US006426186B1

(12) United States Patent
Jones et al.

(10) Patent No.: US 6,426,186 B1
(45) Date of Patent: Jul. 30, 2002

(54) BONE REMODELING GENES

(75) Inventors: Karen A. Jones, Essex (GB); Wayne Volkmuth, Calabasas; Michael G. Walker, Sunnyvale, both of CA (US)

(73) Assignee: Incyte Genomics, Inc, Palo Alto, CA (US)

( * ) Notice: Subject to any disclaimer, the term of this patent is extended or adjusted under 35 U.S.C. 154(b) by 0 days.

(21) Appl. No.: 09/484,970

(22) Filed: Jan. 18, 2000

(51) Int. Cl.[7] .......................... C12Q 1/68; C07H 21/02; C07H 21/04

(52) U.S. Cl. ....................... 435/6; 435/69.1; 435/320.1; 435/440; 536/23.1; 536/24.1; 514/44

(58) Field of Search ......................... 435/6, 440, 320.1, 435/69.1; 536/23.1, 24.1; 514/44

(56) References Cited

PUBLICATIONS

BCCM News, Edition 4, Nov. 1997, http://www,bespo.be. bccm/news/4–97/bccm4b.htm.*
AC004686/c (EST Database Record, Oct. 2, 1998).*
GenEMBL database Record HS774I24/c (Sep. 8, 1998).*
GenEMBL Database Record AL162253/c (Mar. 26, 2000).*
EST Database Record AW292891 (Jan. 6, 2000).*
GenEMBL Database Record HSMX1_2/c and HSMX1_3/c (2000).*
GenEMBL Database Record AC005141/c (Jun. 18, 1998).*
GenEMBL Database Record AC018921 (Dec. 23, 1999).*
GenEMBL Database Record AC018552 (Dec. 14, 1999).*
EST Database Record AW665301/c (Jun. 22, 1998).*
GenEMBL Database Record AC018571 (Dec. 14, 1999).*
Manolagas, S. C., "Cellular and molecular mechanisms of osteoporosis", Aging Clin Exp Res 10: 182–190 (1998).
Teitelbaum, S. L. et al., "Osteoclasts, macrophages, and the molecular mechanisms of bone resorption", J Leukoc Biol 61:381–388 (1997).
Masiukiewicz, U. S. and K.L. Insogna, "The role of parathyroid hormone in the pathogenesis, prevention and treatment of postmenopausal osteoporosis", Aging Clin Exp Res 10: 232–239 (1998).
Vortkamp, A. et al., "Regulation of Rate of Cartilage Differentiation by Indian Hedgehog and PTH–Related Protein", Science 273: 613–622 (1996).
Lanske, B. et al., "Ablation of the PTHrP gene or the PTH/PTHrP receptor gene leads to distinct abnormalities in bone development", J Clin Invest 104: 399–407 (1999).
Jilka, R. L. et al., "Increased Osteoclast Development After Esgtrogen Loss: Mediation by Interleukin–6", Science 257: 88–91 (1992).
Poli, V. et al., "Interleukin–6 deficient mice are protected from bone loss caused by estrogen depletion", EMBO J 13: 1189–1196 (1994).
Srivastava, S. et al., "Estrogen Blocks M–CSF Gene Expression and Osteoclast Formation by Regulating Phosphorylation of Egr–1 and Its Interaction with Sp–1", J Clin Invest 102: 1850–1859 (1998).
Kimble, R. B. et al., "Simultaneous Block of Interleukin–1 and Tumor Necrosis Factor Is Required to Completely Prevent Bone Loss in the Early Postovariectomy Period", Endocrinology 136: 3054–3061 (1995).
de Vernejoul, M. C., "Dynamics of Bone Remodelling: Biochemical and Pathophysiological Basis", Eur J Clin Chem Clin Biochem 34: 729–734 (1996).
Strom et al. (1997) Hum Mol Genet 6: 165–171 (abstract only).
Ecarot and Desbarats (1999) Endocrinology 140:1 192–1199 (abstract only).
Jilka et al. (1999) J Clin Invest 104: 439–446 (abstract only).
Mierke and Pellegrini (1999) Curr Pharm Des 5: 21–36 (abstract only).
Hsu et al. (1999) Proc Natl Acad Sci 96: 3540–3545 (abstract only).
Yeh et al. (1997) Immunity 7:715–725 (abstract only).
Darnay et al. (1998) J Biol Chem 273: 20551–20555 (abstract only).
Lacey et al. (1998) Cell 93: 165–176 (abstract only).
Kong et al. (1999) Nature 397: 315–323 (abstract only).
Nakagawa et al. (1998) Biochem Biophys Res Commun 253: 395–400 (abstract only).
Chen et al. (1993) Proc Natl Acad Sci 90: 4543–4547 (abstract only).
St–Arnaud (1999) Bone 25: 127–129 (abstract only).
Suda et al. (1998) Proc Natl Acad Sci 95: 2337–42 (abstract only).
Shozu and Simpson (1998) Mol Cell Endocrinol 139: 117–29 (abstract only).
Eyre et al. (1998) J Bone Miner Res 13: 996–1004 (abstract only).
MacGillivray et al. (1998) Horm Res 49 (Suppl 1): 2–8 (abstract only).
Dealy et al. (1998) Dev Biol 202: 43–55 (abstract only).
Kretzschmar et al. (1997) Nature 389: 618–22 (abstract only).
Tam et al. (1998) Am J Physiol 274: C1686–98 (abstract only).
Sabatini et al. (1988) Proc Natl Acad Sci 85: 5235–9 (abstract only).
Sato et al. (1999) Biochem Biophys Res Commun 254: 384–7 (abstract only).

(List continued on next page.)

*Primary Examiner*—Mary K. Zeman
(74) *Attorney, Agent, or Firm*—Incyte Genomics, Inc.; Lynn E. Murry

(57) ABSTRACT

The invention provides polynucleotides and polypeptides that are co-expressed with genes known to be involved in bone remodeling and osteoporosis. The invention also provides expression vectors, host cells, and methods for making a polypeptide, for screening or purifying ligands, and for diagnosing disorders associated with bone remodeling or osteoporosis.

4 Claims, No Drawings

OTHER PUBLICATIONS

Reddi and Cunningham (1993) J Bone Miner Res 8 (Suppl 2): S499–502 (abstract only).
Chang et al. (1994) J Biol Chem 269: 28227–34 (abstract only).
Bellows et al. (1999) Cell Tissue Res 297: 249–59 (abstract only).
Faccio et al. (1998) Biochem Biophys Res Commun 249: 522–5 (abstract only).
Hodivala–Dilke et al. (1999) J Clin Invest 103: 229–38 (abstract only).
Jahnen–Dechent et al. (1997) J Biol Chem 272: 31496–503 (abstract only).
Simonet et al. (1997) Cell 89: 309–19 (abstract only).
Yasuda et al. (1998) Endocrinology 139: 1329–37 (abstract only).
Bucay et al. (1998) Genes Dev 12: 1260–8 (abstract only).
Nakase et al. (1997) Bone 21: 17–21 (abstract only).
Tondravi et al. (1997) Nature 386: 81–4 (abstract only).
Vu et al. (1998) Cell 93: 411–22 (abstract only).
Roodman (1996) Endocr Rev 17: 308–32 (abstract only).
Lanske et al. (1996) Science 273: 663–6 (abstract only).
Juppner et al. (1991) Science 254: 1024–6 (abstract only).
Amizuka et al. (1999) J Clin Invest 103: 373–81 (abstract only).
Lanske et al. (1999) J Clin Invest 104: 399–407 (abstract only).
Soriano et al. (1991) Cell 64: 693–702 (abstract only).
Hall et al. (1994) Biochem Biophys Res Commun 199: 1237–44 (abstract only).
Wang et al. (1997) Endocrinology 138: 2953–62 (abstract only).
Gerber et al. (1999) Nat Med 5: 623–8 (abstract only).
Abe et al. (1999) Calcif Tissue Int 64: 508–15 (abstract only).
Ishisaki et al. (1999) J Biol Chem 274: 13637–42 (abstract only).
Usdin et al. (1995) J Biol Chem 270: 15455–8 (abstract only).
Clark et al. (1998) Mol Endocrinol 12: 193–206 (abstract only).
LeClerc et al. (1991) J Biol Chem 266: 17333–40 (abstract only).
Johnson et al. (1999) Endocrinology 140: 3245–54 (abstract only).
Okawa et al. (1998) Nat Genet 19: 271–3 (abstract only).
Kobayashi et al. (1998) Calcif Tissue Int 62: 426–36 (abstract only).
Wozney et al. (1988) Science 242: 1528–34 (abstract only).
Gori et al. (1999) J Bone Miner Res 14: 1522–35 (abstract only).
Morrison et al. (1992) Proc Natl Acad Sci 89: 6665–9 (abstract only).
Tao et al. (1998) Arch Dis Child 79: 488–94 (abstract only).
Yoshizawa et al. (1997) Nat Genet 16: 391–6 (abstract only).
Smith et al. (1994) N Engl J Med 331: 1056–61 (abstract only).
Galibert et al. (1998) J Biol Chem 273: 34120–7 (abstract only).
Korach (1994) Science 266: 1524–7 (abstract only).
Wong et al. (1998) J Biol Chem 273:28355–9 (abstract only).
Langdahl et al. (1997) Bone 20: 289–94 (abstract only).
Liu et al. (1999) Calcif Tissue Int 65: 173–80 (abstract only).
Murakami et al. (1998) Biochem Biophys Res Commun 252: 747–52 (abstract only).
Delmas (1993) J Bone Miner Res 8 (Suppl 2): S549–55 (abstract only).
Hayman et al. (1996) Development 122: 3151–62 (abstract only).
Hou et al. (1999) J Clin Invest 103: 731–8 (abstract only).
Saftig et al. (1998) Proc Natl Acad Sci 95: 13453–8 (abstract only).
Rickard et al. (1998) J Clin Invest 101: 413–22 (abstract only).
Chen et al. (1991) Histochem J 23: 281–9 (abstract only).
Wiesmann et al. (1997) Cell 91: 695–704 (abstract only).
Kuivaniemi et al. (1997) Hum Mutat 9: 300–15 (abstract only).
Byers et al. (1997) Am J Med Genet 72: 94–105 (abstract only).
Pereira et al. (1998) Proc Natl Acad Sci 95: 1142–7 (abstract only).
Sly et al. (1983) Proc Natl Acad Sci 80: 2752–6 (abstract only).
Lehenkari et al. (1998) Exp Cell Res 242: 128–37 (abstract only).
Engleman et al. (1997) J Clin Invest 99: 2284–92 (abstract only).
Grant et al. (1996) Nat Genet 14: 203–5 (abstract only).
Xu et al. (1998) Nat Genet 20: 78–82 (abstract only).
Young et al. (1990) Genomics 7: 491–502 (abstract only).
Staal et al. (1996) Mol Endocrinol 10: 1444–56 (abstract only).
Yoshitake et al. (1999) Proc Natl Acad Sci 96: 8156–60 (abstract only).
Kawane and Horiuchi (1999) Endocrinology 140: 871–9 (abstract only).
Kawakami et al. (1998) Biochem Biophys Res Commun 247: 46–51 (abstract only).
Pulkkinen et al. (1990) J Biol Chem 265: 17780–5 (abstract only).
Dyne et al. (1996) Am J Med Genet 63: 161–6 (abstract only).
Blair et al. (1993) Biochem J 290: 873–84 (abstract only).
Soderstrom et al. (1999) Biochim Biophys Acta 1446: 35–46 (abstract only).
Yamane et al. (1997) Blood 90: 3516–23 (abstract only).
Kuro–o et al. (1997) Nature 390: 45–51 (abstract only).
Kawaguchi et al. (1999) J Clin Invest 104: 229–37 (abstract only).

* cited by examiner

SEQUENCE LISTING

<160> NUMBER OF SEQ ID NOS: 172

<210> SEQ ID NO 1
<211> LENGTH: 1170
<212> TYPE: DNA
<213> ORGANISM: Homo sapiens
<220> FEATURE:
<221> NAME/KEY: misc_feature
<223> OTHER INFORMATION: Incyte ID No: 481497.5

<400> SEQUENCE: 1
gttttgccta ccatcgtgac atctccatgg ctgtaccacc ttgtcgggta gcttatcaga 60
ctgatgttga ctgttgaatc tcatggcaac accagtcgat gggctgtctg acattttggt 120
atctttcatc tgaccatcca tatccaatgt tctcatttaa acattaccca gcatcattgt 180
ttataatcag aaactctggt ccttctgtct ggtggcactt agagtctttt gtgccataat 240
gcagcagtat ggagggagga ttttatggag aaatggggat agtcttcatg accacaaata 300
aataaaggaa aactaagctg cattgtgggt tttgaaaagg ttattatact tcttaacaat 360
tctttttttc agggactttt ctagctgtat gactgttact tgaccttctt tgaaaagcat 420
tcccaaaatg ctctatttta gatagattaa cattaaccaa cataattttt tttagatcga 480
gtcagcataa atttctaagt cagcctctag tcgtggttca tctctttcac ctgcatttta 540
tttggtgttt gtctgaagaa aggaaagagg aaagcaaata cgaattgtac tatttgtacc 600
aaatctttgg gattcattgg caaataattt cagtgtggtg tattattaaa tagaaaaaaa 660
aaattttgtt tcctaggttg aaggtctaat tgatacgttt gacttatgat gaccatttat 720
gcactttcaa atgaatttgc tttcaaaata aatgaagagc agctgtcctt ctttcctctt 780
ttaagtgttc agctgtggca tgctcagagg ttcctgctgg attccagctg gagcggtgtg 840

-continued

```
atacccttct ttttcagctg ttcgtgcctt cctttcttgt atccaccaaa gtggagacaa    900

atacatgatc tcaaagatac acagtaccta cttaattcca gctgatggga gaccaaagaa    960

tttgcaagtg gatggtttgg tatcactgta aataaaaaga gggcctggga attcttgcga   1020

ttccatctct actttgtata agtctcattt tgtgccttac acatctgcag tatttatcat   1080

gttccaactt ggtgactgtc aggcagtgca atacatcagc agtttatcac cgaagagctg   1140

aggaatacct cccttaaaac agacaatgtc                                    1170


<210> SEQ ID NO 2
<211> LENGTH: 4117
<212> TYPE: DNA
<213> ORGANISM: Homo sapiens
<220> FEATURE:
<221> NAME/KEY: misc_feature
<223> OTHER INFORMATION: Incyte ID No: 344594 (1794154CB1)

<400> SEQUENCE: 2

taagttaccc cgatgacttg gtttggaagg ggttaaggca ccagtcatcc tcttctaaag     60

tgatttatga tgatgtgtgg agtttaaaaa ctttacccca ccccaaagaa cagccctctc    120

actcctcact gagtccactc tgaacgtgct aaaatgggaa ggaggcggtg ttttgatgat    180

ctgttaaatt cttagtgaag tttccttgat ttccagtggc tgctgttgtt tgagtttggt    240

ttggagcaaa actgaggtag tcctaacatt tctgggactg aatccaggca agagaaagaa    300

gaaaaagaag aagaaaaaga ggaggaaaaa ggtagggaga aataaaggga ggagagaagc    360

acagtgaaaa aaaaaaaaag tcccttttcg acatcacatt cctgtgtttt ccctcagcct    420

ggaaaacata tgaatcccag tgcttttacg cccggaaaca aagagactaa gccagactat    480

gggggaaagg gagataagaa ggatcctgga actttaaaga gggaaagagt gagattcaga    540

aatcgccagg actggacttt aagggacgtc ctgtgtcagc acaagggact ggcacacaca    600

gacacacgag accgaggaga aactgcagac aaatggagat acaaagactt agaaggacag    660

ctcctttcac ctcatcctac ttgtccagaa ggtaaaaaga cacagccaga aagaaaaggc    720

atcggctcag ctctcagatc aggacaggct gtggatctgt ggcggtactc tgaaagctgg    780

agctgcagca caccccttt gtattgctca ccctcggtaa agagagagag ggctgggagg     840

aaaagtagtt catctaggaa actgtcctgg gaaccaaact tctgatttct tttgcaaccc    900

tctgcattcc atctctatga gccaccattg gattacacaa tgacatggag aatgggaccc    960

cgtttcacta tgctgttggc catgtggcta gtgtgtggat cagaacccca cccccatgcc   1020

actattagag gcagccacgg aggacggaaa gtgcctttgg tttctccgga cagcagtagg   1080

ccagctcggt ttctgaggca cactgggagg tctcgcggaa ttgagagatc cactctggag   1140

gaaccaaacc ttcagcctct ccagagaagg aggagtgtgc ccgtgttgag actagctcgc   1200

ccaacagagc cgccagcccg ctcggacatc aatggggccg ccgtgagacc tgagcaaaga   1260

ccagcagcca ggggctctcc gcgtgagatg atcagagatg aggggtcctc agctcggtca   1320

agaatgttgc gtttcccttc ggggtccagc tctcccaaca tccttgccag ctttgcaggg   1380

aagaacagag tatgggtcat ctcagcccct catgcctcgg aaggctacta ccgcctcatg   1440

atgagcctgc tgaaggacga tgtgtactgt gagctggcgg agaggcacat ccaacagatt   1500

gtgctcttcc accaggcagg tgaggaagga ggcaaggtga gaaggatcac cagcgagggc   1560

cagatcctgg agcagcccct ggaccctagc ctcatcccta agctgatgag cttcctgaag   1620

ctggagaagg gcaagtttgg catggtgctg ctgaagaaga cgctgcaggt ggaggagcgc   1680
```

-continued

```
tatccatatc ccgttaggct ggaagccatg tacgaggtca tcgaccaagg ccccatccgt   1740
aggatcgaga agatcaggca gaagggcttt gtccagaaat gtaaggcctc tggtgtagag   1800
ggccaggtgg tggcggaggg gaatgacggt ggagggggag caggaaggcc aagcctgggc   1860
agcgagaaga agaaagagga cccaaggaga gcacaagtcc caccaaccag agagagtcgg   1920
gtgaaggtcc tgagaaaact ggccgccact gcaccagctt tgccccaacc tccctcaacc   1980
cccagagcca ccacccttcc tcctgcccca gccacaacag tgactcggtc cacgtcccgg   2040
gcggtaacag ttgctgcaag acctatgacc accactgcct ttcccaccac gcagaggccc   2100
tggacccccct caccctccca caggccccct acaaccactg aggtgatcac tgccaggaga   2160
ccctcagttt cagagaatct ttaccctcca tcccggaagg atcagcacag ggagaggcca   2220
cagacaacca ggaggcccag caaggccacc agcttggaga gcttcacaaa tgcccctccc   2280
accaccatct cagaacccag cacaagggct gctggcccag gccgtttccg ggacaaccgc   2340
atggacaggc gggaacatgg ccaccgagac ccaaatgtgg tgccaggtcc tcccaagcca   2400
gcaaaggaga aacctcccaa aaagaaggcc caggacaaaa ttcttagtaa tgagtatgag   2460
gagaagtatg acctcagccg gcctactgcc tctcagctgg aggacgagct gcaggtgggg   2520
aatgttcccc ttaaaaaagc aaaggagtct aaaaagcatg aaaagcttga gaaaccagag   2580
aaggagaaga aaaaaaagat gaagaatgag aacgcagaca agttacttaa gagtgaaaag   2640
caaatgaaga agtctgagaa aaagagcaag caagagaaag agaagagcaa gaagaaaaaa   2700
ggaggtaaaa cagaacagga tggctatcag aaacccacca acaaacactt cacgcagagt   2760
cccaagaagt cagtggccga cctgctgggg tcctttgaag gcaaacgaag actccttctg   2820
atcactgctc ccaaggctga gaacaatatg tatgtgcaac aacgtgatga atatctggaa   2880
agtttctgca agatggctac caggaaaatc tctgtgatca ccatcttcgg ccctgtcaac   2940
aacagcacca tgaaaatcga ccactttcag ctagataatg agaagcccat gcgagtggtg   3000
gatgatgaag acttggtaga ccagcgtctc atcagcgagc tgaggaaaga gtacggaatg   3060
acctacaatg acttcttcat ggtgctaaca gatgtggatc tgagagtcaa gcaatactat   3120
gaggtaccaa taacaatgaa gtctgtgttt gatctgatcg atactttcca gtcccgaatc   3180
aaagatatgg agaagcagaa gaaggagggc attgtttgca aagaggacaa aaagcagtcc   3240
ctggagaact tcctatccag gttccggtgg aggaggaggt tgctggtgat ctctgctcct   3300
aacgatgaag actgggccta ttcacagcag ctctctgccc tcagtggtca ggcgtgcaat   3360
tttggtctgc gccacataac cattctgaag cttttaggcg ttggagagga agttggggga   3420
gtgttagaac tgttcccaat taatgggagc tctgttgttg agcgagaaga cgtaccagcc   3480
catttggtga aagacattcg taactatttt caagtgagcc cggagtactt ctccatgctt   3540
ctagtcggaa aagacggaaa tgtcaaatcc tggtatcctt ccccaatgtg gtccatggtg   3600
attgtgtacg atttaattga ttcgatgcaa cttcggagac aggaaatggc gattcagcag   3660
tcactgggga tgcgctgccc agaagatgag tatgcaggct atggttacca tagttaccac   3720
caaggatacc aggatggtta ccaggatgac taccgtcatc atgagagtta tcaccatgga   3780
taccccttact gagcagaaat atgtaacctt agactcagcc agtttcctct gcagctgcta   3840
aaactacatg tggccagctc cattcttcca cactgcgtac tacatttcct gccttttttct   3900
ttcagtgttt ttctaagact aaataaatag caaactttca cctattcatg agttattatt   3960
gaaacctcaa atcataaaga catttaaaag aattgttttt ctaactggag ggctctagt   4020
gctaaataat agtactgaaa attgatatta ttttcctttt cttatatgaa ggaccttatt   4080
```

```
tggcatataa aattttataa aatatgtaaa aaaaaaa                    4117


<210> SEQ ID NO 3
<211> LENGTH: 1222
<212> TYPE: DNA
<213> ORGANISM: Homo sapiens
<220> FEATURE:
<221> NAME/KEY: misc_feature
<223> OTHER INFORMATION: Incyte ID No: 202177  (3001124CB1)

<400> SEQUENCE: 3

agaaatatca tatggttact ttggtatctg acacagccat gacaccaatt gctagtgtag     60

acacaatagc tgtgtgtctt tttgcaggag cctggggagg ggccatggtg ccaatgcact    120

tactggggag actggagaag ccgcttctcc tcctgtgctg cgcctccttc ctactggggc    180

tggctttgct gggcataaag acggacatca cccccgttgc ttatttcttt ctcacattgg    240

gtggcttctt cttgtttgcc tatctcctgg tccggtttct ggaatggggg cttcggtccc    300

agctccaatc aatgcagact gagagcccag ggccctcagg caatgcacgg gacaatgaag    360

cctttgaagt gccagtctat gaagaggccg tggtgggact agaatcccag tgccgccccc    420

aagagttgga ccaaccaccc ccctacagca ctgttgtgat acccccagca cctgaggagg    480

aacaacctag ccatccagag gggtccagga gagccaaact ggaacagagg cgaatggcct    540

cagaggggtc catggcccag gaaggaagcc ctggaagagc tccaatcaac cttcggcttc    600

ggggaccacg ggctgtgtcc actgctcctg atctgcagag cttggcggca gtccccacat    660

tagagcctct gactccaccc cctgcctatg atgtctgctt tggtcaccct gatgatgata    720

gtgtttttta tgaggacaac tgggcacccc cttaaatgac tctcccaaga tttctcttct    780

ctccacacca gacctcgttc atttgactaa cattttccag cgcctactat gtgtcagaaa    840

caagtgtttc tgcctggaca tcataaatgg ggacttggac cctgaggaga gtcaggccac    900

ggtaagccct tcccagctga gatatgggtg gcataatttg agtcttctgg caacatttgg    960

tgacctaccc catatccaat atttccagcg ttagattgag gatgaggtag ggaggtgatc   1020

cagagaaggc ggagaaggaa gaagtaacct ctgagtggcg gctattgctt ctgttccagg   1080

tgctgttcga gctgttagaa cccttaggct tgacagcttt gtgagttatt attgaaaaat   1140

gaggattcca agagtcagag gagtttgata atgtgcacga gggcacactg ctagtaaata   1200

acattaaaat aactcgaatg ac                                            1222


<210> SEQ ID NO 4
<211> LENGTH: 4359
<212> TYPE: DNA
<213> ORGANISM: Homo sapiens
<220> FEATURE:
<221> NAME/KEY: misc_feature
<223> OTHER INFORMATION: Incyte ID No: 331365 (1553795CB1)

<400> SEQUENCE: 4

cggacccaaa ggagcaaaag gagattccag aacaatcaca accaaaggtg agcggggaca     60

gcccggcgtc ccaggtgtgc ccgggatgaa aggtgacgat ggcagcccag gccgcgatgg    120

gctcgatgga ttccccggcc tcccaggccc tcccggtgat ggcatcaagg gccctccagg    180

ggacccaggc tatccaggaa tacctggaac gaagggtact ccaggagaaa tgggcccccc    240

aggactgggc cttcccggcc tcaaaggcca acgtggtttc cctggagacg ccggcttacc    300

tggaccacca ggcttcctgg gccctcctgg ccccgcagga ccccaggaca aatagattgt    360
```

-continued

```
gacacagatg tgaaaagggc cgttggaggt gacagacagg aggccatcca gccaggttgc     420
ataggagggc ccaagggatt gccaggcctg ccaggacccc caggccccac aggtgccaaa     480
ggcctccgag gaatcccagg cttcgcagga gctgatggag gaccagggtc caggggcttg     540
ccaggagacg caggtcgtga aggttcccca ggacccccag ggttcatagg accccgagga     600
tccaaaggtg cagtgggcct ccctggccca gatggatccc caggtcccat cggcctgcca     660
gggccagatg ggcccctgg ggaaaggggc ctccctggag aagtcctggg agctcagccc     720
gggccacggg gagatgctgg tgtgcctgga cagcctgggc ttaaaggcct tcccggagac     780
agaggccccc ctggattcag aggaagccaa gggatgcctg ggatgccagg gctgaagggc     840
cagccaggcc tcccaggacc ttccggccag ccaggcctgt atgggcctcc aggactgcat     900
ggattcccag gagctcctgg ccaagagggg cccttggggc tgccaggaat cccaggccgt     960
gaaggtctgc ctggtgatag aggggaccct ggggacacag gcgctcctgg ccctgtgggc    1020
atgaaaggtc tctctggtga cagaggagat gctggcttca caggggagca aggccatcca    1080
ggaagccctg gatttaaagg aattgatgga atgcctggga cccccgggct aaaaggagat    1140
agaggctcac ctgggatgga tggtttccaa ggcatgcctg gactcaaagg gagacccggg    1200
tttccaggga gcaaaggcga ggctggattt ttcggaatac ccggtctgaa gggtctggct    1260
ggtgagccag gttttaaagg cagccgaggg gaccctgggc ccccaggacc acctcctgtc    1320
atcctgccag gaatgaaaga cattaaagga gagaaaggag atgaagggcc tatggggctg    1380
aaaggatacc tgggcgcaaa aggtatccaa ggaatgccag gcatcccagg gctgtcagga    1440
atccctgggc tgcctgggag gcccggccac atcaaaggag tcaagggaga catcggagtc    1500
cccggcatcc ccggtttgcc aggattccct ggggtggctg gcccccctgg aattacggga    1560
ttcccaggat tcataggaag ccggggtgac aaaggtgccc cagggagagc aggcctgtat    1620
ggcgagattg gcgcgactgg tgatttcggt gacatcgggg acactataaa tttaccagga    1680
agaccaggcc tgaaggggga gcggggcacc actggaatac caggtctgaa gggattcttt    1740
ggagagaagg gaacagaagg tgacatcggc ttccctggga taacaggcgt gactggagtc    1800
caaggccctc ctggacttaa aggacaaaca ggctttccag ggctgactgg gcctccaggg    1860
tcgcagggag agctggggcg gattggactg cctggtggca aaggagatga tggctggccg    1920
ggagctccgg gcttaccagg ttttccggga ctccgtggga tccgcggctt acacggcttg    1980
ccaggcacca agggctttcc aggatcccca ggttctgaca tccacggaga cccaggcttc    2040
ccaggccctc ctggggaaag aggtgaccca ggagaggcca acacccttcc aggccctgtg    2100
ggagtcccag gacagaaagg agaccaagga gctccagggg aacgaggccc acctgggagc    2160
ccaggacttc aggggttccc aggcatcaca ccccccttcca acatctctgg ggcacctggt    2220
gacaaagggg cgccagggat atttggcctg aaaggttatc ggggcccacc agggccacca    2280
ggttctgctg ctcttcctgg aagcaaaggt gacacaggga acccaggagc tccaggaacc    2340
ccagggacca aaggatgggc cggggactcc gggccccagg gcaggcctgg tgtgtttggt    2400
ctcccaggag aaaaagggcc caggggtgaa caaggcttca tggggaacac tggacccacc    2460
ggggcggtgg gcgacagagg ccccaaggga cccaagggag acccaggatt ccctggtgcc    2520
cccgggactg tgggagcccc cggggattgca ggaatccccc agaagattgc cgtccaacca    2580
gggacagtgg gtccccaggg gaggcgaggc cccctgggg caccggggga gatggggccc    2640
cagggccccc ccggagaacc aggttttcgt ggggctccag ggaaagctgg gccccaagga    2700
agaggtggtg tgtctgctgt tcccggcttc cggggagatg aaggacccat aggccaccag    2760
```

```
gggccgattg gccaagaagg tgcaccaggc cgtccaggga gcccgggcct gccgggtatg   2820
ccaggccgca gcgtcagcat cggctacctc ctggtgaagc acagccagac ggaccaggag   2880
cccatgtgcc cggtgggcat gaacaaactc tggagtggat acagcctgct gtacttcgag   2940
ggccaggaga aggcgcacaa ccaggacctg gggctggcgg gctcctgcct ggcgcggttc   3000
agcaccatgc ccttcctgta ctgcaaccct ggtgatgtct gctactatgc cagccggaac   3060
gacaagtcct actggctctc taccactgcg ccgctgccca tgatgcccgt ggccgaggac   3120
gagatcaagc cctacatcag ccgctgttct gtgtgtgagg ccccggccat cgccatcgcg   3180
gtccacagtc aggatgtctc catcccacac tgcccagctg ggtggcggag tttgtggatc   3240
ggatattcct tcctcatgca cacggcggcg ggagacgaag gcggtggcca atcactggtg   3300
tcaccgggca gctgtctaga ggacttccgc gccacaccat tcatcgaatg caatggaggc   3360
cgcggcacct gccactacta cgccaacaag tacagcttct ggctgaccac cattcccgag   3420
cagagcttcc agggctcgcc ctccgccgac acgctcaagg ccggcctcat ccgcacacac   3480
atcagccgct gccaggtgtg catgaagaac ctgtgagccg gcgcgtgcca ggaagggcca   3540
ttttggtgct tattcttaac ttattacctc aggtgccaac ccaaaaattg gttttatttt   3600
tttcttaaaa aaaaaaaagt ctaccaaagg aatttgcatc cagcagcagc acttagacct   3660
gccagccact gtcaccgagc gggtgcaagc actcggggtc cctggagggc aagccctgcc   3720
cacagaaagc caggagcagc cctggccccc atcagccctg ctagacgcac cgcctgaagg   3780
cacagctaac cacttcgcac acacccatgt aaccactgca ctttccaatg ccacagacaa   3840
ctcacattgt tcaactccct tctcggggtg ggacagacga gacaacagca cacaggcagc   3900
cagccgtggc cagaggctcg aggggctcag ggctcaggc acccgtcccc acacgagggc    3960
cccgtgggtg ggcctggccc tgctttctac gccaatgtta tgccagctcc atgttctccc   4020
aaataccgtt gatgtgaatt attttaaagg caaaactgtg ctctttattt taaaaaacac   4080
tgataatcac actgcggtag gtcattcttt tgccacatcc ctatagacca ctgggtttgg   4140
caaaactcag gcagaagtgg agacctttct agacatcact gtcagccttg ctacttgaag   4200
gtacacccca tagggtcgga ggtgctgtcc ccactgcccc acgttgtccc tgagatttaa   4260
cccctccact gctgggggtg agctgtactc ttctgactgc cccctcctgt gtaacgacta   4320
caaaataaaa cttggttctg aatattttta aaaaaaaaa                          4359
```

<210> SEQ ID NO 5
<211> LENGTH: 1946
<212> TYPE: DNA
<213> ORGANISM: Homo sapiens
<220> FEATURE:
<221> NAME/KEY: misc_feature
<223> OTHER INFORMATION: Incyte ID No: 201920 (1975990/2320312CT1)

<400> SEQUENCE: 5

```
cggggcgggg ctgagcgtgt ttacatccgc cgggtgcgcg gcttcgccgc ccgaggtcgt     60
tcggctcggg taccatcctc cgcgccatgg acaccagcga cctgttcgcc agctgcagga    120
agggggatgt gggccgagtg cggtacctgc tggagcagcg agacgtggag gtactatgcc    180
tgcttgtgtg ggcacgagga gctggtactc taccttctgg ccaatggagc ccgctgcgag    240
gccaacacct tcgatggtga gcgctgcctc tatggggcac tgagtgaccc catccgccgg    300
gctctacgcg attacaagca ggtcacggct tcctgcagga ggcgggatta ctatgacgac    360
ttcttgcagc ggcttctaga gcagggcatc cacagtgacg tggtctttgt agtacacggg    420
```

-continued

```
aagccattcc gggtgcatcg ctgcgtcctg ggtgcacgta gcgctacttt gccaacatgc    480

tggacaccaa atggaagggc aagagtgtcg tggttctcag gcacccactg atcaaccccg    540

tggcctttgg ggccctgctg cagtacctgt acacaggccg cctggacatt ggcgtagagc    600

atgtgagtga ctgtgagcgc ctggccaagc aatgccagct gtgggacctg ctcagcgacc    660

tggaggccaa gtgcgagaag gtgtctgagt ttgtggcgtc taagccaggc acgtgtgtga    720

aggtgctgac catcgagccc ccacctgcag acccccgcct ccgggaggac atggcgctgc    780

tggccgattg tgccctgccc cccgagctcc gaggtgatct ttgggagctg cccttccctt    840

gtcctgacgg cttcaacagc tgccctgaca tctgcttccg agtggctggc tgcagcttcc    900

tctgccacaa ggccttttc tgtggccgca gtgactactt ccgagccctg ctggatgacc    960

acttccgaga gagcgaggag ccagcgacct caggggggccc cccagccgtc accctgcatg   1020

gcatctcacc cgacgtcttc actcacgtgc tctactacat gtacagcgac cacactgagc   1080

tgtcccccga ggcagcctat gatgtgctga gcgtcgccga catgtacctg ctgccaggcc   1140

tgaagaggct gtgcggccgc agcctggctc agatgctaga cgaggacact gtggtgggtg   1200

tgtggcgcgt ggccaagctc ttccgcctgg cgcggcttga ggaccagtgc actgagtaca   1260

tggccaaggt cattgagaag ctggtggagc gggaggactt cgtggaggcg gtgaaggagg   1320

aggcagcggc tgtggcagcc cggcaggaga cggactctat cccgctggtg gacgacatcc   1380

gcttccacgt ggccagcacg gtgcagacct acagcgccat agaggaggcg cagcagcgtc   1440

tgcgggcact cgaggacctg ctcgtgtcca tcggtctgga ctgttgagcc cctggctggg   1500

cagccccagg ggccaggagc tctcttggag acaagcatgt gtatgcgttt gtgtgcagct   1560

cttcttcctg ctccctgcac attgagggct tcatgggggg tgcgaggggc tcagtggggc   1620

ttctcttccc tccatgagcc tggagacccc aggggaggat ccatttggga tgagcccccct  1680

ccccccaatg cacaagccag cccccaagac cctgggggtg gacaccactc agggaaacct   1740

ggggtggggg tgggctttgg tcttagcact ttccttctcc agatcccccc tacccacccc   1800

agtcccaaat ccagtcctct ggcccttgcc tagccctgaa ttgcttctct aagctggtgt   1860

tcccatgcac agggccattc aggaagggct gggggagtgt gtgtggcaat aaagcttgaa   1920

ggcaccgtgg gaaaaaaaaa aaaaaa                                         1946
```

<210> SEQ ID NO 6
<211> LENGTH: 1916
<212> TYPE: DNA
<213> ORGANISM: Homo sapiens
<220> FEATURE:
<221> NAME/KEY: misc_feature
<223> OTHER INFORMATION: Incyte ID No: 228058.2
<221> NAME/KEY: unsure
<222> LOCATION: 1860, 1902, 1910
<223> OTHER INFORMATION: a, t, c, g, or other

<400> SEQUENCE: 6

```
ttttttcat attttgtgtg ctgatttttt aatgaacaac ttataatctt acaaaataac     60

tggctgtagc tgttttacat tacaatacag tagatcagct cctttcacta cattcccaat    120

caagccatcc ccttgggtgt taactaatgc actcaatagt gatcacaaag aatacaggaa    180

gtgccaagtt caatgccttg taatagaaaa aagagaagat gagaatcagg aagagctctt    240

tactttcaca atccctttac tttaatttct gtcagtatct gcccattctc ctcaccctgt    300

ccccttacct gcctttctga ttggaggctg tcatgctagt tgttagagcc agctagccct    360
```

-continued

```
gggccacctg ggcacaatca aacacacaga agagtctctg agaaaggctc tcaatgacca    420
catgggtgga taagagtagc agaatgtgga ccaccacatg gattgagtgt gagttgatgt    480
tgctgggatc tgtgaccaca gtgtcttagt ccttccactt tatcagtgac ctgagttgct    540
caaaacatca ggtcccagga acaaagactg gaagaacctg ctgtctctga atagctatag    600
ctgactatgg ctgggaagcc ttatagccta agaggctctt cacacacaac aggaactttc    660
cttttgcttt cccagagcag tggtgaattg cagataataa aatattttaa aatgaaattt    720
aaaacagaaa tgttcttact gttgctcttg tggagagact gcatgaagac acacactggc    780
atgaaccaca ggctccatgt tcctgagctg agtaatgccc aggataacaa ttcctctgcc    840
tcaatctcag acaaagtagg attctccaag gcagaactta gaatgtgtct agcaatttgg    900
acattttccc caataaaaca agtttataaa attttgaaaa tagagtgtct aaacttttcc    960
attgtcctta gcgtattgaa gcctatcaga atcccaagaa taaatatgtt tgtcttcttg   1020
ggggcactaa gcatgaccca agacaatgaa tggtatctga actacatttt ctttacacta   1080
gagattagta gacaaaaggt ttttttgaa tgggtgaact ctgctctttc cttttcccaa   1140
taactttgca accctcattc cacaaaccca cagattaatg tgggtacatc accttattcg   1200
tgttttattc tctttcagga tattgttctt ccctacgtga tagtgtggat aatatttcta   1260
tcattgtggt agtatttcct attcctattt gcacagccat tgctctagtg ttgatgggaa   1320
gagtagaaaa actgtggtca aagcaaaaga gcagaagatg agaagagacc acagctgagc   1380
tctaaatttt gtctgttctt ggtttccatt ggagaagaaa ctttaaagga gacaagcctc   1440
acagccttcc taaaatgagt aaaactagaa tgttaaacag aaactggctc cttactcact   1500
ttccctaggg tctaatccag aaaccgttac aagaaaatgt aactgcagta gaccacatcc   1560
cagtgagcct gggatgtaaa tagagagagg cttaatatgg tcatttcatg tgcattccat   1620
ctattggata agaaagggta aaaacaacaa aatggacatt aaatagttga aattcttctg   1680
tctccccaca gagtgtcacc cttgctccat gcatttccat ggcttgctca agtcaaaatc   1740
tctggctcac agattttgta catgatactt gaagagaatt tatctcagat tcttcattgc   1800
tcaagggacc cactttggtc ttctttggag acttggaaca aggaccgagt ctccctgatn   1860
acttccattc tcatgcccgg gcctggattt aaccctgaca gntcttgcan tgttct       1916
```

<210> SEQ ID NO 7
<211> LENGTH: 1362
<212> TYPE: DNA
<213> ORGANISM: Homo sapiens
<220> FEATURE:
<221> NAME/KEY: misc_feature
<223> OTHER INFORMATION: Incyte ID No: 233014.1

<400> SEQUENCE: 7

```
attcctgatt tgcctttgcc atataatcta atgcttgttt atatagtgtc tggtattgtt     60
taacagttct gtcttttcta tttaaatgcc actaaatttt aaattcatac ctttccatga    120
ttcaaaattc aaaagatccc atgggagatg gttggaaaat ctccacttca tcctccaagc    180
cattcaagtt tcctttccag aagcaactgc tactgccttt cattcatatg ttcttctaaa    240
gatagtctac atttggaaat gtatgttaaa agcacgtatt tttaaaattt ttttcctaaa    300
tagtaacaca ttgtatgtct gctgtgtact ttgctatttt tatttatttt agtgtttctt    360
atatagcaga tggaatgaat ttgaagttcc cagggctgag gatccatgcc ttctttgttt    420
ctaagttatc tttcccatag cttttcatta tctttcatat gatccagtat atgttaaata    480
```

-continued

```
tgtcctacat atacatttag acaaccacca tttgttaagt atttgctcta ggacagagtt    540

tggatttgtt tatgtttgct caaaaggaga cccatgggct ctccagggtg cactgagtca    600

atctagtcct aaaaagcaat cttattatta actctgtatg acagaatcat gtctggaact    660

tttgttttct gctttctgtc aagtataaac ttcactttga tgctgtactt gcaaaatcac    720

attttctttc tggaaattcc ggcagtgtac cttgactgct agctaccctg tgccagaaaa    780

gcctcattcg ttgtgcttga acccttgaat gccaccagct gtcatcacta cacagccctc    840

ctaagaggct tcctggaggt ttcgagattc agatgccctg ggagatccca gagtttcctt    900

tccctcttgg ccatattctg gtgtcaatga caaggagtac cttggctttg ccacatgtca    960

aggctgaaga aacagtgtct ccaacagagc tccttgtgtt atctgtttgt acatgtgcat   1020

ttgtacagta attggtgtga cagtgttctt tgtgtgaatt acaggcaaga attgtggctg   1080

agcaaggcac atagtctact cagtctattc ctaagtccta actcctcctt gtggtgttgg   1140

atttgtaagg cactttatcc cttttgtctc atgtttcatc gtaaatggca taggcagaga   1200

tgatacctaa ttctgcattt gattgtcact ttttgtacct gcattaattt aataaaatat   1260

tcttatttat tttgttactt ggtacaccag catgtccatt ttcttgttta ttttgtgttt   1320

aataaaatgt tcagtttaac atcccagtgg agaaagttaa aa                       1362
```

```
<210> SEQ ID NO 8
<211> LENGTH: 3522
<212> TYPE: DNA
<213> ORGANISM: Homo sapiens
<220> FEATURE:
<221> NAME/KEY: misc_feature
<223> OTHER INFORMATION: Incyte ID No: 249096.3
<221> NAME/KEY: unsure
<222> LOCATION: 656, 658, 663
<223> OTHER INFORMATION: a, t, c, g, or other

<400> SEQUENCE: 8

cgttagtcct taaaacacaa cggacacgtc gtccccgtcc cagacccaaa actacatcaa     60

gtcctgaagt acctcagaac aaatcggttt ctgttacagg ctttgaacct gttgttcata    120

gtactgatgc tccaggaaca acatttgctc tgactgaact gcaaactctt attttgaaac    180

cagtgacatc accaagccta gaaatgacag aaagtcaacc tgtttctgat gggttctgga    240

atcggttaca cttagtactg agtcaccaaa ggagaccata gcaccagcca aaacagacta    300

tgtatatccc actgccaaag caccactctg gccagaggag ccaaagactg aagttgtgga    360

atctattaca tatgtatctg aaccacctga gaccacacta gaaacgtcgc ctctgccttc    420

tcaatctata accctaccca gcccagatga gcctcagact gaacctgctc ccaagcagac    480

accacgtgct cctcctaagc caaaaacatg caccacgccc aagaatccca caaacacaac    540

cagttcctaa ggtgccccag cgtgttactg caaaaccaaa aacgtcacca agtccagaag    600

tgtcatacac cacacctgct ccaaaagatg tgctccttcc tcataaacca tacccncnag    660

gtntctcaga gcgaacctgc tcctctagag acacgaggca tcccttttat acccatgatt    720

tccccaagtc ctagtcaaga ggaactacag accactctgg aagaaacaga ccaatccacc    780

caagaacctt tcacaactaa gattccacga acaactgaac tagcaaagac aactcaggcg    840

ccacacagat tttatactac tgtgaggccc agaacatctg acaagccaca catcagacct    900

gttctgaata ggacaactac aagacctact aggcccaaac ccagtgggat gcccagtggg    960

aatggagtgg gaacaggggt caagcaagca cccaggccat caggtgctga tagaaatgta   1020

tcagtggact ctacccaccc cactaaaaag ccagggactc gccgcccacc cttgccaccc   1080
```

-continued

```
agacctacac acccacgaag aaaaccttta ccaccaaata atgtcactgg aaagccagga   1140
agtgcaggaa tcatttcatc agggcccaat aactacacca cccctgaggt caacacccag   1200
gcctactgga actcccttgg agagaataga gacagatata aagcaaccaa cagttcctgc   1260
ctctggagaa gaactggaaa atataactga ctttagctca agcccaacaa gagaaactga   1320
tcctcttggg aagccaagat tcaaaggacc tcatgtgcga tacatccaaa agcctgacaa   1380
cagtccctgc tccattactg actctgtcaa acggttcccc aaagaggagg ccacagaggg   1440
gaatgccacc agcccaccac agaacccacc caccaacctc actgtggtca ccgtggaagg   1500
gtgccccttc atttgtcatc ttggactggg aaaagccact aaatgacact gtcactgaat   1560
atgaagttat atccagagaa aatgggtcat tcagtgggaa gaacaagtcc attcaaatga   1620
caaatcagac attttccaca gtagaaaatc tgaaaccaaa cacgagttat gaattccagg   1680
tgaaacccaa aaacccgctt ggtgaaggcc cggtcagcaa cacagtggca ttcagtactg   1740
aatcagcgga cccaagagtg agtgagccag tttctgcagg aagagatgcc atctggactg   1800
aaagaccctt taattcagac tcttactcag agtgtaaggg caaacaatat gtcaaaagga   1860
catggtataa aaaatttgta ggagtgcagc tgtgcaactc tctcagatac aagatttact   1920
tgagcgactc cctcacagga aaattttata acataggtga tcagaggggc catggagaag   1980
atcactgcca gtttgtggat tcatttttag atggacgcac tgggcagcaa ctcacttctg   2040
accagttacc aatcaaagaa ggttatttca gagcagttcg ccaggaacct gtccaatttg   2100
gagaaatagg tggtcacacc caaatcaatt atgttcagtg gtatgaatgt gggactacaa   2160
ttcctggaaa atggtagatg ctgcacaaag ttaccttctg tttcatcatt gcaaacaaaa   2220
atcattgaaa atactatgcc gcattcattt aaagctattt tgtttactat gtataaaagt   2280
ctacaatcta attaatagca atactagatg tttattatta gaaaagattg ctgagagtat   2340
ttatcaggtt ttacaaagtc cattttaaga aagcaagata ctgatgttaa cagaataaca   2400
tttttgggga agctggctcc ctattcatgg tattttaaga gatcatttgt atattattta   2460
tcacactgtt gtaatgatgt tttgagatac ttttataaca aaattaacat caaaaaggta   2520
tatacttttt aaaaagtata tacttttatt gatgtgtact cttcctattg atgagttaat   2580
tccataaatc tctacttagt ttaacttatt ggatcaaatt atcttcagca tgtatatctg   2640
gggaaaaaag gtccgaattt tcacatttat atttaaactt caatttttta tatttaaact   2700
tcaatttttt agcaacagct gaatagcttt gcggaggagt ttaatagtta cacattcatg   2760
ctaatataca tttcctttaa acatccacaa attcttaaaa agattgaatc agtaaatttc   2820
atttcagcta aaaatggagt ctaatatatt gtttcaaaag atacattttt acccaccata   2880
aatgttacaa tatctgaata tgctttgtca aactatccct ttatgcaatc gtcttcatat   2940
tgtttttatg attctaatca agctgtatgt agagactgaa tgtgaagtca agtctgagca   3000
caaaaagata atgcacaatg agattgccta ccattttata ggatatttac tatgtattta   3060
tacgttaaga cctctatgaa tgatgtatca gagaatgtct ttgtaactaa ctgtttaatt   3120
caatctgtaa taaaaatcta actaactaac tcatttattt ctattaaaaa ggtattgtcc   3180
tttaggcggg gaatgggaat ccttgctgca ctgttgcagt cattctgaaa ggacctttcc   3240
ctgtacttac ctttcaacat gcttcaatct tatcaacgct acattttgta tttttcaaac   3300
aagtataaat tctgcaataa agagatgtag ttttttttta agattgagtt tttgtttgtt   3360
atttctgaat ggttcatcag tatgttaact atacctttta tcgagaagga aaatcactaa   3420
```

-continued

```
gttttattca ggctctacca acccccatta tatctactgt ttgtttatgt cctaaattaa   3480

cctttcatcc tatgaagtaa taaagttcat tttaaaccaa cg                      3522


<210> SEQ ID NO 9
<211> LENGTH: 1340
<212> TYPE: DNA
<213> ORGANISM: Homo sapiens
<220> FEATURE:
<221> NAME/KEY: misc_feature
<223> OTHER INFORMATION: Incyte ID No: 253776.2CB1

<400> SEQUENCE: 9

gacaacagcc ccacgtgacc ggccaacact gagtgttgtc tcgctctggc gtcagagccg     60

tcgtggctcg ttccattctc ggcggtggta cctgctcccg gtggccctga ggacgtgtgg    120

gccaggggcg gccccgaaat taggaagcgg agggggagca gtctgcaggt ctgcggggct    180

aagtgtcggc ggcggcgcac cttcgcgtca agaatccgga ggaggagact gcaaggatag    240

gcccaggagt aatggagtcc aaagaggaac tagcggcaaa caatctcaac ggggaaaatg    300

cccaacaaga aaacgaagga ggggagcagg cccccacgca gaatgaagaa gaatcccgcc    360

atttgggagg gggtgaaggc cagaagcctg gaggaaatat caggcggggg cgagttaggc    420

gacttgtccc taattttcga tggggccatac ctaataggca tattgagcac aatgaagcga    480

gagatgatgt agaacggttt gtagggcaga tgatggaaat caagagaaag actagggaac    540

agcagatgag gcactatatg cgcttccaaa ctcctgaacc tgacaaccat tatgactttt    600

gcctcatacc ttgaatccta aaagttttcg ctgaggttaa tgtgaacact gctttacaag    660

cttgtatttt tgtgatttac tttttctgta agccttttgg ggtttacact taccagtttc    720

taatggaaat tagaattcta attgaatatt gttttgtctc agcctaaaag ttacggtcag    780

catggcaatt cacctatttt aggaaaaata ctcttttcat aatatgaaat gcataaagca    840

gttcaaaaag cagtctgtat tccatcatct tcctttttca ttccagtcct tatttttgta    900

agtattactt ttcctcctcc ggctacctgg actcaaaatc tcagttgtct ttgacagttt    960

ttttcttgtc cctgaccaaa aaagaatgat catacccaga attcaatgtt tgatatttta   1020

agaatgtatg ttctagtgtt tttcagagtg agtctaccat ctgtataaaa acaccttggg   1080

ggcaggcagg ggcatttaaa aatgtaggac ctatcgtcca gactcacaga gtggggctcc   1140

agaatctcca tttttaacaa actctcttaa gtaattctga tgtgtaccaa aatcagtgcc   1200

attggtgtgt gtgtacgtaa ctatatacat atgtgtgtgt gtgtatatat ataatgtgtc   1260

ataaccgtaa acaataaaca atatcaagat aaatctgact ttgatgggca agtaattaaa   1320

aaagaaaagt atgagacctt                                                1340


<210> SEQ ID NO 10
<211> LENGTH: 1183
<212> TYPE: DNA
<213> ORGANISM: Homo sapiens
<220> FEATURE:
<221> NAME/KEY: misc_feature
<223> OTHER INFORMATION: Incyte ID No: 331906.2CB1
<221> NAME/KEY: unsure
<222> LOCATION: 562
<223> OTHER INFORMATION: a, t, c, g, or other

<400> SEQUENCE: 10

gcggccgctg ggcagcgccc ttcgtccagg ctcgcgcccc agctgccgcc gacgacagcg     60

gccgagagaa gttggggtct gactagacgc ttacggggcc tcggaccccg gcgccgcggc    120
```

-continued

```
gacctccgga gggaaccggc tccttgcgtc ccgcccgcgc agggagctcc gcacgggatt    180
tgcagattta cagaatggct gcacattaat ggaaagagaa gcataaacct atcttctttc    240
attatggagg gaggtttggc agatggggaa cctgatcgaa cttcgcaaac agtgacgaat    300
ctcagcttct gacaccagga aagatgagtc agcgccaagg aaaagaagct tatccaacgc    360
caaccaaaga tttgcatcag ccatctctta gtccagcaag tcctcatagc cagggttttg    420
aaagacggga agcgaacgat atcttctcca aaattaaacg atgaatcttc actttctatg    480
tcaaagagca aggtctgaat ctaaacttta taatggctca gagaaggaca gttcaacttc    540
aagcaaactc acaaaaaaag antctcttaa ggtacaaaag aaaaattacc gagaagaaaa    600
gaaaagagcc acaaaggagc tgctcagtac aatcacagat ccttctgtta ttgttatggc    660
tgattggtta aagattcgtg gtactctaaa gagctggacc aagttatggt gtgtgttgaa    720
acctggggtg ctactgatct ataaaaccca aaaaaatggt cagtgggtag gaacagttct    780
tctgaatgcc tgtgaaatca ttgaacgtcc atcaaaaaag gatggctttt gtttcaaact    840
tttccatcct ttggagcaat ctatttgggc agtgaagggt ccaaaaggtg aagcggttgg    900
atccattact caacccttac ctagcagtta tttgatcatc cgagctactt cacgagtccg    960
atgggaaggt gctgaatgga tgctttgaag ttggctttga aatgtcctag tctccttaaa   1020
ggtacaatga tcagagaagg aaaggaccat gacctgagcg tttcatcaga tagcacacat   1080
gtgacttcca atggcttact acgtgctacc aatctccaca gtggtgataa cttccagtta   1140
aatgatagtg aaattgaccg ccaacatttt aaggaccaag ata                     1183
```

<210> SEQ ID NO 11
<211> LENGTH: 3896
<212> TYPE: DNA
<213> ORGANISM: Homo sapiens
<220> FEATURE:
<221> NAME/KEY: misc_feature
<223> OTHER INFORMATION: Incyte ID No: 009049.1
<221> NAME/KEY: unsure
<222> LOCATION: 12
<223> OTHER INFORMATION: a, t, c, g, or other

<400> SEQUENCE: 11

```
ccggtgcctg anattatgtg cggccccgcg ggctgctttc cgaggtcaga gtgccctgct     60
gctgtctcag aggcatctgt tctgcaaatc ttaggaagaa aaatgtccct agtagcaaac    120
gggtgtcttc tgtgcataaa taagtacaac acaattctcc gaaagttcgg gtaaaaagag    180
atgcggtagc agctgccctg tgtgaagctg tctaccccgc atctctcagg cgctaagctc    240
agtttttgtt tttgtttttg ttttttaaa gaaaagatgt ataattgcag gaattttttt    300
ttattttttt attttccatc attctatata tgtgatggtg aaagatatgc ctggaaaagt    360
tttgttttga aaagtttatt ttctgcttcg tcttcagttg gcaaaagctc tcaattcttt    420
agcttccagt ttcttttctc tctttttctt tgttaggtaa ttaaaggtat gtaaacaaat    480
tatctcatgt agcaggggat tttcatgttg agaggaatct tccgtgtgag ttgtttggtc    540
acacaaataa ccctttctca attttaggag tttggattgt caaatgtagg tttttctcaa    600
agggggcata taactacata ttgactgcca agaactatga ctgtagcact aatcagcaca    660
catagagcca cacaattatt taatttctaa ctctctgtgg tccctagaaa aattccgttg    720
atgtgcttag gttaaagttc tgaagatacc cgttgtaccc ttacttgaaa gtttctaatc    780
ttaagtttta tgaaatgcaa taatatgtat cagctagcaa tatttctgtg atcaccaaca    840
actctcagtt tgatcttaaa gtctgaataa taaaacaaat cccagcagta atacatttct    900
```

-continued

```
taaacctcac agtgcatgat atatcttttc attctgatcc tgtgtttgca aaaatataca    960
catgtatatc atagttcctc actttttatt catttgtttt cctattacct gtagtaaata   1020
tattagttag tacatggaat ttatagcatc agctaccccc aggaacagca cctgacaggc   1080
gggggatttt ttttcaagtt gttctacatt tgcataaatt atttctatta ttattcatgt   1140
atgttattta tttctgaatc acactagtcc tgtgaaagta caactgaagg cagaaagtgt   1200
taggattttg catctaatgt tcattatcat ggtattgatg gacctaagaa aataaaaatt   1260
agactaagcc cccaaataag ctgcatgcat ttgtaacatg attagtagat ttgaatatat   1320
agatgtagta ttttgggtat ctaggtgttt tatcattatg taaaggaatt aaagtaaagg   1380
actttgtagt tgtttttatt aaatatgcat atagtagagt gcaaaaatat agcaaaaata   1440
aaaactaaag gtagaaaagc attttagata tgccttaatt tagaaactgt gccaggtggc   1500
cctcgggaat agatgccagg cagagaccag tgcctgggtg gtgcctcctc ttgtctgccc   1560
tcatgaagaa gcttccctca cgtgatgtag tgcccctcgt aggtgtcatg tggagtagtg   1620
ggaacaggca gtactgttga gaggagagca gtgtgagagt tttctgtag aagcagaact    1680
gtcagcttgt gccttgaggc ttccagaacg tgtcagatgg agaagtccaa gtttccatgc   1740
ttcaggcaac ttagctgtgt acagaagcaa tccagtgtgg taataaaaag caaggattgc   1800
ctgtataatt tattataaaa taaaagggat tttaacaacc aacaattccc aacacctcaa   1860
aagcttgttg catttttttgg tatttgaggt ttttatctga aggttaaagg gcaagtgttt  1920
ggtatagaag agcagtatgt gttaagaaaa gaaaaatatt ggttcgcgta gagtgcaaat   1980
tagaactaga aagttttata cgattatcat tttgagatgt gttaaagtag gttttcactg   2040
taaaatgtat tagtgtttct gcattgccat agggcctggt taaaactttc tcttaggttt   2100
caggaagact gtcacataca gtaagctttt ttccttctga cttataatag aaaatgtttt   2160
gaaagtaaaa aaaaaaaaat ctaatttgga aatttgactt gttagtttct gtgtttgaaa   2220
tcatggttct agaaatgtag aaattgtgta tatcagatac tcatctaggc tgtgtgaacc   2280
agcccaagat gaccaacatc cccacacctc tacatctctg tcccctgtat ctcttccttt   2340
ctaccactaa agtgttccct gctaccatcc tggcttgtcc acatggtgct ctccatcttc   2400
ctccacatca tggaccacag gtgtgcctgt ctaggcctgg ccaccactcc caacttgacc   2460
tagccacatt catctagaga tggttcctga tgctgggcac agactgtgct catggcaccc   2520
attagaaatg cctctagcat ctttgtatgc atcttgattt ttaaaccaag tcattgtaca   2580
gagcattcag ttttggctgt ggtaccaaga gaaaaactaa tcaagaatat aaaccacatt   2640
ccaggctgct gttttctctc catctacagg ccacactttt actgtatttc ttcatacttg   2700
aaattcattc tgctattttc atatcagggt acagacttat aagggtgcat gttccttaaa   2760
ggtgcataat tattcttatt ccgtttgctt atattgctac agaatgctct gttttggtgc   2820
tttgagttct gcagacccaa gaagcagtgt ggaaattcac tgcctgggac acagtcttat   2880
aagaatgttg gcaggtgact ttgtatcaga tgttgcttct cttttctctg tacacagatt   2940
gagagttacc acagtggcct gtcgggtcca ccctgtgggt gcagcacagc tctctgaaag   3000
caagaacctt cctacctatt ctaacgtttt tgccctctaa gaaaaatggc ctcaggtatg   3060
gtatagacat agcaagaggg gaagggctgt ctcactctag caaccatccc tccattacac   3120
acagaaagcc ctcttgaagc aaaagaagaa gaaagaaaga aagcttatct ctaaggctac   3180
tgtcttcaga atgctctgag ctgaatgctc ttgctccttt cccaagaggc agatgaaaat   3240
```

-continued

```
atagccattt tatctatacc cttcctatct gaggaggaga atagaaaagt agggtaaata   3300

tgtaacgtaa aatatgtcat tcaaggacca ccaaaacttt aagtacccta tcattaaaaa   3360

tctggtttta aaagtagctc aagtaaggga tgctttgtga cccagggttt ctgaagtcag   3420

atagccattc ttacctgccc cttactctga cttattggga aagggagaac tgcagtggtg   3480

tttctgttgc agtggcaaag gtaacatgtc agaaaattca gagggttgca taccaataat   3540

cctttggaaa ctggatgtct tactgggtgc tagaatgaaa atgtaggtat ttattgtcag   3600

atgatgaagt tcattgtttt tttcaaaatt ggtgttgaaa tatcactgtc caatgtgttc   3660

acttatgtga aagctaaatt gaatgaggca aaaagagcaa atagtttgta tatttgtaat   3720

accttttgta tttcttacaa taaaaatatt ggtagcaaat aaaaataata aaaacaataa   3780

ctttaaactg ctttctggag atgaattact ctcctggcta ttttcttttt tactttaatg   3840

taaaatgagt ataactgtag tgagtaaaat tcattaaatt ccaagtttta gcaaaa        3896
```

<210> SEQ ID NO 12
<211> LENGTH: 927
<212> TYPE: DNA
<213> ORGANISM: Homo sapiens
<220> FEATURE:
<221> NAME/KEY: misc_feature
<223> OTHER INFORMATION: Incyte ID No: 213109.3CB1

<400> SEQUENCE: 12

```
ctttccgaag cctctaggtc attgtggtgc cttgtagctg tcccgggagc cctcagcagc     60

agttggagct ggtgcacagg aaggatgagg aagaccaggc tctgggggct gctgtggatg    120

ctctttgtct cagaactccg agctgcaact aaattaactg aggaaaagta tgaactgaaa    180

gaggggcaga ccctggatgt gaaatgtgac tacacgctag agaagtttgc cagcagccag    240

aaagcttggc agataataag ggacggagag atgcccaaga ccctggcatg cacagagagg    300

ccttcaaaga attcccatcc agtccaagtg gggaggatca tactagaaga ctaccatgat    360

catggtttac tgcgcgtccg aatggtcaac cttcaagtgg aagattctgg actgtatcag    420

tgtgtgatct accagcctcc caaggagcct cacatgctgt tcgatcgcat ccgcttggtg    480

gtgaccaagg gtttttcagg gacccctggc tccaatgaga attctaccca gaatgtgtat    540

aagattcctc ctaccaccac taaggccttg tgcccactct ataccagccc cagaactgtg    600

acccaagctc cacccaagtc aactgccgat gtctccactc ctgactctga aatcaacctt    660

acaaatgtga cagatatcat cagggttccg gtgttcaaca ttgtcattct cctggctggt    720

ggattcctga gtaagagcct ggtcttctct gtcctgtttg ctgtcacgct gaggtcattt    780

gtaccctagg cccacgaacc cacgagaatg tcctctgact tccagccaca tccatctggc    840

agttgtgcca agggaggagg gaggaggtaa aaggcaggga gttaataaca tgaattaaat    900

ctgtaatcac cagctatttc taaagtc                                        927
```

<210> SEQ ID NO 13
<211> LENGTH: 1707
<212> TYPE: DNA
<213> ORGANISM: Homo sapiens
<220> FEATURE:
<221> NAME/KEY: misc_feature
<223> OTHER INFORMATION: Incyte ID No: 001549.6CB1

<400> SEQUENCE: 13

```
cactgatccc gcctggggcc ggctgagtgg cacttaagcg ggccatgcca tgcaaccttg     60

ggcgctgcca accgtgggcg agctctgggt gtgcgggcgg cctggcgcgg cgcttccggt    120
```

-continued

```
aaggcgtgtg tgcggcaggg cggggacaga accgtcctct cgggctctgg gcgtgtccga    180
gaccgcgctc cccgccgaaa tcaagctccg agtcatccgt gtggggcatt cgtcccccct    240
ggcacagttg gcctctttcc agaagcccgt tttgtttgtt ttacgtctaa attcgcgtcg    300
gttcttattt ctctccctgg caaggtctga agacgggtag gagaataacg tatgtagagc    360
tgtgtcagcg tgttatgatg ccgtcccgta ccaacctggc tactggaatc cccagtagta    420
aagtgaaata ttcaaggctc tccagcacag acgatggcta cattgacctt cagtttaaga    480
aaacccctcc taagatccct tataaggcca tcgcacttgc cactgtgctg tttttgattg    540
gcgcctttct cattattata ggctccctcc tgctgtcagg ctacatcagc aaagggccac    600
cagggggcag accgggccgt tccagtgctg atcattggca ttctggtgtt cctacccgga    660
ttttaccacc tgcgcatcgc ttactatgca tccaaaggct accgtggtta ctcctatgat    720
gacattccag actttgatga ctagcaccca ccccatagct gaggaggagt cacagtggaa    780
ctgtcccagc tttaagatat ctagcagaaa ctatagctga ggactaagga attctgcagc    840
ttgcagatgt ttaagaaaat aatggccaga ttttttgggt ccttcccaaa gatgttaagt    900
gaacctacag ttagctaatt aggacaagct ctatttttca tccctgggcc ctgacaagtt    960
tttccacagg aatatgtatc atggaagaat agaggttatt ctgtaatgga aaagtgttgc   1020
ctgccaccac cctctgtaga gctgagcatt tcttttaaat agtcttcatt gccaatttgt   1080
tcttgtagca aatggaacaa tgtggtatgg ctaatttctt attattaagt aatttatttt   1140
aaaaatatct gagtatatta tcctgtacac ttatccctac cttcatgttc cagtggaaga   1200
ccttagtaaa atcaaagatc agtgagttca tctgtaatat tttttttact tgctttctta   1260
ctgacagcaa ccaggaattt ttttatcctg cagagcaagt tttcaaaatg taaatacttc   1320
ctctgtttaa cagtccttgg accattctga tccagttcac cagtaggttg gacagcatat   1380
aatttgcatc attttgtccc ttgtaaatca agatgttctg cagattattc ctttaacggc   1440
cggacttttg gctgtttcct aatgaaacat gtagtggtta ttatttagag tttatagccg   1500
tattgctagc accttgtagt atgtcatcat tctgctcatg attccaagga tcagcctgga   1560
tgcctagagg actagatcac cttagtttga ttctattttt tagcttgcaa aaagtgactt   1620
atattccaaa gaaattaaaa tgttgaaatc caaatcctag aaataaaatg agttaacttc   1680
aaacatttca gaaaacaaaa aaaaagg                                       1707
```

<210> SEQ ID NO 14
<211> LENGTH: 568
<212> TYPE: DNA
<213> ORGANISM: Homo sapiens
<220> FEATURE:
<221> NAME/KEY: misc_feature
<223> OTHER INFORMATION: Incyte ID No: 009661.1CB1
<221> NAME/KEY: unsure
<222> LOCATION: 462
<223> OTHER INFORMATION: a, t, c, g, or other

<400> SEQUENCE: 14

```
ctcagccaga agaggtaatg taatgctgta gatgggaata ggagcattga tcttgctctt     60
cttcctgact gtagtacttc ctttctatgg ctttaaccag ccacctcctc cctgggaaac    120
atctcctgtg ggcttgttgg gtatagaagc tactctaaga cccaaccaga taccatgatg    180
ccactgttaa ttctgtttgc tcttctaatt aacctaagct agtgtgtatg tggacaggga    240
gggtggacaa aattctacag taaatatttc aaaaattata gcatcataga atcatcttta    300
```

-continued

```
tggctgccag atttgtcatc aacacccca ggatagacag tttcatcttc cgacctatct    360

ggaaaatctc aaggaccatg tccccagacc tcctaactaa ccatagcacc ccaaaatacc   420

caaaccccta ttgtgaagtg gaactcttcc ccacttagtg gntcccccct ggaccctgct   480

gtccccctgc cctgaccact attatcggaa tctgggaagt tgggcatcta tatctccagt   540

gcactcataa ctctaacatt tgcatcca                                      568
```

<210> SEQ ID NO 15
<211> LENGTH: 966
<212> TYPE: DNA
<213> ORGANISM: Homo sapiens
<220> FEATURE:
<221> NAME/KEY: misc_feature
<223> OTHER INFORMATION: Incyte ID No: 034157.1CB1

<400> SEQUENCE: 15

```
attattttaa aagtaggtca catacatggt tgaaaacaat caactggtaa aaaagatatt    60

ggatagaaag gtaagtctgt gttctacttg agtctgagac atatgccctg aagagtttct   120

tctttatctc taagtatgtc cgaggcatga ataactgtct gacatataca catctctaca   180

cagacatttc tcagcttaat ttttctttac ctcagcaatt gttccatatc agcacacata   240

caaaatactt ttacactgct acatttcatc aggaggatgt actaccattt atatgcccag   300

ttcccaagaa taaacagttg ggtcattacc atgcctttgc taaaaactgc tgaaacagac   360

tttgcatcca cagtctgcac acgtgaacat gtttctagat gtggagttgg gggccaaaga   420

gtaaatggat tttcatcttt gacagatttg ccctccaaaa aagacaacac tagtttccat   480

tcccaacaaa actccgtgag cttacctgac agcctttggt aaacagtatc tatgtatatt   540

aaactcctga tctcagttgc tggcacaggt gaaaaatact atctctaggt ggttatttgc   600

atctgtgact gagactgggt ctctttttaa atccacacat ggccatttct atatttattt   660

cctacgggtg tcactgtgtt ttgcacatta ttctatttct cagggtcttg gcattcttct   720

tactgatttc taaaagtaca cactcaatgt taaagaattt atcctttgtt atgtgtgttg   780

caaatatgtc ctccctccct ggtcctctgt ctctggaact caaatgaagt aattgttttt   840

gccacacaga ttattttgta taatttttgt gtagtcagtg gtcaaacaga ccattcttta   900

ccatttctaa gttttgtgtc ttgcttagca agatcctttc cccttcaaaa ttatcattct   960

ttcaaa                                                              966
```

<210> SEQ ID NO 16
<211> LENGTH: 842
<212> TYPE: DNA
<213> ORGANISM: Homo sapiens
<220> FEATURE:
<221> NAME/KEY: misc_feature
<223> OTHER INFORMATION: Incyte ID No: 064612.1CB1

<400> SEQUENCE: 16

```
gtcaagctct acctgagcga caaccacctc aatagcctgc ctccggagct ggggcagcta    60

cagaacctgc agattctggc cttggatttc aacaacttca aggctctgcc ccaggtggtg   120

tgcaccttga aacagctctg catcctctac ctgggcaaca acaaactctg cgacctcccc   180

agtgagctga gcctgctcca gaacctcagg accctgtgga tcgaggccaa ctgcctcacc   240

cagctgccgg atgtggtctg tgagctgagt ctccttaaga ctctgcatgc cggctccaac   300

gccctgcgtt tgctgccagg ccagctccgg cgcctccagg agctgaggac catctggctc   360

tcgggcaacg gctaactgac tttcccactg tgctgcttca catgcccttc ctggaggtga   420
```

```
ttgatgtgga ctggaacagc atccgttact tccccagcct ggcgcacctg tcaagtctga    480

agctggtcat ctatgaccac aatccttgca ggaacgcacc caaggtggcc aaaggtgtgc    540

gccgtgtggg gagatgggca gaggagacgc cagagcccga ccctagaaaa gccaggcgct    600

atgcgttggt cagagaggaa agccaggagc tacaggcacc agtccctcta cttcctccta    660

ccaactcctg aggagcttca gttgcaagtc aatggccaag gacccaactg cagcatgttc    720

tggaagcctc tccattggag tggaaaggat ggctctgggt catttgggag tggctctgct    780

aagtagagac tgatggagaa agccaggtgg aatgccataa aatcacactg agaaaatatt    840

tc                                                                   842
```

```
<210> SEQ ID NO 17
<211> LENGTH: 1651
<212> TYPE: DNA
<213> ORGANISM: Homo sapiens
<220> FEATURE:
<221> NAME/KEY: misc_feature
<223> OTHER INFORMATION: Incyte ID No: 126510.2CB1
<221> NAME/KEY: unsure
<222> LOCATION: 767-846
<223> OTHER INFORMATION: a, t, c, g, or other

<400> SEQUENCE: 17

ctcaaagatc cacgtggccc tgggtggcag cctgttcctc ctgaatctgg ccttcttggt     60

caatgtgggg agtggctcaa aggggtctga tgctgcctgc tgggcccggg gggctgtctt    120

ccactacttc ctgctctgtg ccttcacctg gatgggcctt gaagccttcc acctctacct    180

gctcgctgtc agggtcttca acacctactt cgggcactac ttcctgaagc tgagcctggt    240

gggctggggc ctgcccgccc tgatggtcat cggcactggg agtgccaaca gctacggcct    300

ctacaccatc cgtgataggg agaaccgcac ctctctggag ctatgctggt tccgtgaagg    360

gacaaccatg tacgccctct atatcaccgt ccacggctac ttcctcatca ccttcctctt    420

tggcatggtg gtcctggccc tggtggtctg gaagatcttc accctgtccc gtgctacagc    480

ggtcaaggag cgggggaaga accggaagaa ggtgctcacc ctgctgggcc tctcgagcct    540

ggtgggtgtg acatgggggt tggccatctt caccccgttg ggcctctcca ccgtctacat    600

ctttgcactt ttcaactcct tgcaaggtgt cttcatctgc tgctggttca ccatccttta    660

cctcccaagt cagagcacca cagtctcctc ctctactgca agattggacc aggcccactc    720

cgcatctcaa gaataggaag gcacggccct gccaatatgg actcagnnnn nnnnnnnnnn    780

nnnnnnnnnn nnnnnnnnnn nnnnnnnnnn nnnnnnnnnn nnnnnnnnnn nnnnnnnnnn    840

nnnnnngggg agggagagga tgggaccagg ttggaccacg tggcatcaga ggtcccatcc    900

agatccaact ataggtccaa gagtccacgt aagcaggttt gcaaggctct aaagttccta    960

tagtcctgag accccctgcc agcaaagagt gacagtcacc tccatgccct gccctcattg   1020

caaagccctc actcaccttc tggtctcagc aagggaggag agtctgttgc tggcatagcc   1080

ctggaaggag cccccagcct ctcccctcct cctccttgtc actggcctcc cacaactccc   1140

cttctggctg cctgtaacct tgaggggcat tcaggaggcc agcgttccct caggcactgg   1200

gggtttgttt tggggggtgg gagttgatcc tcccacccag tctgcccctg gtctctgccc   1260

atccaatcag agcccaccct cctggaagag acccccgtgt tcagagtgct ggcagccctg   1320

cacgtgtcca gggacactgc atttcaaaga accactgagt gggtgagcta ccttgggcaa   1380

accccccact cctgactctg actgccacgt gggtggcccg acctctgacc tgctgtcatc   1440
```

-continued

```
gtagaggtag aaagcaaaca atctggggct cagcacacct gggggtgctc ccactcattc   1500

agtgtgtggg gcccctgagc agaggctggg cattgccact aggacctgag ctcctagaga   1560

acaaggacct gggtggcctc gcttactgtt ccagcccagg ccaagcacag ggtctggctc   1620

gtggcaaacc ttgaataaat atttgttggc t                                   1651


<210> SEQ ID NO 18
<211> LENGTH: 3059
<212> TYPE: DNA
<213> ORGANISM: Homo sapiens
<220> FEATURE:
<221> NAME/KEY: misc_feature
<223> OTHER INFORMATION: Incyte ID No: 197199.3CB1
<221> NAME/KEY: unsure
<222> LOCATION: 23, 42, 132, 331, 341, 345, 352, 397, 419, 602
<223> OTHER INFORMATION: a, t, c, g, or other

<400> SEQUENCE: 18

gccacccacc ccacgtgcca acntcccctc cccgtgccag cnctgccgct tccacctggg     60

ccacccaccg gaccctcgca cgccgtgcca ggcctgcccc agacgcgtct gcaggccgct    120

tgccctcctg tnccctcccc gcaggggcaa cagtggagac gcaggggctc tgggcccgta    180

ccgccaactc gggtcacacc tgaacgctgc tgccagccga tgccccagcc ctgcacgcca    240

cccactatcc cggcacgctc cctctgcaga tggtcgccgc acctacaagc cctggccgca    300

cccaacctgt gttgttgccg cccggccctt ncctccacag ntctncttcc tnccgcccgg    360

cacttctgtg gaccccttct tagttcacag gcacggntgg ggccggtctg tgctggcgnc    420

tgctggccac tgagggacag ggacacgtgc cacctgctca tctctgccct gaggtcaccc    480

cgtggtccct ccacgtgccc atctctctgc agtgccctcc tcgcctgtgc agcccgccca    540

cccacaggct cacccctcct gccggctgcc agaggccccc tccagcaggg cctctctccg    600

tngccccagc ttcactctct ccctcagcac ctgccctgct ggaggcccca gccctccgtg    660

gacagcaggg gccacgtgga gcccgggccg ctcacccgcc acccagtgct ggccgccttc    720

ttggtgccaa accccttcc cccacccaga gactgggcag ctgtgtctgg ttcgttcttt     780

gcactaacca catttgtcat ctctagggca ggctggggct gcgggctgag ggggaccgct    840

ggcacccccc ttccctccct tcttggttcc atttccatcc atgacaggta cagcatccca    900

ggagcccggc ctgaggggct ggacccgagc cggctgtgaa catccctcag cccctgctgt    960

ccccccttgg gactaaccac taacctcacc cccaaactcc acgggtgccc ctagctggcc   1020

cagagccggc agtgtgagcc caagtccggg ctggagccga ggccggagca gctgtctggg   1080

agtcaaggct gcagtagcgt ttcttcatgg ggtgctccag ggggtgccac agaccgacag   1140

gcagcccaag ggcctggaca cccctcccca ggcaggtgct gccccaggag gactgtcctc   1200

gggaatgaac ctcccgcggg ctttggactg aggtccctgt ggcctcggtc tcctccccat   1260

gaagtgggag cgaggctccc caatggtgct tttggcttta gtgtacgatg tttgctgtgc   1320

ttcccgccgt ggagggcaga gccaccccac atcaggatcg gacgtgctac ccctcccggt   1380

cccggccctg gcccagccag cccagccctc gaggctcgat gcctgtgcca aggccagggg   1440

cagccagagg gcagctggat ggccacgtgc aggggtcaag gctgggccct gcagtggggc   1500

gggccgccag ccccagcagt ttacagacgc atggctcttc ctcccagagc agccggcagc   1560

tacctggacc ggaaatgtcc tcatcccccct ccctggggcc aggctctgcc ctggccttcc  1620

tctgtgaacc cctcctttct ttgtgctggt gtctgggacc aaaaaggggg aatatgggag   1680

ggcagagtgg ggaggggagt ccatgggcct ggggccccaa gccggggcgt ctgagctccc   1740
```

-continued

```
caggcatgac caaacctcag tggaggggcc tctgcttcag gccccgcctg gctgacattc   1800
tgagcccccc tcggaggccc cgccacagcc aacctgccca gtctttcctc tggggcttga   1860
cccgccaggg gagttctcca ggcctagggc caggagagag gccctggcac cctggcgtgg   1920
gtgcccgcca aacgccctgc gaccgctaca gaagcacaaa tgctgtccat ggccgtgagg   1980
ctgcctgcca ggtgaatgga catagcgtga gaggcggtga ggccagggct tccagcctcg   2040
tgctgtctcg ggactcctga ccgtggtgtg cgtgtgtgcc cgtctgtgac tttctactca   2100
ccaaggttga agaaaggaaa cggggaaaat caaaaggggt tcaaacccca cctcagtagg   2160
tggaggggag cgcctgccat tggttgtatt tttgttctga gttttcggtg ccgtgttcct   2220
aactactcca tcccatgacc tcgccacacc tactggggca tctggctggt gcctgctgcc   2280
atggccagcc cccactctca ccctgcacag gggtcttgc agcccccagg cccacagcct   2340
cgttgggagg acagggtggc cctggggaca agagggagga gcccaggggc ttacctcact   2400
gagagtgctc cccagcaggc atccactacc ccagggcccc ccacatgtca tggcaaggtt   2460
ggtagtgaat gggcctggtt gggagcagcc cctggcccat tgcccaccca cccatctcac   2520
tatgcaattc gagttccaag caacatttgc tcctgccctg gggccagctc tgccccagcc   2580
ctgagagggg tggtgaggca gccccctgga ccccagaacc ccagacaagg gggcaggcgg   2640
gggaccaggg cctctcctgt gggatctttg ttttgtgttt aaccataatg gttgtgtact   2700
gaaccacttc atatttgtta tatataatat atatatatat aatctcctta agactcagcc   2760
tcctggttta cccccccggc ctgggcatct gacctccccc accccagtgt gatttaacat   2820
ccaggaactg aggcctgaac cattttgcat ttccccctcc tccagcctct gtagggccat   2880
ggctgtatgt actgtcgctg tgttttttttg tttttttaga actgggtttg ggggctgatt   2940
tttatttctt tgggggcttt ttttcttggc aaatactaaa aatctcgtca atgtaatttc   3000
tgtggtttct attcagcttg ggtttcatgt tttaaaataa attttaaaaa gcaaaaaaa    3059
```

<210> SEQ ID NO 19
<211> LENGTH: 1627
<212> TYPE: DNA
<213> ORGANISM: Homo sapiens
<220> FEATURE:
<221> NAME/KEY: misc_feature
<223> OTHER INFORMATION: Incyte ID No: 200119.1CB1
<221> NAME/KEY: unsure
<222> LOCATION: 1624
<223> OTHER INFORMATION: a, t, c, g, or other

<400> SEQUENCE: 19

```
cctacacgcc actgtggttt gagaagaggc tggatccgct gaccggggag atggcctgtg     60
tgtacaaggg cggctactgg gaggccaagg agaagcaaga ctggcatatg tgccccaaca    120
tcttctgagc gccacccttg caacaaatac aggcgcctgc acagcctggc ccacctgttc    180
attaatgcac tcaatttagt actgaatggt ctttctccca gcccattccc agcccttcct    240
atttcctttc ctattttttt tttctcccca cactttcttg ggactcccac cttggaagga    300
ggaagggctg acctgggttc tctccagccc ccaggtgcgc cgggtcaccc gtgccccttc    360
attatggacc tgggccctac cggaacccct gccccagtta ccacaactca ggccggctgg    420
cccgggccat gggctgcgca aatcaccagc cccaacccca gggaggaact ggcccctcct    480
agggagcctc ttcgactttt ttagaaaaat gatctccatt tctttccagc catgatgttt    540
agtaaatatt tttagtaccg cacttagcag acagctttcc aagtgtgctt tcttgccaca    600
```

-continued

```
aaagtgtcct ggcaagagcc ccttattttt aagacatcag gaagccagac cgctttgagt     660
tgggagaatt ttgtagctca acatatcaag tcctcgatgg tatctgagct gcccacaccc     720
ccacctgcca aggccccaca gagcccaaaa cagaaggggg ctgccccagc ccagcagagc     780
acagagtttc tggagctccc atccacagat gcaggagggg gtactgatgg taaccccat     840
gtggatttga gggcagcagt ccctggcctc accctagcca gcctgggtgg ctccctagcc     900
ccaagaggcc aggaagggct ggaaggcagg gcctgcaggt gctccccgcc ctgagaccca     960
ggccccaaat cagcaataat gaacaaaccc ttggcccagc ctgggctggt gacctgggca    1020
ccagagacct tgcatccctc ctcatcctag gaggccccta ggggtgcccc atctcagtgt    1080
cccctgaact ctttatttgc ctaatttata tatatatata tgagatatat aaatatatat    1140
aaaatagcta ttttgcttaa atttctacag tatgtaaaag tgaaaaaatg atgaagacgg    1200
gtgcacctgt ctgagtttgg ccctcatgtg agctgtgccc ttccctctcc tcatgccccc    1260
ttccagcggc ttctgccaac catggggggc tggaccacca tggccactga cccagcccct    1320
cagaatccca cactccaatc ctttccattt cagtttagtc ctaaaagttc atcacagggt    1380
ctttctttct actccaggac tggttttgtt tttatatata taaaaaaaaa aagtgaaaac    1440
accaatgtgt gaaatgcctt acaatgccca ctggagaggc ggggcggggt ggggcaggat    1500
ggccccacta gggctcctac agagctgtgg aatgtacctc tccccaacac tgttttgtta    1560
gcgagcacct tttgaccagt aataaaaaac cttggctttg gagttttcca aaaaaaaaaa    1620
aaanggg                                                              1627
```

```
<210> SEQ ID NO 20
<211> LENGTH: 1638
<212> TYPE: DNA
<213> ORGANISM: Homo sapiens
<220> FEATURE:
<221> NAME/KEY: misc_feature
<223> OTHER INFORMATION: Incyte ID No: 200145.5CB1
<221> NAME/KEY: unsure
<222> LOCATION: 1554, 1581, 1624
<223> OTHER INFORMATION: a, t, c, g, or other

<400> SEQUENCE: 20
```

```
ggctcgggga ccactggtag cggcagcagc tcgcgcccgc gccctcctcg tacccgtgcg      60
cccccggaga ccgatcccgc cccgcggccc aggccgggcc tgaacccagc gggtgccgct     120
tctccacccg aggcttccac ctccaacgag ccatgttcca ggctgcagga gccgcccagg     180
ccaccccctc tcatgacgcc aaaggcggcg ggcagcagca cggtgcagcg ctccaagtcc     240
ttcagcctgc gggcccaggt gaaggagacc tgcgccgcct gccagaagac cgtgtacccc     300
atggagcggc tggtggccga caagctcatt ttccacaact cttgcttctg ctgcaagcac     360
tgtcacacca agctcagcct gggcagctac gccgcgctgc acggggagtt ctactgcaaa     420
ccccacttcc agcagctgtt taagagcaaa ggcaactacg acgaggggtt tggccgcaag     480
cagcacaagg agctctgggc ccacaaggag gtggaccccg gcaccaagac ggcctgaggc     540
ctctgtaacc ttccaccccc tctgcggaag gcctggagcc ggcaggggga aggtgggaag     600
gaggtcgagc tgggcttgcg tgggggccag gtgggaaggg gatgaggctt gctcaggcgt     660
aggggaccag ggcagggctc tgctccagga ctccttcctt cttccttctc ccgcagccgg     720
tgagggtttg gaaaccagga ttggggtctg cccaccaccc tgcttcctgc ttcgttcagc     780
ctccctcccc acctcacccc aggaccccct gggaggcccc caagcccagc tcccctatct     840
aggtgccttt tctccagcaa ggagtcagca tgccccctc agggtcccaa gctccctcac     900
```

-continued

```
tgccaccgga gactgtgtgg cccccacgtc tccccatcta cctctaccct taacctgttt     960

ctgagccacg gagacaggga ggaaggagcg cgacagtgcc acctgttggg catcataaat    1020

gcccctgcag cccatggggg aggagatggg gaagtggagc caccctgcct ctgcagggca    1080

aggcagggcc tgccccagtg gggcttggga ccatctcgaa ccaccagcgt ggagaagcag    1140

aagcaaaagc actcgccagg ctgcagcctc aggcactggc aggggctggt gcggccccac    1200

tcccctcccc cgctcccatt tgtgcccatc ctgttgtgac caaccccgtt ttaaacatgt    1260

ttcaatagat cccgccccgc ggcccaggcc gggcctgaac ccagcgggtg ccgcttctcc    1320

acccgaggct tccacctcca acgagccatg ttccaggctg caggagccgc ccaggccacc    1380

ccctctcatg acgccaaagg cgcgcggcag cagcacggtg cagcgctcca agtccttcag    1440

cctgcgggcc caggtgaagg agacctgcgc cgcctgccag aagaccgtgt accccatgga    1500

gcggctggtg gccggacaag ctcattttcc acaactcttg cttctgctgc aagnactgtc    1560

acaccaagct tcagcctggg nagctacgcc gcgctgcacg gggaattcta ctgcaaaccc    1620

caanttccaa gcagctgt                                                  1638
```

```
<210> SEQ ID NO 21
<211> LENGTH: 926
<212> TYPE: DNA
<213> ORGANISM: Homo sapiens
<220> FEATURE:
<221> NAME/KEY: misc_feature
<223> OTHER INFORMATION: Incyte ID No: 210741.1CB1

<400> SEQUENCE: 21

gagaacattg gcttatgcca gataccacac cacatctggg cttacattct tgtatctttt      60

ttggtgtgtg ggcggggggg gtggggggca gttcagtgaa gtctagaaga cctgctggac     120

aaattctaaa agagctagag ctgtaacact tattcttgca tcttattaat tttctatgat     180

atttttttcct tcttcgtagg gacttgggac aatctggctt tgctgctttc taactgctag    240

gcacctctct ctaaccctca ttgtcagagg gaattggagg atatccacag tctgttcctg     300

ttctgatatt ctgagcagag aaaaggcact aacggttcct cttagctatt taattatcag     360

aagcaagtaa tctttcccca gataatattt tgccctagaa gaagccgtga tttagctctt     420

ttattgtgct tacttggtcc aaatacatct gtggggtgtt ttgtcatttc ttaatgaatg     480

aatcatagtt ataaccaggg gccaagctgc ccaagaggct cttcagagat catggatgct     540

ctctttctgg aagctgtggc ctgatggagc agccccattc cagggtccca tctgtccgga     600

gttgtgtatg tcaagtccgg ctcagtcttt atttccaaca ctagccgtgg tcctgtgcag     660

tcaagctctc agctagtgtt tagggctgtc tgtcagaaat ggttatacgt gggcaaaaga     720

agatctgaca gctcctatat accttatctt actgaattct taaactttga accagttctt     780

ccacttactg acttgttacc actgctgact ttctgaaaag ttttccagtt tttgtttttt     840

gtttttttgtt ttccagtagg ggattagaat gtttagtcct acttagtaag aaaaatattg    900

tatttttaat cattcatagt gctggt                                          926
```

```
<210> SEQ ID NO 22
<211> LENGTH: 2847
<212> TYPE: DNA
<213> ORGANISM: Homo sapiens
<220> FEATURE:
<221> NAME/KEY: misc_feature
<223> OTHER INFORMATION: Incyte ID No: 215642.2CB1
<221> NAME/KEY: unsure
```

<222> LOCATION: 364-381, 572-597, 1191-1234
<223> OTHER INFORMATION: a, t, c, g, or other

<400> SEQUENCE: 22

```
ccagaatgat tgcctctact gtcctcattg acttgtttga accttagtgc cttaccctgt     60
cctcttccca gttctcttta tagaagctct aggagctttc gaaaagccaa agtctttctg    120
aagaatctgt gctggacaga cataattccc tttctcattg tctccatctt tgttggtcat    180
ggtaaggttt ttccatcagc ctctgaaaaa atagttgtgc acaacatctg ctcactggac    240
tgtctgatcc aatgtaattg gctgcgtctg gctaattcta agcactaaag tctacatcta    300
agctatagat ttaagcttga agctacagat tatatcacta tcaccaccac ccctcaccct    360
atgnnnnnnn nnnnnnnnnn ntcttaagtt aaagatattt gttgtctttg aatgatttgc    420
tgtcacagac tatttggtag aagaaatatt tttcacctga gagaggaaga gaaatttctc    480
tagtaacaca aagagtgagt tctaaaaggc atgcccacat ctctttcgtg ccttaaggat    540
agtgagatgc acacttatat atatactgta tnnnnnnnnn nnnnnnnnnn nnnnnnncat    600
atatatatat aatattgcaa gcttaagttt gcaatttccc aaacaataca aaaagcaaat    660
tacacaccct caccactgtt cttatctcta tagtgatgaa acattaatta gggatcttgc    720
tgcttttctt tttctacacg aagttttcat taaagccaca gaataattga tagggcagct    780
gtttgagaac aggtcccatt ttcacattag ggctttaaat gaattagaaa ctatttgagg    840
ctataaaaat gtccttgagt ttggagcctg agctctggtg aaatgctgat acatctgatc    900
tatcatggga attgcagtta gagagagtaa ggaataccat ttagtcatct atccgttctt    960
cacttagcag gaatatgaaa gaaaggcaca tgtttaagag gaatacctaa aggtttttct   1020
aaattccaac atttaaaagg caattgtggg ctatttttat tttttaatat tttgaaataa   1080
agtttagtgt ctagggctgg gagccaggac tgatcttcca tttctttttc tttgttccca   1140
gccatgcttt tgtaacttgc caggtggact tgaccaacta cattaccatg nnnnnnnnnn   1200
nnnnnnnnnn nnnnnnnnnn nnnnnnnnnn nnnntaccta cctcacaggg gtgttgtgag   1260
gctctattca tttgctcctt tattctttcc tgtattctct gtatgtccag cactttgtag   1320
ccatgggagg aaagggacta taaaagtgta caatgttaat ggaatgatac ggtacctgaa   1380
agccttgttt tctagtaaga aaatgctacc ttgctgtaca tacttataac cttgtatttg   1440
gaaatgagaa ataggtttat attttcagat ctctcaaaaa tcacatcatt tgaccaaaga   1500
ataatttaag acacatagaa cagatttttt taatttatat tttcatcctg accagcttag   1560
ttctaataat ttttagttgt gagtgattaa aaaactttgg atcaattttg gtcaaacatg   1620
ccaactttgt agtctgagtg acaggcaagg atttttgggt ttaagatgca cttttagcac   1680
acatttgtat ttcccttggc atatcagatt gagctaatgg tgatgttatt tcaatctaac   1740
agccaccaat ctgaaattgt atttcaaatg ttgattctgt agttctttaa ataataatga   1800
agctcatctt atacattttg ctttcaccaa ttgattcctt cttcttttag cccactatta   1860
aaacatttct tactgaatgg ttcatgtagg cttgctgaac agcacgcatt acttgcttcc   1920
tgaagagttc ccccattcat ccatttgtcc cattagttgc tgtggattat caagttttga   1980
aggaactgta catcccaaca gactgaaaca ttctaagtga aatgagtata atccaagtaa   2040
ctggtgaact ttggaggttt ggagcttgaa gagaatggct aagaagattt gaattatagg   2100
gagggaacag aaatcataca tgaaaaggtt ttactgagaa ggggaaaacc ttagatagag   2160
ggacatgtga aacaaaattc atttgaaatt ttgattcaga catccatttc cagtggcaaa   2220
```

-continued

```
cagcaaagcc tgaacccata aacccaaatg ataggtgaag ttgggtggtt ttatccaatg   2280

tctcaagcaa gcaatgtctg ggaatatcat agagtaacaa gtgctggtca gccaaagaaa   2340

cattcactgc tggtgaacca ataccataag catgtattat ctaagcactt gatcaagaaa   2400

tatacatgtt gtacaagctc tcaattttgt tcatttatta tcaaattttt aaaatacaag   2460

tttggtatgt gatttggaaa agatgccttc tggatcttaa gccagttgtc agtggaggtc   2520

ctcagggctg caaatgtcaa gacataaccc tgttcctcac catcatgata ccagatacag   2580

gtgaatacat aggaactatc tgcctgtgtc ctcaatctcc cttcaaacaa gatgctgatt   2640

tgtagggtac ttggcaggtt aaattaaacc agaagaggtg acttaataaa aaagggaatg   2700

acatttaggg tataaagatc tcataagaaa tgtaatatgt aaattatatc ttgctttatg   2760

ttgtaaaata tacattgttt gcgctagaat agaaatgatt tcttttcaat aaaaagaaag   2820

aaggactcta ccatgtcttt tgttata                                       2847
```

<210> SEQ ID NO 23
<211> LENGTH: 3030
<212> TYPE: DNA
<213> ORGANISM: Homo sapiens
<220> FEATURE:
<221> NAME/KEY: misc_feature
<223> OTHER INFORMATION: Incyte ID No: 218628.2CB1
<221> NAME/KEY: unsure
<222> LOCATION: 9, 64
<223> OTHER INFORMATION: a, t, c, g, or other

<400> SEQUENCE: 23

```
ccttgatgng ctggcggcct cggccgggaa ctccggggta gatgaccgtg gacagcagca     60

tgancagtgg gtactgcagc ctggacgagg aactggaaga ctgcttcttc actgctaaga    120

ctaccttttt cagaaatgcg cagagcaaac atctttcaaa gaatgtctgt aaacctgtgg    180

aggagacaca gcgcccgccc acactggcag gagatcaagc agaagatcga cagctacaac    240

acgcgagaga agaactgcct gggcatgaaa ctgagtgaag acggcaccta cacgggtttc    300

atcaaagtgc atctgaaact ccggcggcct gtgacggtgc ctgctgggat ccggccccag    360

tccatctatg atgccatcaa ggaggtgaac ctggcggcta ccacggacaa gcggacatcc    420

ttctacctgc ccctagatgc catcaagcag ctgcacatca gcagcaccac caccgtcagt    480

gaggtcatcc aggggctgct caagaagttc atggttgtgg acaatcccca gaagtttgca    540

ctttttaagc ggatacacaa ggacggacaa gtgggatgcc ttctccatcc ctgaacttca    600

gaacttccta acaatcctgg aaaaagagga gcaggacaaa atccaacaag tgcaaaagaa    660

gtatgacaag tttaggcaga aactggagga ggccttaaga gaatcccagg gcaaacctgg    720

gtaaccggtc ctgcttcctc tcctcctggt gcattcagat ttatttgtat tattaattat    780

tattttgcaa cagacacttt ttctcaggac atctctggca ggtgcatttg tgcctgccca    840

gcagttccag ctgtggcaaa agtctcttcc atggacaagt gtttgcacga gggttcagct    900

gtgcccgccc ccaggctgtg ccccaccaca gattctgcca aggatcagaa ctcatgtgaa    960

acaaacagct gacgtcctct ctcgatctgc aagcctttca ccaaccaaat agttgcctct   1020

ctcgtcacca aactggaacc tcacaccagc cggcaaagga aggaagaaag gttttagagc   1080

tgtgtgttct ttctctggct ttgattcttc tttgagttct cttacttgcc acgtacagga   1140

ccattattta tgagtgaaaa gttgtagcac attccttttg caggtctgag ctaagcccct   1200

gaaagcaggg taatgctcat aaaaggactg ttcccgcggc cccaaggtgc ctgttgttca   1260

cacttaaggg aagtttataa agctactggc cccagatgct cagggtaagg agcaccaaag   1320
```

```
ctgaggctgg ctcagagatc tccagagaag ctgcagcctg ccctggccct ggctctggcc   1380
ctggcccaca ttgcacatgg aaacccaaag gcatatatct gcgtatgtgt ggtacttagt   1440
cacatctttg tcaacaaact gttcgttttt aagttacaaa tttgaattta atgttgtcat   1500
catcgtcatg tgtttcccca aagggaagcc agtcattgac catttaaaaa gtctcctgct   1560
aagtatggaa atcagacagt aagagaaagc caaaaagcaa tgcagagaaa ggtgtccaag   1620
ctgtcttcag ccttccccag ctaaagagca gaggagggcc tgggctactt gggttcccca   1680
tcggcctcca gcactgcctc cctcctccca ctgcgactct gggatctcca ggtgctgccc   1740
aaggagttgc cttgattaca gagaggggag cctccaattc ggccaacttg gagtcctttc   1800
tgttttgaag catgggccag acccggcact gcgctcggag agccggtggg cctggcctcc   1860
ccgtcgacct cagtgccttt ttgttttcag agagaaatag gagtagggcg agtttgcctg   1920
aagctctgct gctggcttct cctgccagga agtgaacaat ggcggcggtg tgggagacaa   1980
ggccaggaga gcccgcgttc agtatgggtt gagggtcaca gacctccctc ccatctgggt   2040
gcctgagttt tgactccaat cagtgatacc agaccacatt gacagggagg atcaaattcc   2100
tgacttacat ttgcactggc ttcttgttta ggctgaatcc taaaataaat tagtcaaaaa   2160
attccaacaa gtagccagga ctgcagagac actccagtgc agagggagaa ggacttgtaa   2220
ttttcaaagc agggctggtt ttccaaccca gcctctgaga aaccatttct ttgctatcct   2280
ctgccttccc aagtccctct tgggtcggtt caagcccaag cttgttcgtg tagcttcaga   2340
agttccctct ctgacccagg ctgagtccat actgcccctg atcccagaag gaatgctgac   2400
ccctcgtcgt atgaactgtg catagtctcc agagcttcaa aggcaacaca agctcgcaac   2460
tctaagattt ttttaaacca caaaaaccct ggttagccat ctcatgctca gccttatcac   2520
ttccctccct ttagaaactc tctccctgct gtatattaaa gggagcaggt ggagagtcat   2580
tttccttcgt cctgcatgtc tctaacatta atagaaggca tggctcctgc tgcaaccgct   2640
gtgaatgctg ctgagaacct ccctctatgg ggatggctat tttatttttg agaaggaaaa   2700
aaaaagtcat gtatatatac acataaaggc atatagctat atataaagag ataagggtgt   2760
ttatgaaatg agaaaattat tggacaattc agactttact aaagcacagt tagacccaag   2820
gcctatgctg aggtctaaac ctctgaaaaa agtatagtat cgagtacccg ttccctccca   2880
gaggtgggag taactgctgg tagtgccttc tttggttgtg ttgctcagtg tgtaagtgtt   2940
tgtttccagg atattttctt tttaaatgtc tttcttatat gggttttaaa aaaaagtaat   3000
aaaagcctgt tgcaaaaatg aaaaaaaaac                                    3030
```

<210> SEQ ID NO 24
<211> LENGTH: 3597
<212> TYPE: DNA
<213> ORGANISM: Homo sapiens
<220> FEATURE:
<221> NAME/KEY: misc_feature
<223> OTHER INFORMATION: Incyte ID No: 223147.1CB1

<400> SEQUENCE: 24

```
atgaattgtg taaacttaga tccttctccc ttttgggccc aaaagaaccc ttgatttagt     60
tccagaatcc aaccagtttc tttgttaaaa gggtcctttt gaagcaatta agtgctggta    120
agaatatttc tctgttgttg ccaggttacc ttctgctttt aaattgccat cttgtaaagt    180
gtatgtggtt cttaagtgcc agggagatca gccttgccca tgaaggttgc atatgtgtgg    240
tatacagttt ttacctgaaa gcctgagctt tctcttattc ctaaagtggt ggcaaaagaa    300
```

-continued

```
tgaactgggt atgaccctgc ccccttactg ggcttggata ttgaggacca gacgctgcca    360
aatctaggac aagacagacc atcaaagcag acttttgtgg gctcctcttt ggggtgacca    420
ctgctttcaa agccatctgc caaggctctc cagggcagga cctgactggt ggggaatgag    480
tgttcagaag ccttgggaga ggccaaagag ccattctagc atgatctgag aaaaccttcc    540
tgcagaggcc agaaaccttg agcttaggtg cctggggacc agcttcgaca ttctctccag    600
tttctgattc taatttttgc cacgtgtcac aacttttcca gtctctgaga aggtcccagc    660
ctttctcaaa tattctgatt ttgaaaatat gtatccaaag tgggaggccc ctgtgacatt    720
ttgccaactt aaacgagaaa aagacccccc gcacccggca cactcccct tcctccagcc    780
ccgcttcagc cacatgctcc agctgctgcc cagtaaagcc ctgtgccttt ttttcccctg    840
aatactgccc aaagcatccc cttcccatct gcctctcagg agttggggac tttgctagga    900
gattttttaa gtgttcctta ctgggacaac gtggagccac gtttgcagga gctccatttg    960
tatccctgct ggtgttgact tctgtgtagg ggccagttca tgtccctgac tctcacctcc   1020
cattagataa atgaagccca cccccctttt ctagagtgat gagagtcaag aagaggggat   1080
gtatgaacgg ccaaattccc atgtgagagg aagatgacct gatccaccta gccttttctt   1140
ctggatctgt cctccctcac ccctttcacc tgagctgtcc acagtaggaa acataaagaa   1200
acaatgtccc ctacatatcc ccatgactac ataatccatc atcgtaggaa ataggaaagc   1260
aaatttgatt ttggttttgt aaaacgtaca tgcttcaata attctttttt tgtgtcttaa   1320
atactcatag gggaaaaaaa cagctcaccc aaggtgttag gtttcacata tatattcatc   1380
aactatttta gaagatttaa ttctatcaaa tcttgtatta cctcagatca ttttaaatag   1440
caagccaata acgagctttg aaggctattt taccattcct gttcacaaaa ggttctcatg   1500
gtgcctgaca ggttaccctt gagggcttgt gtctactttt taaaagtcaa tggttttttt   1560
tcttgtgttc tagtttccat aataggagag aaaatataga aatatatgca aaaattatag   1620
ttttctttag atcagaaact gatatttttg ggtcagccat atgtattttg tttaaaggat   1680
ttaaaataaa gtgccgtcat gtagccctgt ggaagggagc acataaccag ctgtttggca   1740
tgacaggtga cttagtatat ttgtaattgg ttttaaaacc aatacaccat actttctttc   1800
tgcaaacagc catctttata cttagggaag aaaaattgtt gggttctaga ctttttttaat   1860
ataaattttg ttgatatgga attaggtaag tttaagtgtc tatgtgcata tgttttttat   1920
ataagttttt tctattcagt ttcactgatc caactggcag tgggtaaata tggcataagt   1980
taataacact tttccccaaa atggtgcttt ggatttgaaa agggtctgat ggggagaagg   2040
agaacgtatc atcctagctt cctctcttaa taaacctaga aaaacgggta gtaaactgtg   2100
gatagtcagg aaaacaccca gcaagggaca cagctgtcag gaaatgaatc ttccccccaa   2160
cccccaccat gcagatggat agacagaatc tttcctgact agtcattagg atcaggggcc   2220
tctgttggat ttgtgtttct tgaagaatag ctggcagagt ggtataaaag acacgaatat   2280
ctcctggtct ataaggatac tctgatttgg ggtttgcatt tttcatggtt tttatttcct   2340
gttcccccctg gagttttcca ttagtgagtt tttgtgcaag gatcttattt gtgatgcctt   2400
ccctccccta gaaagatttt gtgcaatata ttaaatgggg acagaattct aaatggataa   2460
aacaatggct ggttctagcc ctgagtgaca gtcttaaggc tagatccttc ccatagtatc   2520
atctgtcctc tggaatgact ctcctgtccc taaaggggtt aagagagaga tcacctagaa   2580
atccctctgg acacttgtgg gttctttagg gtttgagttt cttcttcccc ttgagcttca   2640
```

-continued

```
gagaggagag ttggcatggt taaatctgaa tggttacctc actgctgaaa acccagaggg   2700

gcgtggcaca ctcgcttgtg tggaaaagcc tctaaatgca tcccttcctt tctttcctgc   2760

ttcctttgcc ttacaattga agcagcccgt ggtaccatca cagtatgcag agacttcctc   2820

acctttcata tctagggacc acccccgatg cattggtgag ggtgggcact tataaatgcc   2880

tgctattgtt aagccattcc agcctcttcc tctgaataga ccagacgccc tttcacttag   2940

ttcagtgcca gtccttttgc cttcccaacc ctgctgttag gcctgctgtt ccctttgctc   3000

ttgattagga gagatggaag gagatgagct cccataactg aattggcctt tggttcatgt   3060

tttctcccca tatgtatata tgccatatgt gaatatgcca tatatatgtg ccaacaaatc   3120

tatctacgtt gttcttttca aattagcacg cagataggaa ttttgagttt cttcttcttt   3180

tagtaactag tataacaagc actggtattt ttgtacaaaa aagaaaaaca aaagattgac   3240

tattgtggtc tgcatgacat aaacaaacaa atggtgatat caaagcaacg tataccccag   3300

tccagtgtgt gttgccataa tttgcaattc agcttaacag tgcacccaat ctatatttgc   3360

attttgatat tatttaagct ccatgtacaa ggttttgcat gtatttatat ggttcttagg   3420

gaaaaaaaat gctataaact gcaaatctga aattcaaatg tgttgttcca ctgagaccag   3480

aagaagaaga ggagttttaa aagggataat ttgttggagc caataaagct ttttgctgat   3540

gaacagaaac caatactgct gtgcactgag aataaaaact catgcccact tgtaaaa      3597
```

```
<210> SEQ ID NO 25
<211> LENGTH: 2802
<212> TYPE: DNA
<213> ORGANISM: Homo sapiens
<220> FEATURE:
<221> NAME/KEY: misc_feature
<223> OTHER INFORMATION: Incyte ID No: 231965.4CB1
<221> NAME/KEY: unsure
<222> LOCATION: 38, 55, 108, 1558, 1565
<223> OTHER INFORMATION: a, t, c, g, or other

<400> SEQUENCE: 25

ggaaaaggaa ccacgaaaaa tgtggctata aactgttntc accttcaaga ttctngagag     60

ataactacac ataccctttg ccatagtggg aatgactgtg tagtagtnac tggaggagaa    120

agtttctttg tacacaacta tgctttgatt ttcaagagga ggaatgaaat tgcctcgtaa    180

aattacagag ttaaatacaa tgtacttaag agattatggc atcagaaacc cacaatgtta    240

aaaaacggaa cttttgtaat aagattgagg atcatttcat tgatcttcct agaaaaaaga    300

tctctaattt cactaataag aacatgaagg aggttaagaa atctccaaaa cagttggctg    360

cttacataaa tagaacagtt ggacaaactg tgaaaagccc agataaactt cgtaaagtga    420

tctatcgcag aaagaaagtt catcatccct ttccaaatcc ttgttacaga aaaaaacagt    480

cccctggaag tgggggctgt gacatggcaa ataaagaaaa tgaactggct tgtgcaggcc    540

acctgcctga aaaattacac catgatagtc gaacatattt ggttaactcc agtgattctg    600

gttcttcaca gacagaaagc ccatcatcaa aatatagtgg gttttttttct gaggtttctc    660

aggaccatga aacaatggcc caagttttgt tcagcaggaa tatgagattg aatgtagctt    720

taactttctg gagaaagaga agtataagtg aacttgtagc ttatttgttg aggatagaag    780

atcttggcgt tgtggtagat tgccttcctg tgctcaccaa ttgtttacag gaagaaaaac    840

aatatatctc acttggctgc tgtgttgact tgttgcctct agtaaagtca ctacttaaaa    900

gcaaatttga agaatatgtt atagttggtt taaactggct tcaagcagtc attaaaaggt    960

ggtggtcaga actatcatcc aaaacagaaa ttataaatga tggaaatatt caaattttaa   1020
```

```
aacaacaatt aagtggatta tgggaacagg aaaaccatct tactttggtt ccaggatata   1080

ctggtaatat agctaaggat gtagatgctt atttattaca gttacattga gagatttcat   1140

ctactaaaga gcatttggtt tttcaaaaca tccctgaact gtataattta caaaaaaaaa   1200

agtctcgtct gagaactgtg aactgtggaa gaaatcaaaa ctattttttc ttttaaaaag   1260

ccacgtaatg aaaccactaa tgaaatccca gcaatctgct tcacattgaa gtggaaaaat   1320

atccaaaagg agcagcttca atttcattga ggtgaaagtg cactatgaag attgttcacc   1380

tttgctgcat ttgggagtta tatggttatt tggtaacatt aagaactact ggattttaat   1440

gcaatcctgc ataaaaatat aatttatact atgtgaaaaa ataagacagg acttaccact   1500

aggaaccacc aagaccaatc atcattaact tttttaagat tgtgttttat taaaaaanaa   1560

aaacncttaa atgtgtgcag ctattttctt atgttgaaaa gactgaaagt ttaaaacatg   1620

aaaaaaatca atattaaaca ttttttgttc acactgagat actgtgtatg taaaatgcct   1680

taattattaa taagccaatg tgttatgata ccaatatctg ttttaaaaaa ctaaaaccaa   1740

ccatgcttct ggcatgataa aatcatggaa ttaaatcagg ggtttacatt cttgtagagt   1800

gttcttgaaa cactctctgc accattttta aaacttgaga atagttttag tatctctgat   1860

attttttgcc agaatcatca tgtcatgtat gaatgtgtta tccctatcta aggaaaaagg   1920

tgaatatgtt tttgtatgaa tgtttaactg gaaatgtcca tggacttggc taatttatat   1980

ttacttttta ttgtacatag atttctaata tttttcattc ctgtatcatt taaacttcct   2040

tcatttgagt aaattcacta aatatttcta ttttttgctt ttttaaattc tgattttata   2100

tgaattctaa ttctttttca ctacttatgt tttaaagagt tacatacagt gatttagaat   2160

ggtttacagt taatgctgat cttgtatttt aaattccaac actttgtgtc actacctcct   2220

ctaatggtta gtatgatatg ctagcagact gtatgaggtc tttttttaaa ataccacttt   2280

tagtggtcag tgaaccaaat tctggaatgt cttaacagct ctaaatctta cttgtcttga   2340

aaatgattgg ggtttaatac cactgctggt ggttcacaca tcatcccatc cttaatatgc   2400

ctgacaggca tctgagcaaa ggtttttagt aattgaattt ctctgcagta gtccttcaag   2460

cacttgaatg taaaccttta gcatttattc gtttaatgac tactgatacg aatctcaagc   2520

agatttcttg ctcttaaaag ttatgtttca ctgagttctg gttttgtgta gctatatttt   2580

atatagctag atattcctca cagtgaacat gaattgtaat aattggttat ttccttaagt   2640

ctttagatta taataatttc agattattgc acgtctgtga tttgagaggt gagttattta   2700

agaggccagt tttcaggaca tggaatttg aattgtaaac ctgttatctc tgtgaaactt   2760

ttaacatgat aaaatataac ctttctttgt gcttaaaaaa aa                      2802
```

<210> SEQ ID NO 26
<211> LENGTH: 3017
<212> TYPE: DNA
<213> ORGANISM: Homo sapiens
<220> FEATURE:
<221> NAME/KEY: misc_feature
<223> OTHER INFORMATION: Incyte ID No: 232773.2CB1
<221> NAME/KEY: unsure
<222> LOCATION: 1463-1495
<223> OTHER INFORMATION: a, t, c, g, or other

<400> SEQUENCE: 26

```
gcataagcca ccatgtccaa ctgaaattct taataattaa taatttttga gcaagaggtc     60

cacactttca ttttgcactg ggttcccaaa caggtcctgg gtaggaagga tggctgagga    120
```

-continued

```
taaaacagga gttgctttgg cctggctgaa catttgaacc aatgatcaga gtttcatttt    180
atgattgtgt tactctgaac agatttgcta tttttttcca gctacattta gagttcctca    240
tgtatatatc acccctcttt ttccagtcca tctaacctct cctttttttt gtgcctagaa    300
tcagttctcc ttgccttcaa aatccctgat aagtgtccat ttctttttgt atcctttgat    360
gtagaagcca caagaatggc tttagcagct tattttaatc ttatgaatta ttcattcagg    420
attttttaaa tgattcagat gctttcagtc tgttaacagt atttataaaa catgtttcag    480
tgatacaaca taggtgaact aaaccaaaga tgcaaatgcc ttggaggaaa agaaattgta    540
ttatagagaa tcctgagata tatccttttg ggttgtttaa tttaaagcct atcacaaaac    600
aaagagaatt gtcgcacttt aattccaacc tcctgcagta cttcacaacc cttagcataa    660
gattctgaaa tttgtaatag gtggtaccta gtttgatgca gggttttgca gcagttgtgc    720
gaatgcctct gcgcaacggc ctttcagtca gactaaatga gaaaatccaa actgtcctat    780
caaaactgac ccacaataac tgtactctga ggcgaaacag agcaaatgtg ggtttcctgt    840
tttcattgta aaacattcca ggttctcaga ttgaagagct acattcagct gatagttgac    900
atctgttccc tcacacgtag tggctctcaa cacgggctgc actttggaat cacctgagga    960
cctttcggaa tcttcggttg aatcatcctg gctgtcctgg tgatgcttct tatgtgcagc   1020
taggctggag aaccactaca gggctgacac ctggaatggg agcttgtaac ttttacaaaa   1080
taatagatgt ttatcatctt ttgcaatttt tacttttaag tctatactaa aatgagccaa   1140
agaagtctta acaatgatgt atggcacaat tggttggttg aggctatcat tccatgatta   1200
caaataggtg gttatgtggg gtggttttgc acttgtggca attggactgc aatttggcct   1260
taaaatgaca caattcctcg ttctcagatg gagaggaatt gccttgaaat ttgcatgtac   1320
cagactaagt gccagtatat atatgactga tattttcgtg actcatagaa ggtgtccatg   1380
gtatagagtt tatgcctaca tctctatctt tattttgggc acacatgagc ttttgttaat   1440
tatttctttg tacttgttag aannnnnnnn nnnnnnnnnn nnnnnnnnnn nnnnngattt   1500
gtggtggatt caccttctta aaataataaa tttagaggat attaggaatg acattcaaaa   1560
caaatatagt gagaggtgat tttttaaaaa tttttgttcc tggtttccaa attatgttta   1620
ctttgatttg attatatgtt ggtatctccc aaatataggt taacttagct atttaaatgg   1680
tatcttttga catttaaaaa gaattaagta cctgtcaaat cttgcattga ggttgcagtt   1740
gaataagata aaagcttagg atgtcaaaaa ataatataga gaaatattat aagattttat   1800
gattattctt gaagtttttg atgcaaaagg aaaatatgct gaatagttct tccaaaaaat   1860
attatttccc tcaatatttt atttgtagcc atgtaattta aagagaacag aaaataactg   1920
caatcaaaag tatggtttaa tatcaatcaa agtggcacaa cagaattgat aagatcttta   1980
taacaatcaa ttggctgata ttaaaatatt gattttaatt gatcttttca attaaaatct   2040
ttagggcctg taactcataa aatcagcatc caccacaata tatggtcatt attggtttgt   2100
aagcatagat caccattgac tcctacctgg agagacatgt ctatttctaa aaatccagta   2160
gtttctttgc attctcagta gtacacgttg tatatatata tatgtaacaa atttggtagt   2220
tttcagtatg tgtgatgtcc tttgggggtt atttatcttg ctggtccata ggaggggtac   2280
actaccccaa gaatcaagac atctgagttc tagttctagt tctagctctg ccactgaaga   2340
gccaccttac ctggggcaag ttagccattg tctcccagtc atgtttacca cccatgaaag   2400
gactcgtcgg tttgatgttt ccattaagct caatgagtaa ctctaatagt tactcttgaa   2460
tctggattga aaaacaccat gcatctgatg agataattca taaatgttgc cccttttttta   2520
```

aatgatacaa ccctaaaagt gactgaattg cccaagtgct tgaacatggc agaggtagtt 2580
actcctattt tgcagtttgt gcacttaaaa attcctacag tgattgttac tttactgggg 2640
aaaaaagatg aggtgaaact tcctcccaag gaattaaaat atctgtagaa gccatggctt 2700
gcttttataa tgtggaaatc atttgatttg ctgtaattca cgcagatccc tccttttgtc 2760
agggggaaat gatttgcatc atgttctttt ttcataatgc ttttacttcc tgtttggatc 2820
agttgtatgt aaatgtacat ttttgttact ttggctgtgc ccgttagaat ttatcttcca 2880
taaagtattt ctcccattga gtctaatgat gtatactttg cctaggtctt tccaaaatta 2940
aatttatgta aatgtctatt ttatataaaa tatgattaaa ataagtatgt ctggtttcaa 3000
tctcaaaaaa aaaaaaa 3017

<210> SEQ ID NO 27
<211> LENGTH: 3900
<212> TYPE: DNA
<213> ORGANISM: Homo sapiens
<220> FEATURE:
<221> NAME/KEY: misc_feature
<223> OTHER INFORMATION: Incyte ID No: 233113.4CB1
<221> NAME/KEY: unsure
<222> LOCATION: 256-282
<223> OTHER INFORMATION: a, t, c, g, or other

<400> SEQUENCE: 27
ggcagggagg aggaagcggt ggctgctgcg gatgtcggtg tgagcgagcg gcgcctgaac 60
acacggcggc tgccgagcgc ctgacccggg cctgcgccag agcctgcacc gagctccggg 120
gccccacacc cgctacggtg gccctgcgcc cgttgctact gaggcggcgt gctctgcatt 180
cttcgctgtc caggcctgcc ggctctggtg tctgctggct cctccttgct cgcctgctcc 240
ctcctgcttg cctgannnnn nnnnnnnnnn nnnnnnnnnn nnatggccga gagtggtgaa 300
agcggcggtc ctccgggctc ccaggatagc gccgccggag ccgaaggtgc tggcgccccc 360
gcggccgctg cctccgcggc gcccaaaatc atgaaagtca ccgtgaagac cccgaaggaa 420
aaggaggaat tcgccgtgcc cgagaatagc tccgtccagc agtttaagga agaaatctct 480
aaacgtttta aatcacatac tgaccaactt gtgttgatat ttgctggaaa aattttgaaa 540
gatcaagata ccttgagtca gcatggaatt catgatggac ttactgttca ccttgtcatt 600
aaaacacaaa acaggcctca ggatcattca gctcagcaaa caaatacagc tggaagcaat 660
gttactacat catcaactcc taatagtaac tctacatctg gttctgctac tagcaaccct 720
tttggtttag gtggccttgg gggacttgca ggtctgagta gcttgggttt gaatactacc 780
aacttctctg aactacagag tcagatgcag cgacaacttt tgtctaaccc tgaaatgatg 840
gtccagatca tggaaaatcc ctttgttcag agcatgctct caaatcctga cctgatgaga 900
cagttaatta tggccaatcc acaaatgcag cagttgatac agagaaatcc agaaattagt 960
catatgttga ataatccaga tataatgaga caaacgttgg aacttgccag gaatccagca 1020
atgatgcagg agatgatgag gaaccaggac cgagctttga gcaacctaga aagcatccca 1080
gggggatata atgctttaag gcgcatgtac acagatattc aggaaccaat gctgagtgct 1140
gcacaagagc agtttggtgg taatccattt gcttccttgg tgagcaatac atcctctggt 1200
gaaggtagtc aaccttcccg tacagaaaat agagatccac tacccaatcc atgggctcca 1260
cagacttccc agagttcatc agcttccagc ggcactgcca gcactgtggg tggcactact 1320
ggtagtactg ccagtggcac ttctgggcag agtactactg cgccaaattt ggtgcctgga 1380

-continued

```
gtaggagcta gtatgttcaa cacaccagga atgcagagct tgttgcaaca aataactgaa   1440
aacccacaac ttatgcaaaa catgttgtct gccccctaca tgagaagcat gatgcagtca   1500
ctaagccaga atcctgacct tgctgcacag atgatgctga ataatcccct atttgctgga   1560
aatcctcagc ttcaagaaca aatgagacaa cagctcccaa ctttcctcca acaaatgcag   1620
aatcctgata cactatcagc aatgtcaaac cctagagcaa tgcaggcctt gttacagatt   1680
cagcagggtt tacagacatt agcaacggaa gccccgggcc tcatcccagg gtttactcct   1740
ggcttggggg cattaggaag cactggaggc tcttcgggaa ctaatggatc taacgccaca   1800
cctagtgaaa acacaagtcc cacagcagga accactgaac ctggacatca gcagtttatt   1860
cagcagatgc ttcaggctct tgctggagta aatcctcagc tacagaatcc agaagtcaga   1920
tttcagcaac aactggaaca actcagtgca atgggatttt tgaaccgtga agcaaacttg   1980
caagctctaa tagcaacagg aggtgatatc aatgcagcta ttgaaaggtt actgggctcc   2040
cagccatcat agcagcattt ctgtatcttg aaaaaatgta atttattttt gataacggct   2100
cttaaacttt aaaatacctg ctttatttca ttttgactct tggaattctg tgctgttata   2160
aacaaaccca atatgatgca ttttaaggtg gagtacagta agatgtgtgg gtttttctgt   2220
atttttcttt tctggaacag tgggaattaa ggctactgca tgcatcactt ctgcatttat   2280
tgtaattttt taaaaacatc accttttata gttgggtgac cagattttgt cctgcatctg   2340
tccagtttat ttgcttttta aacattagcc tatggtagta atttatgtag aataaaagca   2400
ttaaaaagaa gcaaatcatt tgcactctat aatttgtggt acagtattgc ttattgtgac   2460
tttggcatgc atttttgcaa acaatgctgt aagatttata ctactgataa ttttgtttta   2520
tttgtataca atatagagta tgcacatttg ggactgcatt tctggaaaca tactgcaata   2580
ggctctctga gcaaaacacc tgtaactaaa aaagtgaaga taagaaaata ctcttaaagc   2640
tgagtatttc ctaattgtat agaatcttac agcatctttg acaaacatct cccagcaaaa   2700
gtgccggtta gtcaggtttg ttgaaaatac agtagaaaag ctgattctgg ttatctcttt   2760
aaggacaatt aattgtacag acacataatg taacattgtc tcaacattca ttcacagatt   2820
gactgtaaat taccttaatc tttgtgcaga ctgaaggaac actgtagtat accccaaagt   2880
gcatttgcct aggacttctc agcttctccc ataggtagtt taacaggcat taaaatttgt   2940
aattgaaatg ttgctttcac tgaaaaagtg tcttgatgtt tcagttattt ttaatcgcca   3000
taaaaaaata gaactatctt ttgggtttat ctgttttctc atgcacaggc aatacacaaa   3060
tttaaaatga gttgtgagcc aattgtttct gaagtgtttt ggtagttcta ttaagaaata   3120
gttaaatatt gtgcttttca gagcctcaga gaaaggggga cggggtgggg gggtggggca   3180
gcggaatctg tcctggatgg ggccagctta aataatactg gcaaccaaga ttctgttagg   3240
atttctgtgc atatagtgta gtaaagaagt atcattcagg ggtgaaaaac aaagagccgt   3300
tttaatgatg ttgagtacat ttggctgttt tatagccttt tcttccctcc cccaaagaat   3360
tctgtttgcc taactcccaa actgttgggg tggtacattc ctttaggacc aattaaaaca   3420
taattgaggg tcagtgatac atttggctga ctctggttca gtattctctt aggtgattat   3480
attctctcat gtacagttac aggaaattaa aatgttaaag taacctaaaa tgaattcaga   3540
ccaataaaat caagggaaat acaagttgat tgcattactt ctgtatgttg cttgctatta   3600
aaaaggttaa gaggccaggt tacccaccag tccttgcact gttctgacac tttccccagg   3660
aggaaaacaa gtacaaaggt tacggtggag gcataagtag aagagattgt taagaagggt   3720
attcatgtgt ctttgctctt tctgctttat gcctcagttt ggtttaaaaa cttctgtact   3780
```

ggcaaatggt ggtattcagt gtgggatagt gtcataacta atttgacaat ttattaatca 3840
taaaataaca ataaatctct agcttttaca cttgagaaaa aaaagaagaa aaaaagaagg 3900

<210> SEQ ID NO 28
<211> LENGTH: 2235
<212> TYPE: DNA
<213> ORGANISM: Homo sapiens
<220> FEATURE:
<221> NAME/KEY: misc_feature
<223> OTHER INFORMATION: Incyte ID No: 235194.5CB1
<221> NAME/KEY: unsure
<222> LOCATION: 1037, 1046, 1087, 2042-2067
<223> OTHER INFORMATION: a, t, c, g, or other

<400> SEQUENCE: 28
gccgggacat ggtgccagtc gcaccccttc cccgccgccg ctgagctcgc cggccgcgcc 60
cgggctggga cgtccgagcg ggaagatgtt ttccgccctg aagaagctgg tggggtcgga 120
ccaggccccg ggccgggaca agaacatccc cgccgggctg cagtccatga accaggcgtt 180
gcagaggcgc ttcgccaagg gggtgcagta caacatgaag atagtgatcc ggggagacag 240
gaacacgggc aagacagcgc tgtggcaccg cctggcaggg ccggccgttc gtggaggagt 300
acatccccac acaggagatc caggtcacca gcatccactg gagctacaag accacggatg 360
acatcgtgaa ggttgaagtc tgggatgtag tagacaaagg aaaatgcaaa aagcgaggcg 420
acggcttaaa gatggagaac gacccccagg aggcggagtc tgaaatggcc ctggatgctg 480
agttcctgga cgtgtacaag aactgcaacg gggtggtcat gatgttcgac attaccaagc 540
agtggacctt acaattacat tctccgggag cttccaaaag tgcccaccca cgtgccagtg 600
tgcgtgctgg ggaactaccg ggacatgggc gagcaccgag tcatcctgcc ggacgacgtg 660
cgtgacttca tcgacaacct ggacagacct ccaggttcct cctacttccg ctatgctgag 720
tcttccatga agaacagctt cggcctaaag taccttcata agttcttcaa tatcccattt 780
ttgcagcttc agagggagac gctgttgcgg cagctggaga cgaaccagct ggacatggac 840
gccacgctgg aggagctgtc ggtgcagcag gagacggagg accagaacta cggcatcttc 900
ctggagatga tggaggctcg cagccgtggc catgcgtccc cactggcggc caacgggcag 960
agcccattcc ccgggctccc agtcaccagt ggtgcctgca ggcgctgtgt ccacggggag 1020
ctccagcccc ggcacanccc agcccncccc acagctgccc ctcaatgctg ccccaccatc 1080
ctctgtnccc cctgtaccac cctcagaggc cctgccccca cctgcgtgcc cctcagcccc 1140
cgccccacgg cgcacatgca tctctaggct gtttgggacg tcacctgcca ccgaggcagc 1200
ccctccacct ccagagccag tcccggccgc acagggccca gcaacggtcc agagtgtgga 1260
ggactttgtt cctgacgacc gcctggaccg cagcttcctg gaagacacaa cccccgccag 1320
ggacgagaag aaggtggggg ccaaggctgc ccagcaggac agcgacagtg atggggaggc 1380
cctgggcggc aacccgatgg tggcagggtt ccaggacgat gtggacctcg aagaccagcc 1440
acgtgggagt cccccgctgc ctgcaggccc cgtccccagt caagacatca ctctttcgag 1500
tgaggaggaa gcagaagtgg cagctcccac aaaaggccct gccccagctc cccagcagtg 1560
ctcagagcca gagaccaagt ggtcctccat accagcttcg aagccacgga gggggacagc 1620
tcccacgagg accgcagcac ccccctggcc aggcggtgtc tctgttcgca caggtccgga 1680
gaagcgcagc agcaccaggc cccctgctga gatggagccg gggaagggtg agcaggcctc 1740
ctcgtcggag agtgaccccg agggacccat tgctgcacaa atgctgtcct tcgtcatgga 1800

-continued

```
tgaccccgac tttgagagcg agggatcaga cacacagcgc agggcggatg actttcccgt   1860

gcgagatgac ccctccgatg tgactgacga ggatgagggc cctgccgagc cgcccccacc   1920

ccccaagctc cctctccccg ccttcagact gaagaatgac tcggacctct tcgggctggg   1980

gctggaggag gccggaccca aggagagcag tgaggaaggt aaggagggca aaaccccctc   2040

tnnnnnnnnn nnnnnnnnnn nnnnnnnagg caaagaggaa gaagaaaaag ctgccaagaa   2100

gaagagcaaa cacaagaaga gcaaggacaa ggaggagggc aaggaggagc ggcgacggcg   2160

gcagcagcgg cccccgcgca cagggagagg acggctgccg atgagctgga ggctttcctg   2220

gggggcgggg ccccg                                                    2235
```

<210> SEQ ID NO 29
<211> LENGTH: 2737
<212> TYPE: DNA
<213> ORGANISM: Homo sapiens
<220> FEATURE:
<221> NAME/KEY: misc_feature
<223> OTHER INFORMATION: Incyte ID No: 235636.1CB1

<400> SEQUENCE: 29

```
caactaacgg tgtttttaag ggggtctaag cctgcctttt caatgattta atttgatttt     60

attttatccg tcaaatctct taagtaacaa cacattaagt gtgaattact tttctctcat    120

tgtttcctga attattcgca ttggtagaaa tatattaggg aaagaaagta gccttctttt    180

tatagcaaga gtaaaaaagt ctcaaagtca tcaaataaga gcaagagttg atagagcttt    240

tacaatcaat actcacctaa ttctgataaa aggaatactg caatgttagc aataagtttt    300

tttcttctgt aatgactcta cgttatcctg tttccctgtg cctaccaaac actgtcaatg    360

tttattacaa aattttaaag aagaatatgt aacatgcagt actgatatta taattctcat    420

tttactttca ttatttctaa taagagatta tgtgacttct ttttctttta gttctattct    480

acattcttaa tattgtatat tacctgaata attcaatttt tttctaattg aatttcctat    540

tagttgacta aaagaagtgt catgtttact catatatgta gaacatgact gcctatcagt    600

agattgatct gtatttaata ttcgttaatt aaatctgcag ttttattttt gaaggaagcc    660

ataactattt aatttccaaa taattgcttc ataaagaatc ccatactctc agtttgcaca    720

aaagaacaaa aaatatatat gtctctttaa atttaaatct tcatttagat ggtaattaca    780

tatccttata tttactttaa aaaatcggct tatttgttta ttttataaaa aatttagcaa    840

agaaatatta atatagtgct gcatagtttg gccaagcata ctcatcattt ctttgttcag    900

ctccacattt cctgtgaaac taacatctta ttgagatttg aaactggtgg tagtttccca    960

ggaaggcaca ggtggagtta tttgtgagaa gcaaagtgtt tactaatgac aaagtagtaa   1020

accattttca agatgaaaac tgatttctat ttattttgct tcaaaggtcc tgaaaaaata   1080

agcaattatc ataacaattt gttattgata ctggaggttt cattgacatg tctctcaaat   1140

taaagctcac actgcctcca taaaagtctt caacatctaa tttataagct ttacaagtat   1200

ttattttata aggcttagac agaattattg gagttttaaa ttaagtgtat tggaaaagaa   1260

aggatggtat gtgtatgaaa tgttaagatc ctacgcaaca ctgctatttt tttcctttaa   1320

tatttgtgct gcataacaaa agccactaga ctgttactgt cttgtctgtc catgtgttaa   1380

cagcatttct taatgatgta tatatggagt ggtcttcaat catagtgaag aatttaaaga   1440

gaaagtcaat tgtattggca tttttaataa gaacaaaatt agttcgtcta aggggactgg   1500

ctggccacat atttgttcct tgcccatatg ctttctactt cttgttctta ttatgaaatt   1560
```

-continued atgaatttga agcctctgaa atggtgatca gtttttcaac atctttcaaa aacaaaatta 1620
ctatttcctc catattgcct tttttagata actttaaagt taggatttta aaatatttgt 1680
aactggctaa attttaaagt cgtgacaaat aattacttag gttcagaaat atacacacac 1740
ttactcttta gccagtttct ttcaaggttt actgtcccat cagatatcta gccattttcc 1800
tttgcaaatt acataccttc ttaagagtgt atttttaaga ttattactta cgctttatga 1860
tgatatagtt tttcaaaatt atttatagct tcatatgatg ttttgtaatt ttttctattg 1920
atacctgttt taaaaatatt ttccaaggaa gttgattaaa attatatttg ttacctttta 1980
gaaaaagcat tgaaatgagt ttctcttgct ttttcatttt ccctctgctt tatatgctct 2040
tcgcaataca tcatgtccaa cgggatacct attgttctca tgacacccaa aattgatgag 2100
agcaaagggg tcgcaccata tggaaatgtt gaaaactatt gtaaagtagt attatgaagt 2160
agcttttgtg tcattcatgt cgatgacatg aaagtgaagt aaatttattc tatgtaaatt 2220
cacactaaaa ccagtacagt accataagta gaatacatgt aagaatcacc tagtcttcac 2280
tatattgagt aaatataaca tgctaatttt acaattaatg aaactaaact tttaaacatc 2340
tccattatat ctacatcctt ttgaaggtat ttatcatagt tgccaatttt aattttagga 2400
ttgactttct ctttctgaat gacttcataa agtttggtgt gaattttgaa gacttgggtt 2460
actaatgatt gtatctttgc tagtcaacaa cttatgaaat atactcaatg cgtctgatgt 2520
gtcattaagt gcagaaataa ctaagacaca aataaccttt gcaaaccttc aagctgtgta 2580
atattccaat gttgtttttt tctttgtata tatacttata tcacgtagga tgtaaaacca 2640
gtatgacctt gtctagtctc caaacttaaa ataaactttt gaaaagctgg gattcttttg 2700
aagcagttgt aattaaacac atttataaga atacaaa 2737

<210> SEQ ID NO 30
<211> LENGTH: 1520
<212> TYPE: DNA
<213> ORGANISM: Homo sapiens
<220> FEATURE:
<221> NAME/KEY: misc_feature
<223> OTHER INFORMATION: Incyte ID No: 235995.2CB1
<221> NAME/KEY: unsure
<222> LOCATION: 248
<223> OTHER INFORMATION: a, t, c, g, or other

<400> SEQUENCE: 30
gaaaaatgta gaaaaacggc agagacagtg tcttacctag aatatctagt gatgttagtc 60
aatacatatt ttttcaaaca tttattctgg tttagttgct tttttctact gtccattttg 120
cttttctgaa gggattagat taaacgtggt tcattgatgc aacacagact tactgattgt 180
ttattgtgtg ccaggtactg ttatggtctg gaggtacaaa aaaatgcaca aaatttactt 240
gctgcctnag ggaagtaatg ttgattggat aattagactt ataagcagac agttcaggtg 300
tacatgtggg gctctggcat aaagaagagg actcagacca agctggggag ttgcttaagg 360
aaggcttcca ggaattggag tctcttaagc tgattttaaa gggtgaataa aagtggacca 420
tgcagataat ctgttggaaa atgggttgga ggttatctca gaggaagtca cttgcctaca 480
tagagaacat gatgaatgta agatgaattt gaatgtacag gtcacatgta ggataggtaa 540
agagtcagtc caaaaacaga atatgagggg cttgtgtccc gtgttgtgga acttgcattc 600
ctgactttcc tcctccaccc cactgagatg ctagagagta actggagaat tttgagtagg 660
gaagtgacct gttgatcagc tattcttgtt taaaagctca ttctaggggt agcatgggat 720
atagctgtga cttaagccaa gagttctgtt agggggatag aagagaatga ggtcctaaag 780

```
ttcagccgcg atagggagaa tgactgtgag agttaactta ggctgaatta gtaggactgt     840

tgatggaata tgcaggtagg aagaagagag tgaattcttg aatgctgtcc ttaggtatct     900

gggtggagcc ctttaccaag atagatgatg caggtaggac aggttttggg gtgttgaatt     960

cagatttagc catgtctgtt tgatgagtct gagtgacaca gaatagaaat agggacatag    1020

agatatctat ttagactaaa tctgtaatat gttctattct aaatggaatt atactccaga    1080

agaaaataaa ctgatttaaa atagcttgtt acagcacttc aggtgttttt ttcttacact    1140

aatgattttg ttttacggct gaaaagtaaa atggccaact tgagaagcct aggtataata    1200

tgccttagat tatattttg aatggaatta ttgttcttta cctgataatt tatattggtt    1260

acttggcctt taaatctttc ttcttaccta actttctatt ctactattta aggggaaaga    1320

taaagggtca ttataagagg gctgtggaat gatttaaaat ggtgggtgaa gggtaaaact    1380

gaaagtgttt attaggaaag taaagctatt catgttttta caggtaactg aagatcaaag    1440

taaagcaaca gaggaatgta catctaccta ataactttct aaaatttaaa tatgtataat    1500

aaaataaatg ttttaaatat                                                1520
```

```
<210> SEQ ID NO 31
<211> LENGTH: 950
<212> TYPE: DNA
<213> ORGANISM: Homo sapiens
<220> FEATURE:
<221> NAME/KEY: misc_feature
<223> OTHER INFORMATION: Incyte ID No: 236378.4CB1
<221> NAME/KEY: unsure
<222> LOCATION: 318, 353, 718
<223> OTHER INFORMATION: a, t, c, g, or other

<400> SEQUENCE: 31

gtggagcaga agccacagtc acttcctgaa ggcagcggcc ccagctcggg tcccactcat      60

cccatggccc atcacctgcc tgcagccatg gagagccatc aggacttccg gagcatcaaa     120

gcaaagttcc aggcctctca gccggagccc agcgacctgc ccaaaaaacc tccgaagcct     180

gagtttggta aactgaagaa gttctcccag cctgagctaa gcgagcaccc ccagaaggcc     240

ccgccgcctg agtttggtgc agtgtccttg aagcccccgc agcctcagtt cactgacctt     300

ccccaagaag gccccgcngc ctgaggtcac tgactccccc aagaagcccc cgncggctga     360

ggtcactgac ctccccaaga agcccccgcc gcctgaggtc actgacctcc ccaagaagcc     420

gtccaaactg gagttgagtg acctctccaa gaagttccca cagctggagg ccactccgtt     480

tccaaggaag cccctgcagc ctgaggtcgg tgaggcccct ttgaaggcct cgctgccgga     540

gcctggtgcg ccggcccgga aacccctgca gcccgacgaa ctcagtcacc ccgccagacc     600

cccctccgaa cccaaatccg gcgcattccc caggaagctc tggcaacccg aggccggtga     660

ggctaccccg aggtccccgc agcctgagtt gagtaccttt cccaagaagc ctgcgcanct     720

ggagttcaac gtgtacccca aaaagcctcc gcagcctcag gtcggtggcc tccctaagaa     780

gtccgtgccg cagcctgagt tcagcgaggc cgctcagact cccctctgga agcctcagtc     840

cagcgagccg aagcgcgact ccagcgcctt tcccaaaaag gcctcccagc ctccgctgag     900

tgactttccc aagaagcctc cgcagcctga gcttggggac ctcaccagga                950
```

```
<210> SEQ ID NO 32
<211> LENGTH: 2497
<212> TYPE: DNA
<213> ORGANISM: Homo sapiens
<220> FEATURE:
```

<221> NAME/KEY: misc_feature
<223> OTHER INFORMATION: Incyte ID No: 238024.1CB1

<400> SEQUENCE: 32

```
ctgcactcca gcctgaacag agtgagatcc tgtcaaaaaa gaaaagaaaa agaaagcagc     60
attcaaatgt aagacaactg taaaatattg agccccactt ggtctaaaat tcaaaaagaa    120
gaacgcctgt ccatcgcctt tttataagtc cttctctcca cacctaaaag cagctgcagc    180
tggaagggca caaattccac tgtgtaaaat aaaatattag ggcaacacac cttcatcaag    240
gcatgcacgg aatgagagag agcagagaag atcaaggatg aagtcttggg tactgaaaaa    300
ttcagtgctg ggcagaaaaa ctgacagggc agtacaagta acaaacagaa tccaagtggg    360
gtggcccttg tgcacagagc tccaggtgac ctctggagag acatgggcat tcacatggaa    420
agctaaaacg gaagctcaag tttcatactc aacataatct tctgtgtgac aaaggacaag    480
ccatgtagcc tctctgtgcc tatttcttca tgcataaact gggactcata atatttgtaa    540
aatgtattga tactctcagg gcaaattcac tatattgcta tacagttgag atcagtgttg    600
taaaattaaa ctgatctggt tctaattgcc tcaaaggcca aagcccaggc atttgaaatg    660
gaaagaagca gagaggaggc tgacttagct gattggtatg gaaacagttg ggccaagagc    720
cagaatttcc ctttgtagca acacggctag ttttactttg agaagctctg ctcagctgct    780
ttataacatt aagtctggcg gaatggatgt cactgtgcac aataaagttt tcacaagtat    840
aaacaatggt gatgtaagtc aacattggct gtagccaggt gtgaaggttg tatggtgtgt    900
gacgaatgta catcatgttt gtaggtttgg atgctaatct tgaattgtag cttaaaaaat    960
acgtattttt gtaactcttt gaaagtttat gaagactgac agctttcctt gtaagcacta   1020
agagaaaaaa aagaaagagg gacatttgac aattttaaag aaacaacaag aaattagaat   1080
gaaaatctgt gacaaacagc gtcagtgtgg ccatgtccac attcctacat gtctctctct   1140
acaagcacct ctctaagaag cctgacatcc cggtggactc tttatagtca tgtacacttg   1200
attccagatg agctctggtc ttatctggat gctcagataa gaggtttcta tctgaggcat   1260
ccagatgttc cctcaggttc caagacattt caccccaggc cctggggttc actctggaat   1320
tcgtaggctt cacgtctctc tagaaatgac gtgtaaaatt taagaccaga cctcagccat   1380
cagcgtccag accatcctag aagtctttcc caatctcaca gagaaagccc tagtatttcc   1440
cagtgacccc aggattccac gttggggtgg ccaaagaaat aggtctctca gggctttgcc   1500
acagcctcca gcccatcctt cagaggcaca cacagcacct ctcggctgct ccagctctgt   1560
aggatagcct cccctggggt ccgtgggacg cgggccacag tgttgaggta gacaaggagg   1620
atcagtgaga ggcctcttcc ctctccacag agactggatt gtcattgttc cttcatttat   1680
atcgtagggc ttaacatttc actcaaaaaa aagcccctct ttttctaatc cttagtcttt   1740
gtttcaagga aagccagttt ttcttctacc acattttcca ggatcgactt taagaaaaat   1800
gcaacatcta ttgaaaaaaa gtggggtgta tgcatgtggt ttaattccag attgcttttg   1860
ggtttaagtg gtatcaaatt tcagtatatt tctgtcttat gtgaaagaaa tatattacta   1920
aaacgtcagt gagcaataat gtcagctgtc aagcactaga tttatttttg caggatatgg   1980
agtgcaatga actgagtcaa tatggcaagg tgtatgtgat ctgtgggagt tatgccattt   2040
aacataggaa gtgcatggga ctttccctct ctgcactcca gctcttactg taccattaga   2100
agatgcagaa ttctgttggt gtgcaaaaag tatagcctta cattcaagca gaatggatct   2160
gaagaaagca gcaatatctg ttactagaga acattcccat gtgtttaaac tcttcacttc   2220
```

-continued

```
ttagatgcat ttaaattctt aatgcaaatg acgtagcaat ttgaaaactt ctccgtatta   2280

cttgtgttta aaatgtcttg ctttaaatac aaaacaaatg gtaaagggga ttatcttttg   2340

tttagatggt taaatattat ttttgcctta gatagctttg taataatttt tctccagaca   2400

gttcaacact tttgaaaaat gacatgaatt ttcattaaaa accctttttcc tatgtttatt   2460

gtatacaaga attatgcaat aaaatttctt tataaaa                             2497
```

<210> SEQ ID NO 33
<211> LENGTH: 2225
<212> TYPE: DNA
<213> ORGANISM: Homo sapiens
<220> FEATURE:
<221> NAME/KEY: misc_feature
<223> OTHER INFORMATION: Incyte ID No: 238544.2CB1

<400> SEQUENCE: 33

```
aacaaggatc ataagagaat gtttggaacc tacttccgag ttggtttctt tggatccaaa     60

tttggggatt tggatgaaca ggaatttgtc tacaaagagc ctgcaattac caagcttcct    120

gagatctcac atagactaga ggcattttat ggtcaatgtt ttggtgcaga atttgtggaa    180

gtgattaaag actccactcc tgtggacaaa accaagttgg atcctaacaa ggcctacata    240

cagatcactt ttgtggagcc ctactttgat gagtatgaga tgaaagacag ggtcacatac    300

tttgagaaga atttcaacct ccggaggttc atgtacacca ccccgttcac cctggagggg    360

cggcctcggg gagagctgca tgagcagtac agaaggaaca cagtcctgac cactatgcac    420

gccttcccct acatcaagac caggatcagc gtcatccaga aggaggagtt tgttttgaca    480

ccgattgaag ttgccattga agacatgaag aagaagaccc tgcagttagc agttgccatt    540

aaccaggagc cgcctgatgc aaagatgctt cagatggtgc tgcaaggctc tgtgggagct    600

actgtaaatc agggaccact ggaagtagcc caagtgtttt tggctgaaat tcctgctgat    660

ccaaaactct atcgacatca caacaagttg aggttatgct ttaaggaatt catcatgaga    720

tgtggtgaag ctgtagagaa aaacaagcgt ctcatcacgg cagaccagag ggaatatcag    780

caggaactca aaaagaacta taacaagcta aaagagaacc tcaggccaat gatcgagcgg    840

aaaattccag aactgtacaa gccaatattc agagttgaga gtcaaaagag ggactccttc    900

cacagatcta gtttcaggaa atgtgaaacc ccagttgtca cagggcagct aagaaaagcc    960

atcttcattc gtggagactg tggccctgca accctggaga aggacttgct ggtacttaaa   1020

aaatgggaca tttgccaccc aggactgact gtacactccc tgatcagcca gcactctggg   1080

aagctttggg atcccaggaa ccatggaatt attcccaaat ggactctgac cagatttttg   1140

ccatactggg gggtggcggg atggaggatg ggtactcagg catgactgcg tatttattaa   1200

agtgtgtttt tccacaatgt accaaacaag gcataagcag cttctcctgc tgactggcca   1260

atcactgccc atctgagaga tgatttcctc tggcccatat ttgaatttat tggagtaact   1320

caaattgcct gaggaaaaat ggaaaaatta tccaccagtc gattcaaact gaatttcact   1380

ctttatagga aggcagggca aacttgtagg agtacgaaac attttcaata aatctacaaa   1440

gggaagcctt actacaattc caaaaatcat catggttgga aatttgggag gagattattt   1500

gtgaacttgt taccctttttg gtaatggtgg actaattgct gtatagttat ttttgtttta   1560

ttattactgt tacattaatt taacatgcat ttatagaaga atacattcaa agcactgatg   1620

taggagatac acggtacttg gagcagtcag ccaaaaatca cagatactgc tttcacttaa   1680

atggaaacaa ttctccgata atgctttgct tttttcttta tgtcactctt gtgtactatc   1740
```

```
tatttttctc ctctctggga ccaagtttct ttttataaag caataatatc tctgttttca   1800

tttcagaaca ttgtgctgtc tgtcagcata tgtatatcag ctacaaaata tattcaactt   1860

tgacttcttt tgacaaagga ctttaggaaa aagaggaaca aagacattat ttgagaatta   1920

aattatatat ttttaatatg actgtgacct tgactgataa taaagatgta ataagaattg   1980

caagctaaat gtttcccttt gcaactcatg ctttgtgttt tgttttgatg acctactcgc   2040

tcgtaatgtt ttgtaaggca cttcagagag aagacagatg catcatcctg gcctccatca   2100

aataacacta tccaaggtgg cacctcttct gcaatgttta accctgctag taatgaacga   2160

tgacttagtt cggatatttc agaacttttt gtttatacca tcaggtatgc atgaatttat   2220

aatct                                                                2225
```

<210> SEQ ID NO 34
<211> LENGTH: 834
<212> TYPE: DNA
<213> ORGANISM: Homo sapiens
<220> FEATURE:
<221> NAME/KEY: misc_feature
<223> OTHER INFORMATION: Incyte ID No: 239382.1CB1

<400> SEQUENCE: 34

```
tcacccactt tcacactcca ctgttaagtt ctgcatatcc tacggttttt taatgcacat     60

ataagcatat ggctcttcac aaatgggatg ataccatata tacattctat aatttaagaa    120

aaaatggctt tcagtatatc tagatctatc tataacagct gtgaggtatt ccactacatg    180

gatgtggcaa aattcattta actaaaacca aactaatagg catgtgttgg ttgtttttac    240

tgggccatta gcaacagtgc tatagtaaac atcattttga ataaatctct atacaattgt    300

tcaagtacgg agggataaat ttctagaaat aaaatttctg gatgaaagaa agcatgggaa    360

tgacttttat ttggatacat atccatcaaa agtgggagaa tgccattttc cccacagcct    420

caccaattct tcaccaatct gacaggtgga aaaagtgtgc cccaactacc ttttagagtt    480

tctctgccca gcagtttcca gtgactgtac atgcaaatgg aaaagtccca ttagaaatag    540

ttgacccaac acagttgcaa tcaagtatct gagctaagta cacaccagca aattactaaa    600

aatatccaga aaaactcaag cttcataaaa cctcaaattt caaaaaaagg atgctaaaat    660

ccacataggt cacttgtgtt ggcctggcct aaacagaccc ctcaaaggaa ctttggaggg    720

aaattgtttc tctaggtaag gaataacagc ataaagggaa aaaaattaaa attgttagat    780

acaggattct ctctagatct gccctgtcca atatagatgc cactaaccct cgtg          834
```

<210> SEQ ID NO 35
<211> LENGTH: 821
<212> TYPE: DNA
<213> ORGANISM: Homo sapiens
<220> FEATURE:
<221> NAME/KEY: misc_feature
<223> OTHER INFORMATION: Incyte ID No: 241145.2CB1
<221> NAME/KEY: unsure
<222> LOCATION: 316, 630, 802, 806, 808
<223> OTHER INFORMATION: a, t, c, g, or other

<400> SEQUENCE: 35

```
ggaaatggga tgggcacctg ggagaatctc cacgtaactt cagaaagggg tggcagatgg     60

ttttcaactg acaagttgaa ttgattggta gtggctccca gaggattctg aggtggtctc    120

catgttgggt gggcaagaga gattgactag tgatgactgc cacagaatgg agaggagggc    180

cctttacttc tttgaaccct aattttctca cgtataagcg gagaccctgg cccctcccgg    240
```

```
gcacagagta agctctgagc aaaggaggca atgctgttcc catcagtaag gctgcggaaa    300

ccaccacctc cctctnccca ccaccccgct ccttaacacc acctccagtc acaacctggt    360

gatgaaacac ctccctgggg ccgaccctga gctcgtgctg ctgggccgcc gctacgagga    420

actagaggtg aggccgtggg aggtgggctg gggcgaggc cagaggcgag gcccagcctg    480

ctgaccccgc ccctcctccg cctcagcgca tcccactcag tgaaatgacc cgcgaagaga    540

tcaatgcgct agtgcaggag ctcggcttct accgcaaggc ggcgcccgac gcgcaggtgc    600

cccccgagta cgtgtgggcg cccgcgaagn ctccagagga aacttcggac cacgctgacc    660

tgtaggtccg gggcgcggc ggagctggga cctacctgcc tgagtcctgg agacagaatg    720

aagcgctcag catcccggga atacttctct tgctgagagc cgatgcccgt ccccgggcca    780

gcagggatgg ggttggggag gntctncnaa ccccactttc t                         821
```

```
<210> SEQ ID NO 36
<211> LENGTH: 4874
<212> TYPE: DNA
<213> ORGANISM: Homo sapiens
<220> FEATURE:
<221> NAME/KEY: misc_feature
<223> OTHER INFORMATION: Incyte ID No: 241732.1CB1
<221> NAME/KEY: unsure
<222> LOCATION: 1668, 3998-4056, 4765, 4812
<223> OTHER INFORMATION: a, t, c, g, or other

<400> SEQUENCE: 36

gaaagccgca gcctcagtcc cgccgccgcc cgctgcgtcc gcccagcgcc agctccgcgt     60

ccccgaccgg cccgcggcag cctgcgccgc gccatggcca cctccccgca gaagtcgcct    120

tctgtcccca agtctcccac tcccaagtcg cccccgtccc gcaagaaaga tgattccttc    180

ttggggaaac ttcggaggga ccctggcccg gaggaagaaa gccaaggagg tgtccgagct    240

gcaggaggag ggaatgaacg ccatcaacct gcccctcagc ccaattccct ttgagctgga    300

ccccgaggac acgatgctgg aggagaatga ggtgcgaaca atggtggatc caaactcacg    360

cagtgacccc aagcttcaag aactgatgaa ggtattaatt gactggatta atgatgtgtt    420

ggttggagaa agaatcattg tgaaagacct agctgaagat ttgtatgatg gacaagtcct    480

gcagaagctt ttcgagaaac tggagagtga gaagctaaat gtggctgagg tcacccagtc    540

agagattgct cagaagcaaa aactgcagac tgtcctggag aagatcaatg aaaccctgaa    600

acttcctccc aggagcatca agtggaatgt ggattctgtt catgccaaga gcctggtggc    660

catcttacac ctgctcgttg ctctgtctca gtatttccgc gcaccaattc gactcccaga    720

ccatgtttcc atccaagtgg ttgtggtcca gaaacgagaa ggaatcctcc agtctcggca    780

aatccaagag gaaataactg gtaacacaga ggctctttcc gggaggcatg aacgtgatgc    840

ctttgacacc ttgttcgacc atgccccaga caagctgaat gtggtgaaaa agacactcat    900

cactttcgtg aacaagcacc tgaataaact gaacctggag gtcacagaac tggaaaccca    960

gtttgcagat ggggtgtacc tggtgctgct catggggctc ctggagggct actttgtgcc   1020

cctgcacagc ttcttcctga ccccggacag ctttgaacag aaggtcttga atgtctcctt   1080

tgcctttgag ctcatgcaag atggagggtt ggaaaagcca aaaccgcggc cagaagacat   1140

agtcaactgt gacctgaaat ctacactacg agtgttgtac aacctcttca ccaagtaccg   1200

taacgtggag tgaggggctg ccctgggccc accactgccc aagagttctt gctgttggcg   1260

tactggaccc tcctccgaac tgccttaccc tgcttattcc tgtctcttgc actgtgctct   1320

cccacaagtc cagctgcaac ccagagatag tggaaactga aattaggaag gaaatcatca   1380
```

-continued

```
ataactcagt gggctgaccc atccctccca ggcgctgggg accaacctag caatgaaggt   1440
tgggaaggtt gttcccttcc cggtgccagg tccagatttc cctccatgat ttgggaacca   1500
ggttaggcaa aagagtcccc acaagatgaa aataaagatc ctagttacca ttcaaaggat   1560
gctaactgtg tgtcaggccc cacactaagt gctctgctct gatatactca aggccattaa   1620
tcttcaggac tcccattgac gtaggtgttt cattcccctt ttacaggntg aggcaactaa   1680
ggcttggagg ttaaatgact tgccagaagt tggaattttt ttcctctttg aacataacct   1740
ctcccttctc cctaaaggta accactattc tgagtccaat catcaaggtt ttgcttttct   1800
ttttagctaa gtatgcattc ctcaatagta gacagtacaa catgtttata acaagccaat   1860
tacattatgt tctttgcatg ttctaaagtt gtgtatgtgt gtgcacatct gagcacgtgc   1920
acatgtacac ctgagccaaa aacacgagaa cccactgatc tcaccactgg ggcaagctag   1980
gtcagagctt agtgattcac actgaaattg gcaaattgga tttaacccaa ttaatagtgt   2040
gtgtgtggca ggagtcatgt ccctcacatc ctttgtacaa atgaaaatta ctcttaattc   2100
cttcagattt ataataactc tgtactttgg tttcagggtg acatttggga aggattttgt   2160
ttagaattaa tggagtggca cattttgcag cctttttgct tgattgcatg taatggaaat   2220
gccctatatt ttcctgcaaa ataagtacta aattcattat cgttaagcaa atgtacaata   2280
tggctcaggc accgcagaga gctgggcacg ggcccatgtg agcatcactt tggaagtagg   2340
gctcttcaac agggaccctt gaactttaaa gaaaggaact tctttttgcc ttctaattga   2400
tcatttagac tattctggct aagtctgccc acatgtaatt accggctaat tcaagcgagg   2460
aaaaatgtaa gtcatttaga ccaaagccaa gcagtttctt tgcgtgggtt actcaagggc   2520
ttgtggttac ttgtatctcc tctatgtgaa cttgactttg aaagacagag ctctagtgtg   2580
ccagcctgct aagtcctgta agaataggga agggcggagg ggggtgggca gtgactaggg   2640
gacgagaagc atggggaaaa tatttgcact ctaaacatac agagatagag gtggggcttg   2700
tggtacttaa cacttgtagc catcaactga ctgagacctt gggctaaata atcaattgtg   2760
ctgatattac atctcgttat ggaatgttcc taaatatgcc aggtagacac cagcccaagt   2820
accctcctcc agaagtctgt gactaccttg tcactacttt aggcccattc cacaaagccc   2880
atctctggtt tgagaattca ttttgatctg tatctacacc acccaaagtt aggcctccta   2940
taatgtccaa aacattcctt tcagcctttt tatttcttac tgtactgtct cttactgtac   3000
tgtctatctg cagtaattga ggacccataa aatttagata actacatgtc tttgctctta   3060
gaattgtcac tcagcataat gagcatttaa catacaaagg caatgtactg ttttgtgttg   3120
atctatgtaa aagaatacaa ttctttttta cataattagt gaaattttat tttttattag   3180
gaaacactaa atagtgtaat atttcttttg cttttaaaaa aattcctggt agcaaatcaa   3240
gataaataat tgcttcattt tcttgagcaa tactgaagca ggatgaagta agaggaatgc   3300
attcatttaa acatgctttg ctttatgaat tttgtctctt ttttggtctc tttttcttat   3360
attcaagtta caaatgtaca agtatcctta ctaagagtgc tccttttgta ttttacatat   3420
atacagtatg aaaatacatt ggaacactag gaaagttttt aaataacagt tctaatttat   3480
cagaaaattg tgttttggga ttgagttctt tgtctcagcc cagaatccca ggtcctgggc   3540
ctggttttct aatgctgtca tctcagttcg atattttact ttagaatctg gaatctccta   3600
cttaatatat gaccatgact ttgaaaggca aaagaggaat caagaataaa taaaacaaac   3660
ttaatcttca tctttaaaaa aaagaaaaaa gaaaccaaaa tgagaatcaa cacttcatag   3720
```

-continued

```
gctcactggg ttttcttttc ttttctgtta atttaaactc agttattttt aatgcttaat   3780

acatacatgg tgcaaaattt aaaaagcgca aataggtatc tagtggaaaa cctaagcctc   3840

cctctctcct ccggcaccca ttacctctcc ctggaggcaa ctgttttgat ccatttctta   3900

cacacactgc cagagatact ctaggcatgt aaagcacaaa catacatata aaatctgcgg   3960

gcttcaaaaa atataagtag gatgtcatct atactgtnnn nnnnnnnnnn nnnnnnnnnn   4020

nnnnnnnnnn nnnnnnnnnn nnnnnnnnnn nnnnnnctgt tctgcagggc ttcagcgtgg   4080

ccttcattcc cgcctcgcct cggcctcttt tcaattaaga agtgatgcca cttgaggcag   4140

ggtctgcatg atcacttctt gggtttgagt ttgaaagctg ccatccctgc gactgcccag   4200

ggcctgtatg ttgggaccga agccaaacac cactgtcctc caggggggctt tcggcccggg   4260

gcagggtccc cagtgcccgc cttcgaatca gactccgcgt ttccgcctct ccctgggcgg   4320

acctgccgct agagggcgct cctcctccgc agccggcgcc ggcctccagc gccccagact   4380

cccgcgctgc cgcccgagcc tgaggtttct cacggcgttc gggattcgcg cttcggaaac   4440

cgggaacaaa gaagcaagca gcacccttca gaaacagtgt tctcgctctc ctagcagctg   4500

gcccgggccc ggaggctggt gccaggagaa ggcagaagag cccgggcagc cggagtgggc   4560

tacggggttc aggcagtgcc aaggaagaag ggcctcacaa tgggcaattc agctgcctcc   4620

cgggccgttg tccccgctgt cttcaaacag ggggtcccctg tcccagctgc cccaggagga   4680

gcgggggagg caggcagggc cgaaaccctc cagagcccag agggggacgc ttggtggccg   4740

ctgcagttac ataaccatag gatgnttttg taccgtggac cttgttctag caggatcctt   4800

tcggaattgc anttttacat gttgggcgaa tttgtgtccg tgctgaagtt tattaaagga   4860

aaatagatgg aaaa                                                     4874
```

<210> SEQ ID NO 37
<211> LENGTH: 1757
<212> TYPE: DNA
<213> ORGANISM: Homo sapiens
<220> FEATURE:
<221> NAME/KEY: misc_feature
<223> OTHER INFORMATION: Incyte ID No: 247384.1CB1

<400> SEQUENCE: 37

```
ccaggagaag gaagccaaca ggatccgacc cggtgttttg tgacaaaggc aagaccccca     60

ggtctactta gagcaaagtt agtagaggag gcagctaggc gtggctctca ttccttccca    120

cagaatggat tataagtcga gcctgatcca ggatgggaat cccatggaga acttggagaa    180

gcagctgatc tgccctatct gcctggagat gtttaccaag ccagtggtca tcttgccgtg    240

ccagcacaac ctgtgccgga agtgtgccaa tgatattttc caggcctcta acccgtattt    300

gcccacaaga ggaggtacca ccatggcatc agggggccga ttccgctgcc catcctgtag    360

acatgaagtg gttttggata gacatggggt atatggactt cagaggaacc tgctggtgga    420

gaacatcatc gacatctaca aacaggagtg ctccagtcgg ccgctgcaga agggcagtca    480

ccccatgtgc aaggagcacg aagatgagaa aatcaacatc tactgtctca cgtgtgaggt    540

gcccacctgc tccatgtgca aggtgtttgg gatccacaag gcctgcgagg tggccccatt    600

gcagagtgtc ttccagggac aaaagactga actgaataac tgtatctcca tgctggtggc    660

ggggaatgac cgtgtgcaga ccatcatcac tcagctggag gattcccgtc gagtgaccaa    720

ggagaacagt caccaggtaa aggaagagct gagccagaag tttgacacgt tgtatgccat    780

cctggatgag aagaaaagtg agttgctgca gcggatcacg caggagcagg agaaaaagct    840
```

-continued

```
tagcttcatc gaggccctca tccagcagta ccaggagcag ctggacaagt ccacaaagct    900

ggtggaaact gccatccagt ccctggacga gcctggggga gccaccttcc tcttgactgc    960

caagcaactc atcaaaagca ttgtggaagc ttccaagggc tgccagctgg ggaagacaga   1020

gcagggcttt gagaacatgg acttctttac tttggattta gagcacatag cagacgccct   1080

gagagccatt gactttggga cagatgagga agaggaagaa ttcattgaag aagaagatca   1140

ggaagaggaa gagtccacag aagggaagga agaaggacac cagtaaggag ctggatgaat   1200

gagaggcccc cagatgcaga gagactggag agggtgggga ggggcccagc ggccttggtg   1260

acaggcccag ggtgggaggg gtcggggccc ctggaggggc aatggggagg tgatgtcttc   1320

tctctgctca gagagcaggg actagggtag gaccctcacc gctgcgtcca gcagacactg   1380

aaccagaatt ggaaacgtgc ttgaaacaat cacacaggac acttttctac attggtgcaa   1440

aatggaatat tttgtacatt tttaaaatgt gatttttgta tatacttgta tatgtatgcc   1500

aatttggtgc tttttgtaaa ggaacttttg tataataatg cctggtcatt gggtgacctg   1560

cgattgtcag aaagagggga aggaagccag gttgatacag ctgcccactt cctttcctga   1620

gcaggaggat ggggtagcac tcacagggac gatgtgctgt atttcagtgt ctatcccaga   1680

catacggggt ggtaactgag tttgtgttat atgttgtttt aataaatgca caatgctctc   1740

ttcctgttct tcaaagg                                                  1757
```

```
<210> SEQ ID NO 38
<211> LENGTH: 1956
<212> TYPE: DNA
<213> ORGANISM: Homo sapiens
<220> FEATURE:
<221> NAME/KEY: misc_feature
<223> OTHER INFORMATION: Incyte ID No: 247608.1CB1

<400> SEQUENCE: 38
```

```
ggctagtgca aggatcagat agcacctgct tggaagttca ctgattaatg atttaacaag     60

ggcggtcaca tgggacaact gctgcttttc tctgccctca tttttcttac taacaggtct    120

gaaaattgaa caagatggac gggtccagga aagaggagga ggaagacagc acattcacca    180

acatttctct tgcagatgac atagaccatt cctcaagaat tttgtatcca aggcccaaaa    240

gtttgttacc caagatgatg aatgctgaca tggatgcagt tgatgctgaa aatcaagtgg    300

aactggagga aaaaacaaga cttattaatc aagtgttgga actccaacac acacttgaag    360

atctctctgc aagagtagat gcagttaagg aagaaaatct gaagctaaaa tcagaaaacc    420

aagttcttgg acaatatata gaaaatctca tgtcagcttc tagtgttttt caaacaactg    480

acacaaaaag caaaagaaag taagggattg acacccttct gttttatgga attgctgctg    540

atcatttttt ctttaaaact tggacagatt ccaaaaagtt acagtacctt tgtggcttca    600

ttgaatattt atgaagataa tgtcagatgt agacaaaaat aacacaataa caggagactt    660

ccataagttt gtgtattatg ttagtctatg aaaacgtgca aatgtattgt agagacttta    720

tgattagaat tgcatatatt tatgaaactt aaagatgaat gttttattga atttgtaggt    780

ttagcactgt cttttattat aggattagta agatatacaa gaaaataacc accgtgttgt    840

gaaaaagtga ccaaaatcat gtactaaatg cacagcttta tgtaccctgt ccaccatctt    900

gtgcctcttc tccatttgcc tcttccttcc tatttccctt ccgctaagga aaaaaattgg    960

tgtcacattt gtaaaagtaa ttttaatagt taatccatct ctgagagtaa cctgtatttt   1020

aattgttgaa acttaaccaa aataagatac tgtctcagct aggggcttgt catttgtgta   1080
```

-continued

```
tttagtgtta agataggaat gctagtgtct ctttaattaa ttggaaatat atggaggcta   1140

aaaatgaagg tttttctttg aaactgaatt aacttgggaa tatttgttgt taaaaacttc   1200

tttttgccca aaataactca ttttgtatta tctgaaaata tataatttct ggtcatgtgt   1260

atgttaaaat agaaaatttt gaggaaaaat ggaaataggg tggaaaagta ctcggtaaac   1320

agtagtaacc aaatattttc actccagatt tgtgttttct ctggcacaga gtagatcttt   1380

tgggaaatat atatgaaagt ggattaagtt tgactaccct tatgttagcc acatctggat   1440

gagaacagtt acaaagagtt tggtctctaa gttgatttgt acccagtggg tcaacttctg   1500

caaaattccg taatggtgta ttagtattag aatagtgaat aaaatgggaa agttatacat   1560

gtatacttat tatcttgctc agtattttat ctcacttgtt ctagaatttt ctgtaaaccc   1620

tgctactggg tttgaagagt tttagtcatc ctttaacaat ttttaaaaat ttagcttcta   1680

gattccattt ggtaaggaaa tcaatattgg aagtattgct aaaatcttat aatatgaaaa   1740

gagatccact aatgtagctt aaggttatta gatttgggct tttaatcatg gaataatctt   1800

atgtattggt gtaagagttg atgaatgact ttagctgtgt gaatatataa tagtcaaact   1860

gcaaacattt tgcatccctt ttgtgaccta atttacagac atttaaattg tgttgcagtt   1920

ctgctttgcc gtttaataaa aagctatttc agaggt                             1956
```

<210> SEQ ID NO 39
<211> LENGTH: 3889
<212> TYPE: DNA
<213> ORGANISM: Homo sapiens
<220> FEATURE:
<221> NAME/KEY: misc_feature
<223> OTHER INFORMATION: Incyte ID No: 251277.1CB1

<400> SEQUENCE: 39

```
atgggggcag tgaatgtcgc caaagggacc gtccagacca gtgtggacac caccaagact     60

gtcctaactg gtaccaagga caccgtctgc agtggggtga ccggtgctgc gaatgtggcc    120

aagggggccg tccagggggg cctggacact acaaagtctg tcctgactgg cactaaagac    180

accgtatcca ctgggctcac aggggctgtg aacttggcca aagggactgt ccagaccggc    240

gtggacacca gcaagactgt cctgaccggt accaaggaca ccgtctgcag tggagtcact    300

ggtgccgtaa atgtggccaa aggcaccgtc cagacaggtg tggacacagc caagacggtg    360

ctgagtggcg ctaaggatgc agtgactact ggagtcacgg gggcagtgaa tgtggccaaa    420

ggaaccgtgc agaccggcgt ggacgcctcc aaggctgtgc ttatgggtac caaggacact    480

gtcttcagtg gggttaccgg tgccatgagc atggccaaag ggccgtcca ggggggcctg     540

gacaccacca agacagtgct gaccggaacc aaagacgcag tgtccgctgg gctcatgggg    600

tcagggaacg tggcgacagg ggccacccac actggcctca gcaccttcca gaactggtta    660

cctagtaccc ccgccacctc ctggggtgga ctcaccagtt ccaggaccac agacaatggt    720

ggggagcaga ctgccctgag cccccaagag gccccgttct ctggcatctc cacgcccccg    780

gatgtgctca gtgtaggccc ggagcctgcc tgggaagccg cagccactac caagggcctt    840

gcgactgacg tggcgacgtt cacccaaggg gccgccccag gcagggagga cacggggctt    900

ttgaccacca cacacggccc cgaagaagcc ccacgcttgg caatgctgca gaatgagttg    960

gaggggctgg gggacatctt ccaccccatg aatgcggagg agcaagctca gctggctgcc   1020

tcccagcccg ggccaaaggt gctgtcggcg gaacagggga gctacttcgt tcgtttaggt   1080

gacctgggtc ccagcttccg ccagcgggca tttgaacacg cggtgagcca cctgcagcac   1140
```

-continued

```
ggccagttcc aagccaggga cactctggcc cagctccagg actgcttcag gctgattgaa   1200
aaggcccagc aggctccaga agggcagcca cgttctggac cagggctcag gtgccagtgc   1260
ggaggacgct gctgtccagg aggagcggga tgccggggtt ctgtccaggg tctgcggcct   1320
tctccggcag ctgcacacgg cctacagtgg cctggtctcc agcctccagg gcctgcccgc   1380
cgagctccag cagccagtgg ggcgggcgcg gcacagcctc tgtgagctct atggcatcgt   1440
ggcctcagct ggctctgtag aggagctgcc cgcagagcgg ctggtgcaga gccgcgaggg   1500
tgtgcaccag gcttggcagg ggttagagca gctgctggag ggcctacagc acaatccccc   1560
gcttcagctg gctggtaggg cccttcgcct tgcccgctgg cgggcagtag ctgtaggagc   1620
ctgcaggccc ggcgcggggt cgccctgctc tgtccaggga ggagctgcct cagaactttc   1680
tccccgcccc caaacctgga tcggttccct aaagccctag acctttgggg ctgcagctgg   1740
ctgagcgccg aggggctgcg gaggcagtga ccttcttaac tgagccaccc cacgccctgc   1800
tccgggcctg cctgcatctc ccacctcctc cccagcgctg cctgcccctc tcggagcctg   1860
gggtcactca gaccaccagc caagagcctt cccttgaagt ccccaagcaa gcactgcaat   1920
taggaaagag aaaaagcagc gtgcccagcc tggaagggca tctgtttgcc ccgctagcaa   1980
ccctttata tctagcaggg gctcttccag tcctgcagca cgggccccca gctatcagcg   2040
gtgcaggcag tgctgtggca tcccaggctc cgggcagctc cgttctcatg ctgaaagtgg   2100
gtctccggcc ttagcacaca caccttgagg gtcttaagaa ccacattccc tcatagtaga   2160
aagtactaga aaaagcgaca ctgccatcat catcccaagg caggctgcta ctgcctttgc   2220
tgacccccgg ggtggcctca cggtggggac aaagctgcca ggagccacag cagccacagc   2280
tgggggcttt gcaccagcct ggcttgagac tgagcagttt gcaggggggtg gggggtgcaa   2340
aaaacaagca aacaggctgc tgctgcctcc agctgcccac cacaggcctg ccccaggcac   2400
ctggggctct gaggcccctg gggaggctgg ggcccagcag ctgcccctgg gaggaacaca   2460
gacaaaggac ttccccgcag ggaactgtgc cctatggagg gatcagacag ggctgggaac   2520
agccacagag gctgcgtgcc tatggcacag cccttcctcc gccgcacact ccccctgggt   2580
cctcaggccc acccaagcgc cgggctgcag aggaagcggg gctggggagg ctgcaggcat   2640
cagagacact ggtggtggcg gacccggccg ccgggccccg tgctctcagg ctagcccagg   2700
tcgtggaggc tggcaggctc aggtcgggtg tgagacgtgc cgtggctgcg ctcagtccag   2760
cggggaggag ccgttcagcc cggcctcccc aggaagccat atccccactc acccggtaag   2820
agaaccttgt acgtcccctt tccatgctct cctaggacac gagcccagga accccagacc   2880
cagggggagg aagggtggag gggccccagg ggtcaccatg tgcaccaggg gccgtgaggg   2940
gccggggcat tcagcttcag ctctgaaccg gggaagctgg cacggcaagg actgcctcag   3000
gtgacgggcc gtgagagggg acgggtcagg agccttccca agccttctcc tcagcccgac   3060
acccatggcc atcggaggct aggatgccag acacagccat ttgcagaaat caggcacagt   3120
gactgcagct cacgtccagc caaccaagca tggggccgca gcttcaggaa gtcccttccc   3180
gccacaccac agcctaattc ttactgggac ggaggcaact cgggctacgc tggggcagga   3240
cgacaaacac gagacgccac tgtggaatga gcaacttcgg agcacggggt gacttgcttg   3300
ggaccgtgcc cacgtgacag ccccttatgc agaggaggaa agagaagccc cgagtgggag   3360
gggaacctgt ccaaagtcac acggtgtgtg ggtgacacag ctggggtgag tcgaggctgg   3420
cccctgaggc ccatgctccc tgaacgctgg agaccactgt cggctagcag cggctctcag   3480
ggaaggcctg gtctccaccc tcccagccta gcctcgcgga ccctcgtcct ccccacatcg   3540
```

```
gacctgctca cctgcctgga ccctgggctg ccagatgcag gaagcatcaa accccccagc   3600

ctcgtgggtg cggggcaggg cgcaggcagc acagcttaga tgccctggtt tgtccctctt   3660

gtctcctggg aagagcttgc tcccgcccag ctctcctgcc actggccttt cagggttggg   3720

ctgggcccag agtgcctttt agtcgcttct cacggtggcc tgatggctca acccagtccc   3780

aaacgggccc agtgacactg ccgactgcac cccagctcag gcccccactg caccagcaat   3840

gctagaaaac caagccaata aaagtgattt ctttttcat taaaaaaaa               3889


<210> SEQ ID NO 40
<211> LENGTH: 1077
<212> TYPE: DNA
<213> ORGANISM: Homo sapiens
<220> FEATURE:
<221> NAME/KEY: misc_feature
<223> OTHER INFORMATION: Incyte ID No: 251482.3CB1
<221> NAME/KEY: unsure
<222> LOCATION: 798-799, 802, 805-806, 810, 1066, 1068-1069, 1074
<223> OTHER INFORMATION: a, t, c, g, or other

<400> SEQUENCE: 40

gcggccgccg cctgcgcccc cctggactcc ggcgcctccg agaacagccg caagccccct     60

tcggcgtcct cggccccggc cctggcgcga gagtgcgtgg tgtgcgccga gggcgaggtg    120

atggctgcgc tggtcccctg cggccacaac ctcttctgca tggactgcgc cgtccgcatc    180

tgcggcaaga gcgagcccga gtgtcccgcc tgccgcacgc cggccaccca ggccattcat    240

atcttttcct agagcgcggc cccgtatcct tcccaggcgg cgccgccttc tccacggcca    300

gtgtttacag atgagcttta actgccgcct caggcgtgga gacggagacc ccgcagcccg    360

gcggcgcctc agcccttcaa cgacagtatt gagtggtcag gttacaataa accggagaga    420

aaaggtccgc ttgcactttt tttagttttc ttatttttag acacccctcc cctccagggt    480

gatctttaaa aaagcaaaac aaaaaacacg acttttccag cgctcagcgt tttttccttt    540

cgtccgaagc cgttttctga tttgactttt ctcgccggcc ggtctcaggc cgcacagacg    600

ttccagagga ggagggtgac atttttactc cctttttggg gctaaccatt tatgcttttg    660

tacatcaacc gtgcgcggcc ggaggggggc aggggggcgg gggcgagggg cgttccaatc    720

aaatttctaa ctttctgtta attattaatc cccttttttac tgcggtttct gttgtcattt    780

ttaaaatttt tttaattnnt tnttnncgtn taacttttac tttttacctc ttgtgtatat    840

gtagggaatt tatagggaaa tatgtacttt atggaataaa ttttaagaac taaaatatat    900

tttattttaa ataaagtaat ggacctttaa tcttacacag ctaaattact gattatatat    960

ttgctgagct gatttaaggg ttaaaaaaat tgtatcaaga gttttatttt ttgacttcaa   1020

agccttctta ataaagcctc ttttctacat gtgagcaaaa aaaaananna aaanaaa      1077


<210> SEQ ID NO 41
<211> LENGTH: 2676
<212> TYPE: DNA
<213> ORGANISM: Homo sapiens
<220> FEATURE:
<221> NAME/KEY: misc_feature
<223> OTHER INFORMATION: Incyte ID No: 253428.1CB1

<400> SEQUENCE: 41

gttctttgat ctatacattt tcattgttta aagtgttcac aggtcaatgc ccatgttacc     60

caaatagcag taagaattat ttatgatgaa atctctcaga tatatctggc gcttagtgtc    120

aaggggtcca agtcatcttg ttgagctgag actctagtgt attttcatag attacaggcg    180
```

-continued

```
tgagccacca cacctggcct ttctgcaaca ttttttttaaa aaaatctaat aaatcttaga    240
tttttaaaaa agaattaaaa tgtgggagtt ctcagaaaga aataaacaca tgagaataag    300
attattacac attttggaag gacttttgag gaatgatgtg atgtgtagag aatagaaaga    360
tttagatata tgcctgtgac aggaatagat tctgggttca ggggtcccca tctgtacaaa    420
tgagaagatt ggattatcta atcttttaga tccttaacaa ctctgatatt ctgagattct    480
ctcatttgta gaatgcccgc tgatgcattg tttatttttt ttgctcataa tataaatatc    540
agattatgtt taggagtgga ttaggtaatt agtgtcacta catgtatcat taaaggtcct    600
aaaaggaatt gttaggcggc aggctttgtg ttacgtgtta catggagtga gggtagatgt    660
gaagatttaa aacgattgat ggatttaagg aagtggtaca taaatatgtc tgttattatg    720
caatcgtagg tcatgataat ttattcagtt atagaaaaca tgccacagaa gccgatgtaa    780
caagtggtgc ttctttagaa agttgtcatt agaatgttct gaggaagtta agcagctgct    840
tcatcaatcc catgacacat gccttgttag catgcccatc aaataatcag atcaaacacc    900
tgctccttat tgccataccc acgaactgtt aaatataaaa aaattcaaag tatttgacat    960
cttaagcaaa tatccagaat atttttaagt aaaaaaccat cttaagtatt caaaatttcc   1020
ttggtttttt aaaggtgata attttgcttt gtgttacttt tttgctcttg aatgtatcgt   1080
tatgatggtc tcttataatc atggtatctt tcacagaata aaaattaaaa ataatgccag   1140
ggtgcaagtg accaaggcct tatcttgaaa gttaaaaaaa aaaagtaaag aaatcacagt   1200
aagttctatt agtgatgata gaaccagata taaaattgtt cagtgatgga gaaaagaaac   1260
gataaatact ttccaaggtt atattgttaa attatcttaa attatcaagg tgtaagatgt   1320
aatgatccca agagttttta tagaatccta aaaaataacg cctgatgtat agattagtta   1380
gcaaattctc agaaatcccc cacataaaag ccttactttg ttcaaaattt attatagtgg   1440
tttaatcatt ttagatttga atgttttaag ataggagaga cttagcagaa aatacttggc   1500
ttgccagggc cacgttctac ttcattgctt tcttttataa gtgcaaggag ttatttccat   1560
cagttgacat agatattatt cactaaaatt ttcagcagac tcaaaataga gaggagactt   1620
taaacttaca tgttagcata aaacagactt ctctctcatt gcatgcacta gatcaatatt   1680
atcatctgta ttaagctatc tgaatttatt cgagacatta agaaaaagac agtacatggt   1740
gggaaagctg cacatttctc acaaggaaaa aaacattcta tatttgtagc agaaatcagt   1800
ggtttgaaaa gtcatacttt gcagatatga acctgaaaat caaagtgcca ttgttaaatc   1860
atcctaaagt gtactgtggg tattctccag catacttgaa aatgaataaa gttagattgc   1920
tcacattgaa gctaatggtt gagacaagac acctgccaga gtgaagtttg attcctatgg   1980
gtgagaagat gtagatgact attgttctca ctaaagttct aaaataatag caagtgtaga   2040
gaagagccgt tgctttgaaa atacatacca catttgttat aaagcatttg tttgttagta   2100
tcaatcacat aggtagaaag agtttgagtt ttactgtgga ttaaaaagcc ttccctaaaa   2160
agagagcatg ccagtcatag agacactaat ttggcacttt tcctccttct taggtttaaa   2220
tgttatacca atgcatgtgt ttgaaatatc cattaagatg atttaaaatt tgtcttgtat   2280
tttgagtttc ttaaatgcgt ggattcttgt tcatttatct ctgaatatgt ctcttttata   2340
ttttggcaca attatacaca ttggaaaggg ccaacctatt agggctcaag tatgtatatg   2400
caaaaaaaaa aagttatatc aaacaggcac agttattaca actagagaga aattccagaa   2460
atatttgttt ttttaagaga aagtaaattt tcacattaga tttctattca aagtactaat   2520
```

-continued

```
atctacatgg tccacacttt tctattttaa aaaattgtgt tctcttgtta aatagattaa   2580

catttccact tctgtttatc acaaaagact gtatttgaaa tatgcatacg gaaaattgaa   2640

attatattag taataaatgt aacttgaaaa atcaaa                             2676


<210> SEQ ID NO 42
<211> LENGTH: 924
<212> TYPE: DNA
<213> ORGANISM: Homo sapiens
<220> FEATURE:
<221> NAME/KEY: misc_feature
<223> OTHER INFORMATION: Incyte ID No: 255839.3CB1

<400> SEQUENCE: 42

cacccttttt gaagtagtct gggcaatgca caaagcagtc catggtggcc ccccagtccc     60

ccaggcttac taccccctt gttgcagagc ccaaagtcca gctcctcatt cccccatcca    120

ctcttctaac tggggaccca ggactcctgc actgccctgt tcttaccccc tatatcccaa    180

tcacctgtac tgttagcttt caggttctta ttggttcctc cactaaggac gggccatgag    240

ggcagggacc ttatctgccc ttcagggcgg aattcccagt accaggcacg cagtaggtgt    300

tccataaatg tttgctgaat gactaaaagc ccaccccaa ggaacaaaga aaaatctctc    360

ctttcacaca cttcccaggg cctgctcagt gccttgctct ggaaacagag cttggtgagc    420

ttcctgggga gggtctctgc ctagggcacc ttcagctcag gtggtgggtg agccgggctg    480

ggggtgggag cccccgccct caccactgct cctgccccca cccccgcggc tccgtctgtg    540

tgcagtgctg atcctggtcg gcgtgggact ggaggcgacc ccctctccag gtgtctccag    600

cgccatcttc ttcgtgccgg gcttcctgtt gttggtgcct ggagtctatc acgtgatctt    660

catctactgc gcggtcaagg gccaccgggg cttccagttc ttctacctgc cctacttcga    720

gaagtgatcg cggcgcagcg tggacccctt gcgcccatgg gggcgcccct cttgccctgt    780

tccgttcccc tcatctcaag ggaagaggcc ctccaggacc ctcgaaaccc cagcccctag    840

ggagtttgct caggaagttc ggggcatgca ggcctggccc tgggaaagcc gcccgtcgcc    900

tgctctgtgc cttaacttat tctc                                           924


<210> SEQ ID NO 43
<211> LENGTH: 3280
<212> TYPE: DNA
<213> ORGANISM: Homo sapiens
<220> FEATURE:
<221> NAME/KEY: misc_feature
<223> OTHER INFORMATION: Incyte ID No: 255840.10CB1
<221> NAME/KEY: unsure
<222> LOCATION: 89, 110, 127, 612
<223> OTHER INFORMATION: a, t, c, g, or other

<400> SEQUENCE: 43

agggtcgtca ttggacaacc gccgcgggcg ccctggtctc tgctacctgt agctgagggt     60

gctgttgatg ggcagcgcgg cgcgctggng aaggctcgtt ctcgcgagan ttcagctccc    120

ttcttanccg tggctgcctc agcacctcga ggatcgacat ggacgctctc gaggactacg    180

tttgggccgc gggcaacctc ggagcttata ctcctcccag tgacgggtct ggagtgcgtg    240

ggggaccggc tgttggcggg tgagggtccc gatgtcctgg tgtacagctt ggactttggt    300

gggcatctgc ggatgataaa gcgagtgcag aacctgcttg gccactatct tatccatggc    360

ttccgggtac ggccagagcc taatggagac cttgacttgg aggccatggt ggctgtgttt    420

ggaagcaagg gactccgagt tgtgaaaatt agctggggac agggccactt ctgggagctt    480
```

-continued

```
tggcgctctg gcctgtggaa catgtctgac tggatttggg atgcacgctg gcttgaggga    540
aatatagcct tggccctggg ccacaactca gtggtgctat atgaccctgt agtagggtgc    600
atcctgcaag angtgccctg cacagacagg tgcaccctct cttcagcctg cctgattgga    660
gacgcctgga aggagctgac catagtggca ggtgctgttt ccaaccagct cttggtctgg    720
tacccagcaa ctgccttagc agacaacaaa cctgtagcac ctgaccgacg aatcagtggg    780
catgtgggca tcatcttcag catgtcatac ctggaaagca agggattgct ggctacagct    840
ttcagaagac cgaagcgttc gtatctggaa ggtgggcgac ctgcgagtgc ctgggggtcg    900
ggtgcagaat attgggcact gctttgggca cagcgcccgt gtgtggcagg tcaagcttct    960
agagaattac cttatcagtg caggagagga ttgtgtctgc ttggtgtgga gccatgaagg   1020
tgagatcctc caggcctttc ggggacacca gggacgtggg atccgggcca tagctgccca   1080
tgagaggcag gcctgggtga tcactggggg tgatgactca ggcattcggc tgtggcactt   1140
ggtagggcgt gggtaccggg gattggggt ctcggctctc tgcttcaagt cccgtagtag   1200
gccaggtaca ctcaaggctg tgactctggc tggctcttgg cgactgctgg cagtgactga   1260
tacaggggcc ctgtatctct atgacgtcga ggtcaagtgc tgggagcagc tgctagagga   1320
taaacatttc cagtcctact gcctgctgga ggcagctcct ggtcccgagg gcttcggatt   1380
gtgtgctatg gccaatgggg aaggtcgtgt caaggttgtt ccccatgcaa cacttccaac   1440
tgctgctgtg gaccagaccc tgtttcctgg gaaggtgcac agcttgagct gggccctgcg   1500
tggttatgag gagctcctgt tgctggcatc gggccctggc ggggtagtag cttgcctaga   1560
gatctcagcc gcaccctctg gcaaggccat ctttgtcaag gaacgttgtc ggtacctgct   1620
gcccccaagc aagcagagat ggcacacatg cagtgccttc ctacccccag gtgacttcct   1680
ggtgtgtggt gaccgccggg gctctgtgct gctattcccc tccagaccag gtctgctcaa   1740
ggaccctggg gtgggaggca aggctcgggc tggtgctggg gcacctgtag tgggtagtgg   1800
tagtagtggg ggtgggaatg ctttcactgg gttgggccca gtgtctaccc tgccctctct   1860
gcacgggaag cagggtgtga cctcagtcac atgccatggt ggctatgtgt ataccacagg   1920
gcgtgatgga gcctactacc agctgtttgt acgagacggc cagctccagc cagtcctaag   1980
gcagaagtcc tgtcgaggca tgaactggct agctgggctc cgtatagtgc ccgatgggag   2040
catggttatc ctgggtttcc atgccaatga gtttgtggtg tggaaccctc ggtcacacga   2100
gaagctgcac atcgtcaact gtggtggagg gcaccgttcg tgggcattct ctgatactga   2160
ggcggccatg gcctttgctt acctcaagga tggggatgtc atgctgtaca gggctctggg   2220
tggctgcacc cggccacacg tgattctccg ggagggtctg catggccgtg agatcacttg   2280
tgtaaagcgt gtgggcacca ttaccctggg gcctgaatat ggagtgccca gcttcatgca   2340
gcctgatgac ctggagcctg gcagtgaggg gcccgacttg actgacattg tgatcacatg   2400
tagtgaggac actactgtct gtgtcctagc actccctaca accacaggct cagcccacgc   2460
actcacagct gtttgtaacc atatctccct cggtacgtgc tgtggctgtg tgggggcatt   2520
ggcaccccag gtggccctca ggatcctcag ccaggcctga ctgcccatgt ggtgtctgcg   2580
ggggggcggg ctgagatgca ctgcttcagc atcatggtta ctccggaccc cagcacccca   2640
aagccgcctc gcctgccatg tcatgcacct ttcgtcccac cggctagatg agtattggga   2700
ccggcaacgc aattcggcat cggatggtta aggtagaccc agagaccagg taatatatgc   2760
tcctgggcag ggtgtggtat gggtcatgca gatgctccca ggcttgcagg ctccacctga   2820
cagctgcatg ttgtctctgc aggtacatgt cccttgctgt gtgtgaactt gaccagcccg   2880
```

-continued

```
gccttggccc ccttgtggct gcagcctgta gtgatggggc cgtaaggtga gagcataggg   2940

cccagtggga caggagacaa aggaagtaag gttgtctagg atgcgttctg agctgggcca   3000

ccccccgccc cccaggctct ttcttttgca ggattctggg cggattctgc agctccttgc   3060

tgaaaccttc caccataagc gatgtgtcct caaggtccac tcctttacac acgaggcacc   3120

caaccagagg cggtgagagg ggctggatga tggtcctgca tgggctgggt tggggggttc   3180

ctgttgagct tcatctctgt tattgaccag gctgtctttt cctggctctc aggaggtcct   3240

cctgtgcagc gcactaactg atggcagctg gcttctggga                         3280
```

<210> SEQ ID NO 44
<211> LENGTH: 2821
<212> TYPE: DNA
<213> ORGANISM: Homo sapiens
<220> FEATURE:
<221> NAME/KEY: misc_feature
<223> OTHER INFORMATION: Incyte ID No: 331395.1CB1

<400> SEQUENCE: 44

```
ctcttttcca ggcacattgt aaactgtgtc tacagtttat ccatataact tctcttctga     60

aaactgagga gtgtcctctg ttcttccagt tcacgagggc aggggggttta aaacaagaat    120

gataggccag gaaggcagtg gggatccacc atcacatgga actgtaaggc catataacta    180

cacaaaactg accaatctgg gttgccaaag cagccaggct tatgctgaaa ccggggaagt    240

ctgacatatg caggaaactc ttttgaaata actttggtgc ccaggccaag tagaatgaga    300

tgagactgag tttggcctct ggctcggttt cctttctttg gtctgatact tcatgtattt    360

gaatatagtt aaatcgtatt atttttttct taacagaaat atttttaaaa atgaaaaagt    420

actcaaaagt gagaagagtt aacttgtcaa agcagaatgg ttctctttga cccactctgg    480

tctattgtgt aaatatttat ttagactatt ttaataatac atattattta ccccactgta    540

acatcatgta aactaagtat gtttttaaac aatttttaag acttgtaatt accctgaaaa    600

taaggtttat aatgcaaaga ccagctcctt tgcggtggca gtgctctagg gctgccatta    660

cacggtcttg tgatgtgact aaaagccact ttgtgactcc cttcatgtaa tcctcttttc    720

ctccccactc ctccacagag ggcagagctc aggacatttg ccagttccag atctcttttt    780

cagcattttg atggaattaa tttacacgta atgagggaag tcctaggatg gatagaaaaa    840

aagcacttac attggggcac acaggaaatc ccagtgtcta gcaatggttt ggtttgcaga    900

gaacacagcc tgatacttaa ttttcttaaa actattttta atgatccact aaacaaagca    960

ggggatcctg aagctgatat aaataagtct agctctataa tccccaagtt ctaaaagtta   1020

tggttagatg ctattctgtg ggttgctttg ataattctta ctaacacaga ttagggtata   1080

ggcatctaga gatgcactgt ccactgtaaa tactataatg agagccacat ctgtaattta   1140

aatgtttcta gtaaccacat ttttttaaaa gtaaaaagaa cccaggtatt gatttaaata   1200

tatttattta acccaatagg ctcaaaaaca ctatcatttc aacataggat caatataaaa   1260

attattaatg agttatttta cttttttca tattaggcct ttgaaattca gtgtgtatta   1320

aacacatctc aattcaaacc atcaccatat ttcaagtctt tgtagccaaa tgtgactagt   1380

ggctaccata ttagacagtg cagatctata ctcattcctt caaatacatt actctgttaa   1440

tctcaaagtg tggccaactc ccatttactt agaggctgat tatctagttt tgtagttcct   1500

caggcctcta atttattttt tgctttctgc tttattgatc ttttgcatgt cccccaaagc   1560

cagaatctgc tcatggagga aggaaggcta agaactgtcc ttgaggaact tcatcagtaa   1620
```

ctctggtaaa gcatcctgtg gagggagagg agagcccagt catttgctta gatggtgttt 1680
gtgggatcac ctggcagatt taaagcctac tctgccacag actcgagtaa gaaaatgttc 1740
tcttgatgac acagtgctcc tactctatcc acattaagta ggcacttttg tggtagaact 1800
gattcttaag gcaggcctga aaggccattt actaatagaa acacagcctt tccaatcctc 1860
tggaacatat tctgtctggg tttttaatgt ctgtggaaaa aaactaaaca agtctctgtc 1920
tcagttaaga gaaatctatt ggtctgaagg tttctgaacc tctttctggt tctcagcaga 1980
agtaactgaa gtagatcagg aaggggctgc ctcaggaaaa ttcctagatc ctaggaattc 2040
agtgagaccc tgggaaggac cagcatgcta atcagtgtca gtgaatccac agtctttact 2100
tcctgcctca taaagggcca ggtctcccca gtaccaagtc ctttcctcat gaagttgtgt 2160
tgcctcaggc tgtttaggga ccattgcctg tcttggtcac atgagtctgt ctccttactt 2220
tagtccctgg gcaatccttg cttaatgctt ttgttgactc aacgagggcc cgaggcctta 2280
ggttttctat taaggtctct gccccaggca tggtgctcta tatcttggcc aaataaatta 2340
ctttccttga atatccagga atcttttagt ctaaagcaat gaggagttat cacctcatcc 2400
tcaaactcca acaagatcta tgccttagtg ttgtttttgt tgtctgcttt gatgtaaaag 2460
caagagtatt tggagcaaga agctgcaatg cgccaaatac acaataggcc ttttctttat 2520
cattcatacg acatttctgg tttaggtgta tgtagttggg ccatgttact tgtccagagg 2580
aagagactaa agatataaga ataatttttt agtcctaaat gctgttttgt ttactttctg 2640
tcaagatatt tacccgtgtc aaattcaaac tacagtactg tgtaattatg tataaagttt 2700
ttttatttat ttgaagttag actagatata cgtttttaaa tttaacatct ggctggacag 2760
tgttctatta actcattgaa tgtgtttcct ttgtcttgtg ttaataaata ttgatgcctg 2820
a 2821

<210> SEQ ID NO 45
<211> LENGTH: 2367
<212> TYPE: DNA
<213> ORGANISM: Homo sapiens
<220> FEATURE:
<221> NAME/KEY: misc_feature
<223> OTHER INFORMATION: Incyte ID No: 331497.1CB1
<221> NAME/KEY: unsure
<222> LOCATION: 1868, 1871
<223> OTHER INFORMATION: a, t, c, g, or other

<400> SEQUENCE: 45
agcgcttcag ttgtcactgc agagccatcg tatgtcagtt gcaatttcca tctgaagcta 60
tgtctttgac ttcactttaa gcagaaaatt ttgtaccctg gtggtcgagt cttcccttaa 120
aaattgttaa atcatttggc tttaatggtt caataatttg gggtggcttc atggtgtttc 180
ttttcttccc agtttaaaaa aaaaactttt taagcgtaaa atctttaagg ggtacacatt 240
tataagtctg gctaatttct aatatgctaa ttaaacattt cccattttaa ggttatatac 300
agtgaggctc ttcaggacaa ttattttctg ggttgattgg gcatatgttt gccgtgtaaa 360
catggatatg ataaagtgtc agtaacaatg gaaaaggtcc cagaggcatt aggcatctaa 420
gaggatgccc tcagaaacgt attctggctt gatttgtgtt attaacttca gaagaacctt 480
ttcaaatgtc ccagtatcgt tcttagtgct ttgggaaaaa atatttaaca cactgttaat 540
aaatttgtta tcagaagttt acaagacgaa gggcttctct cgtctgaatt tctagattta 600
agtcatgaag tgtaaaactg tttcacccag aagtgtaact aagcagaact aggagttttc 660

-continued

```
tctggcttca ccttttttcag agccagcagt gctgttttct caagcacagc gtttgctctt    720

agactctgat ctgcttgtgc ctaagcattg cacaggtttc cgaagacggg cagcttcaga    780

gaagaggatt attcgggaga ttgctggtgt ggcccataga ctctttggca tagactcttt    840

cgcaggcagc cactctgagt gtggccagtt ctataaccat ccccaaacta gctggagcct    900

gatggatagg aacgggtagt ctgtcctctt ccccataaaa atgttccaaa aagttatctc    960

cagagagagt cccttatgaa gacagttgcc aagctgtatt ctcattcttt aaaccaatac   1020

ccaggtcagg gctagttcac actagcactg ttagggacat ggtgtggcta gaaatgaatt   1080

gagtgtgact tctccctaca accccaggcc cagggatagg aggaggcaga ggggtgcctg   1140

gagtttctgc actctcatca gtgatgttca tgttacactt gcacaagggc tgatttccac   1200

gtatgtgtgt gttaatttat tcacttagtt tcaaaagatt ttctctcccc agccattcag   1260

aggtttccaa actaagccac tgagtttgag tcagggaatt ccacgtaaaa agatcagatt   1320

aaggtaaatt ctttgttctg tattgctgct gtgacttcag aaaaaaaaaa ttatgagagc   1380

tcttcctgga attttgaaat ttctatttaa tgaagaagtg tataattcca ttatttattg   1440

tttgaggttt gatttatctg gaagcttaaa aagaatgttt tatttttgtt gttaataaaa   1500

tcccaatcac atttcacaat aactaaaatg tctccaggtg ggttactggt agatgatagt   1560

ggtgacacct gcaggtctgc atttgaattg gattcacaga gaagcattcc atggtcacat   1620

aatgaatagg gagaacagat attttcagaa aaatcaaccg attgtttttt ccagaaacag   1680

aacagaaaat gttcagaata ttttcaaatt tgtcagattc ttttatgttt cctttgaaat   1740

ttattattta agcctattac taaaccttta taaaaatata tttggcaaat acaccaaaga   1800

aaccagctta caaaagatta tgatcattaa tgaactgcaa acctcatctt tcgaaaacaa   1860

ggttttgngt ntttttattt tttgtaaata tttgtgttta taaatgtaca gcagagtaag   1920

agtgtttttt agattattta attcccatat ttctaaacta tttactacac agtaatccat   1980

gcctgttagt ttggaggact tgactgtctc attttttaat tcattgtcag tcatgcttgg   2040

aacagcattt ccactagaga atccagcgtt ctggcagtag caagagtaca catctggagc   2100

atgagggact ctagcatgac tcgtcagatg cacaccccaa gagacaagaa tgtgtagttt   2160

aatgaccggc gtggaccata cgaaattgag attctaactt tcctgcagga gtgctcatga   2220

gcccagaatg tgattgggat aaggccattt gcccacaaat ttagctttca tgtaactcct   2280

agtgtgttat atcataatgt attttgttct tccttttttaa tgtaagtttt gctttgggtc   2340

aatttgaatt aaaaaaatca aatctga                                       2367
```

<210> SEQ ID NO 46
<211> LENGTH: 1769
<212> TYPE: DNA
<213> ORGANISM: Homo sapiens
<220> FEATURE:
<221> NAME/KEY: misc_feature
<223> OTHER INFORMATION: Incyte ID No: 332683.1CB1
<221> NAME/KEY: unsure
<222> LOCATION: 411-478
<223> OTHER INFORMATION: a, t, c, g, or other

<400> SEQUENCE: 46

```
ggagagaggc agtacctgcc gtcagggatg gagcacagca tgcacatgat tagcccttca     60

cccaataacc aacaggcaac caacacttgt gatggccggc agtatggggc agttccaggc    120

tcctcctccc agatgtccgt gcacatggtt taaaggccag tccaaacacc acggagcatt    180

tggcaatcaa ggccccagag tctccgtggt cagatcctcc tctttgggag tcacccaaga    240
```

-continued

```
acaagagata cctttaagcc agtgaaggat acttgcgata gaatcatccg caactcagtg    300
gccattcttc tgccttccca gaccttattg tctgttccag agtggccttt gaagagactg    360
aataatcact tcgtcataat gttaagggag atgctagtgt gtggcagcca nnnnnnnnnn    420
nnnnnnnnnn nnnnnnnnnn nnnnnnnnnn nnnnnnnnnn nnnnnnnnnn nnnnnnnnta    480
ttcatacaca attcatacac atgcaatcat acatgcacac tgactctgaa ctgggtgaac    540
tctgtggagg gaggcccaga atgggtgctt tcaccaagaa tttgtctgtg tacaactcta    600
gatggagtgg gccagcagta gctgccagtc tttctcccct gcagcttcct ctgcttctgg    660
aatgaaccat gtatcctgga gaccctccca atggatgaga gtggaaagac atcagtacaa    720
ctggacttgg cttccggaaa aagattgctt ttgaactttg gctctcttca cttgtatgct    780
atcattgata ttcccagtgg tgcccgtgga aagagggaga aagagaagct gaacaggaga    840
aagacaaaca gaaagaatag agaacaggaa cgaggtggag agcaagactg acagagaaag    900
tgtgagcaat gatgagaatt ttaattcacc aaggagacgt gtttttggtt tgtcccccca    960
aaccccgccc gccccactac aggttatgga aagaatcatg gcattactga ggagtaaacc   1020
tctctggcac actgagcatg gtcagggcat tggtcagagg gacagagcaa ggaatgcatc   1080
ctgagcccac agctttgacc actgtgatcc agaagagagg tgcactacgt gggaagtgct   1140
gattccacag catgcagcct ggtaggggaa ggaaaataaa agggtgtgaa gaaggaatag   1200
ttttataatc tcggaagatg ataccaagag cagaggcaac aaatagaggc ctggcctcca   1260
ggtgccggat ccagacacct gacctagaat gcctgcccgc tatccctgtg gcaggaaata   1320
tcccctcatg tcccagggaa ttgcagatgg gtcttctata cccttctacc tgcccttaga   1380
tctccatttt tatcaaatag tacattgcat tttgaagttt tgggttttgt ccttcatctt   1440
tccctttccc ttcaaatctt ttaatggtaa gaaagcaagt gaagcttggt gcaagctaaa   1500
atttttaaat ggtgtggaaa tgcaaataat accaagtaaa ataatacaga tattattaaa   1560
gtttctggtt ttgaggtgtt gtagataaat gtatttatgt gcctagtggg gaatccaata   1620
ttatgaatat gaaaaagggg gcaataaaag ggtatgtaaa atatgtatga agaaaaggtg   1680
tacaaaaatt tgcccttatg cacggaactc tgtttctaag tgccaagcac agaaagccgc   1740
taaataaaat ctttgcaatt gttttctgc                                     1769
```

<210> SEQ ID NO 47
<211> LENGTH: 1423
<212> TYPE: DNA
<213> ORGANISM: Homo sapiens
<220> FEATURE:
<221> NAME/KEY: misc_feature
<223> OTHER INFORMATION: Incyte ID No: 337015.1CB1

<400> SEQUENCE: 47

```
cgaactcagg gtggcagccc ggagccgggg aatgtgaaga gctctcggct gtgcagtggt     60
accgtcgggg cctgggccgc gaaggatctt ctgccacagc tgcaacatgg gcggcaagaa    120
caagaaacac aaggctccag ggagccccgt gtcaagcaag gtccaaaaat ttatagtttt    180
aattctacaa atgattctag tggtcctgca aatctggata aatctatttt gaaagtggta    240
acttaataac aaactagagc aaagaattat tggagtgatc aatgagcata aaaagcaaaa    300
taatgacaaa ggaatgattt ctggaagact tactgccaaa aaattgcagg atttatacat    360
ggctttacaa gcattttcat ttaagacaaa ggacattgaa gatgccatga ccaatacact    420
cttatatgga ggtgaccttc attctgcctt ggattggctc tgtttaaacc tttcagatga    480
```

-continued

```
tgcacttcct gaaggattca gtcaggaatt tgaagagcag caacctaaaa gtaggcctaa    540

atttcagtct cctcaaatac aagccactat ttcacctcca ttgcaaccta aaacaaaaac    600

atatgaagag gaccctaaga gtaagccaaa aaaggaagaa aaaaatatgg aagtaaatat    660

gaaagagtgg attttacgat atgctgaaca acaaaatgaa gaagaaaaga atgagaattc    720

taaaagttta gaagaggagg aaaaatttga ccctaatgaa aggtacttac atcttgcagc    780

aaaactgctg gatgcaaaag aacaagcagc tacctttaaa ctagaaaaaa acaagcaagg    840

ccaaaaagag gctcaggaaa aaataaggaa atttcaaaga gaaatggaaa ctttagaaga    900

ccatccagta tttaacccag ccatgaagat ttcacatcaa caaaatgaaa ggaaaaagcc    960

tcctgtagcc acagaaggag aaagtgcatt gaattttaat ttatttgaaa aatctgcagc   1020

tgctactgaa gaagagaaag ataaaaagaa agaacctcat gatgtaagaa attttgacta   1080

tactgctcga agttggactg gaaaatctcc caaacaattt ctgattgatt gggtcaggaa   1140

gaatcttccc aagagtccaa atccttcctt tgaaaaagtt ccagtaggta gatactggaa   1200

atgtagggtt agggtaatca agtctgaaga tgatgtcctg gtagtatgcc ctacaatctt   1260

aacagaagat ggcatgcaag ctcagcacct gggagctact ttagccctta ccgtttagtt   1320

aaagggcagg taagactttt taggcctaac tatatctgta tgtggaaggc agtatttaat   1380

tatggttcaa ttttctcttt attgaactgt ttcttctgat aat                     1423
```

```
<210> SEQ ID NO 48
<211> LENGTH: 1651
<212> TYPE: DNA
<213> ORGANISM: Homo sapiens
<220> FEATURE:
<221> NAME/KEY: misc_feature
<223> OTHER INFORMATION: Incyte ID No: 337950.5CB1
<221> NAME/KEY: unsure
<222> LOCATION: 1531, 1570, 1647
<223> OTHER INFORMATION: a, t, c, g, or other

<400> SEQUENCE: 48

agctgctgtc cttccaccac cagcaccgga ccacctgctc caagaccagc ctcctggggg     60

gaccaggcac ccggccttca ctggcaccca gggagccgtc ctcagcagcg tcaacatgtc    120

aaggcccagc agcagagcca tttacttgca ccggaaggag tactcccaga acctcacctc    180

agagcccacc ctcctgcagc acagggtgga gcacttgatg acatgcaagc aggggagtca    240

gagagtccag ggcccgagg atgccttgca gaagctgttc gagatggatg cacagggccg    300

ggtgtggagc caagacttga tcctgcaggt cagggacggc tggctgcagc tgctggacat    360

tgagaccaag gaggagctgg actcttaccg cctagacagc atccaggcca tgaatgtggc    420

gctcaacaca tgttcctaca actccatcct gtccatcacc gtgcaggagc cgggcctgcc    480

aggcactagc actctgctct tccagtgcca ggaagtgggg gcagagcgac tgaagaccag    540

cctgcagaag gctctggagg aagagctgga gcaaagacct cgacttggag gccttcagcc    600

aggccaggac agatggaggg ggcctgctat ggaaaggccg ctccctatgg agcaggcacg    660

ctatctggag ccggggatcc ctccagaaca gccccaccag aggaccctag agcacagcct    720

cccaccatcc ccaaggcccc tgccacgcca caccagtgcc cgagaaccaa gtgcctttac    780

tctgcctcct ccaaggcggt cctcttcccc cgaggaccca gagagggacg aggaagtgct    840

gaaccatgtc ctaagggaca ttgagctgtt catgggaaag ctggagaagg cccaggcaaa    900

gaccagcagg aagaagaaat ttgggaaaaa aaacaaggac cagggaggtc tcacccaggc    960
```

-continued

```
acagtacatt gactgcttcc agaagatcaa gcacagcttc aacctcctgg gaaggctggc   1020

cacctggctg aaggagacaa gtgcccctga gctcgtacac atcctcttca agtccctgaa   1080

cttcatcctg gccaggtgcc ctgaggctgg cctagcagcc caagtgatct caccccctcct   1140

cacccctaaa gctatcaacc tgctacagtc ctgtctaagc tcacctgaga gtaacctttg   1200

gatgggggttg ggcccagcct ggaccactag ccgggccgac tggacaggcg atgagcccct   1260

gccctaccaa cccacattct cggatgactg gcaacttcca gagccctcca gccaagcacc   1320

cttaggatac caggaccctg tttcccttcg gccctccagc cccaaacctg cccagccagc   1380

cctgaaaatg caagtcttgt acgagtttga agctaggaac ccacgggaac tgactgtggt   1440

ccagggagag aagctggagg ttctggacca cagcaagcgg tggtggctgg tgaagaatga   1500

ggcgggacgg agcggctaca ttccaagcaa natcctggag ccctaaaagc cggggacccc   1560

tgggacccan ggccagtcac ctcttgggtt caatgcttcg cttagctcga ggcctgaaga   1620

ggtcacagac tggctgaagc agagaantct t                                  1651
```

<210> SEQ ID NO 49
<211> LENGTH: 1413
<212> TYPE: DNA
<213> ORGANISM: Homo sapiens
<220> FEATURE:
<221> NAME/KEY: misc_feature
<223> OTHER INFORMATION: Incyte ID No: 340819.6CB1
<221> NAME/KEY: unsure
<222> LOCATION: 9
<223> OTHER INFORMATION: a, t, c, g, or other

<400> SEQUENCE: 49

```
gagagagana gagagaaaga ggtttttaaa ttctccatga agtgtactat gttccatcat     60

tccttcccaa agccaccgga agcattcctt ctaggaaagg tggagtcggt agtgagaagc    120

cggaggtgag aagacccctg agcggatgga ttcattcatt ttctgaattt cctatgtgag    180

gacagtatta gagcccagtg aggctttgag aggccccaaa gatgagcgcc aacagtagca    240

gagtgggcca gcttctcttg cagggttcag cgtgcattag gtggaagcag gatgtggaag    300

gggctatcta ccacctagcc aactgcctct tactcctggg cttcatgggg ggcagtgggg    360

tgtatggatg cttctatctt tttggcttcc tgagtgcagg ttacctgtgc tgcgtgctgt    420

ggggctggtt cagtgcctgt ggcctggaca ttgttctttg gagcttcctg ctggctgtgg    480

tctgcctgct ccagctggca cacctggtat accgtctgcg tgaggacacc ctccctgagg    540

agtttgacct cctctacaag acgctgtgcc tgccccttgc aggtgcccct acagacatac    600

aaggagattg ttcactgctg tgaggagcag gtcttaactc tggccactga acagacctat    660

gctgtggagg gtgagacacc catcaaccgc ctgtccctgc tgctctctgg ccgggttcgt    720

gtgagccagg atgggcagtt tctgcactac atctttccat accagttcat ggactctcct    780

gagtgggaat cactacagcc ttctgaggag gggtgttcc aggtcactct gactgctgag     840

acctcatgta gctacatttc ctggccccgg aaaagtctcc atcttcttct gaccaaagag    900

cgatacatct cctgcctctt ctcggctctg ctgggatatg acatctcgga gaagctctac    960

actctcaatg acaagctctt tgctaagttt gggctgcgct ttgacatccg ccttcccagc   1020

ctctaccatg tcctgggtcc cactgctgca gatgctggac cagagtccga gaagggtgat   1080

gaggaagtct gtgagccagc tgtgtcccct cctcaggcca cacccacctc tctccagcaa   1140

acaccccctt gttctacccc tccagctacc accaactttc ctgcacctcc tacccgggcc   1200

aggttgtcca ggccagacag tggcatactg gcttctagaa ttcctctcca gagctactct   1260
```

```
caagttatat ccaggggaca ggcccctttg gctccaaccc acacgcctga actttaagga   1320

tcattggact atcttctctg tggccagcgc agctctcttc tgtgttcaca gaatggccac   1380

tgataggcac gcctcttttc ccacccactg gaa                                1413


<210> SEQ ID NO 50
<211> LENGTH: 1320
<212> TYPE: DNA
<213> ORGANISM: Homo sapiens
<220> FEATURE:
<221> NAME/KEY: misc_feature
<223> OTHER INFORMATION: Incyte ID No: 348160.1CB1
<221> NAME/KEY: unsure
<222> LOCATION: 11, 50, 181
<223> OTHER INFORMATION: a, t, c, g, or other

<400> SEQUENCE: 50

atttactatt nattaaatgg aagtgggtca acataaaagt cttcattctn attgtcttca     60

cattgagtag gcagaggagg agaaagatgg ggaggaagag aaggcgttgg tcttgcagtc    120

ttgtcttagg ggtgtgggga gtgggggaaa gaatattcat gtataagtgg gaccccttgc    180

nattccaagc ccttgttgtt caagggtcaa ctgtaatagg atatagctat ttttcttcct    240

ctatcaacca aatggtaagc atctattttg tagtccactc tactgagcta aattatagat    300

ccagctatgc tatttataat tattttcttg atgaataaat tttcaatttc tcctctgacc    360

atttcagaac atcttccaat aactcataaa acaactgaag taaaattgag tgctggaaaa    420

tatattcacc aaactttggt aatttaagtt gactaaagtt taaaattaag tctaaaatag    480

tttacaccta tactgcataa tccaacaatt ttaatttcag ttgaagacat gttactaata    540

taactattat taaaagagta gaggatgtgt aattaaccat atcttctaaa acatggttac    600

taaaagaata tgtaacatca atattgacct tggtttctta cacaagtgtt gctaactcaa    660

tagtgaagga gacactatta aattttctga acccatgaga gatactagag atggggagtg    720

gaaagtgttt ggttcaggga tatctgaaga acagaagggc agagatttct taagtgacgc    780

ctcatctaca agctggaaat tcctaaaaac aagtagaaag cttataaaca acaggtgata    840

cactcacctc actggtttta gtaaattacc aatacagaaa gtatccctag tcttaaaaac    900

aagtggaaaa tttgaactga ttagtcatat tcctttgatt acactgtttg ttacaatatt    960

tttctcagta aacagaaata actaattttt ttgttcttca ttctttgata gaaattaaaa   1020

tcttattctg tgaggattac agaatactat aactcaaatt ataaagtaga ataaactctt   1080

taaataatta ttcttcatca taaagtgtaa agaataagat ataagaaaac aatttatttt   1140

taaaatttaa tatactaaat gctcaaatat gttctactat agaataagtt cttatcttaa   1200

tttacagggc actaaaaaca attttaaaat gcttaatgtt gccttttata ttttaattgg   1260

ttaagaatat atatttgttt aatgcaaatc agaatcacta tattaaaatg aatgttcttg   1320


<210> SEQ ID NO 51
<211> LENGTH: 1635
<212> TYPE: DNA
<213> ORGANISM: Homo sapiens
<220> FEATURE:
<221> NAME/KEY: misc_feature
<223> OTHER INFORMATION: Incyte ID No: 403869.2CB1
<221> NAME/KEY: unsure
<222> LOCATION: 884, 1049, 1069, 1629, 1632
<223> OTHER INFORMATION: a, t, c, g, or other

<400> SEQUENCE: 51
```

-continued

```
tcgcggccgc aggagccggc gccgggcggc tggggagggc ttgctgacgc tgcgggccaa     60

gccgccctcg gaggccgagt acaccgacgt gctgcagaag atcaagtacg ccttcagcct    120

gctggcccgg ctgcgcggca acatcgccga cccctcctct ccggagctgt tgcacttcct    180

tttcgggcct ctgcagatga ttgtgaacac gtcgggggg ccggagttcg cgagcagtgt     240

gcggcggccg catctgacat cggatgccgt ggcgctgctg cgggacaacg tcactccacg    300

tgaaaacgag ctctggacct cgctggggga ctcgtggacc cgccccgggc tggagctgtc    360

cccggaggag ggacccccat acagacccga gttcttcagc ggctgggagc cgccggtcac    420

tgacccgcag agccgcgcct gggaggaccc agttgagaaa cagctacagc acgagcggag    480

gcgccggcag caaagcgccc ccgaggtcgc tgtcaatggt caccgaggac ttgggagcca    540

gaatctgagc ctcagctgga gtcagagaca gcaggaaaat gggtcctgtg taattatgac    600

ttccaggccc gcaacagcag tgagctgtcg gtcaagcagc gggacgtact ggaggtcctg    660

gatgacagtc gtaagtggtg gaaggttcgg gacccagcgg ggcaggaggg atatgtgccc    720

tacaacatcc tgacacccta ccccggaccc cggctgcacc acagccaaag ccctgcccgc    780

agcctgaaca gcactcctcc tccaccacca gccccagccc cggccccacc tccagctctg    840

gctcggcccc gctgggacag gccccgctgg gacagctgcg atanctcaac ggcttggacc    900

ccagcgagaa ggagaaattc tcccagatgc tcatcgtcaa cgaggaactg caggcgcgcc    960

tggcccaggg ccgctcggga ccgagccgcg cagtcccagg gccccgcgcc ccggaaccgc   1020

agctcagccc gggctcggac gcctccgang tccgcgcctg gctgcaggnc aagggcttta   1080

gctccgggac cgtggacgcg ctgggtgtgc tgaccggggc gcacttttct cgctgcagaa   1140

ggaggagctg cgggcggtga gccccgagga gggggcacgt gtgtacagcc aggtcaccgt   1200

gcagcgcttc gctgctggag gacaaagaga aagtgtcaga gctggaggca gtgatggaga   1260

agcaaaagaa gaaggtggaa ggcgaggtgg aaatggaggt catttgacct gccaggcgcc   1320

cttcgcaaag agtgacgagg ccccgtggga gaacggactc ctcagactct ccccaatagc   1380

ggaagtcgat cttctgaagg atggccaatc tgctccggcc ctggtcttcc cccatcccgg   1440

tggacagact taacgatcct tgctgcagtc cctccggaga ggatctggac tggctgggag   1500

tggggagggc gtggagacag tctacggaaa gcgctagcag acccccgaga gggtgcagtg   1560

gagccctgag cattgtaata tgcggcccag cctataaaca gcctccgtgc ttagcagatg   1620

gtgtgccant tnaaa                                                    1635
```

<210> SEQ ID NO 52
<211> LENGTH: 5226
<212> TYPE: DNA
<213> ORGANISM: Homo sapiens
<220> FEATURE:
<221> NAME/KEY: misc_feature
<223> OTHER INFORMATION: Incyte ID No: 475350.1CB1
<221> NAME/KEY: unsure
<222> LOCATION: 1221-1238, 3365, 5189
<223> OTHER INFORMATION: a, t, c, g, or other

<400> SEQUENCE: 52

```
ttttcaaaca caaagtggat ggtggtatga gacaatgttt aatgtccttc taactccgag     60

agtccttgat tctggagagg cacaggatga acatctgttg ctactgctga gtatacacac    120

tcttgcctct gagatggcgt gaccagcaga aaagaaagct cagggctgtg gcttcagaat    180

tcatggaaac agagccactg tcaagaagga atctgctcag agcagattct gagttttcac    240

actccacaaa tcctcagatt tagtgggaag ctggaaaaag gaactcttaa ttccaattga    300
```

-continued

```
ggagaaacaa gaaaacatta caaatcagtt tcccaagctg agaaggatta gccttgaccc    360
cttgggtctg cctctgttgc cctcaccagt ttaccttcta caacagtttc tcaggaacat    420
gtgtatttcc ccattcagct ttcagcattg ctccacgcca cagcataagc atagatccca    480
agtccacagg ctccattttg caggtcatct tctgatccta gcaaatgtcc tttccccata    540
gttgtcctat gcctttgggc tttagtctat cccaggacta actgtggaga aatcattggt    600
ttgagagtca agagagcatt ggtttgggag ctttaatcct ctttctgctt cacactaagt    660
gtgtcatctt ggctaaatca cttggtcttt ctgcattttg ttttcttatt tataggatga    720
ggaaattaga ttaaatggtt ttgaggtcct ttcttgttct gatatgtcca gtactcactg    780
gaaaattgga tctataactg atgggtttag taatctgctc atttcttgct ctgaaaattg    840
tagtcagcaa aagagatcat ggaagaaatc actgtaatgg tagtaatagt aacacatgcc    900
atttgtattg tgccttaggt ttaccaggtg tttccaaata cattagcata tttgatatgt    960
gcaggactag ataccttggg acctgccaca ctccactttc aagatatgta ttagcttcat   1020
tagaattaaa gggacttgaa ctcaggacct gcagcctatt ctttatccac atgtctctgg   1080
tagggctaca tccagatcac accatgactt cttatagagc aagagaaaat aatattatta   1140
tatcttcctt tgcctaaaat ctctccactt attctttttt atgattctgc accagttcac   1200
tgggttattc tatgattcca nnnnnnnnnn nnnnnnnntc atatttaaaa tgaacttaca   1260
atgtctgaat tttcctggcc ttgagtcaca gaagtaatat gtttcagatg gctgcccaat   1320
atgtattatc atgtaataca tatctgtgtc cttttctggg atgaggaagg cttcaacttc   1380
tggcactgag aactttgtat tacagacaca ggtttagttt ctagcttagt catgccttta   1440
gagtttagta gcacaaatcc atgcaaccca acagaataca tggtgagggc ctagtatgta   1500
gaatttgaaa gtagttcaaa tttgaattag aagaatgaag ctaggactta tttggaaaag   1560
gagatagaaa aaaaatgatc agaaactgtg gggccttatt acctttgcag taagttatct   1620
tcttcatgat atatgtgaat tattttatgt gcagattgtg ttttgggatt gtcagatcta   1680
aacttatatt cttgctggct aatgtgctga tagccaggtc tgaaacttga tgtgctatcc   1740
agacacatat gatcagaaaa gatctagagt gcaaagaggt gtctgaggag caaaatgtgg   1800
ttttaatgtt gtggaaagat cacttgcaag tatataagac tgtataaaga agaggactgt   1860
gtgcaagtgg ggtgaaaaaa aaggatacgc gaatgtgcat atgactgaat agggaggaag   1920
gtcagggcta gaaaggaggc tacataaaaa ggggcaatgg agagtgcaca ggaaagacac   1980
aggggaaggt caagtcgagc aaggtagaaa caggagtagc tagagccatt gggaatccat   2040
tttgaaacaa gaaggagttt tgaaagggaa taggaaagta agtgtcttga agtaaaagat   2100
aaatatggat ggagaaagaa gaaattctgg atgatagaga tgataaaaat atttattaag   2160
aaatgaagtc aggttcagtg tatgaaatgg aaaggaattt ttcagaattt taagaaaggg   2220
gaagttcctc ttggaaaaga tatagcaacc attggggaat gaccttttca tttcagaagt   2280
ggatgaggaa ggtggtgtga gcatcaggta tattctggac catttcaagt gctggtgaga   2340
agaaaggaac tctttgcctg aactgggctt ggttttccaa gtgctgcttt ggaaatgaag   2400
acccagagat gcagagctta tggtagttca taaatcttca tgttctatta tctttcatct   2460
gccaataaag ttcattttca ataatgtcca ccattgctgt gcccagaata accacaggca   2520
aacatcaaaa caatacgcat aagttagaca agattaaatc ttgtctgata tctgcacaaa   2580
cagatatgca ccatgttgga aacatgtgtt ttcctagtcc catccaggct tcccacaaga   2640
```

-continued

```
aagccatgat gtgggtctaa accatatgtt ttgagtaaag gagaatagaa gaaggggagt   2700
gtccgcaaaa tggaaagaga tgaagatgtt ccaaggaaat atgctgaaac agaacagtga   2760
atgttttgcc caaaactaca aaaataaaag aaaaaaagaa aattgcaata catggctact   2820
aagtctttga tcataagtcg aatttataga cctggaattt gccatcctag tctttccttt   2880
ttagtaagac ttctgtcctc tggcagtgca tatggtaggt ctctaatgtt tctgcatctc   2940
caggaagatg cagatcctta tttttgctgg gaaatccttc taaatagaaa tgtaacattt   3000
ttataaaaac agattaatgt gtttttcact tagtaaatgt tttcaagagc tgaattgaga   3060
aggaaagaga ctggagtggt taatggtgat ttgatttctg gcattctgag ttttctgcta   3120
caattagctg cattacttgg tgccaaagag cagtggggaa ttgttgagtt gctgtatcct   3180
ttaaaaaaaa acaaaaaact tgttattttg aaagaactta aggctcacaa gatgttacaa   3240
aaatagtaga gtggccttac cctagatcca gttttcccca tttataacat ttcacttagt   3300
ccattttcgg aaccagaaaa ttaacattgg cataatgcta taactaaact acagaccttt   3360
ttcanttcgc cagtttttcc acacatattc atttagttgc tggatacttt taattcttgc   3420
tgatttgtaa actggccttg cttggataca acaggaaaga tactatctgg ataaagttct   3480
acagttttag agagactatt aacacattaa tgtgttcctt tgtgcatgag caataccctg   3540
cctacactgc ttctaaattt tctgatttgt ttggctgttt ggcatctgaa acaatccaag   3600
acaaacttag aaagattagg caacacaaaa cacagtaaga cctgttcata gcttgttgcc   3660
tagaaaacca ggtagcagga tattctagat gcttcctgct gcttctacgt gagtaggatt   3720
agcactgggg acaaaataag gagtttagag taaaccagta tttcagtcaa gagttagttg   3780
gcacttagtt aatggcactg gaaatagctt gtggagagaa tagaatacaa tggtatagac   3840
tcctaatgtt tgataaaata ctattttcag agtggtagag aggttttatt tgcctaaata   3900
gccgttatta aatggaataa caaccacatt agaccaaatt aattgcaaac acagcggcaa   3960
cctggggaga agttgaaact ccagttttgt ggattacagt tttgagtttt atgattgaca   4020
tttttaagtc ccctatttaa ggggtcaaga ttataaaaat gtgtgtctta ctaagtttct   4080
aggtcattgt gagcacttga taaatatttg ctgaatgttg tttttttgaa tgaacataag   4140
atagaaacaa aaacttctca tccagttaac tagagtgaat gtagggagaa ttgttttgct   4200
tgtaacatgg agagtttatt ttcaagtgag gaaagagaaa aaaattactc agacttgttc   4260
ctggtgaagt gcattctctg tttgtatact ttttgatgga gaaattgatc tatagaactg   4320
cttaattttt tgaggcattt agacagcaat gaaaggtagt tctccacagg acaccgaatc   4380
aaaaggagag accagactct ggcctcatac ccagcctatt tgaaacaagc tatctagttt   4440
ctcctgcaga caccttgtca acaacatgca acagtgtcag gtgccttgca ggaaaataat   4500
ctgagtccca agctagcctg tgctcatcca caatcacaat gaacatgtca aggaagaatt   4560
tgcagagact caagggaagc acaatgggat aaggtaatca ctttcagtga aaaactgttt   4620
tcttgaaaac aggcttggac acaattgaaa gctggcttcc tgcaaacaca ccaagagtct   4680
gtaatctagc ctatccatta tatgtccttt attattcatg atatcctatt cttctacctt   4740
gttgcctggt aactttttct gaggactgag tttctgcagc gatgtggtgc actcttcctg   4800
tgatgaggaa acatctgggc ccccttctgc aggctttgga agatgatgtg tcttgtcaag   4860
gggtaaaggg caaatggatt taatttctgc ttaaaactat catagacgtt ccaaatagaa   4920
tatgtaaaat ttctctgtat tagaaaaaga aacgtgatac caattgtata ttttcttttc   4980
tttatttatt ctctgtaagt ctgtcagatg ataaattgta aataacaatg attaaagagt   5040
```

```
catgctactg atggatctcc ctttctgtat aaacagtgcc agttctgggc tttgtaacct   5100

ttgctcttta tagtctttca ttcctgggga agtgatgggg catgggccca gagctggggt   5160

gtatgtggta tggacacctg tttgtgggnt ttccagcaaa ggattattta aatagacctc   5220

taacat                                                              5226
```

<210> SEQ ID NO 53
<211> LENGTH: 1490
<212> TYPE: DNA
<213> ORGANISM: Homo sapiens
<220> FEATURE:
<221> NAME/KEY: misc_feature
<223> OTHER INFORMATION: Incyte ID No: 016193.3
<221> NAME/KEY: unsure
<222> LOCATION: 25
<223> OTHER INFORMATION: a, t, c, g, or other

<400> SEQUENCE: 53

```
gccattctcc tatcccgtgt ctgtncccat ccctgtgacc cctgacccct ggcctttgcc     60

actccccagg gaccgatgat gtggcgacca tcagttctgc tgcttctgtt gctactgagg    120

cacggggccc aggggaagcc atccccagac gcaggccctc atggccaggg gagggtgcac    180

caggcggccc ccctgagcga cgctccccca tgatgacgcc cacgggaact tccagttacg    240

accatgaggc tttcctggga cgggaagtgg ccaaggaatt cgaccaactc accccagagg    300

aaagccaggc ccgtctgggg cggatcgtgg accgcatgga ccgcgcgggg gacggcgacg    360

gctgggtgtc gctggccgag cttcgcgcgt ggatcgcgca acacgcagca gcggcacata    420

cgggactcgg tgagcgcggc ctggggacac gtacgacacg gaccgcgacg ggcgtgtggg    480

ttgggaggag ctgcgcaacg ccacctatgg ccactacgcg cccggtgaag aatttcatga    540

cgtggaggat gcagagacct acaaaaagat gctggctcgg gacgagcggc gtttccgggt    600

ggccgaccag gatggggact cgatggccac tcgagaggag ctgacagcct tcctgcaccc    660

cgaggagttc cctcacatgc gggacatcgt gattgctgaa accctggagg acctggacag    720

aaacaaagat ggctatgtcc aggtggagga gtacatcgcg gatctgtact cagccgagcc    780

tggggaggag gagccggacg tgggtgcaag acggagaggc agcagttccg ggacttccgg    840

gatctgaaca aggatgggca cctggatggg agtgaggtgg gccactgggt gctgccccct    900

gcccaggacc agcccctggt ggaagccaac cacctgctgc acgagagcga cacggacaag    960

gatgggcggc tgagcaaagc ggaaatcctg ggtaattgga acatgtttgt gggcagtcag   1020

gccaccaact atggcgagga cctgacccgg caccacgatg agctgtgagc accgcgcacc   1080

tgccacagcc tcagaggccc gcacaatgac cggaggaggg gccgctgtgg tctggccccc   1140

tccctgtcca ggccccgcag gaggcagatg cagtcccagg catcctcctg cccctgggct   1200

ctcagggacc ccctgggtcg gcttctgtcc ctgtcacacc cccaacccca gggaggggct   1260

gtcatagtcc cagaggataa gcaataccta tttctgactg agtctcccag cccagaccca   1320

gggacccttg gccccaagct cagctctaag aaccgcccca acccctccag ctccaaatct   1380

gagcctccac cacatagact gaaactcccc tggccccagc cctctcctgc ctggcctggc   1440

ctgggacacc tcctctctgc caggaggcaa taaaagccag cgccgggaaa              1490
```

<210> SEQ ID NO 54
<211> LENGTH: 401
<212> TYPE: DNA
<213> ORGANISM: Homo sapiens
<220> FEATURE:

-continued

<221> NAME/KEY: misc_feature
<223> OTHER INFORMATION: Incyte ID No: 127748.1
<221> NAME/KEY: unsure
<222> LOCATION: 26
<223> OTHER INFORMATION: a, t, c, g, or other

<400> SEQUENCE: 54
tcaaaagatc ttttatttta caattngttc atttaaatca ggagctcaaa actgtacaca 60
cacagtgatt gatagataat gtctttttaa taggttcctt tttttcccct cagttttgta 120
atttatttgt tgaagaaaca gatcatttgg cctataacat ttcccagagt ctggatttcg 180
ctggccagca attttaaatt aaagctttta tggtcaataa atcacatttc ctgtccctct 240
gtgctatcat tggatccaac ccccaaatca tatgcaataa gtttagtgtt attctcttca 300
gatgcaagaa acaaagattc cctcaggata cctctagcag gaagttttat tgtaaagata 360
cacatgggat gggattaaag gatataggac ctcaaatggt g 401

<210> SEQ ID NO 55
<211> LENGTH: 1098
<212> TYPE: DNA
<213> ORGANISM: Homo sapiens
<220> FEATURE:
<221> NAME/KEY: misc_feature
<223> OTHER INFORMATION: Incyte ID No: 200512.1
<221> NAME/KEY: unsure
<222> LOCATION: 927, 961, 987, 1048
<223> OTHER INFORMATION: a, t, c, g, or other

<400> SEQUENCE: 55
cacgagagtg actctcctat gaaggtaaag gccacccctc ttcagttcca gtgactgaga 60
tacatttttc baatcctggg ggcaaataca gacacagcaa gttccttctt ccctttggaa 120
atttggcagc tgccttcacc agtgagcaca aagccacatt tcaaaggaaa ctgacaaatt 180
atccccagct gccagaagaa gaaatcctca ctggacggct tcctgtttcc tgtggttcat 240
tatctgattg gctgcaggga tgaaagtttt taagttcata ggactgatga tcctcctcac 300
ctctgcgttt tcagccggtt caggacaaag tccaatgact gtgctgtgct ccatagactg 360
gttcatggtc acagtgcacc cttcatgcta aacaacgatg tgtgtgtaca ctttcatgac 420
tacattgggc ctgggttgcc cccaaaccat gttcagccac acgcctacca gttcactacc 480
gtgttactga atgtggcatc agggccaaag ctgtctctca ggacatggtt atctacagca 540
ctgagataca ctactcttct aagggcacgc catctaagtt tgtgatccca gtgtcatgtg 600
ctgcccccca aaagtcccca tgggctcacc aagccctgct ccatgagagt agccagcaag 660
agcagggcca cagccagtaa ggatgagaaa tgctacgagg tgttcagctt gtcacagtcc 720
agtcaaaggc ccaactgcga ttgtccacct tgtgtcttca gtgaagaaga gcatacccag 780
gtcccttgtc accaagcagg ggctcaggag gctcaacctc tgcagccatc tcactttctt 840
gatatttctg aggattggtc tcttcacaca gatgatatga ttgggtccat gtgatcctca 900
ggtttggggt ctcctgaaga tgctatntct agaattagta tatagtgtac aaatgtctga 960
naaataagtg ctcttgtgac cctcatntga gcacttttga gaaagagaaa cctatagcaa 1020
cttcatgaat taagcctttt tctatatntt tatattcatg tgtaaacaaa aaataaaata 1080
aaattctgat cgcataaa 1098

<210> SEQ ID NO 56
<211> LENGTH: 2346
<212> TYPE: DNA
<213> ORGANISM: Homo sapiens -continued
<220> FEATURE:
<221> NAME/KEY: misc_feature
<223> OTHER INFORMATION: Incyte ID No: 236360.5

<400> SEQUENCE: 56

```
cagggaagag cctggctacg gtggactgtg agactcagtg cactgtcctc ctcccagcga     60
cgcccacgct ggaccccccct gccggaccct ccacccttcg gcccccaagc ttcccagggg    120
cttcctttgg actggactgt ccctgctcat ccattctcct gccaccccca gacctcctca    180
gctccaggtt gccacctcct ctcgccagag tgatgaggtc ccgggcttct gctctccgtg    240
gcccatctgc ccacaattcg ggagaccacg gaggagatgc tgcttggggg tcctgggaca    300
gggagccccc accctactcc tagcctggat gactacgtga ggtctatatc tcgactggca    360
cagcccacct ctgtgctgga caaggccacg gcccagggcc aacccaggcc accccacagg    420
ccagcccagg cctgccggaa gggccgccct gctgtgtccc tgcgagacat caccgcacgt    480
ttcagtggcc agcagcccac actgcccatg gctgatactg tggacccccct ggactggctt    540
tttggggagt cccaggaaaa gcagccaagc cagagggacc tgccaaggag gactggcccc    600
tctgctggcc tctggggtcc acatagacag atggacagca gcaagcccat gggggccccc    660
agagggaggc tctgtgaagc caggatgcct gggcattccc tggcaagacc accgcaggat    720
gggcagcaga gctctgacct aagaagctgg acttttgggc agtctgccca agccatggcc    780
tcccgccacc gcccccgccc cagcagtgtc ctcagaacac tctactcgca cctcccggtg    840
atccatgaac tctgacccct ccccagtaaa ggcttctgta gagagcatgc tgggtctgca    900
tctcctgctc gtactcctcc atggtggtca ctgcccctgg caggtctctg aaagggaaat    960
gcttttctgc agaggcccct ggcttgggca gttcacagtg agaccgaccc cctctgaata   1020
tgataacagc ctgtttcaca tgaggagatg ttaccaatcc cgttcgctct gacccttgct   1080
ggctgatcac cttgagcaac ttacttaaca tctgtgttcc tcagtttctc atgggtaata   1140
tagggataat tactggcacc tgcctcccag gccattctga cgtgtaaccc gcatatagga   1200
gcccactggc tgagtagcta ccatcatcgc tggtggggaa actggtggta ggggtgtgag   1260
ggtagtgggg gtgtcagccc cccaggtgtt tcagaacaag gcctcgggca ctcccaagtc   1320
tgcctcttgg ctcccaccct caaagcccat gttctgtgag gcccaagaga acacatggag   1380
tcttagcaaa tgcactaatg tattccgggg gactgtcacc tggcaccact ggggcactct   1440
gctggctaca actcatacgt cctgtggtgg cattgggaga gttcccccat gatgagggcc   1500
aagatagaat ctgtaccact cagtgctacc atccccaccc ctacaccact tccacacagg   1560
ggcctcatgg catggtcagg gtcccagctg tgggtgagag cagggcactg tccagctgtc   1620
cactggggaa gtcaagatgt cctaaggccc aggccagggc atctggagtc tgaaggaccc   1680
tagttcctag aggcatctgg cagcaagaag gtgaggcatc agggaacggg aatcaggctg   1740
ggactgatca gaggtgaagg gacagagaga ggagaggagg aagattgagc tgggggcaac   1800
agccaagctc acctgggcag gtctctgcca cctccttgct ctgtgagctg tcagtctagg   1860
ttattctctt tttttgtggc tatttttaat tgctttggat ttgttaaatg ttttctgtct   1920
tctgttaagt gtgttttctc tggagataga atgtaaacca tattaaaagg aaaaagagaa   1980
taacctagac tgacagctca cagagcaagg aggtggcaga gacctgccca ggtgagcttg   2040
gctgttgccc ccagctcaat cttcctcctc tcctctctct gtcccttcac ctctgatcag   2100
tcccagcctg attcccgttc cctgatgcct caccttcttg ctgccagatg cctctaggaa   2160
ctagggtcct tcagactcca gatgccctgg cctgggcctt aggacatctt gacttcccca   2220
```

gtggacagct ggacagtgcc ctgctctcac ccacagctgg gaccgtgacc atgccatgag 2280
gcccctgtgt ggaagtggtg tagggccaag atagaatctg taccactcag tgctaccatc 2340
cccacc 2346

<210> SEQ ID NO 57
<211> LENGTH: 1026
<212> TYPE: DNA
<213> ORGANISM: Homo sapiens
<220> FEATURE:
<221> NAME/KEY: misc_feature
<223> OTHER INFORMATION: Incyte ID No: 334145.1

<400> SEQUENCE: 57
gataaatggc tattggttgc gtatctctct ggatgtatct gtatctccag attttggggt 60
ggcagtttgc tcaggacctt ggttctctaa taggtctaat aagaaaagtc attgattttc 120
agctttccaa ctttccagct ttgtcttgtt ataagcatgg cagcaacatc ttccatgctc 180
ttaacatgat gacactaaag gcagaagtcg atctccatgt ataaacattt taacacatat 240 gtttttgtt atcgtggttt ctgacctgtc tctttgccct gactttctga tactgcacta 300
gggttcctgt tgctggactc cattccatat gacttgctct cgtctaggct gctctttggc 360
tcatctttat aaatcatgat ccaaaatgaa gcacatattt attttttaaa taaatatgaa 420
atgaagtata gacatcaaac tgaagatgag tagatcatac tgagtttcac tgtctgtgct 480
tggatcaaca tcaggcctta tacaaatatt caagtccaga ggcaaaaggt aataaggaaa 540
atttgtagca caagccacaa ggagataaca tgtcaagtct atgcgattgg aaataaacta 600
aagatgaact gctggggatg ctcactcatc acagagctca gtctaaagca ccagatttca 660
caagcatttt ttgggggaaa ttctgttaaa atgaaatatg agtcacatgg tggtgtttca 720
ctcatcatat gtgttcaata ttaattcatt ttaaggttta gttgcacaaa aggtaaatga 780
gaattagaag actccatggg taagaggagc cacagaagta aagcattgtc aagggttcta 840
tgtctatata tttagatatt aggcttctga gaaaaaaaca caataggaag gaagatgaac 900
acaacagagg gcagaaggtc tatacgtcct gaggcctttt atgcaacgtt tgtttgtgga 960
atgtttttta agaatgtgtg agagtcattt taatgtgaaa taaagaccta cgtctacaaa 1020
aaaaaa 1026

<210> SEQ ID NO 58
<211> LENGTH: 3706
<212> TYPE: DNA
<213> ORGANISM: Homo sapiens
<220> FEATURE:
<221> NAME/KEY: misc_feature
<223> OTHER INFORMATION: Incyte ID No: 007074.1
<221> NAME/KEY: unsure
<222> LOCATION: 3634, 3638-3639, 3642-3643, 3647-3648, 3652, 3654-3658, 3664, 3674, 3681
<223> OTHER INFORMATION: a, t, c, g, or other

<400> SEQUENCE: 58
ggcagggcga cgtaggcggc acgtgcgggg tcgtggacga cgagccccgg ccgactggga 60
aagcggagac cgaagacgag gacgaaggga ctgagggcga ggacgaaggg cctcagtggt 120
cgccgcagga cccggcactg caaggcgtag gacagcccac aggaactgga agcataagaa 180
agaagcgatt tgtgtccagt caccgctatg tggaaaccat gcttgtggca gaccagtcga 240
tggcagaatt ccacggcagt ggtctaaagc attaccttct cacgttgttt tcggtggcag 300

-continued

```
ccagattgta caaacacccc agcattcgta attcagttag cctggtggtg gtgaagatct    360
tggtcatcca cgatgaacag aaggggccgg aagtgacctc caatgctgcc ctcactctgc    420
ggaacttttg caactggcag aagcagcaca acccacccag tgaccgggat gcagagcact    480
atgacacagc aattcttttc accagacagg acttgtgtgg gtcccagaca tgtgatactc    540
ttgggatggc tgatgttgga actgtgtgtg atccgagcag aagctgctcc gtcatagaag    600
atgatggttt acaagctgcc ttcaccacag cccatgaatt aggccacgtg tttaacatgc    660
cacatgatga tgcaaagcag tgtgccagcc ttaatggtgt gaaccaggat tcccacatga    720
tggcgtcaat gctttccaac ctggaccaca gccagccttg gtctccttgc agtgcctaca    780
tgattacatc atttctggat aatggtcatg gggaatgttt gatggacaag cctcagaatc    840
ccatacagct cccaggcgat ctccctggca cctcgtacga tgccaaccgg cagtgccagt    900
ttacatttgg ggaggactcc aaacactgcc ccgatgcagc cagcacatgt agcaccttgt    960
ggtgtaccgg cacctctggt ggggtgctgg tgtgtcaaac caaacacttc ccgtgggcgg   1020
atggcaccag ctgtggagaa gggaaatggt gtatcaacgg caagtgtgtg aacaaaaccg   1080
acagaaagca ttttgatacg ccttttcatg gaagctgggg aatgtggggg ccttggggag   1140
actgttcgag aacgtgcggt ggaggagtcc agtacacgat gagggaatgt gacaacccag   1200
tcccaaagaa tggagggaag tactgtgaag gcaaacgagt gcgctacaga tcctgtaacc   1260
ttgaggactg tccagacaat aatggaaaaa cctttagaga ggaacaatgt gaagcacaca   1320
acgagttttc aaaagcttcc tttgggagtg ggcctgcggt ggaatggatt cccaagtacg   1380
ctggcgtctc accaaaggac aggtgcaagc tcatctgcca agccaaaggc attggctact   1440
tcttcgtttt gcagcccaag gttgtagatg gtactccatg tagcccagat tccacctctg   1500
tctgtgtgca aggacagtgt gtaaaagctg gttgtgatcg catcatagac tccaaaaaga   1560
agtttgataa atgtggtgtt tgcgggggaa atggatctac ttgtaaaaaa atatcaggat   1620
cagttactag tgcaaaacct ggatatcatg atatcatcac aattccaact ggagccacca   1680
acatcgaagt gaaacagcgg aaccagaggg gatccaggaa caatgggcag ctttcttgcc   1740
atcaaagctg ctgatggcac atatattctt aatggtgact acactttgtc caccttagag   1800
caagacatta tgtacaaagg tgttgtcttg aggtacagcg gctcctctgc ggcattggaa   1860
agaattcgca gctttagccc tctcaaagag cccttgacca tccaggttct tactgtgggc   1920
aatgcccttc gacctaaaat taaatacacc tacttcgtaa agaagaagaa ggaatctttc   1980
aatgctatcc ccactttttc agcatgggtc attgaagagt ggggcgaatg ttctaagtca   2040
tgtgaattgg gttggcagag aagactggta gaatgccgag acattaatgg acagcctgct   2100
tccgagtgtg caaaggaagt gaagccagcc agcaccagac cttgtgcaga ccatccctgc   2160
ccccagtggc agctgggggga gtggtcatca tgttctaaga cctgtgggaa gggttacaaa   2220
aaaagaagct tgaagtgtct gtcccatgat ggaggggtgt tatctcatga gagctgtgat   2280
cctttaaaga aacctaaaca tttcatagac ttttgcacaa tggcagaatg cagttaagtg   2340
gtttaagtgg tgttagcttt gagggcaagg caaagtgagg aagggctggt gcagggaaag   2400
caagaaggct ggagggatcc agcgtatctt gccagtaacc agtgaggtgt atcagtaagg   2460
tgggattatg ggggtagata gaaaaggagt tgaatcatca gagtaaactg ccagttgcaa   2520
atttgatagg atagttagtg aggattatta acctctgagc agtgatatag cataataaag   2580
ccccgggcat tattattatt atttcttttg ttacatctat tacaagttta gaaaaaacaa   2640
```

-continued

```
agcaattgtc caaaaaaagt tagaactatt acaacccctg tttcctggta cttatcaaat   2700
acttagtatc atgggggttg ggaaatgaaa agtaggagaa aagtgagatt ttactaagac   2760
ctgttttact ttacctcact aacaatgggg ggagaaagga gtacaaatag gatctttgac   2820
cagcactgtt tatggctgct atggtttcag agaatgttta tacattattt ctaccgagaa   2880
ttaaaacttc agattgttca acatgagaga aaggctcagc aacgtgaaat aacgcaaatg   2940
gcttcctctt tccttttttg gaccatctca gtctttattt gtgtaattca ttttgaggaa   3000
aaaacaactc catgtattta ttcaagtgca ttaaagtcta caatggaaaa aaagcagtga   3060
agcattagat gctggtaaaa gctagaggag acacaatgag cttagtacct ccaacttcct   3120
ttctttccta ccatgtaacc ctgctttggg aatatggatg taaagaagta acttgtgtct   3180
catgaaaatc agtacaatca cacaaggagg atgaaacgcc ggaacaaaaa tgaggtgtgt   3240
agaacagggt cccacaggtt tggggacatt gagatcactt gtcttgtggt ggggaggctg   3300
ctgaggggta gcaggtccat ctccagcagc ttgtccaaca gtcgtatcct ggtgaatgtc   3360
tgttcagctc ttctgtgaga atatgatttt ttccatatgt atatagtaaa atatgttact   3420
ataaattaca tgtactttat aagtattggt ttgggtgttc cttccaagaa ggactatagt   3480
tagtaataaa tgcctataat aacatattta tttttataca tttatttcta atgaaaaaaa   3540
cttttaaatt atatcgcttt tgtggaagtg catataaaat agagtattta tacaatatat   3600
gttactagaa ataaaagaac acttttggaa aaanaaanna annaagnnga angnnnnnta   3660
aagntgtatg ccgnggagaa naacccaaat gccgtggtga cgctag                  3706
```

```
<210> SEQ ID NO 59
<211> LENGTH: 3430
<212> TYPE: DNA
<213> ORGANISM: Homo sapiens
<220> FEATURE:
<221> NAME/KEY: misc_feature
<223> OTHER INFORMATION: Incyte ID No: 474317.4

<400> SEQUENCE: 59
```

```
gcgctgggag aaggagagcc atcgccgctc gtacccgctt caacgccgcc agcctaaacg     60
gcgcccccaa ggggggcaag tacgacgacg tcaccctgat gggcgcggag gtagccagcg    120
gcggctgcat gaagaccgga ctctggaaga gcgaaactac cgtctaaggt ggggcgggcg    180
acgcggtaga cgggctggcc acgcggctcg ttcccccgct cctcggggcc ctccaaggtg    240
tctccgtagt cagcaggttg gaggcagagg agccgatggc tggaggaagc ccacaggcgg    300
atgttcccca cttgcctaga gggcatccct ctggggtagc gacagacaat cccagaaaca    360
cgcataatac atttccgtcc agcccggggc agtctgactg tcggtgccct cccaggaacg    420
gggaaggcct ccgtctgtgt gaaagggcac agcacatccc aggtgcaccc tccccaagta    480
ctcccacccc gcctactgta ccatgcggcc tcactggggg ccatcagcct caccagcaaa    540
gcagagatga gagcgtggga actgtgttct ttcctccctg ccctctactg atttcagccc    600
agcccctgcc tagatcctag gtccctttc ctcccgagtt tggctggcac gagagctagc     660
ccagcacatg aagcaggtga tgttaagtca caaggtgctg cttttcagat ccactatgca    720
agaggggagg gtggggccac gtgaaaggca gctctagaca tcaaccagtc ctgggggagg    780
ggagtgggaa ccgggcacaa ctaggaacaa tgccaccatt cccacaggag tggtacttaa    840
accagacagc agggttcaga ggtggcacac cgggacaaag ctgaggccct gcacctcaac    900
agctgactgc caggtgcctg tgggtgaact gaggggagta gagggagagg gcaggtggaa    960
```

-continued

```
ctggggcaga atctagtcat gccctaaagc tagtcctgta aacaatggtg ccccagaaag   1020
ctgcaggtgg tgtttggaga agcagttact tttcagttac aagacccatc tccctagtct   1080
cagccttaca acaccacggg actaaggaag agcacttcct tgcctccgta aggccagagg   1140
aagaaccatc ccaatcattt gatctccagc tccacagtag agagaaacct acaaaatgtc   1200
aaaccagctt cccgactccc aggagctcaa gccaagccca gaggcagtgg ctggggtccc   1260
tgcaggtcat gaggggccta tgcctttact ccttttaaac accagcaccc gtcttttccc   1320
caacctaaaa ccaaccacca gcatttcact acaggaccaa atggaaaccg agggaaccct   1380
gggtcttggg aagaacaaca ggaaaccaag gtctgaccta gggttccctc ccagtcttca   1440
catcactctg gcctcatcac caaggtgaca gaggacacag gggaggggga aaacccacac   1500
acactccttg gaatgggtcc tgttatttat gcttgctgca cagacatatt agaagaaaaa   1560
aaaaagcttt gtattattct tccacatatg ctggctgctg tttacacacc ctgccaatgc   1620
cttagcactg gagagctttt tgcaatatgc tggggaaagg ggagggaggg aatgaaagtg   1680
ccaaagaaaa catgttttta agaactcggg ttttatacaa tagaatgttt tctagcagat   1740
gcctcttgtt ttaatatatt aaaattttgc aaagcccttt gagctactgc cttagtctac   1800
ccactgtcct tttgttatga ggtagaggat ctcatgacac catacacaca aacccatcat   1860
tgcctgtgaa tgcacgtagg gccagaattc cccagttccc gctcctctga gggttgatac   1920
tgctgggaat gccaaccact ccacaagcag agggaagccc cctcaggcct gcaggaggag   1980
ccgcagcagt gtgtccaatt caaaccagca gcaaagagcc tgacattttc ccatccatct   2040
atgaggaaag ccatctcaca gaacatggac ataggcaact tgctctccca caccaaggga   2100
tgggaatctc tcctacctat agtcatccct gcactcctga ctttactcca ggacccaggg   2160
tccaactaat ggcagagccc ctcttggttc cttcaaacaa gaaaagcaat acctacggac   2220
tggtgtacac ttccatcctt ggttataaca ggaatgttat caagctgtca gaacaggatg   2280
aagtgctccc agtggatatc catcagggag ggttagggac actcgtggca gcctgtctag   2340
cagcctgggc tctctgaaag tccctaactt cctgaggggt acgcaaatac tgttctattt   2400
cactatcaga aatgttctca tctccagtga cagtggagac agggggtaca gggcagatcc   2460
gcttcgggga cttcaacatg cagggtggca agagaagggc aggactggcc ggccgcttcc   2520
cctggggtaa acctaaggaa ttatttccca cctccccttc tccttgcccc tgtccccacc   2580
ccggtggctc cttctctcgg gtctccactt ctgctgtccc atcccgaaag gcagagcgga   2640
ccagtgactg gcggtgctgg agaaggtcac cgatgtgctt caccacagac cgtttgtcaa   2700
gtctcagaac tcgtaaccag gccagctgct cagccatccg cagcagcaca gccagcagct   2760
cctgcaggcg ggaggacgcc gggtagggca ggtccacatt tgccaattta caaaatcggg   2820
caagggaaca tgaaagccga tctgcaggct gcagcgactg ccaagccagg aaagtcgcag   2880
cagtgatgac gggcaaggga tgcctcccgg tcaccagcca cgtctcattt gccagctcca   2940
ccaactgcat tgttcgagac agcatcttct ctttgtcttc cacgtatttg gctggcacag   3000
aaggtgaagc ttggaacagt ttgaagctga aataaccaaa atgagggttg gatcttaatg   3060
atatagggc tgctctccca cagtgaggaa agacagccca ctcaagatgg ggaagctatt   3120
ctgccctcag gaatactcaa gctcactggg cagcaagtta ataaaggtag tgagagaaaa   3180
cagggcgtct tccgcttgtt aggggaaggt ggagggatgg aggagagcac gaacatttat   3240
tgggcgcctc ccaatcacca ttattctgag tgctttacaa cgttctcatt taatctacgt   3300
gcacgtgcac catcttatgt gcatgtatag ttaaaaaact ttcccatagt catccagcca   3360
```

-continued

```
ggcagtaacc aagcttcaaa tacaaggcta tttgacacca acagcctcta ctttcaacgt   3420

tatttatcag                                                          3430
```

<210> SEQ ID NO 60
<211> LENGTH: 13977
<212> TYPE: DNA
<213> ORGANISM: Homo sapiens
<220> FEATURE:
<221> NAME/KEY: misc_feature
<223> OTHER INFORMATION: Incyte ID No: 229357.11CB1
<221> NAME/KEY: unsure
<222> LOCATION: 11721-11761, 12294, 13969
<223> OTHER INFORMATION: a, t, c, g, or other

<400> SEQUENCE: 60

```
gggattccct cactttcccc ctacaggact cagatctggg aggcaattac cttcggagaa     60

aaacgaatag gaaaaactga agtgttactt tttttaaagc tgctgaagtt tgttggtttc    120

tcattgtttt taagcctact ggagcaataa agtttgaaga acttttacca ggtttttttt    180

atcgctgcct tgatatacac ttttcaaaat gctttggtgg gaagaagtag aggactgtta    240

tgaaagagaa gatgttcaaa agaaaacatt cacaaaatgg gtaaatgcac aattttctaa    300

gtttgggaag cagcatattg agaacctctt cagtgaccta caggatggga ggcgcctcct    360

agacctcctc gaaggcctga cagggcaaaa actgccaaaa gaaaaaggat ccacaagagt    420

tcatgccctg aacaatgtca acaaggcact gcgggttttg cagaacaata atgttgattt    480

agtgaatatt ggaagtactg acatcgtaga tggaaatcat aaactgactc ttggtttgat    540

ttggaatata atcctccact ggcaggtcaa aaatgtaatg aaaaatatca tggctggatt    600

gcaacaaacc aacagtgaaa agattctcct gagctgggtc cgacaatcaa ctcgtaatta    660

tccacaggtt aatgtaatca acttcaccac cagctggtct gatggcctgg ctttgaatgc    720

tctcatccat agtcataggc cagacctatt tgactggaat agtgtggttt gccagcagtc    780

agccacacaa cgactggaac atgcattcaa catcgccaga tatcaattag gcatagagaa    840

actactcgat cctgaagatg ttgataccac ctatccagat aagaagtcca tcttaatgta    900

catcacatca ctcttccaag ttttgcctca acaagtgagc attgaagcca tccaggaagt    960

ggaaatgttg ccaaggccac ctaaagtgac taaagaagaa cattttcagt tacatcatca   1020

aatgcactat tctcaacaga tcacggtcag tctagcacag ggatatgaga gaacttcttc   1080

ccctaagcct cgattcaaga gctatgccta cacacaggct gcttatgtca ccacctctga   1140

ccctacacgg agcccatttc cttcacagca tttggaagct cctgaagaca agtcatttgg   1200

cagttcattg atggagagtg aagtaaacct ggaccgttat caaacagctt tagaagaagt   1260

attatcgtgg cttctttctg ctgaggacac attgcaagca caaggagaga tttctaatga   1320

tgtggaagtg gtgaaagacc agtttcatac tcatgagggg tacatgatgg atttgacagc   1380

ccatcagggc cgggttggta atattctaca attgggaagt aagctgattg gaacaggaaa   1440

attatcagaa gatgaagaaa ctgaagtaca agagcagatg aatctcctaa attcaagatg   1500

ggaatgcctc agggtagcta gcatggaaaa acaaagcaat ttacatagag ttttaatgga   1560

tctccagaat cagaaactga aagagttgaa tgactggcta acaaaaacag aagaaagaac   1620

aaggaaaatg gaggaagagc ctcttggacc tgatcttgaa gacctaaaac gccaagtaca   1680

acaacataag gtgcttcaag aagatctaga acaagaacaa gtcagggtca attctctcac   1740

tcacatggtg gtggtagttg atgaatctag tggagatcac gcaactgctg ctttggaaga   1800
```

-continued

```
acaacttaag gtattgggag atcgatgggc aaacatctgt agatggacag aagaccgctg   1860
ggttctttta caagacatcc ttctcaaatg gcaacgtctt actgaagaac agtgcctttt   1920
tagtgcatgg ctttcagaaa aagaagatgc agtgaacaag attcacacaa ctggctttaa   1980
agatcaaaat gaaatgttat caagtcttca aaaactggcc gttttaaaag cggatctaga   2040
aaagaaaaag caatccatgg gcaaactgta ttcactcaaa caagatcttc tttcaacact   2100
gaagaataag tcagtgaccc agaagacgga agcatggctg gataactttg cccggtgttg   2160
ggataattta gtccaaaaac ttgaaaagag tacagcacag atttcacagg ctgtcaccac   2220
cactcagcca tcactaacac agacaactgt aatggaaaca gtaactacgg tgaccacaag   2280
ggaacagatc ctggtaaagc atgctcaaga ggaacttcca ccaccacctc cccaaaagaa   2340
gaggcagatt actgtggatt ctgaaattag gaaaaggttg gatgttgata taactgaact   2400
tcacagctgg attactcgct cagaagctgt gttgcagagt cctgaatttg caatctttcg   2460
gaaggaaggc aacttctcag acttaaaaga aaaagtcaat gccatagagc gagaaaaagc   2520
tgagaagttc agaaaactgc aagatgccag cagatcagct caggccctgg tggaacagat   2580
ggtgaatgag ggtgttaatg cagatagcat caaacaagcc tcagaacaac tgaacagccg   2640
gtggatcgaa ttctgccagt tgctaagtga gagacttaac tggctggagt atcagaacaa   2700
catcatcgct ttctataatc agctacaaca attggagcag atgacaacta ctgctgaaaa   2760
ctggttgaaa atccaaccca ccaccccatc agagccaaca gcaattaaaa gtcagttaaa   2820
aatttgtaag gatgaagtca accggctatc aggtcttcaa cctcaaattg aacgattaaa   2880
aattcaaagc atagccctga aagagaaagg acaaggaccc atgttcctgg atgcagactt   2940
tgtggccttt acaaatcatt ttaagcaagt cttttctgat gtgcaggcca gagagaaaga   3000
gctacagaca atttttgaca ctttgccacc aatgcgctat caggagacca tgagtgccat   3060
caggacatgg gtccagcagt cagaaaccaa actctccata cctcaactta gtgtcaccga   3120
ctatgaaatc atggagcaga gactcgggga attgcaggct ttacaaagtt ctctgcaaga   3180
gcaacaaagt ggcctatact atctcagcac cactgtgaaa gagatgtcga agaaagcgcc   3240
ctctgaaatt agccggaaat atcaatcaga atttgaagaa attgagggac gctggaagaa   3300
gctctcctcc cagctggttg agcattgtca aaagctagag gagcaaatga ataaactccg   3360
aaaaattcag aatcacatac aaaccctgaa gaaatggatg gctgaagttg atgtttttct   3420
gaaggaggaa tggcctgccc ttggggattc agaaattcta aaaaagcagc tgaaacagtg   3480
cagactttta gtcagtgata ttcagacaat tcagcccagt ctaaacagtg tcaatgaagg   3540
tgggcagaag ataaagaatg aagcagagcc agagtttgct tcgagacttg agacagaact   3600
caaagaactt aacactcagt gggatcacat gtgccaacag gtctatgcca gaaaggaggc   3660
cttgaaggga ggtttggaga aaactgtaag cctccagaaa gatctatcag agatgcacga   3720
atggatgaca caagctgaag aagagtatct tgagagagat tttgaatata aaactccaga   3780
tgaattacag aaagcagttg aagagatgaa gagagctaaa gaagaggccc aacaaaaaga   3840
agcgaaagtg aaactcctta ctgagtctgt aaatagtgtc atagctcaag ctccacctgt   3900
agcacaagag gccttaaaaa aggaacttga aactctaacc accaactacc agtggctctg   3960
cactaggctg aatgggaaat gcaagacttt ggaagaagtt tgggcatgtt ggcatgagtt   4020
attgtcatac ttggagaaag caaacaagtg gctaaatgaa gtagaattta aacttaaaac   4080
cactgaaaac attcctggcg gagctgagga aatctctgag gtgctagatt cacttgaaaa   4140
tttgatgcga cattcagagg ataacccaaa tcagattcgc atattggcac agaccctaac   4200
```

-continued

```
agatggcgga gtcatggatg agctaatcaa tgaggaactt gagacattta attctcgttg   4260
gagggaacta catgaagagg ctgtaaggag gcaaaagttg cttgaacaga gcatccagtc   4320
tgcccaggag actgaaaaat ccttacactt aatccaggag tccctcacat tcattgacaa   4380
gcagttggca gcttatattg cagacaaggt ggacgcagct caaatgcctc aggaagccca   4440
gaaaatccaa tctgatttga caagtcatga gatcagttta gaagaaatga agaaacataa   4500
tcaggggaag gaggctgccc aaagagtcct gtctcagatt gatgttgcac agaaaaaatt   4560
acaagatgtc tccatgaagt ttcgattatt ccagaaacca gccaattttg agctgcgtct   4620
acaagaaagt aagatgattt tagatgaagt gaagatgcac ttgcctgcat tggaaacaaa   4680
gagtgtggaa caggaagtag tacagtcaca gctaaatcat tgtgtgaact tgtataaaag   4740
tctgagtgaa gtgaagtctg aagtggaaat ggtgataaag actggacgtc agattgtaca   4800
gaaaaagcag acggaaaatc ccaaagaact tgatgaaaga gtaacagctt tgaaattgca   4860
ttataatgag ctgggagcaa aggtaacaga aagaaagcaa cagttggaga aatgcttgaa   4920
attgtcccgt aagatgcgaa aggaaatgaa tgtcttgaca gaatggctgg cagctacaga   4980
tatggaattg acaaagagat cagcagttga aggaatgcct agtaatttgg attctgaagt   5040
tgcctgggga aaggctactc aaaaagagat tgagaaacag aaggtgcacc tgaagagtat   5100
cacagaggta ggagaggcct tgaaaacagt tttgggcaag aaggagacgt tggtggaaga   5160
taaactcagt cttctgaata gtaactggat agctgtcacc tcccgagcag aagagtggtt   5220
aaatcttttg ttggaatacc agaaacacat ggaaactttt gaccagaatg tggaccacat   5280
cacaaagtgg atcattcagg ctgacacact tttggatgaa tcagagaaaa agaaacccca   5340
gcaaaaagaa gacgtgctta agcgtttaaa ggcagaactg aatgacatac gcccaaaggt   5400
ggactctaca cgtgaccaag cagcaaactt gatggcaaac cacggtgacc actgcaggaa   5460
attagtagag ccccaaatct cagagctcaa ccatcgattt gcagccattt cacacagaat   5520
taagactgga aaggcctcca ttcctttgaa ggaattggag cagtttaact cagatataca   5580
aaaattgctt gaaccactgg aggctgaaat tcagcagggg gtgaatctga aagaggaaga   5640
cttcaataaa gatatgaatg aagacaatga gggtactgta aaagaattgt tgcaaagagg   5700
agacaactta caacaaagaa tcacagatga gagaaagaga gaggaaataa agataaaaca   5760
gcagctgtta cagacaaaac ataatgctct caaggatttg aggtctcaaa gaagaaaaaa   5820
ggctctagaa atttctcatc agtggtatca gtacaagagg caggctgatg atctcctgaa   5880
atgcttggat gacattgaaa aaaaattagc cagcctacct gagcccagag atgaaaggaa   5940
aataaaggaa attgatcggg aattgcagaa gaagaaagag gagctgaatg cagtgcgtag   6000
gcaagctgag ggcttgtctg aggatggggc cgcaatggca gtggagccaa ctcagatcca   6060
gctcagcaag cgctggcggg aaattgagag caaatttgct cagtttcgaa gactcaactt   6120
tgcacaaatt cacactgtcc gtgaagaaac gatgatggtg atgactgaag acatgccttt   6180
ggaaatttct tatgtgcctt ctacttattt gactgaaatc actcatgtct cacaagccct   6240
attagaagtg gaacaacttc tcaatgctcc tgacctctgt gctaaggact ttgaagatct   6300
ctttaagcaa gaggagtctc tgaagaatat aaaagatagt ctacaacaaa gctcaggtcg   6360
gattgacatt attcatagca agaagacagc agcattgcaa agtgcaacgc ctgtggaaag   6420
ggtgaagcta caggaagctc tctcccagct tgatttccaa tgggaaaaag ttaacaaaat   6480
gtacaaggac cgacaagggc gatttgacag atctgttgag aaatggcggc gttttcatta   6540
```

-continued

```
tgatataaag atatttaatc agtggctaac agaagctgaa cagtttctca gaaagacaca   6600
aattcctgag aattgggaac atgctaaata caaatggtat cttaaggaac tccaggatgg   6660
cattgggcag cggcaaactg ttgtcagaac attgaatgca actggggaag aaataattca   6720
gcaatcctca aaaacagatg ccagtattct acaggaaaaa ttgggaagcc tgaatctgcg   6780
gtggcaggag gtctgcaaac agctgtcaga cagaaaaaag aggctagaag aacaaaagaa   6840
tatcttgtca gaatttcaaa gagatttaaa tgaatttgtt ttatggttgg aggaagcaga   6900
taacattgct agtatcccac ttgaacctgg aaaagagcag caactaaaag aaaagcttga   6960
gcaagtcaag ttactggtgg aagagttgcc cctgcgccag ggaattctca aacaattaaa   7020
tgaaactgga ggacccgtgc ttgtaagtgc tcccataagc ccagaagagc aagataaact   7080
tgaaaataag ctcaagcaga caaatctcca gtggataaag gtttccagag ctttacctga   7140
gaaacaagga gaaattgaag ctcaaataaa agaccttggg cagcttgaaa aaaagcttga   7200
agaccttgaa gagcagttaa atcatctgct gctgtggtta tctcctatta ggaatcagtt   7260
ggaaatttat aaccaaccaa accaagaagg accatttgac gttcaggaaa ctgaaatagc   7320
agttcaagct aaacaaccgg atgtggaaga gattttgtct aaagggcagc atttgtacaa   7380
ggaaaaacca gccactcagc cagtgaagag gaagttagaa gatctgagct ctgagtggaa   7440
ggcggtaaac cgtttacttc aagagctgag ggcaaagcag cctgacctag ctcctggact   7500
gaccactatt ggagcctctc ctactcagac tgttactctg gtgacacaac ctgtggttac   7560
taaggaaact gccatctcca aactagaaat gccatcttcc ttgatgttgg aggtacctgc   7620
tctggcagat ttcaaccggg cttggacaga acttaccgac tggctttctc tgcttgatca   7680
agttataaaa tcacagaggg tgatggtggg tgaccttgag gatatcaacg agatgatcat   7740
caagcagaag gcaacaatgc aggatttgga acagaggcgt ccccagttgg aagaactcat   7800
taccgctgcc caaaatttga aaaacaagac cagcaatcaa gaggctagaa caatcattac   7860
ggatcgaatt gaaagaattc agaatcagtg ggatgaagta caagaacacc ttcagaaccg   7920
gaggcaacag ttgaatgaaa tgttaaagga ttcaacacaa tggctggaag ctaaggaaga   7980
agctgagcag gtcttaggac aggccagagc caagcttgag tcatggaagg agggtcccta   8040
tacagtagat gcaatccaaa agaaaatcac agaaaccaag cagttggcca aagacctccg   8100
ccagtggcag acaaatgtag atgtggcaaa tgacttggcc ctgaaacttc tccgggatta   8160
ttctgcagat gataccagaa aagtccacat gataacagag aatatcaatg cctcttggag   8220
aagcattcat aaaagggtga gtgagcgaga ggctgctttg gaagaaactc atagattact   8280
gcaacagttc cccctggacc tggaaaagtt tcttgcctgg cttacagaag ctgaaacaac   8340
tgccaatgtc ctacaggatg ctacccgtaa ggaaaggctc ctagaagact ccaagggagt   8400
aaaagagctg atgaaacaat ggcaagacct ccaaggtgaa attgaagctc acacagatgt   8460
ttatcacaac ctggatgaaa acagccaaaa aatcctgaga tccctggaag gttccgatga   8520
tgcagtcctg ttacaaagac gtttggataa catgaacttc aagtggagtg aacttcggaa   8580
aaagtctctc aacattaggt cccatttgga agccagttct gaccagtgga agcgtctgca   8640
cctttctctg caggaacttc tggtgtggct acagctgaaa gatgatgaat taagccggca   8700
ggcacctatt ggaggcgact ttccagcagt tcagaagcag aacgatgtac atagggcctt   8760
caagagggaa ttgaaaacta aagaacctgt aatcatgagt actcttgaga ctgtacgaat   8820
atttctgaca gagcagcctt tggaaggact agagaaactc taccaggagc ccagagagct   8880
gcctcctgag gagagagccc agaatgtcac tcggcttcta cgaaagcagg ctgaggaggt   8940
```

-continued

```
caatactgag tgggaaaaat tgaacctgca ctccgctgac tggcagagaa aaatagatga   9000
gacccttgaa agactccagg aacttcaaga ggccacggat gagctggacc tcaagctgcg   9060
ccaagctgag gtgatcaagg gatcctggca gcccgtgggc gatctcctca ttgactctct   9120
ccaagatcac ctcgagaaag tcaaggcact tcgaggagaa attgcgcctc tgaaagagaa   9180
cgtgagccac gtcaatgacc ttgctcgcca gcttaccact ttgggcattc agctctcacc   9240
gtataacctc agcactctgg aagacctgaa caccagatgg aagcttctgc aggtggccgt   9300
cgaggaccga gtcaggcagc tgcatgaagc ccacagggac tttggtccag catctcagca   9360
ctttctttcc acgtctgtcc agggtccctg ggagagagcc atctcgccaa acaaagtgcc   9420
ctactatatc aaccacgaga ctcaaacaac ttgctgggac catcccaaaa tgacagagct   9480
ctaccagtct ttagctgacc tgaataatgt cagattctca gcttatagga ctgccatgaa   9540
actccgaaga ctgcagaagg ccctttgctt ggatctcttg agcctgtcag ctgcatgtga   9600
tgccttggac cagcacaacc tcaagcaaaa tgaccagccc atggatatcc tgcagattat   9660
taattgtttg accactattt atgaccgcct ggagcaagag cacaacaatt tggtcaacgt   9720
ccctctctgc gtggatatgt gtctgaactg gctgctgaat gtttatgata cgggacgaac   9780
agggaggatc cgtgtcctgt cttttaaaac tggcatcatt tccctgtgta aagcacattt   9840
ggaagacaag tacagatacc ttttcaagca agtggcaagt tcaacaggat tttgtgacca   9900
gcgcaggctg ggcctccttc ctgcatgatt ctatccaaat tccaagacag ttgggtgaag   9960
ttgcatcctt tgggggcagt aacattgagc caagtgtccg gagctgcttc caatttgcta  10020
ataataagcc agagatcgaa gcggccctct tcctagactg gatgagactg gaaccccagt  10080
ccatggtgtg gctgcccgtc ctgcacagag tggctgctgc agaaactgcc aagcatcagg  10140
ccaaatgtaa catctgcaaa gagtgtccaa tcattggatt caggtacagg agtctaaagc  10200
actttaatta tgacatctgc caaagctgct ttttttctgg tcgagttgca aaaggccata  10260
aaatgcacta tcccatggtg gaatattgca ctccgactac atcaggagaa gatgttcgag  10320
actttgccaa ggtactaaaa aacaaatttc gaaccaaaag gtattttgcg aagcatcccc  10380
gaatgggcta cctgccagtg cagactgtct tagaggggga caacatggaa actcccgtta  10440
ctctgatcaa cttctggcca gtagattctg cgcctgcctc gtcccctcag ctttcacacg  10500
atgatactca ttcacgcatt gaacattatg ctagcaggct agcagaaatg gaaaacagca  10560
atggatctta tctaaatgat agcatctctc ctaatgagag catagatgat gaacatttgt  10620
taatccagca ttactgccaa agtttgaacc aggactcccc cctgagccag cctcgtagtc  10680
ctgcccagat cttgatttcc ttagagagtg aggaaagagg ggagctagag agaatcctag  10740
cagatcttga ggaagaaaac aggaatctgc aagcagaata tgaccgtcta aagcagcagc  10800
acgaacataa aggcctgtcc ccactgccgt cccctcctga aatgatgccc acctctcccc  10860
agagtccccg ggatgctgag ctcattgctg aggccaagct actgcgtcaa cacaaaggcc  10920
gcctggaagc caggatgcaa atcctggaag accacaataa acagctggag tcacagttac  10980
acaggctaag gcagctgctg gagcaacccc aggcagaggc caaagtgaat ggcacaacgg  11040
tgtcctctcc ttctacctct ctacagaggt ccgacagcag tcagcctatg ctgctccgag  11100
tggttggcag tcaaacttcg gactccatgg gtgaggaaga tcttctcagt cctccccagg  11160
acacaagcac agggttagag gaggtgatgg agcaactcaa caactccttc cctagttcaa  11220
gaggaagaaa tacccctgga aagccaatga gagaggacac aatgtaggaa gtcttttcca  11280
```

-continued

```
catggcagat gatttgggca gagcgatgga gtccttagta tcattcatga cagatgaaga 11340
aggagcagaa taaatgtttt acaactcctg attcccgcat ggtttttata atattcatac 11400
aacaaagagg attagacagt aagagtttac aagaaataaa tctatatttt tgtgaagggt 11460
agtggtatta tactgtagat ttcagtagtt tctaagtctg ttattgtttt gttaacaatg 11520
gcaggtttta cacgtctatg caattgtaca aaaaagttat aagaaaacta catgtaaaat 11580
cttgatagct aaataacttg ccatttcttt atatggaacg cattttgggt tgtttaaaaa 11640
tttataacag ttataaagaa agattgtaaa ctaaagtgtg ctttataaaa aaaagttgtt 11700
tataaaaacc cctaaaaaca nnnnnnnnnn nnnnnnnnnn nnnnnnnnnn nnnnnnnnnn 11760
nactttgagg cagcgcattg ttttgcatcc ttttggcgtg atatccatat gaaattcatg 11820
gctttttctt tttttgcata ttaaagataa gacttcctct accaccacac caaatgacta 11880
ctacacactg ctcatttgag aactgtcagc tgagtggggc aggcttgagt tttcatttca 11940
tatatctata tgtctataag tatataaata ctatagttat atagataaag agatacgaat 12000
ttctatagac tgactttttc catttttttaa atgttcatgt cacatcctaa tagaaagaaa 12060
ttacttctag tcagtcatcc aggcttacct gcttggtcta gaatggattt ttcccggagc 12120
cggaagccag gaggaaacta caccacacta aaacattgtc tacagctcca gatgtttctc 12180
attttaaaca actttccact gacaacgaaa gtaaagtaaa gtattggatt tttttaaagg 12240
gaacatgtga atgaatacac aggacttatt atatcagagt gagtaatcgg ttgnttggtt 12300
gattgattga ttgattgata cattcagctt cctgctgcta gcaatgccac gatttagatt 12360
taatgatgct tcagtggaaa tcaatcagaa ggtattctga ccttgtgaac atcagaaggt 12420
attttttaac tcccaagcag tagcaggacg atgatagggc tggagggcta tggattccca 12480
gcccatccct gtgaaggagt aggccactct ttaagtgaag gattggatga ttgttcataa 12540
tacataaagt tctctgtaat tacaactaaa ttattatgcc ctcttctcac agtcaaaagg 12600
aactgggtgg tttggttttt gttgcttttt tagatttatt gtcccatgtg ggatgagttt 12660
ttaaatgcca caagacataa tttaaaataa ataaactttg ggaaaaggtg taaaacagta 12720
gccccatcac atttgtgata ctgacaggta tcaacccaga agcccatgaa ctgtgtttcc 12780
atcctttgca tttctctgcg agtagttcca cacaggtttg taagtaaagt aagtaagaaa 12840
gaaggcaaat tgattcaaat gttacaaaaa aacccttctt ggtggattag acaggttaaa 12900
tatataaaca aacaaacaaa aattgctcaa aaaagaggag aaaagctcaa gaggaaaagc 12960
taaggactgg taggaaaaag ctttactctt tcatgccatt ttatttcttt ttgattttta 13020
aatcattcat tcaatagata ccaccgtgtg acctataatt ttgcaaatct gttacctctg 13080
acatcaagtg taattagctt ttggagagtg ggctgacatc aagtgtaatt agcttttgga 13140
gagtgggttt tgtccattat taataattaa ttaattaaca tcaaacacgg gcttctcatg 13200
ctatttctac ctcactttgg ttttggggtg ttcctgataa ttgtgcacac ctgagttcac 13260
agcttcacca cttgtccatt gcgttatttt ctttttcctt tataattctt tctttttcct 13320
tcataatttt caaaagaaaa cccaaagctc taaggtaaca aattaccaaa ttacatgaag 13380
atttggtttt tgtcttgcat ttttttcctt tatgtgacgc tggacctttt ctttacccaa 13440
ggatttttaa aactcagatt taaaacaagg ggttacttta catcctacta agaagtttaa 13500
gtaagtaagt ttcattctaa aatcagaggt aaatagagtg cataaataat tttgttttaa 13560
tctttttgtt tttcttttag acacattagc tctggagtga gtctgtcata atatttgaac 13620
aaaaattgag agctttattg ctgcatttta agcataatta atttggacat tatttcgtgt 13680
```

```
tgtgttcttt ataaccacca agtattaaac tgtaaatcat aatgtaactg aagcataaac  13740

atcacatggc atgttttgtc attgttttca ggtactgagt tcttacttga gtatcataat  13800

atattgtgtt ttaacaccaa cactgtaaca tttacgaatt atttttttaa acttcagttt  13860

tactgcattt tcacaacata tcagacttca ccaaatatat gccttactat tgtattatag  13920

tactgcttta ctgtgtatct caataaagca cgcagttatg ttacaaaana aaaaaaa     13977
```

```
<210> SEQ ID NO 61
<211> LENGTH: 1229
<212> TYPE: DNA
<213> ORGANISM: Homo sapiens
<220> FEATURE:
<221> NAME/KEY: misc_feature
<223> OTHER INFORMATION: Incyte ID No: 480668.3
<221> NAME/KEY: unsure
<222> LOCATION: 650, 660, 665, 676-677
<223> OTHER INFORMATION: a, t, c, g, or other

<400> SEQUENCE: 61

tcgggatcga tctggagctc cgggaatttc cctggcccgg gactccgggc tttccagccc     60
caaccatgca taaaaggggt tcgccgttct cggagagcca cagagcccgg gccacaggca    120
gctccttgcc agctctcccg cttctcgcac agccgctgcg aaccgcctgc tgagccccca    180
tggcccgcgc cacgctctcc gccgccccca gcaatccccg gctcctgcgg gtggcgctgc    240
tgctcctgct cctggtggcc gccagccggc gcgcagcagg agcgcccctg gccactgcaa    300
ctgcgctgcc agtgccttgc agaccctgcc agggaattca ccttcaagaa catccaaagt    360
gtgaaggtga agtcccccgg accccactgc gcccaaaccg aagtcatagc cacactcaag    420
aatgggcaga aagcttgtct caaccccgca tcgcccatgg ttaagaaaat catcgaaaag    480
atgctgaaaa atggcaaatc caactgacca gaaggaagga ggaagcttat tggtggctgt    540
tcctgaagga ggccctgccc ttacaggaac agaagaggaa agagagacac agctgcagag    600
gccacctggg attgcgccta atgtgtttga gcatcactta ggagaaggcn ccgattaatn    660
aattnattaa tttatnnatt ggttggtttt agaagattct atgttaatat tttatgtgta    720
aaataaggtt atgattgaat ctacttgcac actctcccat tatatttatt gtttatttta    780
ggtcaaaccc aagttagttc aatcctgatt catatttaat ttgaagatag aaggtttgca    840
gatattctct agtcatttgt taatatttct tcgtgatgac atatcacatg tcagccactg    900
tgatagaggc tgaggaatcc aagaaaatgg ccagtaagat caatgtgacg gcagggaaat    960
gtatgtgtgt ctattttgta actgtaaaga tgaatgtcag ttgttattta ttgaaatgat   1020
ttcacagtgt gtggtcaaca tttctcatgt tgaagcttta agaactaaaa tgttctaaat   1080
atcccttgga cattttatgt ctttcttgta aggcatactg ccttgtttaa tgttaattat   1140
gcagtgtttc cctctgtgtt agagcagaga ggtttcgata tttattgatg ttttcacaaa   1200
gaacaggaaa ataaaatatt taaaaatat                                     1229
```

```
<210> SEQ ID NO 62
<211> LENGTH: 1981
<212> TYPE: DNA
<213> ORGANISM: Homo sapiens
<220> FEATURE:
<221> NAME/KEY: misc_feature
<223> OTHER INFORMATION: Incyte ID No: 245334.1

<400> SEQUENCE: 62

cctagctggg atattggagc agcaagaggc tgggaagcca tcacttacct tgcactgaga     60

aagaagacaa aggccagtat gcacagcttt cctccactgc tggctgctgc tgttctgggg    120

tgtggtgtct cacagcttcc cagcgactct agaaacacaa gagcaagatg tggacttagt    180

ccagaaatac ctggaaaaat actacaacct gaagaatgat gggaggcaag ttgaaaagcg    240

gagaaatagt ggcccagtgg ttgaaaaatt gaagcaaatg caggaattct ttgggctgaa    300

agtgactggg aaaccagatg ctgaaaccct gaaggtgatg aagcagccca gatgtggagt    360

gcctgatgtg gctcagtttg tcctcactga ggggaaccct cgctgggagc aaacacatct    420

gacctacagg attgaaaatt acacgccaga tttgccaaga gcagatgtgg accatgccat    480

tgagaaagcc ttccaactct ggagtaatgt cacacctctg acattcacca aggtctctga    540

gggtcaagca gacatcatga tatcttttgt caggggagat catcgggaca actctccttt    600

tgatggacct ggaggaaatc ttgctcatgc ttttcaacca ggcccaggta ttggaggggga    660
```

```
tgctcatttt gatgaagatg aaaggtggac caacaatttc agagagtaca acttacatcg     720
tgttgcggct catgaactcg gccattctct tggactctcc cattctactg atatcggggc     780
tttgatgtac cctagctaca ccttcagtgg tgatgttcag ctagctcagg atgacattga     840
tggcatccaa gccatatatg gacgttccca aaatcctgtc cagcccatcg gcccacaaac     900
cccaaaagcg tgtgacagta agctaacctt tgatgctata actacgattc ggggagaagt     960
gatgttcttt aaagacagat tctacatgcg cacaaatccc ttctacccgg aagttgagct    1020
caatttcatt tctgttttct ggccacaact gccaaatggg cttgaagctg cttacgaatt    1080
tgccgacaga gatgaagtcc ggtttttcaa agggaataag tactgggctg ttcagggaca    1140
gaatgtgcta cacggatacc ccaaggacat ctacagctcc tttggcttcc ctagaactgt    1200
gaagcatatc gatgctgctc tttctgagga aaacactgga aaaacctact tctttgttgc    1260
taacaaatac tggaggtatg atgaatataa acgatctatg gatccaggtt atcccaaaat    1320
gatagcacat gactttcctg gaattggcca caaagttgat gcagttttca tgaaagatgg    1380
atttttctat ttctttcatg gaacaagaca atacaaattt gatcctaaaa cgaagagaat    1440
tttgactctc cagaaagcta atagctggtt caactgcagg aaaaattgaa cattactaat    1500
ttgaatggaa aacacatggt gtgagtccaa agaaggtgtt ttcctgaaga actgtctatt    1560
ttctcagtca tttttaacct ctagagtcac tgatacacag aatataatct tatttatacc    1620
tcagtttgca tattttttta ctatttagaa tgtagccctt tttgtactga tataatttag    1680
ttccacaaat ggtgggtaca aaaagtcaag tttgtggctt atggattcat ataggccaga    1740
gttgcaaaga tcttttccag agtatgcaac tctgacgttg atcccagaga gcagcttcag    1800
tgacaaacat atcctttcaa gacagaaaga gacaggagac atgagtcttt gccggaggaa    1860
aagcagctca agaacacatg tgcagtcact ggtgtcaccc tggataggca agggataact    1920
cttctaacac aaaataagtg ttttatgttt ggaataaagt caaccttgtt tctactgttt    1980
t                                                                    1981
```

```
<210> SEQ ID NO 63
<211> LENGTH: 1734
<212> TYPE: DNA
<213> ORGANISM: Homo sapiens
<220> FEATURE:
<221> NAME/KEY: misc_feature
<223> OTHER INFORMATION: Incyte ID No: 201752.1
<221> NAME/KEY: unsure
<222> LOCATION: 1444, 1455, 1457, 1461, 1463, 1465, 1467, 1497, 1500,
      1506, 1521, 1534-
<223> OTHER INFORMATION: a, t, c, g, or other

<400> SEQUENCE: 63
```

```
gaattcgcac tgctctgaga atttgtgagc agcccctaac aggctgttac ttcactacaa      60
ctgacgatat gatcatctta atttacttat ttctcttgct atgggaagac actcaaggat     120
ggggattcaa ggatggaatt tttcataact ccatatggct tgaacgagca gccggtgtgt     180
accacagaga agcacggtct ggcaaataca agctcaccta cgcagaagct aaggcggtgt     240
gtgaatttga aggcggccat ctcgcaactt acaagcagct agaggcagcc agaaaaattg     300
gatttcatgt ctgtgctgct ggatggatgg ctaagggcag agttggatac cccattgtga     360
agccagggcc ccaactgtgg atttggaaaa actggcatta ttgattatgg aatccgtctc     420
aataggagtg aaagatggga tgcctattgc tacaacccac acgcaaagga gtgtggtggc     480
gtctttacag atccaaagca aatttttaaa tctccaggct tcccaaatga gtacgaagat     540
```

-continued

```
aaccaaatct gctactggca cattagactc aagtatggtc agcgtattca cctgagtttt    600

ttagattttg accttgaaga tgacccaggt tgcttggctg attatgttga aatatatgac    660

agttacgatg atgtccatgg ctttgtggga agatactgtg gagatgagct tccagatgac    720

atcatcagta caggaaatgt catgaccttg aagtttctaa gtgatgcttc agtgacagct    780

ggaggtttcc aaatcaaata tgttgcaatg gatcctgtat ccaaatccag tcaaggaaaa    840

aatacaagta ctacttctac tggaaataaa aactttttag ctggaagatt tagccactta    900

taaaaaaaaa aaaaggatga tcaaaacaca cagtgtttat gttggaatct tttggaactc    960

ctttgatctc actgttatta ttaacattta tttattattt ttctaaatgt gaaagcaata   1020

cataatttag ggaaaattgg aaaatatagg aaactttaaa cgagaaaatg aaacctctca   1080

taatcccact gcatagaaat aacaagcgtt aacattttca tatttttttc tttcagtcat   1140

ttttctattt gtggtatatg tatatatgta cctatatgta tttgcatttg aaattttgga   1200

atcctgctct atgtacagtt ttgtattata ctttttaaat cttgaacttt ataaacattt   1260

tctgaaatca ttgattattc tacaaaaaca tgattttaaa cagctgtaaa atattctatg   1320

atatgaatgt tttatgcatt atttaagcct gtctctattg ttggaatttc aggtcatttt   1380

cataaatatt gttgcaataa atatccttga acacacatat tgtgcacctc tctaattatt   1440

taanacaagg acctngnaat ngnantnctg aatcaaaggt taattccaat aaaattntcn   1500

gttttnatag gcaaaaatga ngcctcactg tagnntgaat tngcatnnct ttattcatga   1560

ganngatggt tntntaantt tttgttaatt ttttttgtga annatttttc catgccnttt   1620

ngtcactatt tttaaaaact gatataatct tcnctattga tttgttagaa antattanat   1680

atgtccatgt ttgtcatata tgctntaatt taatttttag tttatatttt gtct         1734
```

<210> SEQ ID NO 64
<211> LENGTH: 831
<212> TYPE: DNA
<213> ORGANISM: Homo sapiens
<220> FEATURE:
<221> NAME/KEY: misc_feature
<223> OTHER INFORMATION: Incyte ID No: 028779.3

<400> SEQUENCE: 64

```
gcactcccaa agaactgggt actcaacact gagcagatct gttctttgag ctaaaaacca     60

tgtgctgtac caagagtttg ctcctggctg ctttgatgtc agtgctgcta ctccacctct    120

gcggcgaatc agaagcagca agcaactttg actgctgtct tggatacaca gaccgtattc    180

ttcatcctaa atttattgtg ggcttcacac ggcagctggc caatgaaggc tgtgacatca    240

atgctatcat ctttcacaca aagaaaaagt tgtctgtgtg cgcaaatcca aaacagactt    300

gggtgaaata tattgtgcgt ctcctcagta aaaaagtcaa gaacatgtaa aaactgtggc    360

ttttctggaa tggaattgga catagcccaa gaacagaaag aaccttgctg gggttggagg    420

tttcacttgc acatcatgga gggtttagtg cttatctaat ttgtgcctca ctggacttgt    480

ccaattaatg aagttgattc atattgcatc atagtttgct ttgtttaagc atcacattaa    540

agttaaactg tattttatgt tatttatagc tgtaggtttt ctgtgtttag ctatttaata    600

ctaattttcc ataagctatt ttggtttagt gcaaagtata aaattatatt tggggggggaa    660

taagattata tggactttct tgcaagcaac aagctatttt ttaaaaaaaa ctatttaaca    720

ttcttttgtt tatattgttt tgtctcctaa attgttgtaa ttgcattata aaataagaaa    780

aatattaata agacaaatat tgaaaataaa gaaacaaaaa gttaaaaaaa a             831
```

<210> SEQ ID NO 65
<211> LENGTH: 8257
<212> TYPE: DNA
<213> ORGANISM: Homo sapiens
<220> FEATURE:
<221> NAME/KEY: misc_feature
<223> OTHER INFORMATION: Incyte ID No: 285840.2
<221> NAME/KEY: unsure
<222> LOCATION: 7391, 8247
<223> OTHER INFORMATION: a, t, c, g, or other

<400> SEQUENCE: 65

```
acgcggcgcg gaggctggcc cgggacgcgc ccggagccca gggaaggagg gaggagggga     60
gggtcgcggc cggccgccat ggggccgggg gcccgtggcc gccgccgccg ccgtcgcccg    120
atgtcgccgc caccgccacc gccacccgtg cgggcgctgc ccctgctgct gctgctagcg    180
gggccggggg ctgcagcccc cccttgcctg gacggaagcc cgtgtgcaaa tggaggtcgt    240
tgcacccagc tgccctcccg ggaggctgcc tgcctgtgcc cgcctggctg ggtgggtgag    300
cggtgtcagc tggaggaccc ctgtcactca ggcccctgtg ctggccgtgg tgtctgccag    360
agttcagtgg tggctggcac cgcccgattc tcatgccggt gcccccgtgg cttccgaggc    420
cctgactgct ccctgccaga tccctgcctc agcagccctt gtgcccacgg tgcccgctgc    480
tcagtggggc ccgatggacg cttcctctgc tcctgcccac ctggctacca gggccgcagc    540
tgccgaagcg acgtggatga gtgccgggtg ggtgagccct gccgccatgg tggcacctgc    600
ctcaacacac ctggctcctt ccgctgccag tgtccagctg gctacacagg gccactatgt    660
gagaaccccg cggtgccctg tgcgccctca ccatgccgta acgggggcac ctgcaggcag    720
agtggcgacc tcacttacga ctgtgcctgt cttcctgggt ttgagggtca gaattgtgaa    780
gtgaacgtgg acgactgtcc aggacaccga tgtctcaatg gggggacatg cgtggatggc    840
gtcaacacct ataactgcca gtgccctcct gagtggacag gccagttctg cacggaggac    900
gtggatgagt gtcagctgca gcccaacgcc tgccacaatg gggtacctg cttcaacacg    960
ctgggtggcc acagctgcgt gtgtgtcaat ggctggacag gcgagagctg cagtcagaat   1020
atcgatgact gtgccacagc cgtgtgcttc catggggcca cctgccatga ccgcgtggct   1080
tctttctact gtgcctgccc catgggcaag actggcctcc tgtgtcacct ggatgacgcc   1140
tgtgtcagca acccctgcca cgaggatgct atctgtgaca caaatccggt gaacggccgg   1200
gccatttgca cctgtcctcc cggcttcacg ggtggggcat gtgaccagga tgtggacgag   1260
tgctctatcg gcgccaaccc ctgcgagcac ttgggcaggt gcgtgaacac gcagggctcc   1320
ttcctgtgcc agtgcggtcg tggctacact ggacctcgct gtgagaccga tgtcaacgag   1380
tgtctgtcgg ggccctgccg aaaccaggcc acgtgcctcg accgcatagg ccagttcacc   1440
tgtatctgta tggcaggctt cacaggaacc tattgcgagg tggacattga cgagtgtcag   1500
agtagcccct gtgtcaacgg tggggtctgc aaggaccgag tcaatggctt cagctgcacc   1560
tgcccctcgg gcttcagcgg ctccacgtgt cagctggacg tggacgaatg cgccagcacg   1620
ccctgcagga atggcgccaa atgcgtggac cagcccgatg gctacgagtg ccgctgtgcc   1680
gagggctttg agggcacgct gtgtgatcgc aacgtggacg actgctcccc tgacccatgc   1740
caccatggtc gctgcgtgga tggcatcgcc agcttctcat gtgcctgtgc tcctggctac   1800
acgggcacac gctgcgagag ccaggtggac gaatgccgca gccagccctg ccgccatggc   1860
ggcaaatgcc tagacctggt ggacaagtac ctctgccgct gcccttctgg gaccacaggt   1920
```

-continued

```
gtgaactgcg aagtgaacat tgacgactgt gccagcaacc cctgcacctt tggagtctgc   1980
cgtgatggca tcaaccgcta cgactgtgtc tgccaacctg gcttcacagg gcccctttgt   2040
aacgtggaga tcaatgagtg tgcttccagc ccatgcggcg agggaggttc ctgtgtggat   2100
ggggaaaatg gcttccgctg cctctgcccg cctggctcct tgcccccact ctgcctcccc   2160
ccgagccatc cctgtgccca tgagccctgc agtcacggca tctgctatga tgcacctggc   2220
gggttccgct gtgtgtgtga gcctggctgg agtggccccc gctgcagcca gagcctggcc   2280
cgagacgcct gtgagtccca gccgtgcagg gccggtggga catgcagcag cgatggaatg   2340
ggtttccact gcacctgccc gcctggtgtc cagggacgtc agtgtgaact cctctccccc   2400
tgcaccccga accccctgtga gcatgggggc cgctgcgagt ctgcccctgg ccagctgcct   2460
gtctgctcct gcccccaggg ctggcaaggc ccacgatgcc agcaggatgt ggacgagtgt   2520
gctggccccg caccctgtgg ccctcatggt atctgcacca acctggcagg gagtttcagc   2580
tgcacctgcc atggagggta cactggccct tcctgtgatc aggacatcaa tgactgtgac   2640
cccaacccat gcctgaacgg tggctcgtgc caagacggcg tgggctcctt ttcctgctcc   2700
tgcctccctg gtttcgccgg cccacgatgc gcccgcgatg tggatgagtg cctgagcaac   2760
ccctgcggcc cgggcacctg taccgaccac gtggcctcct tcacctgcac ctgcccgccg   2820
ggctacggag gcttccactg cgaacaggac ctgcccgact gcagccccag ctcctgcttc   2880
aatggcggga cctgtgtgga cggcgtgaac tcgttcagct gcctgtgccg tcccggctac   2940
acaggagccc actgccaaca tgaggcagac ccctgcctct cgcggccctg cctacacggg   3000
ggcgtctgca gcgccgccca ccctggcttc cgctgcacct gcctcgagag cttcacgggc   3060
ccgcagtgcc agacgctggt ggattggtgc agccgccagc cttgtcaaaa cgggggtcgc   3120
tgcgtccaga ctggggccta ttgcctttgt ccccctggat ggagcggacg cctctgtgac   3180
atccgaagct tgccctgcag ggaggccgca gcccagatcg gggtgcggct ggagcagctg   3240
tgtcaggcgg gtgggcagtg tgtggatgaa gacagctccc actactgcgt gtgcccagag   3300
ggccgtactg gtagccactg tgagcaggag gtggacccct gcttggccca gccctgccag   3360
catgggggga cctgccgtgg ctatatgggg ggctacatgt gtgagtgtct tcctggctac   3420
aatggtgata actgtgagga cgacgtggac gagtgtgcct cccagccctg ccagcacggg   3480
ggttcatgca ttgacctcgt ggcccgctat ctctgctcct gtcccccagg aacgctgggg   3540
gtgctctgcg agattaatga ggatgactgc ggcccaggcc caccgctgga ctcagggccc   3600
cggtgcctac acaatggcac ctgcgtggac ctggtgggtg gtttccgctg cacctgtccc   3660
ccaggataca ctggtttgcg ctgcgaggca gacatcaatg agtgtcgctc aggtgcctgc   3720
cacgcggcac acacccggga ctgcctgcag gacccaggcg gaggtttccg ttgcctttgt   3780
catgctggct tctcaggtcc tcgctgtcag actgtcctgt ctccctgcga gtcccagcca   3840
tgccagcatg gaggccagtg ccgtcctagc ccgggtcctg gggtgggct gaccttcacc   3900
tgtcactgtg cccagccgtt ctggggtccg cgttgcgagc gggtggcgcg ctcctgccgg   3960
gagctgcagt gcccggtggg cgtcccatgc cagcagacgc ccgcgggccc gcgctgcgcc   4020
tgcccccccag ggttgtcggg accctcctgc cgcagcttcc cggggtcgcc gccgggggcc   4080
agcaacgcca gctgcgcggc cgccccctgt ctccacgggg gctcctgccg ccccgcgccg   4140
ctcgcgccct tcttccgctg cgcttgcgcg cagggctgga ccgggccgcg ctgcgaggcg   4200
cccgccgcgg cacccgaggt ctcggaggag ccgcggtgcc cgcgcgccgc ctgccaggcc   4260
aagcgcgggg accagcgctg cgaccgcgag tgcaacagcc caggctgcgg ctgggacggc   4320
```

-continued

```
ggcgactgct cgctgagcgt gggcgacccc tggcggcaat gcgaggcgct gcagtgctgg   4380
cgcctcttca acaacagccg ctgcgacccc gcctgcagct cgcccgcctg cctctacgac   4440
aacttcgact gccacgccgg tggccgcgag cgcacttgca acccggtgta cgagaagtac   4500
tgcgccgacc actttgccga cggccgctgc gaccagggct gcaacacgga ggagtgcggc   4560
tgggatgggc tggattgtgc cagcgaggtg ccggccctgc tggcccgcgg cgtgctggtg   4620
ctcacagtgc tgctgccgcc ggaggagcta ctgcgttcca gcgccgactt tctgcagcgg   4680
ctcagcgcca tcctgcgcac ctcgctgcgc ttccgcctgg acgcgcacgg ccaggccatg   4740
gtcttccctt accaccggcc tagtcctggc tccgaacccc gggcccgtcg ggagctggcc   4800
cccgaggtga tcggctcggt agtaatgctg gagattgaca accggctctg cctgcagtcg   4860
cctgagaatg atcactgctt ccccgatgcc cagagcgccg ctgactacct gggagcgttg   4920
tcagcggtgg agcgcctgga cttcccgtac ccactgcggg acgtgcgggg ggagccgctg   4980
gagcctccag aacccagcgt cccgctgctg ccactgctag tggcgggcgc tgtcttgctg   5040
ctggtcattc tcgtcctggg tgtcatggtg gcccggcgca agcgcgagca cagcaccctc   5100
tggttccctg agggcttctc actgcacaag gacgtggcct ctggtcacaa gggccggcgg   5160
gaacccgtgg gccaggacgc gctgggcatg aagaacatgg ccaagggtga gagcctgatg   5220
ggggaggtgg ccacagactg gatggacaca gagtgcccag aggccaagcg gctaaaggta   5280
gaggagccag gcatgggggc tgaggaggct gtggattgcc gtcagtggac tcaacaccat   5340
ctggttgctg ctgacatccg cgtggcacca gccatggcac tgacaccacc acagggcgac   5400
gcagatgctg atggcatgga tgtcaatgtg cgtggcccag atggcttcac cccgctaatg   5460
ctggcttcct tctgtggggg ggctctggag ccaatgccaa ctgaagagga tgaggcagat   5520
gacacatcag ctagcatcat ctccgacctg atctgccagg gggctcagct tggggcacgg   5580
actgaccgta ctggcgagac tgctttgcac ctggctgccc gttatgcccg tgctgatgca   5640
gccaagcggc tgctggatgc tggggcagac accaatgccc aggaccactc aggccgcact   5700
cccctgcaca cagctgtcac agccgatgcc cagggtgtct tccagattct catccgaaac   5760
cgctctacag acttggatgc ccgcatggca gatggctcaa cggcactgat cctggcggcc   5820
cgcctggcag tagagggcat ggtggaagag ctcatcgcca gccatgctga tgtcaatgct   5880
gtggatgagc ttgggaaatc agccttacac tgggctgcgg ctgtgaacaa cgtggaagcc   5940
actttggccc tgctcaaaaa tggagccaat aaggacatgc aggatagcaa ggaggagacc   6000
cccctattcc tggccgcccg cgagggcagc tatgaggctg ccaagctgct gttggaccac   6060
tttgccaacc gtgagatcac cgaccacctg gacaggctgc cgcgggacgt agcccaggag   6120
agactgcacc aggacatcgt gcgcttgctg gatcaaccca gtgggccccg cagccccccc   6180
ggtccccacg gcctggggcc tctgctctgt cctccagggg ccttcctccc tggcctcaaa   6240
gcggcacagt cggggtccaa gaagagcagg aggccccccg ggaaggcggg gctggggccg   6300
caggggcccc gggggcgggg caagaagctg acgctggcct gcccgggccc cctggctgac   6360
agctcggtca cgctgtcgcc cgtggactcg ctggactccc cgcggccttt cggtgggccc   6420
cctgcttccc ctggtggctt ccccccttgag ggccctatg cagctgccac tgccactgca   6480
gtgtctctgg cacagcttgg tggcccaggc cgggcgggtc tagggcgcca gcccccctggg   6540
aggatgtgta ctcagcctgg gcctgctgaa ccctgtggct gtgcccctcg attgggcccg   6600
gctgccccca cctgcccctc caggcccctc gttcctgctg ccactggcgc cgggacccca   6660
```

-continued

```
gctgctcaac ccagggaccc ccgtctcccc gcaggagcgg cccccgcctt acctggcagt   6720

cccaggacat ggcgaggagt acccggcggc tggggcacac agcagccccc caaaggcccg   6780

cttcctgcgg gttcccagtg agcaccctta cctgacccca tcccccgaat cccctgagca   6840

ctgggccagc ccctcacctc cctccctctc agactggtcc gaatccacgc ctagcccagc   6900

cactgccact ggggccatgg ccaccaccac tggggcactg cctgcccagc cacttccctt   6960

gtctgttccc agctcccttg ctcaggccca gacccagctg gggccccagc cggaagttac   7020

ccccaagagg caagtgttgg cctgagacgc tcgtcagttc ttagatcttg gggcctaaa    7080

gagacccccg tcctgcctcc tttctttctc tgtctcttcc ttccttttag tctttttcat   7140

cctcttctct ttccaccaac cctcctgcat ccttgccttg caagcgtgac cgagataggt   7200

catcagccca gggcttcagt cttcctttat ttataatggg tgggggctac cacccaccct   7260

ctcagtcttg tgaagagtct gggacctcct tcttccccac ttctctcttc cctcattcct   7320

ttctctctcc ttctggcctc tcatttcctt acactctgac atgaatgaat tattattatt   7380

tttctttttc ntttgttttt ttacattttg tatagaaaca aattcattta aacaaactta   7440

ttattattat tttttacaaa atatatatat ggagatgctc cctccccctg tgaacccccc   7500

agtgcccccg tggggctgag tctgtgggcc cattcggcca agctggattc tgtgtaccta   7560

gtacacaggc atgactggga tcccgtgtac cgagtacacg acccaggtat gtaccaagta   7620

ggcacccttg ggcgcaccca ctggggccag gggtcggggg agtgttggga gcctcctccc   7680

caccccacct ccctcacttc actgcattcc agattggaca tgttccatag ccttgctggg   7740

gaagggccca ctgccaactc cctctgcccc agccccaccc ttggccatct ccctttggga   7800

actagggggc tgctggtggg aaatgggagc cagggcagat gtatgcattc ctttatgtcc   7860

ctgtaaatgt gggactacaa gaagaggagc tgcctgagtg gtactttctc ttcctggtaa   7920

tcctctggcc cagccttatg gcagaataga ggtattttta ggctattttt gtaatatggc   7980

ttctggtcaa aatccctgtg tagctgaatt cccaagccct gcattgtaca gccccccact   8040

cccctcacca cctaataaag gaatagttaa cactcagtgt tgttggtctg tgtctaggta   8100

aggtggggag tggtggcagt gggacttcta tctcccccac ccagggctaa cttgagctcc   8160

catcttgggg taaatacatt tgacttgcca gtctacttat gcttcctctt ttggcagatg   8220

actaccgatt ggattagtgg ttgtcanctg acttaag                             8257
```

<210> SEQ ID NO 66
<211> LENGTH: 6814
<212> TYPE: DNA
<213> ORGANISM: Homo sapiens
<220> FEATURE:
<221> NAME/KEY: misc_feature
<223> OTHER INFORMATION: Incyte ID No: 199882.3
<221> NAME/KEY: unsure
<222> LOCATION: 1838, 5528
<223> OTHER INFORMATION: a, t, c, g, or other

<400> SEQUENCE: 66

```
gggagccggc cgtggtggct ccgtgcgtcc gagcgtccgt ccgcgccgtc ggccatggcc     60

aagcgctcca ggggccccgg gcgccgctgc ctgttggcgc tcgtgctgtt ctgcgcctgg    120

gggacgctgg ccgtggtggc ccagaagccg ggcgcagggt gtccgagccg ctgcctgtgc    180

ttccgcacca ccgtgcgctg catgcatctg ctgctggagg ccgtgcccgc cgtggcgccg    240

cagacctcca tcctagatct tcgctttaac agaatcagag agatccaacc tggggcattc    300

aggcggctga ggaacttgaa cacattgctt ctcaataata atcagatcaa gaggatacct    360
```

```
agtggagcat ttgaagactt ggaaaattta aaatatctct atctgtacaa gaatgagatc    420
cagtcaattg acaggcaagc atttaaggga cttgcctctc tagagcaact atacctgcac    480
tttaatcaga tagaaacttt ggacccagat tcgttccagc atctcccgaa gctcgagagg    540
ctatttttgc ataacaaccg gattacacat ttagttccag ggacatttaa tcacttggaa    600
tctatgaaga gattgcgact ggactcaaac acacttcact gcgactgtga aatcctgtgg    660
ttggcggatt tgctgaaaac ctacgcggag tcggggaacg cgcaggcagc ggccatctgt    720
gaatatccca gacgcatcca gggacgctca gtggcaacca tcaccccgga agagctgaac    780
tgtgaaaggc cccggatcac ctccgagccc caggacgcag atgtgacctc ggggaacacc    840
gtgtacttca cctgcagagc cgaaggcaac cccaagcctg agatcatctg gctgcgaaac    900
aataatgagc tgagcatgaa gacagattcc cgcctaaact tgctggacga tgggaccctg    960
atgatccaga acacacagga gacagaccag ggtatctacc agtgcatggc aaagaacgtg   1020
gccggagagg tgaagacgca agaggtgacc ctcaggtact tcgggtctcc agctcgaccc   1080
acttttgtaa tccagccaca gaatacagag gtgctggttg ggagagcgt cacgctggag   1140
tgcagcgcca caggccaccc cccgccgcgg atctcctgga cgagaggtga ccgcacaccc   1200
ttgccagttg acccgcgggt gaacatcacg ccttctggcg ggctttacat acagaacgtc   1260
gtacaggggg acagcggaga gtatgcgtgc tctgcgacca acaacattga cagcgtccat   1320
gccaccgctt tcatcatcgt ccaggctctt cctcagttca ctgtgacgcc tcaggacaga   1380
gtcgttattg agggccagac cgtggatttc cagtgtgaag ccaagggcaa cccgccgccc   1440
gtcatcgcct ggaccaaggg agggagccag ctctccgtgg accggcggca cctggtcctg   1500
tcatcgggaa cacttagaat ctctggtgtt gccctccacg accagggcca gtacgaatgc   1560
caggctgtca acatcatcgg ctcccagaag gtcgtggccc acctgactgt gcagcccaga   1620
gtcaccccag tgtttgccag cattcccagc gacacaacag tggaggtggg cgccaatgtg   1680
cagctcccgt gcagctccca gggcgagccc gagccagcca tcacctggaa caaggatggg   1740
gttcaggtga cagaaagtgg aaaatttcac atcagccctg aaggattctt gaccatcaat   1800
gacgttggcc ctgcagacgc aggtcgctat gagtgtgngg cccggaacac cattgggtcg   1860
gcctcggtga gcatggtgct cagtgtgaat gttcctgacg tcagtcgaaa tggagatccg   1920
tttgtagcta cctccatcgt ggaagcgatt gcgactgttg acagagctat aaactcaacc   1980
cgaacacatt tgtttgacag ccgtcctcgt tctccaaatg atttgctggc cttgttccgg   2040
tatccgaggg atccttacac agttgaacag gcacgggcgg gagaaatctt tgaacggaca   2100
ttgcagctca ttcaggagca tgtacagcat ggcttgatgg tcgacctcaa cggaacaagt   2160
taccactaca acgacctggt gtctccacag tacctgaacc tcatcgcaaa cctgtcgggc   2220
tgtaccgccc accggcgcgt gaacaactgc tcggacatgt gcttccacca gaagtaccgg   2280
acgcacgacg gcacctgtaa caacctgcag caccccatgt ggggcgcctc gctgaccgcc   2340
ttcgagcgcc tgctgaaatc cgtgtacgag aatggcttca acacccctcg gggcatcaac   2400
ccccaccgac tgtacaacgg gcacgccctt cccatgccgc gcctggtgtc caccaccctg   2460
atcgggacgg agaccgtcac acccgacgag cagttcaccc acatgctgat gcagtggggc   2520
cagttcctgg accacgacct cgactccacg gtggtggccc tgagccaggc acgcttctcc   2580
gacggacagc actgcagcaa cgtgtgcagc aacgaccccc cctgcttctc tgtcatgatc   2640
ccccccaatg actcccgggc caggagcggg gcccgctgca tgttcttcgt gcgctccagc   2700
```

-continued

```
cctgtgtgcg gcagcggcat gacttcgctg ctcatgaact ccgtgtaccc gcgggagcag   2760
atcaaccagc tcacctccta catcgacgca tccaacgtgt acgggagcac ggagcatgag   2820
gcccgcagca tccgcgacct ggccagccac cgcggcctgc tgcggcaggg catcgtgcag   2880
cggtccggga agccgctgct ccccttcgcc accgggccgc ccacggagtg catgcgggac   2940
gagaacgaga gccccatccc ctgcttcctg gccggggacc accgcgccaa cgagcagctg   3000
ggcctgacca gcatgcacac gctgtggttc cgcgagcaca accgcattgc cacggagctg   3060
ctcaagctga acccgcactg ggacggcgac accatctact atgagaccag gaagatcgtg   3120
ggtgcggaga tccagcacat cacctaccag cactggctcc cgaagatcct gggggaggtg   3180
ggcatgagga cgctgggaga gtaccacggc tacgaccccg gcatcaatgc tggcatcttc   3240
aacgccttcg ccaccgcggc cttcaggttt ggccacacgc ttgtcaaccc actgctttac   3300
cggctggacg agaacttcca gcccattgca caagatcacc tccccttca caaagctttc    3360
ttctctccct tccggattgt gaatgagggc ggcatcgatc cgcttctcag gggctgttc    3420
ggggtggcgg ggaaaatgcg tgtgccctcg cagctgctga acacggagct cacggagcgg   3480
ctgttctcca tggcacacac ggtggctctg gacctggcgg ccatcaacat ccagcggggc   3540
cgggaccacg ggatcccacc ctaccacgac tacagggtct actgcaatct atcggcggca   3600
cacacgttcg aggacctgaa aatgagatt aaaaaccctg agatccggga gaaactgaaa    3660
aggttgtatg gctcgacact caacatcgac ctgtttccgg cgctcgtggt ggaggacctg   3720
gtgcctggca gccggctggg ccccaccctg atgtgtcttc tcagcacaca gttcaagcgc   3780
ctgcgagatg gggacaggtt gtggtatgag aaccctgggg tgttctcccc ggcccagctg   3840
actcagatca agcagacgtc gctggccagg atcctatgcg acaacgcgga caacatcacc   3900
cgggtgcaga gcgacgtgtt cagggtggcg gagttccctc acggctacgg cagctgtgac   3960
gagatcccca gggtggacct ccgggtgtgg caggactgct gtgaagactg taggaccagg   4020
gggcagttca atgcctttc ctatcatttc cgaggcagac ggtctcttga gttcagctac    4080
caggaggaca agccgaccaa gaaaacaaga ccacggaaaa tacccagtgt tgggagacag   4140
ggggaacatc tcagcaacag cacctcagcc ttcagcacac gctcagatgc atctgggaca   4200
aatgacttca gagagtttgt tctggaaatg cagaagacca tcacagacct tcagaacaca   4260
gataaagaaa cttgaatcac ggctcagtac cacagagtgc gtggatgccg ggggcgaatc   4320
tcacgccaac aacaccaagt ggaaaaaaga tgcatgcacc atttgtgaat gcaaagacgg   4380
gcaggtcacc tgcttcgtgg aagcttgccc ccctgccacc tgtgctgtcc ccgtgaacat   4440
cccaggggcc tgctgtccag tctgcttaca gaagagggcg gaggaaaagc cctaggctcc   4500
tgggaggctc ctcagagttt gtctgctgtg ccatcgtgag atcgggtggc cgatggcagg   4560
gagctgcgga ctgcagacca ggaaacaccc agaactcgtg acatttcatg acaacgtcca   4620
gctggtgctg ttacagaagg cagtgcagga ggcttccaac cagagcatct gcggagaagg   4680
aggcacagca ggtgcctgaa gggaagcagg caggagtcct agcttcacgt tagacttctc   4740
aggtttttat ttaattcttt taaaatgaaa aattggtgct actattaaat tgcacagttg   4800
aatcatttag gcgcctaaat tggttttgcc tcccaacacc atttcttttt aaataaagca   4860
ggatacctct atatgtcagc cttgccttgt tcagatgcca ggagccggca gacctgtcac   4920
ccgcaggtgg ggtgagtctt ggagctgcca gaggggctca ccgaaatcgg ggttccatca   4980
caagctatgt ttaaaaagaa aattggtgtt tggcaaacgg aacagaacct ttgatgagag   5040
cgttcacagg gacactgtct gggggtgcag tgcaagcccc cggcctcttc cctgggaacc   5100
```

```
tctgaactcc tccttcctct gggctctctg taacatttca ccacacgtca gcatctaatc   5160

ccaagacaaa cattcccgct gctcgaagca gctgtatagc ctgtgactct ccgtgtgtca   5220

gctccttcca cacctgatta gaacattcat aagccacatt tagaaacaga tttgctttca   5280

gctgtcactt gcacacatac tgcctagttg tgaaccaaat gtgaaaaaac ctccttcatc   5340

ccattgtgta tctgatacct gccgagggcc aagggtgtgt gttgacaacg ccgctcccag   5400

ccggccctgg ttgcgtccac gtcctgaaca agagccgctt ccggatggct cttcccaagg   5460

gaggaggagc tcaagtgtcg ggaactgtct aacttcaggt tgtgtgagtg cgttaaaaaa   5520

aaaaaaanaa aaaagaatcc ctatacctca tttgtatttt taaaatgcgt gatgttttat   5580

gaaattgtgt ccatttttta ggtattagat atggcagaaa aaccatttcc actatgcaaa   5640

gttcttttag acgtcagtga aaatcaactc tcatacctca tggtctctct ttaattgacc   5700

aaaaccttcc atttttctct aaatacaaag cgatctgtgt tctgagcaac ctttccccga   5760

acacacagct tcagtgcagc acgctgacct gagtatccac catgtgccag gcacagtgct   5820

gggcacacga ggcaccaagg tccgggccac ctgcccgcag caaggcccag ctgaggtggt   5880

ggagggagcc cctgaggtca ggggccgttt cggttcaggg tggcaggtgt ccagcactgg   5940

ggtatggcgt cgaggcttcc atggggtggg ggaggccagc ttccttctga caggatgggc   6000

gcatacagtg cctggtgtga tttgtgcaca acccgtgttc caggtgcaca tcctcccaag   6060

gagacaccca gacccttcca gcacgggccg gccaagttgc tgcggcggag gcagcatttc   6120

agctgtgagg aaggtcattg gattcatgtg ttttatctgt aaaaatggtt gtcttaactt   6180

cttaacctca tattggtaag tgattgataa aaattggttg gtgtttcatg acatgtggac   6240

ttcttttgaa atagcaagtc aaatgtagtg accaaattgt ggaagagatt tctgtcaaat   6300

aggaaatgtg taagttcgtc taaaagctga tggttatgta agttgctcag gcactcagat   6360

gacagcagat tctgggttct gggagtgttc tgtgcctctt acatgccctg gaggcctcat   6420

ggtctcagtg ctgaggcggc acacctgtag cacacctgcg taatgtgcgg tctgggccag   6480

tcacaaggaa ttgtgttgtc taagccaaag gggaagctg actgtgattt accaaaaaaa   6540

attctgtaat tcaaaccaaa atgtctgcgg aatcaccagt ttgatactct ctgtaatcag   6600

aacagtgggc agtgcctggg tgaacgtgtc tagcagccac tgtgcgggat cgctgtaaca   6660

ggagtggaat gtacatattt atttactttt ctaactgctc caacagccaa atgccttttt   6720

tatgaccatt gtattcagtt cattaccaaa gaaatgtttg cactttgtaa tgatgccttt   6780

cagttcaaat aaatgggtca cattttcaaa tgga                               6814
```

<210> SEQ ID NO 67
<211> LENGTH: 1790
<212> TYPE: DNA
<213> ORGANISM: Homo sapiens
<220> FEATURE:
<221> NAME/KEY: misc_feature
<223> OTHER INFORMATION: Incyte ID No: 198309.5CB1
<221> NAME/KEY: unsure
<222> LOCATION: 1241-1260
<223> OTHER INFORMATION: a, t, c, g, or other

<400> SEQUENCE: 67

```
tcggtgagct acccctctct ttggccgctt gcaccaagca gtgggatgtg gtaagctacc     60

tcctggagaa cccacaccag cccgccagcc tgccaggcca ctgactccca gggcaacaca    120

gtcctgcatg ccctagtgat gatctcggac aactcagctg agaacattgc actggtgacc    180
```

-continued

```
agcatgtatg atgggctcct ccaagctggg gcccgcctct gccctaccgt gcagcttgag    240

gacatccgca acctgcagga tctcacgcct ctgaagctgg ccgccaagga gggcaagatc    300

gagattttca ggcacatcct gcagcgggag ttttcaggac tgagccacct ttcccgaaag    360

ttcaccgagt ggtgctatgg gcctgtccgg gtgtcgctgt atgacctggc ttctgtggac    420

agctgtgagg agaactcagt gctggagatc attgcctttc attgcaagag cccgcaccga    480

caccgaatgg tcgttttgga gcccctgaac aaactgctgc aggcgaaatg ggatctgctc    540

atccccaagt tcttcttaaa cttcctgtgt aatctgatct acatgttcat cttcaccgct    600

gttgcctacc atcagcctac cctgaagaag caggccgccc ctcacctgaa agcggaggtt    660

ggaaactcca tgctgctgac gggccacatc cttatcctgc taggggggat ctacctcctc    720

gtgggccagc tgtggtactt ctggcggcgc cacgtgttca tctggatctc gttcatagac    780

agctactttg aaatcctctt cctgttccag gccctgctca cagtggtgtc ccaggtgctg    840

tgtttcctgg ccatcgagtg gtacctgccc ctgcttgtgt ctgcgctggt gctgggctgg    900

ctgaacctgc tttactatac acgtggcttc cagcacacag gcatctacag tgtcatgatc    960

cagaaggtca tcctgcggga cctgctgcgc ttccttctga tctacttagt cttccttttc   1020

ggcttcgctg tagccctggt gagcctgagc caggaggctt ggcgccccga agctcctaca   1080

ggccccaatg ccacagagtc agtgcagccc atggagggac aggaggacga gggcaacggg   1140

gcccagtaca ggggtatcct ggaagcctcc ttggagctct tcaaattcac catcggcatg   1200

ggcgagctgg ccttccagga gcagctgcac ttccgcggca nnnnnnnnnn nnnnnnnnnn   1260

gcctacgtgc tgctcaccta catcctgctg ctcaacatgc tcatcgccct catgagcgag   1320

accgtcaaca gtgtcgccac tgacagctgg agcatctgga agctgcagaa agccatctct   1380

gtcctggaga tggagaatgg ctattggtgg tgcaggaaga agcagcgggc aggtgtgatg   1440

ctgaccgttg gcactaagcc agatggcagc ccggatgagc gctggtgctt cagggtggag   1500

gaggtgaact gggcttcatg ggagcagacg ctgcctacgc tgtgtgagga cccgtcaggg   1560

gcaggtgtcc ctcgaactct cgagaaccct gtcctggctt cccctcccaa ggaggatgag   1620

gatggtgcct ctgaggaaaa ctatgtgccc gtccagctcc tccagtccaa ctgatggccc   1680

agatgcagca ggaggccaga ggacagagca gaggatcttt ccaaccacat ctgctggctc   1740

tggggtccca gtgaattctg gtggcaaata tatattttca ctaactcaaa              1790
```

```
<210> SEQ ID NO 68
<211> LENGTH: 3882
<212> TYPE: DNA
<213> ORGANISM: Homo sapiens
<220> FEATURE:
<221> NAME/KEY: misc_feature
<223> OTHER INFORMATION: Incyte ID No: 331276.3CB1
<221> NAME/KEY: unsure
<222> LOCATION: 141
<223> OTHER INFORMATION: a, t, c, g, or other

<400> SEQUENCE: 68

acacacactg catgcagcac acacacacca gggacgcacc acacagagca cgcacagcac     60

acaccacaca gcgcacgcac cacacagagc acacgcggca cacacagcac acacagcgca    120

cgcaccacgc agagcacaca nggcacatgc agcatacaca ccaaacagcg catgcaccac    180

acagagcaca cgcggcacac gcagcacaca caccacacag agcacctgga gcacccacag    240

cacacacacc acgcagagta cacgcggcac acacaccaca cacagcgcat gcacaacaca    300

gagcacacac agcacatgca ccacacgtag cgcgcacact gcaggcagca cacacaccac    360
```

-continued

```
acacagcgcg tgcaccacac agagcacctg cggcacacac agcacacacc gcacgcacca    420
cacagagcac atgtggcaca cacagtgcac gcaccacaca gcacccgcgg cgcacacagc    480
acacgtggca tatggcctcc atgaccctgt gtcttgaggg caggtcctac tttttgcttt    540
gttgtgttgg agcggaattt ctcccctggc ttctattgga gtcctagatt atttaaatca    600
cttcctctgt taattgtgcc tggaattaac ctgttagatt tacttcctag cagttagttg    660
ctcagtatgg gtttctacac tattaaagca acctagcggt agtacacaag gttttgttag    720
gatagctgtg agattttttt tctctaacaa tcatcattat ttctgtgtct gctccgtttt    780
tcttcagtgt tttatatgat attaataggg gatgtctaat tttgtatctt taaaaaaact    840
ttatcaaatc tgaagcattt ttcgtgttat agcttctcta taatttttca tggatattga    900
atatttggtg ttgatattct tcactcagtt ttgaacattg agttttcttc taatgttttg    960
tgcttatgaa aaccatttct gtgtaacgtg tttaagtagc ttatttatct gaaagaactc   1020
taataatgaa aagaaataaa aagtttttca gaagcatgat catattcttc cagaagagtc   1080
aggaaccatg tgtgccagga aagggaaacg ggactgagcg tctcgtagcg aaacgcctgc   1140
tgcagacttg acgcggctcc cctccaggac gggctggcgg cacacagact gtgcacttac   1200
ctcactgccg gcctcataat agtaatcagt gtaaatggtg tttctctttc gttttgttat   1260
ttcgtggcgt acgtgttaaa gtgtgtgaaa ctacaaggcc agctagtcct ttcatcattc   1320
cctttggtgc aggttttgga gcagcaccac agggcacacc cctcgccact ctttatgggg   1380
aatttttgcc caggcaggca gaggagtcat cttggtcaca agtctccctt ttcccccctcc  1440
ccagcatctt cgatcctgtc cccacccctc cagatgcatc caggggttgc aagcctgccc   1500
cccaaccagt ccccgtgagg aacagtggcc gggattgtcc cagggcccct tccagcaggg   1560
ggacctcctg acttgagagt ccccaaagcc ttcccagggc agctagaatc tgcctggaga   1620
gaagggatct tgtccccaag ggttagaggc agtaaactaa tagcaaggac agctgccttt   1680
agcaattgtg tgtgtcgcat ggccggtccc tgcatttttc ttcagttcca aagctgcact   1740
ggcattttta tggtcatctc tggagtccct ttgattcaag aaattatacc tctaggatgc   1800
caactaaacg aacaacaaac agaaactcca cctgtttgct agcataacag gcgtgaaggc   1860
ggcagtgtcg ccggcgtcct tccgcggaag cccagtgtgt gcagacagca cggggtggcg   1920
ctgctctcag gtgctctggc tgcttgggtt cctggcatgc tgatttgtga cttaagatta   1980
aaatcacatt gccagggatt accacgcaac cacgaccttg gctgctcctc cagaaaccgt   2040
ggtcgcgctc actgcagatt ggagaacagg tgcatctcgt agctcttctt tggaaacaaa   2100
agaagccacc agctgaggaa gatgctcacc ggtcaccgtc cctttattta tgcccagcga   2160
tgacctctct aacaaggtgc agagcttagc tgattggtga acagtgattg gtttccgctt   2220
tgttcacagt ggctaagttc tgcacctgaa gagaaggtga gatggggaca gttaagttgg   2280
agccgctggg gcagaggccg ttgctgacgg gccggccgct gctgcacagt cagcttgggt   2340
gcggacgcga tcctggagga tgagagacca cttgacccca aggatgcact gtctcctgct   2400
gggaatgcta gccatgtact gagtccttaa gtctgtccac agaaacatcc actaatcgga   2460
catctgtctg aaaggtcaaa tgtattgaaa gttgcaaaaa ttcttcttac aaaaaactaa   2520
aaccaaatgc atcacctaag tcgtgtgaaa tcatgtggta gctcatggct gtgagcgggg   2580
cggggcgggg ctttcggagg agctcctgtt gttctgggcg cggtgaactc tctcttgtat   2640
ttgcagtcca ggccttcgcg tctcctgcgc cagcagacgg tgcccacgga gctcccagct   2700
```

-continued

```
gaggcgctgc ttctccgggc tgtcgattgg acccgccctc cggtgcctac tgagctgata   2760

tcagttctca ttttacacac tggctcagtt cagcaggaac aggagtcgag cccttgagca   2820

aaaagccttc gtgtctgtaa gtgcccgagg ctcaggagag ctgggggctc ccactcgcgg   2880

cagacaggcc cgcgtaccac cctgcgtcca ccccggcccg gcggcagcaa cggtgccagt   2940

catctgcatg tgctcctgcg gcgtgggggt ttgtagactt ggaaaaccct gttggcagaa   3000

agttaagagc tcccaggcct gaaggcagga cacagtgcca gcaggggccc gtttgccccc   3060

atgtgtaagg gaggcagggc ccagctctcc cacggcgagg tgagctgaga ctttctgaga   3120

atagttagag tgggtgcgtg tctgaaatgg gtactcctag cagctattgt gtacgcaaag   3180

cctgagtaca gcctgctggt gtcatggcca cgtgtgagca ggccagcgtc acacggctcg   3240

ctgtgacccg tcccggagac tgaaatgggc ctgggtcttc tccttgtcct gtgattaaag   3300

tcctctcttg aaagtggaga gcaaaggcac acagaggtgc gcgctcacaa gaattcctcc   3360

cggtgactgg gtaatcaatg ttactgctgt ttcctttgca ggaaagacca cagcaagatt   3420

ctttcattcg tctcctccta gcctggggga ccaggctcga actgaccctg gacatcaaag   3480

gagggattat gtggctgcta aagccatcgg cccacagccc tgttcacgtc ttggtgcttc   3540

tctttcccag aggctggtcc cagccaggca cacacaaaag gcagattctc gtaaacgcag   3600

cctccctccc tggaggctgc ctcctgccct ggatctggag tggagctgct ctgagatttt   3660

gagttcttct gcagagatga ttaaatatat ccaagagaca ttggaaaacc tgctgaacat   3720

tttacattgg tctgctcagc acatggctgg atgcggatat ttctataatt ccagaaagtc   3780

acacagctcc tctgtatgag accagtgggc gccatttaaa agaacaggat gagaatctaa   3840

gatatattat taataaatgt aatggatttt ttttttgtaa aa                       3882
```

```
<210> SEQ ID NO 69
<211> LENGTH: 1484
<212> TYPE: DNA
<213> ORGANISM: Homo sapiens
<220> FEATURE:
<221> NAME/KEY: misc_feature
<223> OTHER INFORMATION: Incyte ID No: 344071.1CB1
<221> NAME/KEY: unsure
<222> LOCATION: 47
<223> OTHER INFORMATION: a, t, c, g, or other

<400> SEQUENCE: 69

cagggcagcg acgcgactct ggtgcgggcc gtcttcttcc ccccganctg ggcgtgcgcg     60

gccgcaatga actgggagct gctgctgtgg ctgctggtgc tgtgcgcgct gctcctgctc    120

ttggtgcagc tgctgcgctt cctgagggct gacggcgacc tgacgctact atgggccgag    180

tggcagggac gacgcccaga atgggagctg actgatatgg tggtgtgggt gactggagcc    240

tcgagtggaa ttggtgagga gctggcttac cagttgtcta aactaggagt ttctcttgtg    300

ctgtcagcca gaagagtgca tgagctggaa agggtgaaaa gaagatgcct agagaatggc    360

aatttaaaag aaaaagatat acttgttttg ccccttgacc tgaccgacac tggttcccat    420

gaagcggcta ccaaagctgt tctccaggag tttggtagaa tcgacattct ggtcaacaat    480

ggtggaatgt cccagcgttc tctgtgcatg gataccagct tggatgtcta cagaaagcta    540

atagagctta actacttagg gacggtgtcc ttgacaaaat gtgttctgcc tcacatgatc    600

gagaggaagc aaggaaagat tgttactgtg aatagcatcc tgggtatcat atctgtacct    660

ctttccattg gatactgtgc tagcaagcat gctctccggg gttttttttaa tggccttcga    720

acagaacttg ccacataccc aggtataata gtttctaaca tttgcccagg acctgtgcaa    780
```

```
tcaaatattg tggagaattc cctagctgga gaagtcacaa agactatagg caataatgga    840

gaccagtccc acaagatgac aaccagtcgt tgtgtgcggc tgatgttaat cagcatggcc    900

aatgatttga aagaagtttg gatctcagaa caacctttct tgttagtaac atatttgtgg    960

caatacatgc caacctgggc ctggtggata accaacaaga tggggaagaa aaggattgag   1020

aactttaaga gtggtgtgga tgcagactct tcttatttta aaatctttaa gacaaaacat   1080

gactgaaaag agcacctgta cttttcaagc cactggaggg agaaatggaa aacatgaaaa   1140

cagcaatctt cttatgcttc tgaataatca aagactaatt tgtgatttta ctttttaata   1200

gatatgactt tgcttccaac atggaatgaa ataaaaaata aaatcacaaa ttagtctttg   1260

attattcaga agcataagaa gattgctgtt ttcatgtttt ccatttctcc ctccagtggc   1320

ttgaaaagta caggtgctct tttcagtcat gttttgtctt aaagatttta aaataagaag   1380

agtctgcatc cacaccactc ttaaagttct caatcctttt cttccccatc ttgttggtta   1440

tccaccaggc ccaggttggc atgtattgcc acaaatatgt tact                    1484
```

<210> SEQ ID NO 70
<211> LENGTH: 3871
<212> TYPE: DNA
<213> ORGANISM: Homo sapiens
<220> FEATURE:
<221> NAME/KEY: misc_feature
<223> OTHER INFORMATION: Incyte ID No: 481723.1CB1
<221> NAME/KEY: unsure
<222> LOCATION: 2910-2932, 3791, 3794, 3813, 3815, 3827, 3843, 3850-3851, 3860
<223> OTHER INFORMATION: a, t, c, g, or other

<400> SEQUENCE: 70

```
caaaatttgg cgtgatacat tcctagtgga aagaggcaaa tttctacgta agaaggaaga     60

atccagcaag aatatccaac agtcaaatca cttgcccaaa tatgaacggg tcaaagaact    120

atgccagcag gccaggtacc agacagcctg tgaacaaccg gggcagaagt ggcaatgcat    180

tgaggataca tctggcaagc ttcgaattca caagtgtaaa ggacccagtg acctgctcac    240

agtccggcag agcacgcgga acctctacgc tcgcggcttc catgacaaag acaaagagtg    300

cagttgtagg gagtctggtt accgtgccag cagaagccaa agaaagagtc aacggcaatt    360

cttgagaaac caggggactc caaagtacaa gcccagattt gtccatactc ggcagacacg    420

ttccttgtcc gtcgaatttg aaggtgaaat atatgacata aatctggaag aagaagaaga    480

attgcaagtg ttgcaaccaa gaaacattgc taagcgtcat gatgaaggcc acaaggggcc    540

aagagatctc caggcttcca gtggtggcaa caggggcagg atgctggcag atagcagcaa    600

cgccgtgggc ccacctacca ctgtccgagt gacacacaag tgttttattc ttcccaatga    660

ctctatccat tgtgagagag aactgtacca atcggccaga gcgtggaagg accataaggc    720

atacattgac aaagagattg aagctctgca agataaaatt aagaatttaa gagaagtgag    780

aggacatctg aagagaagga agcctgagga atgtagctgc agtaaacaaa gctattacaa    840

taaagagaaa ggtgtaaaaa agcaagagaa attaaagagc catcttcacc cattcaagga    900

ggctgctcag gaagtagata gcaaactgca actttttcaa ggagaacaac cgtaggagga    960

agaaggagag gaaggagaag agacggcaga ggaaggggga agagtgcagc ctgcctgggc   1020

ctcacttgct tcacgcatga caacaaccac tggcagacag ccccgttctg gaacctggga   1080

tctttctgtg cttgcacgag ttctaacaat aacacctact ggtgtttgcg tacagttaat   1140

gagacgcata attttctttt ctgtgagttt gctactggct tttggagta ttttgatatg    1200
```

-continued

```
aatacagatc cttatcagct cacaaataca gtgcacacgg tagaacgagg cattttgaat   1260
cagctacacg tacaactaat ggagctcaga agctgtcaag gatataagca gtgcaaccca   1320
agacctaaga atcttgatgt tggaaataaa gatggaggaa gctatgacct acacagagga   1380
cagttatggg atggatggga aggttaatca gccccgtctc actgcagaca tcaactggca   1440
aggcctagag gagctacaca gtgtgaatga aaacatctat gagtacagac aaaactacag   1500
acttagtctg gtggactgga ctaattactt gaaggattta gatagagtat ttgcactgcc   1560
tgaagagtca ctatgagcaa aataaaacaa ataagactca aactgctcaa agtgacgggt   1620
tcttggttgt ctctgctgag cacgctgtgt caatggagat ggcctctgct gactcagatg   1680
aagacccaag gcataaggtt gggaaaacac ctcatttgac cttgccagct gaccttcaaa   1740
ccctgcattt gaaccgacca acattggttt ttctccagag agtaaacttg aatggaataa   1800
cgacattcca gaagttaatc atttgaattc tgaacactgg agaaaaaccg aaaaatggac   1860
ggggcatgaa gagactaatc atctggaaac cgatttcagt ggcgatggca tgacagagct   1920
agagctcggg cccagcccca ggctgcagcc cattcgcagg cacccgaaag aacttcccca   1980
gtatggtggt cctggaaagg acatttttga agatcaacta tatcttcctg tgcattccga   2040
tggaatttca gttcatcaga tgttcaccat ggccaccgca gaacaccgaa gtaattccag   2100
catagcgggg aagatgttga ccaaggtgga gaagaatcac gaaaaggaga agtcacagca   2160
cctagaaggc agcacctcct cttcactctc ctctgattag atgaaactgt taccttaccc   2220
taaacacagt atttcttttt aacttttttta tttgtaaact aataaaggta atcacagcca   2280
ccaacattcc aagctaccct gggtaccttt gtgcagtaga agctagtgag catgtgagca   2340
agcggtgtgc acacggagac tcatcgttat aatttactat ctgccaagag tagaaagaaa   2400
ggctggggat atttgggttg gcttggtttt gattttttgc ttgtttgttt gttttgtact   2460
aaaacagtat tatcttttga atatcgtagg gacataagta tatacatgtt atccaatcaa   2520
gatggctaga atggtgcctt tctgagtgtc taaaacttga cacccctggt aaatctttca   2580
acacacttcc actgcctgcg taatgaagtt ttgattcatt tttaaccact ggaatttttc   2640
aatgccgtca ttttcagtta gatgattttg cactttgaga ttaaaatgcc atgtctattt   2700
gattagtctt atttttttat ttttacaggc ttatcagtct cactgttggc tgtcattgtg   2760
acaaagtcaa ataaaccccc aaggacgaca cacagtatgg atcacatatt gtttgacatt   2820
aagcttttgc cagaaaatgt tgcatgtgtt ttacctcgac ttgctaaaat cgattagcag   2880
aaaggcatgg ctaataatgt tggtggtgan nnnnnnnnnn nnnnnnnnnn nnatgaagat   2940
tgcctgctct ctctgtgcct agcctcaaag cgttcatcat acatcatacc tttaagattg   3000
ctatattttg ggttattttc ttgacaggag aaaaagatct aaagatcttt tattttcatc   3060
ttttttggtt ttcttggcat gactaagaag cttaaatgtt gataaaatat gactagtttt   3120
gaatttacac caagaacttc tcaataaaag aaaatcatga atgctccaca atttcaacat   3180
accacaagag aagttaattt cttaacattg tgttctatga ttatttgtaa gaccttcacc   3240
aagttctgat atcttttaaa gacatagttc aaaattgctt ttgaaaatct gtattcttga   3300
aaatatcctt gttgtgtatt aggtttttaa ataccagcta aaggattacc tcactgagtc   3360
atcagtaccc tcctattcag ctccccaaga tgatgtgttt ttgcttaccc taagagaggt   3420
tttcttctta tttttagata attcaagtgc ttagataaat tatgttttct ttaagtgttt   3480
atggtaaact cttttaaaga aaatttaata tgttatagct gaatcttttt ggtaacttta   3540
```

aatctttatc atagactctg tacatatgtt caaattagct gcttgcctga tgtgtgtatc 3600
atcggtggga tgacagaaca aacatattta tgatcatgaa taatgtgctt tgtaaaaaga 3660
tttcaagtta ttaggaagca tactctgttt tttaatcatg tataatattc catgatactt 3720
ttatagaaca attctggctt caggaaagtc tagaagcaat atttcttcaa ataaaaggtg 3780
tttaaacttt ncanaaataa aaatacaaat aananaaaaa cttaaanaag gtttgaaaaa 3840
ganatgtatn nggggatctn aaagtgttta c 3871

<210> SEQ ID NO 71
<211> LENGTH: 735
<212> TYPE: DNA
<213> ORGANISM: Homo sapiens
<220> FEATURE:
<221> NAME/KEY: misc_feature
<223> OTHER INFORMATION: Incyte ID No: 004485.2CB1
<221> NAME/KEY: unsure
<222> LOCATION: 631, 637
<223> OTHER INFORMATION: a, t, c, g, or other

<400> SEQUENCE: 71
cctgcctcaa tgctgagcag aaccagcacc tccgggcctc cctcagccgc ctgcatcggg 60
tggcacagta tgcccgggcc cagcacgtgc ggctcctggt ggatgcggag tacacctcac 120
tgaaccctgc gctctcgctg ctggtggctg ccctggctgt gcgctggaac agcccgggtg 180
aaggcgggcc ctgggtgtgg aacacctacc aggcctgtct aaaggacaca ttcgagcggc 240
tggggaggga tgcagaggct gcgcacaggg ccggcctggc cttcggagtg aagctggtac 300
gaggtgcata tctggacaag gagagagcgg tggcccagct ccatgggatg gaagacccca 360
ctcagcctga ctatgaggcc accagtcaga gttacagccg ctgcctggaa ctgatgctga 420
cgcacgtggc ccgccatggc cccatgtgcc acctcatggt ggcttcccac aatgaggaat 480
ctgttcgcca ggcaaccaag cgggcaggcc ggctatgtag tgtataagtc cattccctat 540
ggctccttgg aggaggtaat cccctacctg atccggaggg cccaggagaa ccggagcgtg 600
cttcagggtg cccgcaggga acaggagctg ntcagcnaag aactgtggcg gcggctgctg 660
ccaggatgcc gaaggatacc ccactagcac ccctgagggg gtcatgtggt caataaaagt 720
ccttaggtgc tgcct 735

<210> SEQ ID NO 72
<211> LENGTH: 1649
<212> TYPE: DNA
<213> ORGANISM: Homo sapiens
<220> FEATURE:
<221> NAME/KEY: misc_feature
<223> OTHER INFORMATION: Incyte ID No: 012432.7CB1
<221> NAME/KEY: unsure
<222> LOCATION: 148
<223> OTHER INFORMATION: a, t, c, g, or other

<400> SEQUENCE: 72
ggtgggctgg tggaggcggg gtcgagatgg cggcgccttt gaggattcag agcgactggg 60
cgcaagcctc aggaaggatg aaggggaggc ctggctgagc tgtcatcccc cagtggaagc 120
agcctgaggc tctcatcaga agcagatnct ggtgccatgc ttcttgtaca gtctgcagaa 180
ccggaaacca tctttgtatg gcagcctgac ttgtcaagga attggcctag atggcatccc 240
agaggttaca gcttcagaag gatttactgt gaatgaaata aacaagaaaa gcattcatat 300
ttcatgtcca aaggaaaatg catcttctaa gtttttggca ccatatacta ctttttccag 360
aattcataca aagagtataa catgcctgga catttccagc agaggaggtc ttggtgtgtc 420

```
ttctagtact gacgggacca tgaaaatctg gcaggcttcc aatggagaac tcaggagagt    480

attggaagga catgtgtttg atgtgaattg ttgcaggttt ttcccatcag gccttgtggt    540

cctgagtggg ggaatggatg cccagctgaa gatatggtca gctgaagatg ctagctgccg    600

tggtgacctt caaaggtcac aaaggaggta tcctgggata cagccatcgt tgatcggggg    660

aggaatgtgg tgtctgcttc tcgagatggg acagcacgac tttgggattg tgggcgctca    720

ggctgcttgg gagtccttgc agattgtggt tcttctatca atggagtggc ggtgggtgct    780

gctgacaact ccataaacct tgggctcccc tgagcagatg cccagtgaac gggaggttgg    840

aacagaggcc aaaatgctgc tcttggcccg ggaagataag aaacttcagt gcttgggact    900

acagagcagg cagctggtgt tcctctttat tggctcagac gctttcaact gctgtacttt    960

tctctctggc ttcttgctat tggctgggac tcaagatgga aacatttatc agctggatgt   1020

gaggagtcca agggctccgg tacaagtcat ccacagatca ggagcaccag ttctatccct   1080

gctaagtgtc agagatggat tcattgctag ccaaggtgat ggaagctgtt ttattgtcca   1140

gcaagactta gactatgtca ctgagctcac tggggctgac tgtgaccctg tgtacaaggt   1200

agccacatgg gagaagcaga tctacacatg ctgtcgagac ggtcttgtac gacgctacca   1260

gctttctgac ctctgacttc ttggaaagag cagtcccggt tagtgaaaag gtttgaccct   1320

gatcaacaat gagcagaaac atcatcagtc cttcccaagg accatggcgt ttaatgtctt   1380

gggcacccct tggaaatcac agaaagtcag ctgtactggc cgtgtggaac tctcatccca   1440

agacctactt tgaactgagt aagaaggtca ttgtgcccac tgcatttgtt ccaacttctc   1500

cttgtataaa ctcaccccag caacacaggg caaggatata gatgctttta gtttgttctt   1560

aaaccagttt tgttaaatgt ttacaaggac ctcagtacta aagcctgttc tctggaggaa   1620

ataaagaaaa tatgtttgga ggtgcctga                                    1649
```

<210> SEQ ID NO 73
<211> LENGTH: 1629
<212> TYPE: DNA
<213> ORGANISM: Homo sapiens
<220> FEATURE:
<221> NAME/KEY: misc_feature
<223> OTHER INFORMATION: Incyte ID No: 019238.3CB1

<400> SEQUENCE: 73

```
ggcgttccca ctgcaccctg ggagaacgag cctttgcggg gtttctcctg gctgtcctcc     60

gaccccggcg gtctcgaaag cgacacgctg cagtgggtgg aggagcccca acgctcctgc    120

accgcgcgga gatgcgcggt actccaggcc accggtgggg tcgagcccgc aggctggaag    180

gagatgcgat gccacctgcg cgccaacggc tacctgtgca agtaccagtt tgaggtcttg    240

tgtcctgcgc cgcgccccgg ggccgcctct aacttgagct atcgcgcgcc cttccagctg    300

cacagcgccg ctctggactt cagtccacct gggaccgagg tgagtgcgct ctgccgggga    360

cagctcccga tctcagttac ttgcatcgcg gacgaaatcg gcgctcgctg ggacaaactc    420

tcgggcgatg tgttgtgtcc ctgccccggg aggtacctcc gtgctggcaa atgcgcagag    480

ctccctaaac tgcctaggac ggacttggga ggctttgcct gcgaatgtgc tacgggcttc    540

gagctgggga aggacggccg ctcttgtgtg accagtgggg aaggacagcc gacccttggg    600

gggaccgggg tgcccaccag gcgcccgccg gccactgcaa ccagccccgt gccgcagaga    660

acatggccaa tcagggtcga cgagaagctg ggagagacac cacttgtccc tgaacaagac    720

aattcagtaa catctattcc tgagattcct cgatggggat cacagagcac gatgtctacc    780
```

cttcaaatgt cccttcaagc cgagtgcaaa ggccactatc accccatcag ggagcgtgat 840
ttccaagttt aattctaacg acttcctctg ccactcctca ggctttcgac tcctcctctg 900
ccgtggtctt catatttgtg agcacagcag tagtagtgtt ggtgatcttg accatgacag 960
tactggggct tgtcaagctc tgctttcacg aaagcccctc ttcccagcca aggaaggagt 1020
ctatgggccc gccgggcctg gagagtgatc ctgagcccgc tgctttgggc tccagttctg 1080
cacattgcac aaacaatggg gtgaaagtcg ggactgtgga tctgcgggac agagcagagg 1140
gtgccttgct ggcggagtcc cctcttggct ctagtgatgc atagggaaac aggggacatg 1200
ggcactcctg tgaacagttt ttcacttttg atgaaacggg gaaccaagag gaacttactt 1260
gtgtaactga caatttctgc agaaatcccc cttcctctaa attcccttta ctccactgag 1320
gagctaaatc agaactgcac actccttccc tgatgataga ggaagtggaa gtgcctttag 1380
gatggtgata ctgggggacc gggtagtgct ggggagagat attttcttat gtttattcgg 1440
agaatttgga gaagtgattg aacttttcaa gacattggaa acaaatagaa cacaatataa 1500
tttacattaa aaaataattt ctaccaaaat ggaaaggaaa tgttctatgt tgttcaggct 1560
aggagtatat tggttcgaaa tcccagggaa aaaaataaaa ataaaaaatt aaaggattgt 1620
tgataaccc 1629

<210> SEQ ID NO 74
<211> LENGTH: 1862
<212> TYPE: DNA
<213> ORGANISM: Homo sapiens
<220> FEATURE:
<221> NAME/KEY: misc_feature
<223> OTHER INFORMATION: Incyte ID No: 021651.1CB1
<221> NAME/KEY: unsure
<222> LOCATION: 1842
<223> OTHER INFORMATION: a, t, c, g, or other

<400> SEQUENCE: 74
gagacccaga gatcaggaga gaaggcaccg cccccacccc gcctccaaag ctaaccctcg 60
ggcttgaggg gaagaggctg actgtacgtt ccttctactc tggcaccact ctccaggctg 120
ccatggggcc cagcacccct ctcctcatct tgttcctttt gtcatggtcg ggacccctcc 180
aaggacagca gcaccacctt gtggagtaca tggaacgccg actagctgct ttagaggaac 240
ggctggccca gtgccaggac cagagtagtc ggcatgctgc tgagctgcgg gacttcaaga 300
acaagatgct gccactgctg gaggtggcag agaaggagcg ggaggcactc agaactgagg 360
ccgacaccat ctccgggaga gtggatcgtc tggagcggga ggtagactat ctggagaccc 420
agaacccagc tctgccctgt gtagagtttg atgagaaggt gactggaggc cctggggacc 480
aaaggcaagg gaagaaggaa tgagaagtac gatatggtga cagactgtgg ctacacaatc 540
tctcaagtga gatcaatgaa gattctgaag cgatttggtg gcccagctgg tctatggacc 600
aaggatccac tggggcaaac agagaagatc tacgtgttag atgggacaca gaatgacaca 660
gcctttgtct tcccaaggct gccgtgactt cacccttgcc atggctgccc ggaaagcttc 720
ccgagtccgg gtgcccttcc cctgggtagg cacagggcag ctggtatatg gtggctttct 780
ttattttgct cggaggcctc ctggaagacc tggtggaggt ggtgagatgg agaacacttt 840
gcagctaatc aaattccacc tgggcaaacc gaacagtggt ggacagctca gtattcccag 900
cagaggggct gatccccccc tacggcttga cagcagacac ctacatcgac ctggcagctg 960
atgaggaagg tctttgggct gtctatgcca cccgggagga tgacaggcac ttgtgtctgg 1020

-continued

```
ccaagttaga tccacagaca ctggacacag agcagcagtg ggacacacca tgtcccagag   1080

agaatgctga ggctgccttt gtcatctgtg ggaccctcta tgtcgtctat aacacccgtc   1140

ctgccagtcg ggcccgcatc cagtgctcct ttgatgccag cggcaccctg acccctgaac   1200

gggcagcact cccttatttt ccccgcagat atggtgccca tgccagcctc cgctataacc   1260

cccgagaacg ccagctctat gcctgggatg atggctacca gattgtctat aagctggaga   1320

tgaggaagaa agaggaggag gtttgaggag ctagccttgt tttttgcatc tttctcactc   1380

ccatacattt atattatatc cccactaaat ttcttgttcc tcattcttca aatgtgggcc   1440

agttgtggct caaatcctct atatttttag ccaatggcaa tcaaattctt tcagctcctt   1500

tgtttcatac ggaactccag atcctgagta atcctttttag agcccgaaga gtcaaaaccc  1560

tcaatgttcc ctcctgctct cctgccccat gtcaacaaat ttcaggctaa ggatgaccca   1620

gacccagggc tctaaccttg tatgcgggca ggcccaggga gcaggcagca gtgttcttcc   1680

cctcagagtg acttggggag ggagaaatag gaggagacgt ccagctctgt cctctcttcc   1740

tcactcctcc cttcagtgtc ctgaggaaca ggactttctc cacattgttt tgtattgcaa   1800

cattttgcat taaaaggaaa atccactgct aaaaaaaaaa anaaaaaaaa agggcggccg   1860

cc                                                                  1862
```

<210> SEQ ID NO 75
<211> LENGTH: 1855
<212> TYPE: DNA
<213> ORGANISM: Homo sapiens
<220> FEATURE:
<221> NAME/KEY: misc_feature
<223> OTHER INFORMATION: Incyte ID No: 021763.7CB1
<221> NAME/KEY: unsure
<222> LOCATION: 1826
<223> OTHER INFORMATION: a, t, c, g, or other

<400> SEQUENCE: 75

```
gtgtctttaa gagggtggaa cggggcttcg cgtctgtgct tcctgtggct gacgtcatct     60

ggaggagatt tgctttcttt ttctccaaaa ggggaggaaa ttgaaactga gtggcccacg    120

atgggaagag gggaaagccc aggggtacag gaggcctctg ggtgaaggca gaggctaaca    180

tggggttcgg agcgaccttg ggccgttggc ctgaccatct ttgtgctgtc tgtcgtcact    240

atcatcatct gcttcacctg ctcctgctgc tgcctttaca agacgtgccg ccgaccacgt    300

ccggttgtca ccaccaccac atccaccact gtggtgcatg cccttatcc tcagcctcca     360

agtgtgccgc ccagctaccc tggaccaagc taccagggct accacaccat gccgcctcag    420

ccagggatgc cagcagcacc ctacccaatg cagtacccac caccttaccc agcccagccc    480

atgggcccac cggcctacca cgagaccctg gctggaggag cagccgcgcc ctaccccgcc    540

agccagcctc cttacaaccc ggcctacatg gatgccccga aggcggccct ctgagcattc    600

cctggcctct ctggctgcca cttggttatg ttgtgtgtgt gcgtgagtgg tgtgcaggcg    660

cggttcctta cgccccatgt gtgctgtgtg tgtccaggca cggttcctta cgccccatgt    720

gtgctgtgtg tgtcctgcct gtatatgtgg cttcctctga tgctgacaag gtggggaaca    780

atccttgcca gagtgggctg ggaccagact ttgttctctt cctcacctga aattatgctt    840

cctaaaatct caagccaaac tcaaagaatg gggtggtggg gggcaccctg tgaggtggcc    900

cctgagaggt gggggcctct ccagggcaca tctggagttc ttctccagct taccctaggg    960

tgaccaagta gggcctgtca caccagggtg gcgcagcttt ctgtgtgatg cagatgtgtc   1020

ctggtttcgg cagcgtagcc agctgctgct tgaggccatg gctcgtcccc ggagttgggg   1080
```

```
gtacccgttg ccagagccag ggacatgatg caggcgaagc ttgggatctg gccaagttgg   1140

actttgatcc tttgggcaga tgtcccattg ctccctggag cctgtcatgc ctgttgggga   1200

tcaggcagcc tcctgatgcc agaacacctc aggcagagcc ctactcagct gtacctgtct   1260

gcctggactg tcccctgtcc ccgcatctcc cctgggacca gctggagggc cacatgcaca   1320

cacagcctag ctgcccccag ggagctctgc tgcccttgct ggccctgccc ttcccacagg   1380

tgagcagggc tcctgtccac cagcacactc agttctcttc cctgcagtgt tttcatttta   1440

ttttagccaa acattttgcc tgttttctgt ttcaaacatg atagttgata tgagactgaa   1500

acccctgggt tgtggaggga aattggctca gagatggaca acctggcaac tgtgagtccc   1560

tgcttcccga caccagcctc atggaatatg caacaactcc tgtaccccag tccacggtgt   1620

tctggcagca gggacacctg ggccaatggg ccatctggac caaaggtggg gtgtggggcc   1680

ctggatggca gctctggccc agacatgaat acctcgtgtt cctcctccct ctattactgt   1740

ttcaccagag ctgtcttagc tcaaatctgt tgtgtttctg agtctagggt ctgtacactt   1800

gtttataata aatgcaatcg tttggngctg ctgcccccctt tcttcctggc ctcgg      1855
```

<210> SEQ ID NO 76
<211> LENGTH: 497
<212> TYPE: DNA
<213> ORGANISM: Homo sapiens
<220> FEATURE:
<221> NAME/KEY: misc_feature
<223> OTHER INFORMATION: Incyte ID No: 023103.1CB1

<400> SEQUENCE: 76

```
tttttttttg gaaagaacag tttgtgctgt gctttattaa aatgtgcatc attcttttat     60

tttaaaatgt gcatcattgt ctcgtgctcg gcgcatgcga cctcagcgtg gtggcccgct    120

gggggcctcg ttcccgccca gctcccgcgg agccgcaggg agcaggcgca ctcacgtggc    180

gcgggcccgg gggctcccgc ccatggcgag gtagacgtcg atgggcacgt gcagcagcgt    240

caggcagtgg catccagggc agcgacgaag cggcctgacc gggttgtgct ccgtcgctac    300

cgcctccggg ctgtcctggg actcggggc ggcggcaagg ccacgggagt ctccggcctc    360

aatggggaat ctccgaccct gcgggggctc ctgggcgctc atgtccaagc cccggggcgc    420

tctcccggcg gttgagaccg gtcccaggct agaagcagct gccggagccc tggccgcggg    480

agaacgctcc ggtccag                                                   497
```

<210> SEQ ID NO 77
<211> LENGTH: 506
<212> TYPE: DNA
<213> ORGANISM: Homo sapiens
<220> FEATURE:
<221> NAME/KEY: misc_feature
<223> OTHER INFORMATION: Incyte ID No: 033977.1CB1

<400> SEQUENCE: 77

```
gcggccgccg ggcggacgcg ctgctccgtc cacggccagc actggggcgg ccgggccccg     60

gtcccagaag ggaagcggga ggacggccac gcacacacgt cccgccgccg gtcatgctgc    120

tcagcctcgg gccgcgcgct taccaggcca ctcaaattca actactagag acatccctcc    180

aaccactggc ggtcctcgcg ctcgcccgga ggtgctgtta agggaaccag accacaaaga    240

ctgtgcgatt agcggcttct ggctggcgcc gtccacacgt gggcctccac agccctgtcc    300

taccactgcc ctggccaagc ctgctctgtg gacgtggcgt cccctctccc gggaagggcc    360
```

```
cctgacctgg cactcgagtg cccagtccgc ccaggctgcc gccgtggatg cggagcctgc    420

ctgggaaggt ggtgtgggca tgcagtcgct ggggaaccaa gaccaagcgt ttgaatacct    480

gcagcttgag gaatggcaaa ggtggg                                         506
```

<210> SEQ ID NO 78
<211> LENGTH: 744
<212> TYPE: DNA
<213> ORGANISM: Homo sapiens
<220> FEATURE:
<221> NAME/KEY: misc_feature
<223> OTHER INFORMATION: Incyte ID No: 037739.1CB1
<221> NAME/KEY: unsure
<222> LOCATION: 5, 8
<223> OTHER INFORMATION: a, t, c, g, or other

<400> SEQUENCE: 78

```
gacgntgnct ttttttaatt tatttcaaaa atacttgttt attgcatggt tctctccaga     60

ttttatgtct aggcttactt ttatcataaa gtacttcagc aaagaagaga aactggcatt    120

caaacatggc cggccaatca ttgccaggct aattgcacaa gagcttctcc aagcaaatat    180

ttctcaccta ttacaaaccc cacattgata taggtgccac aaataataaa tgggataaaa    240

cagaagcccc tgtgcaaggg ggaagtcagt gaggaagagg gaaggaaaca agaggcaagg    300

agaccacgca catcactagt gtttctcttc atatggcaat ttaacattgc tgttctttgt    360

ctttatgaaa aatggggtta ggtcaggttc cttgtcatca caagtctcag aaatcatcta    420

gaaaacatat attttacaca ctagtctcac aactagacaa catattcagt acttcaagtg    480

gtagaatctt cagcttttca caccttaggc agttcttcca ccatctattt ctgtttcttc    540

attctcagtt cccaagaagg catagatcag gtcctagata ggttagcatt tcacatgtct    600

actccatttc atttgcaaca atgacaatga aaacccagca tgcaatgtgg ctgaggtgct    660

gggaacccca aacaatgtgg gggaaaaagc agagggcact tcacacccca gacgggacag    720

gtttccattc cttactgagg gtgg                                           744
```

<210> SEQ ID NO 79
<211> LENGTH: 898
<212> TYPE: DNA
<213> ORGANISM: Homo sapiens
<220> FEATURE:
<221> NAME/KEY: misc_feature
<223> OTHER INFORMATION: Incyte ID No: 196556.3CB1

<400> SEQUENCE: 79

```
gtgggatggg agcaggggca gagacgggca gagggcagag ggcggacggc gccggagcgg     60

gcgtcatggc gcggctcctc tggttgctcc ggggcctgac cctcggaact gcgcctcggc    120

gggcggtgcg gggccaagcg ggcggcggcg ggcccggcac cgggccggga ctgggggagg    180

cagggtctct tgcaacgtgt gagctgcctc ttgccaagag tgagtggcaa aagaaactaa    240

ccccggagca gttctacgtc acaagagaaa agggaacgga accgcctttc agtgggatct    300

acctgaataa caaggaagca ggaatgtatc attgcgtgtg ctgcgacagt ccactcttca    360

gttctgagaa aaagtactgc tctggcactg ggtggccttc gttttccgag gctcatggta    420

cgtctggctc tgatgaaagc cacacaggga tcctgagacg tctggatacc tcgttaggat    480

cagctcgcac agaggttgtc tgcaagcagt gtgaagctca tctaggtcac gtgtttcctg    540

atggacctgg gcccaatggt cagaggtttt gcatcaacag tgtggctttg aagttcaaac    600

caaggaaaca ctgaccatct tcaagagtcc cgttcccttg ccacccottc acgtgcaccc    660
```

-continued

```
tcaatttcca caattcactt gaatgacttg ttttatttgc aataaaactg ggctgaattt    720

gctgctgtct ccagcgagtc attgcttctc ttaatttatt tacctggaat caacttaatc    780

ctgtgtgtta ggctgttctt gtgttgctat aaagaagtac ctgatcagga tctgggagat    840

ttgaaaaaaa agaaaaacta gaaaaataaa caaaattaaa agaaaaaaaa atacctga      898
```

<210> SEQ ID NO 80
<211> LENGTH: 612
<212> TYPE: DNA
<213> ORGANISM: Homo sapiens
<220> FEATURE:
<221> NAME/KEY: misc_feature
<223> OTHER INFORMATION: Incyte ID No: 197271.1CB1

<400> SEQUENCE: 80

```
gcggccgcgg ccaatcggag ccgctcttgc tgcgacgcag cggtcggaag cggacaaggt     60

cgaggccggg ttggcgccgg agccggggcc gcttggagct cgtgtggggt ctccggtcca    120

ggggcgcggc atgggcgtcc tgggccgcag cggcgcgctg cctggtccgg ggtgcggacc    180

gaatgagcaa gtggacgagc aagcggggcc cgcgcagctt caggggccgc aagggccggg    240

gcgccaaggg catcggcttc ctcacctcgg gctggaggtt cgtgcagatc aaggagatgg    300

tcccggagtt cgtcgtcccg gatctgaccg gcttcaagct caagccctac gtgagctacc    360

tcgcccctga gagcgaggag acgcccctga cggccgcgca gctcttcagc gaagccgtgg    420

cgcctgccat cgaaaaggac ttcaaggacg gtaccttcga ccctgacaac ctggaaaagt    480

acggcttcga gcccacacag gagggaaagc tcttccagct ctaccccagg aacttcctgc    540

gctagctggg cgggggaggg gcggcctgcc ctcatctcat ttctattaaa cgcctttgcc    600

agctaaaaaa aa                                                        612
```

<210> SEQ ID NO 81
<211> LENGTH: 1154
<212> TYPE: DNA
<213> ORGANISM: Homo sapiens
<220> FEATURE:
<221> NAME/KEY: misc_feature
<223> OTHER INFORMATION: Incyte ID No: 197886.1CB1
<221> NAME/KEY: unsure
<222> LOCATION: 17-37
<223> OTHER INFORMATION: a, t, c, g, or other

<400> SEQUENCE: 81

```
tcggcaggat gttaggnnnn nnnnnnnnnn nnnnnnnctc gtcggctgcg ctcctgaccg     60

gggagcggac cggctgctca cctgctacgt gcaggactac cttgagtgcg tggagtcgct    120

gccccacgac atgcagagga acgtgtctgt gctgcgagac tggacaacaa atatcaaggt    180

cggggctgtg ccgggggcgt tggttcggcc ccagcggagt ccgaatcggg gtttgcagca    240

tgttttgcgg tgatgtttcc aacctctttc ccagtcaatg gatcaggacg gcgatcagca    300

gctcggaccg tcgcggatcc tggctccgca aacgttaaag gaaattgatg atgtctacga    360

aaaatataag aaagaagatg atttaaacca gaagaaacgt ctacagcagc ttctccagag    420

agcactaatt aatagtcaag aattgggaga tgaaaaaata cagattgtta cacaaatgct    480

cgaattggtg gaaaatcggg caagacaaat ggagttacac tcacagtgtt tccaagatcc    540

tgctgaaagt gaacgagcct cagataaagc aaagatggat tccagccaac cagaaagatc    600

ttcaagaaga ccccgcaggc agcggaccag tgaaagccgt gatttatgtc acatggcaaa    660

tgggattgaa gactgtgatg atcagccacc taaagaaaag aaatccaagt cagcaaagaa    720
```

```
aaagaaacgc tccaaggcca agcaggaaag ggaagcttca cctgttgagt ttgcaataga    780

tcctaatgaa cctacatact gcttatgcaa ccaagtgtct tatggggaga tgataggatg    840

tgacaatgaa cagtgtccaa ttgaatggtt tcacttttca tgtgtttcac ttacctataa    900

accaaagggg aaatggtatt gcccaaagtg caggggagat aatgagaaaa caatggacaa    960

aagtactgaa aagacaaaaa aggatagaag atcgaggtag taaaggccat ccacatttta   1020

aagggttatt tgtcttttat ataattcgtt tgctttcaga aaatgtttta gggtaaatgc   1080

ataagactat gcaataattt ttaatcatta gtattaatgg tgtattaaaa gttgttgtac   1140

tttgaaaaaa aaaa                                                     1154
```

```
<210> SEQ ID NO 82
<211> LENGTH: 776
<212> TYPE: DNA
<213> ORGANISM: Homo sapiens
<220> FEATURE:
<221> NAME/KEY: misc_feature
<223> OTHER INFORMATION: Incyte ID No: 199069.2CB1

<400> SEQUENCE: 82

ggtcgtgcca gatccgccgg acgccggaag tggttctccg cccctgccac tgggccatgg     60

agactgtggg cacagtagac tgtagtgtga ggctcgcggg gggcagtggc catggaggcc    120

cgtgctgaac gagctggtgt ctgtggagga cctgctgaag tttgaaaaga aatttcagtc    180

tgagaaggca gcaggctcgg tgtccaagag cacgcagttt gagtacgcct ggtgcctggt    240

gcggagcaag tacaatgatg acatccgtaa aggcatcgtg ctgctcgagg agctgctgcc    300

caaagggagc aaggaggaac agcgggatta cgtcttctac ctggccgtgg ggaactaccg    360

gctcaaggaa tacgagaagg ccttaaagta cgtccgcggg ttgctgcaga cagagcccca    420

gaacaaccag gccaaggaac tggagcggct cattgacaag gccatgaaga aagatggact    480

cgtgggcatg gccatcgtgg gaggcatggc cctgggtgtg gcgggactgg ccggactcat    540

cggacttgct gtgtccaagt ccaaatcctg aaggagacgc gggagcccac ggagaacgct    600

ccaggagggc ctgtccatcc tcgctgtcct ttccctgttc tccccctgtt ctccccctgc    660

cccccgtctc tatcctctgt ggccttcagc taatttctgc tcccctgaga ttcgtccttc    720

agccccatca tgtgctttgg gatgagtgta aataaaacgg ggctgtggct tgggaa        776
```

```
<210> SEQ ID NO 83
<211> LENGTH: 1744
<212> TYPE: DNA
<213> ORGANISM: Homo sapiens
<220> FEATURE:
<221> NAME/KEY: misc_feature
<223> OTHER INFORMATION: Incyte ID No: 206250.6CB1

<400> SEQUENCE: 83

acagaagtag ctctggctgt gatgggggatc ttactgggcc tgctactcct ggggcaccta     60

acagtggaca cttatggccg tcccatcctg gaagtgccag agagtgtaac aggaccttgg    120

aaaggggatg tgaatcttcc ctgcacctat gaccccctgc aaggctacac ccaagtcttg    180

gtgaagtggc tggtacaacg tggctcagac cctgtcacca tctttctacg tgactcttct    240

ggagaccata tccagcaggc aaagtaccag ggccgcctgc atgtgagcca caaggttcca    300

ggagatgtat ccctccaatt gagcaccctg gagatggatg accggagcca ctacacgtgt    360

gaagtcacct ggcagactcc tgatggcaac caagtcgtga gagataagat tactgagctc    420

cgtgtccaga aactctctgt ctccaagccc acagtgacaa ctggcagcgg ttatggcttc    480
```

```
acggtgcccc agggaatgag gattagcctt caatgccagg ctcggggttc tcctcccatc    540
agttatattt ggtataagca acagactaat aaccaggaac ccatcaaagt agcaacccta    600
agtaccttac tcttcaagcc tgcggtgata gccgactcag gctcctattt ctgcactgcc    660
aagggccagg ttggctctga gcagcacagc gacattgtga agtttgtggt caaagactcc    720
tcaaagctac tcaagaccaa gactgaggca cctacaacca tgacataccc cttgaaagca    780
acatctacag tgaagcagtc ctgggactgg accactgaca tggatggcta ccttggagag    840
accagtgctg ggccaggaaa gagcctgcct gtctttgcca tcatcctcat catctccttg    900
tgctgtatgg tggtttttac catggcctat atcatgctct gtcggaagac atcccaacaa    960
gagcatgtct acgaagcagc cagggcacat gccagagagg ccaacgactc tggagaaacc   1020
atgagggtgg ccatcttcgc aagtggctgc tccagtgatg agccaacttc ccagaatctg   1080
ggcaacaact actctgatga gccctgcata ggacaggagt accagatcat cgcccagatc   1140
aatggcaact acgcccgcct gctggacaca gttcctctgg attatgagtt tctggccact   1200
gagggcaaaa gtgtctgtta aaaatgcccc attaggccag gatctgctga cataattgcc   1260
tagtcagtcc ttgccttctg catggccttc ttccctgcta cctctcttcc tggatagccc   1320
aaagtgtccg cctaccaaca ctggagccgc tgggagtcac tggctttgcc ctggaatttg   1380
ccagatgcat ctcaagtaag ccagctgctg gatttggctc tgggcccttc tagtatctct   1440
gccgggggct tctggtactc ctctctaaat accagaggga agatgcccat agcactagga   1500
cttggtcatc atgcctacag acactattca actttggcat cttgccacca gaagacccga   1560
gggaggctca gctctgccag ctcagaggac cagctatatt caggatcatt tctctttctt   1620
cagggccaga cagcttttaa ttgaaattgt tatttcacag gccagggttc agttctgctc   1680
ctccactata agtctaatgt tctgactctc tcctggtgct caataaatat ctaatcataa   1740
cagc                                                                1744
```

<210> SEQ ID NO 84
<211> LENGTH: 1831
<212> TYPE: DNA
<213> ORGANISM: Homo sapiens
<220> FEATURE:
<221> NAME/KEY: misc_feature
<223> OTHER INFORMATION: Incyte ID No: 207220.1CB1

<400> SEQUENCE: 84

```
ctggagccgc cctgggtgtc agcggctcgg ctcccgcgca cgctccggcc gtcgcgcacc     60
tcgggcacct gcaggtccgt ggcgtcccgc ggctgggcgc ccctgactcc gtcccggcca    120
gggagggcca tgatttccct cccggggccc ctggtgacca acttgctgcg gtttttgttc    180
ctggggctga gtgccctcgc gcccccctcg cgggcccagc tgcaactgca cttgcccgcc    240
aaccggttgc aggcggtgga gggaggggaa gtggtgcttc cagcgtggta caccttgcac    300
ggggaggtgt cttcatccca gccatgggag gtgccctttg tgatgtggtt cttcaaacag    360
aaagaaaagg aggatcaggt gttgtcctac atcaatgggg tcacaacaag caaacctgga    420
gtatccttgg tctactccat gccctcccgg aacctgtccc tgcggctgga gggtctccag    480
gagaaagact ctggccccta cagctgctcc gtgaatgtgc aagacaaaca aggcaaatct    540
aggggccaca gcatcaaaac cttagaactc aatgtactgg ttcctccagc tcctccatcc    600
tgccgtctcc agggtgtgcc ccatgtgggg gcaaacgtga ccctgagctg ccagtctcca    660
aggagtaagc ccgctgtcca ataccagtgg gatcggcagc ttccatcctt ccagactttc    720
```

```
tttgcaccag cattagatgt catccgtggg tctttaagcc tcaccaacct ttcgtcttcc    780

atggctggag tctatgtctg caaggcccac aatgaggtgg gcactgccca atgtaatgtg    840

acgctggaag tgagcacagg tcagtgaggg ggcctggagc tgcagtggtt gctggagctg    900

ttgtgggtac cctggttgga ctggggttgc tggctgggct ggtcctcttg taccaccgcc    960

ggggcaaggc cctggaggag ccagccaatg atatcaagga ggatgccatt gctccccgga   1020

ccctgccctg gcccaagagc tcagacacaa tctccaagaa tgggaccctt tcctctgtca   1080

cctccgcacg agccctccgg ccaccccatg gccctcccag gcctggtgca ttgaccccca   1140

cgcccagtct ctccagccag gccctgccct caccaagact gcccacgaca gatggggccc   1200

accctcaacc aatatccccc atccctggtg ggtttcttc ctctggcttg agccgcatgg    1260

gtgctgtgcc tgtgatggtg cctgcccaga gtcaagctgg ctctctggta tgatgacccc   1320

accactcatt ggctaaagga tttggggtct ctccttccta taagggtcac ctctagcaca   1380

gaggcctgag tcatgggaaa gagtcacact cctgaccctt agtactctgc cccacctct    1440

ctttactgtg ggaaaaccat ctcagtaaga cctaagtgtc caggagacag aaggagaaga   1500

ggaagtggat ctggaattgg gaggagcctc cacccacccc tgactcctcc ttatgaagcc   1560

agctgctgaa attagctact caccaagagt gaggggcaga gacttccagt cactgagtct   1620

cccaggcccc cttgatctgt accccacccc tatctaacac caccccttggc tcccactcca  1680

gctccctgta ttgatataac ctgtcaggct ggcttggtta ggttttactg gggcagagga   1740

tagggaatct cttattaaaa ctaacatgaa atatgtgttg ttttcatttg caaatttaaa   1800

taaagataca taatgtttgt atgagataag a                                  1831


<210> SEQ ID NO 85
<211> LENGTH: 453
<212> TYPE: DNA
<213> ORGANISM: Homo sapiens
<220> FEATURE:
<221> NAME/KEY: misc_feature
<223> OTHER INFORMATION: Incyte ID No: 207591.1CB1

<400> SEQUENCE: 85

ctttcatcta ccaatccatg tgcattggat tgcacactaa gatgtatttt cttacgaaat     60

agttctgtgt ttatttttta attatagaaa ttccaaagaa cagcacatca gaatgctcct    120

ctcttttcag taattgtttt agttcagaga tcttcccgct cagcctccat aaatctaatg    180

tcattttttt tttaataagt cctaggagct ggggcttcat tcctccagcg ggagtccagt    240

cagggtcctg aagtttgctg gttcaggaaa gaacaggaaa gagaaaagcc ttctgtgccc    300

aggctaaagc tgttacattt ccacagtgtg gatgcagtca gaatccctgc acattctggt    360

cataaggatt agagtcacca gatgaggctc taaacagatc gcatcccttg gaattagaaa    420

gcagtggaga ccgggcgcag tgactcacac ctg                                 453


<210> SEQ ID NO 86
<211> LENGTH: 1268
<212> TYPE: DNA
<213> ORGANISM: Homo sapiens
<220> FEATURE:
<221> NAME/KEY: misc_feature
<223> OTHER INFORMATION: Incyte ID No: 232653.3CB1
<221> NAME/KEY: unsure
<222> LOCATION: 1226
<223> OTHER INFORMATION: a, t, c, g, or other

<400> SEQUENCE: 86
```

```
tttttcaca tttctttaca tttaatgtaa ataccaacag tggtcaccta tcaacatcat      60
ggaagagcac acttcacagg tttcataatc aaattttaaa ataatcacat gtaataaaaa    120
caaatgacta aaatacaaaa atgtaatgta tttatttact aaatggttag ctataaagat    180
acaatttctg ccttggagtt taaagcagtt tcatttttg ccatagttac tttttctgat      240
aatatgctag aatcacagtc ttctctgttt tatctggatt gtagggattg tttacatttt    300
atatgtttgt tcacttgaga accaaatttt tttttcttca tgatgatgga agctctgtaa    360
tataaaaatg tcattgtgct catatatttg aataataccg atcacggttt tcaaagtctc    420
tatgagcata tcttgcataa gtcttgttat gtgggatcct tccaaaaggt tcatggtcat    480
tgaaacaaga ttcaaaaact tcatcaacag cctttttagc tacttctttg ctgatattcc    540
taacagccag gatagaaaga gtggctctgt ctcgcacaca agtctggtgg tgttgtttta    600
atccaaaatg taacctgaat atttcattga caagtgagca gtctccacta aggttagcag    660
ctcgaacctc tgagcacgcc aaatgtctga tgttggtgaa ccagtcgaca tgggcacgac    720
aatgatcaaa tgcatgaata agctcgtgtg tgaccactct gttcatatgg gcctgattat    780
ggatattatt ctggcacaaa actatctgag atgttgaagc atcaaaacct ccactgacat    840
ttccattaca gtcttcgcaa gaaaagtgtc tatctttgtt aacagcacaa cctgagtgtt    900
tcatagcatc aagcagaagt ttgacatatg gatttgtctc cagcgtcttc aggagcctaa    960
gctggcactt ctggttgctg gtgaagaagc tggagaagaa cccttgctgg ggattcccct   1020
gggccagacg ctcggggaag acctggcaag agacgtgttg ctgctgcagc tgctcccctg   1080
ccgcggggcc ccgccggcgc tcgtccggag ctcccgccat gcctcccgca gacctcgccg   1140
ctgcttcctc ctggctcagg cggccagagc gagactggga aaggtaacct ccctcccgcc   1200
aacgcgaccg cccaggccct ccctcngcag ggaagaaggg cagcctggct gggctgaaga   1260
cgttaggc                                                            1268
```

```
<210> SEQ ID NO 87
<211> LENGTH: 1885
<212> TYPE: DNA
<213> ORGANISM: Homo sapiens
<220> FEATURE:
<221> NAME/KEY: misc_feature
<223> OTHER INFORMATION: Incyte ID No: 232968.10CB1

<400> SEQUENCE: 87

gggcgaagag gggcgcaagt tcattgcgtt ttgagtctcg ggacccctgt tggagagact     60
atggcgctca acaagaatca ctcggagggc ggcggagtga tcgtcaataa caccgagagc    120
atcctaatgt cctatgatca cgtggaactc acattcaatg acatgaagaa cgtgccagaa    180
gccttcaaag ggaccaagaa aggcactgtc taccttaccc cttaccgggt catctttctg    240
tccaagggca aggatgccat gcagtccttc atgatgccat tttatctcat gaaagactgt    300
gagatcaagc agcccgtatt tggtgcaaac tacatcaagg gaacagtgaa ggcggaagcg    360
ggaggtggct gggaaggctc tgcttcctac aagttgactt tcacggcagg gggcgccatt    420
gagttcggac agcggatgct ccaggtggca tctcaagcct ccagaggtga agtccccagt    480
ggagcctatg gctactctta catgcccagc ggggcctatg tctatccccc gccagtcgcc    540
aatggaatgt acccctgccc tcctggctac ccctatccac cgcccccacc tgagttctat    600
ccaggacccc ccatgatgga cggggccatg ggatacgtgc agcccccacc accgccctac    660
cctgggccca tggaacctcc ggttcagcgg ccccgatgtc ccctccactc ctgcagccga    720
```

```
agccaaggcc gcagaagcag ccgccagcgc ctattacaac ccaggcaatc ctcacaacgt    780

ctacatgccc acgagccagc cgccgccacc tccctactac ccaccggaag ataagaagac    840

ccagtaggcc ctcctgcctc cctgcctccc accctcatct ctctacccta cccctcccat    900

cggggctgtg ctggggcttg gggaggggag ggggcgcctt gttctccctc caggtctgat    960

cataaacaat taccaggaac tagcattgtg ggacattagg gcccccggcc tcgggagagg   1020

tgccgcccag cttcccatgc cagcccggag cccacagtgc tgcccagcgt acctccctca   1080

ccgtctgggg ctcttctggg agcacggagc atcccctgtt cctgtttcac tctcagcttc   1140

tcccctcgaa gggactctct ggccacctcc tccaccgcag tccagctccc tcagtctggg   1200

cacccactgc tacactcagc ctcatgagcc acttcagacc agccaggtgt cttcccgggc   1260

cctgccagac cctgctcaca ttccctctgc tggtctgtgc tggtctcaga aggccaccgc   1320

gcccgcattc cactcagcca gggtccagct gcagcccccg ccacccttcc ttcccttccc   1380

tgtcctgggt catgttgttg ccaccctgtg tgacttttga agctgtaaaa tgagcttcca   1440

gggcttgggt ggcgtcgggg cagggccgcc gaggctggga ggaagccctt ctgccttttg   1500

ctggtgtttc tggaatttgc tttccctcac ctctcacttc cttctagaag gagcttcctg   1560

actggaacca gagaatgcat gtctgtccac ttggtggctg ctgggtgggg ccgggaacaa   1620

gggcccctga ccctgtgtgc tggccgggac ctgccaccag ccccccagcc tgcttcttcc   1680

ccttaagctt tgtgcccctg gatgcgctaa cattcactct tgtttgtccc tggactggcc   1740

atgaagtgag gagatggtta tttaaagaga attccctatt tatttgacaa aaaatccagt   1800

taatatatta atgtgaaata aaccctgttt gcacctcgat ttgtttgctg aaaatgtgaa   1860

atagtaaaaa tgaaataact ggaaa                                          1885
```

```
<210> SEQ ID NO 88
<211> LENGTH: 753
<212> TYPE: DNA
<213> ORGANISM: Homo sapiens
<220> FEATURE:
<221> NAME/KEY: misc_feature
<223> OTHER INFORMATION: Incyte ID No: 235464.2CB1
<221> NAME/KEY: unsure
<222> LOCATION: 657
<223> OTHER INFORMATION: a, t, c, g, or other

<400> SEQUENCE: 88
```

```
caccettgcc acctgtcatt cccacttgga ccaggccagc agcctccctg gtctctctga     60

ccctccccct gagttcgttc accaaaggca gtaacggaga cacccctca acacacacag    120

gaagcagatg gccttgacac cagcagggtg acatccgcta ttgctacttc tctgctcccc    180

cacagttcct ctggacttct ctggaccaca gtcctctgcc agacccctgc cagaccccag    240

tccaccatga tccatctggg tcacatcctc ttcctgcttt tgctcccagt ggctgcagct    300

cagacgactc caggagagag atcatcactc cctgcctttt accctggcac ttcaggctct    360

tgttccggat gtgggtccct ctctctgccg ctcctggcag gcctcgtggc tgctgatgcg    420

gtggcatcgc tgctcatcgt gggggcggtg ttcctgtgcg cacgcccacg ccgcagcccc    480

gcccaagaag atggcaaagt ctacatcaac atgccaggca ggggctgacc ctcctgcagc    540

ttggaccttt gacttctgac cctctcatcc tggatggtgt gtggtggcac aggaaccccc    600

gccccaactt ttggattgta ataaaacaat tgaaacacca aaaaaaaaaa agtgcanaga    660

catgagaaga caccagcgca aggcccacac aaaaggggcg gccgccgact aagtagccct    720
```

tcgcccgggg acttaattcc ggacgggtgc ctt 753

<210> SEQ ID NO 89
<211> LENGTH: 1168
<212> TYPE: DNA
<213> ORGANISM: Homo sapiens
<220> FEATURE:
<221> NAME/KEY: misc_feature
<223> OTHER INFORMATION: Incyte ID No: 245000.1CB1
<221> NAME/KEY: unsure
<222> LOCATION: 34, 55
<223> OTHER INFORMATION: a, t, c, g, or other

<400> SEQUENCE: 89
ggagcgcagg tgaggcggcg ccccactccc ggcngccccc gggcctcctt ccgcncgcac 60
cccgagctgc ctccgcacag ttggaggagc gtaggaggga cccccaccca gggatgacac 120
tccaggaagg ggactgcaga ggaagccagc cgttcctctc tggtgctccc ttcctcatag 180
actgtgtccc tgacaatggg aacagcccga ccagtgatga gatggccccg gaggccccac 240
agcacaccca cattcgatgt gcacatccac caggagtctg ccctggccaa gctcctgctc 300
acctgctgct ctgcgctgcg gccccgggcc acccaggcca gggggcagca gccggctgct 360
ggtggcctca tgggtgatgc agatcgtgct ggggatcttg agtgcagtcc taggaggatt 420
tttctacatc cgcgactaca ccctcctcgt cacctcggga gctgccatct ggacaggggc 480
tgtggctgtg ctgggctgga gctgctgcct tcatttacga gaaacggggt ggtacatact 540
gggccctgct gaggactctg ctagcgctgg cagctttctc cacagccatc gctgccctca 600
aactttggaa tgaagatttc cgatatggct actcttatta caacagtgcc tgccgcatct 660
ccagctcgag tgactggaac actccagccc ccactcagag tccagaagaa gtcagaaggc 720
tacacctatg tacctccttc atggacatgc tgaaggcctt gttcagaacc cttcaggcca 780
tgctcttggg tgtctggatt ctgctgcttc tggcatctct ggcccctctg tggctgtact 840
gctggagaat gttcccaacc aaagggggtga gtccctaaga aaagagacca gaaggaaatg 900
ttggaagtga gtggaatcta gccatgcctc tcctgattat tagtgcctgg tgcttctgca 960
ccgggcgtcc ctgcatctga ctgctggaag aagaaccaga ctgaggaaaa gaggctcttc 1020
aacagcccca gttatcctgg ccccatgacc gtggccacag ccctgctcca gcagcacttg 1080
cccattcctt acaccccttc cccatcctgc tccgcttcat gtcccctcct gagtagtcat 1140
gtgataataa actctcatgt tattgaaa 1168

<210> SEQ ID NO 90
<211> LENGTH: 2798
<212> TYPE: DNA
<213> ORGANISM: Homo sapiens
<220> FEATURE:
<221> NAME/KEY: misc_feature
<223> OTHER INFORMATION: Incyte ID No: 245084.3CB1
<221> NAME/KEY: unsure
<222> LOCATION: 126, 129, 199, 204
<223> OTHER INFORMATION: a, t, c, g, or other

<400> SEQUENCE: 90
ctccactccc caccagaaac tcttattttt tccccccctat gtggtcatga attcctcctg 60
ggtgcatagc tccctaagtt gttctgtgtt ttagtgctta taatttccca catcccatga 120
tgcccnttna tagaattatt ttttctgtac tcacacgaaa tggaaacaga agagatgaaa 180
aaccctgggg atgcggccnc tcangtctca aactgatcgg ctgctaagca caacctgcat 240
atctcttggc tgagttcctt tcttggctca gttagatttt gcatgaccta ggaggcttag 300

-continued

```
gacccagggg gcgcctttca gctgaaaaac agtctcgcgc tgcagcaagc tagctgggaa    360
gctcccagtt ctaaagagag gctgtttacc agaacagcat aacaagggca ggtctgactg    420
caaggctggg actgggaggc agagccgccg ccaagggggc ctcggttaaa cactggtcgt    480
tcaatcacct gcaagacgaa ggaggcaagg atgctgttgg cctgggtaca agcattcctc    540
gtcagcaaca tgctcctagc agaagcctat ggatctggag gctgtttctg ggacaacggc    600
cacctgtacc gggaggacca gacctccccc gcgccgggcc tccgctgcct caactggctg    660
gacgcgcaga gcgggctggc ctcggccccc gtgtcggggg ccggcaatca cagttactgc    720
cgaaacccgg acgaggaccc gcgcgggccc tggtgctacg tcagtggcga ggccggcgtc    780
cctgagaaac ggccttgcga ggacctgcgc tgtccagaga ccacctccca ggccctgcca    840
gccttcacga cagaaatcca gtaagcgtct gaagggccag gtgcagatga ggtgcaggtg    900
ttcggctcct gccaacgccc tgcccgctcg gagtgaggcg gcagctgtgc agccagtgat    960
tgggatcagc cagcgggtgc ggatgaactc caaggagaaa aaggacctgg gaactctggg   1020
ctacgtgctg ggcattacca tgatggtgat catcattgcc atcggagctg gcatcatctt   1080
gggctactcc tacaagaggg ggaaggattt gaaagaacag catgatcaga aagtatgtga   1140
gagggagatg cagcgaatca ctctgccctt gtctgccttc accaacccca cctgtgagat   1200
tgtggatgag aagactgtcg tggtccacac cagccagact ccagttgacc ctcaggaggg   1260
cagcaccccc cttatgggcc aggccgggac tcctggggcc tgagcccccc cagtgggcag   1320
gagcccatgc agacactggt gcaggacagc ccaccctcct acagctagga ggaactacca   1380
ctttgtgttc tggttaaaac cctaccactc cccgcttttt ttggcgaatc ctagtaagag   1440
tgacagaagc aggtggccct gtgggctgag ggtaaggctg ggtagggtcc taacagtgct   1500
ccttgtccat cccttggagc agattttgtc tgtggattga gacagtggca gctcccacag   1560
tgatgctgct gctaagggct tccaaacatt gcctgcaccc ctggaactga accagggata   1620
gacggggagc tcccccaggc tcctctgtgc tttactaaga tggcctcagt ctccactgtg   1680
ggcttgagtg gcatacactg ttattcatgg ttaaggtaaa gcaggtcaag ggatggcatt   1740
gaaaaaatat atttagtttt taaaatattt gggatggaac tccctactga cctctgagaa   1800
ctggaaacga gtttgtacag aagtcagaac tttgggttgg gaatgagatc taggttgtgg   1860
ctgctggtat gcttcagctt gctggcaatg atgtgccttg acaaccgtgg gccaggcctg   1920
ggcccagggg actcttcctg tttcataagg aaaggaagaa ttgcactgag cattccactt   1980
aggaagagga tagagaagga tctgctccgc ctttggccac aggagcagag gcagacctgg   2040
ggatgcccca gtttctcttc agggatggat agtgacctgt cttcattttg cacaggtaag   2100
agagtagtta gctaacctat gggaattata ctgtggggcc ttgtgagctg cttctaagag   2160
gctaacctgg aaactaagct cagagggcaa ggtaataaag cacttcaggg cttgctcccc   2220
aagtgggcct gatttagcag gtggtcctgc gggcgtccag gtcagcacct tcctgtaggg   2280
cactggggct agggtcacag cccctaactc ataaagcaat caaagaacca ttagaaaggg   2340
ctcattaagc cttttggaca caggacccca gagaggaaaa agtgacttgc ccaaggtcgt   2400
aagcaagcta ctggcatggc aagagcccag cttcctgacg gagcgcaaca tttctccact   2460
gcactgtgct agcagctcag cagggcctct aacctgtgat gtcacactca agaggccttg   2520
gcagctccta gccatagagc ttcctttcca gaacccttcc actgcccaat gtggagacag   2580
gggttagtgg ggctttctat ggagccatct gctttgggga cctagacctc aggtggtctc   2640
```

ttggtgttag tgatgctgga gaagagaata ttactggttt ctacttttct ataaaggcat 2700
ttctctatat acatgtttta tatacctcat tctgacacct gcatatagtg tgggaaattg 2760
ctctgcattt gacttaatta aaaaaaaaaa aaaagggc 2798

<210> SEQ ID NO 91
<211> LENGTH: 503
<212> TYPE: DNA
<213> ORGANISM: Homo sapiens
<220> FEATURE:
<221> NAME/KEY: misc_feature
<223> OTHER INFORMATION: Incyte ID No: 249553.1CB1

<400> SEQUENCE: 91
agggagagaa aaaaattgta aaaataaaaa tagtaaaaga aactgataaa gaaaagtaat 60
ggaagacagg aagaaaagaa gagaaggaag taaagaggaa aacttataaa tattcccaca 120
gatagacaaa gtcaagcata aaactggagc ttgagaagga aatgaaaggc cgtggcacct 180
tcttataccc tagaagaaga cctccataca ggaagacttg tgtgtggggt tgggacatta 240
gaatcatcca caagtcaccc caaaccttgg aactgtcagg gtcagagggg aaccaccatt 300
tattaagcat ttgccatgtg ccaggcacta acccagatgc attataaata ccacgttgtt 360
tcacctgtgt gtggcatcta cagaccttag atcatagctg tgagaacaac gtaagcactg 420
ccaaagttat cagctaccca tatctcatgt ttttgatgtt atctactctt cctagaatca 480
aatattaaaa taattttaaa acc 503

<210> SEQ ID NO 92
<211> LENGTH: 2885
<212> TYPE: DNA
<213> ORGANISM: Homo sapiens
<220> FEATURE:
<221> NAME/KEY: misc_feature
<223> OTHER INFORMATION: Incyte ID No: 249997.2CB1
<221> NAME/KEY: unsure
<222> LOCATION: 8
<223> OTHER INFORMATION: a, t, c, g, or other

<400> SEQUENCE: 92
ggtgaggnaa aaaaaaatta aaaaaaaaat gcaagctgtc aggatgctta agctcttttc 60
agacatctgc agtttcatcc ctaccttgtt cacataccat ccaagaggca cataggctac 120
ccaagagagc cttggattca gtggtacact ccttgggccc aagggcttta gcagctggat 180
atggggttcc ttgattttcc tctgggccca aatatagccc tcacactctt ggaatttcca 240
ggtatggggg tagccccaaa aggaggaatc tcctatggcc aataaggtat cttgacttta 300
tcaaagtaga agagagggtc acttcggagt caaatcatac actaggcctt tgatgcttta 360
attcttcttc agttcattaa aagtaactac taaggaaagg ttaaaaactt cccctcaaaa 420
aggaatcaac cccaggaagt aattatttac aacgattttc ccaaattttg tacaatctgt 480
cctggaaagc aaaccccttt taaaatctaa tgtctgggct ttgagtatta gctcatttag 540
ggtggacaaa tgcattactg ttttcaaact gctcacattt attcagtatt tctccaagtt 600
gctatctact cagccttatg aatgcccctc gcttttctaa ggccatgtga aaatcacggc 660
actgccctta gccttgtgtc atctgctttt tcgttctgcg atatgcccag ttcccaaatc 720
aattataggt acctgtttag gagagaggaa gattttacct ctcaaagggt gagatttgaa 780
atttacacta aaaagacaac tttacattta atgcttcact taatgagaca ttcttttttt 840
tataagtcta tttttctact cagtttcaga acactaatct gattttcact ctgattttta 900

-continued

```
acgtttcttt aaatatttat aatgtagctt ctttcaaaat attttcatga aaaattactt    960
ttattatacc attatgtgca tgttattggt agcaggcata gtttattatt tagtactgaa   1020
acatgctctt ttacctaaca gtaaaaccaa gtatgttttg ataatatatc tgttaatatg   1080
cttatagtgg taagaaatgg acttgaggtc ccaggagatt tcattttatt caccctggtc   1140
agatacaata aaggctatga gtataaatac ataacttcct aaccaggtgt agggcatgtt   1200
catgaatatc aaatcttttg atgctggacc caagagagga aaagttgtag ctaaatgttg   1260
atttacttat aactagacgt ctatgtgaga aaatatatgt atacatatat atgatatgca   1320
gaagtcactt tttttatcag gctttattct ccttacaaag ccacagttta actgtctgca   1380
acagttggtt tatgttaatg atagacaaat acccagtgtt tgttactttt tccaactacc   1440
actgtaatga taatctttct cacgtatata catgcaactt cttggcttca tttccatgaa   1500
gctgtttcaa tatattcagt atactttgtc cttaatgctg cttctgttaa cagtgatctc   1560
tttctttttt tcattcttat atcttcatta gttcatcata aatctgtcca gttgaggcct   1620
caggaccacg gcatgatttc atgactccga agtattttac agaaacattt tttaaataag   1680
ggaaatattt tatataccag atggttcaca agtgatggct catagctagt tttttttttc   1740
ttctaaaaaa tgtcaggttt ttaaaatcat ttaccttatt aaaatgaaaa gtgccatact   1800
taacttttaa aggaaagacc tgacttgctt tttctctatt tagactgttt ttgtacttta   1860
ctaatcttta aactatcagg aaaaaaacca aaactttata ccaatgattt agtaattttg   1920
aggcataggg tagcttacgt agtgggagga tgtgccaaat attctcttca aatgccacct   1980
tctcaattta taactaaaat agtgttatct gactaattcc tctgaatttt gatgtaagat   2040
ctatataggc ccccaaaatg atcgtagtac atgccagtca tttctcagtg aaataaatac   2100
aataccagag tacattatga gttttattgc tttcttttat ggtagacctg ttaatgggga   2160
aaaaatacat caaatcaaat agaatcttat atctgtatgt taaaatagag cacttacctg   2220
aagtcagtgg cctgggatca tagccctgga tcatttccca gtctgtcctg tgctgtgtga   2280
ccttggacaa ggcgcttcat ctctctgggc ctctatttct ccatttgtaa aacaagtggc   2340
tgcagtagat gatggctgag agcccttcct gttcccagat gccttggtcc aaagacccca   2400
cccctctgct ggtcctgcca acgtgttggt gctataagct gcttcagata taaaattggt   2460
ttatctataa tgtttgttca tttaatagct tctaaaaggc ctttttgtta tacagtgctt   2520
tttttctagt tttatggact tggttactgt aataatgtct tgtttttagc catgtaacta   2580
caaacagata ttctcttgat gtcttagtaa atttgcattt gatatatcat tgatgagatt   2640
ttgttgttat gtaatattct ttggctacgc atctgtccag catcttatta accataatac   2700
tgtgatcatt atttggaaat atgtcctatg gaaagaataa aagcatgtac ttcacagcta   2760
gcatgttcac agatttgaaa gaagtttcat taaaagcacc attgctttct gtactgcgtc   2820
agtgcctcat tgtatcatcc tacttgtgtt ttgctcaata aatgaataaa agaccatttc   2880
tcttc                                                               2885
```

<210> SEQ ID NO 93
<211> LENGTH: 3446
<212> TYPE: DNA
<213> ORGANISM: Homo sapiens
<220> FEATURE:
<221> NAME/KEY: misc_feature
<223> OTHER INFORMATION: Incyte ID No: 252234.3CB1
<221> NAME/KEY: unsure
<222> LOCATION: 1432, 1435
<223> OTHER INFORMATION: a, t, c, g, or other

<400> SEQUENCE: 93

```
gtttcaaagg acacaaagag agatgtggac tcaaagtcac cggggatgcc tttatttgaa     60
gcagaggaag gagttctatc acgaacccag atatttccta ccactattaa agtcattgat    120
ccagaatttc tggaggagcc acctgcactt gcatttttat ataaggatct gtatgaagaa    180
gcagttggag agaaaaagaa ggaagaggag acagcttctg aaggtgacag tgtgaattct    240
gaggcatcat ttcccagcag aaattctgac actgatgatg gaacaggaat atattttgag    300
aagtacatac tcaaagatga cattctccat gacacatctc taactcaaaa ggaccagggc    360
caaggtctgg aagaaaaacg agttggtaag gatgattcat accaaccgat agctgcagaa    420
ggggaaattt ggggaaagtt tggaactatt tgcagggaga agagtctgga agaacagaaa    480
ggtgtttatg gggaaggaga atcagtagac catgtggaga ccgttggtaa cgtagcgatg    540
cagaagaaag ctcccatcac agaggacgtc agagtggcta cccagaaaat aagttatgcg    600
gttccatttg aagacaccca tcatgttctg gagcgtgcag atgaagcagg cagtcacggt    660
aatgaagtcg gaaatgcaag tccagaggtc aatctgaatg tcccagtaca agtgtccttc    720
ccggaggaag aatttgcatc tggtgcaact catgttcaag aaacatcact agaagaacct    780
aaaatcctgg tcccacctga gccaagtgaa gagaggctcc gtaatagccc tgttcaggat    840
gagtatgaat ttacagaatc cctgcataat gaagtggttc ctcaagacat attatcagaa    900
gaactgtctt cagaatccac acctgaagat gtcttatctc aaggaaagga atcctttgag    960
cacatcagtg aaaatgaatt tgcgagtgag gcagaacaaa gtacacctgc tgaacaaaaa   1020
gagttgggca gcgagaggaa agaagaagac caattatcat ctgaggtagt aactgaaaag   1080
gcacaaaaag agctgaaaaa gtcccagatt gacacatact gttacacctg caaatgtcca   1140
atttctgcca ctgacaaggt gtttgggcac ccacaaagac catgaagttt caacgcttga   1200
cacaagctat aagtgctgta aaggttcaat tagcagaatt tctagaaaat ttacaagaaa   1260
agtccttgag gattgaagcc tttgttagtg agatagaatc ctttttttaat accattgagg   1320
aaaactgtag taaaaatgag aaaaggctag aagaacagaa tgaggaaatg atgaagaagg   1380
ttttagcaca gtatgatgag aaagcccaga gctttgagga agtgaagaag angangatgg   1440
agttcctgca tgagcagatg gtccactttc tgcagagcat ggacactgcc aaagacaccc   1500
tggagaccat cgtgagagaa gcagaggagc ttgatgaggc cgtcttcctg acttcgtttg   1560
aggaaatcaa tgaaaggttg ctttctgcaa tggagagcac tgcttcttta gagaaaatgc   1620
ctgctgcgtt ttccctttttt gaacattatg atgacagctc ggcaagaagt gaccagatgt   1680
taaaacaagt ggctgttcca cagcctccta gattagaacc tcaggaacca aattctgcca   1740
ccagcacaac aattgcagtt tactggagca tgaacaagga agatgtcatt gattcatttc   1800
aggtttactg catggaggag ccacaagatg atcaagaagt aaatgagttg gtagaagaat   1860
acagactgac agtgaaagaa agctactgca tttttgaaga tctggaacct gaccgatgct   1920
atcaagtgtg ggtgatggct gtgaacttca ctggatgtag cctgcccagt gaaagggcca   1980
tctttaggac agcaccctcc accctgtga tccgcgctga ggactgtact gtgtgttgga   2040
acacagccac tatccgatgg cggcccacca ccccagaggc cacggagacc tacactctgg   2100
agtactgcag acagcactct cctgagggag agggcctcag atctttctct ggaatcaaag   2160
gactccagct gaaagttaac ctccaaccca atgataacta ctttttctat gtgagggcca   2220
tcaatgcatt tgggacaagt gaacagagtg aagctgctct catctccacc agaggaacca   2280
```

-continued

```
gatttctctt gttgagagaa acagctcatc ctgctctaca catttcctca agtgggacag   2340

tgatcagctt tggtgagagg agacggctga cggaaatccc gtcagtgctg ggtgaggagc   2400

tgccttcctg tggccagcat tactgggaaa ccacagtcac agactgcccc agcatattcg   2460

actcggcatc tgctccagct tcggctgtgc aggcaggtgc cctaggacaa ggggagacct   2520

catggtacat gcactgctct gagccacaga gatacacatt tttctacagt ggtattgtga   2580

gtgatgttca tgtgactgag cgtccagcca gagtgggcat cctgctggac tacaacaacc   2640

agagacttat cttcatcaac gcagagagcg agcagttgct cttcatcatc aggcacaggt   2700

ttaatgaggg tgtccaccct gcctttgccc tggagaaacc tggaaaatgt actttgcacc   2760

tggggataga gccccggat tctgtaaggc acaagtgatc cttggctttc agaatttgca   2820

agaacagcga tttgaatttt gggggggtct gctgttcatt cctttaggtg ctatacatta   2880

ttcaaaaagt ctcccgcgca tttgcactaa tgatggctgc atgcatagca atcagcatgt   2940

gagcaaaatc gacaagaaaa ccttgacttt acagagcagt gtgtgagtaa acagaatgaa   3000

aacaacaacc tccactcttt agtttatata agtttgagtt ctttcctaaa ttaaaagatc   3060

tacacttgag ttgggaaccg aaagagaaaa atggacttcc atctgtttta ctggtaaagg   3120

aaatcctctg atggacaggt cagagtgaag gaaggttgtg ctggtaagac atctctgacg   3180

aagagccatg gatgctttcc acaaaatgtc acctcgctgc actaaaggat gatgaatcct   3240

aatcattaaa ggaattgttt cagctgattt aaatttataa tgaactcttt tgtaataatg   3300

tatactgtag aacatgagtc tctcctccct aaaattttaa atgtagaaaa gtgctatata   3360

ttagaaattt ccattttgtt aaataaatgg ttagagtcta taaagccagt catgttatgt   3420

gaacttactc catgtaactt actggc                                        3446
```

<210> SEQ ID NO 94
<211> LENGTH: 458
<212> TYPE: DNA
<213> ORGANISM: Homo sapiens
<220> FEATURE:
<221> NAME/KEY: misc_feature
<223> OTHER INFORMATION: Incyte ID No: 254173.1CB1

<400> SEQUENCE: 94

```
tgatttcatt cattcattta ttcaattttt tttaaaaaag ctattacgtt aaactcttag     60

gatgaggaca agccttacaa tggtgtgtga gtgtgagtat gtgttcatgc atacactcac    120

atccctgtgt ctgagtgttg tgggtgtgtg tgatgtctgt gcatttctat gtggtatgta    180

ttcatatgca tgtgtattgg ggtacactaa atttgggttt gcacagaaaa gaataaacag    240

aattgtactg gaatagttta cctagtgctt cctctaagaa cagcacacag ctcattcagt    300

tttgctgatt ttcatcctct gcatccacaa agcacactga ggtctctcct atcaccttga    360

caatggggat ttgaccccaa ccatctccac cgcagttgga ctgacaggca gcaagtggtg    420

ctcatcaaag acagctctga ggaggctttc gggagaca                            458
```

<210> SEQ ID NO 95
<211> LENGTH: 373
<212> TYPE: DNA
<213> ORGANISM: Homo sapiens
<220> FEATURE:
<221> NAME/KEY: misc_feature
<223> OTHER INFORMATION: Incyte ID No: 256852.1CB1

<400> SEQUENCE: 95

```
ggcctatgga gcagccctga tctgcaagga gcggcatctc tggcgctgct gtgcacagct     60
```

gcttccatga aagctgctgc ctaacaccac cagctcaccc ttgaatcttt gggcaaatcc 120
aagaactctc ccaggctaag ccccagtctt ggggcttgcc tgtcctgcat catctggcaa 180
ccagcaaagg gacaaggaca gcggagatgg tggcaattgg cagagaggca agacagcaga 240
gacagagagg cagcaattgg tgagagacaa gagacagcag ttggcaagac agcaagagac 300
ggtgaagcag tctgtgattg aggatgtaag atctgtaaca ctgaggaagt accaataaag 360
agctgctaac act 373

<210> SEQ ID NO 96
<211> LENGTH: 4487
<212> TYPE: DNA
<213> ORGANISM: Homo sapiens
<220> FEATURE:
<221> NAME/KEY: misc_feature
<223> OTHER INFORMATION: Incyte ID No: 330852.1CB1
<221> NAME/KEY: unsure
<222> LOCATION: 1985, 1992, 1997
<223> OTHER INFORMATION: a, t, c, g, or other

<400> SEQUENCE: 96
gcgaccgctc gtccgccggc ttgaggcccg cggggaggcg cgcaattcgt cggcccgcgg 60
gggggcggcc atcccggcag tcttcgcggc gaccaaggac taccaggaag gggagcggct 120
gggatggcgc gtccgcggcc ccgcgagtac aaagcgggcg acctggtctt cgccaagatg 180
aagggctacc cgcactggcc ggcccggatt gatgaactcc cagagggcgc tgtgaagcct 240
ccagcaaaca agtatcctat cttctttttt ggcacccatg aaactgcatt tctaggtccc 300
aaagaccttt ttccatataa ggagtacaaa gacaagtttg gaaagtcaaa caaacggaaa 360
ggatttaacg aaggattgtg ggaaatagaa aataacccag gagtaaagtt tactggctac 420
caggcaattc agcaacagag ctcttcagaa actgagggag aaggtggaaa tactgcagat 480
gcaagcagtg aggaagaagg tgatagagta gaagaagatg gaaaaggcaa aagaaagaat 540
gaaaaagcag gctcaaaacg gaaaaagtca tatacttcaa agaaatcctc taaacagtcc 600
cggaaatctc caggagatga agatgacaaa gactgcaaag aagaggaaaa caaaagcagc 660
tctgagggtg gagatgcggg caacgacaca agaaacacaa cttcagactt gcagaaaacc 720
agtgaaggga cctaactacc ataatgaatg ctgcatatta agagaaacca caaggaaggt 780
tatatgtttg gttgtctaat attcttggat ttgatatgaa ccaacacata gtccttgttg 840
tcattgacag aaccccagtt tgtatgtaca ttattcatat tcctctctgt tgtgtttcgg 900
ggggaaaaga cattttagcc ttttttaaaa gttactgatt taatttcatg ttatttggtt 960
gcatgaagtt gcccttaacc actaaggatt atcaagattt ttgcgcagac ttatacatgt 1020
ctaggatcct tttatcaagg cagttatgat catcgttttc ctgccttgac ccccaccatca 1080 tcaaacactc agttaaatat aaattaacat tttttagatg accactcaac ataatgctta 1140
agaatggaat ttcctctctg tgacagaacc caggaattaa ttcctaaata cataacgttg 1200
gtatattgaa gacgaaatta aaattgtcct tcagttttga ggccatgtgt aaagtttaac 1260
catattgtaa aatatctatt ccgtattaga aatagctagt tgacagctta tacttctcaa 1320
aattcatatt gttatgtaca caaactaagt ttctatatgt gaagttagtg agtctttttg 1380
tgttactcca aaataaaggc aatgatttat ttttttccca gtgccaatac aattttgagc 1440
taagcactca aggtggatac tttacatttt aaagctggaa tcagcaacag ccctatggga 1500
aaccagacaa agcattgact tttaaatgta gacttttaaa ataaactgtt ttcttttgga 1560

-continued

```
actacaatta gaatagttaa tattcatcct taaaccatta ttatgtgtac attattgttg   1620
ctattgtgat aatagagaat tttatttatt tttatgccag cttatattgt gagaacacat   1680
ttagtcagtt tgggttttat caatcctgtt aatgcttgtc cttggaacat ctttcgcgta   1740
ttcacggttt gtagttgaaa agtttactgt aaaaaaatca aaaacaaaaa aatgtattgt   1800
ttttacagaa taaatttatt ggaatgtgta ctgggagtaa gatttgaggt tgtaagcaaa   1860
ctaagttagt gtaatttggc ttcatatatg taacgtgagg tattaatgta attcatatat   1920
taaagcaaaa attgttcaca gcaagctgac aatagaatca agtgcaggtg agggtttttc   1980
tttanctttc tntaatnttt tttaaacact ctctgggttt tagattattt gaaaacactg   2040
taggggatga tggggagatg actacatgat ttgcttacac ttacatattt accagcccag   2100
tggaccctag attttgtaat ttgatattat ccatgcattg atttgtatcc cattttcttt   2160
tggttttctt gatgagagct aataaaaaca tgagaaaatg tgagcagacc taaaagccta   2220
gggccgttaa taatgatgat ggtgatgatg gcagctaagg gtatgaaagc accagtccat   2280
ttatcattcc agggcacagt gaggaggtgg ctgtttgtat ttttggtgtg tttctttcat   2340
ttagtgaata ctgattttct ctagtatact caacatacaa tcccaaacat gaaaagttca   2400
taaaaagata gtagggatgt cgatctaata cttcttcctt aaaaggtcct ttttaatttt   2460
gaatatttga atgtattttt taattaatga aatttaattc atcaaaagac ctcttcattg   2520
ctcacactga aacataaggg gaatgtagat ggcattttga attggaatat acaactcaca   2580
aattttcttt aaaagcgttt tatgtgtata tatgaaatgt ttcaaattta ataagatttg   2640
tctttataag aggccaaaaa taattttatt aaaaatatac acagaaatac aatagaaata   2700
tttccagcca ccaataaaac aaatgttcat taaggataga gataaagtta ctgatcccta   2760
tttagctgtt taaattcaca caaaaaaatt tagtaaaagt aattttcttg aaacagcagc   2820
aaataataaa ctttccttgg gaaaacattt ttcaaacaac atttaaaaat attctgatga   2880
tttgcctttt atattgagtt taataatgaa gcatattcat cttatttgca aaagttactc   2940
ctccagtctg cattcactgt tttgaatttt ttaatatgca caggccatat tctcttttga   3000
atagtttcat ttcatgctca ctactgttgg cactaaattg taattttta cacttataat   3060
tattttatat gtcaaacaat attgagatgg atgatcaagt ttattcacaa atgattttga   3120
atatatttct ttaaacaaac tgtttctcaa gaatttccat tttccttcaa aaaaaattta   3180
cacaatacca tatagctcac acatacagtg cagagcaaga atgtacatat tcttaagtac   3240
tcacgtatga gaagagagtg aaatgggaca aaatatcagt accagtataa caaaagttag   3300
taatttagaa aggaggaaca tgaagtaata tttttattcc actttttctt ctgcctttgt   3360
ttttatgaag aactctggtt tgtagataca acgataggcc aagagctgag gaagaactcc   3420
atatgctatg tttaatgcta aaaaaaggat ttttgcttct tcagggactc tgtagacata   3480
agcagttcta gcatgaagag atgcaccaat gtgagaaaac tgagcctgag ccagacctcc   3540
agcatgtatc aatgtgatgt caggcatcca ggaacatcca ggaaccacta agccatacag   3600
tgcagtcaca aagtaaggaa cagaatagaa catatatgcc agcatctgaa ttttaggata   3660
agcagcagga tcctttagat agggctcttg aaattgcgta tataatcggc agagctcaga   3720
tgggcaatcc aaagcaatca aacctctgaa caggcaaaat ccagttgcca ggaggagaca   3780
cacaaccaac attaaatcaa atggtcttct cagcaggtct ttcgcttggg cttcttgaat   3840
aacctttgag ggtaattat aattttctga tggctgatta tagattctga aaccagccca   3900
gacaggaaga caagtatatg gtatgcttaa gaaaaaagca gggcaaattc gtgttccata   3960
```

-continued

```
cttccctaca atgtttcctg gcacaaaaac aacaacactc ataataatag atccaaccca   4020

atataggcca atggttctat aagtttcctc ccatgctatg gctgccacca tcaccaggta   4080

catcagataa tgagcagagc catcccagta gcagatcatg tgcccatatg cggtgttcag   4140

atacggttca ccctctctca agtagtgtgt catgaacccg tcaatgattc catcttgctc   4200

cagtcctatg atgaggttca ccacgctggt aaatccaaaa actgcataca catagaacag   4260

tgggtcccgg ggtggttttc ttttgacgag gacacgagcc agcagtgcta ccaggaacag   4320

gatgagggca gcaaccccta caatagtcca ggaatcatgc tgggccgcca ggtggttgaa   4380

gacataggtg accgggatgg ccgagcaggg acagcacgaa gaccccggtg gccgcagagg   4440

cactcatcgc agccgccgcg ccgctcgccc ttcaccgcat cccgctg                 4487
```

<210> SEQ ID NO 97
<211> LENGTH: 1056
<212> TYPE: DNA
<213> ORGANISM: Homo sapiens
<220> FEATURE:
<221> NAME/KEY: misc_feature
<223> OTHER INFORMATION: Incyte ID No: 334405.3CB1

<400> SEQUENCE: 97

```
atacaaataa tgccagactt aaaatttaaa gacatcatat tattttagaa gccgtttaat     60

tatggtatga agtagaaggt tcctctagcg agacaactgc cagtcatacc agcttctgcc    120

aacggaccac ctcacagggt tgttgtgagg agcatatgaa accaaatcag gaaacagccc    180

atcacagcac tgcagcacag aataaaatcc atgctggttg agatgtccca ttatatttgc    240

acaaatgtgg ttcatcgctg gtcgaagact ttcacctttt ccccgaagaa ttttccacgt    300

tgaagtgtct gtgaaggtga caagcatcgt gaggtacagg gtgatgagtc gggagtcctg    360

caggatttca ggcttgagct gcttgagaaa atcacagcag taccacaaaa tgttcttgat    420

ctgttgaatc caaaggaggg tgaggtcctt agaacaagcc agggacacat accacacctt    480

aggctcattc tcagcatcca tgctgctcag gatgctgcga cacaacttct caaatctctc    540

attatcctct ttgattctga ataggaacag cagtttcctg gcaatcttga aaatacaaag    600

tgcacttctt ttagtggact cagggtcatc tgctttaaaa aagtcatcaa tctctctcct    660

gatatctctc tgcagtcgac tccgacagag aaaactccgg acatgggcct ggatcacaac    720

agctgcccgc tcccgttcct tctgcacaag cctttcttct cgtgctgacg ggctctatcg    780

atgaaccatg ctctcgaggt ctgagacagg gtgaacatgt ttgcaaactt gcacaaaccc    840

tgaggacctg cctgtgtcgc agaaatgcca ggtaatcatt agtgatcttg cacaggactc    900

gtggctgaga acagcttctc acttcagaaa agcttgttat tttttcttta ttcgccggag    960

gtccccgcac ttggggtcgg ggccgcagct gccactgtct cagcccaaaa cacccgagtt   1020

ctgccagacc cggggcagca gccgacgcac taccgc                             1056
```

<210> SEQ ID NO 98
<211> LENGTH: 2027
<212> TYPE: DNA
<213> ORGANISM: Homo sapiens
<220> FEATURE:
<221> NAME/KEY: misc_feature
<223> OTHER INFORMATION: Incyte ID No: 337179.1CB1

<400> SEQUENCE: 98

```
gcggccgcgg ccgtgagcct gcccccaact cgccctcagc cgggctggcc ggcgcggcca     60
```

-continued

```
tggaggtcta catcccgtcc tttcgctatg aagagagcga cctggagcgg ggatacacgg    120

tgtttaagat agaagtgcta atgaatggaa gaaaacattt tgttgaaaag agatacagcg    180

aatttcatgc tttgcacaaa aagcttaaga aatgtataaa aactccagaa atcccttcta    240

aacatgttag gaactgggtc cccaaagtct tggaacagcg acgacaaggc ttggaaacat    300

acttacaggc tgtcatttta gaaaatgaag aacttcccaa actgtttctt gatttcctaa    360

atgtgcgaca cttgccctct ctaccaaagg cagaaagttg tggatctttt gatgaaacag    420

agtctgaaga gtcaagcaaa ctgtcccacc agcctgtgct gctgttcctc agggatccat    480

atgtcttgcc tgcagccagc gattttccaa atgtggttat tgaaggagtc ctccatggga    540

tattttaccc tcatctacag cccaggtaga aatcctacat ggctaaaaga agcagaagca    600

agtttcgaag tcacagtcaa ggaaatcaat acctaccaat ttaacctaaa cgctatgata    660

tataacagct ctagctagtg gtaaagtgca cagtcccagc ttaattcagg gcagggacat    720

ttccattaga atggtgctct taaaaataga aactgaaccg gggcggtggt caggctaagg    780

ccaagtgttt aagaagtaga gtgtagctgc cagcgtagaa acccatgaaa aggaggccac    840

aggagattcc tgggagcact gggtgtagca aaacaaagcc actctctgct tcagtcgcac    900

catttgctaa ttgaaaatca tatcctgaat catactgaga ctgatcaact ttggtagctt    960

ttttgttcag atcttatgac acactactct tctcaccgtg agattttctc agccagtgat   1020

agtacattct gaaatgctgg caccaggaga cggccacaga cacacactgc taaatgtgaa   1080

gatggaacta aactggaaat taaattatac tgacaatatt atggcatttt taagatcatg   1140

gcattttaat ttacattaga gtggagttgc atcatactca ggggttagct tccaaggtca   1200

gtacataggt aaaatgggct attaggatga tccttgaaag ccctttagaa gggtgccatg   1260

ttggaaacct gtacatccac aacaagtagc ttttcctcct atgttggaaa aaaagactgt   1320

ttctttgttt gaagaccaag tgaagttgtt ggtgtttgtt taggggccat tttgttaaaa   1380

aaaaaaaaaa aaaaagcaca taacttttaa cactagaatc agcccgcaag atgcttgccc   1440

cgctagtggc agatgtgaac tgacaaggag tgaagcgccc acccagcgga tggacagcac   1500

ccacctgggt ttactcaagg gtgtgcattc attttaggtg ggatcgccac aggatttcat   1560

gttattttcc ttacggcttc cttttcactg acctcatttg ttgagttaat gtaagttaaa   1620

tgtgtttatg atataactcc actgtacatc atcctttgag tagtaaagga taaaagcata   1680

tatactacct atatgtatgt gctgtatgtg ggcatttcat tgagatctaa ttaatagcta   1740

gcctatttat ggttattcgt tttagtaagt tctgtgggag caaggtattt aaaatcaaaa   1800

ctaataacta catcatggtt tttgattagg atctaaatat tcaggtttta agcctgctgc   1860

aaacttttaa aatattatga tagattctgt actacatgtg ggaaacaagc aagaactaaa   1920

taatcaaatg ttgtcaacca aaagtaatag ttgggtattg gagatttttt taaaatgttt   1980

ttatgttatt agctatttgg agttaaataa aaacagaaca aggaaac                  2027
```

<210> SEQ ID NO 99
<211> LENGTH: 1477
<212> TYPE: DNA
<213> ORGANISM: Homo sapiens
<220> FEATURE:
<221> NAME/KEY: misc_feature
<223> OTHER INFORMATION: Incyte ID No: 337314.1CB1
<221> NAME/KEY: unsure
<222> LOCATION: 46, 661
<223> OTHER INFORMATION: a, t, c, g, or other

<400> SEQUENCE: 99

```
cacaacgggg ccgctgagcc cgagcctgag gccgagactg ccagangaca tccagggggc     60
agtaccacac cctgcaggct ggcttcagct ctcgctctca gggcctgagt ggggacaaga    120
cctcgggctt ccggcccatc gccaagccgg cctacagccc agcctcctgg tcctcccgct    180
ccgccgtgga tctgagctgc agtcggaggc tgagttcagc ccacaacggg ggcagcgcct    240
ttggggccgc tgggtacggg ggtgcccagc ccacccctcc catgcccacc aggcccgtgt    300
ccttccatga gcgcggtggg gttgggagcc gggccgacta tgacacactc tccctgcgct    360
cgctgcggct ggggcccggg ggcctggacg accgctacag cctggtgtct gagcagctgg    420
agcccgcggc cacctccacc tacagggcct ttgcgtacga gcgccaggcc agctccagct    480
ccagccgggc aggggggctg gactggcccg aggccactga ggtttccccg agccggacca    540
tccgtgcccc tgccgtgcgg accctgcagc gattccagag cagccaccgg agccgcgggg    600
taggcggggc agtgccgggg gccgtcctgg agccagtggc tcgagcgcca tctgtgcgca    660
nctcagcctc agcctggctg actcgggcca cctgccggac gtgcatgggt tcaacagcta    720
cggtagccac cgaaccctgc agagactcag cagcggtttt gatgacattg acctgccctc    780
agcagtcaag tacctcatgg cttcagaccc caacctgcag gtgctgggag cggcctacat    840
ccagcacaag tgctacagcg atgcagccgc caagaagcag gcccgcagcc ttcaggccgt    900
gcctaggctg gtgaagctct tcaaccacgc caaccaggaa gtgcagcgcc atgccacagg    960
tgccatgcgc aacctcatct acgacaacgc tgacaacaag ctggccctgg tggaggagaa   1020
cgggatcttc gagctgctgc ggacactgcg ggagcaggat gatgagcttc gcaaaaatgt   1080
cacagggatc ctgtggaacc tttcatccag cgaccacctg aaggaccgcc tggccagaga   1140
cacgctggag cagctcacag acctggtgtt gagcccccctg tcgggggctg ggggtccccc   1200
cctcatccag cagaacgcct cggaggcaga gatcttctac aacgccaccg gcttcctcag   1260
gaacctcagc tcagcctctc aggccactcg ccagaagatg cgggagtgcc acgggctggt   1320
ggacgccctg gtcacctcta tcaaccacgc cctggacgcg ggcaaatgcg aggacaagag   1380
cgtggagaac gcggtgtgcg tcctgcggaa cctgtcctac cgcctctacg acgagatgcc   1440
gccgtccgcg ctgcagcggc tggagggtcg cggtcgc                             1477
```

```
<210> SEQ ID NO 100
<211> LENGTH: 610
<212> TYPE: DNA
<213> ORGANISM: Homo sapiens
<220> FEATURE:
<221> NAME/KEY: misc_feature
<223> OTHER INFORMATION: Incyte ID No: 338091.2CB1
<221> NAME/KEY: unsure
<222> LOCATION: 10, 19, 48, 89, 117, 124, 136
<223> OTHER INFORMATION: a, t, c, g, or other

<400> SEQUENCE: 100

gaaaattctn gaaaaattnt taaagcctcc gttaagggtc caattccnag caaaacaggc     60
ttgttcacca agcaaagggt tgatccctna cgtgaaggcc acaagcagcg ccggccncgg    120
ctgntctggc gatctnactt ttgggccttc ttcctcttct gctcgctccc tctccccgca    180
ctacaggccc agtgagaagg cggtcaaaca tcgactcagg aacaaaacca gactgcttaa    240
ctatatcagt ccagtctgga gcaactgcaa attcaggatt ttcttccagc cacctggggt    300
agatccttca ttggaggcgc catagctcca cccatcttct tcccatttcg tttattgaca    360
acagggcacc ctttcttctc ctgtcaaagt gtttatatcc aatttattag ggtttccgac    420
```

-continued

```
atctatgtcg tttctgtttc ggtttctgaa atgaggaaaa cagcacatct gcattctttg    480

gtacataact tggcatatca acagtgtaag tagggtgcag cttcagccat tcaactaaat    540

ccttattttt aggagcatct tcccccacca gcctagtccc atcttcaaga ttgataacag    600

ggatccgtgt                                                           610


<210> SEQ ID NO 101
<211> LENGTH: 2409
<212> TYPE: DNA
<213> ORGANISM: Homo sapiens
<220> FEATURE:
<221> NAME/KEY: misc_feature
<223> OTHER INFORMATION: Incyte ID No: 404040.2CB1
<221> NAME/KEY: unsure
<222> LOCATION: 11-13, 15-17, 25, 35, 1273, 1281, 1288, 2402
<223> OTHER INFORMATION: a, t, c, g, or other

<400> SEQUENCE: 101

ctacagcttc nnngnnnttt ttttnttttt tttcnatttt tgccagactc ttgatactct     60

taaaacttgt ttgtggtcag cacaacaagg aacaaaacaa agctttgaaa aaaactttaa    120

catgaaaaaa cgcactgaca ttttttttta tttaatatag cctggacttt acctgcgtat    180

gcacatgctc aagaattgtc tactaggctg actatgtatc acctcttcag cttggatcca    240

attgtggatt tatttacaaa catcaaatgc cttcaagcca atccttttttg ctgtatgttt   300

tgcagcctac tgtagtagat acgcaacaga taatgtggga aaaaaagaga taagaggagg    360

aagctaataa gagactgtca agattgtata ccttcttggt ttcttttaag aatttgttgc    420

ctttctacta ttacagcaaa gcagcatttt gttactgact gcctaaaatc acttaatctc    480

aggtgaacgc atcacttgcc aaactgttgg aatgctattt gtgttttgtt gcactggttt    540

ttttcggttg tttgtttgtt tatttggttg gctttttgga gagggaaatt tggaaacggg    600

acatacacaa aaggttacac acccacattc cctttttatc atgacataca agaagaaact    660

agcagagcta agaatggagt gaagaaaggc agtatggcag gcaccagcaa agagttgagg    720

gctgttgctc ttaaaaaatt attttttttta ttattatttt gaaagtatgg aagttttcca   780

ttcactgggg aaaggaggga aaagtgcatt tatttttata cagagttact taattacctc    840

caaaacacat atgttggaaa tcgcttttgc tggtgcaaag tatattaatg agcaggaata    900

catacattga ggttatgaat agagagctca atttgtacct ttgctgtctt gctcaagctt    960

ggtatggcat gaaaactcga ctttattcca aaagtaactt caaaatttaa aatactagaa   1020

cgtttgctgc gataaatctt ttggattttt gtgtttttct aatgagaata ctgtttttca   1080

ttacctaaag aacaatttgc taaacatgag aaatcactca ctttgattat gtatagatta   1140

cataggaaga acaatcacat cagtaagtta tagtttatat taaaggtaat tttctgttgg   1200

ctcataacaa atataccagc attcatgata gcatttcagc attttccaag gtaccaagtg   1260

tacttatttt gtngttgttg ntgttgtngt attttagaag gaattcagct ctgatgtttt   1320

taaagaaaac cagcatctct gatgttgcaa catacgtgta aaatgggtgt tacatctatc   1380

ctgccattta accccacagt taataaagtg gctgaaaata atagtagctc tggcttggtg   1440

cttgacctgg ttaaatactg tcttaaagct catacaaaac aaataggctt ttccataagt   1500

ggcctttaag aaaacatgga agacaattca tgtttgacaa atgctgacag ggtgaagaaa   1560

gcccagtgta aaaatgaatc gcgttttaag tgattcggtt aaagagtttg gggctcccgt   1620

agcaaactaa tactagataa taaggaaatg ggggtgaaat atttttttat tgttgaatca   1680

ttttgtgaat gtccccctca aaaaaagcta atggaatatt tggcataaag ggcatttggt   1740
```

ggttttattt ttgtttgagg gggattgtca gaaaatccct tttctctctt acgtctaact 1800
gactagggaa caattgttga tatgcatagc attggaatac ttgtcattat atactcttac 1860
aaataacaca tgaagcaaga atgaccaata ttctgataat tggcactgga tcacaaaatg 1920
tgataaaact ttaaatgtat aaaactttat caaataaagt tttattttcc cctttaaaat 1980
gtatttcttt agaggcatta cttttttaaa aatattggtc aattcctgac ataagatgtg 2040
aggttcacag ttgtattcca gtattcaaga tagattcctg atttttcaat taggaaaagt 2100
aaaatccaaa atgttagcaa aacaaagtgc aatattaaat gtttgcttta tagattatat 2160
tctatggctg tttgtaattt ctcttttttt cctttttat ttggtgctga atatgtcctt 2220
gtaggctctg ttttaagaaa acaatatgtg ggaaatgatt taatttttcc tattgctctt 2280
ccttgtggaa aataaagtgt tttgtttttt tctgttttgt ataattgttt ggagatttat 2340
ttgaatcttg atcatattag taactcacca tacatgcaaa cacattaaat taaactatta 2400 anctctatt 2409

<210> SEQ ID NO 102
<211> LENGTH: 548
<212> TYPE: DNA
<213> ORGANISM: Homo sapiens
<220> FEATURE:
<221> NAME/KEY: misc_feature
<223> OTHER INFORMATION: Incyte ID No: 406280.3CB1
<221> NAME/KEY: unsure
<222> LOCATION: 16
<223> OTHER INFORMATION: a, t, c, g, or other

<400> SEQUENCE: 102
aagaagctag tgcggncagg cagagaagat gggctacaag gccatatttg tgacagtgga 60
cacaccttac ctgggcaacc gtctggatga tgtgcgtaac agattcaaac tgccgccaca 120
actcaggatg aaaaattttg aaaccagtac tttatcattt tctcctgagg aaaattttgg 180
agacgacagt ggacttgctg catatgtggc taaagcaata gacccatcta tcagctggga 240
agatatcaaa tggctgagaa gcactgacat cattgccaat tgttgcaaag ggcattttga 300
gaggtgatga tgcccaggga ggctgttaaa catggcttga atgggatctt ggtgtcgaat 360
catggggctc gacaactcga tggggtgcca gccactattg atgttctgcc agaaattgtg 420
gaggctgtgg aagggaaggt ggaagtcttc ctggacgggg gtgtgcggaa aggcactgat 480
gttctgaaag ctctgctctt gtgccaaggc tgtgtttgtg gggagaccaa tcgtttgggg 540
cttagcta 548

<210> SEQ ID NO 103
<211> LENGTH: 2281
<212> TYPE: DNA
<213> ORGANISM: Homo sapiens
<220> FEATURE:
<221> NAME/KEY: misc_feature
<223> OTHER INFORMATION: Incyte ID No: 406568.1CB1
<221> NAME/KEY: unsure
<222> LOCATION: 446, 874, 1360
<223> OTHER INFORMATION: a, t, c, g, or other

<400> SEQUENCE: 103
cagcctgcca cttgcctccc tgcctgcttc tggctgcctt gaatgcctgg tccttcaagc 60
tccttctggg tctgacaaag cagggaccat gtctaccttt ggctaccgaa gaggactcag 120
taaatacgaa tccatcgacg gaggatgaac tcctcgcctc cctgtcagcc gaggagctga 180

-continued

```
aggagctaga gagagagttg gaagacattg aacctgaccg caaccttccc gtggggctaa    240
ggcaaaagag cctgacagag aaaaccccca cagggacatt cagcagagag gcactgatgg    300
cctattggga aaaggagtcc caaaaactct tggagaagga gaggctgggg gaatgtggaa    360
aggttgcaga agacaaagag gaaagtgagg aagagcttat ctttactgaa agtaacagtg    420
aggtttctga ggaagtgtat acagangagg aggaggagga gtcccaggag gaagaggagg    480
aagaagacag tgacgaagag gaaagaacaa ttgaaactgc aaaagggatt aatggaactg    540
taaattatga tagtgtcaat tctgacaact ctaagccaaa gatatttaaa agtcaaatag    600
agaacataaa tttgaccaat ggcagcaatg ggaggaacac agagtcccca gctgccattc    660
acccttgtgg aaatcctaca gtgattgagg acgcttggac aagattaaaa gcaatgaccc    720
tgacaccaca gaagtcaatt tgaacaacat tgagaacatc acaacacaga cccttacccg    780
ctttgctgaa gccctcaagg acaacactgt ggtgaagacg ttcagtctgg ccaacacgca    840
tgccgacgac agtgcagcca tggccattgc aganatgctc aaagtcaatg agcacatcac    900
caacgtaaac gtcgagtcca acttcataac gggaaagggg atcctggcca tcatgagagc    960
tctccagcac aacacggtgc tcacggagct gcgtttccat aaccagaggc acatcatggg   1020
cagccaggtg gaaatggaga ttgtcaagct gctgaaggag aacacgacgc tgctgaggct   1080
gggataccat tttgaactcc caggaccaag aatgagcatg acgagcattt tgacaagaaa   1140
tatggataaa cagaggcaaa aacgtttgca ggagcaaaaa cagcaggagg gatacgatgg   1200
aggacccaat cttaggacca aagtctggca aagaggaaca cctagctctt caccttatgt   1260
atctcccagg cactcaccct ggtcatcccc aaaactcccc aaaaaagtcc agactgtgag   1320
gagccgtcct ctgtctcctg tggccacacc tcctcctccn cgggactcct ccactcccag   1380
agaaaaagct cattaccaga aacattgcag aagtcatcaa acaacaggag agtgcccaac   1440
gggcattaca aaatggacaa aaaaaagaaa aaagggaaaa aggtcaagaa acagccaaac   1500
agtattctaa aggaaataaa aaattctctg aggtcagtgc aagagaagaa aatggaagac   1560
agttcccgac cttctacccc acagagatca gctcatgaga atctcatgga agcaattcgg   1620
ggaagcagca taaaacagct aaagcgggtg gaagttccag aagccctgcg ataaaaacat   1680
gatctttaga agaggatgca gaactgttca gtggtattac atgaaatgca ttgtgagatg   1740
tttctaaaat accttcttca attcaaaatg atccctgact ttaaaaataa tctcacccat   1800
taattccaaa gagaatctta agaaacaatc agcatgtttc ttctgtaaat atgaaaataa   1860
atttcttttt tatgtcgtga gatttgtatt ggcaagaagc agttaattta aagatgctct   1920
tcctatctgt ggatgtgttg gtaactccga gttgtaatga gttcatgaaa tgtgctgtta   1980
tttttgtaat ctcaataaat gtggattgaa gttttttccc ttttttttaaa gccaaactaa   2040
tatttttctg tgacttgata catctgtcag atttttgtaa tctcgataaa tgtgtattga   2100
agtttttttcc cttttttttaa aaagccaaac taatattttt ctgtgagtta atacatctgt   2160
caggtgtgta tgtaacatta ctggacatta aaaaaaatta ttacattctc acccaaaaag   2220
ggtttgggtc ctaagcattt gcctttcttt gtttcctctt gttcaagaaa atctgattag   2280
a                                                                    2281
```

<210> SEQ ID NO 104
<211> LENGTH: 3521
<212> TYPE: DNA
<213> ORGANISM: Homo sapiens
<220> FEATURE:
<221> NAME/KEY: misc_feature

```
<223> OTHER INFORMATION: Incyte ID No: 407143.2CB1
<221> NAME/KEY: unsure
<222> LOCATION: 3139
<223> OTHER INFORMATION: a, t, c, g, or other

<400> SEQUENCE: 104

ggtgtccatg gcccgcaccc ccaagctgcc actgcagcag tcagagtggc agctgaaggc     60

tcggttcatg ccgtgccccc gggcagttct ggtgaggcta agcaagaggc ctctgcatct    120

tgacacctag gagagcaggg acggagtctc ccagggtgga ggaccatgct gcgccgcaag    180

ccctccaatg ccagtgagaa ggagcccact cagaagaaaa agctctccct tcagcgctcc    240

agcagcttca aggattttgc caaatccaaa cccagctccc ccgtggtgag cgagaaggag    300

tttaatctgg atgataacat tccagaagat gactcaggtg tccccacccc agaagatgct    360

gggaagagtg gcaaaaagct ggggaagaag tggagggcag tgatttcccg aaccatgaac    420

aggaagatgg gcaagatgat ggtgaaggcc ctgtcagaag agatggcaga cactctggag    480

gagggctctg cctccccgac atctccagac tacagcctgg acagccctgg ccctgagaag    540

atggcgctgg cctttttctga gcaagaggag catgaacttc cggtgctcag ccgccaggca    600

tcaacaggca gtgagctctg cagccccagc ccaggttctg gcagcttcgg ggaggaacca    660

cctgcccccc agtacacagg gcctttctgt ggccgggcac gagtccacac cgacttcact    720

cccagcccct atgaccacga ctcgctgaaa ctgcagaaag gagatgtgat ccagatcatt    780

gaaaagccac ctgtgggcac gtggctgggc ctactcaatg gcaaggtggg ctctttcaaa    840

ttcatctatg tggatgtgct gcccgaggag gccgtggggc atgcccgccc cagccgccga    900

cagagcaagg gcaagaggcc caagcctaag accctggcat gagctgctgg agcgcatcgg    960

cctggaggag cacacatcca ccctcctgct caatggctac cagacactgg aagacttcaa   1020

agagctgcga gaaacacacc tcaatgagct gaacatcatg gatccacagc accgggccaa   1080

gctgctcacg gccgccgagc tgctgctgga ctatgacact ggcagtgagg aggctgaaga   1140

gggcgccgag agcagccagg agccagtggc acacacagtg tcggaaccca aggtggacat   1200

cccgcgcgac tcaggctgct ttgagggctc ggagagcggg cgcgatgacg cagagctggc   1260

aggcactgag gagcagctgc aaggcctctc cctggccggg gcaccttgag gtggcggtgg   1320

caataggcca aggctgggac ccagctgcaa aggctgtagg agtgggccca gcctcccgtg   1380

gtggcccagg ccctgaggac tggcactgag cctggccctg cttccccagg gacacttagg   1440

gccacagagg ccaggccagg gccctacagg ttccaggctc agctggagtg gttggggagt   1500

cgcccaaggg cacatcccac ctgcctgagc cccgcccttc caccagcgac tgacagcgca   1560

gccctcctgg caccaactgc tcccctgcca tggccacggc cacagcaagt ggggcactgg   1620

gaaaccctgc ccatgtccct caccaacaag gcctccaaat cctcctcacc cccacaccac   1680

ctacccctgt cgcactgctc ctgaaaaggg ggccaagtca atgtttcagg tcagtctaaa   1740

aaccctaggg aagctggcca tttaaaagaa cccaaactga ccatgggtaa atccagttcc   1800

cctaaataag gcctgaagaa atccacaggt accattccca ctttccttct ccctagcttt   1860

cttagaggtt tggccactaa atcttatgag acttgaacca agtggcttcc tctttctagg   1920

cttaggacgg gttggggtta gaaagggtga tcactgaagg ccttgcctgc tctgacattc   1980

tgtgacatta aatgtctatt ctcctgttac ctgtggcctg ggacaccagt ggggtttatc   2040

gaggggacca gaggggcctc aggctttcag atgaaatggc tcctcctact cacccacttt   2100

attcctctcc atgtaattca ggacaagctg caacttcccc cagcttaaca caatgcccat   2160
```

```
acctcatacg atatgcgccc tcccgttcca tccctggccc cctcaaacga gacttctcac   2220

aaggctgatt acagatggtc aaacctggct tccaaggaca gaattgcctc tcggaagcca   2280

gctgtggatc tgagtccaga gttggccact tgtgtgggtc ctcacaagca aagagagcac   2340

taaacttgac attgggggtc caccactcca actttgcttt ctgaaggttt tggtgtacat   2400

tgagccccag aaggaaagga gagtatctgt gagtgggggc ctcccttgac cccagtacga   2460

agtctatgcc ctgaatcccc agagtagccc ttcctggtgc ccaactggcc tggggacaaa   2520

cagcgtccac tacatctagg actgccggct aagtggacac acttcttgac ctcctaccag   2580

gaactttggt aaaagctagc tttggggaag gggttgggtg taaatatgag agggtggagg   2640

gagaccagct ggtagcaata aacatgggta gaactaaatt accgtctcca gttatctttt   2700

ctatggagag agtgttgtgg ggaggggcag accggtctcc ttcaaagctg gcctcagcaa   2760

agtgtccctc actgtccttt caggtccatc tttcccttcc cttaaatgtt cagtgccctt   2820

gactctgctg acctaaagct ccagtctgaa gccctagctg gctctgccct cccctctaac   2880

cagccctcct cagaacaagg ctcaagctcc catgaccacg ggctttgctg gggtccaaga   2940

ggtgtagggg ggaatggcta tttccctcat ccaataactg ttcattttaa cagggccctt   3000

aaagaccttc acccgtgtga agaaaggcct gcactgagga gctgtccagg atctaagagg   3060

gggagatttg gggtcagcat ggcctttcct ctgaagtcac cttttcctgg cccccaccct   3120

gtacccacta aagcagtgnc atctcctggg agaaaaggag aacatataca tagaataaag   3180

actatgaaga tctgcaccaa atgactacta ctggtgatct tgtgaggcgt gtggggtggg   3240

actaggggag tgagggagaa aaatgctcac tttctacatt cttcttttat ttgcacttca   3300

aaagtattat ttttatatct atgaagaaaa ggaaactgca tttcaatttt tgaaaaaaaa   3360

aataaaacta aattaacaaa taaatagggc ccacgcctct ggcctccaat acgggacagt   3420

agcagcaaaa tcattatcct gctgcctttt ggtacacggt tctggaaaga tgagaggtga   3480

ataatggcca aagtgcttaa aatccatgca tgccagcgtg c                       3521
```

```
<210> SEQ ID NO 105
<211> LENGTH: 2396
<212> TYPE: DNA
<213> ORGANISM: Homo sapiens
<220> FEATURE:
<221> NAME/KEY: misc_feature
<223> OTHER INFORMATION: Incyte ID No: 414171.7CB1
<221> NAME/KEY: unsure
<222> LOCATION: 80, 2377, 2382, 2386-2387
<223> OTHER INFORMATION: a, t, c, g, or other

<400> SEQUENCE: 105

gcacgttgtg acatcaaaga aagggctcgt gctgggaaag cgggcggggc tgagagcggc     60

cctgcagccg acgcgcatgn cttctatcga cctgcggctg ggtgggggt gcactgggaa    120

aaggggcggg gtcctcagag ctgccgcgct ggcacatctt cctggagaag gggagggtgc    180

ggctgcagag aattgagact tagaagcttt gaattcctgt atctgagaac ggagttcgtt    240

gggggtggtg gagggggttg gaattgggga cctacggaag gtgaggatca gcctccaggc    300

acaacagggg agaggacgtt cagtgggctt caacttgacc caggccttct cccttcagg    360

ctcagctctt gccaggccaa attgagacat gtctgacaca agcgagagtg gtgcaggtct    420

aactcgcttc caggctgaag cttcagaaaa ggacagtagc tcgatgatgc agactctgtt    480

gacagtgacc cagaatgtgg aggtcccaga gacaccgaag gcctcaaagg cactggaggt    540

ctcagaggat gtgaaggtct caaaagcctc tggggtctca aaggccacag aggtctcaaa    600
```

```
gaccccagag gctcgggagg cacctgccac ccaggcctcg tctactactc agctgactga    660

tacccaggtt ctggcagctg aaaacaagag tctagcagct gacaccaaga aacagaatgc    720

tgacccgcag gctgtgacaa tgcctgccac tgagaccaaa aaggtcagcc atgtggctga    780

tacgaaggtc aatacaaagg ctcaggagac tgaggctgca ccctctacag gccccagcag    840

atgaacctga gcctgagagt gcagctgccc agtctcagga gaatcaggat actcggccca    900

aggtcaaagc caagaaagcc cgaaaggtga agcatctgga tggggaagag gatggcagca    960

gtgatcagag tcaggcttct ggaaccacag gtggccgaag ggtctcaaag gctctaatgg   1020

cctcaatggc ccgcagggct tcaaggggtc ccatagcctt ttgggcccgc agggcatcaa   1080

ggactcggtt ggctgcttgg gcccggagag ccttgctctc cctgagatca cctaaagccc   1140

gtaggggcaa ggctcgccgt aggagctgcc aagctccagt tcatcccaag agcctgaagc   1200

accaccacct cggggatgtg gcccttttgc aagggagggc aaatgatttg gtgaagtacc   1260

ttttggctaa agaccagacg aagattccca tcaagcgctc ggacatgctg aaggacatca   1320

tcaaagaata cactgatgtg taccccgaaa tcattgaacg agcaggctat tccttggaga   1380

aggtatttgg gattcaattg aaggaaattg ataagaatga ccacttgtac attcttctca   1440

gcaccttaga gcccactgat gcaggcatac tgggaacgac taaggactca cccaagctgg   1500

gtctgctcat ggtgcttctt agcatcatct tcatgaatgg aaatcggtcc agtgaggctg   1560

tcatctggga ggtgctgcgc aagttggggc tgcgccctgg ggatacatca ttcactcttt   1620

ggggacgtga agaagctcat cactgatgag tttgtgaagc agaagtacct gggactatgc   1680

cagagtcccc aatagcaatc cccctgaata tgagttcttc tggggcctgc gctcttacta   1740

tgagaccagc aagatgaaag tcctcaagtt tgcctgcaag gtacaaaaga aggatcccaa   1800

ggaatgggca gctcagtacc gagaggcgat ggaagcggat ttgaaggctg cagctgaggc   1860

tgcagctgaa gccaaggcta gggccgagat tagagctcga atgggcattg ggctcggctc   1920

ggagaatgct gccgggccct gcaactggga cgaagctgat atcggaccct gggccaaagc   1980

ccggatccag gcgggagcag aagctaaagc caaagcccaa gagagtggca gtgccagcac   2040

tggtgccagt accagtacca ataacagtgc cagtgccagt gccagcacca gtggtggctt   2100

cagtgctggt gccagcctga ccgccactct cacatttggg ctcttcgctg gccttggtgg   2160

agctggtgcc agcaccagtg gcagctctgg tgcctgtggt ttctcctaca agtgagattt   2220

tagatattgt taatcctgcc agtctttctc ttcaagccag ggtgcatcct cagaaaccta   2280

ctcaacacag cactctaggc agccactatc aatcaattga agttgacact ctgcattaaa   2340

tctatttgcc atttctgaaa aaaaaaaaaa aaaaaanaaa anaagnnaaa aaaaag       2396
```

```
<210> SEQ ID NO 106
<211> LENGTH: 4822
<212> TYPE: DNA
<213> ORGANISM: Homo sapiens
<220> FEATURE:
<221> NAME/KEY: misc_feature
<223> OTHER INFORMATION: Incyte ID No: 444857.15CB1
<221> NAME/KEY: unsure
<222> LOCATION: 33, 51, 79, 211, 369, 483-484, 731, 748, 4803,
      4805-4806, 4808-4809,
<223> OTHER INFORMATION: a, t, c, g, or other

<400> SEQUENCE: 106

gagtccgctg gcctcactcc tagctcatct ggnccggcgg cggcaactgg nttcagggtt     60

agggtttaaa gaaaggacnc ggaggcagga ggagcagtct cattgttccg ggagccgtca    120
```

-continued

```
ccacagtagg tccctcggct cagtcggccc agcccctctc agtcctcccc aacccccaca    180
accgcccgcg gctctgagac gcggccccgg nggcggcggc agcagctgca gcatcatctc    240
caccctccag ccatggaaga cctggaccag tctcctctgg tctcgtcctc ggacagccca    300
ccccggccgc agcccgcgtt caagtaccag ttcgtgaggg agcccgagga cgaggaggaa    360
gaagaggang atgaagagga ggacgaggac gaagacctgg aggagctgga ggtgctggag    420
aggaagcccg ccgccgggct gtccgcggcc ccagtgccca ccgcccctgc cgccggcgcg    480
ccnntaatgg acttcggaaa tgacttcgtg ccgccggcgc cccggggacc cctgccggcc    540
gctcccccccg tcgccccgga gcggcagccg tcttgggacc cgagcccggt gtcgtcgacc    600
gtgcccgcgc catccccgct gtctgctgcc gcagtctcgc cctccaagct ccctgaggac    660
gacgagcctc cggcccggcc tccccctcct cccccggcca gcgtgagccc ccaggcagag    720
cccgtgtgga ncccgccagc cccggctncc gccgcgcccc cctccacccc ggccgcgccc    780
aagcgcaggg gctcctcggg ctcagtggat gagacccttt ttgctcttcc tgctgcatct    840
gagcctgtga tacgctcctc tgcagaaaat atggacttga aggagcagcc aggtaacact    900
atttcggctg gtcaagagga tttcccatct gtcctgcttg aaactgctgc ttctcttcct    960
tctctgtctc ctctctcagc cgcttctttc aaagaacatg aataccttgg taatttgtca   1020
acagtattac ccactgaagg aacacttcaa gaaaatgtca gtgaagcttc taaagaggtc   1080
tcagagaagg caaaaactct actcatagat agagatttaa cagagttttc agaattagaa   1140
tactcagaaa tgggatcatc gttcagtgtc tctccaaaag cagaatctgc cgtaatagta   1200
gcaaatccta gggaagaaat aatcgtgaaa aataaagatg aagaagagaa gttagttagt   1260
aataacatcc ttcataatca acaagagtta cctacagctc ttactaaatt ggttaaagag   1320
gatgaagttg tgtcttcaga aaaagcaaaa gacagtttta atgaaaagag agttgcagtg   1380
gaagctccta tgagggagga atatgcagac ttcaaaccat ttgagcgagt atgggaagtg   1440
aaagatagta aggaagatag tgatatgttg gctgctggag gtaaaatcga gagcaacttg   1500
gaaagtaaag tggataaaaa atgttttgca gatagccttg agcaaactaa tcacgaaaaa   1560
gatagtgaga gtagtaatga tgatacttct ttccccagta cgccagaagg tataaaggat   1620
cgttcaggag catatatcac atgtgctccc tttaacccag cagcaactga gagcattgca   1680
acaaacattt ttcctttgtt aggagatcct acttcagaaa ataagaccga tgaaaaaaaa   1740
aatagaagaa aagaaggccc aaatagtaac agagaagaat actagcacca aaacatcaaa   1800
cccttttact tgtagcagca caggattctg agacagatta tgtcacaaca gataatttaa   1860
caaaggtgac tgaggaagtc gtggcaaaca tgcctgaagg cctgactcca gatttagtac   1920
aggaagcatg tgaaagtgaa ttgaatgaag ttactggtac aaagattgct tatgaaacaa   1980
aaatggactt ggttcaaaca tcagaagtta tgcaagagtc actctatcct gcagcacagc   2040
tttgcccatc atttgaagag tcagaagcta ctccttcacc agttttgcct gacattgtta   2100
tggaagcacc attgaattct gcagttccta gtgctggtgc ttccgtgata cagcccagct   2160
catcaccatt agaagcttct tcagttaatt atgaaagcat aaaacatgag cctgaaaacc   2220
ccccaccata tgaagaggcc atgagtgtat cactaaaaaa agtatcagga ataaaggaag   2280
aaattaaaga gcctgaaaat attaatgcag ctcttcaaga aacagaagct ccttatatat   2340
ctattgcatg tgatttaatt aaagaaacaa agctttctgc tgaaccagct ccggatttct   2400
ctgattattc agaaatggca aaagttgaac agccagtgcc tgatcattct gagctagttg   2460
```

-continued

```
aagattcctc acctgattct gaaccagttg acttatttag tgatgattca atacctgacg   2520
ttccacaaaa acaagatgaa actgtgatgc ttgtgaaaga aagtctcact gagacttcat   2580
ttgagtcaat gatagaatat gaaaataagg aaaaactcag tgctttgcca cctgagggag   2640
gaaagccata tttggaatct tttaagctca gtttagataa cacaaaagat accctgttac   2700
ctgatgaagt ttcaacattg agcaaaaagg agaaaattcc tttgcagatg gaggagctca   2760
gtactgcagt ttattcaaat gatgacttat ttatttctaa ggaagcacag ataagagaaa   2820
ctgaaacgtt ttcagattca tctccaattg aaattataga tgagttccct acattgatca   2880
gttctaaaac tgattcattt tctaaattag ccagggaata tactgaccta gaagtatccc   2940
acaaaagtga aattgctaat gccccggatg gagctgggtc attgccttgc acagaattgc   3000
cccatgacct ttctttgaag aacatacaac ccaaagttga agagaaaatc agtttctcag   3060
atgacttttc taaaaatggg tctgctacat caaaggtgct cttattgcct ccagatgttt   3120
ctgctttggc cactcaagca gagatagaga gcatagttaa acccaaagtt cttgtgaaag   3180
aagctgagaa aaaacttcct tccgatacag aaaaagagga cagatcacca tctgctatat   3240
tttcagcaga gctgagctaa aacttcagtt gttgacctcc tgtactggag agacattaag   3300
aagactggag tggtgtttgg tgccagccta ttcctgctgc tttcattgac agtattcagc   3360
attgtgagcg taacagccta cattgccttg gccctgctct ctgtgaccat cagctttagg   3420
atatacaagg gtgtgatcca agctatccag aaatcagatg aaggccaccc attcagggca   3480
tatctggaat ctgaagttgc tatatctgag gagttggttc agaagtacag taattctgct   3540
cttggtcatg tgaactgcac gataaaggaa ctcaggcgcc tcttcttagt tgatgattta   3600
gttgattctc tgaagtttgc agtgttgatg tgggtattta cctatgttgg tgccttgttt   3660
aatggtctga cactactgat tttggctctc atttcactct tcagtgttcc tgttatttat   3720
gaacggcatc aggcacagat agatcattat ctaggacttg caaataagaa tgttaaagat   3780
gctatggcta aaatccaagc aaaaatccct ggattgaagc gcaaagctga atgaaaacgc   3840
ccaaaataat tagtaggagt tcatctttaa aggggatatt catttgatta tacgggggag   3900
ggtcagggaa gaacgaacct tgacgttgca gtgcagtttc acagatcgtt gttagatctt   3960
tatttttagc catgcactgt tgtgaggaaa aattacctgt cttgactgcc atgtgttcat   4020
catcttaagt attgtaagct gctatgtatg gatttaaacc gtaatcatat ctttttccta   4080
tctgaggcac tggtggaata aaaaacctgt atattttact ttgttgcaga tagtcttgcc   4140
gcatcttggc aagttgcaga gatggtggag ctagaaaaaa aaaaaaaaaa aagccctttt   4200
cagtttgtgc actgtgtatg gtccgtgtag attgatgcag attttctgaa atgaaatgtt   4260
tgtttagacg agatcatacc ggtaaagcag gaatgacaaa gcttgctttt ctggtatgtt   4320
ctaggtgtat tgtgactttt actgttatat taattgccaa tataagtaaa tatagattat   4380
atatgtatag tgtttcacaa agcttagacc tttaccttcc agccacccca cagtgcttga   4440
tatttcagag tcagtcattg gttatacatg tgtagttcca aagcacataa gctagaagaa   4500
gaaatatttc taggagcact accatctgtt ttcaacatga aatgccacac acatagaact   4560
ccaacaacat caatttcatt gcacagactg actgtagtta attttgtcac agaatctatg   4620
gactgaatct aatgcttcca aaaatgttgt ttgtttgcaa atatcaaaca ttgttatgca   4680
agaaattatt aattacaaaa tgaagattta taccattgtg gtttaagctg tactgaacta   4740
aatctgtgga atgcattgtg aactgtaaaa gcaaagtatc aataaagctt atagacttaa   4800
aangnnanna gngaaaaaag gg                                             4822
```

<210> SEQ ID NO 107
<211> LENGTH: 351
<212> TYPE: DNA
<213> ORGANISM: Homo sapiens
<220> FEATURE:
<221> NAME/KEY: misc_feature
<223> OTHER INFORMATION: Incyte ID No: 002715.1CB1

<400> SEQUENCE: 107

```
cttgtgagtc ctccccttc ctgacatgag tctcagtgcc ggcaaacacg gctggttgaa     60

ccctgagcta gcccagctgc tttgttcacc ttacgtttgg ggaaggctga aattttattg    120

agcaccgact gtattccaca cactcttcta ggtgcccgaa atatgctgtt aaacaaatac    180

tcagccctca tggggctgag agtctggtgg ggaagacctg ttgaaaaaca atcatattaa    240

atgaattgca ttgcatgtta gaagatcgta agtactctgg gggaaaatga gagtagaaca    300

ggataagggg gtgatggagg gaatgagtgg tgattttaaa tgtagttatc a             351
```

<210> SEQ ID NO 108
<211> LENGTH: 349
<212> TYPE: DNA
<213> ORGANISM: Homo sapiens
<220> FEATURE:
<221> NAME/KEY: misc_feature
<223> OTHER INFORMATION: Incyte ID No: 004516.1CB1

<400> SEQUENCE: 108

```
ggcaccagtt ggtgtctgag atgccctcca gtctggggaa tcccgtagat tcttagacta     60

ctttgaactg aagtatgtgc agtctgccat ctcacattaa aatgtaggca ttttgtcaat    120

tgcttttctt tcatctgcac aagaggaagg agagaacgaa tcaatacaac cactcttttc    180

cttgagactg caaagaaaat ggttctatag tttgatggtt ctacttccca gatgctacct    240

ctcagattta ttctcaacag aaaatttttt gattacagca gaccagatct ttatctgtca    300

ataagttaaa aaagataatc tgggctggat gtggtggctc acgcctgtt                349
```

<210> SEQ ID NO 109
<211> LENGTH: 1082
<212> TYPE: DNA
<213> ORGANISM: Homo sapiens
<220> FEATURE:
<221> NAME/KEY: misc_feature
<223> OTHER INFORMATION: Incyte ID No: 005028.2CB1
<221> NAME/KEY: unsure
<222> LOCATION: 875
<223> OTHER INFORMATION: a, t, c, g, or other

<400> SEQUENCE: 109

```
agcttagcca tgactcagta actaaaaagt tcaaaaaatc cagttatgta atgtgcagag     60

taacaaattg caagaaaaac aacttaatct tccagtgact aagtaagaaa aactgttgtc    120

actattaaac atgtaggaaa ttgataatta ttacaaacaa agcaatactc taccctaaat    180

ctagacaaat cactggacag atgataagat tttcagcttt ctcctttaaa gagctgtgcc    240

tggctggatg atgggtttta tacacgtttt tatgttattt tagaatgtac agattttttt    300

gtaaacatgc aaagggaagg ttacaaactc cttaaacttt aaaaaaccat aaatcctttc    360

tttgctactt atattctatg ccaattataa tattccaaga cttacctttc ttcagaatgc    420

ttacatatgg aaaggtttat ttataaatat ttgataggta aatattccat atgtattttc    480

tagcccgtct ttctctgtcc ctccctcaaa taacttcatt accctctcct ttttaaacga    540
```

```
aatatcttga taataagaaa acaaaatcat ttttttgtga aataatacat atggacaaaa    600

aatacaagtt gtattttact tctggttcat taaaatattg tgtttagttg gatttttttcc   660

tcctttattt tcagaaacat aaaagaaatt gttttatttc ctaaaggata aaattggata    720

tagcctcttt agtagacact atcacagttc tgttgtttgc tgtgttcatt tgcttaatga    780

attgcgtgag aacagtcact gtaatgaaat atgtgtgctg ggggtggggg gaagggcatg    840

ggaaatgttt tatgaaaaaa agttataagc ctaaactat gaagtaacat ctaatgcagt     900

tctttttaag tgcaatatat ttatttctgc tagaaatata ttatcaacct tatgtaatat    960

ttgaagcatt acatattatt tgtaaacagc ttaaaattat atattacccc aattgtacat   1020

aagtacaaat gtgtggatat tagtgctgag attacaatga tatggatttc tggtgtagtc   1080

at                                                                  1082
```

<210> SEQ ID NO 110
<211> LENGTH: 763
<212> TYPE: DNA
<213> ORGANISM: Homo sapiens
<220> FEATURE:
<221> NAME/KEY: misc_feature
<223> OTHER INFORMATION: Incyte ID No: 009051.5CB1

<400> SEQUENCE: 110

```
aaaagttgct gttaggactt tattactatt ctcttttagg atacatcaac atttgaattt     60

taccagcata tgtgacttag ttttcttagt ttttgtcatt tttaagaatc ctggcaaata    120

attttaaata atttatttgt tactaaaatt tgatataacc ttaatgatct ttcagcacat    180

tatcaaatta tttagccatc ctaaaatact tgatgaataa attaatagaa gttaatgttt    240

ctagtttgcc tcacttttct ggaattattc ttattttgca gattagtctt gccaactacc    300

gatgccacag aatttaatta ccaattgcaa agccattttc atagtcataa ttatattcta    360

ggcaatattt tttggtcagg ttctcctcca gtctgcagtc aatgtcctct gcatcactac    420

aaaatgatgg gaccattttt cccagggtcg tctcaaatgc ttcagaaaac ttcttcatca    480

gatctgtgtc atcacaacga gctgctttgt agaacatctc aaaggacttg aacccgtggt    540

ttgcaaaacg ttttttggca cagtctggcc attcagtggt atatgttggt ttccagacgc    600

catcttcata agcacaataa tacttgtcag tagacccttc tgtgaaatca tagccctcca    660

agcaagttaa tgtacagttg actccagtat tatctggagt gcatataaaa tccccattta    720

caggtgtgaa tggaatttca cagggagaac cttttatgac aat                      763
```

<210> SEQ ID NO 111
<211> LENGTH: 909
<212> TYPE: DNA
<213> ORGANISM: Homo sapiens
<220> FEATURE:
<221> NAME/KEY: misc_feature
<223> OTHER INFORMATION: Incyte ID No: 021656.2CB1

<400> SEQUENCE: 111

```
ggtttaagtt cccctccagc cccgagccag gagcagttct caataccggg agaggcacag     60

agctatttca gccacatgaa aagcatcgga attgagatcg cagctcagag gacaccgggg    120

cgccccttcc accttccaag gagctttgta ttcttgcatc tgggctgcct gggacttccc    180

ttaggcagta aacaaataca taaagcaggg ataagactgc atgaaaaatg tcgaaacagc    240

cagtttccaa tgttagagcc atccaggcaa atatcaatat tccaatggga gcctttcggc    300

caggagcagg tcaacccccc agaagaaaag aatgtactcc tgaagtggag gagggtgttc    360
```

ctcccacctc ggatgaggag aagaagccaa ttccaggagc gaagaaactt ccaggacctg 420
cagtcaatct atcggaaatc cagaatatta aaagtgaact aaaatatgtc cccaaagctg 480
aacagtagta ggaagaaaaa aggattgatg tgaagaaata aagaggcaga agatggattc 540
aatagctcac taaaatttta tatatttgta tgatgattgt gaacctcctg aatgcctgag 600
actctagcag aaatggcctg tttgtacatt tatatctctt ccttctagtt ggctgtattt 660
cttactttat cttcattttt ggcacctcac agaacaaatt agcccataaa ttcaacacct 720
ggagggtgtg gttttgagga gggatatgat tttatggaga atgatatggc aatgtgccta 780
acgattttga tgaaaagttt cccaagctac ttcctacagt attttggtca atatttggaa 840
tgcgttttag ttcttcacct tttaaattat gtcactaaac tttgtatgag ttcaaataaa 900
tatttgact 909

<210> SEQ ID NO 112
<211> LENGTH: 703
<212> TYPE: DNA
<213> ORGANISM: Homo sapiens
<220> FEATURE:
<221> NAME/KEY: misc_feature
<223> OTHER INFORMATION: Incyte ID No: 023303.1CB1

<400> SEQUENCE: 112
caggaggtgg gcctggagca gggcctcaga agtctcctgg cctttcccat caggaagcac 60
atcctgttgg tgtctggctg ccgcggcagg gccgctattt gttgcggttg gctacgcctt 120
ccagctcacc aaaaacagtc tcaaaaacaa ccatttcctc tctgctgaga gccagggaag 180
gcgagctctg cgcacacggg cgtccctgca gcagccactc tgctttccag gaccggccaa 240
ctgccctgga ggcatccaca caggggccca ggcagcacag aggagctgtg aacccgctcc 300
acaccggcca ccctgcccgg agcctggcac tcacagcagg ccggtgctaa ggagtgtggc 360
gcgggctcga ctcccactgc tgccggcctc ccgagtgact ctgttttcca ctgctgcagg 420
cgagaagagg cacgcgcggc acaggccggc ctccgcttcc cgggaagacg gcgcactcct 480
ggccctgggt tcttgctgct gcccaccctc tgctccctgg gatgggcccc gaggcgagca 540
gcttcagcac aggcctggcc ctgctccagg tgcaggaagg aggataaggc cgggccgaga 600
ggcggcacac ctggaccatc ccatgggcct ccgcccgcgc cgccccgagg atgagtggtg 660
atgtcctcta gccaccccta gcagcgtcgg ctctccctgg acg 703

<210> SEQ ID NO 113
<211> LENGTH: 704
<212> TYPE: DNA
<213> ORGANISM: Homo sapiens
<220> FEATURE:
<221> NAME/KEY: misc_feature
<223> OTHER INFORMATION: Incyte ID No: 040200.1CB1

<400> SEQUENCE: 113
gtggtattat acccaagcct agtgtgtatt acaacttcaa cactcccctt tggcttatat 60
taccatgtgc atagctaaag tcttctattt ttagaacacc ttctgtctgt tctttcccca 120
tcaactcctt cctcatcctt cttggtgttc tgtcatgggc catgggcttg ctatggccag 180
ccttactgat gccaagcagc ttatgggatg ttctttattg tgtgtgatgg tattggtttg 240
tttggtagat aagtgggagg aaaagtactg ttgctacact attataggca tgtttgatac 300
tagcagctaa cactggtcac tccaaagcac tgtttctata ggaacattga agctattaag 360

-continued

```
atgttttgat tatcctaatt acataatgac cgatttgaga tagaggcctt taaatacatt    420

ccatgccctc cccagaaaat agtctgtggg agtcagttgc cttggtgcca ggtatgtgtt    480

ctgatgtagg tcatgagtct ttctacttaa tgggaaggga agaacatttg tttccaggat    540

gactttctgg ccagaatacc ggaaagcttt taggaagctt cgttcacatg ctatttaaat    600

gcacaaaata gacagtaagg atttatctgt tcagtttttc ttcccagtga attaatttca    660

gcttatatgg gtgtcttcat tgaacatgag gaatattagg ttat                      704
```

<210> SEQ ID NO 114
<211> LENGTH: 6349
<212> TYPE: DNA
<213> ORGANISM: Homo sapiens
<220> FEATURE:
<221> NAME/KEY: misc_feature
<223> OTHER INFORMATION: Incyte ID No: 179654.7CB1

<400> SEQUENCE: 114

```
ggccgccctg ttgttttgat gaataatact tggtggggcg aggggggaaag agtaggggtg     60

gaggggtagg aggatttact cttccagcga gagctacgcg catcccatcc tccccctccc    120

ccctacccgg gctccggcgt ggaggcgggg cgtggccggc ctgctttggg aggggagggg    180

cttcccttac agtgctgggc tctgccagga cggctgtggg gtcgccttac ctcggggtat    240

ccactctgca gtcgaccagt tcccgccagg agcaaagggt aggaaggaga gcaggatctg    300

ctgtaggaac gcagctaccg cgccactatc acgaagaaac agcaggctcg gggcacgaga    360

cgaactggag accgcgctgc ctagctgggt aacctgggaa gcagagggta ataagtggcg    420

ccttaagaca accctgtagc agcagcagtg gcggccaaag gaggctgctc agggaacaag    480

cggctgtagt agtctgtggg gcgactggag tgaccgaagc caaggcagtt tagtgcctct    540

cgtgttctta ttttttaacc tctgactatg caattctgaa acctccccca ttcgggggac    600

cagacagcct gatagacacc ttccactctc cttcctcccg ccgtggtctc gagaacagaa    660

ggatctctcc ttaacgcctt tcaccattaa gaggaaagcg atggaggagc tgagcgctga    720

tgagattcga cggaggcgcc ttgcacgact tgctggtgga cagacctctc agccaaccac    780

cccactcacc tctccccaga gggagaaccc tccggggcct cccatagcgg catcagcccc    840

aggaccctct cagagtcttg gtctcaatgt ccacaacatg accccagcta cctccccaat    900

aggtgcatca ggagtagccc atcgaagcca gagcagtgaa ggagtcagtt ctctcagcag    960

ctcgccctct aatagccttg aaacgcaatc tcagtctctc tcacgttccc agagcatgga   1020

tatcgatggt gtctcatgtg agaaaaagcat gtcccaggtg gatgtggatt caggaattga   1080

aaacatggag gttgatgaaa atgatcgaag agaaaagcgg agcctcagtg ataaggagcc   1140

ttcctcgggc cctgaagtgt ctgaagagca ggccttacag ctggtctgta agatcttccg   1200

tgtctcttgg aaggaccggg acagagatgt catctttctt tcttctcttt ctgcacagtt   1260

taagcagaac ccaaaaagaag tattctccga ttttaaggac ttgattggcc agattttaat   1320

ggaagtgcta atgatgtcca ctcagaccag agatgaaaac ccatttgcca gtctgacagc   1380

cacatcacag ccaattgctg cagcagcacg gtcaccagac agaaatctct tgctaaacac   1440

tggctccaat ccaggaacaa gccccatgtt ctgcagcgtg gcttcctttg gtgccagctc   1500

tttgtctagt ttgggagcct ctggtggagc aagtaattgg gattcctaca gtgaccattt   1560

caccattgaa acctgcaaag agacagatat gctgaactac ctcatcgagt gtttcgaccg   1620

agttggaata gaggaaaaaa aagcaccaaa gatgtgcagc cagccagcag tcagccagct   1680
```

-continued

```
tctgagcaac atccgctcac agtgcatatc ccatactgct ttagtactac aaggctccct   1740
aacacagccc aggtccttgc agcagccgtc cttcctagtg ccgtatatgc tgtgtaggaa   1800
tctcccatat ggcttcattc aggaactggt gagaaccact caccaggatg aagaagtgtt   1860
caagcagata tttatcccca ttttacaagg cctggctctt gctgccaaag agtgctccct   1920
cgacagtgac tactttaaat accccctcat ggcactaggt gagctctgtg aaaccaagtt   1980
tgggaagaca caccctgtgt ggcaatttgg ttgcttcttt gcggttgtgg ttgccgaaat   2040
ccttaagtcc tggctgtggg cgggagctgc agagactctc ttacttaggg gctttcttta   2100
gcttctcagt ctttgcagaa gatgatgtta aagtggttga aaaatacttc tcagggcctg   2160
ccattaccct ggaaaacact cgtgtggtta gccaatcatt gcagcattac ttagagctcg   2220
gaaggcaaga gctttttaag attctgcata gtattttgtt aaatggcgaa acccgtgagg   2280
ctgctctcag ttacatggcg gctgtcgtca atgccaatat gaagaaagca cagatgcaga   2340
cagatgatag attggtgtct acagatggat ttatgctgaa tttcctttgg gtactgcagc   2400
agctaagtac aaaaatcaag ttagaaacag ttgatcccac gtatattttt cacccaagat   2460
gtcggattac tcttcccaat gatgagacgc gtgtgaatgc aacgatggaa gatgtgaatg   2520
actggctgac tgaactctat ggcgatcagc ctccattttc tgagccgaaa ttccctacgg   2580
agtgcttctt tctcaccctg catgctcacc acctctctat tctgcctagt tgccgtcgct   2640
atatccgcag actccgggct atccgggagc tcaatagaac tgtagaagat ttgaaaaata   2700
atgaaagcca atggaaagat tccccactgg caactagaca ccgcgaaatg ctgaagcgct   2760
gtaaaactca gcttaagaaa ctggtacggt gcaaggcctg tgctgatgct ggcctacttg   2820
acgagagctt cctgagaaga tgtctgaatt tttatggcct tctcattcag ctgctgctcc   2880
gcatcctgga ccccgcatat cccgatataa cactgccttt aaattcagat gtccccaagg   2940
tatttgcagc gttgcctgag ttttatgtag aagatgttgc agaatttttta tttttttattg   3000
tacaatactc tccccaggcg ctttatgagc cctgtactca ggatattgtg atgttccttg   3060
ttgtgatgtt gtgcaaccag aactacatcc gaaacccata tttggtggcc aaactggtag   3120
aagtcatgtt tatgaccaac cctgctgttc agccacgaac ccagaagttt tttgaaatga   3180
ttgagaacca tcctctctcc accaagttgt tggtaccttc cctgatgaag ttttatacag   3240
atgttgagca taccggagcc accagtgagt tttatgacaa gttcacaatt cgctatcata   3300
ttagcaccat ttttaaaagc ctttggcaaa acatagctca ccatggcacc tttatggagg   3360
agttcaactc cgggaagcag tttgttcgct atataaacat gttgataaac gacacgacgt   3420
tttgctcga tgaaagtctg gagtctctga agcgaatcca tgaagtgcag gaagagatga   3480
agaacaaaga acagtgggac cagttgcccc gggatcagca gcaggctcgt cagtctcagc   3540
ttgctcagga tgagcgtgtg tcccgctctt acctcgccct ggccaccgaa accgtggaca   3600
tgttccacat cctcacgaag caggtccaga agcccttcct cagaccgctt ctcaacagtg   3660
aaatacagga gtactctgtg caaaagcaaa ttcttgaaaa gctaagtata tgttgaattt   3720
gtataaatcc agttattaca tttcatgaaa accttgtgac ttaaaggaat gctttcgtga   3780
ctccctttta tggccagtgt ttaatgctct ctaagccaca tcttcctgtt tcaggtttgc   3840
ttaaaaccat gtatgcccaa ccgtagtggg tactgagtca ccttgtgaga ttacagcata   3900
gattattact attttccagg tgtttcattt aagtttactc tgtctcattg actagattta   3960
aaactattca aggcataact tttatcttct ttccttgcat tactttgtta tttgtatctg   4020
ataagtacat aagaatgaca cagactgaac tgccaggggc ttttaacatt tatggggaaa   4080
```

-continued

```
aaagtttatg aaatactggc tggaagagct gactcaaaac tttttttgct cagataatgg   4140
taagatttgt ataattttct ctcttttact tgtttctcaa tgaatttgga gtgatacttt   4200
ttttaattaa aagcataaat gtaaagaaaa gtttggcttc ttttggtatt tataaataaa   4260
tatttcatca gcctgcaaca ttccattaag tattagaatt atcagatcag aaatggggag   4320
taaagttgaa atataatgtt gtctttcttc agcttatgat acacagcacc tgtaaggatt   4380
ctttgaagat taatccaacc aattcctgtt cctccactga aatgggagtt tttggtcctt   4440
ttcacttgtc tcaacagcat gaattgtcct attatcctgt gatttcctag gagcttggac   4500
cccgattggc tgcaatgctg aactttaatc ttcagcaact ttgtggcccc aagtgccgtg   4560
acctgaaagt tgaaaaccct gagaaatacg gctttgaacc aaagaagctg ttggaccaac   4620
tgacggatat ttacttacag ctggactgtg ctcggttcgc gaaagccatt gctgacgacc   4680
agagatccta cagtaaggaa ttgtttgaag aagttatttc aaagatgcgg aaggcaggga   4740
tcaaatccac aatagcaata gaaaaattta agctgctcgc cgagaaagtg gaggagatag   4800
tggccaagaa cgcacgcgca gaaatcgact acagcgacgc tcctgatgag ttcagagacc   4860
ctctgatgga caccctcatg acagaccccg tgcggctgcc ctctggcacc atcatggacc   4920
gctccatcat cctgcggcac ctgctcaact cccccacgga ccccttcaac cggcagacgc   4980
tgacagagag catgctggaa ccagtgccag aactgaaaga gcagattcag gcgtggatga   5040
gagagaaaca gaacagcgat cactaaaccg ttccgccgcc caccctctgc tagacacagc   5100
caaggccaac gaggcaagca gaagcagcgg cccgcagcga agctgccgtt catgtgttgg   5160
aggccaaatg tggcaaacca accccaggcc cacccagagc gagcaaacgc tgagacctga   5220
aaggacatgg atgagaagag gagcccgctt cctgtacata tatttaagtg acaaacacgg   5280
tcaaaagctt aagggacagg ttttatggtt gcttgtgtaa taaagcatgt ccttcgtatg   5340
tcacagtttg gggcaacgga agtcttttag tgatggctaa tgggtctggg cagcatccct   5400
tcatgaattt ttttttaatc caatatccgt tgatttgatt gtgattagag aaccttggac   5460
attttgctgc taaagaatct tttttcccct ctccccccttc ctgaccctac ttgcactgct   5520
gtggattttt ttaagagaag caaaaacaaa agtaaactcc tttccctggc cctccaaaca   5580
tatattctgt gagataactg tgcctgctac caagtgttaa tcctgggatc gtatttttat   5640
atcatattca catatttgtt tttttaattg gtgttagatg acatgattaa taaaaaaggc   5700
aagatatttt cagaatttga atttcagttt ttttttttct tttgaaatgt ccctttaaga   5760
tttttttatt ctaaacaaaa taaagaaaat cctgctgctc tggtccttgt gataagcctc   5820
tcttcggcat ctgaggagca gctgcagcaa aatctagggg tgtaagtgta tcaggactta   5880
tgtgacttat attttgggga gatgagggtt gggttttttt tttaatgcta cgtgacagtt   5940
tgaaaccttc acagttatcc tctgggggta aatcaattct tcaacccttg ggtgtgtgag   6000
tttgaggcag ggtcatttgt gtgatgtgtt tggccttacc aaagcaaaag agggtgcaag   6060
aatgtgggag tatgtctgcc ggtttcaaca cacacagaca aacacagcca cacgcgcaca   6120
caagtataag actttttgta ttactgctcc ctacttaaca tacttgaatt ctcaaatttc   6180
ctttggggta aaaaaaaaaa aaggatttga aaccataaag tgttctgaag aaattaagtc   6240
tataaaaagc atactttctt ttttcttttc cttttttccc tccacagaca atgtcctctg   6300
ttcaattcct aacgcaaact acaataaatg gtgacacacg ttcagaaga               6349
```

<210> SEQ ID NO 115

<211> LENGTH: 2408
<212> TYPE: DNA
<213> ORGANISM: Homo sapiens
<220> FEATURE:
<221> NAME/KEY: misc_feature
<223> OTHER INFORMATION: Incyte ID No: 198067.1CB1
<221> NAME/KEY: unsure
<222> LOCATION: 2138
<223> OTHER INFORMATION: a, t, c, g, or other

<400> SEQUENCE: 115

```
ggagctgcca gcggggaggc tgcagccgcg ggttgttaca gctgctggag cagcagcggg     60
cccccgctcc cgggaaccgt ttcccgggcc gttgatcttc ggccccacac gaacagcaga    120
gaggggcagc aggatgaatg tgggcacagc gcacagcgag gtgaacccca acacgcgggt    180
gatgaacagc cgtggcatct ggctctccta cgtgctggcc atcggtctcc tccacatcgt    240
gctgctgagc atcccgtttg tgagtgtccc tgtcgtctgg accctcacca acctcattca    300
caacatgggc atgtatatct tcctgcacac ggtgaagggg acaccctttg agaccccgga    360
ccagggcaag gcgaggctgc taacccactg ggagcagatg gattatgggg tccagttcac    420
ggcctctcgg aagttcttga ccatcacacc catcgtgctg tacttcctca ccagcttcta    480
cactaagtac gaccagatcc attttgtgct caacaccgtg tccctgatga gcgtgcttat    540
ccccaagctg ccccagctcc acggagtccg gatttttgga atcaataagt actgagagtg    600
cagccccttc ccctgcccag ggtggcaggg gaggggtagg gtaaaaggca tgtgctgcaa    660
cactgaagac agaaagaaga agcctctgga cactgccaga gatgggggtt gagcctctgg    720
cctaatttcc cccctcgctt cccccagtag ccaacttgga gtagcttgta gtggggttgg    780
ggtaggcccc ctgggctctg accttttctg aattttttga tcttttcctt ttgctttttg    840
aatagagact ccatggagtt ggtcatggaa tgggctgggc tcctgggctg aacatggacc    900
acgcagttgc gacaggaggc caggggaaaa accccctgctc acttgtttgc cctcaggcag    960
ccaaagcact ttaacccctg catagggagc agagggcggt acggcttctg gattgtttca   1020
ctgtgattcc taggtttttt cgatgccacg cagtgtgtgc ttttgtgtat ggaagcaagt   1080
gtgggatggg tctttgcctt tctgggtagg gagctgtcta atccaagtcc caggcttttg   1140
gcagcttctc tgcaacccac cgtgggtcct ggttgggagt ggggagggtc aggttgggga   1200
aagatggggt agagtgtaga tggcttggtt ccagaggtga gggggccagg gctgctgcca   1260
tcctggcctg gtggaggttg gggagctgta ggagagctag tgagtcgaga cttagaagaa   1320
tggggccaca tagcagcaga ggactggtgt aagggaggga ggggtaggga cagaagctag   1380
acccaatctc ctttgggatg tgggcaggga gggaagcagg cttggagggt taatttaccc   1440
acagaatgtg atagtaatag gggagggagg ctgctgtggg tttaactcct gggttggctg   1500
ttgggtagac aggtggggaa aaggcccgtg agtcattgta agcacaggtc caacttggcc   1560
ctgactcctg cgggggtatg gggaagctgt gacagaaacg atgggtgctg tggtcctctg   1620
caggccctca ccccttaact tcctcataca gactggcact gggcagggcc tctcatgtgg   1680
cagccacatg tggcgttgtg aggccacccc atgtggggtc tgtggtgaga gtcctgtagg   1740
atccctgctc aagcagcaca gaggaagggg caagacgtgg cctgtaggca ctgtctcagc   1800
ctgcagagaa gaaagtgagg ccgggagcct gagcctgggc tggagccttc tcccctcccc   1860
agttggacta ggggcagtgt taattttgaa aaggtgtggg tccctgtgtc ctcttccagg   1920
ggtccaaggg aacaggagag gtcactgggc ctgttttctc cctcctgacc ctgcatctcc   1980
caccccgtgt atcataggga actttcacct taaaatcttt ctaagcaaag tgtgaatagg   2040
```

```
atttttactc cctttgtaca gtattctgag aaacgcaaat aaaagggcaa catgtttctg   2100

tttccctgtg tctggccttc gcttcctgga aggctgangg gagggggcag ggtgtgggc    2160

agcggctccc gctgaggtgc tggtggggca tcagtgcagc tctgacggtg gcaggagggg   2220

cgctgggact gctgggcttt ctgctggctt cagcagggaa atcccccaag ggggctgtga   2280

gggaactggc ggcggcacgg tagtcagaga gcaaaattct ctgtgctttt gcctggctgt   2340

tctccgacag tcttgcgcct tggccccaga ggctggggtg acctgtgcca tggccaagga   2400

aggggaca                                                            2408
```

<210> SEQ ID NO 116
<211> LENGTH: 553
<212> TYPE: DNA
<213> ORGANISM: Homo sapiens
<220> FEATURE:
<221> NAME/KEY: misc_feature
<223> OTHER INFORMATION: Incyte ID No: 200039.1CB1

<400> SEQUENCE: 116

```
tctactccag agctccgact tatttccaaa tattatgatc ctgcatgttt gctatttcac     60

aatcaatgac attttgaggc cacattgact ataaataatc acatctgtct ttggaaaagc    120

cacattttgt ttcacactaa ttcttttttt tgtccttgca aagttggctt tctggatgga    180

gagaatgatg tgtctggcaa tagggatctg tacatttcct atttcaagag cacacaaagt    240

attgacatct gaaatgaaaa cacaaaagga aaagcttaaa cttgccacat aggaagttct    300

tcatgcttga atagtgtctt cataaccata atgggatttt ttaggattat aatagttctt    360

tttaaatgct ttatttactt aacaaatagt aatcaaatca ttgcaaattc ttatatggaa    420

gatttaggcg ctggcagcaa tagttacata aattataatg tcaactatga caaactttcc    480

tatgtgtcta gagctagaat ataaaataga agtgtgccat catggctaca aatggttaag    540

aatatagatt cta                                                       553
```

<210> SEQ ID NO 117
<211> LENGTH: 3191
<212> TYPE: DNA
<213> ORGANISM: Homo sapiens
<220> FEATURE:
<221> NAME/KEY: misc_feature
<223> OTHER INFORMATION: Incyte ID No: 201843.4CB1
<221> NAME/KEY: unsure
<222> LOCATION: 826
<223> OTHER INFORMATION: a, t, c, g, or other

<400> SEQUENCE: 117

```
gagccctggg ccaaaatggc ggcctacctg cagtggcggc gcttcgtttt cttcgacaag     60

gagctggtga aggagccgct gaggcaatga tggggccgct cccggggcca cacctgcttc    120

tggatccgct gcttccaagt tcctttgcct ccctcctggc atcactgtct gcgactcagg    180

ccgagggagc ctggtctttg gagatatgga aggccagatc tggttcttgc cacgttccct    240

acagcttaca ggcttccaag cctacaaact acgggtgaca cacctgtacc aactgaagca    300

gcacaatatt ctggcatctg ttggagaaga tgaagagggc atcaacccct tggttaagat    360

ctggaacctg gagaagagag atggtggcaa tccactctgc actcgaatct tccctgctat    420

tccaggaaca gagccaactg ttgtatcttg tttgactgtc catgaaaatc tcaactttat    480

ggccattggt ttcacagatg ggagtgttac attgaacaaa ggagacatca cccgggaccg    540

gcatagcaag acccagattt tgcacaaggg caactatcct gtaactggat tggcctttcg    600
```

-continued

```
ccaagcagga aagaccactc acttgtttgt tgtgacaaca gagaacgtcc agtcctatat    660
agtttctgga aaagactacc ctcgcgtgga gttggacacc catggttgtg gcctgcgctg    720
ctcagcccta agtgaccctt ctcaggacct gcagttcatt gtggccgggg atgagtgtgt    780
ctacttgtac cagcctgatg aacgtgggcc ctgcttcgcc tttganggcc ataagctcat    840
tgcccactgg tttagaggct accttatcat tgtctcccgt gaccggaagg tttctcccaa    900
gtcagagttt accagcaggg attcacagag ctccgacaag cagattctaa acatctatga    960
cctgtgcaac aagttcatag cctatagcac cgtctttgag gatgtagtgg atgtgcttgc   1020
tgagtggggc tccctgtacg tgctgacgcg ggatgggcgg gtccacgcac tgcaggagaa   1080
ggacacacag accaaactgg agatgctgtt taagaagaac ctatttgaga tggcgattaa   1140
ccttgccaag agccagcatc tggacagtga tgggctggcc cagattttca tgcagtatgg   1200
agaccatctc tacagcaagg gcaaccacga tggggctgtc cagcaatata tccgaaccat   1260
tggaaagttg gagccatcct acgtgatccg caagtttctg gatgcccagc gcattcacaa   1320
cctgactgcc tacctgcaga ccctgcaccg acaatccctg gccaatgccg accataccac   1380
cctgctcctc aactgctata ccaagctcaa ggacagctcg aagctggagg agttcatcaa   1440
gaaaaagagt gagagtgaag tccactttga tgtggagaca gccatcaagg tcctccggca   1500
ggctggctac tactcccatg ccctgtatct ggcggagaac catgcacatc atgagtggta   1560
cctgaagatc cagctagaag acattaagaa ttatcaggaa gcccttcgat acatcggcaa   1620
gctgcctttt gagcaggcag agagcaacat gaagcgctac ggcaagatcc tcatgcacca   1680
cataccagag cagacaactc agttgctgaa gggactttgt actgattatc ggcccagcct   1740
cgaaggccgc agcgataggg aggccccagg ctggcagggc caactctgag gagttcatcc   1800
ccatctttgc caataacccg cgagagctga aagccttcct agagcacatg agtgaagtgc   1860
agccagactc accccagggg atctacgaca cactccttga gctggcgact gcagaactgg   1920
gcccacgaga aggatccaca ggtcaaagag aagcttcacg cagaggccat ttccctgctg   1980
aagagtggtc gcttctgcga cgtctttgac aaggccctgg tcctgtgcca gatgcacgac   2040
ttccaggatg gtgtccttta cctttatgag cagggggaagc tgttccagca gatcatgcac  2100
taccacatgc agcacgagca gtaccggcag gtcatcagcg tgtgtgagcg ccatggggag   2160
caggacccct ccttgtggga gcaggccctc agctacttcg ctcgcaagga ggaggactgc   2220
aaggagtatg tggcagctgt cctcaagcat atcgagaaca agaacctcat gccacctctt   2280
ctagtggtgc agaccctggc ccacaactcc acagccacac tctccgtcat cagggactac   2340
ctggtccaaa aactacagaa acagagccag cagattgcac aggatgagct gcgggtgcgg   2400
cggtaccgag aggagaccac ccgtatccgc caggagatcc aagagctcaa ggccagtcct   2460
aagattttcc aaaagaccaa gtgcagcatc tgtaacagtg ccttggagtt gccctcagtc   2520
cacttcctgt gtggccactc cttccaccaa cactgctttg agagttactc ggaaagtgat   2580
gctgactgcc ccacctgcct ccctgaaaac cggaaggtca tggatatgat ccgggcccag   2640
gaacagaaac gagatctcca tgatcaattc cagcatcagc tcaagtgctc caatgacagc   2700
ttttctgtga ttgctgacta ctttggcaga ggtgttttca acaaattgac tctgctgacc   2760
gaccctccca cagccagact gacctccagc ctggaggctg ggctgcaacc gcgacctact   2820
catgcactcc aggaggggca cttaagcagc ctggaggaag atgtgggcaa cagtggagga   2880
ccgagagaac agacacaatg ggacctgggc gggcgttaca cagaaggctg gctgacatgc   2940
```

-continued

```
ccagggctcc actctcatct aatgtcacag ccctcagaac taaagcggac tttctttccc   3000

tgccttctta tttagtcagc ttgccatccc tcctcttcac tagcagtgta gatcattcca   3060

gatcagtggg ggagggcacc tcagcaacct ctgagtgtgg acaatagctg ctttcttctc   3120

tatccaagag caccaggctg tgcttgggtc cttgctctca gagtctataa ataaaagaat   3180

ataatgattt g                                                        3191
```

<210> SEQ ID NO 118
<211> LENGTH: 520
<212> TYPE: DNA
<213> ORGANISM: Homo sapiens
<220> FEATURE:
<221> NAME/KEY: misc_feature
<223> OTHER INFORMATION: Incyte ID No: 213764.1CB1

<400> SEQUENCE: 118

```
agcctccatt tttctccaga tggttgaaat aaccagcctc tgaaggagcc caatggtttg     60

gtcactgctc tctcagcaaa ttacagtcac tgtcacttag catggagagt ggacgttgca    120

catcactgtg aaaccttgca gaggaggaga gggcaggttc atcagaagaa agaaaggaca    180

aaatgactcc ttatgaagca ttttgtgcct tctgtgagaa aacatgtatt tagatcagat    240

aaactctagt caaaatacaa aaaggaaaaa tgaaagacct ctgaaatagg aacaatctct    300

tgaagaggca aatgactcaa aactgctcag tggctctttc agaaaatcta agtaaagttc    360

cctgacaaca gaaactgaag agattgcctg gttcatcttg tagtcttcca aaacagcaga    420

taatttctga atctcagatg ttgaatcagt gcaacgggat ggatttcttg ttcctaagtg    480

ttaaatgatc acatacataa aagagtctga gcctgagcaa                          520
```

<210> SEQ ID NO 119
<211> LENGTH: 2343
<212> TYPE: DNA
<213> ORGANISM: Homo sapiens
<220> FEATURE:
<221> NAME/KEY: misc_feature
<223> OTHER INFORMATION: Incyte ID No: 216188.1CB1
<221> NAME/KEY: unsure
<222> LOCATION: 2323, 2332, 2337
<223> OTHER INFORMATION: a, t, c, g, or other

<400> SEQUENCE: 119

```
gttccgtgga ctccgctggc cccaggcctg aagttgagga ggaaaatggg gaggaagttt     60

tcctgagtgc ctatgatgac ctaagtcccc ttctgggacc taaacccccca atctggaagg    120

gttcagggag tctggaggga gaggcagcag gatgtggaag gcaggctctg ggacagggtg    180

gggaagagca ggcatgctgg gaagttgggg aggacaagca ggctgagcct ggaggcaggc    240

tagacatcag ggaagaggca gagggaagtc cagagaccaa ggtggaggct ggaaaggcca    300

gtgaggatag aggggaggct gggggaagcc aagagacaaa agtcagattg agagaaggga    360

gtagggaaga gacagaggcc aaggaagaga agtccaaagg tcagaagaag gctgacagta    420

tggaggctaa aggtgtggag gaaccaggag gagatgagta tacagatgag aaggaaaaag    480

aaattgagag agaagaggat gaacaaagag aggaagccca ggtagaagct ggaagggacc    540

tagagcaagg ggcccaggaa gatcaagttg ctgaggagaa atgggaagtt gtacagaaac    600

aagaggctga gggagtcaga gaggatgagg acaaaggaca gagggagaag gggtaccatg    660

aagcaagaaa agaccaagga gatggtgaag acagcagaag cccagaagca gcaactgaag    720

gaggagcagg ggaggtcagc aaggaacggg agagtgggga tggagaggct gagggagacc    780
```

-continued

```
agagggctgg agggtactat ttagaagagg acaccctctc tgaaggttca ggtgtagcgt    840
ccctggaggt tgactgtgcc aaagagggca atcctcactc ttctgagatg gaagaggtag    900
ccccacagcc acctcagcca gaggagatgg agcctgaggg gcagcccagt ccagacggct    960
gtctatgccc ctgttctctt ggcctgggtg gcgtgggcat gcgtctagct tccactctgg   1020
ttcaggtcca acaggtccgc tctgtgcctg tggtgccccc caagccacag tttgccaaga   1080
tgcccagtgc aatgtgtagc aagattcatg tggcacctgc aaatccatgc ccgagggcct   1140
ggccggcttg atgggactcc tggagaaagg gcttgggggt cccgagcttc tcgatcctct   1200
tggaggaatg ggggtagtct ttcctttgat gctgctgtgg ccctagcccg ggaccgccaa   1260
aggactgagg ctcaaggagt tcggcgaacc cagacctgta ctgagggtgg ggattactgc   1320
ctcatcccca gaacctcccc ttgtagcatg atctctgccc attctcctcg gcccccttagc  1380
tgcctggagc tcccatctga aggtgcagaa gggtctggat cccggagtcg tcttagtctg   1440
ccccccagag aaccccaggt tcctgacccc ctgttgtcct ctcagcgcag atcatatgca   1500
tttgaaacac aggctaaccc tgggaaaggt gaaggactgt gattaggacc acagccctgg   1560
gcaaagggga ccagcaagtt gtcttgaatc tccagggttc ctgactagct gtctcctctg   1620
cagcatgagc agctgtagtg cccaactcta taggctttgg ccctccagct tctctctttg   1680
actgtgggag gcactgcctt ggttggttta cctgaacttg tctccgacac aaagcactta   1740
tctcttagga gattcccaag aaagtcaaca agatcttgtt cccagggagt gggtcattgg   1800
ccaaagggaa cataaggtag gcagaaaact taaaagagtt tgttaaagtg aagactggag   1860
aaattcctcc cttcctctga gctgtgaatc tctcttcatg aaagccaaag gtagagacag   1920
ggaggacagg gccaggttag ggccttccac acacaaacac ttctagagtt gcccattcct   1980
gttatgttct tggaccctaa gatacctcct gtccctttta aatccagatt aagagaaacg   2040
tccaggaaga gctctttgaa gccctcaata tttgttggag ggactggact cctctccagc   2100
tccccaccct ctgcctccag tcaccatgtg caagagaggt cctgtacaga tctctctggg   2160
ctctcctttc tcctttggaa taacttgttc ctatttcagg aaagggaaat ggtgtcactc   2220
aggccctggg actgcttctc cagccaggct ggggccacag gtcccactct agtgaaggtc   2280
aatgtctcaa aataaaagct gtatttttac acataaaaaa aanaaaaaaa anctcgnggg   2340
ggg                                                                 2343
```

<210> SEQ ID NO 120
<211> LENGTH: 485
<212> TYPE: DNA
<213> ORGANISM: Homo sapiens
<220> FEATURE:
<221> NAME/KEY: misc_feature
<223> OTHER INFORMATION: Incyte ID No: 218996.1CB1

<400> SEQUENCE: 120

```
aaacgaggtc aagtagtaag agaagcggta agagtgacgg gaacaggagt cattgacctc     60
ttgggagagg agacattgga ggtggtgatg atttgctgaa gcagccacac acgttcagct    120
tgtgaggaca gcagttgtta ggcaggggat gagggaggaa gctggcagat ctgtgcaggt    180
gagaggtacc tgtggccttg ggctcatgga agtgggaggt gatgggattc taatgtgctt    240
gggtacagtt tacaaataca acctctctta gtttgcccaa tacctccaaa ttcctggggt    300
ggcacacctg aggttcaggt ggcatgactg agccacagtc acacatcccc actgtaggat    360
accaccacgg ttgggttagg ttccagcaca tgggcggtcg cggcctggcc ctcttggtcc    420
```

```
cacctcacct ggtgactagt gcagaccact ctgttcttgc ctgtttcagg cagcgcgagg    480

aggag                                                                485


<210> SEQ ID NO 121
<211> LENGTH: 1447
<212> TYPE: DNA
<213> ORGANISM: Homo sapiens
<220> FEATURE:
<221> NAME/KEY: misc_feature
<223> OTHER INFORMATION: Incyte ID No: 227709 (1221361CB1)

<400> SEQUENCE: 121

cgcgggcgcg tcgccctctg cccccgccgg caccctggcc atgacaggca agtcggtgaa     60

ggacgtggat cggtaccagg ctgtcctggc caacctgctg ctggaggagg ataacaagtt    120

ttgtgccgat tgccagtcta aagggccgcg atgggcctct tggaacattg gtgtgttcat    180

ctgcattcga tgtgctggaa tccacaggaa tctgggggtg cacatatcca gggtaaagtc    240

agttaacctc gaccagtgga ctcaagaaca gattcagtgc atgcaagaga tgggaaatgg    300

aaaggcaaac cgactttatg aagcctatct tcctgagacc tttcggcgac ctcagataga    360

cccagctgtt gaaggattta ttcgagacaa atatgagaag aagaaataca tggaccgaag    420

tctggacatc aatgccttta ggaaagaaaa agatgacaag tggaaaagag ggagcgaacc    480

agttccagaa aaaaaattgg aacctgttgt ttttgagaag gtgaaaatgc cacagaaaaa    540

agaagaccca cagctacctc ggaaaagctc ccgaaatcc acagcgcctg tcatggattt    600

gttgggcctt gatgctcctg tggcctgctc cattgcaaat agtaagacca gcaataccct    660

agagaaggat ttagatctgt tggcctctgt tccatcccct tcttcttcgg gttccagaaa    720

ggttgtaggt tccatgccaa ctgcagggag tgccggctct gttcctgaaa atctgaacct    780

gtttccggag ccagggagca aatcagaaga aataggcaag aaacagctct ctaaagactc    840

cattctttca ctgtatggat cccagacgcc tcaaatgcct actcaagcaa tgttcatggc    900

tcccgctcag atggcatatc ccacagccta ccccagcttc cccggggtta cacctcctaa    960

cagcataatg ggagcatga tgcctccacc agtaggcatg gttgctcagc caggagcttc   1020

tgggatggtt gcccccatgg ccatgcctgc aggctatatg ggtggcatgc aggcatcaat   1080

gatgggtgtg ccgaatggaa tgatgaccac ccagcaggct ggctacatgg caggcatggc   1140

agctatgccc cagactgtgt atggggtcca gccagctcag cagctgcaat ggaaccttac   1200

tcagatgacc cagcagatgg ctgggatgaa cttctatgga gccaatggca tgatgaacta   1260

tggacagtca atgagtggcg gaaatggaca ggcagcaaat cagactctca gtcctcagat   1320

gtggaaataa aaacaaaaca cctgtatggc tgccattctc ttcagccctc gctctacccc   1380

tttccacagc ctcaacccct gacccatcct cttttcctac ctctctgttt ggtttagaaa   1440

ttgctca                                                             1447


<210> SEQ ID NO 122
<211> LENGTH: 2116
<212> TYPE: DNA
<213> ORGANISM: Homo sapiens
<220> FEATURE:
<221> NAME/KEY: misc_feature
<223> OTHER INFORMATION: Incyte ID No: 228623 (3284695CT1)

<400> SEQUENCE: 122

gaggacccat tcatgccaga aagctggtaa ctccctccca gcatccctgc ggaaggagtc     60

agtttctgag agtgtgactt ttcaaggcga atgatgggga agggttcccc agtccccaca    120
```

```
gtggccccac ctctgggccc tgcaccagag cccttctgtg tcacggcggg ctgtgcaccc    180
atgcacacac ctacgcacac acaacactcc gcactgcagt atattcttgc caaagatttc    240
ctttaaaagc aagcactttt actaattatt attttgtaaa tgtttatctt cttctgtctt    300
ctccctccct gaatctattt tactgttgtt tattgttgaa tctgtgtgtc agccaggaga    360
gcgctgtctg gccttgaaca tgggctggga tgggaaaggg tctgggagaa gatgggcaac    420
aaagagccag ggagtcatgg acatcgcagc gacgcagacc ccagcaggtt cagtcccgtg    480
ctgccaccag ctgtccagct gggtgtctgg agggaagagg gcagaggagg gtcatgtccc    540
ttcagctggg ggaggggccc agtgagctcc acgtggcttt ttcccaaagg gagcaagagg    600
gaaggattgg gcgagaaaac aatggagagg ggacctgcga aggaaaacag ggaggaagtg    660
agcggtttga tcagcctgct atcacggtgt tctggctctc ttatttagcc aggcgcttaa    720
gggacagata catcacatcc taagtttggg aaaggccttt gacccatgtc atctgagcgt    780
ctcctccagt agctctgaaa gctgtggaca ccaatggcca ggattccttc tcccctggtt    840
tttgaggatc cctgggtctt ctgagactgg ccaggagagg gatggtgggg ccagtggttg    900
tgtgaaagca ggaggggcag ccctcctgga caagtgtgat cccccctataa acggctctca    960
ggaggttagt gagtaggaga ttctgccttg ttctgatgag cctgtgcagg ggctccaggg   1020
gagcatgctg tccagggggc acagaagggt ggtgagtgtg atcaaatcta gtctcactcc   1080
cactttttta gtctcactcc tacttttgtc caccacccct gcctcctgga tcttctccca   1140
cttttttttt cagctttagg acctggggag atcctgtgag tcaaggcaga cacccaatcc   1200
tgcccccaca ctcggggtcc tccaagaggt tgggggggcag agtcccagag cagcccttta   1260
ccccaggtcc aggccctgga atcctgagac tcgcgtttcc ttggccagtg gtaacacagg   1320
acgtgtgtgc gcatgtgcaa gtgtggatgt atgtgtgtgc gtgtgttttg ctcatttctt   1380
tagggaactt gggagtcggg gttggaggtg ctgggcaatg gaacttcaaa ttcaatgtcg   1440
cccagcagtg aggggagtcg ggaggtgagg cctgtaggcc aaccaattgg tggagtctca   1500
gcgatagccc aggtgagaag tggttcaccc agaggggcag ggtgggggcc tcgggcagat   1560
ctgtccctct tggcccctct gtcctcaaat gtccaaaatg ttggaggacc tctgttcata   1620
tcccacgcct gggctcttgc cagcagtgga gttactgtag agggatgtcc caagcttgtt   1680
ttccaatcag tgttaagctg tttgaaactc tcctgtgtct gtgttttgtt tgtgcgtgtg   1740
tgtgagagca catcagtgtg tgcaggctgt gtttccccat ttctctcctc ccttcagacc   1800
catcattgag aacaaatgta agaaatccct tcccaccacc ctccctgcct cccaggccct   1860
ctgcggggga aacaagatca cccagcatcc ttccccaccc cagctgtgta tttatataga   1920
tggaaatata ctttatattt tgtatcatcg tgcctatagc cgctgccacc gtgtataaat   1980
cctggtgtat gctccttatc ctggacatga atgtattgta cactgacgcg tccccactcc   2040
tgtacagctg ctttgtttct ttgcaatgca ttgtatggct ttataaatga taaagttaaa   2100
gaaaaaaaaa aaaaaa                                                   2116
```

<210> SEQ ID NO 123
<211> LENGTH: 1386
<212> TYPE: DNA
<213> ORGANISM: Homo sapiens
<220> FEATURE:
<221> NAME/KEY: misc_feature
<223> OTHER INFORMATION: Incyte ID No: 231861.3CB1

<400> SEQUENCE: 123

```
ttcggcacag cacggaaccc cctcctctca cagaaccccc tcctctcaca cagaaccccc     60

tcctctcaca cagaaccccc tcctctcacg gaaccccctc ctctcacgga accccctcct    120

ctcacggaac gccctcctct cacacagaac cccctcctct caccgaatcc catctcagtc    180

ttgagttttc cctcgactct gttgcttccg ctcacatctt agtgagtccc cagggcctct    240

gcggggcatg gaatcacacg tgcagtgttc cggcatgttc agcctggtgt gtgacagtgg    300

ggttccctgc caggccagca gtgtgctctg actcggggca gggaccaggt tctgtgtagc    360

tttgtgctca agtgctgagc agagtagact ctcagcagat gtttgaatga atgggtgaac    420

caatggctgc acaaatgaac gagcctgact ctccctcatg atttggtcca tagtgtgttt    480

aaataccctc ctagtgggct tttagctcct tgaagatgga aacaggtttg catagtaagt    540

ttgttttatt gaatggaatg gacttaaagt cttcggactt gggagaatta ggacagatct    600

gtttccccgt tggtaaagta aaggttgggc ctgatgatct cagaaactca ggaagagtga    660

tggtcggccc cagggtcgag agtgagttac tgccaggtcc agggctgtcc ctgtgttctg    720

gctcccagac cacagtgttt cttcctgaag ccggtggttg cagccacttt gccttgctcc    780

tctacgcctt tcctgaagga tgaggtgggg ccagtctgcc tctgggagct cggtcaagtt    840

cacccgcctg cctgcctgtc cagccaagta cctggcccag atcattgtga tgggcgtgca    900

ggtggtgggc agggcctttg cacgggcctt gcggcaggag tttgcagggg tgagccacca    960

actcggaagg cccagggtga agtgtgggct gctgaggact gagcgatcac ccacatgtcc   1020

acacagccag ccgggccgca gctgatgccc gaggacgcgc tggacaccgg tctgcagccg   1080

cttccaacct ctccggcctc agcctccagg aggcacagca gattctcaac gtgtccaagc   1140

tgagccctga ggaggtccag aagaactatg aacacttatt taaggtgaat gataaatccg   1200

tgggtggctc cttctacctg cagtcaaagg tggtccgcgc aaaggagcgc ctggatgagg   1260

aactcaaaat ccaggcccag gaggacagag aaaaagggca gatgccccat acgtgactgc   1320

tcggctcccc ccgcccaccc cgccgcctct aatttatagc ttggtaataa atttcttttc   1380

tgcaaa                                                              1386
```

<210> SEQ ID NO 124
<211> LENGTH: 938
<212> TYPE: DNA
<213> ORGANISM: Homo sapiens
<220> FEATURE:
<221> NAME/KEY: misc_feature
<223> OTHER INFORMATION: Incyte ID No: 232573.1CB1
<221> NAME/KEY: unsure
<222> LOCATION: 599, 620
<223> OTHER INFORMATION: a, t, c, g, or other

<400> SEQUENCE: 124

```
ttttagccct tgttgtttat ttttcaataa acaaggtttt tttgcatgtc tggactggta     60

gtaaacggga aagctaaaaa gagcgccaag gacatttttt ttaacatttt ggtgacaaaa    120

ttgatactcc tcttcctcct ctcctaattt gggaccaaat tgctgatcat gtcttggatc    180

gctgtctttg agcttttccg tttgtttcgt aaactacaca ctacaccaga cacacacaag    240

gtgcggctgg gcagtcaagg atcccgacac tctcagcaga atctggtggc catagaacat    300

ggaatgacca tttctgcatg acgtgaagac cgtggcgagg ctgctgacac tgcttctgtt    360

gcacgggggg ggtagtgcga gtggtgggca ctgtggaatt tgggagggac ggcctcatcg    420

ggtgctggta atagataatt tgttgcgtgg gaaggtgaga tggtggctct tctccaaggg    480
```

-continued

```
aggcgtctgc tcaagaccct ccactcccac ggcatgtgac cggcaccgcg ctgggctccc    540

tggggacagc tgtgtgtcca ccccccttcca gactgccccc tcgtcctgcc tgccctgcng    600

cttccgcaca ctgcctagtn tccgcaggtg cctggaaatg cttcctgatc agatgggttg    660

tggacggtga acaaatgaat ggatggggag ttggtcaagg atacctcgac cgtgggacgt    720

ctttttcttg ttatcagggg aacatggctg ttctctatag catcaagatc gaaaacatag    780

ataatttgat catctgacca atcttagaat tttctatttg ggaaactga ggaacagaat    840

cgttagcagg ctcagtccag gtctcacgct gagagaggcc aggcagggta ccagacgccc    900

gcctgacaca tgccaacaat tcttttttt gtcttttt                              938
```

```
<210> SEQ ID NO 125
<211> LENGTH: 1287
<212> TYPE: DNA
<213> ORGANISM: Homo sapiens
<220> FEATURE:
<221> NAME/KEY: misc_feature
<223> OTHER INFORMATION: Incyte ID No: 234545.3CB1
<221> NAME/KEY: unsure
<222> LOCATION: 11, 24, 55, 81, 97, 107, 1273
<223> OTHER INFORMATION: a, t, c, g, or other

<400> SEQUENCE: 125

gtttttaggg naggaaaagt gtgnggctgc tgatctgagc tctctggcca ggagnaggga     60

agggggtggg ggtggagagg ngggaggagg gggtaanaag gggaggngat gcgaggaggg    120

agtggagaga gggcaggtaa ttcggaggag ggaagaggca gcccccctgcc cggccagctc    180

gtgactaatt taggcaaaag gcagcctgga gctatttcca ttcggcggcg ggaacaggtg    240

ccggcgcctc cgccccatcc ccaggggccg cctcccccgg ggcggcctcc aggctgccga    300

gacctataaa ggcgccaggt tttctcaatg aagccgggac gcactccgga gcgcactgcg    360

tggtcgcacc ctacccgggc tgccttggaa gtcgtccccg ccgcccctcc gcaccggcat    420

gaagctcatc gtgggcatcg gaggcatgac caacggcggc aagaccacgc tgaccaacag    480

cctgctcaga gccctgccca actgctgcgt gatccatcag gatgacttct tcaaggctcc    540

tctgtttcag ccccaagacc aaatagcagt tggggaagac ggcttcaaac agtgggacgt    600

gctggagtct ctggacatgg aggccatgct ggacaccgtg caggcctggc tgagcagccc    660

gcagaagttt gcccgtgccc acggggtcag cgtccagcca gaggcctcgg acacccacat    720

cctcctcctg gaaggcttcc tgctctacag ctacaagccc ctggtggact tgtacagccg    780

ccggtacttc ctgaccgtcc cgtatgaaga gtgcaagtgg aggagaagta cccgcaacta    840

cacagtccct gatcccccg gcctcttcga tggccacgtg tggcccatgt accagaagta    900

taggcaggag atggaggcca acggtgtgga agtggtctac ctggacggca tgaagtcccg    960

agaggagctc ttccgtgaag tcctggaaga cattcagaac tcgctgctga accgctccca   1020

ggaatcagcc ccctccccgg ctcgcccagc caggacacag ggacccggac gcggatgcgg   1080

ccacagaacg gccaggcctg cagcgtccca gcaggacagc atgtgagcgt ttccctatgg   1140

gggtgtctgt acgtaggaga gtggaggccc cactcccagt tgggcgtccc ggagctcagg   1200

gactgagccc caagacgcct ctgtaacctc gctgcagctt cagtagtaaa ctgggtcctg   1260

tttttttata aangcaaaag tacttaa                                        1287
```

```
<210> SEQ ID NO 126
<211> LENGTH: 2172
<212> TYPE: DNA
<213> ORGANISM: Homo sapiens
```

-continued

<220> FEATURE:
<221> NAME/KEY: misc_feature
<223> OTHER INFORMATION: Incyte ID No: 237549.1CB1
<221> NAME/KEY: unsure
<222> LOCATION: 1219, 1233
<223> OTHER INFORMATION: a, t, c, g, or other

<400> SEQUENCE: 126

```
tgccttaaag aaaataataa gagaagggtg tgttctcttc caagtaatga gccgatcaag     60
gggaagcaac ccaaggctag caggctcttt tcaattccca gctctgccac tcttagcatg    120
gcagagagtt ggcctcatta tgccagtatg gctgccacag tgtcagacat cacattccag    180
gcagtggaaa ggagaaagaa ccaaagggca tccctttctc ttgaagcagt ccctgtgagg    240
ggggattatc tggaagcccc aacccaattt ctgcttccaa ccattatcca tagaaacaac    300
tggaagttga gaagtgcagt cttttaggtg ggcacctggc tgccctgtat gaaaccagaa    360
ttaggttggt cagcaggaaa acaagaaaac acttactgtg ttgactgagg tttttgacgc    420
atcgctttat tgtcaaatta aacaactcta tctcattctg cactgaaaca cgtactacca    480
ttgcctataa ttggaaaatg atcctcagag gcacagaaga tgccctgatg gaaagtttgc    540
cccttgggca aagagacagc catgggaacc ttcagacata gagagagaag gtggcttttc    600
tccctacatt cctcaaatag ctaagatttg gccagtgtgt tttctaagtc aattctagtg    660
tgtttcatcc tcacctcttc cctctgtggc tttgatgatg gaagtgtagt cctaacctac    720
tgcacagctg ggaccccctg cccctagatc ccaatactgg ggatgggagg accttgcact    780
attcccctca gtccatctat cgaggtcttt gcaggaagca tactgggaat tgaaacgaga    840
gcctaaatga catctaagaa aggcagtgtt caataccagg tattaggtga ggatgggatt    900
ctaaggacat cagtgggagg cagggagcca ccttcagacc tcagcatgga agcttccaag    960
atccagagga agaggcaaca gcactgagag tcataggtag aagaatcatc acagccctgc   1020
taaccaggca gctgatgccc ctctcccctg gctccctgtg tccaaatcct acaggggcat   1080
ctgttggctg aactcaacct gaagccaaag agaagatgag tggagagagg caacatttat   1140
agagctcagg tttctagggc tggagaggga tctggaggga cacacaggag acacctggca   1200
taaccaaaaa atgattaana aaaaaaaaaa aanaaacatc tatggagcat gggacacggg   1260
gagtggaggc agctaaaagc catctcatct ttcaccgtat tcaacaagcc cattataaca   1320
agtctttcac gctcaaccat tcaaacaatc ccaacaatcc cagcctaaga atttcctggc   1380
atttgatgaa aatggctgtg ggttttgcta tctttaagct ccctggggaa gcaggatata   1440
agcccagggg ctggcaggct ctttctagct acctgctctt gcacatagag tttgcctcat   1500
ggttgcaaga aggctgccat agctccagat ggcacataga cattccaggc agcaggaaaa   1560
aggaaggagc acttaaccga aggaggtcag ggagttggtt agtctccacc tgaagaagag   1620
agccatgaac cagcttcagt tgactaacgg gctcctgtga gtgcatcttt ggacttttct   1680
ggaggttgaa atctagatgt ggtatgtgtc ttaaagcagc caccaactcc tcccattacc   1740
ttccaagtga gcccaactac acgatggagc ctcttccctg cccttggatc tgggctgagc   1800
ctctgacttg cgttgaccaa cagaatgcag tgaaagtgat gccgatacta ccctccctgc   1860
cctagacttg ggatacctgg cagctatatt cttccattcc tcaggacttg caaaaacggg   1920
tctcagcatg ccttcccaga gccatgaggt gtttctttgc ccattcattg atctgagaag   1980
tgagtgtaag gagtttaaat caacctctgt tctgtgctag ttaaggtaat aaagttgctg   2040
cagtccaggg ggtaggtacc tgtggacggc tctgcgaata ggacagttgc atttcttggg   2100
```

```
aatcaagtgc atccctaggc tggcagtgca gcagaaatac tgaataaaat gtgacaaatc   2160

tccctgaaaa aa                                                       2172


<210> SEQ ID NO 127
<211> LENGTH: 1886
<212> TYPE: DNA
<213> ORGANISM: Homo sapiens
<220> FEATURE:
<221> NAME/KEY: misc_feature
<223> OTHER INFORMATION: Incyte ID No: 237709.6CB1
<221> NAME/KEY: unsure
<222> LOCATION: 1852, 1856, 1858-1859, 1863-1865, 1867, 1869, 1872, 1880
<223> OTHER INFORMATION: a, t, c, g, or other

<400> SEQUENCE: 127

ctcgagccgg ggtgcggcag cactggccag gggaagaggg tgatccgacc cggggaaggt     60

cgctggggca gggcgagttg ggaaagcggc agccccccgcc gcccccgcag ccccttctcc   120

tcctttctcc cacgtcctat ctgcctctcg ctggaggcca ggccgtgcag catcgaagac    180

caggaggaac tggagcctca ttggccggcc cggggcgccg gcctcgggct taaataggag    240

ctccgggctc tggctgggac ccgaccgctg ccggccgcgc tcccgctgct cctgccgggt    300

gatggaaaac cccagcccgg ccgcacgccc tgggcaaggc cctcctgcgc tctcctgcct    360

ggccactctc ggcgccgccg gccagcctct tgggggagag tccatctgtt ccgccagagc    420

cccggccaaa tacagcatca ccttcacggg caagtggagc cagacggcct tccccaaggc    480

agtacccccct gttccgcccc cctgcgcagt ggtcttcgct gctgggggcc gcgcatagct   540

ccgactacag catgtggagg aagaaccagt acgtcagtaa cgggctgcgc gactttgcgg    600

agcgcggcga ggcctgggcg ctgatgaagg agatcgaggc ggcgggggag gcgctgcaga    660

gcgtgcacga ggtgttttcg gcgcccgccg tccccagcgg caccgggcag acgtcggcgg    720

agctggaggt gcagcgcagg cactcgctgg tctcgtttgt ggtgcgcatc gtgcccagcc    780

ccgactggtt cgtgggcgtg gacagcctgg acctgtgcga cggggaccgt tggcgggaac    840

aggcggcgct ggacctgtac ccctacgacg ccgggacgga cagcggcttc accttctcct    900

cccccaactt cgccaccatc ccgcaggaac acggtgaccg agataacgtc ctcctctccc    960

agccacccgg ccaactcctt ctactaccca cggctgaagg ccctgcctcc catcgccagg   1020

gtgacactgg tgcggctgcg acagagcccc cagggccttc atccctcccg ccccagtcct   1080

gcccagcagg gacaatgaga ttgtagacag cgcctcagtt ccagaaacgc cgctggactg   1140

cgaggtctcc ctgtggtcgt cctggggact gtgcggaggc cactgtggga ggctcgggac   1200

caagagcagg actcgctacg tccgggtcca gcccgccaac aacgggagcc cctgccccga   1260

gctcgaagaa gaggctgagt gcgtccctga taactgcgtc taagaccaga gccccgcagc   1320

ccctggggcc ccccggagcc atggggtgtc gggggctcct gtgcaggctc atgctgcagg   1380

cggccgaggg cacaggggggt ttcgcgctgc tcctgaccgc ggtgaggccg cgccgaccat  1440

ctctgcactg aagggccctc tggtggccgg cacgggcatt gggaaacagc ctcctccttt   1500

cccaaccttg cttcttaggg ggcccccgtg tcccgtctgc tctcagcctc ctcctcctgc   1560

aggataaagt catccccaag gctccagcta ctctaaatta tgtctcctta taagttattg   1620

ctgctccagg agattgtcct tcatcgtcca ggggcctggc tcccacgtgg ttgcagatac   1680

ctcagacctg gtgctctagg ctgtgctgag cccactctcc cgagggcgca tccaagcggg   1740

ggccacttga gaagtgaata aatggggcgg tttcggaagc gtcagtgttt ccatgttatg   1800

gatctctctg cgtttgaata aagactatct ctgttgctca caaaaaaaaa anatananna   1860
```

aannnanana anccaaattn atcaaa 1886

<210> SEQ ID NO 128
<211> LENGTH: 2018
<212> TYPE: DNA
<213> ORGANISM: Homo sapiens
<220> FEATURE:
<221> NAME/KEY: misc_feature
<223> OTHER INFORMATION: Incyte ID No: 238413.3CB1
<221> NAME/KEY: unsure
<222> LOCATION: 8, 24
<223> OTHER INFORMATION: a, t, c, g, or other

<400> SEQUENCE: 128
cagccagncc ccgcgccgcc cgcnccccgc tcgactccgg aggctcccgc agccccggcg 60
tccgccccgc tggcccctcc cccgggggcc atgggggcgc cccgggcta ccggccctca 120 gcttgggtgc atctcctcca ccagctgccc cgcgccgact tccagctccg cccggtgccc 180
agcgttttcg cgccccaaga gcaggaatac cagcaggcct tgttgctggt ggcggccttg 240
gcgggcctgg gcttgggcct gagcctcatt ttcatcgctg tctacctcat ccgcttctgc 300
tgctgccggc cccccgagcc ccccgggtcc aagatcccct cgcccggggg aggctgcgtc 360
acctggagct gcattgtcgc ccttctcgcc ggctgcactg gcattggcat cggtttctat 420
ggcaacagtg agaccagtga tggggtgtcc cagctcagct ctgcgctgct gcacgccaac 480
cacacactca gcaccattga ccacctggtg ttggagacgg tggagaggct gggcgaggcg 540
gtgaggacag agctgaccac cctggaggag gtgctcgagc cgcgcacgga gctggtggct 600
gccgcccgag gggctcgacg gcaggcggag gctgcggccc agcagctgca ggggctggcc 660
ttctggcagg gagtgcccct gagcccccctg caggtggctg aaaatgtgtc ctttgtggag 720
gagtacaggt ggctggccta tgtcctcctg ctgctcctgg agctgctggt ctgcctcttc 780
accctcctgg gcctggcgaa gcagagcaag tggctggtga tcgtgatgac agtcatgagt 840
ctcctggttc tcgtcctgag ctggggctcc atgggcctgg aggcagccac ggccgtgggc 900
ctcagtgact tctgctccaa tccagaccct tatgttctga acctgaccca ggaggagaca 960
gggctcagct cagacatcct gagctattat ctcctctgca accgggccgt ctccaacccc 1020
ttccaacaga ggctgactct gtcccagcga gctctggcca acatccactc ccagctgctg 1080
ggcctggagc gagaagctgt gcctcagttc ccttcagcgc agaagcctct gctgtccttg 1140
gaggagactc tgaatgtgac agaaggaaat ttccaccagt tggtggcact gctacactgc 1200
cgcagcctgc acaaggacta tggtgcagcc ctgcggggcc tgtgcgaaga cgccctggga 1260
aggcctgctc ttcctgctac tcttctccct gctgtctgca ggagcgctgg ccactgccct 1320
ctgcagcctg ccccgagcct gggccctctt cccacccagt gacgactacg atgacacaga 1380
cgatgacgac cctttcaacc ctcaggaatc caagcgcttt gtgcagtggc agtcgtctat 1440
ctgagcccct cctcccggct ggactggagc ctggctcccc tcttcgttcc ttccctggct 1500
gccggaggag accccactaa cccagcctgc ctgggctctg accactaaca ctcttggcca 1560
tggacagcct gcacaggacc gcctccctgc tcttggccac tgtgctccca tttctgtcct 1620
tggccttggg agtagctgag gggcagact agggagtagg gctggcaggg gagggggcag 1680
acagcctcgc ctcgcaccct tcatccctgg ctgccggtcc catccttgga gggactaagc 1740
tgggggtggg ggacatgagt ccccctgctg cccctgccac atcccagtgg gctctgaccc 1800
cctgatctca actcgtggca ctaacttgga aaagggttga tttaaaataa aagggaagac 1860

```
tattttacaa gcagctgggt cctccttatt tctcctctcc cttgattcgg cctcctggcc   1920

agggctggga catcctccct gctgtcctct ctcccccggc ctcccagctg ccaggaattt   1980

ctgcgcctgt ccaggctcag caaggggtcc aaagacat                           2018
```

<210> SEQ ID NO 129
<211> LENGTH: 1160
<212> TYPE: DNA
<213> ORGANISM: Homo sapiens
<220> FEATURE:
<221> NAME/KEY: misc_feature
<223> OTHER INFORMATION: Incyte ID No: 238469.4CB1

<400> SEQUENCE: 129

```
tatttttttc atgatatatg ccatattcca ctgtgtaatg tagattacac cacagggttt     60

ttaatttcct aaaggcaaga gctataacct agtcatcttc ctctcctaag tggggagtat    120

caccatgatt tgaccaagta gctatgatat gggtgctatc tccataaatg aatgagcagt    180

gaggaaaaag gagatgatta tgagtgaatg aagaatctta ataaggaaag tttattccac    240

agtgaagcag tgttggtggc tccaaaacct ctctttagga aggatttagg acagcatcct    300

aatcaaaagg gcctggaagc actttataaa agagagagac aagatcgcat gtcaaactag    360

aaggaaggag gtgagaggag atagggctcc agagtggagc aagccccttc tgtccccttg    420

aacttcctgc cggtgcatgg gttacctctc attaaattta atagtacttg ttgctttggt    480

gtagtgaaat gaatgccttg atgaaattgc attgcaccat ttttgaaaga gagaatactc    540

aaacgtgtca cttctgtttc ttgcaagcaa ctgtgatcct gagctgtgca cacttctggt    600

tgggattatt tctggtttct acttcctgtt tgaagatgtg gcatggagag tgctctgctt    660

tgacctgaag tattttatct atcctcagtc tcaggacact gttgatggaa ttaaggccaa    720

gcacatctgc aaaaaagaca ttgctggagg aggtgcaaag agctggaaac caagtctcca    780

gtcctgggaa aagcagtggt atggaaaagc aatggaaaga gcattttgaa aatgccattc    840

cactgttttc tggcctttat gatttctgct gagaaatcca ctgttagtct tgatggggtc    900

tccttcatag caccaatgac ctgaagagcc ttgttgaagg aagactccat ctgatgactc    960

agagcaagta ttttttagtg tgttattgtt attagcagaa agagggccat aaaatacatg   1020

gggcaagctg aatatatctt aggcaaaaga agaaaatatt caaattctta tgttatttta   1080

tctaattatt ttatctcttt ttgtgtgtga cttataatgt gtgtattgta ttaataaaag   1140

tatataaaca tgtagtttac                                               1160
```

<210> SEQ ID NO 130
<211> LENGTH: 1037
<212> TYPE: DNA
<213> ORGANISM: Homo sapiens
<220> FEATURE:
<221> NAME/KEY: misc_feature
<223> OTHER INFORMATION: Incyte ID No: 239347 (1880193CT1)

<400> SEQUENCE: 130

```
caggcaccca ccgtcacacc cggctaattt ttttgtattt tagtagagac agggtttcac     60

cgtgttagcc aggatggtct tgatctcctg accttgtgat ccaccagcct cagcctccca    120

aagtgctggg attacaggcg tgagccactg tgcccggcca agaatttttt tatcgataac    180

atagtgagct ctctgcctct tcggaacgat gtccactttg cttatgatca acccaagcag    240

gactcttctc tccctggacg cctctcccct ggtctggaat cttccagttc tgccagaatt    300

ggcctttccc agatgctgca aacttccagt tgaacccctt tttctgtgtg gcccctgggg    360
```

```
ctgcgagacc aaaatccatg agttctgtgt accctagacc tttggaaggt gagagcaggg    420

ccctgagaaa aggcagccac ctcctctccc tggctgaacc cctgccaccc tactcctcac    480

cagaattgtc agtggccttt caccacagtg gtccttcctg cctgagccct gcactgtccc    540

agaccacaca gaagtctggt cacctctggg cgcctgggat ggtcaccgaa gagaagcacg    600

ctgtccccgt ctctcctggc ttctgccaga aaatcgaaca agtgcaatta acacactgtt    660

actgccgaag cctgaaactc ccaggacttg tccttgatcc ttccagaaac caccaggtcc    720

ggcacttgga gccccccgga gagggacctc ccagccgagc cctcaaagaa ctccatgaaa    780

tcaggaactg cttgatgaaa tgtatctcct tgtacctgga agatgaagcc caaacaccca    840

cacctctgtc tcccccaggg ctcgggatgt ctccagcagc ccggccacgc agcttcccag    900

gtgggctcgg ggaggtggga gcagggacca tctctgtccc ctccaccctc actccatcca    960

cctcggagac caccctcccc cagccagata cggaataaaa ctacagacgc agacgtcgga   1020

ataaaaaaaa aaaaaaa                                                   1037
```

<210> SEQ ID NO 131
<211> LENGTH: 1167
<212> TYPE: DNA
<213> ORGANISM: Homo sapiens
<220> FEATURE:
<221> NAME/KEY: misc_feature
<223> OTHER INFORMATION: Incyte ID No: 241599 (4331016CT1)

<400> SEQUENCE: 131

```
gaacattcct actcgagcct gggcctcaag gccaagatgg atgctggttg gacaggcctg     60

caagcctctg atataatgtg gaccatatca gacacaggtt ggatactgaa catcttgggc    120

tcacttttgg aatcttggac attaggagca tgcacatttg ttcatctctt gccaaagttt    180

gacccactgg ttattctaaa gacactctcc agttatccaa tcaagagtat gatgggtgcc    240

cctattgttt accggatgtt gctacagcag gatctttcca gttacaagtt cccccatcta    300

cagaactgcc tcgctggagg ggagtccctt cttccagaaa ctctggagaa ctggagggcc    360

cagacaggac tggacatccg agaattctat ggccagacag aaacgggatt aacttgcatg    420

gtttccaaga caatgaaaat caaaccagga tacatgggaa cggctgcttc ctgttatgat    480

gtacaggtta tagatgataa gggcaacgtc ctgccccccg gcacagaagg agacattggc    540

atcagggtca aacccatcag gcctataggc atcttctctg gctatgtgga aaatcccgac    600

aagacagcag ccaacattcg aggagacttt tggctccttg gagaccgggg aatcaaagat    660

gaagatgggt atttccagtt tatgggacgg gcagatgata tcattaactc cagcgggtac    720

cggattggac cctcggaggt agagaatgca ctgatgaagc accctgctgt ggttgagacg    780

gctgtgatca gcagcccaga ccccgtccga ggagaggtgg tgaaggcatt tgtgatactg    840

gcctcgcagt tcctatccca tgacccagaa cagctcacca aggagctgca gcagcatgtg    900

aagtcagtga cagccccata caagtaccca agaaagatag agtttgtctt gaacctgccc    960

aagactgtca cagggaaaat tcaacgaacc aaacttcgag acaaggagtg gaagatgtcc   1020

ggaaaagccc gtgcgcagtg aggcgtctag gagacattca tttggattcc cctcttcttt   1080

ctctttcttt tccctttggg cccttggcct tactatgatg atatgagatt ctttatgaaa   1140

gaacatgaat gtaaaaaaaa aaaaaaa                                        1167
```

<210> SEQ ID NO 132
<211> LENGTH: 1766

```
<212> TYPE: DNA
<213> ORGANISM: Homo sapiens
<220> FEATURE:
<221> NAME/KEY: misc_feature
<223> OTHER INFORMATION: Incyte ID No: 245065.1CB1

<400> SEQUENCE: 132

cacacacata taatttgaaa gaggtgagta tgtactctga cttcagctct caggttttaa     60

aaattatatt agtgggacca gttatgacaa gaataatcat tatagtactt ttcagatttt    120

ataacctgga gcagattatt ttaagttgat tagtaggttc tgttacagtt tttcttttgt    180

tcgtgcactt atagtcttca tttaattcct catagaatcc ccagtcacct ttatatatca    240

tattattgga agagattcat cttcataatc tccagttttt tcacagtgcc tcacagagtt    300

aatcatgcct tttggagcta gaaggacttt agaacttatc tagttatgct cctttatatt    360

ataagtaagg gaatagaatc aataagacag tttctgccca aagtcatgtt accagttggt    420

gacagagctg gaaatacgta gagatctata cccttaaatc tctccactca catgctgata    480

tactttctac tacaatatgc tatagcttta tggaactcag ggtgatgatc agacgtgtca    540

ttagaacatg agtcctctgc ttctgattca ggcatacttt tgggattctt ccatctttaa    600

aggaaaaagg aagccattca tctatattta gtaacccagt aatatctcac ttagtttagg    660

gttagatctt tagttaattc aaccttatag atcatactta tgaaggtgat aactgacacg    720

tgttccctga attttaattt gataggcaat acatctaccc actccattat tttttaaaac    780

ttcatttaat agtttaaaca agattggttt tgttttcaat ttttattcac tcttcataga    840

atcacaatta cctttatata tcatatgtta ttggaagaga ttcctcagta atctccaatc    900

tctcatagtg cctcacaggg ttggtcaatg gcttttggaa ctggaaggac cttagaactt    960

atctgttatg ctcctgatag ccaatagcag atagaagctt gcaatcaaga gggtaggaca   1020

tgtgttcttc aatggatatc aaaggaagag gttgcaaacc aaagccattt ggcaagccct   1080

gtagcctggg ccatttaaga caggggcggt ctcagccaaa ttgcacccat ttaactatcc   1140

caaagagcca cagtgcctac aacccaggcc ctaagttgat gaagaaaaag tcaaggaagg   1200

aggtgataca attggaaata ttcccatcaa atggttaatc ttatttagaa aatgggcata   1260

ttagaaaaag tccttccaag atgattttgg ataataaaag ttgtatttgt ggaaattggt   1320

attatctctg ttttatgcac ttacatttat cccttacatt ttgtttttag tgaccctaca   1380

tgacattaaa tttaaagtaa aacattgttt aatgttacct tttggcttga gaatgtcttt   1440

cagctccaga attattgtta ctcatatttt aatcagtaag tcatttaagc tatgacagag   1500

taggaattga gaaattattt catatgctac agtattgaaa tgtggatgct gccttgtttt   1560

ataagaagat gatcaaggtt tgtgtgccca ttacctttcc tctgcctgaa agacgtgtct   1620

caagaaaaat aaattctatt ttagatgcag gtactgcatt ttattctaag aattgatatc   1680

aattcaaaac atagaaaact gtaaaagata aatcaggaga tggctgattc ataatgggta   1740

ataaaataaa tagcactttc gagctg                                         1766

<210> SEQ ID NO 133
<211> LENGTH: 4772
<212> TYPE: DNA
<213> ORGANISM: Homo sapiens
<220> FEATURE:
<221> NAME/KEY: misc_feature
<223> OTHER INFORMATION: Incyte ID No: 245487.3CB1
<221> NAME/KEY: unsure
<222> LOCATION: 3196-3488
<223> OTHER INFORMATION: a, t, c, g, or other
```

<400> SEQUENCE: 133

```
gccaaggacc ccgatccacc ctactccgtg gagacccccct atggctaccg cctggacctg     60
gacttcctca agtacgtgga tgacatcgag aagggccaca cgctgcgacg cgtggcagtg    120
cagcgccgcc cccgcctgag ctcgctgccc cgtggccctg gctcctggtg gacgtccact    180
gagtcgctgt gctccaatgc cagtggggac agccgccact cagcctattc ctactgcggc    240
cgtggcttct accctcagta tggtgctctg gagacccgcg gtggcttcaa tccgcgggtg    300
gagcgcacgc tcgctggatg cccgtcgccg tctcgaggac caggcggcca cacccaccgg    360
cctgggctcc ctgaccccca gtgcggccgg ctcgacagcc tccctggtgg gcgtggggtt    420
gccacccccg acaccacgga gttcaggact gtccacaccg gtgcctccca gtgccgggca    480
cctggcccac gtgcgggagc agatggcggg tgccctgcgg aagctgcggc agtggaggag    540
caggtgaagc tgatccctgt gctccaggtg aagctctcgg tgctccagga ggaaaagcgg    600
cagctcacag tacaacttaa gagccagaag ttcctgggcc accccacagc gggccggggt    660
cgcagcgagc tctgcctgga cctccccgat cccccagagg acccagtggc actggagacc    720
cggagtgtgg gcacctgggt tcgagaacgg gacttgggca tgcctgatgg ggaggctgcc    780
ctcgccgcca aggtcgctgt gctggagacc cagctcaaga aggcgctgca ggagctgcag    840
gcagctcagg cccggcaggc tgacccccag ccccaggcct ggccaccgcc ggacagcccg    900
gtccgcgtgg atacagtccg ggtggtagaa gggccacggg aggtggaggt ggtggccagc    960
acagccgctg gcgcccccgc acagcgggcc cagagcctgg agccttacgg cacagggctg   1020
agggccctgg caatgcctgg taggcctgag agcccacctg tgttccgcag ccaggaggtg   1080
gtggagacaa tgtgcccagt gcccgctgca gctaccagca acgtccatat ggtgaagaag   1140
attagcatca cagagcgaac tgccgatgga gcagcaggcc tcccagaagt tcctgccgaa   1200
tcgtcttcgt cacccccggg gtccgaggta gcctccctta cacagcctga gaagagcaca   1260
ggccgagtgc ccacccagga gcccacccac agggagccca ccaggcaagc agcctcccaa   1320
gagtccgagg aggccggggg caccggcggg cccccgggca ggcgtgcgat ctatcatgaa   1380
acggaaagag gaggttgcag accccacggc ccaccggagg agcctccagt tcgtgggggt   1440
caacggcggg tatgagtcgt catccgagga ctccagcaca gcagagaaca tctcagacaa   1500
cgacagcaca gagaacgagg ccccagagcc gagggagagg gttccgagtg tggccgaagc   1560
cccccagctt caggcctgca gggacggcag cggccaagac cagccggcag gagtgtcagc   1620
tgtctcgaga atctcagcac atacccactg ctgagggggc atcaggatca aacacggagg   1680
aggagatcag ggatgggagc taagccctga cctcatctca gcctgcttgg ccctggaaaa   1740
gtacctggac aatcccaacg ccctcacaga gcgggagctg aaagtggcct acaccacagt   1800
gctgcaggag tggctgcgcc tggcctgccg cagcgacgca caccccgagc tggtgcggcg   1860
gcacctggtc acgttccggg ccatgtctgc gcggctgctg gactacgtgg tcaacatcgc   1920
cgacagcaac ggcaacacag ccctgcacta ctccgtgtct catgccaact tccccgtggt   1980
gcagcagctg ctcgacagcg gtgtctgcaa ggtggacaaa cagaaccgtg ctggctacag   2040
ccctattatg ctcaccgccc tggccaccct gaagacccag gacgacatcg agactgtcct   2100
tcagctcttc cggcttggca acatcaatgc caaagccagc caggcaggac agacggccct   2160
gatgctggcc gtcagccacg ggcgggtgga cgttgtcaaa gccctgctgg cctgtgaggc   2220
agatgtcaac gtgcaagatg atgacggctc cacggccctc atgtgcgcct gtgagcacgg   2280
```

-continued

```
ccacaaggag atcgcggggc tgctgctggc cgtgcccagc tgtgacatct cactcacaga   2340
ttcgcgatgg gagcacagct ctgatggtgg ccttggacgc agggcagagt gagattgcgt   2400
cccatgctgt attcccgcat gaacatcaag tgctcgtttg ccccaatgtc agatgaccga   2460
gagccctaca tcatcctcgg cagaagagta gccgtgaggg aggcggggac cagccagacc   2520
gggagcaaac cgtcccttgt ccccgtctcc tccctgttcc cgttcctccc tggcccaccc   2580
cactcacact ccccaaggcc cacggctcaa aggcaagcga gctctccctc tgcttccctg   2640
ggggagcccc aacggccaca ggactccagc tccaagtggg ttttcttggc tcccctgttc   2700
aaagtggcca cagcgcagac cgaagcaaaa ttcttgtata cattggcgcc agggctgatg   2760
ctggggtgtg ggttttatga agaacattga gaacaatcag ctggtaatta tggatggagg   2820
aagagggaga ggaaaaaaat attgtatttt tgaatcattg ttgcaggagg gggtgggaat   2880
cttaggattt gttgccagat ttgaaagtca ctggaacttg catattttca ttttaatcct   2940
aagtgttatt acgcaccagt tggggttcac ccttcatccc tcacatttaa ttgtctgata   3000
tagaatagtg ttgtgtccac tgccccgcta gacggctttc ttaggggaat tttcttctgg   3060
ttgtttcaca agacagattc tgtccttgtc acccgggaca gaaaactcag tcttttcacc   3120
ctcattcaga tgaagggact caggacaggc tctgtgactt acagggaccc aatcaattca   3180
caatgagaaa ttaccnnnnn nnnnnnnnnn nnnnnnnnnn nnnnnnnnnn nnnnnnnnnn   3240
nnnnnnnnnn nnnnnnnnnn nnnnnnnnnn nnnnnnnnnn nnnnnnnnnn nnnnnnnnnn   3300
nnnnnnnnnn nnnnnnnnnn nnnnnnnnnn nnnnnnnnnn nnnnnnnnnn nnnnnnnnnn   3360
nnnnnnnnnn nnnnnnnnnn nnnnnnnnnn nnnnnnnnnn nnnnnnnnnn nnnnnnnnnn   3420
nnnnnnnnnn nnnnnnnnnn nnnnnnnnnn nnnnnnnnnn nnnnnnnnnn nnnnnnnnnn   3480
nnnnnnnncc cagaaacccc tcccttcccc acatggaggc cttggcaaat gttaattttc   3540
ctagaaaatc cttcagacct gaagacgcag gaaaagaatc tggctctcag ggtggcttct   3600
gcgtccccgc cgccaggccc cagactatgg tcacagggcc gtcctgttcc tccccgggac   3660
tccagaattt ctctcctcaa aggaaagaaa acagggcatg cgcttgttgg caaaacgcag   3720
ggccggctcc caaaaacccc atgtgtgtac gattaaaagt tggccgtccc caggcctccc   3780
agcgcaaact taaagagaca gggctttgct gaaaaccaaa catgggccag ctgggctttt   3840
taacaaccta gagactttcc ggagctgcct ggaacagagc ctgcgggaaa cggggcttgc   3900
cagagacact cacagtttcc ttcatgggcc tgttttggtc ccctaagaat ctccacatca   3960
ttgtctttct tgtgcctttt ccttggtgag caacagaaag ggaagggttc caagcctcta   4020
aaaatgtgct ttgtgatcag gagtgcgctc caaaccaaat acgcgcgctg ccctttcgag   4080
gccagtgagc tcagcctcca aggctttaaa gccacatttc agcaagagaa agcgctgaga   4140
gctcgcaggt tcattaaaga aggcaaagca ctggtttctc tccttagaaa agtaggtttc   4200
ttggcttgat gtagactggc ttgctttgat ttttagtgaa gggaatgtac gtaaaacaaa   4260
atagggcttg gctggtcaaa ggagacaagc aggatggatg gatggctggg tggatggatg   4320
tatggatgaa tagatagatg gtgtttgcat gtaaattgca gagaaaacaa aaccaaagct   4380
gattggaaac aattaattgt gggtgtctga gggggaaggt cgcagctttg ggcagctttg   4440
agaagcggta caagagttct gtgcctgtgt gtccagccct ggagccagcc agtgcattta   4500
ttttaagctc ttagaagcaa ctccttggcc caggaatgcg tgacccctga gatgggtcca   4560
cgcatctctc tacacttcct tctctccgtg ggatactgga ctcgtgcctc tgcgcccatt   4620
ctcttctcac gcatatccat gagctttaat ttcactttct gatcacggta cgtccataaa   4680
```

gccagtatta cacttaaatg aagtattctt ttttgtaatc gttttttttta gaaggtaaac 4740 aaatttaata aagctaccaa taatgttgaa aa 4772

<210> SEQ ID NO 134
<211> LENGTH: 2435
<212> TYPE: DNA
<213> ORGANISM: Homo sapiens
<220> FEATURE:
<221> NAME/KEY: misc_feature
<223> OTHER INFORMATION: Incyte ID No: 247789.2CB1
<221> NAME/KEY: unsure
<222> LOCATION: 93, 128, 132, 143-144, 2419, 2427, 2429
<223> OTHER INFORMATION: a, t, c, g, or other

<400> SEQUENCE: 134
ctccctctcc tgggcacctg ccgagcagca gaatgtgagg gagatgaaca gctggactcg 60
ggctgcagtg ctcgggccaa cgtgacgtca ccnggcggag agatgagttc ccggtggggc 120
tctggggngg gntcctgaac ggnnattcct tcctgaagcc tcatccccgc tcagccctgc 180
tcagcccctc ctcctactcc cctccccctc cccctcctgc cgggccagga attgggtttg 240
gggcgggttc tgcttccaaa gccatctctt ccagcaggag agggctctac tctgagctcc 300
tattttccaa ggctccgggc cgcgctcggc gctgggcctg ctgccccggc gggttccgcc 360
ggccggaggc gggagtcaca ggaagagccc tccacaaaag gaggcctcgg cggatcagga 420
cagctgcagg tgggtgtgca gactggtgag ctgccagcag gggcccagac gcgccaggcc 480
tggagatggc tggaaactgc tcctgggagg cccatcccgg caacaggaac aggatgtgcc 540
ctggcctgag cgaggccccg gaactctaca gccggggctt cctgaccatc gagcagatcg 600
cgatgctgcc gcctccggcc gtcatgaact acatcttcct gctcctctgc ctgtgtggcc 660
tggtgggcaa cgggctggtc ctctggtttt tcggcttctc catcaagagg aacccccttct 720 ccatctactt cctgcacctg gccagcgccg atgtgggcta cctcttcagc aaggcggtgt 780
tctccatcct gaacacgggg ggcttcctgg gcacgtttgc cgactacatc cgcagcgtgt 840
gccgggtcct ggggctctgc atgttcctta ccggcgtgag cctcctgccg gccgtcagct 900
ccgagcgctg cgccttcggt catcttcccc gcctggtact gggcgccggc ggcccaagcg 960
cctgtcggcc gtggtgtgcg ccctgctgtg ggtcctgtcc ctcctggtca cctgcctgca 1020
caactacttc tgcgtgttcc tgggccgcgg ggcccccggc gcggcctgca ggcacatgga 1080
catcttcctg ggcatcctcc tgttcctgct ctgctgcccg ctcatggtgc tgccctgcct 1140
ggccctcatc ctgcacgtgg agtgccgggc ccgacggcgc cagcgctctg ccaagctcaa 1200
ccacgtcatc ctggccatgg tctccgtctt cctggtgtcc tccatctact tagggatcga 1260
ctggttcctc ttctgggtct tccagatccc ggccccccttc cccgagtacg tcactgacct 1320
gtgcatctgc atcaacagca gcgccaagcc catcgtctac ttcctggccg ggagggacaa 1380
gtcgcagcgg ctgtgggagc cgctcagggt ggtcttccag cgggccctgc gggacggcgc 1440
tgagctgggg gaggccgggg gcagccacgc ccaacacagt caccatggag atgcagtgtc 1500 cccggggggaa cgcctcctga gactccagcg cctggaggag gcaggggcag gaagcggcct 1560
ccaagaccct tcgccttggg acaggaatgg gcacctgctt ctgagtccat acaggagaag 1620
aaagatctgt ttcctctcct cgggcctcct tctccctggg ctggggactc caggggtggc 1680
tgggagactg ggcagccacc agcaaacaga ccctgtggcc cctgcccggc tcccccaccc 1740
attctgctcc cctagagacc tcttgtacag aagttgcccc caggtggtgg ggcccctcct 1800

```
tgccctaggc tggttggtaa aagagaggag gtcaacaccc agcctagcca cctctgcctc   1860

ttgggtcagc cctccttgac tgtgtcccag ccagcaccag gccagcagcc tcatccctgc   1920

cattcagggc tgttccagag attcgatcct cttaaggcat tatcagtgag caaatgtgaa   1980

ggaaatggtg tctggaagaa agttctggtt cacatgcctt gtagctaagt ctttctgcaa   2040

acaacctccc ttccccccgt cgagtcattt ggtgactttg atggggggat ttctggttat   2100

gtcaaggctc tggagacagg aagggccttt ggccgccttg ggtagttgac ctgccttttc   2160

tgactccggg acgagccagt cctaggctgc ctccgggagc acttgaggta tcccgcaggc   2220

catgaggacc cactgggcag ctcctggaca gcctcttggc tccagccccc acccgaaagt   2280

ggacactggc tccgccctgg ccacctgggg actggcactg tggtgcacag tggcccaatg   2340

tggccaacgg aagttttata aaagacaaaa tgtatatcaa taaacatttt ataacttgca   2400

gccaggaagg cttcatgcnc acaaaantna gcgtg                              2435
```

```
<210> SEQ ID NO 135
<211> LENGTH: 4402
<212> TYPE: DNA
<213> ORGANISM: Homo sapiens
<220> FEATURE:
<221> NAME/KEY: misc_feature
<223> OTHER INFORMATION: Incyte ID No: 252875 (2874502CB1)

<400> SEQUENCE: 135
```

```
ggcggtggcg ctggtggctg cggcggcggc ggcggcagcg gcgctcgagc ggttcctgtc     60

agggtcagcc ggcgggcccc ctgggtggtc cacctgcaaa tcgcggagcg ggcgccccag    120

ggatcgatgg cgatgaacta taacgcgaag gatgaagtgg acggtgggcc cccgtgtgct    180

ccgggggggca ccgcgaagac tcggagaccg gataacacgg ccttcaaaca gcaacggctg    240

ccagcttggc agcccatcct tacggctggc acggtgctac ctattttctt catcatcggt    300

ctcatcttca ttcccatcgg cattggcatt tttgtcacct ccaacaacat ccgcgagatc    360

gagattgatt ataccggaac agagccttcc agtccctgta ataaatgttt atctccggat    420

gtgacacctt gcttttgtac cattaacttc acactggaaa agtcatttga gggcaacgtg    480

tttatgtatt atggactgtc taatttctat caaaaccatc gtcgttacgt gaaatctcga    540

gatgatagtc aactaaatgg agattctagt gctttgctta atcccagtaa ggaatgtgaa    600

ccttatcgaa gaaatgaaga caaaccaatt gctccttgtg gagctattgc caacagcatg    660

tttaatgata cattagaatt gtttctcatt ggcaatgatt cttatcctat acctatcgct    720

ttgaaaaaga aaggtattgc ttggtggaca gataaaaatg tgaaattcag aaatccccct    780

ggaggagaca acctggaaga acgatttaaa ggtacaacaa agcctgtgaa ctggcttaaa    840

ccagtttaca tgctggattc tgacccagat aataatggat tcataaatga ggattttatt    900

gtttggatgc gtactgcagc attacctact tttcgcaagt tgtatcgtct tatagaaagg    960

aaaagtgatt tacatccaac attaccagct ggccgatact ctttgaatgt cacatacaat   1020

taccctgtac attattttga tggacgaaaa cggatgatct tgagcactat ttcatggatg   1080

ggaggaaaaa atccattttt ggggattgct tacatcgctg ttggatccat ctccttcctt   1140

ctgggagttg tactgctagt aattaatcat aaatatagaa acagtagtaa tacagctgac   1200

attaccattt aattttatat tatgaaagca aatcatctgc atgtgcatca aggccagtcc   1260

tattcaacct agctttcgaa tgctgatatc tggttagtat gtcattttga agttggcaca   1320

taacttttct aaaaaaaagc agtctttgtt gtttgcttct tccctacgga tgacttctaa   1380
```

-continued

```
aaatatatga cgggtataaa aaaattagct atattgatca tatcaacact gtaactgctg   1440
aaatggcatt ctaatgtttg ctttttattc ggacaggcca catgatgcat agagcctctt   1500
tcatgtgact tgtgtctact gcttaaatct ttatgctgtg ttgatgatat tatattgaca   1560
tatgaagctg tatatgtgta tgtattttgt ggagaaaggg attacaagat gtatgagtat   1620
aatgacttgc taacctttca ggattcagag aaagatgaag aaagaccata tctaaataat   1680
acacttcatc attttcatgt gtataaatgc ttaaagtacc atctttgttg aggtggttca   1740
tgtatccagt ttatccagta cagttatttg tcaagcttag ctttgatttc aaaggacacg   1800
cttaccttgt ctggcataag aattaatgct catgtctgca gtggttgggt aggtcctgct   1860
taggagaatt aaaaaattcc tctttccgtt tggttgaatg ttgcagtcag gaaccccaac   1920
tcacttggaa tgtttttata tgtaatcatt tcccttgaag cttatacttt ataagggaag   1980
aaagaattca ggtgatatgg gaaaactgct tggcagacct tcatcttctg cctcaactgt   2040
aaaccacatg taaatgctta atggagactg ttttcattct tgtgatattt aacattcaga   2100
aaattacttc agctttggaa atactcaggc tgtttttatt ctgcaggtaa gtgttttgac   2160
ttaagtacta atattccaga aatttttgaa agcagtaacc ttaatttcct atgtatttca   2220
ttccactttt gcatataggt caaatagcaa tgtgtatgca cattctcttt agttaaggca   2280
ccaattgttt tggttggttt tcctaagaca tactttaaaa agatgttcta taaatttcct   2340
agttaaatta tggggatttt ggagtatgta catgataaat tataatacgt atatggttga   2400
agttatttta ttttttacta atgaattatt ttaatattcc ttattgaata aatgctgtaa   2460
cttgtttgct atggaactta ttcttaaagt tctagttaaa aataattttt ccacatgcat   2520
gaaaatatgt attaatcaga ggtggcttaa ttacattgaa attgcttttt tgttgttgtt   2580
tttttactga aataactcat gtttgtgtag aagaatgcct gtttactcag agtttatatt   2640
ttccttcagt tatattttaa atcaaaaggt ctgggtaatg tatacttttg attaatatat   2700
acttttttta aaaaacaaaa aacaatgtaa tggttaatag tagaaatgtg ccacactttt   2760
caagttttat ataacatatg aaattcagtt aaaagaatgt gtgtttcata atgactttta   2820
actggtaaaa atattacttg cacgaagtac ttgatgtatg gttatcctga aatttcggag   2880
tatttggtgt gttctttgtc taaaaatagt ctgttttgtc agtccttcag aatattattt   2940
attctgaaga ttgtccctct tgcacttggc agtttatttt cggggataca ttgttggggg   3000
agaggggttt ctgccactct ttccagattg agtctgtgct gtttaaggag gactaccatc   3060
ctgcaactct ttttctaatt ggggcacaga ggatgtcgct aaagaaaagt tgaagagccc   3120
tttcagcact ttctcatctg tggagaagat ggaatcttaa aatacatttg gagttttatc   3180
tgttttacaa gtccattgat ggcctaagtt cctcctgttt tctgctgttt gatctctaag   3240
gaactcctgt tgctaaatat gaagagtatg gaacattcat atagtctctg tgaagcatgg   3300
ggggagggaa gacatttctt tttcttatag gctttatgct caaatgtcat agtctccttt   3360
caaagaattg tgttgcattt taaatgcacc cagcttaagt agaagacatt gaaggatgca   3420
ttaattttca ggaactattt tgaattatga aaagattccc aattgaaaaa attattcaac   3480
aagtaaaagc taagaaattt cattgaaatc ataaggcagt ttaagcataa attgataaaa   3540
atagctgtgt actactaatt aatagaaaat cattcaacca agagaagagt caagtgaata   3600
tcgtttgttt atttgctagt gagtttcttt gtaacgttga ttttattaaa tgataatatt   3660
tggttagtat gtcctatgtt aataaaaatg aacaaaatta attttgctat gttcaggtgt   3720
cttgataaaa taacaatgct ccagtgttgt tgcttacatt tagcactaaa ttttaacaca   3780
```

```
gggtcagtga gtccaggttt taacttcttc atgcctggat gggataaaat gtaattcatt   3840

gttaaattaa ttcatatttg tatttattaa tcactgtgac aacattaacc atttgttctt   3900

accaggaagt ggtcagatta tcatctgagt tacagttaga ctggctaagt ttggtattag   3960

atcaagggga atgtccagta aacagagagg taagcatgat ggaaataatg aagtggggta   4020

cacaggaaaa acctgactag tgaggaggag cagctgagag atagggtcag tgaatgcggt   4080

tcagcctgct acctctcctg tcttcataga accattgcct tagaattatt gtatgacacg   4140

tttttgttg gttaagctgt aaggttttgt tctttgtgaa catgggtatt ttgaggggag   4200

ggtggaggga gtagggaagt ggtcctttta caagaatttt gatgcataag tgtctattgt   4260

agggtttgga tgatctagta aagtgtttta gaaccccttt ttatcccatg caccattcag   4320

taaacataaa aatcacaatt ctgctaatgt catttggaac ttcaaaataa atatcttgtc   4380

taaaaacaaa aaaaaaaaaa aa                                              4402
```

<210> SEQ ID NO 136
<211> LENGTH: 937
<212> TYPE: DNA
<213> ORGANISM: Homo sapiens
<220> FEATURE:
<221> NAME/KEY: misc_feature
<223> OTHER INFORMATION: Incyte ID No: 253384.4CB1
<221> NAME/KEY: unsure
<222> LOCATION: 285
<223> OTHER INFORMATION: a, t, c, g, or other

<400> SEQUENCE: 136

```
ttttacaaca caagaaatgg tactgaatat atttgttaca tcctgaatca acccaataga     60

ctatcttgta aacaaaatag taaggtaaca cttcaaaaac agatgaacaa tttatccacc    120

aagaatgtat atagtaagcc aaaagctcac tgtggaaata cacttagcat ggttattaga    180

aaatcacaaa gagtaatgta acaagttacc aaattttatg gtcatgttct gcttgataat    240

tcaaatagga tggatggtag ttactagttt tctatttgtg ttgtnttaac atctccattg    300

atttttaatg ctttattttt tatttgaatt tgctggctgg caggtttgct ttgcttaata    360

cattgactgc aacacgctta ttgttgtgtt ggtagaataa gacatacgag aatatatata    420

gaaaggccat atggaggttt ccatggaaag attctgatac tccataactc tgctgttcag    480

aatttcagct gattgcctgt agttggtgca gcgaacggaa cgctggtggc aggtgttgtt    540

gctgcagaca cagtggtagg tgtagcaccg tgcatcatgg gcacaatatt tgaagcgggt    600

gccatgcaca gtattggccc tgcagggata aatgccggct gtgggagctg caggttagtc    660

agagcctgtt ggcagtggaa aacagtggga ttaaagaccg gggtggcacc attgggcttt    720

tccagtgctg atctctttgg tatcagttgc agtgtaccag gctgcagggc catggcagag    780

gcagctgaat ggttcatctg atgatgagct gccttgagtc tggcttgcaa gtgtgcagga    840

ggatgaaagt acttgcattt ctcccgcgag catcgacctt tgatgtaatc catgcagatt    900

gtcacagtat tatcactcgc ctagttctag atccgag                             937
```

<210> SEQ ID NO 137
<211> LENGTH: 977
<212> TYPE: DNA
<213> ORGANISM: Homo sapiens
<220> FEATURE:
<221> NAME/KEY: misc_feature
<223> OTHER INFORMATION: Incyte ID No: 332290.1CB1

<400> SEQUENCE: 137

```
ctaaaggaaa ttcacagtaa tgctgcatta aacactaagc tcacttaggt cactttctag     60
tgagctaacc gtaacagaga gcctacagga tacacgtgag ataatgtcac gtgtagaaga    120
tcgttgtgaa ttaaagttca aaattaagac ttcttagatt atgatgtaga ttttagagct    180
ccttaaaaca taaagcgaat cttataaatg ttcaattcta aagttattcc acttggaaaa    240
attagctttt gggacaattt ttaagaactt ttgtgtaaaa tgcagctcca tgtttagcat    300
aatctaaaaa taatttcaag caatccagaa tcttccaaga atttattaaa gctttaaaac    360
aaagcaaaac aaaaagaccc ttttgtgcct tatatgggaa gactccaaaa acagaaaaaa    420
atagaggaaa acaccacttc aatttgacat tcaatgcatt cacatcagaa actaagaaga    480
taacaagcct gagatgtcag gtgataaaaa ttcatgtttc ttccaaggac agaaggctat    540
tagattgtcc caggccatat ctattcccag ttctttgtga gtagtcttct tactttttct    600
gtggtaggta agaagcatat ttccaccaaa agaaagcatg cattgtttga ctagccagct    660
ttctagaaaa aatgagatcc ttgagaggat aaacaaatcc aacctattca tggtgtcctc    720
acttattgtg gtcaatttgg aaggcttaaa acacaaaaaa tgggatggat aactttgaac    780
actaaaatta gtggagccaa aggcacgtct tcaccattct gttatgtgac ttaaaattca    840
atttcacgaa acccacttcc acaagcttaa tgaactgtga gctacatgag ggcataaacc    900
atgtcttctt tgtatggtat tcctgcttcc tagcaggaca gctggcaaag agtttatcat    960
taaatgtttg ctgaatt                                                   977
```

```
<210> SEQ ID NO 138
<211> LENGTH: 3054
<212> TYPE: DNA
<213> ORGANISM: Homo sapiens
<220> FEATURE:
<221> NAME/KEY: misc_feature
<223> OTHER INFORMATION: Incyte ID No: 336987.1CB1

<400> SEQUENCE: 138
```

```
gtggccaagg acgccggagt ggccgccttc cccgcgcctg agcgcagtgg ggcgagacaa     60
agagacctgg gcccccagcg cacccgtctc gggccacggg cgccccagct ccgcggagtc    120
ccgcagtcgc tggcccggga cgcgcccggc ccgggctccc ttggaaggct ccctaggcaa    180
tggccgggtc tctgctccac ccggctctca ggagcgctgc tctctccatc tgatcgccct    240
ccatcctccc cattccctcc ggttccgggc tctcccttcg ctccaagcct caggccaccg    300
gcttggatgg acgctccgag gctacccgtg cgtccagggg tcttgcttcc gaagttggtc    360
ctgctctttg tctacgcaga tgattgcctt gctcagtgtg gcaaagattg caaatcttac    420
tgctgtgatg gaaccacgcc ctactgttgc tcctactacg cttatattgg gaatatcctc    480
tcgggcactg caattgcggg cattgttttt ggaatagtat ttatcatggg ggtcattgct    540
gggattgcca tatgcatctg catgtgcatg aagaaccaca gggcgacccg cgtgggcatc    600
ctcaggacga ctcacatcaa caccgtctcc tcctatcctg gaccaccacc ctacggtcac    660
gaccacgaga tggaatactg tgcagacttg cctcctccat actcccccac cccacagggt    720
ccagcacagc gttctccacc ccctccttat cctggaaacg caaggaaata atctatctcc    780
cagaacagaa catgtgccaa tgggcgatct tgcctggaat aaaatgcctc tactcagaaa    840
caggcaggaa agaattgctc caaggaatac tttttggggt cagataatgt gtcaggtgga    900
atatccctgc taggagatat aggatttcta ctctgctcaa agctgacccc atctggagta    960
ttaatgtttg gttctatgga accacatttt aagagatctg ctgatccacc taagcacatt   1020
```

```
cagggaagag taatgtaatt gacaaaatat ctgataatca tgttgtttaa gggctaggtg   1080
aagaaagttt cagtattgat cctggaaaaa aagaagatct aagtaggatg ggagaatgat   1140
ttggcccaca caaggaagca actttattct atatagcttt aaaagtcaga actagaattg   1200
ttcattcttt cattcatcaa taaatgtatt ttgagtgcct aagagtttac tatgtgccta   1260
gcactgtttg aggtcctgat ggaagttaca ggatgggtac tctggtttta gtacaagaaa   1320
gagcaatgac tagattgctt tgtgaagctc ttggtagaga cacgctccag aagggataac   1380
aaaatcaaat agtagatggg ttcattgggc ctcagaagtt ctgctcgtat tttaggtggg   1440
tgtgaagtga atttctatat gtccaggagt gaatacaaca gaaagagttg gatcttattt   1500
atttaattag ggagttaaaa caagaccaaa aagactcaac agccgcttga agccaagaac   1560
tcttcaatgc cagctactgc cacctaaaaa tcatctggct ttatagtgga tcagaataaa   1620
ggttattcta actgtgggga gaaaaaaaaa attgtatcaa gttccacagg tagcagacac   1680
ttcacttcca agtaaaagat gagaaatcaa ttattcccac aggattttag gtcagggagc   1740
aaaaatctca gaacttgacc atgaagatac acaacagact cgcaaaaata aagtgggaaa   1800
tgaagttcag attcccttct gtagatttcc ttaaaactat tattttttc ttcttcgtaa   1860
aattttgata atctgttctc ttaaaaaagt taatgacaca attaagatac tgacatcaaa   1920
ttgttgcctt ttaccaaaat gcaaatttta tgaagtgcct acctttatat gtataaagca   1980
tttaataaat aattctaatg tgccatattt tgctgtgagt gaccttaaca tttatatttt   2040
tatatgaatt gtttcatgta tttataaaaa ttgtatattg aacattggaa atagatgatt   2100
agatttttgt gtcattttac aattaaatct aaaatgctta atccaatatc atcatcaaaa   2160
ttcagtgaaa tcccaaaaca gtgccaagaa ttttgctgaa tgaaacaatc aaacaaagca   2220
ttttaaggtg taagttatag tacctgtact tgcagataag aagcttacta tatcattatt   2280
ataagtagca tatattactt tcaaatacct atattagaaa gatattgatc tgactgaaat   2340
ataacctacc tgccagtaag gtccaaaggc tgaatttgtt ttgaatgact tccttgatct   2400
ttaagcactg atgattttct tatatatgag gatgcaaagc attcaagagt ttcagcctgt   2460
tctggtgagg ggctccctga cttacataaa gttttcagtg caattttaat agtacatatg   2520
ctttaattta tttttcttct gcgtgtggtc agacccaatt acactgtggc taagactctc   2580
aaagtgccag ggtttctgtg atgattctga gaatgctgaa tacaaatata ccttatattc   2640
tttaaggaaa acggaaagga aagatcagca gaaatagggt tttctcatct tcaccatcaa   2700
taaacattta ttgcgtacct cctatattct gcaaattttc cccaaataga agccagttca   2760
gtccacacca tctcttcttt gagttgttta tggcctccct taaggcattt tacaaaccca   2820
taagcctaca atagatgagt atttttacta tttgtattaa gtgtcataat agcatcaatg   2880
tgcacattac cagtatagac tgttggagtt cactgattgt tttcatagat gatgcttctt   2940
ggggaaaaat agtataggat gtgaaagttt tgaattacgg ttatttaaaa actaacattt   3000
gctatggcca aagtgtttac aataagcaat aaagtgaaag aacctattat aacc         3054
```

<210> SEQ ID NO 139
<211> LENGTH: 2379
<212> TYPE: DNA
<213> ORGANISM: Homo sapiens
<220> FEATURE:
<221> NAME/KEY: misc_feature
<223> OTHER INFORMATION: Incyte ID No: 344516.2CB1
<221> NAME/KEY: unsure
<222> LOCATION: 1047-1270, 1321-1399

<223> OTHER INFORMATION: a, t, c, g, or other

<400> SEQUENCE: 139

```
ccaaagtgaa aaagaggaac aagttctaac ccaatgcagg tttaaaacat aaccaaaaga     60
acaaaagaga gagcttgaca caccaatctt gaggttatca cgctataata gagaatggac    120
tcattaatat gggattacag aggaaggaat ggttaagaaa aagacatggc ctctgactgc    180
tccaaaaaag gataagcagg gcttcacaga agaggtgaca gaaaaggaag tggaatggaa    240
taaaatcccc caatacagta caattataca ttaatggctg taatgtgaag agcatcacac    300
acgaagagag ccatcttcca gaaataagtt tatacactct ctcctctaat tgcatcagga    360
ctttaccaga taatgttctt ccagatctga aaaggaaaat gcctaaaaga gcttccaaac    420
tcatttttga ataatactag gctacaaaga attacactgt gaattcatta agggtaacac    480
caaaccacta aacagcactg tttgtacaga aatgtcgaaa agctgtggaa ataatttagc    540
ggccatttct gtaggaattt cgcttctttt actcttagtg gtttgtggaa ttgggtgtgt    600
ttggcactgg aaacaccgtg ttgccacacg atttacctta ccgaggtttt tacaaaggag    660
aagcagcagg agaaaagtct gtactaaaac attcttgggc ccccgcatca ttggcttaag    720
gcatgaaatc tcagttgaaa cccaagacca caaatctgct gtcaggggaa ataacacaca    780
cgacaactat gaaaatgtgg aagcaggtcc tcccaaagct aaaggaaaaa ccgataagga    840
actatatgaa aacacagggc agtctaattt cgaggagcat atctatggaa atgagacatc    900
ttctgactat tataacttcc agaagcctcg tccttctgaa gttcctcaag atgaagatat    960
atacattctt ccagattcat attagctttt caaaatattg acttttgtta ttggatgata   1020
aatattcact gtaatttttc aacagcnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnnnnnnnnn nnnnnnnnnn nnnnnnnnnn   1260
nnnnnnnnnn acagtggaag gagggagagg ttcagggaaa aaaaaaatat caggtactat   1320
nnnnnnnnnn nnnnnnnnnn nnnnnnnnnn nnnnnnnnnn nnnnnnnnnn nnnnnnnnnn   1380
nnnnnnnnnn nnnnnnnnng taccccctgaa cataaaatta taattaaaat attaaaaata   1440
attcactgtg atttttatgg tactgatgcc attcttaatc aagttctgat aagtggatgg   1500
tctctgccta tctccacctt tctgaatcct atgtgtatcg ctgtggatta attctagata   1560
tcttctccac cctccttgca ccagactaaa tctgtattat gtgatattga ttcttccttc   1620
taaatattac ccgttatctc tttcctttat ttctaccatt atctttatct ggctcagaat   1680
tattgtcata gggctcctaa ctgttcctcc tgcttctagt ttctacccac tcaatcaatt   1740
accgatggtg ttgccagatt tatcttcaga aaatattcct aacagccaca ttatttcttt   1800
cacttaaaat gttttaatgc cccctctttg caaaagacat aatacccata atttgaactc   1860
caaaatttat ggttttccac aattggttcc aattcacttt tccagtgact tctcttacta   1920
tctctcattt ctttgccttc agcagaatca tcttaaaacc tgccaaactt atccttcctt   1980
cacagctttg cttttctgcc tcttctctca agcctgcttc agatcataag ttcttccaca   2040
catctcctga atcactccaa acccgcattt accttttttat tttctgatat aagctttgat   2100
gcctcttcaa ttcttaggac atttaaacat atgaatgttg ccacagcatt ttattaccta   2160
gcttcatatg aaaatgtctt aaattcccac ctaaatgaaa agaaactgcc caaatgccta   2220
gaacatcaca taaggcacta aatgcctcat gttttactga cgggaattga attgtacatt   2280
```

ttgctgagta gttttgagaa aaaaatctaa taaattcatc tgttattcat ccatacaagg 2340
gatatttgtt gtgtcttcta tctacttgct attgtgctg 2379

<210> SEQ ID NO 140
<211> LENGTH: 1492
<212> TYPE: DNA
<213> ORGANISM: Homo sapiens
<220> FEATURE:
<221> NAME/KEY: misc_feature
<223> OTHER INFORMATION: Incyte ID No: 405185.4CB1

<400> SEQUENCE: 140
ctctagtggc taggaatgaa attctgggat aagcttgtgt taaagtagac catgtgcgtt 60
tccaaacagt gagaacaggt cactagcaaa caatggcatt ttgtttgaga aatggagagc 120
gagcaagact ggagcattac catcatgatg gcctgtcagg cttttcagag aagaaatgaa 180
ctgattaacc acaaatgcat tattccaaca agccaaaagt cttccatccc atgggccagg 240
gtaattttcc caggttagat ccagggtttg ggtgaaattt aactttaaga tgtgggtgcc 300
aaaagagaga attggcttgt ggggcctttc accagagacc catgccagtg actgaatgac 360
ctggattagg tatgcatact tgcaagcctc ttatttggga attacactaa tggttacctg 420
ttttgtgtga ccaaaaatgt tgagaactga agacatcaaa ttataactgc agtatagggg 480
cccagaagaa gggaccctca caatctatct acacactcta tttccaaagg ataagattgc 540
aagagccagg aggaccaact ccagcttctg ggatggaagg ttcagcaact ctactacggg 600
gggtcctgtt tagtcacaga gtgggctagg aaaattttgt cccagcccct taattttcca 660
gggtaagggt tgattttctg tgagaagtat ttaatgctat tctttgctaa agagccgggt 720
aaactctgaa aaattaaatc caaagctggt tatttaaaaa taactatgtt cttaacactc 780
ttgcagacaa acctaaatat cagatagaaa gtccttgtat catttctatt tgaaaattga 840
agattttatt gcctcttttc ttatgtactg caccatctta catcagagga ccagggcttg 900
ttttgacagg gattattata attgcagcat aatttgtatt agacccatgt aacaagcctg 960
tctacttcat ggaaattgca gtgggttgcc cagtcattcc agttaatcag acactcatcg 1020
tgtgggaagc ccggcattga gtttggtgct ttgatgcacg tctgagacag tgtgatgtgg 1080
ttaagcatag gaattgtgag cctctgagtg gataacctta cctatctctc atttacaggt 1140
atgtgaaaca agaagttctg ggtcctttca tcataaggga gaagcttcag aaagttccga 1200
ggacctgcta aaatcagcta ctagaatctg ctgccagagg ggacaaagac gtgcactcaa 1260
ccttctacca ggccactctc aggctcacct taaaatcagc ccttgatccc atttctgggc 1320
aatttagaca gtgaaactga ctttgtttac ctcttgcagc atattagaac agacgatcca 1380
tgctaatatt gtattttctc ttaaaacata gctttcctgt aatttaaagt gcttttatga 1440
aaatatttgt aattaattat atatagttgg aaatagcagt aagctttccc at 1492

<210> SEQ ID NO 141
<211> LENGTH: 2233
<212> TYPE: DNA
<213> ORGANISM: Homo sapiens
<220> FEATURE:
<221> NAME/KEY: misc_feature
<223> OTHER INFORMATION: Incyte ID No: 410257.2CB1
<221> NAME/KEY: unsure
<222> LOCATION: 5, 9, 2220
<223> OTHER INFORMATION: a, t, c, g, or other

<400> SEQUENCE: 141

-continued

```
gggancacna tggtaggtac agcagccagg atgccgatga gcaggactgg gagtttcaga      60
agagagatgt gtcactcggc acctatggca gccgggctgc ggatccacag gaacaggagt     120
ttgggaagag cgcttggata agggactaca gcagtggtgg cagctccagg acccttgacg     180
cccaggacag aagctttgga acgagacccc tgagctctgg gttcagcccc gaggaagccc     240
agcaacagga tgaggaattt gagaagaaga ttccaagtgt ggaagacagc cttggagagg     300
gcagcaggga tgctggccgg ccaggagaga gaggatccgg gggcttgttc agtcctagca     360
ctgcccacgt gccggatggg gcactcgggc agagagacca gagcagctgg caaaacagtg     420
atgctagcca ggaggtggga gggcatcagg agagacagca ggcaggggct cagggccctg     480
gcagtgctga cctggaagat ggggagatgg gaaagcgagg ctgggtcggt gagtttagcc     540
tcagtgttgg cccccagcga gaggcagcat ttagcccagg gcagcaggac tggagccggg     600
acttctgcat cgaggccagt gagaggagct atcagtttgg catcattggc aacgacagag     660
tgagtggtgc tggctttagc ccttctagca agatggaagg tggtcacttt gtgcctcctg     720
ggaagaccac agctggctcg gtggactgga ctgaccagct gggtctcagg aacttggaag     780
tgtccagctg tgtgggttct ggggggctcga gcgaggccag ggagagtgcc gtgggacaga     840
tgggctggtc aggtggcctg agcttgagag acatgaacct gaccggctgt ttggaaagtg     900
gagggtctga agagccgggg ggaatcggag ttggggagaa ggactggact tctgatgtta     960
atgtgaagag caaagatttg gctgaggtcg gggagggagg aggccacagc caggccagag    1020
agagtggcgt ggggcagact gactggtcag gtgtggaggc cggagagttc cttaaatcaa    1080
gggagcgtgg agttggacag gcagactgga cacctgacct tgggctgaga aacatggccc    1140
caggggcagt ctgcagtcct ggagagtcca aagagcttgg ggtgggccag atggactggg    1200
gtaacaatct gggcctgagg gatttggagg tgacctgtga cccagactct ggaggttctc    1260
aggggctacg gggatgtgga gtggggcaga tggactggac ccaggacttg gcgccccaga    1320
atgtggagct ctttggggct ccaagtgaag ccagggagca tggggtgggc ggggtgagcc    1380
agtgcccaga gcccggcctg aggcacaatg gcagcttgtc tcctggcctg gaggccagag    1440
acccccttgga ggccagggag ctgggggttg gtgagacaag tggccagag acccagggtg     1500
aagattactc ctcgtcttcc ttggagccac accctgcaga ccctggaatg gagacaggag    1560
aagccctcag cttcggagca agccctggca ggtgcccggc ccgcccccca ccctccggct    1620
cccagggcct gctggaggag atgctggcag ccagcagctc caaggcggtg gctcggaggg    1680
agtcagcggc ctcgggcctt gggggcctgt tggaggagga aggagccggg gcaggtgctg    1740
cccaagagga ggtgctggag cctgggcagg gactctccac cctcctggag gccgcagcct    1800
gatggtgagg ccagccagac agaagacgtg gatggcacct ggggctcttc agcagccagg    1860
tggagcgatc aggggccagc acagacttct cggcgaccct cccaaggccc tcctgccaga    1920
tcccccagtc aggacttctc cttcattgag gacaccgaga tcctcgacag tgccatgtat    1980
cggagccgtg ccaacttggg gcgcaagcgt gggcaccggg ccccggtcat tcggcctggg    2040
ggtaccttgg gcctgtcgga ggcagcagac tcggatgcac acctgttcca ggactctaca    2100
gagccacggg catctcgggt gccatcttca gatgaagagg tagtggagga acctcagagc    2160
cgccggacac ggatgtcgtt gggcacaagg ggctgaaatc aacctctttc ctggcctgan    2220
cccctcagcc ctg                                                       2233
```

<210> SEQ ID NO 142

<211> LENGTH: 2612
<212> TYPE: DNA
<213> ORGANISM: Homo sapiens
<220> FEATURE:
<221> NAME/KEY: misc_feature
<223> OTHER INFORMATION: Incyte ID No: 412477.1CB1

<400> SEQUENCE: 142

```
ctctcgtcca gggacatgac gggcacgcca ggcgccgttg ccacccggga tggcgaggcc     60
cccgagcgct ccccgccctg cagtccgagc tacgacctca cgggcaaggt gatgcttctg    120
ggagacacag gcgtcggcaa aacatgtttc ctgatccaat tcaaagacgg ggccttcctg    180
tccggaacct tcatagccac cgtcggcata gacttcagga acaaggtggt gactgtggat    240
ggcgtgagag tgaagctgca gatctgggac accgctgggc aggaacggtt ccgaagcgtc    300
acccatgctt attacagaga tgctcaggcc ttgcttctgc tgtatgacat caccaacaaa    360
tcttctttcg acaacatcag ggcctggctc actgagattc atgagtatgc ccagagggac    420
gtggtgatca tgctgctagg caacaaggcg gatatgagca gcgaaagagt gatccgttcc    480
gaagacggag agaccttggc cagggagtac ggtgttccct tcctggagac cagcgccaag    540
actggcatga atgtggagtt agcctttctg gccatcgcca aggaactgaa ataccgggcc    600
gggcatcagg cggatgagcc cagcttccag atccgagact atgtagagtc ccagaagaag    660
cgctccagct gctgctcctt catgtgaatc ccagggggca gagaggaggc tctggaggca    720
cacaggatgc agccttcccc ctcccaggcc tggcttattc caagaggctg agccaatggg    780
gagaaagatg gaggactcac tgcacagccg cttcctagca gggagctata ctccaactcc    840
tacttgagtt cctgcggtct ccccgcatcc acagggaggg taaaacactt agcttttatt    900
ttaatagtac ataatttaat accaaaaaag gcgcctggat ccccaaaaaa ccgaggctgg    960
gagctagtgg cccttttgct ttctaggact tggggggccg gccctccctc ctaagcataa   1020
caaaggtggt gttgctccag ctcagcccca ggggacacag atgcactttg ggggtgaggg   1080
caggtaatga ctccatcgca ccctcagttc agctggacag aggctcaggt gaccccagcc   1140
ttcactgtct cccgctctcc aggagcttat cttcgcccca tctcccaaat aagtgggccc   1200
ttgtgctgtg aggaagacca aagcctcagg gaagataaga gatatggaga tgggaggggg   1260
aggacaaggg gcagagagta gggtctagct ggctatctct ggccttacta acacccccct   1320
ggaggcatgc cccttttctc cagcacacaa gcacattggg gcacctggaa atattggttc   1380
caggctcctg ttctctggac ttcagatcct gggggagccc ctcccccccc tgaatccctg   1440
gcttagctac cttcctgcct gtgcacctaa aaacctcagg tcagaactag gaaaagagtt   1500
ttgtttttat ttttttgaaa tggagtctcg ttctgtcgcc caggctgagg tgcagtagtg   1560
caatctccgc tcactacaac ctccactccc tggggctcaa gcgatcctcc cacctcagcc   1620
cccgaagtag ctgggactat aggtgtgtac catcacacct ggctaatttt tgtatttttt   1680
gtagacacag ggtttcgcca tgttgcccag gctggtcttg aattcctgag ctcaagcaac   1740
ctgccggcct cggcctccca aagtactggg attacacgca gaaggcacca tgcccaggct   1800
agatgtgtct tatcccaatc ctttggcagg catgcagctc cacaggcgat ttcttcaagc   1860
agctgaagtg tttagccctc ctgggttaag agccagataa ggagaaatcc ctttcctagg   1920
tttggaatgt gttgtgaaaa aaaagagaaa tccctggctc ctggagctgg tgggagacaa   1980
gattaagcaa acctcccctg acatgtatcc ctttgacccc aagctctgcc tcctccctga   2040
ccacccatgc cctttccttt aacttctcaa acagatacca gggcctaaac tgctttacct   2100
```

-continued

```
cccctcctac tgagtcaggt taggtggtgg gaggtcaccc atttccgagt taaaccaatg   2160

caatatgagt aaaacaaagt catgtgggta tgtctggggt agagagaggg gtagcaagtt   2220

catgtgtcct ccttggtcac atatctccca aagctccgat ccctgccatg ggaagtggac   2280

aggaaacatg aggtcatgac ctgcaggcat ctttactgca gctctgccgg cctggagggg   2340

gagaggggga ggaagaagta tgcgctgcac atttctgagg ctactgcatt tgctttcaag   2400

gcagaaatct tgctctgagc agtcagcggc tccagtttgg gcccgataag gaagttctcc   2460

gtggcctccc tcaggcagag cagggaggag gctgacattg ccagtctctt ctggggccca   2520

aggcaggttg caggagatcc aatcccatag acagctctgg gcctcttgca tttgagtttt   2580

tcagaattaa actgcagtat tttggaaagc ac                                 2612
```

<210> SEQ ID NO 143
<211> LENGTH: 282
<212> TYPE: DNA
<213> ORGANISM: Homo sapiens
<220> FEATURE:
<221> NAME/KEY: misc_feature
<223> OTHER INFORMATION: Incyte ID No: 010205.3

<400> SEQUENCE: 143

```
ctcttgctat gtctatacca tacctgaggc cattttatct atacccttcc tatctgagga     60

ggagaataga aaagtagggt aaatatgtaa cgtaaaatat gtcattcaag gaccaccaaa    120

actttaagta ccctatccat aaaaaatctg ggtttaaaaa gtagttccaa gtaagggatg    180

cctttgtgac ccagggtttc tgaagtcaga tagccattct tacttgcccc ttactctgac    240

ttattgggaa agggagaact gcagtggtgt ttctgttgca gt                       282
```

<210> SEQ ID NO 144
<211> LENGTH: 1839
<212> TYPE: DNA
<213> ORGANISM: Homo sapiens
<220> FEATURE:
<221> NAME/KEY: misc_feature
<223> OTHER INFORMATION: Incyte ID No: 019740.3CB1
<221> NAME/KEY: unsure
<222> LOCATION: 1830
<223> OTHER INFORMATION: a, t, c, g, or other

<400> SEQUENCE: 144

```
ctttttttttc atcttatata taaagggttc tccattagct aataaagtcc cagaaaggct    60

ggctctcctg taagggcaga gcatcgttct gcctagtttc aaagcctctt caagtggaga    120

gcttgacacc aggctgggcg gggcaggcct ggctgaggtg ccctggtgta tatgctcccc    180

ctggcttctg gcctctggtt cccacagtgc tgaggcatgg ggtggccctg ggatgactag    240

gtggtccttc tcgaggcacc tggctcacca cttcctcttc ctaatagtga gatggccttt    300

gtcccaacag aacctgaatg gtgtgccctc gatcaccaac cccatcaaaa ctgcaaacca    360

acaccagggc aagaagcaac acccatccca ggaaaagcca caagtcctga cccccagccc    420

caggaagcag aagctgaaca gaaagtacag gtcccaccat gaccagatga tctgcaagtg    480

cctctccctg agcatatcct actccgctac cattggcggc ctgaccacca tcatcggcac    540

ctccaccagc ctcatcttcc tggaacactt caacaaccag tatccagccg cagaggtggt    600

gaactttggc acctggttcc tcttcagctt ccccatatcc ctcatcatgc tggtggtcag    660

ctgggttctg gatgcactgg ctgttcctgg gctgcaattt taaagagacc tgctctctga    720

gcaagaagaa gaagaccaaa agggaacagt tgtcagagaa gaggatccaa gaagaatatg    780
```

-continued

```
aaaaactggg agacattagc tacccagaaa tggtgactgg atttttcttc atcctgatga    840
ccgtactgtg gtttacccgg gagcctggct ttgtccctgg ctgggattct ttctttgaaa    900
agaaaggcta ccgtactgat gccacagtct ctgtcttcct tggcttcctc ctcttcctca    960
ttccagcgaa gaagccctgc tttgggaaaa agaatgatgg agagaaccag gagcactcac   1020
tggggaccga gcccatcatc acgtggaagg acttccagaa gaccatgccc tgggagattg   1080
tcattctggt tgggggaggc tatgctctgg cttctggtag caagagctct ggcctctcta   1140
catggattgg gaaccagatg ttgtccctga gcagcctccc accgtgggct gtcaccctgc   1200
tggcatgcat cctcgtgtcc attgtcactg agtttgtgag caacccagca accatcacca   1260
tcttcctgcc catcctgtgc agcctgtctg aaacgctgca cattaacccc ctctacaccc   1320
tgatcccagt caccatgtgc atctcctttg cagtgatgct gcctgtgggc aatcccccta   1380
atgccatcgt cttcagctat gggcactgcc agatcaaaga tatggtgaaa gctggcctgg   1440
gagtcaacgt tattggactg gtgatagtaa tggtggccat caacacctgg ggagttagcc   1500
tcttccacct ggacacttac ccagcatggg cgagggtcag caacatcact gatcaagcct   1560
aacgccaagt gtacaaactg gcccaaccac aggagctgcc agtatccagc agtatctgga   1620
ccacaggcaa agaaaaccac taggaccacc aggagcacac aaccccagac ccacgccgga   1680
gggcatccct ccaccagaag attccgccac ctcaagtgaa ctgcaggaat cctccaacaa   1740
ccacaaacac atgcttcgct gttagtgtct tcttcctgcc ctcagcacca cagctcaaga   1800
aaacctaaag tttcaataca agccataggn tcacagaaa                          1839
```

```
<210> SEQ ID NO 145
<211> LENGTH: 512
<212> TYPE: DNA
<213> ORGANISM: Homo sapiens
<220> FEATURE:
<221> NAME/KEY: misc_feature
<223> OTHER INFORMATION: Incyte ID No: 196697.1CB1

<400> SEQUENCE: 145

gcggccgcgg gcaccgccag gagagcgtgc agctcgaaga gaactgcctg tgccgcttcc     60
actggtgctg cgtagtacag tgccaccgct gccgtgtgcg caaggagctc agcctctgcc    120
tgtgacccgc cgcccggccg ctagactgac ttcgcgcagc ggtggctcgc acctgtggga    180
cctcagggca ccggcaccgg gcgcctctcg ccgctcgagc ccagcctctc cctgccaaag    240
cccaactccc agggctctgg aaatggtgag gcgaggggct tgagaggaac gcccacccac    300
gaaggcccag ggcgccagac ggccccgaaa aggcgctcgg ggagcgttta aaggacactg    360
tacaggccct ccctcccctt ggcctctagg aggaaacagt tttttagact ggaaaaaagc    420
cagtctaaag gcctctggat actgggctcc ccagaactgc tggccacagg atggtgggtg    480
aggttagtat caataaagat atttaaacca cc                                 512
```

```
<210> SEQ ID NO 146
<211> LENGTH: 3112
<212> TYPE: DNA
<213> ORGANISM: Homo sapiens
<220> FEATURE:
<221> NAME/KEY: misc_feature
<223> OTHER INFORMATION: Incyte ID No: 198006.3 CB1

<400> SEQUENCE: 146

cgagggcgga cgcaaagaac gcggaggacc tctgggtgcc tgcaggggag ctgctccagc     60
cgggccgccg ggagcggtgg ggagagcatc gcgcagccgc ccctccacgc gcccgcccag    120
```

-continued

```
ccgcgttcgc ccactgggct ctcccggctg cagtgccagg gcgcaggacg cggccgatct    180
cccgctcccg ccacctccgc caccatgctg ctcccccagc tctgctggct gccgctgctc    240
gctgggctgc tcccgccggt gcccgctcag aagttctcgg cgctcacgtt tttgagagtg    300
gatcaagata aagacaagga ttgtagcttg gactgtgcgg gttcgcccca gaaacctctc    360
tgcgcatctg acggaaggac cttcctttcc cgttgtgaat ttcaacgtgc caagtgcaaa    420
gatccccagc tagagattgc atatcgagga aactgcaaag acgtgtccag gtgtgtggcc    480
gaaaggaagt atacccagga gcaagcccgg aaggagtttc agcaagtgtt cattcctgag    540
tgcaatgacg acggcaccta cagtcaggtc cagtgtcaca gctacacggg atactgctgg    600
tgcgtcacgc ccaacgggag gcccatcagc ggcactgccg tggcccacaa gacgccccgg    660
tgcccgggtt ccgtaaatga aaagttaccc caacgcgaag gcacaggaaa aacagatgat    720
gccgcagctc cagcgttgga gactcagcct caaggagatg aagaagatat tgcatcacgt    780
taccctaccc tttggactga acaggttaaa agtcggcaga acaaaaccaa taagaattca    840
gtgtcatcct gtgaccaaga gcaccagtct gccctggagg aagccaagca gcccaagaac    900
gacaatgtgg tgatccctga gtgtgcgcac ggcggcctct acaagccagt gcagtgccac    960
ccctccacgg ggtactgctg gtgcgtcctg gtggacacgg ggcgccccat tcccggcaca   1020
tccacaaggt acgagcagcc gaaatgtgac aacacgggcc agggcccacc cagccaaagc   1080
ccgggacctg tacaagggcc gccagctaca aggttgtccg ggtgccaaaa agcatgagtt   1140
tctgaccagc gttctggacg cgctgtccac ggacatggtc cacgccgcct ccgacccctc   1200
ctcctcgtca ggcaggctct cagaacccga ccccagccat accctagagg agcgggtggt   1260
gcactggtac ttcaaactac tggataaaaa ctccagtgga gacatcggca aaaaggaaat   1320
caaacccttc aagaggttcc ttcgcaaaaa atcaaagccc aaaaaatgtg tgaagaagtt   1380
tgttgaatac tgtgacgtga ataatgacaa atccatctcc gtacaagaac tgatgggctg   1440
cctgggcgtg gcgaaagagg acggcaaagc ggacaccaag aaacgccaca cccccagagg   1500
tcatgctgaa agtacgtcta atagacagcc aaggaaacaa ggataaatgg ctcatacccc   1560
gaaggcagtt cctagacaca tgggaaattt ccctcaccaa agagcaatta agaaaacaaa   1620
aacagaaaca catagtattt gcactttgta ctttaaatgt aaattcactt tgtagaaatg   1680
agctatttaa acagactgtt ttaatctgtg aaaatggaga gctggcttca gaaaattaat   1740
cacatacaat gtatgtgtcc tcttttgacc ttggaaatct gtatgtggtg gagaagtatt   1800
tgaatgcatt taggcttaat ttcttcgcct tccacatgtt aacagtagag ctctatgcac   1860
tccggctgca atcgtatggc tttctctaac ccctgcagtc acttccagat gcctgtgctt   1920
acagcattgt ggaatcatgt tggaagctcc acatgtccat ggaagtttgt gatgtacggc   1980
cgaccctaca ggcagttaac atgcatgggc tggtttgttt cttgggattt tctgttagtt   2040
tgtcttgttt tgctttccag agatcttgct catacaatga atcacgcaac cactaaagct   2100
atccagttaa gtgcaggtag ttcccctgga ggaaataata ttttcaaact gtcgttggtg   2160
tgatactttg gctcaaagga tctttgcttt tccattttaa gcttctgttt tgagttttgc   2220
cctggggctt gaatgagtcc cagagagtcg ttcggatggt gggaggctgc ctaggaggca   2280
gtaaatccag tcacagtgcc tgggaggggc ccatccttcc aaaatgtaaa tccagtcgcg   2340
gtgtgaccga gctggctaac aggcttgtct gcctggtttt cctcctacac gtggacatta   2400
ttctcctgat cctcctacct ggtccacccc agggctaccg gaaggtaaaa tcttcacctg   2460
```

```
aaccaattat gagcagtctc cttactgaag gtacagccgg atacgtggtg cccccggggc   2520

tggtgttggc agccgggggg aggtgcctga gggtccccac ggttcctttc tgcttttctg   2580

aatgcatcaa gggtacgaga acttgccaat gggaaattca tccgagtggc actggcagag   2640

aaggatagga gtggaatgcc cacacagtga ccaacagaac tggtctgcgt gcataaccag   2700

ctgccaccct caggcctggg ccccagagct cagggcaccc agtgtcttaa ggaaccattt   2760

ggaggacagt ctgagagcag gaacttcaag ctgtgattct atctcggctc agacttttgg   2820

ttggaaaaag atcttcatgg ccccaaatcc cctgagacat gccttgtaga atgattttgt   2880

gatgttgtga tgcttgtgga gcatcgcgta aggcttcttg cttatttaaa ctgtgcaagg   2940

taaaaatcaa gcctttggag ccacagaacc agctcaagta catgccaatg ttgtttaaga   3000

aacagttatg atcctaaact ttttggataa tcttttatat ttctgacctt tgaatttaat   3060

cattgttctt agattaaaat aaaatatgct attgaaacta aaaaaaaaaa aa           3112
```

<210> SEQ ID NO 147
<211> LENGTH: 872
<212> TYPE: DNA
<213> ORGANISM: Homo sapiens
<220> FEATURE:
<221> NAME/KEY: misc_feature
<223> OTHER INFORMATION: Incyte ID No: 200386.1CB1
<221> NAME/KEY: unsure
<222> LOCATION: 68-85, 437
<223> OTHER INFORMATION: a, t, c, g, or other

<400> SEQUENCE: 147

```
cgggatcccg tctctctctc tcttctcttg gttcctttga atttcctccc agaaagctca     60

gatttctnnn nnnnnnnnnn nnnnnttctt cttcagtaat ccctcccctc actgatacta    120

gaagagaaga cccacaggca tgagccaagt ctctcaaata cacactcaca aacacacact    180

cctcgctacc tgaagtcatt caaaataatc ttattctcta attttcattt ctttctcttc    240

ttccttccct aggaattacc ttctcttttt gtagtcccta agccaaaata agttcacctt    300

aaaacaaatt gctagaactt ttacacagag acacgcaatt tgatggcttc ttattttaaa    360

atgcaaaaat aatctagggg cacaaaaatg caagctgggt acttaacttt cattctccag    420

atgtcttcag ccagggnccc catccagcct ccagtctgtc tgtgaaggtt agaatgtttc    480

cttcagtttg atgcttgggg ttgttggttg ttgaaggctt ttaatccctc atccaacttg    540

ttgataggtt gcaagtctcc gtaaagttct ttggggtgcc agtttgctgt tcctaataac    600

cttatgagtc tgggagctct taacttcacc ttctgggagt cttgtgggtt ccaagtgttt    660

tgctccttaa tcactgtcac agacaattga tactgccatt gatactcgtg ggcttgggga    720

ggtccccaaa cacccgtagg acctcaatcc tggctggcgt ccaggctctt gacactgttg    780

tgagaaggaa tttaaggatg agttgggaaa atactgaaag tgcagagatg tatcacaaag    840

caaaaagtac acacccggga aaagggagtg tg                                  872
```

<210> SEQ ID NO 148
<211> LENGTH: 1596
<212> TYPE: DNA
<213> ORGANISM: Homo sapiens
<220> FEATURE:
<221> NAME/KEY: misc_feature
<223> OTHER INFORMATION: Incyte ID No: 215998.2CB1
<221> NAME/KEY: unsure
<222> LOCATION: 269-350
<223> OTHER INFORMATION: a, t, c, g, or other

<400> SEQUENCE: 148

-continued

```
gcgcccaagg tcacacagct gggatgtggc agagctgggg ttccagctcc tgttcccatt     60
gctggacagc tgccacatct ggcacccaat ttaggacccc gcggggaggc ccaagccccg    120
ggggtggcgg gggatcctag aggaaagtgg caaggccagg accctggagc agagccagag    180
tagaaaactg aggctctgag agatgaagct acttgccaag gtcacgcagc acagtcacat    240
cctactgaac atcatcctgt tctctgggnn nnnnnnnnnn nnnnnnnnnn nnnnnnnnnn    300
nnnnnnnnnn nnnnnnnnnn nnnnnnnnnn nnnnnnnnnn nnnnnnnnnn caggacaagt    360
gcccagtaaa cacttgggaa gcaatgcaag cgtcctccca gcagctcctg caaacagacc    420
cccgacccaa gcctttcctt ctgcctccac tgccaccact gctgctcatc tctgctggca    480
cagaagtctc ttccctggtc ttccagaaat cccctctcca cactcagcca gagggagcta    540
ttaaaactgc gggccagccc acatcagtcc acagcaaagt cctctctaag ggatctttgt    600
tgcttggaga ataaaccctc ggattccttc cttggctctc ggggcctcct ctctgacctc    660
cctctgtctc ctctcccagc cttcctcctc actcaccctc cagccatgct ggcttcctcc    720
ttgctcctga aacagcctga gagccacact gccccgggcc ctttgcactg gctgtttcct    780
ctgcctggag cacttctcct aggcatccac agggctccct cccacaactc cttcgggtgc    840
ccacatggga agccatccct gaccaccccc ccgacttcct tctgagcaag gtagggtctt    900
tctacctagt catgagggca gggatttttg tctgttgtgt tctctgtgtg cccccagtgg    960
catcccagtg cctggcagat ggtaagtgct cgacacacat tggctgactg cctgaatgaa   1020
caactctatg agccgatggc agataaggac actgaggtcc tctggggtag gtgaccagcc   1080
caaggccaca cagctggtct gagattaggc caggagagga gcccgggttg gtcacatcct   1140
ggagttggcg tcttggaaac tgcatcagga gaataacaaa gatgagacgc aggctctaac   1200
aagtggatac cagtgactct cgccccgcca gccccagccc tgcagccttg ggcccttcca   1260
ggagtcatgg tctgcctgcc tggggcattc caggcttcga cccaggtcct gcactttcta   1320
ttttgagcct cttagtcctg aggactgtgt gttcccagca ggcggcgcgg gccagaggct   1380
gagcctgggt gtggctgtca ccctatctgg ggccagagac ccagattccc gggcccttaa   1440
cctgttggct gctgagggct ctggcataag ccctgttccc tgcttgattg tctccccttc   1500
aagcccctgc cctggtatcg tatcggccca tctcaccttg gattatatcc ctgtttggcc   1560
ccatttgaat cctggctctg cccctttcca gcaatg                             1596
```

```
<210> SEQ ID NO 149
<211> LENGTH: 989
<212> TYPE: DNA
<213> ORGANISM: Homo sapiens
<220> FEATURE:
<221> NAME/KEY: misc_feature
<223> OTHER INFORMATION: Incyte ID No: 227944.2CB1
<221> NAME/KEY: unsure
<222> LOCATION: 12
<223> OTHER INFORMATION: a, t, c, g, or other

<400> SEQUENCE: 149

gcccctgggg tngggacaca atcaccccag gttgagatcc atggagccag gtctgtttgc     60
caccaaggtg taaagctcca ttcccacctt aggagggcta ggaggcagca tcgtggggcc    120
acagaaggcc tgggtttgca gtcagaggac aggatgcaca ttccttcaag atacagaccc    180
agattgttgg gcatctagtt cttgggtttt ctgttgttgc tgttccgttt tgtctgtctt    240
ccctcctttg tttactagca gcctgggaat ttgccacttt ttctaaacga agatttatgg    300
```

```
gaacacttac cacacggctg acgctgcgca ggctaaggtt ctaatacacc gcagctcact    360

taactcttcg caataccata aacggcacac tgtttcatct tggacccttt cttggggaag    420

gtgacagaga ggtaggaggg caaacatctt gtgtgccccg tcccaagggt attaactggt    480

ggaataatat ccgcccccca ccccagtttc taatttgctg taggctgtga cgctgtgggg    540

caagactagg gagtcctgtt gaaattagga ataagtgtgc tgtgagggaa gggctgcctt    600

attttagagc acagattttc tgaatatcta ttttgacagg ttcgatcctc tccccttcct    660

gccttccttc tgtcgatttt caatgtcttg atggtgtccc acctgagtgg cctttagaga    720

tgtgagttgt gaggcactgg ggaggcaggc acacgtcctc cagcccaaga ctgcctaatt    780

taacagggat ttctgcattc tggaacaagc ctccattttc cccaagcagg attactccag    840

agggcaaaac acagcccaat agtatcacat ttcctttctg ctttagcaaa aataaccact    900

gatcattaca ggaagcttca gaaaccgtgg gaccagtgta gaagaatgga ctatctgtcc    960

aaactaagaa taaaaatttt gacacttgt                                      989
```

<210> SEQ ID NO 150
<211> LENGTH: 1992
<212> TYPE: DNA
<213> ORGANISM: Homo sapiens
<220> FEATURE:
<221> NAME/KEY: misc_feature
<223> OTHER INFORMATION: Incyte ID No: 232513.3
<221> NAME/KEY: unsure
<222> LOCATION: 1421
<223> OTHER INFORMATION: a, t, c, g, or other

<400> SEQUENCE: 150

```
ccggcgtccc ctccgtgagg tcgcgcccgt tcgcaccgcc cccgcccgca agaaagatgg     60

cagtggcctg atccgggccc gttggcggcg tcactgacgc ttacgctccg gtcctcggat    120

cccgagcgcg gggaggcaga ccgactgtga gctgcttgtc cccatcctgc ggccgtcctg    180

gggacacaga gccctccgtg gtgcccgggg attggattgg agccaggacc tcacttcctc    240

ctctgcccct gcccctgccc ctcccagcac ctggcccaca ccctgcagcc cgccccatgg    300

tctggccctg ggtggcgatg gcgtccaggt ggggttcccc tcattggcct ggctccgtgc    360

tgcctctggc tcctgggggc agtccttctg atggacgcgt ctgcacggcc tgccaaccac    420

tcgtccactc gagagagagt agccaacagg gaggagaatg agatcctgcc cccagaccac    480

ctgaacgggg tgaagctgga gatggacggg cacctcaatc gcggcttcca ccaggaggtc    540

ttcctaggca aggacctggg tggctttgat gaggacgcgg agccgcggcg gagcgaggaa    600

gctgatggtc atcttttcca aggtggatgt gaacactgac cggaagatca gtgccaagga    660

gatgcagcgc tggatcatgg agaagacggc cgagcacttc caggaggcca tggaggagag    720

caagacacac ttccgcgccg tggaccctga cggggacggt cacgtgtctt gggacgagta    780

taaggtgaag tttttggcga gtaaaggcca tagcgagaag gaggttgccg acgccatcag    840

gctcaacgag gaactcaaag tggacgagga aacacaggaa gtcctggaga acctgaagga    900

ccgctggtac caggcggaca gccccccctgc agacctgctg ctgacggagg aggagttcct    960

gtcgttcctc caccccgagc acagccgggg aatgctcagg ttcatggtga aggagatcgt   1020

ccgggacctg gaccaggacg gtgacaagca gctctctgtg cccgagttca tctccctgcc   1080

cgtgggcacc gtggagaacc agcagggcca ggacattgac gacaactggg tgaaagacag   1140

aaaaaaggag tttgaggagc tcattgactc caaccacgac ggcatcgtga ccgccgagga   1200

gctggagagc tacatggacc ccatgaacga gtacaacgcg ctgaacgagg ccaagcagat   1260
```

```
gatcgccgtc gccgacgaga accagaacca ccacctggag cccgaggagg tgctcaagta   1320

cagcgagttc ttcacgggca gcaagctggt ggactacgcg cgcagcgtgc acgaggagtt   1380

ttgagcgccc ggccgcgccc cgcgccgccc cccacgcacc nccggggcgg cctcgcgggt   1440

gactccgggc tccgtggctg tcccggaccc cacctcttcc ctgccgcccg ccaccggccg   1500

accgaccgcg gctgccccag ttgatgagcg gcgtgtcccc tctgcagcgc gcaccccggc   1560

ggggctttgg ctgtgacgcg gtcggggcgc ggggctgggc tgtggccccg cggcgccgcc   1620

tcctccctgg tccctcgaaa tcgtggcatc tcacttctga gaacgaaatc tcgcttcagt   1680

cactctgccg aaggcgctga cggcatcgcg gccggaacct ctgggcccgg cccctcccag   1740

ggccgccgct ccgtgggaaa aaacagctcc tccatttcct tgaaaactga acgattatta   1800

aaaatagatt aaacttcgct ggaaatgagt agccaggaag ttcaggggag ggtgccgggt   1860

ccttcccggg cctggcgtgt cggagccacc caggtcccgc agctgccgct gagaaaatgc   1920

aaatatttgt tgtgacaaga atcacataca tttactttaa atatagttgc ctttttttggt   1980

cagcttcaaa aa                                                        1992
```

```
<210> SEQ ID NO 151
<211> LENGTH: 1295
<212> TYPE: DNA
<213> ORGANISM: Homo sapiens
<220> FEATURE:
<221> NAME/KEY: misc_feature
<223> OTHER INFORMATION: Incyte ID No: 337832.3CB1
<221> NAME/KEY: unsure
<222> LOCATION: 6, 1252, 1260, 1284
<223> OTHER INFORMATION: a, t, c, g, or other

<400> SEQUENCE: 151

gctgangcca gggcaggggc tgggatgatg gcgcgggaga ggctgtgtcc tcgcgtgtca     60

cccaccagcc ctcgagcaga ggcaggcttg gagtctgcag ccaccctggg aatgtctgtg    120

cttcctcgtg gagctgacat gatggtgaaa taggttcaat cctccaccta cccagggccc    180

agacccttcc ctggttctac cgacctgatg tggacccaga ggtggccaaa gacaaggcca    240

gcttccggaa ctacacgttc aggtcccctc ctggaccgtg tcttcaccac ctacaagctc    300

atgcacacgc accagacagt ggacttcgtc aggagcaagc atgcccagtt tgggggcttc    360

tcctacaaga aatgacagt tcatggaggc cgtggacctg ctggatgggc tggtggatga    420

gtcggacccg gacgtagatt tccccaactc cttccatgcc ttccagacag cggagggcat    480

ccggaaggcc cacccagaca aggactggtt ccacctacgt cgggctcctg cacgacctgg    540

ggaaggtcct ggccctgttc ggggagcccc agtgggctgt cgtcggcgac accttccccg    600

tcggatgccg tccgcaggcc tccgtggttt tctgcgactc caccttccag gacaaccctg    660

acctccagga tcctcgatac agcacagagc tcgggatgta tcagccccac tgtgggctcg    720

acagggtcct catgtcctgg ggccatgatg agtacatgta ccaggtgatg aagtttaaca    780

agttctcact gccccctgag gctttctaca tgatccggtt ccactccttc taccccctggc    840

acacgggccg cgactaccag cagctgtgca gccagcagga cctggccatg ctgccctggg    900

tgcgggagtt caacaagttc gacctctaca ccaagtgccc ggacctgccg gacgtggaca    960

agctgcggcc ctactaccag ggctcattg acaagtactg ccctggcatc ctgagctggt   1020

gaccctcctg ccacccaagc tgctgctgga cctaggcctg gccctccgcc tgcctggaga   1080

ggcctggccc tgggcaaaca gccgccatca gggttcacct cggtgggga ccccactcac   1140
```

```
ccccttaggg tcgccacccc tcacggcaac ttgtgcctgg cgtcaataaa gacctggaag   1200

gatgttgtgc ttctgaagcc ccactgggtg ttactgcagc agggcgtggc cnaggccgan   1260

ggatggtgcc agcagggtgg aggncaagtc ccagg                              1295


<210> SEQ ID NO 152
<211> LENGTH: 2030
<212> TYPE: DNA
<213> ORGANISM: Homo sapiens
<220> FEATURE:
<221> NAME/KEY: misc_feature
<223> OTHER INFORMATION: Incyte ID No: 400799.2CB1
<221> NAME/KEY: unsure
<222> LOCATION: 294-318, 334, 487, 1603-1922
<223> OTHER INFORMATION: a, t, c, g, or other

<400> SEQUENCE: 152

aggacataga agaaggggtt aactggcccg gatctcctcc tcgccttcca agcccgctaa     60

gcactggggt tatctaccca ttccccagaa ggggagactg aggcagccca ccagccaaag    120

gaggcgacca gactggggct gcgttttacc atttcagaag cggcttgagc tggtctgagc    180

tataataata aacactggcg gtggaggcga gggcgaccac agggctgagg tcagggctag    240

gattccggtg tctctacgta ggttgcttga atggggggca ccctggcatg gacnnnnnnn    300

nnnnnnnnnn nnnnnnnnga gtcagacagc ctanaaccgt cgtgcaccgt gtcctccgcg    360

gatgtggact ggaacgcgga gttcagtgcc acgtgcctga atttcagtgg cctcagcctg    420

agcctgcctc acaaccagtc tctgcgggcc agcaacgtga ttctccttga cctgtctggg    480

aacggcntgc gagagcttcc agtgaccttc tttgcccacc tgcagaagct tgaggtcctg    540

aacgtgctac gcaacccctt gtctcgtgtg gatggggcgc tggccgcccg ctgtgacctt    600

gacctgcagg ccgactgcaa ctgtgccctg gagtcctggc acgacatccg ccgagacaac    660

tgctctggcc agaagcctct gctctgctgg gacacaacca gctcccagca caacctctct    720

gccttcctgg aggtcagctg cgcccctggc ctggcctctg caactatcgg ggcagtggtg    780

gtcagcgggt gcctgcttct tggacttgcc atcgctggcc ctgtgctggc ctggagactc    840

tggcgatgcc gagtggccag aagccgggag ctgaacaaac cctgggctgc tcaggatggg    900

cccaagcccg gtttaggctt gcagccacgg tacggcagcc ggagcgcccc caagccccaa    960

gtggccgtgc catcctgccc ctccactccc gactatgaga acatgtttgt gggccagcca   1020

gcagccgagc accagtggga tgaacaaggg gctcaccctt cagaggacaa tgacttttac   1080

atcaactaca aggacatcga cctggcttcc cagcctgtct actgtaacct gcagtcactg   1140

ggccaggccc caatggatga agaggagtac gtgatccccg ggcactgagc ctaagatgtc   1200

ctaacctcca cccagaaccc cttcagtccc tgctgggtga ctcagggcgt cctaacgcct   1260

ccatggcctc agtttcccca tctgaagaat gggtacagga aaggattgtc cttgaggccc   1320

caggaagctc tgccgccccc tccctgtccc tcatgccgct cctcagctcc ctcagctcct   1380

agagggggaa gaggagagac ccccaacaag gggacaggag ggtcactgtg ccaatcctgt   1440

catcaccctc ctgtggatgt acaggcagtg ctcaataaat gcttcgaggc tgatgaggct   1500

gctggctcag ggtgcgtggg ttcctcaagg tggggatttc tgagttctaa gaccaagtct   1560

ccatctgaga ctcccaaatt gctccccacc tcccatccct gtnnnnnnnn nnnnnnnnnn   1620

nnnnnnnnnn nnnnnnnnnn nnnnnnnnnn nnnnnnnnnn nnnnnnnnnn nnnnnnnnnn   1680

nnnnnnnnnn nnnnnnnnnn nnnnnnnnnn nnnnnnnnnn nnnnnnnnnn nnnnnnnnnn   1740

nnnnnnnnnn nnnnnnnnnn nnnnnnnnnn nnnnnnnnnn nnnnnnnnnn nnnnnnnnnn   1800
```

```
nnnnnnnnnn nnnnnnnnnn nnnnnnnnnn nnnnnnnnnn nnnnnnnnnn nnnnnnnnnn   1860

nnnnnnnnnn nnnnnnnnnn nnnnnnnnnn nnnnnnnnnn nnnnnnnnnn nnnnnnnnnn   1920

nncctccctt ctgcccctct cagggcccct tcccaggtcc ctgatctcca ggcttggcct   1980

ccagagcagc ccacaccacc cccaaaataa aaaaatgtat atattccttt              2030
```

<210> SEQ ID NO 153
<211> LENGTH: 2087
<212> TYPE: DNA
<213> ORGANISM: Homo sapiens
<220> FEATURE:
<221> NAME/KEY: misc_feature
<223> OTHER INFORMATION: Incyte ID No: 402117.1CB1
<221> NAME/KEY: unsure
<222> LOCATION: 1320, 1454-1496
<223> OTHER INFORMATION: a, t, c, g, or other

<400> SEQUENCE: 153

```
agcttttcca ccccaggaat ctctgttcct tctctgtctg cctctccaca gcccgtgatc     60

ccctgcttct gggctcctac cactggacag tcattgtgga tagagcagcc tgctgctctc    120

aggaccagag aagggaaatg acttctccag gcagaggcag atctgagtct agaacccagg    180

cttctaaatt tctaggccag tactactgct ctcaaaagag attaactggg attaagtgag    240

atgacgcatg taaagatgct gtgtaaactg taattcttaa taccattatc acgcattact    300

agaatcattt cattatttct gcttcctggg ggaaggatgc agaaggagtc tgatgctcaa    360

catcccttac ctcctttcgc tgatggccaa agcaaaggag agtcctggga gcccacaaga    420

tccaggcaga aggagatggg tttggggctg gccccatcct ggcccagcct cttaacctct    480

tcttaccctg aatgtgtgcc ctatcttttc tcccacctcc ttcctcctac cacccagccc    540

tatccattct ctccttccct ctccagcctg ctgtataagt aacatgtggg tcataccttg    600

aaccccccctc cgcccccatg ctctctgtgg cctccatgcc ttcaagactt ctgtctgtat    660

ctatctcaca ctgcaccaag cacccactgt gcaccaggca ctaagtctct agcctctttc    720

tcccttctgc tcccatccaa gaaagacagt gtataaggaa catctctgta attgtgtccc    780

ctctcatcta tgctctttcc tgtcttcctt gaccaaagct ctctttgagg tccaaaaaag    840

gctgccctgg gccatatgtg ctatggagag gactctccca aacccccaat agctagtgac    900

agccacttgg cctcactacc agaagaaggg tggagtcaga aaccaaagtg acctccagag    960

ctgtcctcct ggcacctgag tgtccttgct ctagaggttc aaaggcagca aggcagtgag   1020

ctatgagccc agcatggatg tgtctcaggc acctcatccc caccccatct caccccaaca   1080

aactcctcta gaagaagcca agaatttctc tctatgtctg tttcactttt tggattgcat   1140

ctccccaaaa actaaatgtg aaatccctac catttctagc ctctattgcc cagattggag   1200

tcagaggtca aaaaaggatt ccaagtgatg gaactccagg ggtggaggga aattggcagt   1260

tcctggcatc tcttgtgtac cagctgctgt gctgggtgcc ttgcatgcac ggggcttatn   1320

tgatcttcct caaacttcag ataggttagg gaaggacaaa ggcccccagc catgaagggt   1380

tttgctattt ccaaagcttc cccttatcgt cccctgtgat tatctcccaa ccccgtgaca   1440

aaggtagagc acannnnnnn nnnnnnnnnn nnnnnnnnnn nnnnnnnnnn nnnnnngact   1500

ggtctaaagt ctcacaggta gtatatggtg gagccaacac ttgcactcag acctttttac   1560

acaaaatccc atgatttttc cactgagaca aatcctaggc tcctgggagg ccctggcaga   1620

agccagaaca catggctggg cctttccagc ccaacccact gtcttgcagt ggacggagag   1680
```

```
ccttggcgag ggcagcaggg tagagaggac aaagaatgtg gggctggttt ctgcccttta   1740

agagcacccg gtcagtcaga gaacagagat cacacacacc aaaccagaca gaggcagggc   1800

agcatggaga caggtagaca gacctccagg tccctaagct ggggacagag aaggttctga   1860

gctgtcccat actcccactt tgtgccaaat gactttgcac ctgcaaatgg tgcttcaatg   1920

tcgttttgta tctttaagct gtgatgttgt atatatacaa tgcctcccag ctagactgta   1980

agccctttgg ggacaagggc tgcttccagt tcttggatgg cgttctccta tctaccttcc   2040

ttcaactgct ctgcatataa taagcactca ataaatgctc atttgcc                  2087
```

```
<210> SEQ ID NO 154
<211> LENGTH: 876
<212> TYPE: DNA
<213> ORGANISM: Homo sapiens
<220> FEATURE:
<221> NAME/KEY: misc_feature
<223> OTHER INFORMATION: Incyte ID No: 406605.3CB1
<221> NAME/KEY: unsure
<222> LOCATION: 185-215, 240
<223> OTHER INFORMATION: a, t, c, g, or other

<400> SEQUENCE: 154

tgctgcccag acaagctgaa ggaccacagg aaaagccatg gagacttcag catcctcctc     60

ccagcctcag gacaacagtc aagtccacag agaaacagaa gatgtagact atggagagac    120

agatttccac aagcaagatg ggaaggctgg actcttttcc caagaacaat atgagagaaa    180

caagnnnnnn nnnnnnnnnn nnnnnnnnnn nnnnncctcc tcatcttctt catcctcctn    240

ctcctcagag agcaatgatg aggaccagca acccagagca accggaaaac atcgacggag    300

cctgggggct ggataccccc acgggaacgg ctcacccggt cctgggcatg gggagcctga    360

cgttttgaag gatgagcttc aactctatgg agatgctcct ggagaggtgg taccctctgg    420

ggaatcagga ctccgaagga gaggctctga cccagcaagt ggagaagtgg aggcctctca    480

gttaagaaga ctgaatataa agaaagatga tgagtttttc catttcgtcc tcctgtgctt    540

tgccatcggg gccttgctgg tgtgttatca ctattacgca gactggttca tgtctcttgg    600

ggtcggcctg ctcaccttcg cctccctgga aaccgttggc atctacttcg gactagtgta    660

ccgtatccac agcgtcctcc aaggcttcat ccccctcttc cagaagttta ggctgacagg    720

gttcaggaag actgactgag gccacttcca ggtgggcagc agaggcaggc cccagtgtga    780

ccaccactgc gacccctgag cccacaaggg cagagcagca ttctgagaga cgcacaggag    840

accaagccag accaataaac agaacacttt tccttc                              876
```

```
<210> SEQ ID NO 155
<211> LENGTH: 419
<212> TYPE: DNA
<213> ORGANISM: Homo sapiens
<220> FEATURE:
<221> NAME/KEY: misc_feature
<223> OTHER INFORMATION: Incyte ID No: 17091.1
<221> NAME/KEY: unsure
<222> LOCATION: 26
<223> OTHER INFORMATION: a, t, c, g, or other

<400> SEQUENCE: 155

gtgagactcc gctgaaaatt aaaaanacaa aaacaaaaaa ccagaaatgg tacttgtgct     60

atgatgattt aaatatgtgt atattcattt atacacaata tgactgtaaa gtaataagac    120

tggttttgtg taaccctgct tacacatttt tttcagacac actgtaacct attatctatt    180

atatgttatt aggttttaaa tttatattat attaagagac tgagtgttat caactttcgt    240
```

```
ttgtttcatt ttatgtaagg caatatacaa gaatatttgg acagcttttt ggaaatgttc    300

ataaattttg atctgttcta ttcatgtaac tatgtatgta catgcacatc tgtatatgca    360

ctatgttata tctatattat agatcttagg taacaacaaa catatttgtg tgagtcaaa     419
```

<210> SEQ ID NO 156
<211> LENGTH: 1497
<212> TYPE: DNA
<213> ORGANISM: Homo sapiens
<220> FEATURE:
<221> NAME/KEY: misc_feature
<223> OTHER INFORMATION: Incyte ID No: 036258.1

<400> SEQUENCE: 156

```
gcgcggaccg ccgggagcta agtggaatcc cggttggctt ggggcgcagg cttccaactt     60

cgtactctgg cctctggcgt ctcggctcgt cggttgggta cccgaaccca gctactgctg    120

cttgaagaga agatggatgg ggactcctcg ccgtcgctgc gccgccggcc ttccctgggc    180

ggacgtacac ctttgcgaac gtcagtgagg acccagggcc cctccttgga atagctctta    240

tttctcaagc gctgcagcgt gaagctcgct ctgcgggtcc gagaggcctg cgatctgaag    300

actgaaaact gggaagagac gctctaccct gtgctcctcg ccggcttcga taggagccgc    360

aggtgcctgg gattttctca aactttgtcc caaacttcag ctgtgggagt ggaggaacaa    420

acaggcctct cccagaattg tgaaagagat cgccctggtg gatgaaacaa aaacaaatgc    480

acttgacttc caccgcctgc ctggcgtgtc acgcgggttt aatgtatgtg tcacatttaa    540

attcaaagta ttttcttcta agggcctgga cacatttctt ttctccctgt atcgtgaatt    600

ggaaaatacc ttaggatatt aaaagttatc taagataacc ccctttcttc tgtaagttaa    660

atactaaacg gcttaagacg aaattttgga atatagagat gatgatgcag actgcagtga    720

attatcaaat atgcatctca ctgttctcca cattaaacat atttttgttg cgtaaattca    780

tgttaagacg tctataacaa ttacactttg gtaaaattgt tggatgttaa catctctgat    840

agctcccaat agaaatctct gatgtactaa ccagactggt aaaccattat catgcacttt    900

gaaaatataa taaaatatta taattaaagc tgccattaat gaaataggct gagcaacaat    960

aaatttacaa aggaaaataa aagtggatag ccttgggagt tctcacataa aatatggaga   1020

tttcaaagtt aaacttgatt aattatgtta gggtaaaaag tgaattaaag caacaggact   1080

atttataaaa taattagatt tagaaagcag tcgtagaaat ataagcctgg agttgcctct   1140

gaattacata tttaacaaac ctagaagcta aatcagtttg tcttttatca aaactgcaac   1200

tcctctaagt tgaaagcaca gtgacaagag aaagcattac aaattcttga gaaataatag   1260

aaattaaagc tcttttcaaa cctgtgaaca agtatagtac cagaagtata agattcagat   1320

aggcccaagt tgtagttctt gttatgagtc ttacaaccct atggactttg gacaaattac   1380

ttctctgcgt ctgtttcctc atctgtaaaa tgaaaataat ttctgtttca tacaggtata   1440

gtctaaatag gggataatta cacctacttc aaagttgtaa aatacacaat tacaact      1497
```

<210> SEQ ID NO 157
<211> LENGTH: 1499
<212> TYPE: DNA
<213> ORGANISM: Homo sapiens
<220> FEATURE:
<221> NAME/KEY: misc_feature
<223> OTHER INFORMATION: Incyte ID No: 230960 (2454666CT1)

<400> SEQUENCE: 157

-continued

```
gtctgggatt attttaaaat tatatatata tatataaaga tatattctta catcttttct     60

ttgccctctg tgctttgaaa gcactggata aattgtttgg ttttgctttt ctctcttcca    120

caaaattgga agcttttttt aaaaatgttt tccccacaag tcatcttgcc ttgtggcatg    180

tctgtctagc ctcttcctcc ctccctcatg atgaagtgcc atttctgtta cgtctccctc    240

tccccaagct cagaggtgct cagaggtacg agatacccaa gtttgtcagt tgagattaaa    300

agtaaggaac agagaatgtg caataccgtc tggctggggg ctgtccctgc cctgccctga    360

gctgagtcct ttccctggga gccaggccac cttagaatgg ggtttggaag taagatgtat    420

agagttgggg aatcatggag aaggaaagcc tatagtcgag tgcctgctta ggtgctgagg    480

tcacagggga gatggtggaa tcttccctgt ttttatcccc tcagggtcag ttacatagaa    540

gctgcttctt gactagtata gctcggtgac cctttgttca accgctgagg tttgatttct    600

taccctttct tctccccatt ttcatactct tcccagggat tagtgatgga ggtgaggtct    660

ccctaatcat ggtaaagtgt taaccttcca cctcctccct tccctcctcc ttcctcatcc    720

ttctgtcttc ctcaattctc cgtctctttt ttttcatcac tgattgcctt gtgtccctcc    780

aagtctactt gttactatcc atctccaggc tctgggccgt gtagacacta aacctcatgc    840

cctaaggaca ggaggaaaga ccctctgttt ggagcattat tagtagagtg aggatcccac    900

cagttctgcc tggcttcctc catccccaga ggcactaaaa gcagtatttt aaggttggtg    960

tcttactccc tggaagcctg aaatgggtgg aatagcggta aggcttgagt aaaactaggg   1020

gacagaggtt cttatttgtc gattttattt tataatttga ccacagcatc tgaactccct   1080

ctctccctgg aataagtatt tttcccacat ttttggatat atgtatggta gacaattttt   1140

ttttaagaca cagagataaa tgttttcctg ctttggttac ctttcctttc ccctttaaaa   1200

ggaattagct atagaactgc tttgtaaaga tgcttcttga tattttactt ttgttccttt   1260

tccctaatca ttccctttc tccccactcc tccagaaggc ataacccttc tctccacacc    1320

ccctaccccc acccccgtcc taggctccca tcctttccat caagaccttc attagcttat   1380

gatatttgct gccgagatgt tataacaagg actcgttcat gtatataagc tatttcttga   1440

tccatttaaa aggaattgta cattgtgtag aaaaaaaaaa aacctgaaaa agagaaaaa    1499
```

<210> SEQ ID NO 158
<211> LENGTH: 755
<212> TYPE: DNA
<213> ORGANISM: Homo sapiens
<220> FEATURE:
<221> NAME/KEY: misc_feature
<223> OTHER INFORMATION: Incyte ID No: 231491.3

<400> SEQUENCE: 158

```
ctgcgctgcc agctcaggtg agccctcgcc aaggtgacct cgcaggacac tggtgaagga     60

gcagtgagga acctgcagag tcacacagtt ggccaccacc atctctagat gggaagacag    120

aaagtagtta ctttcccaag atctccccac aagcaagtgt atccttgggg tttgtacacc    180

tactttcacc atggggctct gcctgccccc gcccctgcct cctctcgctg accaattgag    240

ctgtgagcct ggagcagatc cgtgggctgc agacccccgc cccagtgcct ctccccctgc    300

agccctgccc ctcgaactgt gacatggaga gagtgaccct ggcccttctc ctactggcag    360

gcctgactgc cttggaagcc aatgacccat ttgccaataa agacgatccc ttctactatg    420

actggaaaaa cctgcagctg agcggactga tctgcggagg gctcctggcc attgctggga    480

tcgcggcagt tctgagtggc aaatgcaaat gcaagagcag ccagaagcag cacagtcctg    540
```

tacctgagaa ggccatccca ctcatcactc caggctctgc cactacttgc tgagcacagg 600
actggcctcc agggatggcc tgaagcctaa cactggcccc cagcacctcc tcccctggga 660
ggccttatcc tcaaggaagg acttctctcc aagggcaggc tgttaggccc ctttctgatc 720
aggaggcttc tttatgaatt aaactcgccc cacgc 755

<210> SEQ ID NO 159
<211> LENGTH: 868
<212> TYPE: DNA
<213> ORGANISM: Homo sapiens
<220> FEATURE:
<221> NAME/KEY: misc_feature
<223> OTHER INFORMATION: Incyte ID No: 234571.8
<221> NAME/KEY: unsure
<222> LOCATION: 23, 27
<223> OTHER INFORMATION: a, t, c, g, or other

<400> SEQUENCE: 159
gcgcaggtcc caccccgcct gcncgcnccg cccattggtc ccgagcgcga tgacttggcg 60
ggcggaccag gaaggaaacc gctcccgagc acggcggacg gcgtcgtctc ccggccagtg 120
cagctgccgc taaccgccgc cctctgcccg ccggcccgtc ctgttctacc cccaggcatg 180
agcgggcctg cgcgtctaca gcacgtccgg tcaccggctc ccgcgaaatc aagtcccagc 240
agagcgaggt gacccgaatc ctggatggga agcgcatcca ataccagcta gtggacatct 300
cccaggacaa cgccctgagg gatgagatgc gagccttggc aggcaacccc aaggccaccc 360
caccccagat tgtcaacggg gaccagtact gtggggacta tgagctcttc gtggaggctg 420
tggaacaaaa cacgctgcag gagttcctga agctggcttg agtcaagcct gtccagagtt 480
cccctgctgg actccatcac cacactcccc ccagccttca cctggccatg aaggaccttt 540
tgaccaactc cctgtcattc ctaacctaac cttagagtcc ctcccccaat gcaggccact 600
tctcctccct cctctctaaa tgtagtcccc tctcctccat ctaaaggcaa cattccttac 660
ccattagtct cagaaattgt cttaagcaac agccccaaat gctggctgcc cccagccaag 720
cattggggcc gccatcctgc ctggcactgg ctgatgggca cctctgttgg ttccatcagc 780
cagagctctg ccaaaggccc cgcagtccct ctcccaggag gaccctagag gcaattaaat 840
gatgtcctgt tccattggca aaaaaaaa 868

<210> SEQ ID NO 160
<211> LENGTH: 1340
<212> TYPE: DNA
<213> ORGANISM: Homo sapiens
<220> FEATURE:
<221> NAME/KEY: misc_feature
<223> OTHER INFORMATION: Incyte ID No: 332763.1
<221> NAME/KEY: unsure
<222> LOCATION: 393
<223> OTHER INFORMATION: a, t, c, g, or other

<400> SEQUENCE: 160
tctcagctgt agaatggaaa aatctgtttc agttttaagg attgaattca aatgtgtaaa 60
tagcttaaga gtatccggca taagcactat agaagcgtct gctattactc tgcagagtgg 120
cagtggtgaa ttatctgata ttttttcctt aacttgaata gcaatccaca ttacaatgga 180
taacaatacc cattgtttat gatttgaggc atccaattat aactgtatta ttgaagtgtt 240
atcaaattac caaggctgta gggtatattt agtattccta gttaaaggtt tgaactaatt 300
tgtatactag ggcatgtttc ttaatgggaa gggggtgaag gttataataa aagtcacccc 360
taatgcttgt ttaaaattaa agaggaattt gtnggcctgg gaccaacctt agacttatcc 420

```
aggccaaggt atgttgtttg acgaacaccg caggatacct gatgtgcatc cccgtctgag    480

aactgttaac tataaaagtt tgactttgga aatgaagaaa aattaccttt tagcctaatc    540

atgaagacta ggcgtcaaac caaaacaaga tgcatcagtt actgtagcaa cacatttttt    600

ttaaaaaatt gcttgttgtc acaatgaagg gtgtgtatct gttttccagt atgcaattct    660

aatgccaaat gtctgcctta aaaatagcaa aggagaccat caggttaaca taaaggaaaa    720

ctgtagttgt gtgactcatg tgtctgtaga ttgtaatttt ataattacaa tttttataag    780

ataaaaaact accagttgta aattcaacca aaaaaattta aagctttgat ttagcttttt    840

gctttaactt gggtagtaac tgaaatataa aggaagaaaa tctattaaaa ccaatgaggt    900

tttatatttt tttaaatctt gattcaataa atatcagctg aattaagtat ctgtatggta    960

ctacgaagca atcaattagt ataaatggca atttacaagt tcaacagtaa atgtaaacat   1020

tctttgtatc taggattttt gagttgcaag ttaaactgaa tttttactgc agtagagagg   1080

aggagcatag caggcaaaat aacaggtaat actgtatttt aaacaaacag aaaaacccaa   1140

gtaattggcg ccctttatcc aatcatcttt taaaaggcct atgtatgtgt atagttatgt   1200

tcttaagaaa catcttaaga ggttcagaaa tcaattttat agatggaaca ttttaataat   1260

tcgttttggc ctagccaaaa gagtaaaata aaacaaaata gtgttagatt tctgtgaggt   1320

gttttaattg ccttttctgc                                               1340
```

<210> SEQ ID NO 161
<211> LENGTH: 2184
<212> TYPE: DNA
<213> ORGANISM: Homo sapiens
<220> FEATURE:
<221> NAME/KEY: misc_feature
<223> OTHER INFORMATION: Incyte ID No: 337523.1

<400> SEQUENCE: 161

```
tttgcaaatg tactgtattt ttaactttta tttagaacag aggtctcttg gactctcagc     60

cccaggcttg actactttgt gccactggga gtactccctt tcctcttctt cacaccatca    120

ggaaaggcag gctgagagtt acgctgcttg actctgcctc ggtctatccc acaggtgatc    180

acttactcca gtcgtcatgt ctacaataac ttgactgagg aacagaaggg ccgagtggcc    240

tttgcttcca atttcctggc aggagatgcc tccttgcaga ttgaacctct gaagcccagt    300

gatgagggcc ggtacacctg taaggttaag aattcagggc gctacgtgtg gagccatgtc    360

atcttaaaag tcttagtgag accatccaag cccaagtgtg agttggaagg agagctgaca    420

gaaggaagtg acctgacttt gcagtgtgag tcatcctctg gcacagagcc cattgtgtat    480

tactggcagc gaatccgaga gaaagaggga gaggatgaac gtctgcctcc caaatctagg    540

attgactaca accaccctgg acgagttctg ctgcagaatc ttaccatgtc ctactctgga    600

ctgtaccagt gcacagcagg caacgaagct gggaaggaaa gctgtgtggt gcgagtaact    660

gtacagtatg tacaaagcat cggcatggtt gcaggagcag tgacaggcat agtggctgga    720

gccctgctga ttttcctctt ggtgtggctg ctaatccgaa ggaaagacaa agaaagatat    780

gaggaagaag agagacctaa tgaaattcga gaagatgctg aagctccaaa agcccgtctt    840

gtgaaaccca gctcctcttc ctcaggctct cggagctcac gctctggttc ttcctccact    900

cgctccacag caaatagtgc ctcacgcagc cagcggacac tgtcaaactg acgcagcacc    960

ccagccaggg ctggccaccc aggcatacag cctagtggga ccagaggtga gaggttctga   1020

accaaagaaa gtccaccatg ctaatctgac caaagcagaa accacaccca gcatgatccc   1080
```

-continued

```
cagccagagc agagccttcc aaacggtctg aattacaatg gacttgactc ccacgctttc   1140
ctaggagtca gggtctttgg actcttctcg tcattggagc tcaagtcacc agccacacaa   1200
ccagatgaga ggtcatctaa gtagcagtga gcattgcacg gaacagattc agatgagcat   1260
tttccttata caataccaaa caagcaaaag gatgtaagct gattcatctg taaaaaggca   1320
tcttattgtg cctttagacc agagtaaggg aaagcaggag tccaaatcta tttgttgacc   1380
aggacctgtg gtgagaaggt tggggaaagg tgaggtgaat atacctaaaa cttttaatgt   1440
gggatatttt gtatcagtgc tttgattcac aattttcaag aggaaatggg atgctgtttg   1500
taaattttct atgcatttct gcaaacttat tggattatta gttattcaga cagtcaagca   1560
gaacccacag ccttattaca cctgtctaca ccatgtactg agctaaccac ttctaagaaa   1620
ctccaaaaaa ggaaacatgt gtcttctatt ctgacttaac ttcatttgtc ataaggtttg   1680
gatattaatt tcaaggggag ttgaaatagt gggagatgga gaagagtgaa tgagtttctc   1740
ccactctata ctaatctcac tatttgtatt gagcccaaaa taactatgaa aggagacaaa   1800
aatttgtgac aaaggattgt gaagagcttt ccatcttcat gatgttatga ggattgttga   1860
caaacattag aaatatataa tggagcaatt gtggatttcc cctcaaatca gatgcctcta   1920
aggactttcc tgctagatat ttctggaagg agaaaataca acatgtcatt tatcaacgtc   1980
cttagaaaga attcttctag agaaaaaggg atctaggaat gctgaaagat tacccaacat   2040
accattatag tctcttcttt ctgagaaaat gtgaaaccag aattgcaaga ctgggtggac   2100
tagaaaggga gattagatca gttttctctt aatatgtcaa ggaagtagcc gggcatggtg   2160
ccaggcacct gtaggaaaat ccag                                          2184
```

```
<210> SEQ ID NO 162
<211> LENGTH: 1037
<212> TYPE: DNA
<213> ORGANISM: Homo sapiens
<220> FEATURE:
<221> NAME/KEY: misc_feature
<223> OTHER INFORMATION: Incyte ID No: 351273.2
<221> NAME/KEY: unsure
<222> LOCATION: 418
<223> OTHER INFORMATION: a, t, c, g, or other

<400> SEQUENCE: 162
```

```
ggtgatgtgt cttcaggagt cccaatctat cttttcctgg tcctgggttt cagaaccgcc     60
tggggctgaa ccaaaatgcc cacagctccc atctctcctg gcctactgaa tatcagcccc    120
tgtgtcagtc ctcccagagg atagcctgag gagggtgtgg gatctcccaa aggagcaact    180
gaatttccca aatgggagga gactcctggt acactcttca tctagatagc caaccccttg    240
ggatgctcag cttttctttc ccagtcccag ttttcgtaag ttggagacac atggctggtc    300
agccagttgg atggtgctat tgagggaaag gagaaatgat tcctgtcctc tggattgtgt    360
caactgtgaa ggaagacaaa accccaaaag acaaggaaag cccaccccaa cggggtgnac    420
cagtagcctg caaatcagaa tatgaaattg aggttcacag cggggcatag tgcggtgttg    480
gtggaaagta gtcatgagcg cttcggtgag caggatgggg gtggagagat gtctcatgtg    540
atagggtgac ctgtgctgac acatgagtca gacatcactg tgttccagcc agtattgccc    600
ctctgtgggc ttgtcccttg taaagaattg ttcatagatt gcagcttgag tatttcaaat    660
taactttacg ttgcattttt cactagagcc aaatccaaga atgattgcat agatcaggta    720
agacacagaa gaggcaactc aacaaagccc atgacataca gtgcatggct cacaatccca    780
```

```
ggagatgagg gcagcacagc tgcagagcaa cacagagtgg ggagaacatc caggatgcac    840

attcaaccag caggtgggga gcaagacaga cagggacctg tgggccaaag cgtttctcag    900

ggtccaggga attgaacaag gagagatgtc tcatgtgaaa tgttcagaga atcaccacca    960

gacactcccg tgtgaaaatt tgtatgcatc tcctcctttc atctatccta gaaacagaga   1020

tctttttttt ttgagac                                                  1037


<210> SEQ ID NO 163
<211> LENGTH: 991
<212> TYPE: DNA
<213> ORGANISM: Homo sapiens
<220> FEATURE:
<221> NAME/KEY: misc_feature
<223> OTHER INFORMATION: Incyte ID No: 402939.1

<400> SEQUENCE: 163

ttttagagct acaaaatttt atagtttatg gaacatagca agtatatttc ctacaggatc     60

ttcatctgtg ttttcctttc agaactgtta agttttaaaa tgcagatggc ttcagtttct    120

tcttctgacg cctaagagag agaaaactag agagattaag agatccaagg tcactcatca    180

gacgtggaag aatccaggac tccaggcagt gtggggtctt ctattcacac tcacttcaca    240

ccttaatctc agttttacat ttcatcttct gttttcttta tacaatctgt ccagcttttg    300

aatataattt tccatacttt gagaagagct caaatgatgg taatacagtc tggaaatcct    360

tgtcacagat ccatttctta ggattttcac ttcggaattg ttctttgtaa gaaataggac    420

catacttgct tgataaatgc attgatggga tgtacttttc atttttatgg tatgaagaaa    480

atggcaaaaa catattgtca tttacatttt gcagccattc ctctcttctg agctcctctc    540

tggccaactt taactcatcg attggttctg ccacccgcaa cgttggctcc aaaggcctgt    600

agcgttgttc taatacttcg gtgatatctc ggaagggccc ctgacattgc tttctattaa    660

taggtggtag aatttcagac cgaggaaaag aacgggcgct tgtacaagct agccaatcag    720

taaggctggt ggagtccttc tgcttaactt taggtcttcg gtgtgttaaa ggctttgcct    780

tctgtaattg cagctcccat ggatcaggct cttttctgaa gggtgaattg tatattcctg    840

gaatctgctt tgtgctgagg caggtaatgc atctttcggg cttggtaatc tcttttcttc    900

tcttcccttt cgaggttagc cttcttctct tctctttctt tcatttctgc aaactcctcc    960

agtgccttcc tttggttgcc atgaacttgg a                                   991


<210> SEQ ID NO 164
<211> LENGTH: 4339
<212> TYPE: DNA
<213> ORGANISM: Homo sapiens
<220> FEATURE:
<221> NAME/KEY: misc_feature
<223> OTHER INFORMATION: Incyte ID No: 334392.1
<221> NAME/KEY: unsure
<222> LOCATION: 82, 131, 138, 226, 332, 345, 1186-1280, 3020, 3024,
      3028, 3031-3032
<223> OTHER INFORMATION: a, t, c, g, or other

<400> SEQUENCE: 164

cttcaacaaa ggacactaca tcaaggactg cccccaggca cgccccaaag gcgagggcct     60

gactccatac cagggcaaaa ancgctgctt cggcgagtac aagtgtccca agtgcaagag    120

aaaatggatg ngcggganct cctgggccaa catggggcag gagtgcatca agtgccacat    180

caacgtgtat ccacacaagc agagacccct ggagaagccc gacggnctgg acgtgtccga    240

ccagagcaag gagcacccgc agcacctctg cgaggaagtg caaggtcctg ggctactact    300
```

-continued

```
gccgtcgcgt gcagtgacgg gctgcctgcc cncacccaga gccanccccc gacagcccga    360
ggagacgctg cttccctgtg ctactccgag gggctgcgtg tcgccctgtg catggggtgc    420
cctcgcaggc ctgcggggct gggccggggg ctcttagcgt ccttgtcttg tgtgtgttga    480
caaacagtgt tactgacatt gctgcccccc acaggccagg gaaagcaggg agtctggggc    540
tttttgcagg cgggcctggg gtctcagtgg aggggacaaa ggcaagcaaa agcccatgtc    600
caggagccct gggtgtcccc acaggctcgc ctctgagagc ctctttgggg tgagcagcct    660
tgtattggcc acaggtgcac taaattgact gtgaatccca aacctcccca gaccagccag    720
gccgcctgcc cccacccaga accttccggt ttgccctgta tggaaagcca ctctcggaaa    780
tccctctttc ctgagtcagc aatcgtggca aggggacatg tgttccaaca gcggctgggg    840
agtggacctc tctgtccctt gcccacctta agccccaaat ccagaccccc tctgacatca    900
ctggcattgc acctgggtgt gcccccctcc ccacgctatg gacccagata ggaggggtta    960
ggcatggggg aggcacagaa tgctggagag atgcgtcctg gtgaacgtgg ggcagcccct   1020
cccacgaccc ccaccagact gccttaggtt ttgtcagccc cactcccttt ccttcccctc   1080
tgcctcccac ccactctggg ggtccacatc aagatagctg ggcccagtgt ggaagcccag   1140
cgtgtctgtt ctagcagaaa ggacacaagc ctggtgttct ggagannnnn nnnnnnnnnn   1200
nnnnnnnnnn nnnnnnnnnn nnnnnnnnnn nnnnnnnnnn nnnnnnnnnn nnnnnnnnnn   1260
nnnnnnnnnn nnnnnnnnnn acagcataac actagagagc agagggccca tttcagctct   1320
gttgttctgg gattcaggct ggccggtgct gtgtcctgga gctttatttg gggagtttca   1380
cccagaatgg tgggagaaac ctcccaggtg ccaggtaccc cgcatcgtga cccttcactt   1440
ggtgtcttag gaagtcaagc tgagggatgc tgagtcctcc cctgctggcc cctgcagccc   1500
cagccctgct tttcatcccc cacccctgca aacatggagg agccccctcc ttctcacctc   1560
ggtctcctag cccctgacat ggagaaccct gagacaagcc acagaacccc tcttttctaa   1620
aatggagaca ataatttcct acctcccaag ggagcagaga ggcctcgtgg cacgtccgtg   1680
gccagggagc ccactgtcct ggctggcggc gggatcgtgc gctcctctgt ctcccggatg   1740
agaagccccg tttccatggt cttgaccctt cctttctccc ggctgtcaga actgggtctc   1800
ttgattttgc ccctacatta tgcctctgtg ggaaaaaaaa aaaatcagac caagaaatga   1860
gcctgaaatt cagtgtttac catggctcaa ggatgcccat ctggtgtcca gttgcctttt   1920
gtattcaaat gaaaatgctt tgtacaactg aggagttaca gtgaagtgtt aaccaggggt   1980
ccagggagcg agttgaaaag atggagtgag tgtatttgca gccagggagc tgcagggtgg   2040
atttgagggg ccataccctc tgagcactta acaaaggtat ttgctccagg ccaggcagca   2100
ggctgtggac acccttgcca ccactgggga ctgccactga ggactccccg agcacgttgt   2160
tccccgtctt ctccaaggtg ttgaggtgag ctggggttgg ccccggccca ggcttctgtc   2220
ccaaggagaa gctgccactg acagtcatcc taccgcactg ctaaagagaa tgttcgcagt   2280
ggtgggcggc gtgcctgtgc caacccttcc agggacccgg ccatggggga ccttggccca   2340
aggatgcctg ggcctgcca gctgtgctgc aaaggtgggg ggcccacacc ctaaaactaa   2400
cccaggcccc agaccactgg aggccagggc ttccctgcac gggctaaggg gagttgggat   2460
atcaccccaa agtgaccttg ccagtgagct gttcagcagg tagccactgc cctgccatct   2520
gtgcagagcc agccaccttg ggggctgggg ttcccgcttt gaggcccacc ttccatactc   2580
cccttgactc ggctctggct gaactgggga actctcttgt ggtcagcaaa gcccctgcca   2640
```

-continued

```
tgcaggccag gtgccattga gaattaagtg ctcagagggc caggagccca ggggatggga   2700

aagtgtgtgg ttttagtacg ttcaaaaggg acaatcgctt gcagttggta gatctagcga   2760

tctagttggg agataatggt gtttacccca tatgaagtat tcaatagttc tacttgtgaa   2820

tttgtattta ttttgagtta tacttgacac agaattcctt ttttaaaaaa atatgtgtgt   2880

attttggaaa aaaaattcat agatgttaaa atttctgcat ggttaccagt ttttctcaca   2940

acactgaatt tggtagcttt tcccgaaaaa atcttcacag taatttttttg tctgtatata   3000

tttgagggcc ttttttaaan aaanaaanaa nncaagaaaa atataattgt ttgatttttg   3060

agattaaaac aaacaaaaag agaggcattt tcaaaatttc agaactttca ggagggcaag   3120

agaatatcaa acaaagattt ctggaagtat tttgccaacc ttctggttga gctgcaagaa   3180

aatatttatg gtgagaactt ttctgtttcc cgttattggg tttttggttg gtttttgttt   3240

gtttttttact atgctttggt ctgtaaaaat atgcaactga actacattca gaaggaaata   3300

ttgtctacat agaatattat atgaagttgg tacataattc tgatgaggaa aaaaaatctt   3360

tgcaattctt taagccatat tgttgttttt ctgtgttgtt ttccctggat gaaaatatca   3420

gtattaagta gacagcatat tattcaagtg tttagactta ttaatatgtt cttgtccctg   3480

tatttataca tatgtgtatt ttggaaagta ttgccttttt taagggaagc tataattcga   3540

tacatagtga aaaagggaat ggtgacccct ttgtgcctct tccactgagg ataacaaaca   3600

gcattgtaat ccattctctt gcaccttctt cttcttatct tgttattacg gttttattaa   3660

ttttgtagag ggacagggag tgggcaaggg gaagaagcag cttatttgac taaccagccc   3720

ctctgtggtc caccagcgtc ttggcttggt gggagggctc tcaatcagca gggccccagg   3780

agggaagaag aagtggggca aagcctggcc tcgccgctcg ggagctttgc catctgagcc   3840

acgcctcctc caggccatgc tccttgaact tggaaatgtc aaccggagcc cttacaccag   3900

ccctccagca tctaatagac ttgaatctac tctaaacgaa tatttaatcc aacctcacta   3960

cattgtagct cagtccaacg actaaccctg aaatgggggt gttccagcct tcagcgagat   4020

ggccaagcgg tcccctgggg gctgtggcag cgggcttatc cttctctgtt gccaaccttg   4080

ccgtccgacc tcctccgccc ccatgcggtg accccgtccg tgtctgtgtc tgtccatacg   4140

tgtgagtcca gctaaaaaga caaaacagaa cccgtgggcc cagctcggaa ggtgcgtgga   4200

gaaggctccg acgtctccga agtgcagccc ttgggatggc attccgttgt gtgccttatt   4260

cctggagaat ctgtatacgg ctcgcctata gaaatatagc ctcttcatgc tgtattaaaa   4320

ggacttttaa aagcaaaaa                                                 4339
```

```
<210> SEQ ID NO 165
<211> LENGTH: 2114
<212> TYPE: DNA
<213> ORGANISM: Homo sapiens
<220> FEATURE:
<221> NAME/KEY: misc_feature
<223> OTHER INFORMATION: Incyte ID No: 199021.1
<221> NAME/KEY: unsure
<222> LOCATION: 1907, 1909, 2009, 2014
<223> OTHER INFORMATION: a, t, c, g, or other

<400> SEQUENCE: 165

cagccgagtt gctttcttac taaatcctat taaaatatgc aaaaataagt cagattttaa     60

ggcaaataaa gtgacataag gtgctttata ttttattttg gtatatttaa acagtgaaaa    120

actaactgaa agcacatgaa gagttgtaac ttgggggaaa ataggtaaac atagcttcta    180

gctaacacag gagacctatt cttagccttt actaatttca agcagtgtat cccatatggt    240
```

```
atctcttgct cttccttcaa ctccaataaa tttaatgact aaatgccaag ttaacaaatc    300

aacttccatt tggattgtag gtgtgaaggc acaactctaa ttgctattag tctacatgta    360

tttctgtaat agtattgtgt catatcaatt tttaagatgt ctaaatttta tggtcacaag    420

ttatccctcc tcagtatgaa aaataaatta gatattgaaa aatgtctaaa cttcagtgat    480

ggaaagaata tttcaagaag ttttttaacc taaatacttt tattttgaat ttaagtcttt    540

gcacataaaa tatagcaagc ttacatatta aactatttac gtaaatggaa tgtaagccat    600

gactttaact gaagtgttca cattcactaa ttttgataga ttgctgtcct taataatttt    660

ggaggaaatt aagccaaatg attattgtac tacagtattt tcagaatatg ggaaatcaat    720

taaaaatgta atctaatcta gtttaagatt tttgtttaat catcatggtg gtcctacctg    780

gataatttaa ctataaagac aaagtaattc tattaaatga actaactgaa aataataatt    840

ataggaagtg attattccat tttaagtatt agagctcaaa ttggctttat ttgcatttag    900

ggagatcatg ttttcttaat catgctggaa tttaaaaatt gttttacttg tatcgaaatt    960

aaccttgatt tataactatt tttgtaataa aacaatgaca gctgtagtaa ctatgatggg   1020

tgtaacaaca tttttttaaa gaagggaatc tgtttatcgc ttttcaaaat attttctaaa   1080

gtgggggaag aaagtttata gactttccaa gcacatttat ggttttttat tactattatt   1140

atggttttaa aaagagtaac tttatttctt tttgtaagga attaagtaat atcctttaca   1200

gttctgtgaa aggacttatt ttttaactgt aatatttatt agttttaaaa tatttgtatc   1260

tcatttgtaa caatttgttt taattttttta tatatatgtt tttattttta aaaaacatac   1320

cagttgaatg gggttaaagc tttcaatatc ttaaaatatt tataaaacat ttcactgttg   1380

caaaatcact tccaaaatga tagctatcta acaactaatt actaattttt aaagaacaaa   1440

tcacacattt aaaaaatctg tagaatttat tttaactatg acctttaatt gaaaataaat   1500

aattaaaata tcagacatgt tttggaaaag tcttaatttg agaacaccaa aggaaactac   1560

cccagaatct aatgtagttc gctattaata acaatgcatt attgaaagta tattgcaaat   1620

acatgtttcc tcatgaaatc taagtaattt tgttgtggaa tagtgtcact gttacatttc   1680

ccccatgaag ttcaataaac cagcttagcc acaaaaaaat tacttagatt tcatgaggaa   1740

acatgtattt gcaatatact ttcaataatg cattgttatt aatagctaac tacattagat   1800

tctggggtag tttcctttgg tgttctctaa ttaagacttt tccaaaacat gtctgatatt   1860

ttaattattt attttcaatt aaaggtcata gttaaaataa ataattncna atatcagaca   1920

tgttttggaa aagtcttaat ttgagaacac ccaaggaaac taccccagaa tctaatgtag   1980

ttagctatta ataacaatgc attattgana gtancctgca aatacatgtt tcctcatgaa   2040

atctaagtaa ttttgttgtg gaatagtgtc actgttactt tcccccatga agttcaataa   2100

accagcttag ccac                                                     2114
```

```
<210> SEQ ID NO 166
<211> LENGTH: 763
<212> TYPE: DNA
<213> ORGANISM: Homo sapiens
<220> FEATURE:
<221> NAME/KEY: misc_feature
<223> OTHER INFORMATION: Incyte ID No: 277496.3
<221> NAME/KEY: unsure
<222> LOCATION: 7, 464-598
<223> OTHER INFORMATION: a, t, c, g, or other

<400> SEQUENCE: 166
```

-continued

```
ccaaggngct gggattacag atgtgggcca ccgtgcctgg ccagaaaatc tggattctta     60

ttcctagttc ttcatttctg tcacatgcac ttagttgaca ttacatctac atatattagc    120

tttttcctac atgagccatc tatttactta gtaaccagtg ttcttaatga agtatttagt    180

cttgggtttc ttgtaaaatt tctctgcatt ccttagacag tgtactatac atgaaatatt    240

cttgttgacc tagtaattta tattattcca tttaattctt aaacctatgg ccttttttatt    300

gagcacactc ttaaatcatt atttggcttg taaacattca tctgaattgt ggctacaatc    360

ctctttaaat aatctaggaa aaaagaaaga taaagcttac attttcacag ttttggctct    420

taaacacatt ccacaaatgc cattaagaat ttattttgtt ttannnnnnn nnnnnnnnnn    480

nnnnnnnnnn nnnnnnnnnn nnnnnnnnnn nnnnnnnnnn nnnnnnnnnn nnnnnnnnnn    540

nnnnnnnnnn nnnnnnnnnn nnnnnnnnnn nnnnnnnnnn nnnnnnnnnn nnnnnnnntt    600

ttgttttaga gtcatttaat gtgtttttat gcacaataat agtgggaggt tgttttgttg    660

catttgtttg tttgttttgt tttgttttgt tttgctttcc atgtgggaaa agttaacatt    720

ggaactgttt ctagtaaaag atttttttca ggctgggcac ggt                      763
```

<210> SEQ ID NO 167
<211> LENGTH: 1234
<212> TYPE: DNA
<213> ORGANISM: Homo sapiens
<220> FEATURE:
<221> NAME/KEY: misc_feature
<223> OTHER INFORMATION: Incyte ID No: 333034.1

<400> SEQUENCE: 167

```
aattcggcac gagcggggaa gcttcgcagg cgtgcacgga gcagtgagat cactggcgtt     60

ataaatatcc cggtgccagc gcggagatcc gtcgggtggc ctctctcttc ccctctcccc    120

ttctcttccc cgaggctatg tccacccggt gcggcgaggc gggcagagcc agaggcacgc    180

agccgcacag gggctacaga gcccagaatc agccctacaa gatgcactta ggaccccccgc    240

ggctggaaga atgagcttgt ccttcctcct cctcctcttc ttcagccacc tgatcctcag    300

cgcctgggct cacggggaga agcgtctcgc ccccaaaggg caacccggac ccgctgccac    360

tgataggaac cctagaggct ccagcagcag acagagcagc agtagcgcta tgtcttcctc    420

ttctgcctcc tcctccccccg cagcttctct gggcagccaa ggaagtggct tggagcagag    480

cagtttccag tggagcccct cggggcgccg gaccggcagc ctctactgca gagtgggcat    540

cggtttccat ctgcagatct acccggatgg caaagtcaat ggatcccacg aagccaatat    600

gttaagtgtt ttggaaatat ttgctgtgtc tcaggggatt gtaggaatac gaggagtttt    660

cagcaacaaa tttttagcga tgtcaaaaaa aggaaaactc catgcaagtg ccaagttcac    720

agatgactgc aagttcaggg agcgttttca agaaaatagc tataatacct atgcctcagc    780

aatacataga actgaaaaaa cagggcggga gtggtatgtg gccctgaata aaagaggaaa    840

agccaaacga gggtgcagcc cccgggttaa accccagcat atctctaccc attttcttcc    900

aagattcaag cagtcggagc agccagaact ttctttcacg gttactgttc ctgaaaagaa    960

aaagccacct agccctatca agccaaagat tcccctttct gcacctcgga aaaataccaa   1020

ctcagtgaaa tacagactca agtttcgctt tggataatat taatcttggc cttgtgagaa   1080

accattcttt cccctcagga gtttctatag gtgtcttcag agttctgaag aaaaattact   1140

ggacacagct tcagctatac ttacactgta ttgaagtcac gtcatttgtt tcaatgtgac   1200

tgaaacaaaa tgtttttttga taggaaggaa actg                               1234
```

-continued

<210> SEQ ID NO 168
<211> LENGTH: 3186
<212> TYPE: DNA
<213> ORGANISM: Homo sapiens
<220> FEATURE:
<221> NAME/KEY: misc_feature
<223> OTHER INFORMATION: Incyte ID No: 230316.1
<221> NAME/KEY: unsure
<222> LOCATION: 75, 90-93, 2074, 2141
<223> OTHER INFORMATION: a, t, c, g, or other

<400> SEQUENCE: 168

```
ccccctgactg taagtggtgg gagagggagg ggagttaatg gaactgggtc tgggattatt     60
ttaaaattat atatntatat ataaagatan nnncttacat cttttctttg ccctctgtgc    120
tttgaaagca ctggataaat tgtttggttt tgcttttctc tcttccacaa aattggaagc    180
ttttttaaa aatgttttcc ccacaagtca tcttgccttg tggcatgtct gtctagcctc    240
ttcctccctc cctcatgatg aagtgccatt tctgttacgt ctccctctcc ccaagctcag    300
aggtgctcag aggtacgaga tacccaagtt tgtcagttga gattaaaagt aaggaacaga    360
gaatgtgcaa taccgtctgg ctgggggctg tccctgccct gccctgagct gagtcctttc    420
cctgggagcc aggccacctt agaatggggt ttggaagtaa gatgtataga gttggggaat    480
cattggagaa ggaaagccta tagtcgagtg cctgcttagg tgctgaggtc acaggggaga    540
tggtggaatc ttccctgttt ttatcccctc agggtcagtt acatagaagc tgcttcttga    600
ctagtatagc tcggtgaccc tttgttcaac cgctgaggtt tgatttctta ccctttcttc    660
tccccatttt catactcttc ccagggatta gtgatggagg tgaggtctcc ctaatcatgg    720
taaagtgtta accttccacc tcctcccttc cctcctcctt cctcatcctt ctgtcttcct    780
caattctccg tctcttttt ttcatcactg attgccttgt gtccctccaa gtctacttgt    840
tactatccat ctccaggctc tgggccgtgt agacactaaa cctcatgccc taaggacagg    900
aggaaagacc ctctgtttgg agcattatta gtagagtgag gatcccacca gttctgcctg    960
gcttcctcca tccccagagg cactaaaagc agtattttaa ggttggtgtc ttactccctg   1020
gaagcctgaa atgggtggaa tagcggtaag gcttgagtaa aactagggga cagaggttct   1080
tatttgtcga ttttatttta taatttgacc acagcatctg aactccctct ctccctggaa   1140
taagtatttt tcccacattt ttggatatat gtatggtaga caattttttt ttaagacaca   1200
gagataaacg ttttcctgct ttggttacct ttcctttccc ctttaaaagg aattagctat   1260
agaactgctt tgtaaagatg cttcttgata ttttactttt gttccttttc cctaatcatt   1320
ccctttctc cccactcctc cagaaggcat aacccttctc tccacaaccc ctaccccac    1380
ccccgtccta ggctcccatc ctttccatca agaccttcat tagcttatga tatttgctgc   1440
cgagatgtta taacaaggac tcgttcatgt atataagcta tttcttgatc catttaaaag   1500
gaattgtaca ttgtgtagaa aaaaaaaaaa acctgaaaaa gagaaaaaaa agccctggag   1560
tagtccctcc gggtcaccag cactgccttg gcagagccca ctccctaccc taacctgccc   1620
accctcccta tcccccagca ttaggttgat actgtgggga agtgctgggg gctgggaggt   1680
agccgaggaa tggggcagtt cccgggggca tcgaaaccaa gtattattat gaattgtaat   1740
tgtatttgca ctgtttttt cctctgattg catcagcata tatacaatat acctatataa    1800
caaaattcag tgtcaagctt tcttatgcaa gggatttccc ccaccccacc tcctcaaaaa   1860
agaaagaacc tagtcttatg ggcctttgag ggtggattgt caggggatga tagaaaggat   1920
tttaataagt catcctgagg aaatttcacc tagtgagagc cacatccatc tgcacagcct   1980
```

-continued

```
taggctgcgt gaaccgaggt gaggctgagc tcctgtgaaa gccaagacct cctggtccag   2040

gactttgtag gagtaaaaag aaccaccagc acanaagggg ttgagggggc tacaatctgg   2100

agacctgggg tctcctacta acttgctata tgatctttgg nagagttaat tttctgagta   2160

tcaattttct tatctgtgaa gtgaagaggg ggatcatctg gccaccaagt ttaaaattct   2220

atacttctca cctgccaaaa ccaaaaaaca acttgaggtg aggaaagtgt tgggcccaga   2280

aaccagggag gaactgaaag tgactcgcgt tgaagtggtt atgtgtatga caatgctctt   2340

ggagaactgc cagtcctcta tggttaccct tgatttggga gaggcagcag agtcatgtcc   2400

agggcatcag accagtgaca tctttgcctt tatgcctcta gtcatctgag ggcggggact   2460

aggcctcaag ccccatctca cagccaacca cagagccctt aagggtggtt gacaattgaa   2520

tgccccaggt tggtgcttta gttatttact ccctttgtga gctacaggat gtgtaacttt   2580

tcccccatct tggtgataaa ataggagagc gcagacacag cccacatttt gtctcctttc   2640

ctcagatttc atctgaaccc cgctaaaggc aagctgtttc acagtctgtc tccttcaggg   2700

gcccaatttc cccacagcct gggctgagta ctcctactct cttctttagg ttctgggctg   2760

ataaagcctg gagagggtac agggtgatgg gtgaagccct ggtgaaggtg aaaggataga   2820

ttggggttgg ggggtgggga gcagggaggt gggatgggga atggccttcc ctgaataggg   2880

tgggtgggag gggaacaaga cccttttgca caactctctt taagtttcct ttatttcttt   2940

tttaactcat tctgattttc tgcattgtgt ttgggaaata aaatgaaaaa actaagacca   3000

atagaaactg gttttcaaaa aggcaaatac actcccatct gtttcagatg ctgctgagca   3060

tttcagcagt gacagattca aataataagc taatttttgg agaaaggatt aaaagaaaaa   3120

aaaactttgt aatatttatc acttgcaagc tatgtttaat aaagaaagga atggtttcta   3180

aaaaaa                                                              3186
```

<210> SEQ ID NO 169
<211> LENGTH: 3083
<212> TYPE: DNA
<213> ORGANISM: Homo sapiens
<220> FEATURE:
<221> NAME/KEY: misc_feature
<223> OTHER INFORMATION: Incyte ID No: 237668.3

<400> SEQUENCE: 169

```
cgcccctgca gcagagctga aaaaaaccag gatccgggtt cctcagcccc ttttcacaat     60

atttgattag gaatttgggg cgggaccctg gtctggcaca ggcacgcaca ctctcagtag    120

actctttcac tcctctctct cttcctctct cacacgttct ccaacccaag gaggccagac    180

agagggacgt ggtcactctc tgaaaagttc aacttgagag acaaaatgca gtggacctcc    240

ctcctgctgc tggcagggct cttctccctc tgcccaggcc cagtatgaag atgaccctca    300

ttggtggttc cactacctcc gcagccagca gtgccaccta ctacgatccc tatgaccctt    360

acccgtatga gacctacgag ccttacccct atggggtgga tgaagggcca gcctacacct    420

acggctcttc catcccctcc agatccccgc gactgccccc aggaatgcga ctgcccaccc    480

aacttcccca cggccatgta ctgtgacaat cgcaacctca agtacctgcc cttcgttccc    540

tcccgcatga agtatgtgta cttccagaac aaccagatca cctccatcca ggaaggcgtc    600

tttgacaatg ccacagggct gctctggatt gctctccacg gcaaccagat caccagtgat    660

aaggtgggca ggaaggtctt ctccaagctg aggcacctgg agaggctgta cctggaccac    720

aacaacctga cccggatgcc cggtcccctg cctcgatccc tgagagagct ccatctcgac    780
```

-continued

```
cacaaccaga tctcacgggt ccccaacaat gctctggagg ggctggagaa cctcacggcc    840
ttgtacctcc aacacaatga gatccaggaa gtgggcagtt ccatgagggg cctccggtca    900
ctgatcttgc tggacctgag ttataaccac cttcggaagg tgcctgatgg gctgccctca    960
gctcttgagc agctgtacat ggtgcacaac aatgtctaca ccgtccccga tagctacttc   1020
cggggggcgc ccaagctgct gtatgtgcgg ctgtcccaca acagtctaac caacaatggc   1080
ctggcctcca acaccttcaa ttccagcagc ctccttgagc tagacctctc ctacaaccag   1140
ctgcagaaga tcccccccagt caacaccaac ctggagaacc tctacctcca aggcaatagg   1200
atcaatgagt tctccatcag cagcttctgc accgtggtgg acgtcgtgaa cttctccaag   1260
ctgcaggtgc tgcgcctgga cgggaacgag atcaagcgca gcgccatgcc tgccgacgcg   1320
cccctctgcc tgcgccttgc ccagcctcat cgagatctga gcagccctgg caccgggtac   1380
tgggcggaga gcccccgtgg catttggctt gatggtttgg tttggctttt gctggaaggt   1440
ccaggatgga ccatgtgaca gaagtccacg ggcaccctct gtagtcttct ttcctgtagg   1500
tggggttagg gggggcgatc agggacaggc agccttctgc tgaggacata ggcagaagct   1560
cactcttttc cagggacaga agtggtggta gatggaagga tccctggatg ttccaacccc   1620
ataaatctca cggctcttaa gttcttccca atgatctgag gtcatggaac ttcaaaagtg   1680
gcatgggcaa tagtatataa ccatactttt ctaacaatcc ctgggctgtc tgtgagcagc   1740
acttgacagc tctccctctg tgctggggct ggtcgtgcag ttactctggg ctcccatttg   1800
ttgcttctca aaatatacct cttgcccagc tgcctcttct gaaatccact tcacccactc   1860
cactttcctc cacagatgcc tcttctgtgc cttaagcaga gtcaggagac cccaaggcat   1920
tgtgagcatc tgcccagcaa cctgtggaga caacccacac tgtgtctgag ggtgaaagga   1980
caccaggagt cacttctata cctccctaac ctcacccctg gaaagccacc agattggagg   2040
tcaccagcat gatgataata ttcatgacct gatgtgggag gagacagcca acctcaggct   2100
tagatcaatg tatagggcta tattttggca gctgggtagc tctttgaagg tggataagac   2160
ttcagaagag gaaaggccag actttgctta ccatcagcat ctgcaatggg ccaaacacac   2220
ctgcaaattg gctgagttga gaaagcagcc ccagtagttc cattcttgcc cagcactttc   2280
tgcattccaa acagcatcct acctgggttt ttatccacaa aggtagcggc cacatggttt   2340
ttaaagtatg agaaacacag tttgtcctct cctttttatcc aagcaggaag attctatatc   2400
ctgatggtag agacagactc caggcagccc tggacttgct agcccaaaga aggaggatgt   2460
ggttaatctg tttcacctgg tttgtcctaa ggccatagtt aaaaagtacc agctctggct   2520
ggggtccgtg aagcccaggc caggcagcca aatcttgcct gtgctgggca tacaaccctc   2580
tgctttcaca tctctgagct atatcctcat tagtgaaggt ggcttttgct ttatagtttg   2640
gctggggagc acttaattct tcccatttca aaaggtaatg ttgcctgggg cttaacccac   2700
ctgccctttg ggcaaggttg ggacaaagcc atctgggcag tcaggggcaa ggactgttgg   2760
aggagagtta gcccaagtat aggctctgcc cagatgccat cacatccctg atactgtgta   2820
tgctttgaag caccttccct gagaagggaa gaggggatct ttggactacg ttcttggctc   2880
cagacctgga atccacaaaa gccaaaccag ctcatttcaa caaaggagct ccgatgtgag   2940
gggcaaggct gccccctgcc ccagggctct tcagaaagca tctgcatgtg aacaccatca   3000
tgcctttata aaggatcctt attacaggaa aagcatgagt ggtggctaac ctgaccaata   3060
aagttatttt atgattgcat cta                                           3083
```

```
<210> SEQ ID NO 170
<211> LENGTH: 93
<212> TYPE: PRT
<213> ORGANISM: Homo sapiens
<220> FEATURE:
<221> NAME/KEY: misc_feature
<223> OTHER INFORMATION: Incyte ID No: 2870970CD1 (GENE ID 234571)

<400> SEQUENCE: 170

Met Ser Gly Leu Arg Val Tyr Ser Thr Ser Val Thr Gly Ser Arg
  1               5                  10                  15

Glu Ile Lys Ser Gln Gln Ser Glu Val Thr Arg Ile Leu Asp Gly
                 20                  25                  30

Lys Arg Ile Gln Tyr Gln Leu Val Asp Ile Ser Gln Asp Asn Ala
                 35                  40                  45

Leu Arg Asp Glu Met Arg Ala Leu Ala Gly Asn Pro Lys Ala Thr
                 50                  55                  60

Pro Pro Gln Ile Val Asn Gly Asp Gln Tyr Cys Gly Asp Tyr Glu
                 65                  70                  75

Leu Phe Val Glu Ala Val Glu Gln Asn Thr Leu Gln Glu Phe Leu
                 80                  85                  90

Lys Leu Ala


<210> SEQ ID NO 171
<211> LENGTH: 353
<212> TYPE: PRT
<213> ORGANISM: Homo sapiens
<220> FEATURE:
<221> NAME/KEY: misc_feature
<223> OTHER INFORMATION: Incyte ID No: 3575519CD1 (GENE ID 247384)

<400> SEQUENCE: 171

Met Asp Tyr Lys Ser Ser Leu Ile Gln Asp Gly Asn Pro Met Glu
  1               5                  10                  15

Asn Leu Glu Lys Gln Leu Ile Cys Pro Ile Cys Leu Glu Met Phe
                 20                  25                  30

Thr Lys Pro Val Val Ile Leu Pro Cys Gln His Asn Leu Cys Arg
                 35                  40                  45

Lys Cys Ala Asn Asp Ile Phe Gln Ala Ala Asn Pro Tyr Trp Thr
                 50                  55                  60

Ser Arg Gly Ser Ser Val Ser Met Ser Gly Gly Arg Phe Arg Cys
                 65                  70                  75

Pro Thr Cys Arg His Glu Val Ile Met Asp Arg His Gly Val Tyr
                 80                  85                  90

Gly Leu Gln Arg Asn Leu Leu Val Glu Asn Ile Ile Asp Ile Tyr
                 95                 100                 105

Lys Gln Glu Cys Ser Ser Arg Pro Leu Gln Lys Gly Ser His Pro
                110                 115                 120

Met Cys Lys Glu His Glu Asp Glu Lys Ile Asn Ile Tyr Cys Leu
                125                 130                 135

Thr Cys Glu Val Pro Thr Cys Ser Met Cys Lys Val Phe Gly Ile
                140                 145                 150

His Lys Ala Cys Glu Val Ala Pro Leu Gln Ser Val Phe Gln Gly
                155                 160                 165

Gln Lys Thr Glu Leu Asn Asn Cys Ile Ser Met Leu Val Ala Gly
                170                 175                 180

Asn Asp Arg Val Gln Thr Ile Ile Thr Gln Leu Glu Asp Ser Arg
```

-continued

```
                185                 190                 195

Arg Val Thr Lys Glu Asn Ser His Gln Val Lys Glu Glu Leu Ser
                200                 205                 210

Gln Lys Phe Asp Thr Leu Tyr Ala Ile Leu Asp Glu Lys Lys Ser
                215                 220                 225

Glu Leu Leu Gln Arg Ile Thr Gln Glu Gln Glu Lys Lys Leu Ser
                230                 235                 240

Phe Ile Glu Ala Leu Ile Gln Gln Tyr Gln Glu Gln Leu Asp Lys
                245                 250                 255

Ser Thr Lys Leu Val Glu Thr Ala Ile Gln Ser Leu Asp Glu Pro
                260                 265                 270

Gly Gly Ala Thr Phe Leu Leu Thr Ala Lys Gln Leu Ile Lys Ser
                275                 280                 285

Ile Val Glu Ala Ser Lys Gly Cys Gln Leu Gly Lys Thr Glu Gln
                290                 295                 300

Gly Phe Glu Asn Met Asp Phe Phe Thr Leu Asp Leu Glu His Ile
                305                 310                 315

Ala Asp Ala Leu Arg Ala Ile Asp Phe Gly Thr Asp Glu Glu Glu
                320                 325                 330

Glu Glu Phe Ile Glu Glu Glu Asp Gln Glu Glu Glu Glu Ser Thr
                335                 340                 345

Glu Gly Lys Glu Glu Gly His Gln
                350


<210> SEQ ID NO 172
<211> LENGTH: 574
<212> TYPE: PRT
<213> ORGANISM: Homo sapiens
<220> FEATURE:
<221> NAME/KEY: misc_feature
<223> OTHER INFORMATION: Incyte ID No: 3938992CD1 (GENE ID 207591)

<400> SEQUENCE: 172

Met Pro Gly Tyr Gly Lys Lys Asn Ala Gly Ile Tyr Val Arg Pro
  1               5                  10                  15

Arg Leu Phe Ser Pro Tyr Val Glu Glu Ala Lys Ser Val Leu Asp
                 20                  25                  30

Glu Met Met Val Glu Gln Thr Val Leu Val Arg Leu Arg Met Val
                 35                  40                  45

Arg Met Ser Asn Val Pro Asp Thr Leu Tyr Met Val Asn Asn Ala
                 50                  55                  60

Val Pro Gln Cys Cys His Met Ile Ser His Gln Gln Ile Ser Ser
                 65                  70                  75

Asn Gln Ser Ser Pro Pro Ser Val Val Ala Asn Glu Ile Pro Val
                 80                  85                  90

Pro Arg Leu Leu Ile Met Lys Asp Met Val Arg Arg Leu Gln Glu
                 95                 100                 105

Leu Arg His Thr Glu Gln Val Gln Arg Ala Tyr Ala Leu Asn Cys
                110                 115                 120

Gly Glu Gly Ala Thr Val Ser Tyr Glu Ile Gln Ile Arg Val Leu
                125                 130                 135

Arg Glu Phe Gly Leu Ala Asp Ala Ala Ala Glu Leu Leu Gln Asn
                140                 145                 150

Pro His Lys Phe Phe Pro Asp Glu Arg Phe Gly Asp Glu Ser Pro
                155                 160                 165
```

-continued

```
Leu Leu Thr Met Arg Gln Pro Gly Arg Cys Arg Val Asn Ser Thr
                170                 175                 180

Pro Pro Ala Glu Thr Met Phe Thr Asp Leu Asp Ser Phe Val Ala
                185                 190                 195

Phe His Pro Pro Leu Pro Pro Pro Pro Pro Pro Tyr His Pro Pro
                200                 205                 210

Ala Thr Pro Ile His Asn Gln Leu Lys Ala Gly Trp Lys Gln Arg
                215                 220                 225

Pro Pro Ser Gln His Pro Ser Arg Ser Phe Ser Tyr Pro Cys Asn
                230                 235                 240

His Ser Leu Phe His Ser Arg Thr Ala Pro Lys Ala Gly Pro Pro
                245                 250                 255

Pro Val Tyr Leu Pro Ser Val Lys Ala Ala Pro Pro Asp Cys Thr
                260                 265                 270

Ser Thr Ala Gly Leu Gly Arg Gln Thr Val Ala Ala Ala Ala Ala
                275                 280                 285

Thr Thr Thr Ser Thr Ala Thr Ala Ala Ala Ala Ala Ala Ser Glu
                290                 295                 300

Lys Gln Val Arg Thr Gln Pro Val Leu Asn Asp Leu Met Pro Asp
                305                 310                 315

Ile Ala Val Gly Val Ser Thr Leu Ser Leu Lys Asp Arg Arg Leu
                320                 325                 330

Pro Glu Leu Ala Val Asp Thr Glu Leu Ser Gln Ser Val Ser Glu
                335                 340                 345

Ala Gly Pro Gly Pro Pro Gln His Leu Ser Cys Ile Pro Gln Arg
                350                 355                 360

His Thr His Thr Ser Arg Lys Lys His Thr Leu Glu Gln Lys Thr
                365                 370                 375

Asp Thr Arg Glu Asn Pro Gln Glu Tyr Pro Asp Phe Tyr Asp Phe
                380                 385                 390

Ser Asn Ala Ala Cys Arg Pro Ser Thr Pro Ala Leu Ser Arg Arg
                395                 400                 405

Thr Pro Ser Pro Ser Gln Gly Gly Tyr Phe Gly Pro Asp Leu Tyr
                410                 415                 420

Ser His Asn Lys Ala Ser Pro Ser Gly Leu Lys Ser Ala Tyr Leu
                425                 430                 435

Pro Gly Gln Thr Ser Pro Lys Lys Gln Glu Glu Ala Arg Arg Glu
                440                 445                 450

Tyr Pro Leu Ser Pro Asp Gly His Leu His Arg Gln Lys Asn Glu
                455                 460                 465

Pro Ile His Leu Asp Val Val Glu Gln Pro Pro Gln Arg Ser Asp
                470                 475                 480

Phe Pro Leu Ala Ala Pro Glu Asn Ala Ser Thr Gly Pro Ala His
                485                 490                 495

Val Arg Gly Arg Thr Ala Val Glu Thr Asp Leu Thr Phe Gly Leu
                500                 505                 510

Thr Pro Asn Arg Pro Ser Leu Ser Ala Cys Ser Ser Glu Ala Pro
                515                 520                 525

Glu Glu Arg Ser Gly Arg Arg Leu Ala Asp Ser Glu Ser Leu Gly
                530                 535                 540
```

-continued

```
His Gly Ala Gln Arg Asn Thr Asp Leu Glu Arg Glu Asp Ser Ile
                545                 550                 555

Ser Arg Gly Arg Arg Ser Pro Ser Lys Pro Asp Phe Leu Tyr Lys
                560                 565                 570

Lys Ser Ala Leu
```

BONE REMODELING GENES

FIELD OF THE INVENTION

The invention relates to 169 genes identified by their co-expression with genes known to be involved in bone remodeling and bone diseases. The invention also relates to the use of these genes and their gene products in diagnosis, prognosis, prevention, treatment, and evaluation of therapies for bone diseases such as osteoporosis.

BACKGROUND OF THE INVENTION

Bone Remodeling

Bone remodeling occurs through teams of juxtaposed bone absorbing osteoclast and bone forming osteoblast and osteocyte cells. The development and proliferation of these cells from their progenitors is governed by networks of growth factors and cytokines produced in the bone microenvironment as well as by systematic hormones (Manolagas (1998) Aging 10:182–190; Teitelbaum et al. (1997) J Leukoc Biol 61:381–388). Coordinated balance between absorption and deposition is necessary to maintain bone integrity and requires intimate and complex interactions between osteoclasts and osteoblasts. Under normal states of bone homeostasis, the remodeling activities in bone serve to remove bone mass where the mechanical demands of the skeleton are low and form bone at the those sites where mechanical loads are repeatedly transmitted.

Bone is a composite material composed of an organic and an inorganic phase. By weight, approximately 70% of the tissue is mineral or inorganic matter (mainly calcium phosphate); water comprises 5 to 8%; and, the organic or extracellular matrix makes up the remainder. Approximately 95% of the mineral phase is composed of a specific crystalline hydroxyapatite that is impregnated with impurities which make up the remaining 5% of the inorganic phase. Ninety-eight percent of the organic phase is composed of type I collagen and a variety of non-collagenous proteins; cells make up the remaining 2% of this phase (Einhom (1996) The bone organ system: form and function. In: Marcus et al. eds., Osteoporosis, Academic Press, New York N.Y.). The process of matrix deposition by osteoblasts and osteocytes, subsequent mineralization and the coupling with bone resorbing activity of osteoclasts is governed by a complex interplay of systemic hormones, peptides and downstream signaling pathway proteins, local transcription factors, cytokines, growth factors and matrix remodeling genes.

Parathyroid hormone (PTH) and it's signaling system is the principal regulator of bone remodeling in the adult skeleton (Masiukiewicz and Insogna (1998) Aging 10:232–239; Mierke and Pellegrini (1999) Curr Pharm Des 5:21–36). It has a vital role in the homeostasis of calcium within the blood stream and acute in vivo effect of PTH is to increase bone resorption, although sustained increases in its circulating levels accelerate both formation and resorption. The PTH signaling pathway may also be involved in the regulation of chondrogenesis during bone formation (Vortkamp et al. (1996) Science 273:613–622; Lanske et al. (1999) J Clin Invest 104:399–407).

Several other hormones and local factors are vital to bone health. In a complex pattern of inhibition and stimulation not yet fully understood, growth hormone, insulin-like growth factor-1, the sex steroids, thyroid hormone, calciotrophic hormones such as PTH and prostaglandin E2, various cytokines, such as interleukin-1 beta, interleukin-6, and tumor necrosis factor-alpha, and 1,25-dihydroxyvitamin D (calcitriol) all act coordinately in the bone remodeling process. Estrogen is involved in inhibition of osteoclast activity (Jilka et al. (1992) Science 257:88–91; Poli et al. (1994) EMBO J 13:1189–1196; Srivastava et al. (1998) J Clin Invest 102:1850–1859). Estrogen may prevent bone loss by blocking the production of cytokines in bone or bone marrow (Kimble et al. (1995) Endocrinology 136:3054–3061). Various cytokines, such as interleukin-l beta, interleukin-6, and tumor necrosis factor-alpha, influence bone remodeling (de Vemejoul (1996) Eur J Clin Chem Clin Biochem 34:729–734).

Bone Remodeling and Osteoporosis

Throughout life, old bone is removed (resorption) and new bone is added to the skeleton (formation). During childhood and teenage years, new bone is added faster than old bone is removed. As a result, bones become larger, heavier and denser. Bone formation continues at a pace faster than resorption until peak bone mass is reached during the mid-20s. After age 30, bone resorption slowly begins to exceed bone formation, most rapidly in the first few years after menopause but persistantly until death. Osteoporosis develops when bone resorption occurs too quickly or if replacement occurs too slowly. Two major classes of osteoporosis are primary and secondary osteoporosis. Type I osteoporosis occurs in a subset of postmenopausal women who are between 50 and 70 years of age and is associated with fractures of vertebral bodies and the forearm. Type II osteoporosis occurs in women and men over the age of 70 and is associated with fractures of the femoral neck and proximal humerus and tibia. In some instances, osteoporosis is a manifestation of another disease (Fauci et al. (1998) Harrison's *Principles of Internal Medicine*, McGraw Hill Companies, New York N.Y., pp 2249). Current therapies are designed to interfere with these growth regulatory systems to encourage the growth and function of osteoblasts and inhibit the growth and activity of osteoclasts.

The present invention satisfies a need in the art by providing new compositions that are useful for diagnosis, prognosis, treatment, prevention, and evaluation of therapies for bone remodeling and associated disorders, such as osteoporosis. We have implemented a method for analyzing gene expression patterns and have identified 169 polynucleotides by their co-expression with genes known to be involved in bone remodeling and osteoporosis.

SUMMARY OF THE INVENTION

The invention provides for a combination of substantially purified polynucleotides that are co-expressed with one or more genes known to be involved in bone remodeling and osteoporosis wherein the polynucleotides or the complements thereof are SEQ ID NOs: 1–169. The genes known to be involved in these conditions include genes encoding PHEX (phosphate-regulating gene with homologies to endopeptidases on the X chromosome), human parathyroid hormone, TNF receptor associated factor 2, tumor necrosis factor receptor superfamily member 11/RANK ligand, tumor necrosis factor receptor superfamily member 11A/ receptor activator of NFkB (RANK), vitamin D 24-hydroxylase, natriuretic precursor protein B. human granulocyte macrophage colony stimulating factor 2, cytochrome P450, subfamily XIX, epidermal growth factor, interleukin 1 alpha, microphthalmia-associated transcription factor, bone morphogenic protein 7, human integrin-binding sialoprotein beta-3 integrin, alpha-2-Hs-glycoprotein, osteoprotegerin, interleukin 1 beta, SPI1, matrix metalloprotease 9, parathyroid receptor 1, SRC kinase insert domain receptor, vascular endothelial growth factor receptor, disintegrin and metalloprotease 12, human homolog of Drosophila mothers against decapentaplegic 6, parathyroid hormone receptor 2, glucocorticoid receptor-like 1, phosphodiesterase I, bone morphogenic protein 2, vitamin D receptor, human estrogen receptor 1, TNF receptor associated factor 5,transforming growth factor beta 1, acid phosphatase type 5, cathepsin K, bone morphogenic protein 6, secreted protein, acidic, cysteine-rich, osteonectin, vascular endothelial growth factor A, vascular endothelial growth factor receptor, bone gla protein (osteocalcin), carbonic anhydrase II, alpha-V integrin, early growth response 1, collagen type 1 alpha 2, macrophage colony stimulating factor 1, biglycan, secreted phosphoprotein (osteopontin), insulin growth factor-1, decorin, cathepsin B, colony stimulating factor receptor, and Klotho. The invention also provides a combination wherein the polynucleotides or the complements thereof are SEQ ID NOs: 107–169 that are highly co-expressed with genes known to be involved in bone remodeling and osteoporosis. The invention further provides a combination wherein the polynucleotides or the complements thereof are SEQ ID NOs: 143–169 that are very highly co-expressed with genes known to be involved in bone remodeling and osteoporosis. The invention additionally provides novel polynucleotides or complements thereof selected from SEQ ID NOs: 155–169 which are co-expressed with one or more of the genes known to be involved in bone remodeling and osteoporosis.

The invention provides a method of using a polynucleotide selected from SEQ ID NOs: 155–169 to screen a library of molecules or compounds (DNA molecules, RNA molecules, PNAs, mimetics, and proteins) to identify or purify a ligand which specifically binds the polynucleotide by combining a polynucleotide with a library of molecules or compounds under conditions to allow specific binding, and detecting specific binding, thereby identifying or purifying a ligand which specifically binds the polynuclcotide.

The invention provides for the use of at least one polynucleotide selected from SEQ ID NOs: 1–169 on an array and for the use of that array in a method for diagnosing a bone remodeling disease or disorder by hybridizing the array with a patient sample under conditions to allow complex formation, detecting complex formation, and comparing the amount of complex formation in the patient sample to that of standards for normal and diseased tissues wherein the complex formation in the patient sample indicates the presence of a bone remodeling disease or disorder.

The invention also provides for an expression vector comprising a polynucleotide selected from SEQ ID NOs: 1–169, a host cell transformed with the expression vector and a method for producing a polypeptide, the method comprising: culturing the host cell under conditions for expression of the polypeptide and recovering the polypeptide from cell culture.

The invention further provides for a polypeptide selected from SEQ ID NOs: 170–172, or a portion thereof, comprising the product of a gene that is co-expressed with one or more genes known to be involved in bone remodeling and osteoporosis. The invention additionally provides for the use of the polypeptide or a portion thereof to screen a library of molecules or compounds (DNA molecules, RNA molecules, PNAs, mimetics. proteins, agonists, antagonists, and antibodies) to identify or purify at least one ligand which specifically binds the polypeptide by combining the polypeptide or a portion thereof with the library of molecules or compounds under conditions to allow specific binding, and detecting specific binding between the polypeptide and ligand, thereby identifying or purifying a ligand which specifically binds the polypeptide.

The invention finally provides for a pharmaceutical composition comprising a polynucleotide selected from SEQ ID NOs: 1–169, polypeptide selected from SEQ ID NOs: 170–172, a ligand identified or purified using a selected polynucleotide or polypeptide which modulates the activity of the selected polynucleotide or polypeptide and a suitable pharmaceutical carrier.

BRIEF DESCRIPTION OF THE SEQUENCE LISTING

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The Sequence Listing provides exemplary polynucleotide sequences, SEQ ID NOs: 1–169, and polypeptide sequences, SEQ ID NOs: 170–172, which co-express with genes known to be involved in bone remodeling and osteoporosis. Each sequence is identified by a sequence identification number (SEQ ID NO) and Incyte ID No.

DETAILED DESCRIPTION OF THE INVENTION

It must be noted that as used herein and in the appended claims, the singular forms "a", "an", and "the" include the plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Definitions

"Genes known to be involved in bone remodeling or osteoporosis" have been previously identified as useful in the diagnosis, treatment, prognosis, or prevention of bone diseases and disorders and include the genes which encode PHEX, human parathyroid hormone, TNF receptor associated factor 2, tumor necrosis factor receptor superfamily member 11/RANK ligand, tumor necrosis factor receptor superfamily member 11A/receptor activator of NFkB (RANK), vitamin D 24-hydroxylase, natriuretic precursor protein B, human granulocyte macrophage colony stimulating factor 2, cytochrome P450, subfamily XIX, epidermal growth factor, interleukin 1 alpha, microphthalmia-associated transcription factor, bone morphogenic protein 7, human integrin-binding sialoprotein, beta-3 integrin, alpha-2-Hs-glycoprotein, osteoprotegerin, interleukin 1 beta, SPI 1, matrix metalloprotease 9, parathyroid receptor 1, SRC kinase insert domain receptor, vascular endothelial growth factor receptor, disintegrin and metalloprotease 12, human homolog of Drosophila mothers against decapentaplegic 6, parathyroid hormone receptor 2, glucocorticoid receptor-like 1, phosphodiesterase I, bone morphogenic protein 2, vitamin D receptor, human estrogen receptor 1, TNF receptor associated factor 5,transforming growth factor beta 1, acid phosphatase type 5, cathepsin K, bone morphogenic protein 6, secreted protein, acidic, cysteine-rich, osteonectin, vascular endothelial growth factor A, vascular endothelial growth factor receptor, bone gla protein (osteocalcin), carbonic anhydrase II, alpha-V integrin, early growth response 1, collagen type 1 alpha 2, macrophage colony stimulating factor 1, biglycan, secreted phosphoprotein (osteopontin), insulin growth factor-1, decorin, cathepsin B, colony stimulating factor receptor, and Klotho as presented in Table 3. These genes are expressed at higher levels and have more abundant transcripts in osteoporotic bone tissue than in normal or non-diseased bone or any other tissue.

"Ligand" refers to any molecule, agent, or compound which will bind specifically to a complementary site on a polynucleotide or polypeptide. Such ligands stabilize or modulate the activity of polynucleotides or polypeptides of the invention. For example, ligands may be found among libraries of inorganic and organic molecules or compounds such as nucleic acids, proteins, peptides, mimetics, carbohydrates, fats, and lipids.

"NSEQ" refers generally to a polynucleotide sequence of the present invention and includes SEQ ID NOs:1–169. "PSEQ" refers generally to a polypeptide sequence of the present invention and includes SEQ ID NOs: 170–172.

A "fragment" refers to a nucleic acid sequence that is preferably at least 20 nucleotides in length, more preferably 400 nucleotides, and most preferably 1000 nucleotides in length, and encompasses, for example, fragments consisting of 1–50, 51–400, 401–4000, 4001–12,000 nucleotides, and the like, of SEQ ID NOs: 1–169. Fragment is substantially equivalent to element and probe.

"Gene" refers to the partial or complete coding sequence of a gene including 5' or 3' untranslated, regulatory regions.

"Polynucleotide" refers to a nucleic acid, nucleic acid sequence, oligonucleotide, or any fragment thereof It may be DNA or RNA of genomic or synthetic origin, double-stranded or single-stranded, and combined with carbohydrate, lipids, protein or other materials to perform a particular activity or form a useful composition. "Oligonucleotide" is substantially equivalent to the terms amplimer, primer, and oligomer.

"Polypeptide" refers to an amino acid sequence, oligopeptide, peptide, or protein or portions thereof whether naturally occurring or synthetic.

A "portion" refers to peptide sequence which is preferably at least 5 to about 15 amino acids in length, most preferably at least 10 amino acids long, and which retains some biological or immunological activity of, for example, a portion of SEQ ID NOs: 170–172.

"Sample" is used in its broadest sense. A sample containing nucleic acids may comprise a bodily fluid; an extract from a cell, chromosome, organelle, or membrane isolated from a cell; genomic DNA, RNA, or cDNA in solution or bound to a substrate; a cell; a tissue; a tissue print; and the like.

"Substantially purified" refers to a nucleic acid or an amino acid sequence that is removed from its natural environment and that is isolated or separated, and is at least about 60% free, preferably about 75% free, and most preferably about 90% free, from other components with which it is naturally present.

"Substrate" refers to any rigid or semi-rigid support to which polynucleotides or polypeptides are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

A "variant" refers to a polynucleotide whose sequence diverges from SEQ ID NOs: 1–169. Polynucleotide sequence divergence may result from mutational changes such as deletions, additions, and substitutions of one or more nucleotides; it may also be introduced to accommodate differences in codon usage. Each of these types of changes may occur alone, or in combination, one or more times in a given sequence.

THE INVENTION

The present invention encompasses a method for identifying polynucleotides and polypeptides that are associated with a specific disease, regulatory pathway, subcellular compartment, cell type, tissue type, or species. In particular, the method identifies polynucleotides useful in diagnosis, prognosis, treatment, prevention, and evaluation of therapies for disorders associated with bone remodeling and osteoporosis including, but not limited to, Paget's disease, osteopenia, osteoporosis, osteomalacia, rickets, including vitamin D dependent, type I and II, and x-linked hypophosphatemic rickets, Cushing's disease/syndrome, Turner syndrome, Gaucher disease, hyperparathyroidism, hypoparathyroidism, hyperthyroidism, hypogonadism, thyrotoxicosis, scurvy, calcium deficiency, systemic mastocytosis, adult hypophosphatasia, hyperadrenocorticism, osteogenesis imperfecta, homocystinuria due to cystathionine synthase deficiency, Ehlers-Danlos syndrome, Marfan's syndrome, diabetes, rheumatoid arthritis, epilepsy, primary biliary cirrhosis, chronic obstructive pulmonary disease, Menkes' syndrome, pregnancy and lactation, hepatobiliary disease, distal renal tubular acidosis, chronic renal failure, Fanconi's syndrome, and fibrogenesis imperfecta ossium.

The method entails first identifying polynucleotides that are expressed in a plurality of cDNA libraries. The identified polynucleotides include genes of known or unknown function which are expressed in a specific disease process, subcellular compartment, cell type, tissue type, or species. The expression patterns of the genes with known function are compared with those of genes with unknown function to determine whether a specified co-expression probability threshold is met. Through this comparison, a subset of the polynucleotides having a high co-expression probability with the known genes can be identified. The high co-expression probability correlates with a particular co-expression probability threshold which is preferably less than 0.001 and more preferably less than 0.00001.

The polynucleotides originate from cDNA libraries derived from a variety of sources including, but not limited to, eukaryotes such as human, mouse, rat, dog, monkey, plant, and yeast; prokaryotes such as bacteria; and viruses. These polynucleotides can also be selected from a variety of sequence types including, but not limited to, expressed sequence tags (ESTs), assembled polynucleotide sequences, full length gene coding regions, promoters, introns, enhancers, 5' untranslated regions, and 3' untranslated regions. To have statistically significant analytical results, the polynucleotides need to be expressed in at least three cDNA libraries.

The cDNA libraries used in the co-expression analysis of the present invention can be obtained from adrenal gland, biliary tract, bladder, blood cells, blood vessels, bone marrow, brain, bronchus, cartilage, chromaffin system, colon, connective tissue, cultured cells, embryonic stem cells, endocrine glands, epithelium, esophagus, fetus, ganglia, heart, hypothalamus, immune system, intestine, islets of Langerhans, kidney, larynx, liver, lung, lymph, muscles, neurons, ovary, pancreas, penis, peripheral nervous system, phagocytes, pituitary, placenta, pleurus, prostate, salivary glands, seminal vesicles, skeleton, spleen, stomach, testis, thymus, tongue, ureter, uterus, and the like. The number of cDNA libraries selected can range from as few as 3 to greater than 10,000. Preferably, the number of cDNA libraries is greater than 500.

In a preferred embodiment, genes are assembled from related sequences, such as assembled sequence fragments derived from a single transcript. Assembly of the sequences can be performed using sequences of various types including, but not limited to, ESTs, extensions, or shotgun sequences. In a most preferred embodiment, the polynucleotide sequences are derived from human sequences that have been assembled using the algorithm disclosed in "System and Methods for Analyzing Biomolecular Sequences", Lincoln et al. U.S. Pat. No. 9,276,534, filed Mar. 25, 1999, incorporated herein by reference.

Experimentally, differential expression of the polynucleotides can be evaluated by methods including, but not limited to, differential display by spatial immobilization or by gel electrophoresis, genome mismatch scanning, representational difference analysis, and transcript imaging. Additionally, differential expression can be assessed by microarray technology. These methods may be used alone or in combination.

Genes known to be involved in bone remodeling and osteoporosis are selected based on the published use of the genes or gene products as diagnostic or prognostic markers or as therapeutic targets.

The procedure for identifying novel genes that exhibit a statistically significant co-expression pattern with genes known to be associated with bone remodeling and osteoporosis is as follows. First, the presence or absence of a gene in a cDNA library is defined: a gene is present in a cDNA library when at least one cDNA fragment corresponding to that gene is detected in a cDNA sample taken from the library, and a gene is absent from a library when no corresponding cDNA fragment is detected in the sample.

Second, the significance of gene co-expression is evaluated using a probability method to measure a due-to-chance probability of the co-expression. The probability method can be the Fisher exact test, the chi-squared test, or the kappa test. These tests and examples of their applications are well known in the art and can be found in standard statistics texts (Agresti (1990) *Categorical Data Analysis*, John Wiley & Sons, New York N.Y., Rice (1988) *Mathematical Statistics and Data Analysis*, Duxbury Press, Pacific Grove Calif.). A Bonferroni correction (Rice, supra, p. 384) can also be applied in combination with one of the probability methods for correcting statistical results of one gene versus multiple other genes. In a preferred embodiment, the due-to-chance probability is measured by a Fisher exact test, and the threshold of the due-to-chance probability is set preferably to less than 0.001, more preferably to less than 0.00001.

To determine whether two genes, A and B. have similar co-expression patterns, occurrence data vectors can be generated as illustrated in Table 1. The presence of a gene occurring at least once in a library is indicated by a one, and its absence from the library, by a zero.

TABLE 1

Occurrence data for genes A and B

| | Library 1 | Library 2 | Library 3 | . . . | Library N |
|---|---|---|---|---|---|
| gene A | 1 | 1 | 0 | . . . | 0 |
| gene B | 1 | 0 | 1 | . . . | 0 |

For a given pair of genes, the occurrence data in Table 1 can be summarized in a 2×2 contingency table.

TABLE 2

Contingency table for co-occurrences of genes A and B

| | Gene A present | Gene A absent | Total |
|---|---|---|---|
| Gene B present | 8 | 2 | 10 |
| Gene B absent | 2 | 18 | 20 |
| Total | 10 | 20 | 30 |

Table 2 presents co-occurrence data for gene A and gene B in a total of 30 libraries. Both gene A and gene B occur 10 times in the libraries. Table 2 summarizes and presents: 1) the number of times gene A and B are both present in a library; 2) the number of times gene A and B are both absent in a library; 3) the number of times gene A is present, and gene B is absent; and 4) the number of times gene B is present, and gene A is absent. The upper left entry is the number of times the two genes co-occur in a library, and the middle right entry is the number of times neither gene occurs in a library. The off diagonal entries are the number of times one gene occurs, and the other does not. Both A and B are present eight times and absent 18 times. Gene A is present, and gene B is absent, two times; and gene B is present, and gene A is absent, two times. The probability (p-value) that the above association occurs due to chance as calculated using a Fisher exact test is 0.0003. Associations are generally considered significant if a p-value is less than 0.01 (Agresti, supra; Rice, supra).

This method of estimating the probability for co-expression of two genes makes several assumptions. The method assumes that the libraries are independent and are identically sampled. However, in practical situations, the selected cDNA libraries are not entirely independent, because more than one library may be obtained from a single subject or tissue. Nor are they entirely identically sampled, because different numbers of cDNAs may be sequenced from each library. The number of cDNAs sequenced typically ranges from 5,000 to 10,000 cDNAs per library. In addition, because a Fisher exact co-expression probability is calculated for each gene versus 45,233 other assembled genes, a Bonferroni correction for multiple statistical tests is used.

The present invention identifies 169 novel polynucleotides that exhibit strong association with genes known to be involved in bone remodeling or osteoporosis. The results presented in "Tables 4 and 5" show that the expression of the 169 novel polynucleotides has direct or indirect association with the expression of genes known to be involved in bone remodeling. Therefore, the novel polynucleotides can potentially be used in diagnosis, treatment, prognosis, or prevention of bone diseases or disorders or in the evaluation of therapies for such diseases and disorders. Further, the gene products of the 169 novel polynucleotides are either potential therapeutics or targets of therapeutics against bone diseases and disorders.

Therefore, in one embodiment, the present invention encompasses a polynucleotide sequence comprising the sequence of SEQ ID NOs: 1–169. These 169 polynucleotides are shown by the method of the present invention to have strong co-expression association with genes known to be involved in bone remodeling and osteoporosis and with each other. The invention also encompasses a variant of the polynucleotide sequence, its complement, or 15 consecutive nucleotides of a sequence provided in the above described sequences. Variant polynucleotide sequences typically have at least about 75%, more preferably at least about 85%, and most preferably at least about 95% polynucleotide sequence identity to NSEQ.

NSEQ or the encoded PSEQ may be used to search against the GenBank primate (pri), rodent (rod), mammalian (mam), vertebrate (vrtp), and eukaryote (eukp) databases, SwissProt, BLOCKS (Bairoch et al. (1997) Nucleic Acids Res. 25:217–221), PFAM, and other databases that contain previously identified and annotated motifs, sequences, and gene functions. Methods that search for primary sequence patterns with secondary structure gap penalties (Smith et al. (1992) Protein Engineering 5:35–51) as well as algorithms such as Basic Local Alignment Search Tool (BLAST; Altschul (1993) J Mol Evol 36:290–300; Altschul et al. (1990) J Mol Biol 215:403–410), BLOCKS (Henikoff and Henikoff (1991) Nucleic Acids Res 19:6565–6572), Hidden Markov Models (HMM; Eddy (1996) Cur Opin Str Biol 6:361–365; Sonnhammer et al. (1997) Proteins 28:405–420), and the like, can be used to manipulate and analyze nucleotide and amino acid sequences. These databases, algorithms and other methods are well known in the art and are described in Ausubel et al. (1997*; Short Protocols in Molecular Biology*, John Wiley & Sons, New York N.Y., unit 7.7) and in Meyers (1995*; Molecular Biology and Biotechnology*, Wiley VCH, New York N.Y., p 856–853).

Also encompassed by the invention are polynucleotide sequences that are capable of hybridizing to SEQ ID NOs: 1–169, and fragments thereof under stringent conditions. Stringent conditions can be defined by salt concentration, temperature, and other chemicals and conditions well known in the art. Conditions can be selected, for example, by varying the concentrations of salt in the prehybridization, hybridization, and wash solutions or by varying the hybridization and wash temperatures. With some substrates, the temperature can be decreased by adding formamide to the prehybridization and hybridization solutions.

Hybridization can be performed at low stringency. with buffers such as 5×SSC with 1% sodium dodecyl sulfate (SDS) at 60° C., which permits complex formation between two nucleic acid sequences that contain some mismatches. Subsequent washes are performed at higher stringency with buffers such as 0.2×SSC with 0.1% SDS at either 45° C. (medium stringency) or 68° C. (high stringency), to maintain hybridization of only those complexes that contain completely complementary sequences. Background signals can be reduced by the use of detergents such as SDS, Sarcosyl, or Triton X-100, and/or a blocking agent, such as salmon sperm DNA. Hybridization methods are described in detail in Ausubel (supra, units 2.8–2.11, 3.18–3.19 and 4–6–4.9) and Sambrook et al. (1989*; Molecular Cloning. A Laboratory Manual*, Cold Spring Harbor Press, Plainview N.Y.)

NSEQ can be extended utilizing a partial nucleotide sequence and employing various PCR-based methods known in the art to detect upstream sequences such as promoters and other regulatory elements. (Sec, e.g., Dieffenbach and Dveksler (1995) *PCR Primer, a Laboratory Manual*, Cold Spring Harbor Press, Plainview N.Y.). Additionally, one may use an XL-PCR kit (PE Biosystems, Foster City Calif.), nested primers, and commercially available cDNA libraries (Life Technologies, Rockville Md.) or genomic libraries (Clontech, Palo Alto Calif.) to extend the sequence. For all PCR-based methods, primers may be designed using commercially available software, such as OLIGO 4.06 Primer Analysis software (National Biosciences, Plymouth Minn.) or another program, to be about 15 to 30 nucleotides in length, to have a GC content of about 50%, and to form a hybridization complex at temperatures of about 68° C. to 72° C.

In another aspect of the invention, NSEQ can be cloned in recombinant DNA molecules that direct the expression of PSEQ, or structural or functional portions thereof, in host cells. Due to the inherent degeneracy of the genetic code, other DNA sequences which encode substantially the same or a functionally equivalent amino acid sequence may be produced and used to express the polypeptide encoded by NSEQ. The nucleotide sequences of the present invention can be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In order to express a biologically active polypeptide, NSEQ, or derivatives thereof, may be inserted into an expression vector, i.e., a vector which contains the elements for transcriptional and translational control of the inserted coding sequence in a particular host. These elements include regulatory sequences, such as enhancers, constitutive and inducible promoters, and 5' and 3' untranslated regions. Methods which are well known to those skilled in the art may be used to construct such expression vectors. These methods include in vitro recombinant DNA techniques, synthetic techniques, and in vivo genetic recombination. (See, e.g., Sambrook, supra; and Ausubel, supra).

A variety of expression vector/host cell systems may be utilized to express NSEQ. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long term production of recombinant proteins in mammalian systems, stable expression in cell lines is preferred. For example, NSEQ can be transformed into cell lines using expression vectors which may contain viral origins of replication and/or endogenous expression elements and a selectable or visible marker gene on the same or on a separate vector. The invention is not to be limited by the vector or host cell employed.

In general, host cells that contain NSEQ and that express PSEQ may be identified by a variety of procedures known to those of skill in the art. These procedures include, but are not limited to, DNA—DNA or DNA-RNA hybridizations, PCR amplification, and protein bioassay or immunoassay techniques which include membrane, solution, or chip based technologies for the detection and/or quantification of nucleic acid or amino acid sequences. Immunological methods for detecting and measuring the expression of PSEQ using either specific polyclonal or monoclonal antibodies arc known in the art. Examples of such techniques include enzyme-linked immunosorbent assays (ELISAs), radioimmunoassays (RIAs), and fluorescence activated cell sorting (FACS).

Host cells transformed with NSEQ may be cultured under conditions for the expression and recovery of the polypeptide from cell culture. The polypeptide produced by a transgenic cell may be secreted or retained intracellularly depending on the sequence and/or the vector used. As will be understood by those of skill in the art, expression vectors containing NSEQ may be designed to contain signal sequences which direct secretion of the polypeptide through a prokaryotic or eukaryotic cell membrane.

In addition, a host cell strain may be chosen for its ability to modulate expression of the inserted sequences or to process the expressed polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide may also be used to specify, protein targeting, folding, and/or activity. Different host cells which have specific cellular machinery and characteristic mechanisms for post-translational activities (e.g., CHO, HeLa, MDCK, HEK293, and W138) are available from the American Type Culture Collection (ATCC, Manassas Md.) and may be chosen to ensure the correct modification and processing of the expressed polypeptide.

In another embodiment of the invention, natural, modified, or recombinant nucleic acid sequences are ligated to a heterologous sequence resulting in translation of a fusion polypeptide containing heterologous polypeptide moieties in any of the aforementioned host systems. Such heterologous polypeptide moieties facilitate purification of fusion polypeptides using commercially available affinity matrices. Such moieties include, but are not limited to, glutathione S-transferase, maltose binding protein, thioredoxin, calmodulin binding peptide, 6-His, FLAG, c-myc, hemaglutinin, and monoclonal antibody epitopes.

In another embodiment, the nucleic acid sequences are synthesized, in whole or in part, using chemical or enzymatic methods well known in the art (Caruthers et al. (1980) Nucl Acids Symp Ser 215–233; Ausubel, supra). For example, peptide synthesis can be performed using various solid-phase techniques (Roberge et al. (1995) Science 269:202–204), and machines such as the ABI 431A Peptide synthesizer (PE Biosystems) can be used to automate synthesis. If desired, the amino acid sequence may be altered during synthesis and/or combined with sequences from other proteins to produce a variant protein.

In another embodiment, the invention entails a substantially purified polypeptide comprising the amino acid sequence of SEQ ID NOs: 170–172 and fragments thereof.

SCREENING, DIAGNOSTICS AND THERAPEUTICS

The polynucleotide sequences can be used in diagnosis, prognosis, treatment, prevention, and selection and evaluation of therapies for diseases and disorders involved in bone remodeling or osteoporosis including, but not limited to, Paget's disease, osteopenia, osteoporosis, osteomalacia, rickets, including vitamin D dependent, type I and II, and x-linked hypophosphatemic rickets, Cushing's disease/syndrome, Tumer syndrome, Gaucher disease, hyperparathyroidism, hypoparathyroidism, hyperthyroidism, hypogonadism, thyrotoxicosis, scurvy, calcium deficiency, systemic mastocytosis, adult hypophosphatasia, hyperadrenocorticism, osteogenesis imperfecta, homocystinuria due to cystathionine synthase deficiency, Ehlers-Danlos syndrome, Marfan's syndrome, diabetes, rheumatoid arthritis, epilepsy, primary biliary cirrhosis, chronic obstructive pulmonary disease, Menkes' syndrome, pregnancy and lactation, hepatobiliary disease, distal renal tubular acidosis, chronic renal failure, Fanconi's syndrome. and fibrogenesis imperfecta ossium.

The polynucleotide sequences may be used to screen a library of molecules for specific binding affinity. The assay can be used to screen a library of DNA molecules, RNA molecules, PNAs, peptides, ribozymes, antibodies, agonists, antagonists, immunoglobulins, inhibitors, proteins including transcription factors, enhancers, repressors, and drugs and the like which regulate the activity of the polynucleotide sequence in the biological system. The assay involves providing a library of molecules, combining the polynucleotide sequence or a fragment thereof with the library of molecules under conditions suitable to allow specific binding, and detecting specific binding to identify, at least one molecule which specifically binds the polynucleotide sequence.

Similarly the polypeptides or portions thereof may be used to screen libraries of molecules or compounds in any of a variety of screening assays. The portion of a polypeptide employed in such screening may be free in solution, affixed to an abiotic or biotic substrate (e.g. bome on a cell surface), or located intracellularly. Specific binding between the polypeptide and the molecule may be measured. The assay can be used to screen a library of DNA molecules, RNA molecules, PNAs, peptides, mimetics, ribozymes, antibodies, agonists, antagonists, immunoglobulins, inhibitors, peptides, polypeptides, drugs and the like, which specifically bind the polypeptide. One method for high throughput screening using very small assay volumes and very small amounts of test compound is described in Burbaum et al. U.S. Pat. No. 5,876,946, incorporated herein by reference, which screens large numbers of molecules for enzyme inhibition or receptor binding.

In one preferred embodiment, the polynucleotide sequences are used for diagnostic purposes to determine the absence, presence, or altered-increased or decreased compared to a normal standard-expression of the gene. The polynucleotides may be at least 15 nucleotides long and consist of complementary RNA and DNA molecules, branched nucleic acids, and/or peptide nucleic acids (PNAs). In one alternative, the polynucleotides are used to detect and quantify gene expression in samples in which expression of NSEQ is correlated with disease. In another alternative, NSEQ can be used to detect genetic polymorphisms associated with a disease. These polymorphisms may be detected in the transcript cDNA.

The specificity of the probe is determined by whether it is made from a unique region, a regulatory region, or from a conserved motif. Both probe specificity and the stringency of diagnostic hybridization or amplification (maximal, high, intermediate, or low) will determine whether the probe identifies only naturally occurring, exactly complementary sequences, allelic variants, or related sequences. Probes designed to detect related sequences should preferably have at least 50% sequence identity to any of the polynucleotides encoding PSEQ.

Methods for producing hybridization probes include the cloning of nucleic acid sequences into vectors for the production of mRNA probes. Such vectors are known in the art, are commercially available, and may be used to synthesize RNA probes in vitro by adding RNA polymerases and labeled nucleotides. Hybridization probes may incorporate nucleotides labeled by a variety of reporter groups including, but not limited to, radionuclides such as $^{32}$p or $^{35}$S, enzymatic labels such as alkaline phosphatase coupled to the probe via avidin/biotin coupling systems, fluorescent labels, and the like. The labeled polynucleotide sequences may be used in Southern or northern analysis, dot blot, or other membrane-based technologies; in PCR technologies; and in microarrays utilizing samples from subjects to detect altered PSEQ expression.

NSEQ can be labeled by standard methods and added to a sample from a subject under conditions for the formation and detection of hybridization complexes. After incubation the sample is washed, and the signal associated with hybrid complex formation is quantitated and compared with a standard value. Standard values are derived from any control sample, typically one that is free of the suspect disease. If the amount of signal in the subject sample is altered in comparison to the standard value, then the presence of altered levels of expression in the sample indicates the presence of the disease. Qualitative and quantitative methods for comparing the hybridization complexes formed in subject samples with previously established standards are well known in the art.

Such assays may also be used to evaluate the efficacy of a particular therapeutic treatment regimen in animal studies, in clinical trials, or to monitor the treatment of an individual subject. Once the presence of disease is established and a treatment protocol is initiated, hybridization or amplification assays can be repeated on a regular basis to determine if the level of expression in the patient begins to approximate that which is observed in a healthy subject. The results obtained from successive assays may be used to show the efficacy of treatment over a period ranging from several days to many years.

The polynucleotides may be used for the diagnosis of a variety of diseases or disorders associated with bone remodeling or osteoporosis. These include, but are not limited to, Paget's disease, osteopenia, osteoporosis, osteomalacia, rickets, including vitamin D dependent, type I and II, and x-linked hypophosphatemic rickets, Cushing's disease/syndrome, Tumer syndrome, Gaucher disease, hyperparathyroidism, hypoparathyroidism, hyperthyroidism, hypogonadism, thyrotoxicosis, scurvy, calcium deficiency, systemic mastocytosis, adult hypophosphatasia, hyperadrenocorticism, osteogenesis imperfecta, homocystinuria due to cystathionine synthase deficiency, Ehlers-Danlos syndrome, Marfan's syndrome, diabetes, rheumatoid arthritis, epilepsy, primary biliary cirrhosis, chronic obstructive pulmonary disease, Menkes' syndrome, pregnancy and lactation, hepatobiliary disease, distal renal tubular acidosis, chronic renal failure, Fanconi's syndrome, and fibrogenesis imperfecta ossium.

The polynucleotides may also be used as targets in a microarray. The microarray can be used to monitor the expression patteins of large numbers of genes simultaneously and to identify splice variants, mutations, and polymorphisms. Information derived from analyses of the expression patterns may be used to determine gene function, to understand the genetic basis of a disease, to diagnose a disease, and to develop and monitor the activities of therapeutic agents used to treat a disease. Microarrays may also be used to detect genetic diversity, single nucleotide polymorphisms which may characterize a particular population, at the genome level.

In yet another alternative, polynucleotides may be used to generate hybridization probes useful in mapping the naturally occurring genomic sequence. Fluorescent in situ hybridization (FISH) may be correlated with other physical chromosome mapping techniques and genetic map data as described in Heinz-Ulrich et al. (In: Meyers, supra, pp. 965–968).

In another embodiment, antibodies or Fabs comprising an antigen binding site that specifically binds PSEQ may be used for the diagnosis of diseases characterized by the over-or-under expression of PSEQ. A variety of protocols for measuring PSEQ, including ELISAs, RIAs, and FACS, are well known in the art and provide a basis for diagnosing altered or abnormal levels of expression. Standard values for PSEQ expression are established by combining samples taken from healthy subjects, preferably human, with antibody to PSEQ under conditions for complex formation The amount of complex formation may be quantitated by various methods, preferably by photometric means. Quantities of PSEQ expressed in disease samples are compared with standard values. Deviation between standard and subject values establishes the parameters for diagnosing or monitoring disease. Alternatively, one may use competitive drug screening assays in which neutralizing antibodies capable of binding PSEQ specifically compete with a test compound for binding the polypeptide. Antibodies can be used to detect the presence of any peptide which shares one or more antigenic determinants with PSEQ. In one aspect, the anti-PSEQ antibodies of the present invention can be used for treatment or monitoring therapeutic treatment for bone remodeling disorders or osteoporosis.

In another aspect, the NSEQ, or its complement, may be used therapeutically for the purpose of expressing mRNA and polypeptide, or conversely to block transcription or translation of the mRNA. Expression vectors may be constructed using elements from retroviruses, adenoviruses, herpes or vaccinia viruses, or bacterial plasmids, and the like. These vectors may be used for delivery of nucleotide sequences to a particular target organ, tissue, or cell population. Methods well known to those skilled in the art can be used to construct vectors to express nucleic acid sequences or their complements. (See, e.g., Maulik et al. (1997) *Molecular Biotechnology, Therapeutic Applications and Strategies*, Wiley-Liss, New York N.Y.) Alternatively, NSEQ, or its complement, may be used for somatic cell or stem cell gene therapy. Vectors may be introduced in vivo, in vitro, and ex vivo. For ex vivo therapy, vectors are introduced into stem cells taken from the subject, and the resulting transgenic cells are clonally propagated for autologous transplant back into that same subject. Delivery of NSEQ by transfection, liposome injections, or polycationic amino polymers may be achieved using methods which are well known in the art. (See, e.g., Goldman et al. (1997) Nature Biotechnology 15:462–466.) Additionally, endogenous NSEQ expression may be inactivated using homologous recombination methods which insert an inactive gene sequence into the coding region or other targeted region of NSEQ. (See, e.g. Thomas et al. (1987) Cell 51: 503–512.)

Vectors containing NSEQ can be transformed into a cell or tissue to express a missing polypeptide or to replace a nonfunctional polypeptide. Similarly a vector constructed to express the complement of NSEQ can be transformed into a cell to downregulate the overexpression of PSEQ. Complementary or antisense sequences may consist of an oligonucleotide derived from the transcription initiation site; nucleotides between about positions −10 and +10 from the ATG are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee et al. In: Huber and Carr (1994) *Molecular and Immunologic Approaches*, Futura Publishing Co., Mt. Kisco N.Y., pp. 163–177.)

Ribozymes, enzymatic RNA molecules, may also be used to catalyze the cleavage of mRNA and decrease the levels of particular mRNAs, such as those comprising the polynucleotide sequences of the invention. (See, e.g., Rossi (1994) Current Biology 4: 469–471.) Ribozymes may cleave mRNA at specific cleavage sites. Alternatively, ribozymes may cleave mRNAs at locations dictated by flanking regions that form complementary base pairs with the target mRNA. The construction and production of ribozymes is well known in the art and is described in Meyers (supra).

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiester linkages within the backbone of the molecule. Alternatively, nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases, may be included.

Further, an antagonist, or an antibody that binds specifically to PSEQ may be administered to a subject to treat or prevent diseases or disorders associated with bone remodeling or osteoporosis. The antagonist, antibody, or fragment may be used directly to inhibit the activity of the polypeptide or indirectly to deliver a therapeutic agent to cells or tissues which express the PSEQ. An immunoconjugate comprising a PSEQ binding site of the antibody or the antagonist and a therapeutic agent may be administered to a subject in need to treat or prevent disease. The therapeutic agent may be a cytotoxic agent selected from a group including, but not limited to, abrin, ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, Pseudomonas exotoxin A and 40, radioisotopes, and glucocorticoid.

Antibodies to PSEQ may be generated using methods that are well known in the art. Such antibodies may include, but are not limited to, polyclonal, monoclonal, chimeric, and single chain antibodies, Fab fragments, and fragments produced by a Fab expression library. Neutralizing antibodies, such as those which inhibit dimer formation, are especially preferred for therapeutic use. Monoclonal antibodies to PSEQ may be prepared using any technique which provides for the production of antibody molecules by continuous cell lines in culture. These include, but are not limited to, the hybridoma, the human B-cell hybridoma, and the EBV-hybridoma techniques. In addition, techniques developed for the production of chimeric antibodies can be used. (See, e.g., Pound (1998) *Immunochemical Protocols*, Methods Mol Biol Vol. 80). Alternatively, techniques described for the production of single chain antibodies may be employed. Fabs which contain specific binding sites for PSEQ may also be generated. Various immunoassays may be used to identify antibodies having the desired specificity. Numerous protocols for competitive binding or immunoradiometric assays using either polyclonal or monoclonal antibodies with established specificities are well known in the art.

Yet further, an agonist of PSEQ may be administered to a subject to treat or prevent a disease associated with decreased expression, longevity or activity of PSEQ.

An additional aspect of the invention relates to the administration of a pharmaceutical or sterile composition, in conjunction with a pharmaceutically acceptable carrier, for any of the therapeutic applications discussed above. Such pharmaceutical compositions may consist of PSEQ or antibodies, mimetics, agonists, antagonists, or inhibitors of the polypeptide. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a subject alone or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton Pa.).

For any compound, the therapeutically effective dose can be estimated initially either in cell culture assays or in animal models such as mice, rats, rabbits, dogs, or pigs. An animal model may also be used to determine the concentration range and route of administration. Such information can then be used to determine useful doses and routes for administration in humans.

A therapeutically effective dose refers to that amount of active ingredient which ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and most preferably, humans.

EXAMPLES

It is to be understood that this invention is not limited to the particular devices, machines, materials and methods described. Although particular embodiments are described, equivalent embodiments may be used to practice the invention. The described embodiments are provided to illustrate the invention and are not intended to limit the scope of the invention which is limited only by the appended claims.

I cDNA Library Construction

The cDNA library, BONTNOT01, was selected as an example to demonstrate the construction of cDNA libraries from which the novel polynucleotides were derived. The BONTNOT01 tibial periosteum library was constructed using 7 nanograms of polyA RNA isolated from tibial periosteum removed from a 20-year-old Caucasian male. Pathology for the matched tumor tissue indicated partially necrotic and cystic ostcoblastic grade 3 osteosarcoma (post-chemotherapy). The tumor involved almost the entire length of the femoral shaft along the site of a previously placed metal rod tract.

The frozen tibial periosteum was homogenized and lysed in a guanidinium isothiocyanate solution using a POLYTRON homogenizer (PT-3000, Brinkmann Instruments, Westbury N.J.). The lysate was centrifuged over a 5.7 M CsCl cushion using an SW28 rotor in an L8-70M ultracentrifuge (Beckman Coulter, Fullerton Calif.) for 18 hours at 25,000 rpm at ambient temperature. The RNA was extracted with acid phenol, pH 4.7, precipitated using 0.3 M sodium acetate and 2.5 volumes of ethanol, resuspended in RNAse-free water, and treated with DNase at 37° C. RNA extraction and precipitation was repeated as before. The mRNA was isolated with the OLIGOTEX kit (Qiagen, Chatsworth Calif.) and used to construct the cDNA library.

The mRNA was handled according to the recommended protocols in the SUPERSCRIPT plasmid system (Life Technologies). The cDNAs were fractionated on a SEPHAROSE CL-4B column (Amersham Pharmacia Biotech, Piscataway N.J.), and those cDNAs exceeding 400 bp were ligated into PSPORT I (Life Technologies). The plasmid was subsequently transformed into DH5α competent cells (Life Technologies).

II Isolation and Sequencing of cDNA Clones

Plasmid DNA was released from the cells and purified using the REAL PREP 96 plasmid kit (Qiagen). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Life Technologies) with carbenicillin at 25 mg/l and glycerol at 0.4%; 2) after inoculation, the cells were cultured for 19 hours and lysed with 0.3 ml of Iysis buffer; and 3) following isopropanol precipitation, the DNA pellet was resuspended in 0.1 ml of distilled water. After the last step in the protocol, samples were transferred to a 96-well block for storage at 4° C.

The cDNAs were prepared using a MICROLAB 2200 system (Hamilton, Reno Nev.) in combination with DNA ENGINE thermal cyclers (PTC200; MJ Research, Waltham Mass.). The cDNAs were sequenced by the method of Sanger and Coulson (1975; J. Mol. Biol. 94:441f) using ABI PRISM 377 DNA sequencing systems (PE Biosystems). Most of the sequences were sequenced using standard ABI protocols and kits (PE Biosystems) at solution volumes of 0.25×–1.0×. In the alternative, some of the sequences were sequenced using solutions and dyes from Amersham Pharmacia Biotech.

III Selection, Assembly, and Characterization of Sequences

The sequences used for co-expression analysis were assembled from EST sequences, 5' and 3'long read sequences, and full length coding sequences. Selected assembled sequences were expressed in at least three cDNA libraries.

The assembly process is described as follows. EST sequence chromatograms were processed and verified. Quality scores were obtained using PHRED (Ewing et al. (1998) Genome Res 8:175–185; Ewing and Green (1998) Genome Res 8:186–194), and edited sequences were loaded into a relational database management system (RDBMS). The sequences were clustered using BLAST with a product score of 50. All clusters of two or more sequences created a bin which represents one transcribed gene.

Assembly of the component sequences within each bin was performed using a modification of Phrap, a publicly available program for assembling DNA fragments (Green, P. University of Washington, Seattle Wash.). Bins that showed 82% identity from a local pair-wise alignment between any of the consensus sequences were merged.

Bins were annotated by screening the consensus sequence in each bin against public databases, such as GBpri and GenPept from NCBI. The annotation process involved a FASTn screen against the GBpri database in GenBank. Those hits with a percent identity of greater than or equal to 75% and an alignment length of greater than or equal to 100 base pairs were recorded as homolog hits. The residual unannotated sequences were screened by FASTx against GenPept. Those hits with an E value of less than or equal to $10^{-8}$ were recorded as homolog hits.

Sequences were then reclustered using BLASTn and Cross-Match, a program for rapid amino acid and nucleic acid sequence comparison and database search (Green. supra), sequentially. Any BLAST alignment between a sequence and a consensus sequence with a score greater than 150 was realigned using cross-match. The sequence was added to the bin whose consensus sequence gave the highest Smith-Waterman score (Smith et al. (1992) Protein Engineering 5:35–51) amongst local alignments with at least 82% identity. Non-matching sequences were moved into new bins. and assembly processes were repeated.

IV Co-expression Analyses of Bone Remodeling and Osteoporosis-Associated Genes Fifty-five genes known to be involved in bone remodeling and osteoporosis were selected to identify the novel polynucleotides of the Sequence Listing. The known genes and brief descriptions of their functions are listed in Table 3.

TABLE 3

Descriptions of Genes Known To Be Involved in Bone Remodeling and Osteoporosis

| Gene | Gene Symbol | Description | Reference |
|---|---|---|---|
| phosphate-regulating gene with homologies to endopeptidases on the X chromosome | PHEX | PHEX is a marker for the fully differentiated osteoblast with a role in bone mineralization. Mutations found to be responsible for X-linked vitamin D resistant hypophosphataemic rickets. PHEX gene mutations discovered in naturally occurring mouse models of hypophosphataemic rickets. | Strom et al. (1997) Hum Mol Genet 6: 165–171; Ecarot and Desbarats (1999) Endocrinology 140: 1192–1199 |
| Parathyroid hormone | PTH | Principle regulator of bone remodeling of the adult skeleton and in the homeostasis of calcium within the blood stream. In vivo effect of PTH is to increase bone resorption, sustained increases in PTH increase resorption and formation. Forms of hyperparathyroidism thought to contribute to increased bone loss in post-menopausal women. PTH now used in anabolic therapy for osteoporosis. | Jilka et al. (1999) J Clin Invest 104: 439–446; Mierke and Pellegrini (1999) Curr Pharm Des 5: 21–36 |

TABLE 3-continued

Descriptions of Genes Known To Be Involved in Bone Remodeling and Osteoporosis

| Gene | Gene Symbol | Description | Reference |
|---|---|---|---|
| TNF receptor associated factor 2 | TRAF2 | Binds to the intracellular domain of RANK/TNFRSF11A, which is an essential regulator of osteoclastogenesis. TRAF/RANK interaction is functionally important for the RANK-dependent induction of NF-kappaB and c-Jun NH2-terminal kinase activities during osteoclastogenesis. | Hsu et al. (1999) Proc Natl Acad Sci 96: 3540–3545; Yeh et al. (1997) Immunity 7: 715–725; Darnay et al. (1998) J Biol Chem 273: 20551–20555. |
| tumor necrosis factor receptor superfamily member 11/RANK ligand | TNFSF11 | TNF-related cytokine that binds hematopoietic progenitor cells committed to the osteoclast lineage, and stimulates the rapid induction of genes that typify osteoclast development. Functions as an osteoclast differentiation and activation factor. Knockout mouse is severely osteopetrotic and hypocalcaemic with a defect in tooth eruption. Completely lack osteoclasts and have defects in early T and B lyphocyte differentiation. | Lacey et al. (1998) Cell 93: 165–176; Kong et al. (1999) Nature 397: 315–323. |
| tumor necrosis factor receptor superfamily member 11A/ receptor activator of NFkB. (RANK) | TNFRSF1 1A | Essential for osteoclastogenesis. Interacts with OPG, OPGL/RANKL to control key regulatory events in bone metabolism. Pivotal involvement in bone catabolism: expressed in monocyte/macrophage family, which give rise to osteoclast lineage. Mice that overexpress a soluble RANK fusion protein lacking the activation domain have severe osteopetrosis due to reduction in osteoclastogenesis. | Nakagawa et al. (1998) Biochem Biophys Res Commun 253: 395–400; Hsu et al. (1999) Proc Natl Acad Sci 96: 3540–3545. |
| Vitamin D 24-hydroxylase | CYP24 | Vitamin D metabolizing enzyme which directly affects the level of active vitamin D metabolite 1,25-(OH)2D3. Vitamin D plays a crucial role in bone metabolism. | Chen et al. (1993) Proc Natl Acad Sci 90: 4543–4547; St-Arnaud (1999) Bone 25: 127–129. |
| natriuretic precursor protein B | NPPB | Studies in vitro and with transgenic mice suggest that NPPB affects the process of endochondral ossification and hence longitudinal bone growth. Transgenic mice with elevated plasma BNP concentrations exhibited bone abnormalities resulted from a high turnover of endochondral ossification accompanied by overgrowth of the growth plate. | Suda et al. (1998) Proc Natl Acad Sci 95: 2337–42. |
| granulocyte macrophage colony stimulating factor 2 | CSF2 | Essential cytokine for osteoclast differentiation. Northern analysis and immunoprecipitation on murine osteoclast precursors demonstrated GM-CSF induces cell surface integrins of the mature osteoclast. Negatively regulated by estrogen and may therefore play a role in menopause-associated osteoporosis. | Teitelbaum et al. (1997) J Leukoc Biol 61: 381–8. |
| cytochrome P450, subfamily XIX | CYP19 | Estrogen synthetase which catalyses the formation of C18 estrogens from C19 androgens. Unique transcript noted in bone cells and this enzyme is produced locally in osteoblasts indicating independence from circulating estrogen in bone tissue. Human mutations in CYP19 result in estrogen deficiency with increased bone turnover and osteoporosis in both sexes. | Shozu and Simpson (1998) Mol Cell Endocrinol 139: 117–29; Eyre et al. (1998) J Bone Miner Res 13: 996–1004; MacGillivray et al. (1998) Horm Res 49 (Suppl 1): 2–8. |
| epidermal growth factor | EGF | Regulates chondrogenesis by opposing the action of BMP4. EGF found to be important in outgrowth of limb mesoderm, regulation of limb chondrogeneic and myogenic differentiation. | Dealy et al. (1998) Dev Biol 202: 43–55; Kretzschmar et al. (1997) Nature 389: 618–22. |
| interleukin I alpha | IL1A | IL1A plays a crucial part in bone remodeling by stimulating osteoclast activity. Found to stimulate osteoclast activity in vitro and modulate calcium signalling pathway in osteoblasts. Subcutaneous injections of IL1A in mice cause increase in plasma calcium and an increase in bone resorption surfaces and osteoclast number. | Tam et al. (1998) Am J Physiol 274: C1686–98; Sabatini et al. (1988) Proc Natl Acad Sci 85: 5235–9. |
| Microphthalmia-associated Transcription Factor | MITF | MITF is a transcription factor which is central to osteoclastogenesis. It specifically binds PU.1 (SPI) and c-fos, essential transcription factors in osteoclastogenesis, and regulates their nuclear localization. Mutations in MITF block SPI and c-fos nuclear translocation and result in osteopetrosis in mi/mi mice. Also has a role in transactivation of cathepsin K cooperatively with other transcription factors. | Sato et al. (1999) Biochem Biophys Res Commun 254: 384–7. |

TABLE 3-continued

Descriptions of Genes Known To Be Involved in Bone Remodeling and Osteoporosis

| Gene | Gene Symbol | Description | Reference |
|---|---|---|---|
| Bone morphogenic protein 7 | BMP7 | Expressed in centres of ossification: periosteum, perichondrium and hypertrophic cartilage. Can induce local formation of ectopic bone and cartilage when injected into subcutaneous tissue and muscle in rats. | Reddi and Cunningham (1993) J Bone Miner Res 8 (Suppl 2): S499–502; Chang et al. (1994) J Biol Chem 269: 28227–34. |
| integrin-binding sialoprotein | IBSP | Acidic glycoprotein which makes up 12% of non-collagenous proteins in human bone, synthesized by osteocytes, osteoblasts, osteoclasts, hypertrophic chondrocytes. Marker of osteoblasts. Expression is regulated by vitamin D3 and BMP-2. | Bellows et al. (1999) Cell Tissue Res 297: 249–59. |
| beta-3 integrin | ITGB3 | Essential for osteoclast function, since it mediates osteoclast attachment to bone, and spreading. Mice lacking ITGB3 have 3.5x more osteoclasts than wild type control littermates and have hypocalcaemic and sclerotic bones, decreased bone degradation and fewer resorptive pits and platelet disorder. | Faccio et al. (1998) Biochem Biophys Res Commun 249: 522–5. Hodivala-Dilke et al. (1999) J Clin Invest 103: 229–38. |
| alpha-2-Hs-glycoprotein | AHSG | Possible role in calcium homeostasis and inhibition of unwanted mineralization. Mice lacking AHSG exhibit ectopic calcification in soft tissue, and appear to show a lack of inhibition of apatite formation. | Jahnen-Dechent et al. (1997) J Biol Chem 272: 31496–503. |
| osteoprotegerin | TNFRSF11B | Negative regulator of osteoclastogenesis. Adolescent and adult knockout mice exhibit increased bone porosity, decreased bone density and increased fractures. | Simonet et al. (1997) Cell 89: 309–19; Yasuda et al. (1998) Endocrinology 139: 1329–37; Bucay et al. (1998) Genes Dev 12: 1260–8. |
| interleukin 1 beta | IL1B | Potent regulator of ostoprogenitor cells and fibroblasts, stimulates osteoclast activity in vitro. Subcutaneous injections of IL1B in mice cause increase in plasma calcium and an increase in bone resorption surfaces and osteoclast number. | Nakase et al. (1997) Bone 21: 17–21; Sabatini et al. (1988) Proc Natl Acad Sci 85: 5235–9. |
| SPI1 | SPI1 | SPI1 is a myeloid and B cell transcription factor. Directs tissue specific expression of macrophage colony stimulating factor receptor and integrin B2, both essential for osteoclast function. Expression of SPI1 increases in macrophages as they become osteoclast-like. Development of macrophages and osteoclasts is arrested in SPI1 −/− mice which die 24–48 hours after birth. Bones exhibit osteopetrosis by stage E18. | Tondravi et al. (1997) Nature 386: 81–4; Teitelbaum et al. (1997) J Leukoc Biol 61: 381–8. |
| matrix metalloprotease 9 | MMP9 | Metalloprotease that degrades collagen in the extracellular matrix, growth plates and hypertrophic chondrocytes. Osteoclasts have high MMP9 levels, which are increased in osteosarcomas and Paget's. | Vu et al. (1998) Cell 93: 411–22; Roodman (1996) Endocr Rev 17: 308–32. |
| parathyroid receptor 1 | PTHR1 | PTHR1 binds to two ligands with distinct functions: the calcium-regulating hormone, parathyroid hormone (PTH), and the paracrine factor, PTH-related protein (PTHrP). Osteoblast-specific PTHR1 expression is regulated by 1,25 dihydroxyvitamin D3. Mice lacking PTHR1 usually die mid-gestation, but surviving ones exhibit accelerated chondrocyte differentiation, osteoblast number and increased matrix accumulation. | Lanske et al. (1996) Science 273: 663–6; Juppner et al. (1991) Science 254: 1024–6. Amizuka et al. (1999) J Clin Invest 103: 373–81; Lanske et al. (1999) J Clin Invest 104: 399–407. |
| SRC | SRC | SRC belongs to a conserved family of tyrosine kinases and is highly expressed in osteoclasts where it is thought to have a role in osteoclastic bone resorption. SRC knockout mice exhibit bone remodeling disorder - developing osteopetrosis with death after a few weeks. | Soriano et al. (1991) Cell 64: 693–702. Hall et al. (1994) Biochem Biophys Res Commun 199: 1237–44. |
| kinase insert domain receptor | KDR | High affinity binding receptor for VEGF and likely plays a role in VEGF-mediated bone remodelling under the influence of 1,25 dihydroxyvitamin D3. | Wang et al. (1997) Endocrinology 138: 2953–62. |

TABLE 3-continued

Descriptions of Genes Known To Be Involved in Bone Remodeling and Osteoporosis

| Gene | Gene Symbol | Description | Reference |
|---|---|---|---|
| vascular endothelial growth factor receptor | FLT1 | Receptor for VEGF which is expressed on endothelial cells and which may play a role in VEGF-mediated bone remodelling. Blocking VEGF activity using a soluble chimeric FLT1 receptor in 24-day old mice resulted in cessation of capillary invasion of endochondral bone and inhibition of bone formation and cartilage remodelling. | Wang et al. (1997) Endocrinology 138: 2953–62; Gerber et al. (1999) Nat Med 5: 623–8. |
| disintegrin and metalloprotease 12 | ADAM12 | Disintegrin and metalloprotease family member which appears to regulate the formation of macrophage-derived giant cells and osteoclasts by mediating the effects of dihydroxyvitamin D3 on cell-cell fusion. Addition of ADAM12 to osteoclast precursor cells in vitro results in a 50% decrease in giant cell formation. | Abe et al. (1999) Calcif Tissue Int 64: 508–15. |
| Homolog of Drosophila mothers against decapentaplegic 6 | MADH6 | Prevents ligand-induced activation of signal-transducing Smad proteins in the transforming growth factor-beta family. MADH6 is a human bone morphogenetic protein-2 (hBMP-2)-inducible antagonist of hBMP-2 activity. Consequently, MADH6 is implicated as a regulator of bone remodelling. | Ishisaki et al. (1999) J Biol Chem 274: 13637–42. |
| Parathyroid hormone receptor 2 | PTHR2 | Specific receptor for parathyroid hormone and implicated in calcium homeostasis and bone formation. | Usdin et al. (1995) J Biol Chem 270: 15455–8; Clark et al. (1998) Mol Endocrinol 12: 193–206. |
| glucocorticoid receptor-like 1 | GRLF1 | Inhibitor of glucocorticoid receptor transcription. Glucocorticoids, acting through the glucocorticoid receptor promote osteoblastic differentiation of bone marrow stromal cells. | LeClerc et al. (1991) J Biol Chem 266: 17333–40; Johnson et al. (1999) Endocrinology 140: 3245–54. |
| phosphodiesterase 1 | PDNP1 | Regulates soft tissue calcification and bone mineralization by controlling inorganic pyrophosphate levels, an inhibitor of calcification. Mouse knockout of PDNP1 is a model of osteoporosis. Naturally occurring mouse mutant known as tip-toe walking (ttw) has a PDNP1 nonsense mutation, with loss of 2/3 of protein structure. The ttw mouse exhibits regional osteopenia. | Okawa et al. (1998) Nat Genet 19: 271–3; Kobayashi et al. (1998) Calcif Tissue Int 62: 426–36. |
| bone morphogenic protein 2 | BMP2 | Regulates cartilage formation and induces ectopic bone and cartilage formation when over-expressed in vitro and in vivo. Enhances osteoblast formation in vitro by increasing expression of the osteoblast transcription factor, CBFA1. Therefore BMP2 acts to shunt uncommitted stromal precursor cells from the adipocyte to the osteoblast lineage. | Johnson and Tabin (1997) Cell 90: 979–90; Wozney et al. (1988) Science 242: 1528–34; Kretzschmar et al. (1997) Nature 389: 618–22; Gori et al. (1999) J Bone Miner Res 14: 1522–35. |
| vitamin D receptor | VDR | Mediates effect of vitamin D on bone mineralization. Allelic variance in VDR affects circulating osteocalcin levels (osteocalcin is the most abundant non-collagenous component in bone). Mutations in VDR cause vitamin-D resistant rickets. Variation in VDR genotype also associated with prepubertal bone mineral density. Mice lacking VDR exhibit alopoecia, hypocalcaemia, infertility and bone formation was severely impaired as a typical feature of vitamin D-dependent rickets type II. | Morrison et al. (1992) Proc Natl Acad Sci 89: 6665–9; Tao et al. (1998) Arch Dis Child 79: 488–94; Yoshizawa et al. (1997) Nat Genet 16: 391–6. |
| Estrogen receptor 1 | ESR1 | Mediates effect of estrogen on bone turnover. A human estrogen receptor deficiency caused open epiphyseal growth plates and osteoporotic phenotype. Mice lacking ESR1 are infertile, with reproductive system defects and skeletal disorders including open epiphyseal growth plates. | Smith et al. (1994) N Engl J Med 331: 1056–61; Korach (1994) Science 266: 1524–7. |
| TNF receptor associated factor 5 | TRAF5 | Binds directly to intracellular domain of RANK/tumor necrosis factor receptor superfamily member 11A, which has a key role in osteoclastogenesis. TRAF5 is involved in RANK signal transduction. | Galibert et al. (1998) J Biol Chem 273: 34120–7; Wong et al. (1998) J Biol Chem 273: 28355–9. |

TABLE 3-continued

Descriptions of Genes Known To Be Involved in Bone Remodeling and Osteoporosis

| Gene | Gene Symbol | Description | Reference |
|---|---|---|---|
| Transforming growth factor beta 1 | TGFB1 | TGFB1 encodes a multifunctional peptide that controls proliferation, differentiation, and other functions in many cell types. Regulates osteoclast and osteoblast activity in vitro. Acts with 1.25 dihydroxyvitamin D3 to stimulate differentiation of bone marrow stromal cells to the osteoblast lineage. TGFbeta also stimulates apoptosis of osteoclast cells, possibly by regulation of osteoprotegerin expression. Intronic polymorphism in TGFB1 associated with osteoporosis and very low bone mineral density. | Langdahl et al. (1997) Bone 20: 289–94; Liu et al. (1999) Calcif Tissue Int 65: 173–80; Murakami et al. (1998) Biochem Biophys Res Commun 252: 747–52. |
| acid phosphatase type 5 | ACP5 | Osteoclast enzyme involved in catabolism of extracellular matrix and used as a biochemical marker of bone turnover. Mice lacking ACP5 exhibit bone remodelling defects; chondrocyte arrangement and osteoclast turnover are disrupted and mineralization of cartilage is delayed. This results is skeletal malformations such as foreshortening of long bones, shortened vertebrae and defects in cartilagenous growth plates. | Delmas (1993) J Bone Miner Res 8 (Suppl 2): S549–55. Hayman et al. (1996) Development 122: 3151–62. |
| cathepsin K | CTSK | Cysteine protease critical for bone remodeling by osteoclasts. Mutations in cathepsin K cause osteopetrosis and pycnodysostosis, a autosomal recessive osteosclerotic skeletal dysplasia. Cathepsin K −/− mice survive and are fertile, but display an osteopetrotic phenotype. | Hou et al. (1999) J Clin Invest 103: 731–8; Saftig et al. (1998) Proc Natl Acad Sci 95: 13453–8. |
| bone morphogenic protein 6 | BMP6 | BMP6 expression is concentrated in the hypertrophic cartilage during skeletal development. Probable role in endochondral bone formation. It's expression is influenced by estrogen levels and is repressed by estrogen antagonists in vitro. Therefore, BMP6 is a likely mediator of osteochondrogenic action of estrogen. | Rickard et al. (1998) J Clin Invest 101: 413–22. |
| secreted protein, acidic, cysteine-rich (osteonectin) | SPARC | SPARC is an adhesive, cell, and extracellular matrix-binding glycoprotein. It is one of the major protein components in mineralized bone matrix and cartilage. | Chen et al. (1991) Histochem J 23: 281–9. |
| vascular endothelial growth factor A | VEGFA | Hypertrophic chondrocytes in the epiphyseal growth plate express VEGF which is an essential regulator of chondrocyte death, extracellular matrix remodelling, angiogenesis and bone formation and resorption in the growth plate. Systemic administration of VEGF inhibitor to 24 day-oid mice resulted in disruption of bone formation and turnover. | Gerber et al. (1999) Nat Med 5: 623–8. |
| vascular endothelial growth factor receptor | FLT1 | High affinity binding receptor for VEGF. May participate in bone formation and remodelling as demonstrated by in vitro studies | Wiesmann et al. (1997) Cell 91: 695–704; Wang et al. (1997) Endocrinology 138: 2953–62. |
| collagen type I alpha 2 | COL1A2 | Major collagen component of bone. Polymorphisms in COL1A2 associated with bone mineral density levels and osteoporosis. Mutations found to cause related disorders osteogenesis imperfecta and Ehlers-Danlos syndrome. | Kuivaniemi et al. (1997) Hum Mutat 9: 300–15; Byers et al. (1997) Am J Med Genet 72: 94–105; Pereira et al. (1998) Proc Natl Acad Sci 95: 1142–7. |
| bone gla protein (osteocalcin) | BGLAP | Osteocalcin is the most abundant non-collagenous component of bone. It's expression is regulated by vitamin D. | Morrison et al. (1992) Proc Natl Acad Sci 89: 6665–9. |
| carbonic anhydrase II | CA2 | CA2 has a role in osteoclast function and bone resorption. Generates protons in the mature osteoclast ruffled border which are pumped across the membrane by the H + ATPase. Carbonic anhydrase inhibitors block the normal parathyroid hormone-induced release of calcium from bone. Mutations in CA2 found to be responsible for osteopetrosis with renal tubular acidosis in some families. | Sly et al. (1983) Proc Natl Acad Sci 80: 2752–6; Lehenkari et al. (1998) Exp Cell Res 242: 128–37. |

TABLE 3-continued

Descriptions of Genes Known To Be Involved in Bone Remodeling and Osteoporosis

| Gene | Gene Symbol | Description | Reference |
|---|---|---|---|
| alpha-V integrin | ITGAV | Essential adhesion integrin for osteoclast function and attachment to bone surface. Blocking ITGAV action in vitro prevents bone resorption. | Teitelbaum et al. (1997) J Leukoc Biol 61: 381–8. Engleman et al. (1997) J Clin Invest 99: 2284–92. |
| early growth response 1 | EGR1 | Transcription factor that mediates antiosteoclastogenic action of estrogen. Estrogen facilitates EGR1/SP1 complex formation which prevents SP1 from transactivating the osteoclastogenic CSF1 promoter. Mouse knockout of EGR1 exhibits low bone mineral density and estrogen treatment fails to block CSF1 expression and osteoclast formation in egr −/− mice. | Srivastava et al. (1998) J Clin Invest 102: 1850–9. |
| collagen type I alpha2 | COL1A1 | Major structural component of bone, skin, tendons. Polymorphisms in COL1A1 are associated with bone mineral density and osteoporotic fracture. Mutations found to cause related disorders osteogenesis imperfecta and Ehlers-Danlos syndrome. | Grant et al. (1996) Nat Genet 14: 203–5. |
| Macrophage colony stimulating factor 1 | CSF1 | Essential cytokine for osteoclast differentiation. Negatively regulated by estrogen and may therefore play a role in menopause-associated osteoporosis. | Teitelbaum et al. (1997) J Leukoc Biol 61: 381–8. |
| Biglycan | BGN | Biglycan is an ECM proteoglycan that is enriched in bone and other non-skeletal connective tissues. In vitro studies indicate that Bgn may function in connective tissue metabolism by binding to collagen fibrils and TGF-beta. BGN knockout mice have reduced growth rate, and decreased bone mass and strength when compared to wild type - ie an osteoporotic phenotype. | Xu et al. (1998) Nat Genet 20: 78–82. |
| secreted phosphoprotein (osteopontin) | SPP1 | Calcification-regulating gene. Osteopontin is the principal phosphorylated glycoprotein of bone and is expressed in a limited number of other tissues. Expression is influenced by the bone regulatory peptide, 1,25 dihydroxyvitamin D3. Osteopontin-knockout mice are resistant to ovariectomy-induced osteoporosis, indicating osteopontin function is an important mediator of post-menopausal osteoporosis. | Young et al. (1990) Genomics 7: 491–502; Staal et al. (1996) Mol Endocrinol 10: 1444–56; Yoshitake et al. (1999) Proc Natl Acad Sci 96: 8156–60: Gerstenfeld (1999) J Bone Miner Res 14: 850–5. |
| insulin growth factor-1 | IGF1 | Osteoblastogenic cytokine which suppresses expression of PTH/PTHrP in culture. Upregulates both bone resorption and bone formation in vivo. | Kawane and Horiuchi (1999) Endocrinology 140: 871–9; Kawakami et al. (1998) Biochem Biophys Res Commun 247: 46–51. |
| decorin | DCN | Extracellular matrix proteoglycan that binds collagen. Deficient expression of DCN invoived in Marfan syndrome, a connective tissue disorder and osteogenesis imperfecta. | Pulkkinen et al. (1990) J Biol Chem 265: 17780–5: Dyne et al. (1996) Am J Med Genet 63: 161–6. |
| cathepsin B | CTSB | Osteoclast-residing lysosomal enzyme that degrades bone collagen. Important in bone resorption/bone remodelling. | Blair et al. (1993) Biochem J 290: 873–84; Soderstrom et al. (1999) Biochim Biophys Acta 1446: 35–46. |
| colony stimulating factor receptor | CSF1R | Receptor for colony stimulating factor and mediates development of bone marrow progenitor cells. It is essential for osteoclastogenesis. | Yang et al. (1998) Blood 92: 4632–40; Yamane et al. (1997) Blood 90: 3516–23. |
| Klotho | KL | Defect in klotho gene in mice causes osteoblast and osteoclast differentiation leading to low turnover osteopenia. Mutant kl/kl mice exhibit typical senile osteoporosis and premature ageing. | Kuro-o et al. (1997) Nature 390: 45–51; Kawaguchi et al. (1999) J Clin Invest 104: 229–37. |

V Novel Genes Co-Expressed with Genes Involved with Bone Remodeling and Osteoporosis Using the co-expression analysis method, 169 polynucleotides, including 18 novel polynucleotides, have been identified.

Polynucleotides comprising the consensus sequences of SEQ ID NOs: 1–169 of the present invention were first identified from Incyte bins and assembled as described in Example III. BLAST and other motif searches were performed for SEQ ID NOs: 1–169 according to Example VI. The full length and 5'-complete sequences were translated, and sequence identity was investigated using the methods described in Example VI.

SEQ ID NO: 170 of the present invention was encoded by the polynucleotide of SEQ ID NO: 159. SEQ ID NO: 170 has 93 amino acids. Motif analyses of SEQ ID NO: 170 shows one potential casein kinase II phosphorylation site at residue T85. BLOCKS identifies a potential single-strand binding protein domain from S2 to V11.

SEQ ID NO: 171 of the present invention was encoded by the polynucleotide of SEQ ID NO:37. SEQ ID NO: 177 has 353 amino acids. Motif analyses of SEQ ID NO: 171 shows two potential cAMP- and cGMP-dependent protein kinase phosphorylation sites at residues T198 and S240, respectively; six potential casein kinase II phosphorylation sites at residues T189, S240, S266, S285, and T326, respectively; seven potential protein kinase C phosphorylation sites at residues T60, T77, S110, S194, S210, S256, and T278, respectively. Additionally, SEQ ID NO:171 contains a potential zinc finger C3HC4 type signature sequence from residue C39 to C47. BLOCKS identifies a potential zinc finger C3HC4 type domain at C39 to C47, and Pfam identifies a potential zinc finger C3HC4 type domain at C23 to C47.

SEQ ID NO: 172 of the present invention was encoded by the polynucleotide of SEQ ID NO:85. SEQ ID NO: 178 has 574 amino acids. Motif analyses of SEQ ID NO: 172 shows three potential N-glycosylation sites at residues N76, N240, and N488, respectively; one potential cAMP- and cGMP-dependent protein kinase phosphorylation site at residue T370; seven potential casein kinase II phosphorylation sites at residues S27, T188, S324, S342, T500, T547, and S563, respectively; and nine potential protein kinase C phosphorylation sites at residues T168, S261, S299, S324, T364, S365, S403, S440, and S529, respectively.

VI Homology Searching of the Co-Expressed Polynucleotides and Polypeptides

The polynucleotide sequences, SEQ ID NOs: 1–169, and polypeptide sequences, SEQ ID NOs: 170–172, were queried against databases derived from sources such as GenBank and SwissProt. These databases, which contain previously identified and annotated sequences, were searched for regions of similarity using BLAST (Altschul, supra). BLAST searched for matches and reported only those that satisfied the probability thresholds of $10^{-25}$ or less for nucleotide sequences and $10^{-8}$ or less for polypeptide sequences.

The polypeptide sequence was also analyzed for known motif patterns using MOTIFS, SPSCAN, BLIMPS, and HMM-based protocols. MOTIFS (Genetics Computer Group, Madison Wis.) searches polypeptide sequences for patterns that match those defined in the Prosite Dictionary of Protein Sites and Patterns (Bairoch, supra) and displays the patterns found and their corresponding literature abstracts. SPSCAN (Genetics Computer Group) searches for potential signal peptide sequences using a weighted matrix method (Nielsen et al. (1997) Prot. Eng. 10:1–6). Hits with a score of 5 or greater were considered. BLIMPS uses a weighted matrix analysis algorithm to search for sequence similarity between the polypeptide sequences and those contained in BLOCKS, a database consisting of short amino acid segments, or blocks of 3–60 amino acids in length, compiled from the PROSITE database (Henikoff; supra; Bairoch, supra), and those in PRINTS, a protein fingerprint database based on non-redundant sequences obtained from sources such as SwissProt, GenBank, PIR, and NRL-3D (Attwood et al. (1997) J Chem Inf Comput Sci 37:417–424). For the purposes of the present invention, the BLIMPS searches reported matches with a cutoff score of 1000 or greater and a cutoff probability value of $1.0\times10^{-3}$. HMM-based protocols were based on a probabilistic approach and searched for consensus primary structures of gene families in the protein sequences (Eddy, supra; Sonnhammer, supra). More than 500 known protein families with cutoff scores ranging from 10 to 50 bits were selected for use in this invention.

VII Labeling of Probes and Hybridization Analyses

Substrate Preparation

Polynucleotides are isolated from a biological source and applied to a substrate for standard hybridization protocols by one of the following methods. A mixture of target nucleic acids, a restriction digest of genomic DNA, is fractionated by electrophoresis through an 0.7% agarose gel in 1×TAE [Tris-acetate-ethylenediamine tetraacetic acid (EDTA)] running buffer and transferred to a nylon membrane by capillary transfer using 20× saline sodium citrate (SSC). Alternatively, the target nucleic acids are individually ligated to a vector and inserted into bacterial host cells to form a library. Target nucleic acids are arranged on a substrate by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 beads (Amersham Pharmacia Biotech). Purified target nucleic acids are robotically arrayed onto a glass microscope slide (Coming Science Products, Coming N.Y.). The slide is previously coated with 0.05% aminopropyl silane (Sigma-Aldrich, St. Louis Mo.) and cured at 110° C. The arrayed glass slide (microarray) is exposed to UV irradiation in a STRATALINKER UV-crosslinker (Stratagene).

Probe Preparation cDNA probes are made from mRNA templates. Five micrograms of mRNA is mixed with 1 μg random primer (Life Technologies), incubated at 70° C. for 10 minutes, and lyophilized. The lyophilized sample is resuspended in 50 μl of 1× first strand buffer (cDNA Synthesis systems; Life Technologies) containing a dNTP mix, [$\alpha$-$^{32}$P]dCTP, dithiothreitol, and MMLV reverse transcriptase (Stratagene), and incubated at 42° C. for 1–2 hours. After incubation, the probe is diluted with 42 μl $dH_2O$, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 microcolumn (Amersham Pharmacia Biotech). Probes can be labeled with fluorescent markers, Cy3-dCTP or Cy5-dCTP (Amersham Pharmacia Biotech), in place of the radionucleotide, [$^{32}$P] dCTP.

Hybridization

Hybridization is carried out at 65° C. in a hybridization buffer containing 0.5 M sodium phosphate (pH 7.2), 7% SDS, and 1 mM EDTA. After the substrate is incubated in hybridization buffer at 65° C. for at least 2 hours, the buffer is replaced with 10 ml of fresh buffer containing the probes.

After incubation at 65° C. for 18 hours, the hybridization buffer is removed, and the substrate is washed sequentially under increasingly stringent conditions, up to 40 mM sodium phosphate, 1% SDS, 1 mM EDTA at 65° C. To detect signal produced by a radiolabeled probe hybridized on a membrane, the substrate is exposed to a PHOSPHORIMAGER cassette (Amersham Pharmacia Biotech), and the image is analyzed using IMAGEQUANT data analysis software (Amersham Pharmacia Biotech). To detect signals produced by a fluorescent probe hybridized on a microarray, the substrate is examined by confocal laser microscopy, and images are collected and analyzed using GEMTOOLS gene expression analysis software (Incyte Pharmaceuticals).

VIII Complementary Polynucleotides

Molecules complementary to the polynucleotide, or a fragment thereof, are used to detect, decrease, or inhibit gene expression. Although use of oligonucleotides comprising from about 15 to about 60 base pairs is described, the same procedure is used with larger or smaller fragments or their derivatives (PNAs). Oligonucleotides are designed using OLIGO 4.06 software (National Biosciences) and SEQ ID NOs: 1–169 or fragments thereof. To inhibit transcription by preventing promoter binding, a complementary oligonucleotide is designed to bind to the most unique 5' sequence, most preferably about 10 nucleotides before the initiation codon of the open reading frame. To inhibit translation, a complementary oligonucleotide is designed to prevent ribosomal binding to the mRNA encoding the polypeptide.

IX Production of Specific Antibodies

The polypeptides encoded by SEQ ID NOs: 1–1 69, or portions thereof, substantially purified using polyacrylamide gel electrophoresis or other purification techniques, are used to immunize rabbits and to produce antibodies using standard protocols as described in Pound (1998; Immunochemical Protocols, Methods Mol. Biol. Vol. 80).

Alternatively, the amino acid sequence is analyzed using LASERGENE software (DNASTAR, Madison Wis.) to determine regions of high immunogenicity, and a corresponding oligopeptide is synthesized and used to raise antibodies by means known to those of skill in the art. Methods for selection of epitopes, such as those near the C-terminus or in hydrophilic regions are well described in the art. Typically, oligopeptides 15 residues in length are synthesized using an ABI 431A Peptide synthesizer (PE Biosystems) using fmoc-chemistry and coupled to keyhole limpet hemocyanin (KLH, Sigma-Aldrich) by reaction with N-maleimidobenzoyl-N-hydroxysuccinimide ester (Ausubel supra) to increase immunogenicity. Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

X Screening Molecules for Specific Binding with the Polynucleotide or Polypeptide The polynucleotide, or fragments thereof, or the polypeptide, or portions thereof, are labeled with $^{32}$P-dCTP, Cy3-dCTP, or Cy5-dCTP (Amersham Pharmacia Biotech), or with BIODIPY or FITC (Molecular Probes, Eugene Oreg.), respectively. Libraries of candidate molecules previously arranged on a the substrate are incubated in the presence of labeled polynucleotide or polypeptide. After incubation under conditions for either a nucleic acid or amino acid sequence, the substrate is washed, and any position on the substrate retaining label, which indicates specific binding or complex formation, is assayed, and the binding molecule is identified. Data obtained using different concentrations of the polynucleotide or polypeptide are used to calculate affinity between the labeled nucleic acid or protein and the bound molecule.

TABLE 4

| Incyte ID NO | PHEX 212786 | PTH 27686 | TRAF2 28174 | TNFSF11 334504 | TNFRSF11A 406015 | CYP24 207524 | NPPB 21736 | CSF2 275416 | CYP19 31314 | EGF 333073 | IL1A 335942 | MITF 345480 |
|---|---|---|---|---|---|---|---|---|---|---|---|---|
| 16193 | 0 | 0 | 0 | 0 | 1 | 1 | 2 | 1 | 1 | 1 | 0 | 0 |
| 17091 | 6 | 0 | 0 | 0 | 0 | 0 | 0 | 0 | 1 | 0 | 0 | 0 |
| 36258 | 1 | 1 | 0 | 5 | 0 | 0 | 0 | 0 | 3 | 1 | 0 | 0 |
| 127748 | 0 | 6 | 0 | 0 | 0 | 1 | 0 | 0 | 0 | 1 | 0 | 0 |
| 200512 | 1 | 0 | 0 | 0 | 0 | 0 | 1 | 0 | 12 | 0 | 0 | 0 |
| 228058 | 0 | 1 | 0 | 0 | 1 | 1 | 0 | 0 | 11 | 0 | 0 | 2 |
| 230960 | 1 | 0 | 0 | 6 | 0 | 0 | 1 | 0 | 3 | 1 | 2 | 0 |
| 231491 | 0 | 1 | 0 | 0 | 0 | 5 | 0 | 0 | 1 | 9 | 1 | 1 |
| 233014 | 0 | 1 | 0 | 0 | 0 | 0 | 0 | 6 | 4 | 0 | 2 | 0 |
| 234571 | 1 | 0 | 0 | 1 | 1 | 0 | 0 | 3 | 1 | 1 | 4 | 1 |
| 236360 | 1 | 0 | 0 | 1 | 0 | 1 | 1 | 0 | 1 | 2 | 0 | 1 |
| 249096 | 0 | 0 | 0 | 1 | 1 | 0 | 0 | 0 | 1 | 0 | 0 | 2 |
| 332763 | 0 | 0 | 0 | 5 | 0 | 0 | 0 | 0 | 0 | 0 | 1 | 0 |
| 334145 | 0 | 5 | 0 | 0 | 0 | 0 | 0 | 0 | 2 | 0 | 0 | 1 |
| 337523 | 1 | 1 | 0 | 0 | 0 | 0 | 0 | 0 | 1 | 0 | 1 | 1 |
| 351273 | 0 | 0 | 0 | 5 | 0 | 0 | 0 | 0 | 1 | 0 | 1 | 0 |
| 402939 | 1 | 6 | 0 | 0 | 0 | 0 | 0 | 0 | 2 | 1 | 2 | 0 |
| 9049 | 0 | 0 | 0 | 0 | 0 | 0 | 0 | 0 | 6 | 0 | 0 | 1 |
| 10205 | 0 | 1 | 0 | 1 | 1 | 1 | 1 | 4 | 2 | 1 | 2 | 1 |
| 19740 | 0 | 1 | 0 | 1 | 0 | 1 | 0 | 0 | 6 | 1 | 1 | 0 |
| 196697 | 0 | 1 | 0 | 0 | 1 | 1 | 0 | 0 | 4 | 1 | 1 | 0 |
| 198006 | 0 | 0 | 0 | 1 | 1 | 1 | 1 | 0 | 1 | 0 | 1 | 1 |
| 198309 | 0 | 0 | 0 | 2 | 1 | 0 | 0 | 0 | 1 | 0 | 1 | 0 |
| 200386 | 0 | 0 | 0 | 0 | 0 | 1 | 0 | 0 | 9 | 0 | 0 | 1 |
| 202177 | 0 | 1 | 0 | 0 | 1 | 1 | 0 | 0 | 7 | 2 | 2 | 0 |
| 213109 | 0 | 0 | 0 | 0 | 0 | 0 | 0 | 0 | 1 | 0 | 3 | 0 |
| 215998 | 0 | 0 | 0 | 1 | 0 | 1 | 0 | 0 | 1 | 0 | 2 | 0 |

TABLE 4-continued

| | | | | | | | | | | | | |
|---|---|---|---|---|---|---|---|---|---|---|---|---|
| 227944 | 1 | 1 | 0 | 0 | 0 | 0 | 0 | 0 | 9 | 0 | 1 | 0 |
| 232513 | 0 | 1 | 0 | 1 | 2 | 0 | 2 | 0 | 1 | 1 | 1 | 6 |
| 253776 | 1 | 1 | 0 | 2 | 0 | 0 | 0 | 1 | 1 | 1 | 0 | 1 |

| Incyte ID NO | BMP7 346943 | IBSP 350961 | ITGB3 351122 | AHSG 199151 | TNFRSF11B 201571 | IL1B 21870 | SPI1 235903 | MMP9 238213 | PTHR1 243080 | SRC 245512 | KDR 247817 |
|---|---|---|---|---|---|---|---|---|---|---|---|
| 16193 | 2 | 3 | 1 | 0 | 3 | 1 | 1 | 2 | 2 | 1 | 1 |
| 17091 | 1 | 1 | 0 | 1 | 1 | 0 | 1 | 0 | 1 | 0 | 0 |
| 36258 | 1 | 1 | 1 | 2 | 2 | 0 | 1 | 0 | 2 | 3 | 1 |
| 127748 | 1 | 0 | 1 | 0 | 1 | 0 | 0 | 0 | 1 | 1 | 0 |
| 200512 | 1 | 1 | 3 | 4 | 0 | 0 | 1 | 1 | 4 | 1 | 3 |
| 228058 | 2 | 0 | 5 | 4 | 0 | 0 | 2 | 0 | 5 | 1 | 3 |
| 230960 | 2 | 1 | 0 | 1 | 1 | 1 | 2 | 0 | 2 | 1 | 3 |
| 231491 | 1 | 0 | 1 | 0 | 1 | 0 | 0 | 1 | 5 | 2 | 1 |
| 233014 | 1 | 0 | 4 | 1 | 1 | 1 | 1 | 1 | 1 | 0 | 1 |
| 234571 | 3 | 1 | 2 | 1 | 1 | 7 | 10 | 5 | 1 | 2 | 1 |
| 236360 | 1 | 0 | 2 | 1 | 1 | 1 | 1 | 1 | 2 | 0 | 2 |
| 249096 | 1 | 1 | 1 | 0 | 2 | 1 | 1 | 0 | 0 | 1 | 4 |
| 332763 | 2 | 0 | 1 | 0 | 0 | 0 | 0 | 0 | 0 | 0 | 1 |
| 334145 | 1 | 0 | 1 | 0 | 1 | 0 | 0 | 0 | 1 | 0 | 0 |
| 337523 | 0 | 3 | 0 | 0 | 6 | 1 | 1 | 0 | 0 | 0 | 1 |
| 351273 | 1 | 0 | 2 | 1 | 0 | 0 | 1 | 0 | 1 | 0 | 0 |
| 402939 | 1 | 1 | 1 | 1 | 1 | 0 | 0 | 1 | 1 | 0 | 1 |
| 9049 | 0 | 0 | 4 | 2 | 0 | 0 | 1 | 0 | 2 | 0 | 3 |
| 10205 | 3 | 1 | 8 | 1 | 3 | 1 | 2 | 1 | 2 | 1 | 1 |
| 19740 | 3 | 0 | 1 | 2 | 0 | 0 | 2 | 1 | 2 | 0 | 2 |
| 196697 | 7 | 0 | 3 | 2 | 2 | 0 | 0 | 0 | 4 | 1 | 1 |
| 198006 | 1 | 1 | 1 | 0 | 1 | 2 | 0 | 0 | 1 | 1 | 2 |
| 198309 | 1 | 0 | 3 | 1 | 1 | 0 | 7 | 7 | 2 | 2 | 2 |
| 200386 | 1 | 0 | 6 | 1 | 1 | 0 | 0 | 0 | 2 | 0 | 2 |
| 202177 | 3 | 0 | 8 | 2 | 1 | 1 | 1 | 0 | 4 | 1 | 2 |
| 213109 | 0 | 0 | 2 | 0 | 0 | 11 | 2 | 1 | 0 | 0 | 0 |
| 215998 | 1 | 0 | 2 | 0 | 1 | 2 | 8 | 3 | 1 | 2 | 0 |
| 227944 | 0 | 1 | 3 | 4 | 0 | 0 | 1 | 1 | 3 | 0 | 2 |
| 232513 | 3 | 1 | 1 | 1 | 4 | 1 | 2 | 1 | 1 | 5 | 4 |
| 253776 | 2 | 0 | 1 | 1 | 1 | 1 | 0 | 0 | 1 | 3 | 1 |

| Incyte ID NO | FLT1 322303 | ADAM12 331582 | MADH6 333398 | PTHR2 336338 | GRLF1 336588 | PDNP1 344785 | BMP2 346680 | VDR 348162 | ESR1 349438 | TRAF5 401610 | TGFB1 121174 |
|---|---|---|---|---|---|---|---|---|---|---|---|
| 16193 | 1 | 3 | 1 | 2 | 1 | 5 | 2 | 1 | 3 | 1 | 3 |
| 17091 | 0 | 0 | 1 | 1 | 1 | 1 | 0 | 1 | 0 | 0 | 0 |
| 36258 | 2 | 1 | 1 | 1 | 1 | 2 | 1 | 3 | 0 | 0 | 3 |
| 127748 | 0 | 0 | 2 | 1 | 1 | 2 | 0 | 3 | 0 | 0 | 1 |
| 200512 | 5 | 6 | 4 | 0 | 1 | 6 | 0 | 1 | 1 | 1 | 2 |
| 228058 | 9 | 7 | 9 | 5 | 1 | 7 | 1 | 3 | 2 | 1 | 2 |
| 230960 | 0 | 2 | 2 | 1 | 3 | 1 | 1 | 2 | 1 | 1 | 4 |
| 231491 | 1 | 0 | 2 | 1 | 1 | 1 | 0 | 2 | 0 | 0 | 0 |
| 233014 | 3 | 2 | 2 | 1 | 1 | 2 | 1 | 3 | 0 | 1 | 2 |
| 234571 | 1 | 2 | 2 | 0 | 1 | 1 | 2 | 5 | 0 | 1 | 5 |
| 236360 | 4 | 2 | 5 | 1 | 4 | 4 | 1 | 1 | 1 | 1 | 4 |
| 249096 | 3 | 2 | 2 | 1 | 1 | 1 | 3 | 1 | 2 | 3 | 2 |
| 332763 | 1 | 0 | 0 | 0 | 1 | 0 | 0 | 0 | 2 | 3 | 0 |
| 334145 | 1 | 1 | 1 | 3 | 0 | 3 | 1 | 2 | 0 | 2 | 1 |
| 337523 | 1 | 1 | 3 | 2 | 0 | 1 | 2 | 1 | 0 | 1 | 1 |
| 351273 | 1 | 0 | 0 | 0 | 1 | 1 | 0 | 0 | 1 | 1 | 1 |
| 402939 | 2 | 0 | 4 | 2 | 2 | 2 | 0 | 3 | 0 | 1 | 1 |
| 9049 | 5 | 5 | 6 | 2 | 1 | 5 | 1 | 2 | 0 | 2 | 1 |
| 10205 | 3 | 3 | 7 | 3 | 1 | 6 | 0 | 6 | 1 | 2 | 1 |
| 19740 | 3 | 3 | 1 | 1 | 3 | 2 | 0 | 1 | 1 | 1 | 1 |
| 196697 | 2 | 3 | 5 | 3 | 1 | 4 | 1 | 5 | 1 | 0 | 3 |
| 198006 | 4 | 1 | 1 | 3 | 1 | 2 | 2 | 1 | 3 | 1 | 4 |
| 198309 | 0 | 0 | 2 | 1 | 1 | 3 | 1 | 2 | 1 | 1 | 3 |
| 200386 | 8 | 7 | 6 | 1 | 0 | 9 | 1 | 3 | 0 | 1 | 2 |
| 202177 | 3 | 5 | 6 | 3 | 2 | 5 | 2 | 3 | 0 | 0 | 3 |
| 213109 | 1 | 2 | 1 | 1 | 0 | 2 | 2 | 1 | 1 | 1 | 5 |
| 215998 | 3 | 0 | 3 | 1 | 1 | 2 | 1 | 1 | 0 | 1 | 5 |
| 227944 | 3 | 5 | 3 | 0 | 0 | 5 | 0 | 3 | 0 | 1 | 2 |
| 232513 | 1 | 1 | 5 | 4 | 4 | 2 | 1 | 3 | 5 | 2 | 2 |
| 253776 | 1 | 0 | 1 | 0 | 1 | 0 | 1 | 1 | 1 | 3 | 1 |

| Incyte ID NO | ACP5 215481 | CTSK 219975 | BMP6 233926 | SPARC 234507 | VEGFA 242681 | FLRG 243362 | COL1A2 244935 | BGLAP 246251 | CA2 248306 | ITGAV 250203 | EGR1 251715 |
|---|---|---|---|---|---|---|---|---|---|---|---|
| 16193 | 1 | 5 | 1 | 7 | 2 | 6 | 10 | 3 | 1 | 2 | 1 |
| 17091 | 0 | 0 | 0 | 0 | 0 | 0 | 1 | 1 | 0 | 0 | 0 |
| 36258 | 1 | 2 | 2 | 2 | 1 | 1 | 1 | 6 | 1 | 1 | 2 |
| 127748 | 1 | 0 | 1 | 1 | 1 | 0 | 1 | 2 | 1 | 1 | 0 |

TABLE 4-continued

| | | | | | | | | | | | |
|---|---|---|---|---|---|---|---|---|---|---|---|
| 200512 | 1 | 1 | 3 | 1 | 0 | 2 | 1 | 1 | 0 | 0 | 1 |
| 228058 | 0 | 2 | 2 | 2 | 2 | 1 | 1 | 1 | 1 | 2 | 0 |
| 230960 | 1 | 1 | 6 | 1 | 1 | 3 | 1 | 4 | 2 | 1 | 2 |
| 231491 | 1 | 1 | 1 | 1 | 2 | 1 | 0 | 1 | 4 | 2 | 3 |
| 233014 | 1 | 1 | 1 | 0 | 1 | 0 | 0 | 1 | 0 | 2 | 0 |
| 234571 | 4 | 1 | 6 | 2 | 4 | 3 | 2 | 5 | 2 | 2 | 4 |
| 236360 | 2 | 8 | 5 | 14 | 2 | 8 | 6 | 3 | 1 | 5 | 2 |
| 249096 | 0 | 8 | 4 | 8 | 3 | 9 | 10 | 1 | 0 | 7 | 5 |
| 332763 | 0 | 1 | 1 | 1 | 1 | 0 | 1 | 1 | 0 | 1 | 0 |
| 334145 | 0 | 0 | 0 | 0 | 1 | 0 | 1 | 1 | 0 | 1 | 1 |
| 337523 | 1 | 2 | 1 | 1 | 0 | 4 | 1 | 0 | 1 | 1 | 0 |
| 351273 | 0 | 2 | 1 | 1 | 0 | 0 | 0 | 2 | 2 | 1 | 0 |
| 402939 | 0 | 1 | 1 | 1 | 2 | 1 | 0 | 1 | 1 | 0 | 0 |
| 9049 | 0 | 2 | 2 | 1 | 0 | 1 | 1 | 1 | 0 | 0 | 1 |
| 10205 | 1 | 1 | 2 | 2 | 4 | 2 | 1 | 2 | 1 | 2 | 1 |
| 19740 | 0 | 3 | 2 | 0 | 1 | 2 | 0 | 0 | 4 | 1 | 1 |
| 196697 | 0 | 1 | 2 | 1 | 1 | 0 | 1 | 3 | 1 | 2 | 1 |
| 198006 | 1 | 13 | 2 | 9 | 3 | 11 | 12 | 3 | 0 | 3 | 7 |
| 198309 | 4 | 1 | 2 | 1 | 2 | 0 | 1 | 1 | 2 | 0 | 5 |
| 200386 | 1 | 2 | 1 | 1 | 0 | 1 | 1 | 2 | 0 | 0 | 0 |
| 202177 | 1 | 1 | 1 | 1 | 2 | 0 | 1 | 2 | 1 | 2 | 2 |
| 213109 | 1 | 3 | 2 | 0 | 1 | 0 | 1 | 1 | 1 | 1 | 1 |
| 215998 | 3 | 0 | 3 | 0 | 0 | 1 | 0 | 0 | 0 | 0 | 1 |
| 227944 | 1 | 3 | 2 | 1 | 0 | 1 | 1 | 1 | 1 | 0 | 1 |
| 232513 | 3 | 4 | 6 | 6 | 5 | 4 | 4 | 5 | 2 | 4 | 4 |
| 253776 | 1 | 2 | 4 | 7 | 1 | 4 | 1 | 15 | 0 | 6 | 1 |

| Incyte ID NO | COL1A1 257184 | CSF1 333948 | BGN 345168 | SPP1 352406 | IGF1 399413 | DCN 427953 | CTSB 429609 | CSF1R 64333 | KL 215078 | maximum − log pvalue |
|---|---|---|---|---|---|---|---|---|---|---|
| 16193 | 9 | 1 | 16 | 1 | 2 | 6 | 6 | 4 | 0 | 16 |
| 17091 | 0 | 0 | 0 | 0 | 0 | 0 | 1 | 0 | 0 | 6 |
| 36258 | 1 | 0 | 2 | 1 | 2 | 1 | 1 | 2 | 1 | 6 |
| 127748 | 1 | 0 | 0 | 0 | 0 | 0 | 0 | 2 | 4 | 6 |
| 200512 | 2 | 0 | 3 | 2 | 2 | 1 | 1 | 4 | 1 | 12 |
| 228058 | 1 | 1 | 3 | 2 | 4 | 1 | 0 | 3 | 4 | 11 |
| 230960 | 1 | 1 | 3 | 1 | 2 | 1 | 1 | 2 | 1 | 6 |
| 231491 | 0 | 0 | 4 | 4 | 0 | 1 | 1 | 1 | 10 | 10 |
| 233014 | 0 | 6 | 0 | 3 | 1 | 0 | 2 | 1 | 1 | 6 |
| 234571 | 1 | 11 | 4 | 1 | 1 | 1 | 8 | 3 | 1 | 11 |
| 236360 | 4 | 2 | 12 | 5 | 3 | 7 | 6 | 4 | 2 | 14 |
| 249096 | 4 | 2 | 7 | 1 | 5 | 12 | 3 | 3 | 1 | 12 |
| 332763 | 0 | 0 | 0 | 0 | 1 | 0 | 0 | 0 | 0 | 5 |
| 334145 | 0 | 0 | 1 | 0 | 1 | 1 | 0 | 1 | 3 | 5 |
| 337523 | 2 | 3 | 1 | 0 | 1 | 2 | 1 | 0 | 0 | 6 |
| 351273 | 0 | 1 | 0 | 0 | 1 | 0 | 1 | 1 | 0 | 5 |
| 402939 | 0 | 0 | 0 | 1 | 2 | 1 | 0 | 2 | 3 | 6 |
| 9049 | 0 | 0 | 0 | 2 | 2 | 1 | 1 | 1 | 2 | 6 |
| 10205 | 1 | 2 | 1 | 2 | 2 | 1 | 1 | 2 | 1 | 8 |
| 19740 | 0 | 2 | 1 | 2 | 1 | 1 | 1 | 5 | 2 | 6 |
| 196697 | 1 | 2 | 1 | 1 | 2 | 0 | 1 | 2 | 5 | 7 |
| 198006 | 9 | 1 | 9 | 2 | 10 | 12 | 3 | 3 | 1 | 13 |
| 198309 | 1 | 2 | 3 | 2 | 1 | 1 | 3 | 8 | 0 | 8 |
| 200386 | 1 | 1 | 1 | 3 | 2 | 0 | 1 | 2 | 3 | 9 |
| 202177 | 1 | 1 | 2 | 2 | 1 | 1 | 0 | 5 | 5 | 8 |
| 213109 | 0 | 1 | 2 | 0 | 0 | 0 | 2 | 1 | 0 | 11 |
| 215998 | 0 | 2 | 0 | 0 | 0 | 1 | 2 | 2 | 1 | 8 |
| 227944 | 3 | 1 | 1 | 1 | 2 | 0 | 1 | 3 | 1 | 9 |
| 232513 | 4 | 2 | 9 | 1 | 3 | 5 | 7 | 3 | 0 | 9 |
| 253776 | 0 | 1 | 1 | 4 | 1 | 2 | 3 | 2 | 1 | 15 |

| Incyte ID NO | PHEX 212786 | PTH 27686 | TRAF2 28174 | TNFSF11 334504 | TNFRSF11A 406015 | CYP24 207524 | NPPB 21736 | CSF2 275416 | CYP19 31314 | EGF 333073 | IL1A 335942 | MITF 345480 |
|---|---|---|---|---|---|---|---|---|---|---|---|---|
| 331276 | 0 | 1 | 0 | 0 | 0 | 3 | 2 | 0 | 1 | 3 | 0 | 2 |
| 331906 | 0 | 1 | 0 | 1 | 1 | 1 | 1 | 0 | 3 | 1 | 4 | 2 |
| 337832 | 0 | 1 | 0 | 0 | 0 | 6 | 0 | 0 | 0 | 6 | 0 | 0 |
| 344071 | 1 | 1 | 0 | 0 | 0 | 1 | 0 | 1 | 1 | 1 | 1 | 1 |
| 344594 | 0 | 1 | 0 | 1 | 1 | 1 | 0 | 0 | 1 | 0 | 0 | 4 |
| 400799 | 0 | 0 | 0 | 1 | 0 | 0 | 0 | 0 | 1 | 0 | 1 | 0 |
| 402117 | 0 | 0 | 0 | 0 | 0 | 3 | 0 | 0 | 0 | 7 | 0 | 0 |
| 406605 | 0 | 1 | 0 | 0 | 0 | 1 | 0 | 0 | 8 | 0 | 2 | 0 |
| 481497 | 0 | 0 | 1 | 1 | 0 | 2 | 0 | 1 | 0 | 3 | 1 | 0 |
| 1549 | 0 | 0 | 1 | 1 | 2 | 1 | 1 | 0 | 1 | 1 | 0 | 1 |
| 2715 | 0 | 0 | 0 | 0 | 0 | 0 | 6 | 0 | 0 | 0 | 0 | 0 |
| 4485 | 0 | 0 | 0 | 0 | 0 | 4 | 0 | 0 | 0 | 5 | 0 | 0 |
| 4516 | 0 | 0 | 0 | 0 | 0 | 1 | 0 | 0 | 0 | 7 | 0 | 1 |
| 5028 | 0 | 0 | 0 | 1 | 0 | 0 | 7 | 0 | 0 | 1 | 1 | 0 |
| 9051 | 0 | 1 | 0 | 0 | 0 | 0 | 0 | 0 | 6 | 0 | 1 | 0 |

TABLE 4-continued

| | | | | | | | | | | | | |
|---|---|---|---|---|---|---|---|---|---|---|---|---|
| 9661 | 0 | 0 | 0 | 0 | 0 | 1 | 0 | 0 | 7 | 0 | 0 | 0 |
| 12432 | 2 | 1 | 1 | 1 | 1 | 0 | 1 | 1 | 2 | 0 | 1 | 1 |
| 19238 | 0 | 2 | 0 | 0 | 0 | 0 | 0 | 0 | 1 | 0 | 0 | 1 |
| 21651 | 0 | 0 | 0 | 0 | 1 | 0 | 0 | 1 | 0 | 1 | 2 | 3 |
| 21656 | 0 | 0 | 0 | 1 | 1 | 0 | 10 | 0 | 0 | 0 | 0 | 0 |
| 23103 | 0 | 1 | 0 | 0 | 0 | 1 | 0 | 1 | 4 | 3 | 1 | 0 |
| 23303 | 1 | 1 | 0 | 0 | 1 | 2 | 1 | 0 | 2 | 1 | 1 | 1 |
| 33977 | 0 | 1 | 0 | 1 | 0 | 0 | 0 | 0 | 1 | 1 | 6 | 0 |
| 34157 | 0 | 0 | 0 | 0 | 0 | 1 | 0 | 0 | 1 | 1 | 0 | 1 |
| 37739 | 0 | 1 | 0 | 0 | 0 | 0 | 0 | 0 | 6 | 0 | 0 | 0 |
| 40200 | 0 | 0 | 0 | 1 | 0 | 2 | 0 | 0 | 1 | 1 | 1 | 3 |
| 64612 | 0 | 0 | 0 | 0 | 0 | 0 | 6 | 0 | 0 | 0 | 0 | 0 |
| 126510 | 0 | 0 | 0 | 1 | 0 | 0 | 0 | 0 | 0 | 0 | 0 | 0 |
| 179654 | 1 | 1 | 0 | 0 | 1 | 1 | 0 | 0 | 4 | 1 | 2 | 1 |
| 196556 | 0 | 1 | 0 | 0 | 0 | 3 | 0 | 0 | 3 | 0 | 1 | 1 |
| 197199 | 1 | 0 | 1 | 1 | 1 | 1 | 1 | 1 | 1 | 1 | 0 | 1 |
| 197271 | 0 | 1 | 0 | 1 | 0 | 0 | 2 | 1 | 2 | 1 | 1 | 2 |

| Incyte ID NO | BMP7 346943 | IBSP 350961 | ITGB3 351122 | AHSG 199151 | TNFRSF11B 201571 | IL1B 21870 | SPI1 235903 | MMP9 238213 | PTHR1 243080 | SRC 245512 | KDR 247817 |
|---|---|---|---|---|---|---|---|---|---|---|---|
| 331276 | 2 | 2 | 1 | 1 | 5 | 1 | 0 | 1 | 4 | 3 | 3 |
| 331906 | 3 | 0 | 8 | 2 | 0 | 0 | 1 | 1 | 2 | 1 | 1 |
| 337832 | 0 | 0 | 0 | 0 | 2 | 0 | 0 | 0 | 3 | 0 | 0 |
| 344071 | 0 | 1 | 4 | 0 | 1 | 1 | 0 | 1 | 1 | 0 | 2 |
| 344594 | 1 | 2 | 2 | 1 | 4 | 0 | 0 | 1 | 2 | 1 | 1 |
| 400799 | 0 | 0 | 0 | 0 | 1 | 4 | 8 | 3 | 1 | 1 | 1 |
| 402117 | 1 | 0 | 0 | 0 | 1 | 0 | 1 | 1 | 4 | 0 | 1 |
| 406605 | 1 | 0 | 3 | 2 | 1 | 0 | 0 | 0 | 1 | 0 | 1 |
| 481497 | 2 | 1 | 2 | 0 | 1 | 1 | 0 | 1 | 1 | 4 | 3 |
| 1549 | 0 | 1 | 2 | 0 | 3 | 0 | 1 | 1 | 3 | 2 | 3 |
| 2715 | 1 | 0 | 0 | 0 | 1 | 1 | 0 | 0 | 0 | 0 | 1 |
| 4485 | 0 | 0 | 0 | 1 | 0 | 0 | 0 | 0 | 3 | 0 | 1 |
| 4516 | 0 | 0 | 0 | 0 | 0 | 0 | 0 | 0 | 3 | 0 | 0 |
| 5028 | 1 | 0 | 1 | 0 | 0 | 0 | 0 | 1 | 0 | 1 | 0 |
| 9051 | 1 | 1 | 2 | 2 | 0 | 0 | 0 | 0 | 1 | 1 | 2 |
| 9661 | 0 | 0 | 1 | 0 | 0 | 0 | 0 | 0 | 1 | 0 | 0 |
| 12432 | 6 | 0 | 2 | 1 | 0 | 0 | 2 | 0 | 4 | 0 | 2 |
| 19238 | 1 | 1 | 1 | 0 | 0 | 0 | 1 | 0 | 3 | 1 | 8 |
| 21651 | 1 | 2 | 2 | 1 | 0 | 1 | 0 | 0 | 4 | 1 | 3 |
| 21656 | 1 | 0 | 0 | 0 | 0 | 1 | 0 | 1 | 0 | 1 | 1 |
| 23103 | 2 | 0 | 6 | 2 | 2 | 0 | 2 | 0 | 2 | 1 | 1 |
| 23303 | 2 | 1 | 3 | 2 | 1 | 0 | 1 | 1 | 4 | 0 | 4 |
| 33977 | 2 | 0 | 2 | 1 | 0 | 0 | 2 | 0 | 1 | 0 | 0 |
| 34157 | 2 | 1 | 6 | 0 | 2 | 1 | 0 | 0 | 3 | 0 | 0 |
| 37739 | 1 | 0 | 4 | 1 | 1 | 0 | 0 | 0 | 2 | 0 | 0 |
| 40200 | 3 | 0 | 7 | 0 | 3 | 0 | 0 | 0 | 1 | 0 | 0 |
| 64612 | 1 | 0 | 0 | 0 | 1 | 0 | 1 | 0 | 0 | 0 | 1 |
| 126510 | 0 | 0 | 0 | 0 | 0 | 2 | 8 | 1 | 0 | 1 | 0 |
| 179654 | 1 | 1 | 4 | 1 | 1 | 0 | 2 | 1 | 2 | 2 | 4 |
| 196556 | 1 | 1 | 3 | 1 | 2 | 1 | 1 | 0 | 2 | 1 | 2 |
| 197199 | 3 | 1 | 2 | 1 | 1 | 1 | 2 | 5 | 1 | 1 | 4 |
| 197271 | 5 | 2 | 1 | 2 | 3 | 1 | 1 | 1 | 3 | 1 | 1 |

| Incyte ID NO | FLT1 322303 | ADAM12 331582 | MADH6 333398 | PTHR2 336338 | GRLF1 336588 | PDNP1 344785 | BMP2 346680 | VDR 348162 | ESR1 349438 | TRAF5 401610 | TGFB1 121174 |
|---|---|---|---|---|---|---|---|---|---|---|---|
| 331276 | 2 | 1 | 3 | 2 | 1 | 4 | 3 | 3 | 6 | 2 | 2 |
| 331906 | 2 | 3 | 6 | 5 | 6 | 4 | 1 | 5 | 2 | 4 | 2 |
| 337832 | 0 | 0 | 1 | 0 | 0 | 0 | 0 | 1 | 0 | 0 | 0 |
| 344071 | 2 | 2 | 7 | 1 | 1 | 3 | 2 | 4 | 1 | 1 | 1 |
| 344594 | 2 | 3 | 4 | 2 | 5 | 2 | 3 | 3 | 6 | 4 | 2 |
| 400799 | 1 | 2 | 1 | 1 | 1 | 0 | 0 | 0 | 1 | 0 | 6 |
| 402117 | 0 | 1 | 1 | 0 | 1 | 1 | 0 | 0 | 0 | 0 | 0 |
| 406605 | 5 | 3 | 4 | 1 | 1 | 5 | 0 | 2 | 0 | 0 | 1 |
| 481497 | 1 | 1 | 1 | 0 | 1 | 2 | 2 | 2 | 4 | 1 | 1 |
| 1549 | 4 | 1 | 2 | 2 | 2 | 2 | 0 | 4 | 2 | 1 | 3 |
| 2715 | 1 | 0 | 0 | 0 | 2 | 0 | 1 | 0 | 0 | 1 | 0 |
| 4485 | 0 | 0 | 0 | 0 | 0 | 0 | 0 | 0 | 0 | 0 | 0 |
| 4516 | 0 | 0 | 0 | 0 | 0 | 1 | 0 | 0 | 0 | 0 | 0 |
| 5028 | 1 | 1 | 2 | 0 | 1 | 0 | 0 | 0 | 0 | 1 | 0 |
| 9051 | 2 | 2 | 2 | 0 | 0 | 2 | 1 | 1 | 1 | 0 | 1 |
| 9661 | 2 | 4 | 2 | 0 | 0 | 2 | 0 | 1 | 0 | 0 | 0 |
| 12432 | 4 | 0 | 2 | 3 | 3 | 4 | 1 | 1 | 1 | 1 | 2 |
| 19238 | 2 | 0 | 5 | 1 | 1 | 2 | 1 | 1 | 1 | 1 | 1 |
| 21651 | 3 | 2 | 2 | 2 | 1 | 1 | 1 | 1 | 3 | 1 | 3 |
| 21656 | 0 | 1 | 0 | 0 | 1 | 0 | 1 | 0 | 0 | 0 | 0 |
| 23103 | 1 | 2 | 4 | 5 | 3 | 4 | 1 | 3 | 2 | 1 | 1 |
| 23303 | 2 | 2 | 8 | 2 | 2 | 3 | 1 | 6 | 1 | 1 | 2 |

TABLE 4-continued

| | | | | | | | | | | | |
|---|---|---|---|---|---|---|---|---|---|---|---|
| 33977 | 0 | 1 | 2 | 2 | 3 | 0 | 0 | 3 | 2 | 0 | 2 |
| 34157 | 1 | 3 | 3 | 2 | 1 | 5 | 2 | 3 | 0 | 0 | 2 |
| 37739 | 3 | 5 | 3 | 1 | 0 | 3 | 1 | 2 | 1 | 0 | 1 |
| 40200 | 1 | 1 | 3 | 2 | 4 | 4 | 1 | 3 | 0 | 3 | 2 |
| 64612 | 0 | 0 | 0 | 0 | 2 | 0 | 0 | 0 | 0 | 0 | 0 |
| 126510 | 0 | 0 | 1 | 1 | 0 | 0 | 0 | 0 | 1 | 0 | 2 |
| 179654 | 2 | 2 | 11 | 2 | 1 | 3 | 1 | 2 | 1 | 2 | 2 |
| 196556 | 3 | 2 | 7 | 1 | 0 | 6 | 1 | 4 | 0 | 2 | 2 |
| 197199 | 3 | 0 | 2 | 1 | 2 | 3 | 2 | 3 | 1 | 1 | 11 |
| 197271 | 2 | 1 | 10 | 2 | 2 | 4 | 2 | 6 | 1 | 1 | 3 |

| Incyte ID NO | ACP5 215481 | CTSK 219975 | BMP6 233926 | SPARC 234507 | VEGFA 242681 | FLRG 243362 | COL1A2 244935 | BGLAP 246251 | CA2 248306 | ITGAV 250203 | EGR1 251715 |
|---|---|---|---|---|---|---|---|---|---|---|---|
| 331276 | 2 | 5 | 3 | 8 | 3 | 12 | 9 | 4 | 1 | 5 | 3 |
| 331906 | 0 | 4 | 2 | 1 | 1 | 1 | 1 | 3 | 1 | 2 | 0 |
| 337832 | 1 | 1 | 0 | 0 | 3 | 1 | 0 | 0 | 1 | 2 | 1 |
| 344071 | 2 | 4 | 1 | 2 | 1 | 0 | 1 | 1 | 0 | 0 | 2 |
| 344594 | 3 | 19 | 5 | 22 | 5 | 22 | 29 | 5 | 0 | 4 | 11 |
| 400799 | 3 | 0 | 2 | 1 | 0 | 0 | 0 | 0 | 0 | 0 | 1 |
| 402117 | 1 | 0 | 0 | 1 | 1 | 1 | 0 | 1 | 3 | 1 | 1 |
| 406605 | 1 | 1 | 2 | 0 | 1 | 0 | 0 | 2 | 0 | 0 | 0 |
| 481497 | 6 | 6 | 5 | 9 | 7 | 6 | 5 | 7 | 2 | 11 | 5 |
| 1549 | 2 | 6 | 6 | 10 | 3 | 3 | 6 | 5 | 1 | 6 | 2 |
| 2715 | 0 | 0 | 0 | 0 | 0 | 0 | 0 | 1 | 0 | 1 | 0 |
| 4485 | 0 | 0 | 0 | 0 | 1 | 1 | 0 | 0 | 2 | 2 | 0 |
| 4516 | 0 | 1 | 0 | 0 | 1 | 0 | 1 | 0 | 1 | 2 | 0 |
| 5028 | 1 | 1 | 0 | 2 | 2 | 0 | 1 | 1 | 1 | 1 | 1 |
| 9051 | 0 | 1 | 2 | 1 | 0 | 1 | 0 | 0 | 1 | 0 | 0 |
| 9661 | 0 | 1 | 1 | 1 | 1 | 1 | 0 | 0 | 0 | 0 | 1 |
| 12432 | 1 | 1 | 1 | 3 | 2 | 1 | 0 | 5 | 3 | 2 | 1 |
| 19238 | 1 | 3 | 6 | 8 | 2 | 4 | 3 | 1 | 0 | 1 | 1 |
| 21651 | 3 | 7 | 4 | 11 | 4 | 13 | 17 | 4 | 0 | 5 | 4 |
| 21656 | 1 | 0 | 0 | 1 | 0 | 4 | 3 | 1 | 0 | 1 | 1 |
| 23103 | 1 | 2 | 1 | 1 | 2 | 0 | 0 | 2 | 4 | 1 | 1 |
| 23303 | 2 | 2 | 1 | 3 | 1 | 1 | 1 | 4 | 0 | 1 | 1 |
| 33977 | 0 | 3 | 1 | 0 | 1 | 0 | 0 | 1 | 2 | 1 | 0 |
| 34157 | 1 | 1 | 2 | 1 | 1 | 0 | 0 | 2 | 1 | 2 | 0 |
| 37739 | 0 | 0 | 0 | 1 | 0 | 0 | 1 | 1 | 0 | 0 | 0 |
| 40200 | 1 | 1 | 1 | 0 | 0 | 0 | 0 | 1 | 1 | 1 | 0 |
| 64612 | 0 | 0 | 0 | 0 | 0 | 0 | 0 | 1 | 0 | 0 | 0 |
| 126510 | 1 | 1 | 1 | 1 | 0 | 1 | 1 | 0 | 0 | 0 | 1 |
| 179654 | 1 | 1 | 2 | 2 | 4 | 2 | 3 | 2 | 1 | 2 | 4 |
| 196556 | 3 | 4 | 2 | 4 | 2 | 0 | 3 | 4 | 1 | 2 | 2 |
| 197199 | 4 | 5 | 3 | 6 | 4 | 3 | 5 | 6 | 1 | 4 | 2 |
| 197271 | 2 | 3 | 3 | 2 | 3 | 2 | 2 | 4 | 3 | 2 | 3 |

| Incyte ID NO | COL1A1 257184 | CSF1 333948 | BGN 345168 | SPP1 352406 | IGF1 399413 | DCN 427953 | CTSB 429609 | CSF1R 64333 | KL 215078 | maximum − log pvalue |
|---|---|---|---|---|---|---|---|---|---|---|
| 331276 | 6 | 2 | 10 | 4 | 5 | 11 | 5 | 4 | 3 | 12 |
| 331906 | 0 | 1 | 0 | 1 | 3 | 1 | 1 | 2 | 2 | 8 |
| 337832 | 0 | 0 | 2 | 5 | 0 | 0 | 1 | 1 | 6 | 6 |
| 344071 | 1 | 0 | 1 | 1 | 2 | 1 | 0 | 1 | 0 | 7 |
| 344594 | 21 | 4 | 13 | 0 | 13 | 26 | 11 | 5 | 0 | 29 |
| 400799 | 1 | 3 | 1 | 0 | 1 | 0 | 3 | 3 | 0 | 8 |
| 402117 | 0 | 0 | 1 | 2 | 0 | 1 | 1 | 0 | 5 | 7 |
| 406605 | 0 | 1 | 0 | 1 | 1 | 1 | 1 | 2 | 3 | 8 |
| 481497 | 4 | 3 | 4 | 7 | 3 | 9 | 9 | 4 | 2 | 11 |
| 1549 | 3 | 3 | 8 | 4 | 3 | 12 | 8 | 2 | 2 | 12 |
| 2715 | 0 | 0 | 0 | 0 | 0 | 0 | 0 | 1 | 0 | 6 |
| 4485 | 1 | 0 | 2 | 2 | 1 | 0 | 0 | 0 | 8 | 8 |
| 4516 | 0 | 0 | 0 | 3 | 0 | 0 | 0 | 0 | 4 | 7 |
| 5028 | 0 | 1 | 0 | 0 | 0 | 1 | 1 | 1 | 1 | 7 |
| 9051 | 0 | 2 | 2 | 1 | 1 | 1 | 1 | 3 | 3 | 6 |
| 9661 | 1 | 0 | 2 | 2 | 0 | 0 | 0 | 2 | 2 | 7 |
| 12432 | 1 | 1 | 2 | 1 | 1 | 2 | 1 | 1 | 1 | 6 |
| 19238 | 1 | 0 | 4 | 1 | 1 | 3 | 4 | 2 | 1 | 8 |
| 21651 | 12 | 1 | 10 | 2 | 7 | 17 | 7 | 3 | 0 | 17 |
| 21656 | 1 | 1 | 1 | 0 | 1 | 5 | 0 | 1 | 0 | 10 |
| 23103 | 0 | 0 | 1 | 1 | 2 | 1 | 1 | 5 | 3 | 6 |
| 23303 | 1 | 1 | 2 | 1 | 3 | 1 | 1 | 1 | 3 | 8 |
| 33977 | 0 | 0 | 0 | 1 | 1 | 0 | 0 | 1 | 1 | 6 |
| 34157 | 0 | 0 | 0 | 2 | 1 | 0 | 0 | 1 | 2 | 6 |
| 37739 | 2 | 1 | 0 | 2 | 1 | 0 | 0 | 2 | 2 | 6 |
| 40200 | 0 | 1 | 1 | 1 | 1 | 0 | 1 | 0 | 2 | 7 |
| 64612 | 0 | 0 | 1 | 0 | 0 | 0 | 0 | 0 | 0 | 6 |
| 126510 | 0 | 2 | 0 | 1 | 1 | 2 | 1 | 1 | 0 | 8 |
| 179654 | 1 | 1 | 2 | 1 | 2 | 3 | 1 | 2 | 3 | 11 |

TABLE 4-continued

| | | | | | | | | | | |
|---|---|---|---|---|---|---|---|---|---|---|
| 196556 | 2 | 1 | 4 | 1 | 1 | 3 | 2 | 5 | 2 | 7 |
| 197199 | 3 | 1 | 7 | 4 | 1 | 2 | 8 | 6 | 1 | 11 |
| 197271 | 2 | 1 | 2 | 0 | 2 | 2 | 1 | 1 | 1 | 10 |

| Incyte ID NO | PHEX 212786 | PTH 27686 | TRAF2 28174 | TNFSF11 334504 | TNFRSF11A 406015 | CYP24 207524 | NPPB 21736 | CSF2 275416 | CYP19 31314 | EGF 333073 | IL1A 335942 | MITF 345480 |
|---|---|---|---|---|---|---|---|---|---|---|---|---|
| 197886 | 1 | 1 | 0 | 1 | 0 | 0 | 0 | 1 | 2 | 0 | 0 | 1 |
| 198067 | 0 | 3 | 1 | 1 | 3 | 0 | 0 | 1 | 2 | 2 | 0 | 0 |
| 199069 | 0 | 1 | 1 | 1 | 0 | 0 | 1 | 0 | 1 | 0 | 1 | 0 |
| 200039 | 0 | 0 | 0 | 1 | 0 | 0 | 0 | 0 | 3 | 0 | 1 | 0 |
| 200119 | 1 | 2 | 0 | 1 | 2 | 0 | 0 | 0 | 3 | 0 | 1 | 0 |
| 200145 | 0 | 0 | 1 | 1 | 1 | 0 | 1 | 3 | 0 | 0 | 2 | 1 |
| 201843 | 1 | 4 | 0 | 3 | 1 | 0 | 0 | 1 | 3 | 1 | 0 | 1 |
| 201920 | 1 | 1 | 0 | 0 | 2 | 0 | 0 | 1 | 2 | 0 | 2 | 1 |
| 205855 | 0 | 0 | 0 | 1 | 0 | 0 | 0 | 0 | 6 | 0 | 1 | 1 |
| 206250 | 0 | 1 | 0 | 0 | 0 | 0 | 0 | 0 | 1 | 0 | 0 | 1 |
| 207220 | 0 | 1 | 0 | 0 | 1 | 1 | 1 | 0 | 2 | 1 | 0 | 1 |
| 207591 | 0 | 1 | 0 | 0 | 0 | 1 | 0 | 0 | 4 | 1 | 2 | 1 |
| 210741 | 0 | 1 | 0 | 1 | 0 | 0 | 0 | 0 | 4 | 0 | 1 | 0 |
| 213764 | 0 | 0 | 0 | 0 | 0 | 3 | 0 | 0 | 0 | 7 | 0 | 0 |
| 215642 | 0 | 0 | 0 | 0 | 1 | 0 | 2 | 1 | 1 | 1 | 1 | 2 |
| 216188 | 0 | 1 | 1 | 1 | 4 | 0 | 1 | 2 | 1 | 1 | 3 | 0 |
| 218628 | 0 | 0 | 0 | 1 | 2 | 1 | 1 | 2 | 1 | 0 | 2 | 1 |
| 218996 | 0 | 0 | 0 | 1 | 0 | 1 | 0 | 0 | 3 | 1 | 2 | 0 |
| 223147 | 0 | 0 | 0 | 2 | 1 | 0 | 1 | 0 | 1 | 0 | 1 | 2 |
| 227709 | 1 | 1 | 0 | 1 | 1 | 1 | 2 | 0 | 2 | 0 | 1 | 0 |
| 228623 | 0 | 0 | 0 | 0 | 1 | 0 | 2 | 1 | 0 | 1 | 1 | 0 |
| 229357 | 1 | 1 | 0 | 0 | 1 | 0 | 0 | 1 | 1 | 0 | 1 | 1 |
| 231861 | 0 | 0 | 0 | 0 | 0 | 0 | 0 | 0 | 1 | 0 | 1 | 1 |
| 231965 | 0 | 1 | 1 | 1 | 0 | 1 | 0 | 0 | 7 | 1 | 1 | 1 |
| 232573 | 0 | 1 | 0 | 0 | 0 | 0 | 0 | 0 | 7 | 0 | 1 | 0 |
| 232653 | 1 | 1 | 0 | 1 | 3 | 0 | 0 | 0 | 3 | 2 | 2 | 0 |
| 232773 | 0 | 0 | 0 | 0 | 0 | 3 | 0 | 0 | 1 | 1 | 0 | 2 |
| 232968 | 0 | 0 | 1 | 1 | 0 | 0 | 0 | 0 | 0 | 1 | 0 | 1 |
| 233113 | 1 | 1 | 0 | 1 | 2 | 0 | 0 | 1 | 1 | 1 | 1 | 1 |
| 234545 | 0 | 0 | 0 | 0 | 1 | 0 | 10 | 0 | 0 | 1 | 0 | 0 |
| 235194 | 0 | 1 | 0 | 4 | 0 | 0 | 1 | 0 | 0 | 0 | 2 | 0 |
| 235464 | 0 | 0 | 1 | 1 | 0 | 0 | 0 | 2 | 1 | 0 | 2 | 1 |

| Incyte ID NO | BMP7 346943 | IBSP 350961 | ITGB3 351122 | AHSG 199151 | TNFRSF11B 201571 | IL1B 21870 | SPI1 235903 | MMP9 238213 | PTHR1 243080 | SRC 245512 | KDR 247817 |
|---|---|---|---|---|---|---|---|---|---|---|---|
| 197886 | 1 | 0 | 4 | 1 | 0 | 0 | 2 | 1 | 0 | 0 | 2 |
| 198067 | 1 | 0 | 2 | 2 | 3 | 0 | 2 | 1 | 1 | 3 | 4 |
| 199069 | 2 | 0 | 1 | 1 | 1 | 1 | 0 | 1 | 1 | 2 | 5 |
| 200039 | 2 | 0 | 6 | 1 | 1 | 0 | 2 | 0 | 2 | 0 | 0 |
| 200119 | 1 | 1 | 1 | 4 | 0 | 0 | 1 | 1 | 7 | 1 | 2 |
| 200145 | 0 | 1 | 0 | 0 | 0 | 3 | 10 | 3 | 0 | 1 | 2 |
| 201843 | 1 | 1 | 2 | 1 | 0 | 1 | 3 | 2 | 1 | 0 | 2 |
| 201920 | 3 | 0 | 2 | 0 | 0 | 1 | 5 | 3 | 2 | 2 | 3 |
| 205855 | 2 | 1 | 4 | 2 | 1 | 0 | 2 | 0 | 3 | 1 | 1 |
| 206250 | 0 | 1 | 0 | 0 | 1 | 2 | 4 | 3 | 1 | 2 | 3 |
| 207220 | 1 | 0 | 1 | 1 | 0 | 0 | 1 | 0 | 3 | 0 | 6 |
| 207591 | 1 | 0 | 7 | 1 | 1 | 0 | 1 | 1 | 5 | 0 | 1 |
| 210741 | 1 | 0 | 6 | 2 | 0 | 0 | 1 | 0 | 2 | 1 | 2 |
| 213764 | 1 | 0 | 1 | 0 | 1 | 0 | 0 | 0 | 3 | 1 | 0 |
| 215642 | 1 | 1 | 1 | 0 | 2 | 1 | 0 | 1 | 0 | 1 | 3 |
| 216188 | 1 | 0 | 2 | 1 | 0 | 4 | 10 | 6 | 1 | 1 | 0 |
| 218628 | 0 | 0 | 1 | 1 | 1 | 4 | 10 | 6 | 1 | 1 | 1 |
| 218996 | 2 | 0 | 5 | 1 | 1 | 0 | 2 | 0 | 1 | 0 | 0 |
| 223147 | 2 | 0 | 1 | 1 | 1 | 0 | 2 | 1 | 2 | 2 | 2 |
| 227709 | 3 | 0 | 1 | 0 | 0 | 2 | 10 | 2 | 1 | 2 | 1 |
| 228623 | 1 | 0 | 1 | 0 | 1 | 0 | 1 | 0 | 2 | 3 | 3 |
| 229357 | 1 | 1 | 2 | 0 | 1 | 0 | 0 | 2 | 0 | 4 | 3 |
| 231861 | 2 | 0 | 3 | 3 | 1 | 0 | 1 | 1 | 2 | 2 | 1 |
| 231965 | 2 | 0 | 3 | 1 | 0 | 1 | 2 | 0 | 2 | 0 | 3 |
| 232573 | 1 | 0 | 3 | 4 | 0 | 0 | 1 | 0 | 2 | 2 | 2 |
| 232653 | 2 | 1 | 3 | 3 | 1 | 0 | 1 | 1 | 2 | 1 | 2 |
| 232773 | 1 | 1 | 2 | 1 | 4 | 0 | 1 | 1 | 2 | 0 | 1 |
| 232968 | 2 | 0 | 1 | 1 | 1 | 1 | 8 | 1 | 3 | 3 | 2 |
| 233113 | 3 | 0 | 6 | 1 | 2 | 3 | 4 | 1 | 2 | 1 | 2 |
| 234545 | 3 | 0 | 2 | 1 | 1 | 0 | 1 | 0 | 1 | 0 | 1 |
| 235194 | 4 | 0 | 1 | 0 | 0 | 0 | 3 | 1 | 0 | 3 | 1 |
| 235464 | 1 | 0 | 0 | 1 | 1 | 5 | 10 | 8 | 1 | 1 | 0 |

TABLE 4-continued

| Incyte ID NO | FLT1 322303 | ADAM12 331582 | MADH6 333398 | PTHR2 336338 | GRLF1 336588 | PDNP1 344785 | BMP2 346680 | VDR 348162 | ESR1 349438 | TRAF5 401610 | TGFB1 121174 |
|---|---|---|---|---|---|---|---|---|---|---|---|
| 197886 | 1 | 3 | 4 | 2 | 0 | 2 | 1 | 7 | 1 | 1 | 2 |
| 198067 | 1 | 1 | 4 | 1 | 1 | 7 | 1 | 2 | 1 | 2 | 2 |
| 199069 | 0 | 2 | 1 | 1 | 0 | 2 | 3 | 2 | 2 | 2 | 1 |
| 200039 | 1 | 3 | 1 | 1 | 1 | 2 | 2 | 1 | 1 | 0 | 3 |
| 200119 | 1 | 1 | 4 | 2 | 1 | 1 | 1 | 2 | 1 | 0 | 1 |
| 200145 | 0 | 1 | 1 | 1 | 0 | 1 | 1 | 6 | 1 | 1 | 6 |
| 201843 | 2 | 1 | 2 | 1 | 2 | 3 | 2 | 2 | 1 | 2 | 3 |
| 201920 | 4 | 1 | 5 | 5 | 1 | 3 | 2 | 4 | 0 | 2 | 12 |
| 205855 | 2 | 4 | 2 | 2 | 1 | 3 | 0 | 2 | 0 | 1 | 1 |
| 206250 | 4 | 3 | 1 | 2 | 2 | 1 | 3 | 3 | 1 | 0 | 4 |
| 207220 | 5 | 2 | 4 | 0 | 1 | 2 | 2 | 1 | 2 | 2 | 2 |
| 207591 | 2 | 2 | 4 | 2 | 2 | 3 | 0 | 2 | 1 | 1 | 1 |
| 210741 | 3 | 2 | 2 | 3 | 1 | 3 | 2 | 3 | 0 | 1 | 1 |
| 213764 | 0 | 0 | 1 | 0 | 1 | 1 | 0 | 1 | 0 | 0 | 0 |
| 215642 | 4 | 1 | 0 | 1 | 1 | 3 | 0 | 3 | 3 | 2 | 1 |
| 216188 | 0 | 1 | 1 | 1 | 0 | 1 | 1 | 4 | 0 | 2 | 3 |
| 218628 | 1 | 1 | 0 | 1 | 2 | 1 | 2 | 3 | 0 | 1 | 4 |
| 218996 | 1 | 4 | 4 | 1 | 1 | 2 | 0 | 3 | 2 | 0 | 2 |
| 223147 | 3 | 1 | 1 | 2 | 1 | 1 | 2 | 2 | 3 | 1 | 3 |
| 227709 | 1 | 1 | 1 | 2 | 1 | 2 | 1 | 3 | 0 | 1 | 4 |
| 228623 | 2 | 1 | 1 | 1 | 3 | 2 | 2 | 1 | 3 | 0 | 5 |
| 229357 | 5 | 0 | 2 | 3 | 1 | 1 | 2 | 2 | 3 | 1 | 4 |
| 231861 | 2 | 3 | 4 | 2 | 2 | 1 | 1 | 8 | 1 | 2 | 2 |
| 231965 | 4 | 2 | 3 | 2 | 1 | 6 | 1 | 3 | 0 | 2 | 1 |
| 232573 | 3 | 3 | 3 | 1 | 1 | 4 | 0 | 2 | 1 | 1 | 1 |
| 232653 | 1 | 1 | 3 | 1 | 2 | 2 | 0 | 8 | 1 | 0 | 1 |
| 232773 | 4 | 2 | 4 | 2 | 2 | 3 | 1 | 1 | 1 | 0 | 2 |
| 232968 | 1 | 0 | 3 | 1 | 1 | 1 | 0 | 1 | 2 | 2 | 3 |
| 233113 | 3 | 1 | 7 | 2 | 1 | 6 | 2 | 5 | 1 | 2 | 2 |
| 234545 | 1 | 2 | 1 | 2 | 2 | 1 | 1 | 1 | 0 | 0 | 0 |
| 235194 | 0 | 1 | 1 | 1 | 3 | 1 | 0 | 1 | 2 | 1 | 5 |
| 235464 | 0 | 1 | 0 | 0 | 0 | 0 | 0 | 2 | 1 | 1 | 3 |

| Incyte ID NO | ACP5 215481 | CTSK 219975 | BMP6 233926 | SPARC 234507 | VEGFA 242681 | FLRG 243362 | COL1A2 244935 | BGLAP 246251 | CA2 248306 | ITGAV 250203 | EGR1 251715 |
|---|---|---|---|---|---|---|---|---|---|---|---|
| 197886 | 1 | 2 | 2 | 0 | 1 | 1 | 0 | 4 | 1 | 2 | 1 |
| 198067 | 7 | 2 | 3 | 2 | 7 | 2 | 4 | 4 | 2 | 3 | 14 |
| 199069 | 3 | 1 | 2 | 8 | 5 | 4 | 3 | 4 | 1 | 11 | 2 |
| 200039 | 0 | 1 | 1 | 1 | 0 | 0 | 0 | 1 | 1 | 1 | 1 |
| 200119 | 0 | 2 | 2 | 1 | 1 | 1 | 1 | 2 | 3 | 1 | 1 |
| 200145 | 5 | 2 | 0 | 0 | 1 | 1 | 1 | 3 | 0 | 0 | 3 |
| 201843 | 3 | 3 | 3 | 1 | 3 | 2 | 2 | 6 | 3 | 2 | 1 |
| 201920 | 1 | 2 | 2 | 1 | 3 | 1 | 1 | 4 | 1 | 2 | 2 |
| 205855 | 0 | 1 | 1 | 1 | 0 | 0 | 1 | 2 | 2 | 0 | 0 |
| 206250 | 5 | 5 | 4 | 9 | 3 | 6 | 3 | 3 | 2 | 3 | 3 |
| 207220 | 2 | 1 | 3 | 7 | 4 | 3 | 4 | 2 | 2 | 2 | 2 |
| 207591 | 1 | 2 | 2 | 1 | 0 | 0 | 1 | 1 | 1 | 0 | 1 |
| 210741 | 0 | 2 | 3 | 1 | 2 | 0 | 1 | 4 | 2 | 4 | 1 |
| 213764 | 0 | 0 | 0 | 1 | 1 | 0 | 1 | 0 | 2 | 2 | 0 |
| 215642 | 2 | 8 | 1 | 12 | 2 | 13 | 14 | 4 | 0 | 5 | 6 |
| 216188 | 3 | 1 | 2 | 1 | 1 | 1 | 0 | 1 | 1 | 1 | 6 |
| 218628 | 3 | 0 | 2 | 1 | 1 | 0 | 1 | 0 | 0 | 0 | 2 |
| 218996 | 0 | 2 | 1 | 0 | 1 | 1 | 1 | 1 | 2 | 0 | 0 |
| 223147 | 3 | 8 | 3 | 7 | 7 | 12 | 9 | 6 | 1 | 7 | 5 |
| 227709 | 4 | 0 | 3 | 1 | 6 | 0 | 0 | 3 | 3 | 3 | 3 |
| 228623 | 1 | 5 | 7 | 15 | 8 | 14 | 19 | 4 | 0 | 6 | 10 |
| 229357 | 1 | 6 | 3 | 9 | 4 | 17 | 18 | 4 | 1 | 2 | 7 |
| 231861 | 2 | 2 | 2 | 2 | 2 | 2 | 1 | 6 | 5 | 1 | 2 |
| 231965 | 1 | 2 | 2 | 3 | 3 | 2 | 1 | 3 | 1 | 3 | 1 |
| 232573 | 1 | 3 | 2 | 1 | 0 | 1 | 1 | 2 | 2 | 0 | 1 |
| 232653 | 1 | 3 | 2 | 1 | 1 | 1 | 0 | 2 | 3 | 1 | 1 |
| 232773 | 0 | 1 | 2 | 5 | 3 | 4 | 3 | 2 | 1 | 4 | 1 |
| 232968 | 1 | 2 | 2 | 6 | 6 | 1 | 1 | 4 | 4 | 6 | 6 |
| 233113 | 1 | 3 | 2 | 2 | 1 | 1 | 1 | 5 | 2 | 5 | 1 |
| 234545 | 1 | 0 | 0 | 2 | 1 | 2 | 1 | 3 | 0 | 2 | 0 |
| 235194 | 1 | 1 | 2 | 2 | 4 | 1 | 1 | 2 | 2 | 1 | 4 |
| 235464 | 6 | 0 | 1 | 1 | 0 | 1 | 1 | 2 | 1 | 0 | 1 |

| Incyte ID NO | COL1A1 257184 | CSF1 333948 | BGN 345168 | SPP1 352406 | IGF1 399413 | DCN 427953 | CTSB 429609 | CSF1R 64333 | KL 215078 | maximum − log pvalue |
|---|---|---|---|---|---|---|---|---|---|---|
| 197886 | 1 | 2 | 1 | 1 | 1 | 1 | 1 | 1 | 0 | 7 |
| 198067 | 1 | 0 | 5 | 1 | 2 | 6 | 4 | 5 | 3 | 14 |
| 199069 | 2 | 0 | 5 | 2 | 2 | 6 | 4 | 4 | 1 | 11 |
| 200039 | 1 | 2 | 0 | 0 | 1 | 1 | 0 | 2 | 1 | 6 |

TABLE 4-continued

| | | | | | | | | | | |
|---|---|---|---|---|---|---|---|---|---|---|
| 200119 | 1 | 1 | 1 | 0 | 2 | 1 | 0 | 1 | 1 | 7 |
| 200145 | 0 | 3 | 1 | 0 | 1 | 0 | 2 | 2 | 0 | 10 |
| 201843 | 1 | 1 | 1 | 3 | 1 | 1 | 2 | 3 | 2 | 6 |
| 201920 | 2 | 2 | 3 | 3 | 3 | 1 | 2 | 5 | 2 | 12 |
| 205855 | 1 | 2 | 0 | 1 | 1 | 1 | 0 | 2 | 1 | 6 |
| 206250 | 2 | 0 | 12 | 7 | 4 | 10 | 9 | 7 | 3 | 12 |
| 207220 | 1 | 1 | 12 | 3 | 2 | 3 | 3 | 4 | 1 | 12 |
| 207591 | 1 | 1 | 1 | 1 | 4 | 1 | 1 | 2 | 2 | 7 |
| 210741 | 0 | 1 | 1 | 0 | 1 | 1 | 1 | 2 | 2 | 6 |
| 213764 | 0 | 0 | 1 | 2 | 0 | 0 | 0 | 0 | 6 | 7 |
| 215642 | 8 | 1 | 7 | 3 | 3 | 18 | 4 | 2 | 0 | 18 |
| 216188 | 2 | 4 | 1 | 0 | 1 | 0 | 2 | 4 | 0 | 10 |
| 218628 | 1 | 2 | 1 | 0 | 0 | 1 | 2 | 4 | 0 | 10 |
| 218996 | 1 | 2 | 0 | 2 | 1 | 0 | 0 | 3 | 1 | 5 |
| 223147 | 6 | 2 | 5 | 1 | 5 | 12 | 9 | 2 | 1 | 12 |
| 227709 | 0 | 1 | 2 | 4 | 0 | 1 | 2 | 7 | 1 | 10 |
| 228623 | 10 | 2 | 11 | 0 | 8 | 17 | 5 | 3 | 1 | 19 |
| 229357 | 11 | 2 | 4 | 2 | 14 | 21 | 3 | 3 | 0 | 21 |
| 231861 | 1 | 1 | 2 | 3 | 2 | 2 | 3 | 3 | 1 | 8 |
| 231965 | 0 | 0 | 1 | 2 | 3 | 3 | 1 | 1 | 1 | 7 |
| 232573 | 1 | 1 | 1 | 1 | 2 | 1 | 0 | 5 | 3 | 7 |
| 232653 | 1 | 0 | 1 | 1 | 1 | 1 | 1 | 2 | 1 | 8 |
| 232773 | 1 | 2 | 1 | 2 | 2 | 6 | 3 | 1 | 1 | 6 |
| 232968 | 1 | 5 | 4 | 6 | 3 | 3 | 7 | 3 | 1 | 8 |
| 233113 | 1 | 1 | 2 | 1 | 1 | 1 | 3 | 6 | 5 | 7 |
| 234545 | 1 | 1 | 1 | 0 | 0 | 1 | 1 | 1 | 0 | 10 |
| 235194 | 1 | 2 | 4 | 0 | 1 | 1 | 1 | 1 | 0 | 5 |
| 235464 | 1 | 3 | 1 | 1 | 0 | 1 | 2 | 5 | 1 | 10 |

| Incyte ID NO | PHEX 212786 | PTH 27686 | TRAF2 28174 | TNFSF11 334504 | TNFRSF11A 406015 | CYP24 207524 | NPPB 21736 | CSF2 275416 | CYP19 31314 | EGF 333073 | IL1A 335942 | MITF 345480 |
|---|---|---|---|---|---|---|---|---|---|---|---|---|
| 235636 | 0 | 0 | 0 | 1 | 0 | 1 | 1 | 1 | 1 | 1 | 1 | 2 |
| 235995 | 0 | 2 | 1 | 0 | 2 | 0 | 1 | 0 | 2 | 1 | 1 | 0 |
| 236378 | 0 | 0 | 0 | 0 | 0 | 0 | 0 | 0 | 0 | 1 | 0 | 0 |
| 237549 | 0 | 1 | 3 | 0 | 0 | 1 | 0 | 0 | 1 | 1 | 2 | 0 |
| 237709 | 0 | 1 | 0 | 1 | 0 | 1 | 1 | 0 | 0 | 1 | 0 | 2 |
| 238024 | 0 | 1 | 0 | 1 | 0 | 1 | 2 | 1 | 1 | 1 | 0 | 1 |
| 238413 | 0 | 0 | 0 | 0 | 1 | 1 | 0 | 0 | 1 | 0 | 1 | 0 |
| 238469 | 0 | 0 | 1 | 1 | 1 | 0 | 0 | 0 | 0 | 0 | 0 | 0 |
| 238544 | 0 | 0 | 0 | 3 | 0 | 0 | 0 | 1 | 2 | 0 | 1 | 0 |
| 239347 | 0 | 0 | 0 | 1 | 0 | 0 | 1 | 1 | 1 | 2 | 1 | 1 |
| 239382 | 0 | 0 | 0 | 0 | 0 | 0 | 6 | 0 | 0 | 0 | 1 | 0 |
| 241145 | 1 | 1 | 0 | 0 | 0 | 0 | 0 | 1 | 0 | 2 | 0 | 1 |
| 241599 | 0 | 0 | 0 | 0 | 0 | 5 | 0 | 0 | 0 | 3 | 0 | 0 |
| 241732 | 0 | 1 | 0 | 1 | 0 | 2 | 1 | 0 | 1 | 0 | 0 | 4 |
| 245000 | 0 | 1 | 1 | 1 | 2 | 2 | 1 | 0 | 2 | 2 | 0 | 1 |
| 245065 | 0 | 2 | 0 | 0 | 1 | 2 | 1 | 0 | 3 | 1 | 0 | 1 |
| 245084 | 0 | 2 | 0 | 0 | 1 | 0 | 0 | 1 | 1 | 1 | 2 | 1 |
| 245487 | 0 | 0 | 0 | 1 | 1 | 1 | 2 | 0 | 1 | 1 | 0 | 2 |
| 247384 | 1 | 0 | 0 | 0 | 0 | 0 | 6 | 0 | 1 | 1 | 0 | 0 |
| 247608 | 1 | 1 | 0 | 1 | 1 | 2 | 1 | 1 | 0 | 2 | 1 | 1 |
| 247789 | 0 | 0 | 0 | 1 | 2 | 0 | 0 | 0 | 0 | 0 | 0 | 1 |
| 249553 | 0 | 0 | 0 | 0 | 0 | 5 | 0 | 0 | 1 | 4 | 0 | 0 |
| 249997 | 0 | 2 | 0 | 1 | 0 | 2 | 0 | 1 | 3 | 1 | 1 | 1 |
| 251277 | 0 | 0 | 0 | 1 | 1 | 0 | 1 | 1 | 0 | 0 | 0 | 1 |
| 251482 | 2 | 0 | 0 | 0 | 5 | 1 | 0 | 0 | 4 | 1 | 2 | 1 |
| 252234 | 1 | 0 | 0 | 0 | 0 | 0 | 12 | 0 | 1 | 1 | 0 | 0 |
| 252875 | 1 | 1 | 2 | 1 | 1 | 0 | 0 | 0 | 0 | 1 | 1 | 1 |
| 253384 | 0 | 1 | 0 | 1 | 0 | 1 | 0 | 0 | 8 | 1 | 2 | 0 |
| 253428 | 0 | 0 | 0 | 1 | 0 | 0 | 0 | 1 | 0 | 0 | 0 | 1 |
| 254173 | 0 | 0 | 0 | 0 | 0 | 0 | 0 | 0 | 7 | 0 | 0 | 0 |
| 255839 | 0 | 0 | 1 | 0 | 0 | 1 | 0 | 0 | 2 | 1 | 1 | 1 |
| 255840 | 0 | 0 | 0 | 1 | 0 | 1 | 0 | 1 | 1 | 0 | 0 | 1 |
| 256852 | 0 | 0 | 0 | 0 | 0 | 1 | 0 | 0 | 8 | 0 | 0 | 0 |

| Incyte ID NO | BMP7 346943 | IBSP 350961 | ITGB3 351122 | AHSG 199151 | TNFRSF11B 201571 | IL1B 21870 | SPI1 235903 | MMP9 238213 | PTHR1 243080 | SRC 245512 | KDR 247817 |
|---|---|---|---|---|---|---|---|---|---|---|---|
| 235636 | 2 | 5 | 1 | 1 | 4 | 0 | 1 | 0 | 2 | 0 | 1 |
| 235995 | 3 | 2 | 6 | 3 | 1 | 1 | 2 | 1 | 1 | 2 | 3 |
| 236378 | 0 | 0 | 0 | 0 | 0 | 1 | 9 | 5 | 1 | 1 | 1 |
| 237549 | 3 | 0 | 2 | 1 | 1 | 0 | 2 | 1 | 2 | 2 | 3 |
| 237709 | 1 | 1 | 0 | 0 | 2 | 0 | 1 | 1 | 1 | 3 | 1 |
| 238024 | 1 | 0 | 1 | 0 | 2 | 0 | 1 | 1 | 0 | 1 | 1 |
| 238413 | 3 | 0 | 1 | 0 | 0 | 0 | 1 | 0 | 1 | 1 | 1 |
| 238469 | 2 | 0 | 0 | 0 | 1 | 0 | 0 | 1 | 0 | 0 | 1 |
| 238544 | 0 | 0 | 2 | 1 | 0 | 4 | 10 | 2 | 1 | 1 | 1 |
| 239347 | 2 | 1 | 3 | 1 | 1 | 3 | 8 | 1 | 1 | 2 | 1 |

TABLE 4-continued

| | | | | | | | | | | | |
|---|---|---|---|---|---|---|---|---|---|---|---|
| 239382 | 1 | 0 | 0 | 0 | 1 | 0 | 0 | 0 | 0 | 0 | 0 |
| 241145 | 0 | 0 | 0 | 1 | 4 | 1 | 1 | 1 | 0 | 5 | 2 |
| 241599 | 0 | 1 | 1 | 5 | 0 | 1 | 0 | 0 | 2 | 1 | 2 |
| 241732 | 2 | 0 | 2 | 0 | 2 | 0 | 0 | 1 | 1 | 1 | 5 |
| 245000 | 0 | 0 | 1 | 3 | 1 | 0 | 3 | 5 | 2 | 6 | 2 |
| 245065 | 1 | 1 | 2 | 1 | 1 | 0 | 1 | 1 | 2 | 1 | 2 |
| 245084 | 3 | 0 | 1 | 0 | 0 | 3 | 4 | 5 | 2 | 3 | 4 |
| 245487 | 2 | 1 | 2 | 1 | 2 | 1 | 0 | 0 | 1 | 6 | 2 |
| 247384 | 0 | 1 | 0 | 0 | 0 | 0 | 0 | 0 | 0 | 0 | 1 |
| 247608 | 2 | 1 | 1 | 0 | 1 | 0 | 1 | 1 | 0 | 1 | 4 |
| 247789 | 1 | 0 | 2 | 0 | 2 | 0 | 0 | 1 | 1 | 5 | 2 |
| 249553 | 1 | 0 | 1 | 2 | 0 | 0 | 0 | 0 | 3 | 1 | 1 |
| 249997 | 2 | 0 | 2 | 1 | 3 | 1 | 0 | 1 | 2 | 2 | 4 |
| 251277 | 1 | 1 | 1 | 1 | 1 | 0 | 1 | 1 | 0 | 1 | 1 |
| 251482 | 3 | 0 | 4 | 1 | 1 | 1 | 1 | 1 | 3 | 1 | 1 |
| 252234 | 3 | 0 | 1 | 1 | 1 | 1 | 1 | 2 | 2 | 0 | 1 |
| 252875 | 2 | 0 | 1 | 0 | 0 | 1 | 3 | 2 | 2 | 2 | 7 |
| 253384 | 3 | 0 | 4 | 1 | 1 | 0 | 1 | 0 | 4 | 0 | 1 |
| 253428 | 0 | 0 | 2 | 1 | 1 | 0 | 0 | 1 | 1 | 0 | 1 |
| 254173 | 0 | 0 | 4 | 4 | 0 | 0 | 2 | 0 | 3 | 0 | 2 |
| 255839 | 3 | 0 | 3 | 2 | 0 | 1 | 1 | 1 | 0 | 1 | 3 |
| 255840 | 8 | 0 | 1 | 1 | 1 | 0 | 2 | 2 | 2 | 2 | 2 |
| 256852 | 0 | 0 | 2 | 2 | 0 | 0 | 1 | 0 | 1 | 0 | 2 |

| Incyte ID NO | FLT1 322303 | ADAM12 331582 | MADH6 333398 | PTHR2 336338 | GRLF1 336588 | PDNP1 344785 | BMP2 346680 | VDR 348162 | ESR1 349438 | TRAF5 401610 | TGFB1 121174 |
|---|---|---|---|---|---|---|---|---|---|---|---|
| 235636 | 1 | 1 | 1 | 1 | 1 | 1 | 3 | 1 | 1 | 1 | 0 |
| 235995 | 1 | 2 | 2 | 2 | 3 | 3 | 1 | 4 | 1 | 2 | 1 |
| 236378 | 0 | 1 | 1 | 0 | 0 | 0 | 0 | 1 | 0 | 0 | 1 |
| 237549 | 1 | 1 | 8 | 1 | 4 | 5 | 3 | 3 | 2 | 2 | 4 |
| 237709 | 1 | 1 | 0 | 0 | 0 | 4 | 0 | 1 | 3 | 0 | 2 |
| 238024 | 3 | 0 | 0 | 1 | 1 | 1 | 1 | 1 | 2 | 1 | 0 |
| 238413 | 1 | 0 | 0 | 3 | 1 | 0 | 0 | 1 | 0 | 0 | 1 |
| 238469 | 3 | 1 | 0 | 0 | 2 | 3 | 0 | 1 | 8 | 2 | 1 |
| 238544 | 2 | 0 | 1 | 1 | 2 | 1 | 1 | 2 | 0 | 5 | 1 |
| 239347 | 1 | 2 | 2 | 1 | 1 | 1 | 1 | 2 | 2 | 1 | 3 |
| 239382 | 0 | 0 | 0 | 0 | 3 | 0 | 0 | 0 | 0 | 0 | 0 |
| 241145 | 0 | 1 | 0 | 0 | 0 | 0 | 3 | 2 | 5 | 1 | 3 |
| 241599 | 1 | 0 | 1 | 0 | 1 | 2 | 0 | 0 | 0 | 0 | 1 |
| 241732 | 3 | 3 | 4 | 3 | 4 | 3 | 3 | 2 | 4 | 2 | 1 |
| 245000 | 2 | 2 | 1 | 1 | 1 | 4 | 1 | 4 | 2 | 1 | 4 |
| 245065 | 8 | 2 | 3 | 1 | 1 | 5 | 2 | 3 | 0 | 1 | 1 |
| 245084 | 1 | 1 | 3 | 2 | 2 | 3 | 1 | 3 | 2 | 7 | 3 |
| 245487 | 2 | 2 | 2 | 2 | 1 | 1 | 2 | 1 | 5 | 1 | 2 |
| 247384 | 1 | 0 | 0 | 0 | 2 | 0 | 0 | 0 | 0 | 0 | 0 |
| 247608 | 1 | 0 | 3 | 2 | 3 | 1 | 0 | 1 | 3 | 2 | 0 |
| 247789 | 2 | 0 | 1 | 1 | 1 | 1 | 2 | 0 | 4 | 1 | 5 |
| 249553 | 1 | 0 | 3 | 0 | 1 | 1 | 0 | 0 | 0 | 1 | 0 |
| 249997 | 4 | 2 | 3 | 3 | 3 | 3 | 3 | 4 | 1 | 1 | 3 |
| 251277 | 3 | 1 | 2 | 0 | 2 | 0 | 0 | 0 | 1 | 0 | 0 |
| 251482 | 1 | 1 | 7 | 2 | 1 | 7 | 1 | 3 | 1 | 1 | 2 |
| 252234 | 2 | 2 | 1 | 1 | 1 | 2 | 1 | 1 | 1 | 1 | 0 |
| 252875 | 5 | 1 | 2 | 1 | 1 | 2 | 2 | 4 | 1 | 3 | 5 |
| 253384 | 5 | 4 | 4 | 2 | 1 | 3 | 0 | 2 | 1 | 0 | 1 |
| 253428 | 2 | 1 | 1 | 2 | 0 | 1 | 2 | 0 | 1 | 1 | 4 |
| 254173 | 4 | 4 | 3 | 1 | 1 | 5 | 0 | 1 | 0 | 1 | 2 |
| 255839 | 2 | 4 | 7 | 2 | 2 | 4 | 1 | 4 | 3 | 0 | 3 |
| 255840 | 2 | 1 | 3 | 3 | 2 | 2 | 1 | 4 | 2 | 2 | 3 |
| 256852 | 3 | 5 | 1 | 0 | 0 | 3 | 0 | 0 | 0 | 0 | 1 |

| Incyte ID NO | ACP5 215481 | CTSK 219975 | BMP6 233926 | SPARC 234507 | VEGFA 242681 | FLRG 243362 | COL1A2 244935 | BGLAP 246251 | CA2 248306 | ITGAV 250203 | EGR1 251715 |
|---|---|---|---|---|---|---|---|---|---|---|---|
| 235636 | 1 | 3 | 0 | 8 | 1 | 2 | 1 | 6 | 3 | 9 | 1 |
| 235995 | 3 | 2 | 5 | 1 | 1 | 1 | 1 | 5 | 4 | 3 | 1 |
| 236378 | 1 | 0 | 1 | 1 | 1 | 1 | 2 | 1 | 2 | 1 | 0 |
| 237549 | 2 | 3 | 3 | 2 | 7 | 1 | 4 | 3 | 2 | 2 | 5 |
| 237709 | 2 | 6 | 5 | 8 | 6 | 11 | 9 | 5 | 2 | 3 | 6 |
| 238024 | 0 | 7 | 1 | 8 | 3 | 10 | 6 | 6 | 1 | 6 | 2 |
| 238413 | 0 | 1 | 0 | 2 | 0 | 1 | 2 | 6 | 1 | 3 | 1 |
| 238469 | 2 | 5 | 2 | 4 | 1 | 4 | 3 | 3 | 0 | 2 | 4 |
| 238544 | 3 | 0 | 2 | 1 | 0 | 1 | 1 | 0 | 2 | 1 | 0 |
| 239347 | 1 | 1 | 1 | 0 | 1 | 0 | 1 | 2 | 0 | 0 | 2 |
| 239382 | 0 | 0 | 0 | 0 | 0 | 1 | 1 | 0 | 0 | 1 | 1 |
| 241145 | 2 | 6 | 5 | 13 | 4 | 16 | 12 | 5 | 1 | 11 | 6 |
| 241599 | 1 | 0 | 0 | 1 | 2 | 0 | 1 | 0 | 3 | 3 | 2 |
| 241732 | 0 | 11 | 4 | 10 | 6 | 12 | 13 | 2 | 1 | 3 | 5 |
| 245000 | 6 | 7 | 5 | 5 | 5 | 2 | 6 | 3 | 4 | 2 | 10 |

TABLE 4-continued

| | | | | | | | | | | | |
|---|---|---|---|---|---|---|---|---|---|---|---|
| 245065 | 3 | 3 | 3 | 3 | 2 | 3 | 2 | 6 | 3 | 5 | 1 |
| 245084 | 2 | 2 | 1 | 3 | 1 | 2 | 1 | 4 | 2 | 4 | 4 |
| 245487 | 2 | 6 | 3 | 13 | 3 | 11 | 14 | 4 | 1 | 5 | 6 |
| 247384 | 0 | 0 | 0 | 2 | 0 | 2 | 1 | 1 | 0 | 0 | 1 |
| 247608 | 1 | 2 | 2 | 6 | 3 | 4 | 1 | 7 | 6 | 11 | 1 |
| 247789 | 2 | 8 | 4 | 11 | 2 | 13 | 14 | 3 | 0 | 3 | 6 |
| 249553 | 0 | 0 | 0 | 0 | 0 | 1 | 1 | 1 | 3 | 1 | 0 |
| 249997 | 1 | 7 | 4 | 10 | 4 | 14 | 11 | 6 | 1 | 5 | 5 |
| 251277 | 1 | 6 | 2 | 7 | 2 | 7 | 8 | 2 | 3 | 1 | 3 |
| 251482 | 0 | 2 | 3 | 3 | 2 | 1 | 1 | 4 | 0 | 1 | 0 |
| 252234 | 1 | 1 | 0 | 5 | 1 | 1 | 1 | 2 | 0 | 2 | 1 |
| 252875 | 4 | 7 | 4 | 7 | 6 | 4 | 2 | 6 | 2 | 12 | 4 |
| 253384 | 0 | 3 | 1 | 1 | 0 | 0 | 1 | 1 | 1 | 1 | 0 |
| 253428 | 1 | 4 | 1 | 8 | 1 | 8 | 7 | 3 | 1 | 2 | 4 |
| 254173 | 1 | 3 | 2 | 1 | 0 | 1 | 1 | 1 | 1 | 0 | 0 |
| 255839 | 1 | 2 | 2 | 2 | 2 | 1 | 0 | 3 | 2 | 1 | 1 |
| 255840 | 4 | 2 | 2 | 7 | 8 | 8 | 7 | 5 | 1 | 6 | 7 |
| 256852 | 1 | 1 | 1 | 1 | 0 | 1 | 0 | 0 | 0 | 1 | 0 |

| Incyte ID NO | COL1A1 257184 | CSF1 333948 | BGN 345168 | SPP1 352406 | IGF1 399413 | DCN 427953 | CTSB 429609 | CSF1R 64333 | KL 215078 | maximum − log pvalue |
|---|---|---|---|---|---|---|---|---|---|---|
| 235636 | 1 | 1 | 2 | 6 | 2 | 4 | 1 | 1 | 1 | 9 |
| 235995 | 0 | 2 | 0 | 2 | 2 | 3 | 3 | 2 | 1 | 6 |
| 236378 | 2 | 3 | 0 | 3 | 1 | 1 | 1 | 3 | 0 | 9 |
| 237549 | 3 | 0 | 3 | 2 | 5 | 5 | 1 | 3 | 2 | 8 |
| 237709 | 8 | 3 | 7 | 0 | 8 | 12 | 5 | 2 | 0 | 12 |
| 238024 | 4 | 1 | 2 | 1 | 5 | 11 | 1 | 1 | 0 | 11 |
| 238413 | 1 | 0 | 1 | 5 | 1 | 0 | 1 | 2 | 1 | 6 |
| 238469 | 2 | 0 | 1 | 1 | 1 | 5 | 1 | 1 | 0 | 8 |
| 238544 | 2 | 1 | 1 | 0 | 0 | 1 | 1 | 2 | 0 | 10 |
| 239347 | 0 | 2 | 1 | 1 | 1 | 0 | 3 | 3 | 0 | 8 |
| 239382 | 0 | 0 | 0 | 0 | 0 | 0 | 0 | 1 | 0 | 6 |
| 241145 | 7 | 3 | 12 | 1 | 5 | 15 | 11 | 3 | 1 | 16 |
| 241599 | 1 | 0 | 2 | 3 | 0 | 2 | 1 | 1 | 4 | 5 |
| 241732 | 10 | 2 | 8 | 1 | 10 | 13 | 2 | 1 | 0 | 13 |
| 245000 | 7 | 2 | 5 | 4 | 2 | 11 | 7 | 9 | 2 | 11 |
| 245065 | 1 | 1 | 1 | 1 | 1 | 4 | 2 | 3 | 5 | 8 |
| 245084 | 2 | 3 | 2 | 2 | 1 | 3 | 6 | 4 | 0 | 7 |
| 245487 | 9 | 3 | 9 | 1 | 10 | 22 | 4 | 3 | 0 | 22 |
| 247384 | 0 | 0 | 1 | 1 | 1 | 1 | 0 | 1 | 0 | 6 |
| 247608 | 0 | 2 | 0 | 3 | 1 | 6 | 5 | 1 | 3 | 11 |
| 247789 | 9 | 2 | 7 | 1 | 6 | 13 | 6 | 3 | 0 | 14 |
| 249553 | 1 | 1 | 1 | 2 | 0 | 0 | 1 | 1 | 6 | 6 |
| 249997 | 11 | 3 | 7 | 1 | 5 | 12 | 6 | 4 | 2 | 14 |
| 251277 | 7 | 0 | 3 | 1 | 5 | 10 | 3 | 1 | 0 | 10 |
| 251482 | 1 | 0 | 1 | 1 | 2 | 1 | 1 | 0 | 2 | 7 |
| 252234 | 0 | 1 | 0 | 1 | 4 | 5 | 0 | 1 | 0 | 12 |
| 252875 | 1 | 1 | 4 | 3 | 2 | 6 | 6 | 7 | 2 | 12 |
| 253384 | 0 | 1 | 2 | 2 | 2 | 1 | 1 | 2 | 4 | 8 |
| 253428 | 4 | 1 | 5 | 1 | 6 | 13 | 2 | 1 | 0 | 13 |
| 254173 | 1 | 1 | 0 | 1 | 2 | 0 | 1 | 3 | 1 | 7 |
| 255839 | 2 | 1 | 2 | 1 | 1 | 1 | 1 | 5 | 2 | 7 |
| 255840 | 7 | 3 | 5 | 0 | 3 | 5 | 4 | 3 | 2 | 8 |
| 256852 | 1 | 0 | 1 | 3 | 0 | 0 | 0 | 2 | 1 | 8 |

| Incyte ID NO | PHEX 212786 | PTH 27686 | TRAF2 28174 | TNFSF11 334504 | TNFRSF11A 406015 | CYP24 207524 | NPPB 21736 | CSF2 275416 | CYP19 31314 | EGF 333073 | IL1A 335942 | MITF 345480 |
|---|---|---|---|---|---|---|---|---|---|---|---|---|
| 330852 | 2 | 4 | 0 | 0 | 1 | 0 | 1 | 2 | 0 | 3 | 1 | 1 |
| 331365 | 0 | 0 | 0 | 0 | 0 | 0 | 0 | 0 | 1 | 0 | 0 | 1 |
| 331395 | 1 | 0 | 1 | 0 | 2 | 2 | 0 | 0 | 3 | 0 | 1 | 0 |
| 331497 | 2 | 1 | 0 | 1 | 1 | 1 | 0 | 0 | 2 | 2 | 2 | 1 |
| 332290 | 0 | 0 | 0 | 0 | 0 | 3 | 0 | 0 | 0 | 7 | 0 | 0 |
| 332683 | 1 | 0 | 0 | 0 | 0 | 0 | 0 | 0 | 0 | 1 | 0 | 0 |
| 334405 | 1 | 1 | 0 | 1 | 0 | 0 | 0 | 0 | 7 | 0 | 1 | 0 |
| 336987 | 1 | 1 | 0 | 0 | 0 | 0 | 0 | 0 | 1 | 0 | 0 | 2 |
| 337015 | 1 | 2 | 0 | 1 | 1 | 0 | 1 | 1 | 2 | 0 | 1 | 0 |
| 337179 | 0 | 2 | 0 | 0 | 0 | 1 | 0 | 0 | 3 | 3 | 1 | 0 |
| 337314 | 1 | 0 | 0 | 0 | 2 | 0 | 0 | 0 | 2 | 0 | 2 | 0 |
| 337950 | 0 | 1 | 0 | 1 | 0 | 0 | 0 | 0 | 0 | 0 | 1 | 0 |
| 338091 | 0 | 0 | 0 | 1 | 0 | 1 | 0 | 0 | 1 | 1 | 2 | 1 |
| 340819 | 1 | 0 | 0 | 0 | 0 | 0 | 9 | 0 | 1 | 0 | 0 | 0 |
| 344516 | 0 | 0 | 0 | 2 | 1 | 1 | 0 | 0 | 0 | 0 | 1 | 0 |
| 348160 | 0 | 0 | 0 | 0 | 0 | 0 | 8 | 0 | 1 | 1 | 0 | 0 |
| 403869 | 0 | 1 | 0 | 0 | 1 | 1 | 1 | 0 | 3 | 0 | 1 | 0 |
| 404040 | 0 | 1 | 0 | 0 | 1 | 1 | 0 | 1 | 1 | 1 | 2 | 0 |
| 405185 | 0 | 3 | 1 | 0 | 0 | 1 | 1 | 0 | 2 | 0 | 1 | 1 |
| 406280 | 0 | 0 | 0 | 0 | 0 | 0 | 0 | 0 | 1 | 0 | 0 | 0 |

TABLE 4-continued

| | | | | | | | | | | | | |
|---|---|---|---|---|---|---|---|---|---|---|---|---|
| 406568 | 0 | 0 | 0 | 0 | 0 | 0 | 7 | 0 | 0 | 1 | 0 | 0 |
| 407143 | 0 | 0 | 0 | 2 | 2 | 0 | 0 | 1 | 1 | 1 | 2 | 0 |
| 410257 | 0 | 1 | 0 | 0 | 0 | 1 | 0 | 2 | 2 | 1 | 0 | 0 |
| 412477 | 0 | 0 | 0 | 1 | 0 | 1 | 0 | 0 | 2 | 0 | 2 | 0 |
| 414171 | 1 | 1 | 0 | 1 | 1 | 0 | 1 | 2 | 0 | 1 | 0 | 1 |
| 444857 | 0 | 0 | 1 | 0 | 0 | 0 | 0 | 2 | 1 | 2 | 1 | 1 |
| 475313 | 0 | 1 | 0 | 0 | 0 | 0 | 0 | 0 | 6 | 0 | 1 | 2 |
| 475350 | 2 | 1 | 0 | 1 | 1 | 0 | 0 | 1 | 1 | 0 | 0 | 1 |
| 481723 | 0 | 0 | 0 | 1 | 2 | 1 | 0 | 1 | 1 | 0 | 1 | 0 |
| maximum – log Pvalue | 6 | 6 | 3 | 6 | 5 | 6 | 12 | 6 | 12 | 9 | 6 | 6 |

| Incyte ID NO | BMP7 346943 | IBSP 350961 | ITGB3 351122 | AHSG 199151 | TNFRSF11B 201571 | IL1B 21870 | SPI1 235903 | MMP9 238213 | PTHR1 243080 | SRC 245512 | KDR 247817 |
|---|---|---|---|---|---|---|---|---|---|---|---|
| 330852 | 1 | 1 | 1 | 0 | 1 | 0 | 1 | 0 | 1 | 1 | 2 |
| 331365 | 1 | 0 | 1 | 0 | 3 | 0 | 0 | 1 | 0 | 1 | 0 |
| 331395 | 4 | 1 | 4 | 3 | 1 | 1 | 1 | 3 | 2 | 0 | 1 |
| 331497 | 3 | 0 | 3 | 2 | 1 | 0 | 2 | 0 | 3 | 2 | 2 |
| 332290 | 0 | 1 | 0 | 0 | 0 | 0 | 0 | 0 | 2 | 0 | 1 |
| 332683 | 0 | 5 | 0 | 0 | 3 | 0 | 0 | 1 | 0 | 0 | 0 |
| 334405 | 3 | 2 | 2 | 2 | 1 | 1 | 1 | 0 | 3 | 1 | 2 |
| 336987 | 1 | 1 | 2 | 0 | 3 | 1 | 1 | 1 | 3 | 0 | |
| 337015 | 6 | 1 | 2 | 2 | 0 | 0 | 1 | 0 | 2 | 0 | 3 |
| 337179 | 2 | 0 | 3 | 3 | 0 | 0 | 2 | 0 | 2 | 0 | 1 |
| 337314 | 1 | 0 | 1 | 1 | 1 | 0 | 1 | 1 | 2 | 1 | 1 |
| 337950 | 0 | 0 | 1 | 0 | 0 | 1 | 0 | 1 | 1 | 2 | 0 |
| 338091 | 1 | 0 | 6 | 0 | 0 | 0 | 2 | 0 | 2 | 0 | 0 |
| 340819 | 1 | 0 | 1 | 1 | 2 | 1 | 1 | 0 | 0 | 1 | 2 |
| 344516 | 0 | 0 | 0 | 0 | 0 | 1 | 9 | 1 | 0 | 0 | 0 |
| 348160 | 2 | 0 | 2 | 0 | 2 | 1 | 1 | 2 | 0 | 0 | 2 |
| 403869 | 1 | 0 | 1 | 1 | 1 | 0 | 0 | 0 | 1 | 2 | 2 |
| 404040 | 2 | 0 | 0 | 0 | 0 | 1 | 0 | 1 | 2 | 1 | 3 |
| 405185 | 1 | 3 | 7 | 1 | 2 | 0 | 3 | 1 | 2 | 0 | 2 |
| 406280 | 0 | 0 | 1 | 7 | 0 | 0 | 1 | 0 | 1 | 0 | 0 |
| 406568 | 1 | 0 | 0 | 0 | 0 | 0 | 0 | 1 | 0 | 0 | 1 |
| 407143 | 1 | 1 | 2 | 1 | 0 | 4 | 10 | 3 | 2 | 1 | 0 |
| 410257 | 1 | 1 | 1 | 1 | 0 | 1 | 1 | 1 | 1 | 3 | 2 |
| 412477 | 1 | 0 | 1 | 0 | 0 | 1 | 9 | 1 | 1 | 1 | 1 |
| 414171 | 2 | 0 | 0 | 0 | 1 | 0 | 1 | 1 | 3 | 2 | 3 |
| 444857 | 1 | 1 | 0 | 1 | 3 | 2 | 1 | 1 | 2 | 2 | 4 |
| 475313 | 1 | 0 | 3 | 2 | 0 | 0 | 0 | 0 | 0 | 0 | 3 |
| 475350 | 1 | 3 | 2 | 0 | 2 | 1 | 0 | 1 | 2 | 1 | 8 |
| 481723 | 3 | 0 | 3 | 0 | 2 | 0 | 1 | 3 | 1 | 2 | 3 |
| maximum – log Pvalue | 8 | 5 | 8 | 7 | 6 | 11 | 10 | 8 | 7 | 6 | 8 |

| Incyte ID NO | FLT1 322303 | ADAM12 331582 | MADH6 333398 | PTHR2 336338 | GRLF1 336588 | PDNP1 344785 | BMP2 346680 | VDR 348162 | ESR1 349438 | TRAF5 401610 | TGFB1 121174 |
|---|---|---|---|---|---|---|---|---|---|---|---|
| 330852 | 0 | 3 | 3 | 4 | 1 | 3 | 1 | 2 | 1 | 1 | 0 |
| 331365 | 2 | 1 | 2 | 2 | 1 | 1 | 3 | 3 | 6 | 2 | 1 |
| 331395 | 2 | 2 | 3 | 1 | 2 | 5 | 1 | 8 | 0 | 1 | 3 |
| 331497 | 3 | 2 | 6 | 3 | 2 | 5 | 2 | 8 | 1 | 1 | 3 |
| 332290 | 0 | 0 | 0 | 0 | 0 | 0 | 0 | 0 | 0 | 1 | 0 |
| 332683 | 2 | 0 | 1 | 1 | 0 | 1 | 0 | 0 | 1 | 0 | 1 |
| 334405 | 3 | 2 | 4 | 2 | 1 | 3 | 0 | 3 | 1 | 0 | 2 |
| 336987 | 8 | 1 | 5 | 2 | 2 | 3 | 3 | 1 | 1 | 4 | 2 |
| 337015 | 2 | 1 | 5 | 2 | 2 | 3 | 1 | 5 | 2 | 2 | 1 |
| 337179 | 3 | 3 | 9 | 1 | 1 | 4 | 3 | 5 | 1 | 2 | 4 |
| 337314 | 1 | 2 | 2 | 1 | 0 | 2 | 2 | 8 | 1 | 0 | 2 |
| 337950 | 0 | 0 | 1 | 0 | 0 | 1 | 2 | 5 | 1 | 1 | 0 |
| 338091 | 0 | 1 | 3 | 1 | 3 | 2 | 0 | 1 | 1 | 2 | 1 |
| 340819 | 0 | 1 | 1 | 0 | 1 | 1 | 1 | 2 | 0 | 0 | 1 |
| 344516 | 0 | 0 | 0 | 1 | 0 | 0 | 0 | 3 | 0 | 1 | 2 |
| 348160 | 1 | 0 | 2 | 1 | 1 | 0 | 1 | 1 | 1 | 0 | 1 |
| 403869 | 2 | 2 | 7 | 1 | 1 | 2 | 0 | 6 | 4 | 2 | 0 |
| 404040 | 1 | 2 | 2 | 1 | 0 | 3 | 2 | 1 | 2 | 0 | 2 |
| 405185 | 8 | 4 | 8 | 2 | 1 | 4 | 5 | 4 | 1 | 1 | 4 |
| 406280 | 1 | 0 | 0 | 0 | 0 | 5 | 1 | 0 | 0 | 0 | 0 |
| 406568 | 1 | 2 | 0 | 0 | 2 | 1 | 0 | 1 | 0 | 0 | 1 |
| 407143 | 1 | 1 | 1 | 1 | 1 | 1 | 0 | 2 | 1 | 3 | 4 |
| 410257 | 2 | 1 | 1 | 0 | 1 | 2 | 0 | 1 | 3 | 1 | 2 |
| 412477 | 1 | 0 | 1 | 1 | 2 | 0 | 0 | 2 | 1 | 2 | 4 |
| 414171 | 1 | 1 | 2 | 1 | 2 | 2 | 1 | 1 | 5 | 3 | 2 |
| 444857 | 2 | 1 | 1 | 1 | 3 | 2 | 1 | 2 | 1 | 1 | 3 |
| 475313 | 4 | 3 | 3 | 3 | 1 | 3 | 0 | 1 | 0 | 1 | 2 |
| 475350 | 5 | 1 | 3 | 3 | 2 | 3 | 2 | 1 | 1 | 1 | 2 |
| 481723 | 5 | 5 | 2 | 2 | 1 | 3 | 1 | 4 | 6 | 2 | 3 |

TABLE 4-continued

| maximum –log Pvalue | 9 | 7 | 11 | 5 | 6 | 9 | 5 | 8 | 8 | 7 | 12 |
|---|---|---|---|---|---|---|---|---|---|---|---|

| Incyte ID NO | ACP5 215481 | CTSK 219975 | BMP6 233926 | SPARC 234507 | VEGFA 242681 | FLRG 243362 | COL1A2 244935 | BGLAP 246251 | CA2 248306 | ITGAV 250203 | EGR1 251715 |
|---|---|---|---|---|---|---|---|---|---|---|---|
| 330852 | 1 | 1 | 3 | 3 | 3 | 2 | 0 | 4 | 2 | 8 | 2 |
| 331365 | 3 | 7 | 2 | 8 | 2 | 7 | 12 | 2 | 1 | 3 | 7 |
| 331395 | 3 | 2 | 2 | 2 | 1 | 0 | 0 | 4 | 4 | 3 | 1 |
| 331497 | 1 | 4 | 1 | 2 | 3 | 2 | 2 | 3 | 2 | 3 | 2 |
| 332290 | 1 | 1 | 0 | 0 | 2 | 1 | 1 | 0 | 3 | 2 | 3 |
| 332683 | 0 | 2 | 1 | 3 | 0 | 1 | 2 | 2 | 1 | 1 | 1 |
| 334405 | 1 | 3 | 1 | 1 | 1 | 1 | 2 | 1 | 1 | 2 | 1 |
| 336987 | 2 | 3 | 4 | 4 | 5 | 5 | 6 | 3 | 0 | 3 | 3 |
| 337015 | 0 | 1 | 3 | 0 | 1 | 1 | 0 | 2 | 1 | 1 | 1 |
| 337179 | 1 | 3 | 5 | 6 | 2 | 1 | 1 | 4 | 5 | 2 | 3 |
| 337314 | 0 | 2 | 2 | 1 | 2 | 1 | 2 | 2 | 1 | 1 | 1 |
| 337950 | 1 | 2 | 2 | 0 | 1 | 0 | 2 | 1 | 11 | 1 | 1 |
| 338091 | 0 | 3 | 1 | 1 | 0 | 0 | 0 | 1 | 1 | 1 | 0 |
| 340819 | 0 | 0 | 0 | 1 | 2 | 2 | 1 | 2 | 1 | 1 | 1 |
| 344516 | 0 | 0 | 0 | 2 | 1 | 1 | 2 | 1 | 2 | 0 | 0 |
| 348160 | 0 | 1 | 1 | 2 | 1 | 6 | 3 | 1 | 1 | 5 | 1 |
| 403869 | 1 | 3 | 3 | 1 | 1 | 1 | 2 | 1 | 1 | 0 | 3 |
| 404040 | 3 | 3 | 1 | 9 | 5 | 4 | 3 | 6 | 0 | 12 | 3 |
| 405185 | 3 | 3 | 5 | 6 | 3 | 1 | 2 | 1 | 2 | 1 | 3 |
| 406280 | 1 | 0 | 0 | 1 | 0 | 0 | 0 | 0 | 0 | 0 | 1 |
| 406568 | 1 | 0 | 1 | 2 | 0 | 2 | 0 | 1 | 0 | 1 | 1 |
| 407143 | 2 | 1 | 2 | 1 | 1 | 0 | 1 | 1 | 1 | 1 | 2 |
| 410257 | 2 | 3 | 3 | 6 | 1 | 5 | 6 | 3 | 1 | 2 | 9 |
| 412477 | 0 | 1 | 1 | 1 | 2 | 1 | 1 | 0 | 2 | 0 | 1 |
| 414171 | 2 | 4 | 4 | 10 | 5 | 9 | 6 | 9 | 1 | 8 | 2 |
| 444857 | 2 | 3 | 5 | 13 | 5 | 10 | 2 | 7 | 1 | 12 | 3 |
| 475313 | 1 | 2 | 1 | 1 | 1 | 1 | 1 | 1 | 0 | 1 | 1 |
| 475350 | 2 | 8 | 5 | 11 | 3 | 11 | 7 | 4 | 2 | 3 | 4 |
| 481723 | 3 | 17 | 4 | 12 | 4 | 12 | 12 | 6 | 2 | 4 | 3 |
| maximum –log Pvalue | 7 | 19 | 7 | 22 | 8 | 22 | 29 | 15 | 11 | 12 | 14 |

| Incyte ID NO | COL1A1 257184 | CSF1 333948 | BGN 345168 | SPP1 352406 | IGF1 399413 | DCN 427953 | CTSB 429609 | CSF1R 64333 | KL 215078 | maximum –log pvalue |
|---|---|---|---|---|---|---|---|---|---|---|
| 330852 | 1 | 1 | 1 | 2 | 1 | 3 | 4 | 2 | 1 | 8 |
| 331365 | 15 | 0 | 5 | 1 | 6 | 14 | 3 | 2 | 0 | 15 |
| 331395 | 1 | 2 | 1 | 5 | 1 | 1 | 1 | 2 | 1 | 8 |
| 331497 | 1 | 0 | 1 | 1 | 2 | 2 | 0 | 3 | 3 | 8 |
| 332290 | 0 | 0 | 2 | 3 | 0 | 2 | 0 | 0 | 4 | 7 |
| 332683 | 0 | 1 | 1 | 1 | 1 | 3 | 0 | 1 | 0 | 5 |
| 334405 | 2 | 2 | 2 | 1 | 2 | 1 | 1 | 2 | 2 | 7 |
| 336987 | 2 | 0 | 5 | 1 | 4 | 8 | 2 | 3 | 1 | 8 |
| 337015 | 1 | 0 | 0 | 2 | 2 | 1 | 1 | 2 | 2 | 6 |
| 337179 | 1 | 1 | 1 | 1 | 1 | 1 | 2 | 3 | 5 | 9 |
| 337314 | 3 | 1 | 0 | 0 | 1 | 2 | 3 | 1 | 1 | 8 |
| 337950 | 2 | 1 | 1 | 0 | 0 | 3 | 1 | 0 | 0 | 11 |
| 338091 | 0 | 1 | 0 | 0 | 1 | 0 | 0 | 1 | 1 | 6 |
| 340819 | 1 | 1 | 0 | 0 | 1 | 1 | 0 | 1 | 1 | 9 |
| 344516 | 1 | 3 | 0 | 0 | 1 | 1 | 1 | 1 | 0 | 9 |
| 348160 | 1 | 0 | 0 | 1 | 1 | 8 | 0 | 1 | 1 | 8 |
| 403869 | 1 | 1 | 1 | 1 | 1 | 1 | 2 | 2 | 2 | 7 |
| 404040 | 3 | 1 | 2 | 3 | 2 | 6 | 5 | 1 | 3 | 12 |
| 405185 | 1 | 4 | 4 | 2 | 1 | 3 | 2 | 4 | 2 | 8 |
| 406280 | 1 | 0 | 0 | 0 | 0 | 1 | 0 | 1 | 0 | 7 |
| 406568 | 0 | 0 | 1 | 0 | 0 | 4 | 1 | 1 | 0 | 7 |
| 407143 | 1 | 3 | 1 | 1 | 1 | 2 | 2 | 3 | 1 | 10 |
| 410257 | 4 | 3 | 11 | 1 | 3 | 5 | 6 | 4 | 1 | 11 |
| 412477 | 1 | 2 | 0 | 0 | 1 | 1 | 0 | 1 | 0 | 9 |
| 414171 | 6 | 0 | 10 | 4 | 4 | 11 | 4 | 2 | 2 | 11 |
| 444857 | 1 | 5 | 4 | 4 | 3 | 10 | 12 | 3 | 5 | 13 |
| 475313 | 1 | 0 | 0 | 0 | 4 | 2 | 0 | 2 | 1 | 6 |
| 475350 | 4 | 1 | 4 | 4 | 6 | 15 | 4 | 4 | 1 | 15 |
| 481723 | 7 | 2 | 6 | 1 | 7 | 12 | 6 | 4 | 3 | 17 |
| maximum –log Pvalue | 21 | 11 | 16 | 7 | 14 | 26 | 12 | 9 | 10 | |

TABLE 5

| Incyte ID No | PHEX 212786 | PTH 27686 | TRAF2 73440 | TNFSF11 334504 | TNFRSF11A 406015 | CYP24 207524 | NPPB 21736 | CSF2 275416 | CYP19 31314 | EGF 333073 | IL1A 335942 |
|---|---|---|---|---|---|---|---|---|---|---|---|
| 7074 | >0.001 | >0.001 | >0.001 | >0.001 | >0.001 | >0.001 | >0.001 | >0.001 | >0.001 | >0.001 | >0.001 |
| 334392 | >0.001 | >0.001 | >0.001 | >0.001 | >0.001 | >0.001 | >0.001 | >0.001 | >0.001 | >0.001 | >0.001 |
| 474317 | >0.001 | >0.001 | >0.001 | >0.001 | >0.001 | >0.001 | >0.001 | >0.001 | >0.001 | >0.001 | >0.001 |
| 481723 | >0.001 | >0.001 | >0.001 | >0.001 | >0.001 | >0.001 | >0.001 | >0.001 | >0.001 | >0.001 | >0.001 |
| 229357 | >0.001 | >0.001 | >0.001 | >0.001 | >0.001 | >0.001 | >0.001 | >0.001 | >0.001 | >0.001 | >0.001 |
| 199021 | >0.001 | >0.001 | >0.001 | >0.001 | >0.001 | >0.001 | >0.001 | >0.001 | >0.001 | 7.04E−04 | >0.001 |
| 480668 | >0.001 | >0.001 | >0.001 | >0.001 | >0.001 | >0.001 | >0.001 | >0.001 | >0.001 | >0.001 | 1.69E−05 |
| 277496 | >0.001 | >0.001 | >0.001 | >0.001 | >0.001 | >0.001 | >0.001 | >0.001 | >0.001 | >0.001 | >0.001 |
| 332683 | >0.001 | >0.001 | >0.001 | >0.001 | >0.001 | >0.001 | >0.001 | >0.001 | >0.001 | >0.001 | >0.001 |
| 245334 | >0.001 | >0.001 | >0.001 | >0.001 | >0.001 | >0.001 | >0.001 | >0.001 | >0.001 | >0.001 | >0.001 |
| 333034 | >0.001 | >0.001 | >0.001 | >0.001 | >0.001 | >0.001 | >0.001 | >0.001 | >0.001 | >0.001 | >0.001 |
| 337523 | >0.001 | >0.001 | >0.001 | >0.001 | >0.001 | >0.001 | >0.001 | >0.001 | >0.001 | >0.001 | >0.001 |
| 230316 | >0.001 | >0.001 | >0.001 | 2.27E−07 | >0.001 | >0.001 | >0.001 | >0.001 | >0.001 | >0.001 | >0.001 |
| 237668 | >0.001 | >0.001 | >0.001 | >0.001 | >0.001 | >0.001 | >0.001 | >0.001 | >0.001 | >0.001 | >0.001 |
| 201752 | >0.001 | >0.001 | >0.001 | >0.001 | >0.001 | >0.001 | >0.001 | >0.001 | >0.001 | >0.001 | 2.36E−06 |
| 28779 | >0.001 | >0.001 | >0.001 | >0.001 | >0.001 | >0.001 | >0.001 | 7.01E−09 | >0.001 | >0.001 | 5.58E−09 |
| 285840 | >0.001 | >0.001 | >0.001 | >0.001 | >0.001 | >0.001 | >0.001 | >0.001 | >0.001 | >0.001 | >0.001 |
| 199882 | >0.001 | >0.001 | >0.001 | >0.001 | >0.001 | >0.001 | >0.001 | >0.001 | >0.001 | >0.001 | >0.001 |

| Incyte ID No | MITF 345480 | BMP7 380722 | IBSP 350961 | ITGB3 351122 | AHSG 199151 | TNFRSF11B 201571 | IL1B 21870 | SPI1 235903 | MMP9 238213 | PTHR1 137252 | SRC 245512 |
|---|---|---|---|---|---|---|---|---|---|---|---|
| 7074 | >0.001 | >0.001 | >0.001 | >0.001 | >0.001 | >0.001 | >0.001 | >0.001 | >0.001 | >0.001 | >0.001 |
| 334392 | >0.001 | >0.001 | >0.001 | >0.001 | >0.001 | >0.001 | >0.001 | >0.001 | >0.001 | >0.001 | >0.001 |
| 474317 | >0.001 | >0.001 | >0.001 | >0.001 | >0.001 | >0.001 | >0.001 | >0.001 | >0.001 | >0.001 | >0.001 |
| 481723 | >0.001 | >0.001 | >0.001 | >0.001 | >0.001 | >0.001 | >0.001 | >0.001 | >0.001 | >0.001 | >0.001 |
| 229357 | >0.001 | >0.001 | >0.001 | >0.001 | >0.001 | >0.001 | >0.001 | >0.001 | >0.001 | >0.001 | >0.001 |
| 199021 | >0.001 | >0.001 | >0.001 | >0.001 | >0.001 | >0.001 | >0.001 | >0.001 | >0.001 | >0.001 | >0.001 |
| 480668 | >0.001 | >0.001 | >0.001 | >0.001 | >0.001 | >0.001 | 1.75E−08 | >0.001 | >0.001 | >0.001 | >0.001 |
| 277496 | >0.001 | >0.001 | >0.001 | >0.001 | >0.001 | >0.001 | >0.001 | >0.001 | >0.001 | >0.001 | >0.001 |
| 332683 | >0.001 | >0.001 | 3.59E−05 | >0.001 | >0.001 | 3.01E−04 | >0.001 | >0.001 | >0.001 | >0.001 | >0.001 |
| 245334 | >0.001 | >0.001 | >0.001 | >0.001 | >0.001 | 4.13E−09 | 9.19E−06 | >0.001 | >0.001 | >0.001 | >0.001 |
| 333034 | >0.001 | >0.001 | >0.001 | >0.001 | >0.001 | 2.92E−07 | >0.001 | >0.001 | >0.001 | >0.001 | >0.001 |
| 337523 | >0.001 | >0.001 | 8.77E−04 | >0.001 | >0.001 | 5.44E−07 | >0.001 | >0.001 | >0.001 | >0.001 | >0.001 |
| 230316 | >0.001 | 2.78E−04 | >0.001 | >0.001 | >0.001 | >0.001 | >0.001 | >0.001 | >0.001 | >0.001 | >0.001 |
| 237668 | >0.001 | >0.001 | 1.53E−06 | >0.001 | >0.001 | >0.001 | >0.001 | >0.001 | >0.001 | >0.001 | >0.001 |
| 201752 | >0.001 | >0.001 | 3.88E−07 | >0.001 | >0.001 | 6.65E−05 | >0.001 | >0.001 | >0.001 | >0.001 | >0.001 |
| 28779 | >0.001 | >0.001 | >0.001 | >0.001 | >0.001 | >0.001 | 7.65E−09 | >0.001 | >0.001 | >0.001 | >0.001 |
| 285840 | >0.001 | >0.001 | >0.001 | 9.36E−06 | >0.001 | >0.001 | >0.001 | >0.001 | >0.001 | 4.07E−05 | 1.40E−04 |
| 199882 | >0.001 | >0.001 | >0.001 | >0.001 | >0.001 | >0.001 | >0.001 | >0.001 | >0.001 | >0.001 | >0.001 |

| Incyte ID No | KDR 247817 | FLT1 322303 | ADAM12 331582 | MADH6 333398 | PTHR2 336338 | GRLF1 198342 | PDNP1 344785 | BMP2 346680 | VDR 348162 | ESR1 349438 | TRAF5 408769 |
|---|---|---|---|---|---|---|---|---|---|---|---|
| 7074 | 1.13E−06 | 8.18E−06 | 1.36E−04 | 6.57E−05 | 9.68E−05 | >0.001 | 1.32E−07 | >0.001 | >0.001 | >0.001 | >0.001 |
| 334392 | >0.001 | 5.09E−05 | >0.001 | >0.001 | >0.001 | 2.05E−06 | >0.001 | 1.39E−04 | >0.001 | >0.001 | >0.001 |
| 474317 | 6.64E−05 | 4.74E−06 | >0.001 | >0.001 | >0.001 | 5.87E−08 | 1.49E−04 | >0.001 | 1.92E−05 | >0.001 | >0.001 |
| 481723 | >0.001 | 3.09E−06 | 1.73E−05 | >0.001 | >0.001 | >0.001 | >0.001 | >0.001 | >0.001 | 8.10E−05 | >0.001 |
| 229357 | 6.80E−05 | >0.001 | >0.001 | 1.89E−05 | >0.001 | >0.001 | >0.001 | >0.001 | >0.001 | 3.21E−05 | >0.001 |
| 199021 | >0.001 | >0.001 | >0.001 | >0.001 | >0.001 | >0.001 | >0.001 | >0.001 | >0.001 | >0.001 | >0.001 |
| 480668 | >0.001 | >0.001 | >0.001 | >0.001 | >0.001 | >0.001 | >0.001 | >0.001 | >0.001 | >0.001 | >0.001 |
| 277496 | >0.001 | 9.41E−05 | >0.001 | >0.001 | >0.001 | >0.001 | >0.001 | >0.001 | >0.001 | >0.001 | >0.001 |
| 332683 | >0.001 | >0.001 | >0.001 | >0.001 | >0.001 | >0.001 | >0.001 | >0.001 | >0.001 | >0.001 | >0.001 |
| 245334 | >0.001 | >0.001 | >0.001 | >0.001 | >0.001 | >0.001 | >0.001 | 4.74E−05 | >0.001 | >0.001 | >0.001 |
| 333034 | >0.001 | >0.001 | 2.02E−04 | >0.001 | >0.001 | >0.001 | >0.001 | >0.001 | >0.001 | >0.001 | >0.001 |
| 337523 | >0.001 | >0.001 | >0.001 | 8.73E−04 | >0.001 | >0.001 | >0.001 | >0.001 | >0.001 | >0.001 | >0.001 |
| 230316 | >0.001 | >0.001 | >0.001 | >0.001 | >0.001 | 5.26E−05 | >0.001 | >0.001 | >0.001 | >0.001 | >0.001 |
| 237668 | >0.001 | >0.001 | >0.001 | >0.001 | 3.92E−06 | >0.001 | 1.00E−05 | >0.001 | >0.001 | >0.001 | >0.001 |
| 201752 | >0.001 | >0.001 | 9.41E−05 | >0.001 | 3.12E−05 | >0.001 | >0.001 | 1.23E−06 | >0.001 | >0.001 | >0.001 |
| 28779 | >0.001 | >0.001 | >0.001 | >0.001 | >0.001 | >0.001 | >0.001 | 6.21E−05 | >0.001 | >0.001 | >0.001 |
| 285840 | 8.49E−05 | 6.37E−06 | 7.85E−06 | 4.49E−05 | 9.95E−05 | 8.82E−08 | 1.30E−08 | >0.001 | >0.001 | 2.77E−05 | 6.23E−05 |
| 199882 | >0.001 | >0.001 | 2.19E−06 | >0.001 | >0.001 | >0.001 | >0.001 | >0.001 | >0.001 | >0.001 | >0.001 |

| Incyte ID No | TGFB1 481410 | ACP5 215481 | CTSK 267825 | BMP6 289783 | SPARC 234507 | VEGFA 53488 | FSTL1 243362 | COL1A2 244935 | BGLAP 239544 | CA2 248306 | ITGAV 250203 |
|---|---|---|---|---|---|---|---|---|---|---|---|
| 7074 | >0.001 | >0.001 | 5.39E−11 | >0.001 | 1.07E−15 | 2.31E−07 | 1.52E−17 | 4.09E−20 | 4.31E−06 | >0.001 | 9.16E−08 |
| 334392 | 1.18E−04 | >0.001 | 1.52E−10 | 3.91E−07 | 9.42E−14 | >0.001 | 1.37E−08 | 3.09E−06 | 1.67E−05 | >0.001 | 6.08E−05 |
| 474317 | 1.34E−05 | >0.001 | 6.33E−06 | >0.001 | 2.34E−06 | 1.27E−08 | 3.13E−10 | 2.00E−09 | >0.001 | >0.001 | >0.001 |
| 481723 | >0.001 | >0.001 | 2.83E−11 | >0.001 | 2.97E−15 | >0.001 | 1.29E−14 | 4.40E−17 | >0.001 | >0.001 | 2.23E−07 |
| 229357 | 2.00E−06 | >0.001 | 1.57E−08 | 1.48E−07 | 1.23E−21 | 2.02E−09 | 3.29E−20 | 7.71 E−17 | 1.80E−09 | >0.001 | 2.75E−10 |
| 199021 | >0.001 | >0.001 | >0.001 | >0.001 | >0.001 | >0.001 | >0.001 | >0.001 | >0.001 | >0.001 | >0.001 |
| 480668 | >0.001 | >0.001 | >0.001 | >0.001 | >0.001 | 3.93E−05 | >0.001 | >0.001 | >0.001 | >0.001 | >0.001 |
| 277496 | >0.001 | >0.001 | >0.001 | >0.001 | 2.35E−05 | 4.98E−05 | 1.54E−05 | >0.001 | >0.001 | >0.001 | >0.001 |
| 332683 | >0.001 | >0.001 | >0.001 | >0.001 | >0.001 | >0.001 | >0.001 | >0.001 | >0.001 | >0.001 | >0.001 |
| 245334 | >0.001 | >0.001 | >0.001 | 3.11E−05 | >0.001 | >0.001 | >0.001 | >0.001 | >0.001 | >0.001 | >0.001 |

TABLE 5-continued

| | | | | | | | | | | | |
|---|---|---|---|---|---|---|---|---|---|---|---|
| 333034 | >0.001 | >0.001 | >0.001 | >0.001 | >0.001 | >0.001 | >0.001 | >0.001 | >0.001 | >0.001 | >0.001 |
| 337523 | >0.001 | >0.001 | >0.001 | >0.001 | >0.001 | >0.001 | 7.79E−05 | >0.001 | >0.001 | >0.001 | >0.001 |
| 230316 | >0.001 | >0.001 | >0.001 | 5.64E−06 | >0.001 | >0.001 | >0.001 | >0.001 | 8.64E−06 | >0.001 | >0.001 |
| 237668 | >0.001 | >0.001 | 2.21E−15 | >0.001 | 2.15E−11 | 1.58E−06 | 1.96E−22 | 3.36E−18 | 5.16E−05 | >0.001 | 6.96E−06 |
| 201752 | >0.001 | >0.001 | >0.001 | >0.001 | >0.001 | >0.001 | >0.001 | >0.001 | >0.001 | >0.001 | >0.001 |
| 28779 | >0.001 | >0.001 | >0.001 | >0.001 | >0.001 | >0.001 | >0.001 | >0.001 | >0.001 | >0.001 | >0.001 |
| 285840 | 7.53E−08 | >0.001 | 4.28E−11 | 1.18E−05 | 5.01E−10 | 4.98E−06 | 1.47E−05 | 3.34E−15 | 8.35E−06 | >0.001 | >0.001 |
| 199882 | >0.001 | >0.001 | >0.001 | 5.12E−09 | 7.60E−14 | >0.001 | 7.93E−23 | 8.47E−15 | >0.001 | >0.001 | 2.20E−08 |

| Incyte ID No | EGR1 251715 | COL1A1 257184 | CSF1 333948 | BGN 345168 | SPP1 352406 | IGF1 399413 | DCN 427953 | CTSB 428976 | CSF1R 64333 | KL 215078 |
|---|---|---|---|---|---|---|---|---|---|---|
| 7074 | 9.44E−10 | 2.10E−14 | >0.001 | 1.01E−06 | >0.001 | 1.85E−09 | 3.52E−28 | 2.09E−06 | >0.001 | >0.001 |
| 334392 | 6.42E−08 | 1.77E−05 | >0.001 | 3.06E−07 | >0.001 | 9.52E−08 | 3.21E−09 | 2.12E−05 | 1.10E−09 | >0.001 |
| 474317 | 1.17E−07 | 1.24E−10 | >0.001 | 1.56E−08 | >0.001 | 6.82E−12 | 2.86E−08 | 6.16E−06 | >0.001 | >0.001 |
| 481723 | >0.001 | 6.42E−11 | >0.001 | 9.41E−06 | >0.001 | 1.40E−05 | 4.54E−10 | 1.06E−05 | >0.001 | >0.001 |
| 229357 | 2.90E−09 | 5.24E−11 | >0.001 | 1.22E−06 | >0.001 | 1.06E−14 | 2.12E−21 | 7.34E−11 | >0.001 | >0.001 |
| 199021 | >0.001 | >0.001 | >0.001 | >0.001 | >0.001 | >0.001 | >0.001 | >0.001 | >0.001 | >0.001 |
| 480668 | >0.001 | >0.001 | 2.47E−04 | >0.001 | >0.001 | >0.001 | >0.001 | >0.001 | >0.001 | >0.001 |
| 277496 | >0.001 | >0.001 | >0.001 | >0.001 | >0.001 | 1.31 E−06 | 1.62E−08 | >0.001 | >0.001 | >0.001 |
| 332683 | >0.001 | >0.001 | >0.001 | >0.001 | >0.001 | >0.001 | >0.001 | >0.001 | >0.001 | >0.001 |
| 245334 | >0.001 | >0.001 | >0.001 | >0.001 | >0.001 | >0.001 | >0.001 | 7.44E−07 | >0.001 | >0.001 |
| 333034 | >0.001 | >0.001 | >0.001 | >0.001 | >0.001 | >0.001 | >0.001 | >0.001 | >0.001 | >0.001 |
| 337523 | >0.001 | >0.001 | 4.91E−05 | >0.001 | >0.001 | >0.001 | >0.001 | >0.001 | >0.001 | >0.001 |
| 230316 | >0.001 | >0.001 | >0.001 | >0.001 | >0.001 | >0.001 | >0.001 | >0.001 | >0.001 | >0.001 |
| 237668 | 2.55E−10 | 4.08E−16 | >0.001 | 1.38E−14 | >0.001 | 2.17E−15 | 3.42E−29 | 1.00E−07 | 1.75E−06 | >0.001 |
| 201752 | >0.001 | >0.001 | >0.001 | >0.001 | >0.001 | >0.001 | >0.001 | >0.001 | >0.001 | >0.001 |
| 28779 | >0.001 | >0.001 | 1.75E−04 | >0.001 | >0.001 | >0.001 | >0.001 | >0.001 | >0.001 | >0.001 |
| 285840 | 5.59E−10 | 3.04E−19 | >0.001 | 9.42E−16 | >0.001 | 5.88E−06 | 1.99E−10 | 1.40E−08 | 1.00E−07 | >0.001 |
| 199882 | >0.001 | 3.33E−12 | 2.59E−05 | 3.89E−08 | >0.001 | 3.25E−06 | 1.17E−07 | 2.93E−11 | >0.001 | >0.001 |

What is claimed is:

1. A combination comprising a plurality of substantially purified and isolated polynucleotides, wherein the polynucleotides are SEQ ID NOs: 1–169 that are co-expressed with one or more genes known to be involved in bone remodeling and osteoporosis or the complements of the polynucleodes.

2. An array comprising the combination of claim 1 and a substrate.

3. A method of using a polynucleotide array to detect the presence of at least one polynucleotide in a sample, the method comprising:

(a) contacting the array of claim 2 with a sample containing polynucleotides under conditions which allow for the formation of hybridization complexes between the polynucleotides in the sample and those of the polynucleotide array; and (b) detecting any formed hybridization complexes.

4. A method of screening for the presence of polynucleotides in a sample that are co-expressed with one or more genes known to be involved in bone remodeling and osteoporosis, the method comprising:

a) providing a nucleic acid sample;

b) contacting the sample with the array of claim 2; and c) detecting the formation of any hybridization complexes, whereby the presence of the hybridization complexes indicates the presence of polynucleotides in the sample that are co-expressed with one or more genes known to be involved in bone remodeling and osteoporosis.

* * * * *

UNITED STATES PATENT AND TRADEMARK OFFICE

CERTIFICATE OF CORRECTION

PATENT NO. : 6,426,186 B1
DATED : July 30, 2002
INVENTOR(S) : Jones et al.

It is certified that error appears in the above-identified patent and that said Letters Patent is hereby corrected as shown below:

Column 407,
Line 18, replace “polynucleodes” with -- polynucleotides --.

Signed and Sealed this

Twenty-first Day of January, 2003

JAMES E. ROGAN
*Director of the United States Patent and Trademark Office*